(12) United States Patent
Yang et al.

(10) Patent No.: US 8,877,474 B2
(45) Date of Patent: Nov. 4, 2014

(54) GH61 GLYCOSIDE HYDROLASE PROTEIN VARIANTS AND COFACTORS THAT ENHANCE GH61 ACTIVITY

(75) Inventors: Jie Yang, Foster City, CA (US); Xiyun Zhang, Fremont, CA (US); Jungjoo Yoon, Foster City, CA (US); Kripa Rao, San Mateo, CA (US); John H. Grate, Los Altos, CA (US); David Elgart, San Mateo, CA (US); Dipnath Baidyaroy, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 143 days.

(21) Appl. No.: 13/592,024

(22) Filed: Aug. 22, 2012

(65) Prior Publication Data

US 2013/0052713 A1    Feb. 28, 2013

Related U.S. Application Data

(63) Continuation-in-part of application No. 13/215,193, filed on Aug. 22, 2011, now Pat. No. 8,298,795.

(60) Provisional application No. 61/375,788, filed on Aug. 20, 2010, provisional application No. 61/526,224, filed on Aug. 22, 2011, provisional application No. 61/601,997, filed on Feb. 22, 2012.

(51) Int. Cl.
| | |
|---|---|
| *C12N 9/96* | (2006.01) |
| *C12N 9/16* | (2006.01) |
| *C12N 9/20* | (2006.01) |
| *C12N 15/00* | (2006.01) |
| *C12N 1/00* | (2006.01) |
| *C07H 21/04* | (2006.01) |
| *C12P 19/14* | (2006.01) |
| *C12N 9/30* | (2006.01) |
| *C12P 7/10* | (2006.01) |
| *C12N 9/42* | (2006.01) |

(52) U.S. Cl.
CPC . *C12P 7/10* (2013.01); *C12P 19/14* (2013.01); *C12N 9/242* (2013.01); *C12N 9/2434* (2013.01); *C12Y 302/01021* (2013.01); *C12Y 302/01091* (2013.01); *C12N 9/2437* (2013.01); *C12N 9/2445* (2013.01); *Y02E 50/16* (2013.01)
USPC ........ 435/188; 435/196; 435/198; 435/320.1; 435/254.11; 435/254.2; 536/23.2

(58) Field of Classification Search
CPC .... C12N 9/242; C12N 9/2434; C12N 9/2437; C12N 9/2445; C12Y 302/01021; C12Y 302/01091; C12P 19/14; C12P 7/10; C12P 19/00
USPC ................. 435/188, 196, 198, 320.1, 254.11, 435/254.2; 536/23.2
See application file for complete search history.

(56) References Cited

U.S. PATENT DOCUMENTS

| | | |
|---|---|---|
| 3,990,944 A | 11/1976 | Gauss et al. |
| 3,990,945 A | 11/1976 | Huff et al. |
| 4,356,196 A | 10/1982 | Hultquist |
| 4,461,648 A | 7/1984 | Foody |
| 4,556,430 A | 12/1985 | Converse et al. |
| 4,600,590 A | 7/1986 | Dale |
| 5,037,663 A | 8/1991 | Dale |
| 5,171,592 A | 12/1992 | Holtzapple et al. |
| 5,605,793 A | 2/1997 | Stemmer |
| 5,789,210 A | 8/1998 | Ho et al. |
| 5,811,238 A | 9/1998 | Stemmer et al. |
| 5,811,381 A | 9/1998 | Emalfarb et al. |
| 5,830,721 A | 11/1998 | Stemmer et al. |
| 5,834,252 A | 11/1998 | Stemmer et al. |
| 5,837,458 A | 11/1998 | Minshull et al. |
| 5,866,382 A | 2/1999 | Hallborn et al. |
| 5,928,905 A | 7/1999 | Stemmer et al. |
| 5,939,544 A | 8/1999 | Karstens et al. |
| 6,015,707 A | 1/2000 | Emalfarb et al. |
| 6,096,548 A | 8/2000 | Stemmer |
| 6,106,888 A | 8/2000 | Dale et al. |
| 6,117,679 A | 9/2000 | Stemmer |
| 6,132,970 A | 10/2000 | Stemmer |
| 6,165,793 A | 12/2000 | Stemmer |
| 6,176,176 B1 | 1/2001 | Dale et al. |
| 6,180,406 B1 | 1/2001 | Stemmer |
| 6,251,674 B1 | 6/2001 | Tobin et al. |
| 6,277,638 B1 | 8/2001 | Stemmer |

(Continued)

FOREIGN PATENT DOCUMENTS

| | | |
|---|---|---|
| EP | 0137280 B1 | 3/1992 |
| EP | 0450430 B1 | 6/1997 |

(Continued)

OTHER PUBLICATIONS

Altschul, S.F., et al., "Basic Local Alignment Search Tool," J. Mol. Biol., 215: 403-410 [1990].

Altschul, S.F., et al., "Gapped BLAST and PSI-BLAST: a new generation of protein database search programs," Nucleic Acids Res., 25(17):3389-3402 (1997).

Badhan, A.K., et al., "Production of multiple xylanolytic and cellulolytic enzymes by thermophilic fungus *Myceliophthora* sp. IMI 387099," Biores. Technol., 98:504-10 [2007].

Blaiseau, P-L., et al., "Primary structure of a chitinase-encoding gene (chi1) from the filamentous fungus *Aphanocladium album*: similarity to bacterial chitinases," Gene, 120(2):243-248 (1992).

(Continued)

*Primary Examiner* — Chih-Min Kam
(74) *Attorney, Agent, or Firm* — Codexis, Inc.

(57) ABSTRACT

The present invention provides various GH61 protein variants comprising various amino acid substitutions. The GH61 protein variants have an improved ability to synergize with cellulase enzymes, thereby increasing the yield of fermentable sugars obtained by saccharification of biomass. In some embodiments, sugars obtained from saccharification are fermented to produce numerous end-products, including but not limited to alcohol.

23 Claims, 5 Drawing Sheets

(56) References Cited

U.S. PATENT DOCUMENTS

| | | |
|---|---|---|
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | del Cardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,475,768 B1 | 11/2002 | Otero et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,573,086 B1 | 6/2003 | Emalfrab et al. |
| 6,573,098 B1 | 6/2003 | Stemmer |
| 6,576,467 B1 | 6/2003 | Stemmer |
| 6,579,678 B1 | 6/2003 | Patten et al. |
| 6,582,944 B1 | 6/2003 | Hallborn et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,773,900 B2 | 8/2004 | Short et al. |
| 6,939,689 B2 | 9/2005 | Short et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,399,627 B2 | 7/2008 | Emalfarb et al. |
| 7,421,347 B2 | 9/2008 | Selfinov et al. |
| 7,430,477 B2 | 9/2008 | Selfinov et al. |
| 7,465,791 B1 | 12/2008 | Hallberg et al. |
| 7,527,927 B1 | 5/2009 | Ho et al. |
| 7,534,564 B2 | 5/2009 | Patten et al. |
| 7,620,500 B2 | 11/2009 | Mundorff et al. |
| 7,620,502 B2 | 11/2009 | Selfinov et al. |
| 7,622,284 B2 | 11/2009 | Den Camp et al. |
| 7,629,170 B2 | 12/2009 | delCardayre et al. |
| 7,647,184 B2 | 1/2010 | Vega et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,754,457 B2 | 7/2010 | Foody et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 7,981,614 B2 | 7/2011 | Stemmer et al. |
| 8,088,608 B2 | 1/2012 | Yang et al. |
| 8,206,960 B1 | 6/2012 | Yang et al. |
| 8,236,551 B2 | 8/2012 | Dhawan et al. |
| 2007/0031953 A1 | 2/2007 | Dunson, Jr. et al. |
| 2007/0238155 A1 | 10/2007 | Gusakov et al. |
| 2008/0057541 A1 | 3/2008 | Hill et al. |
| 2008/0104724 A1 | 5/2008 | Sticklen et al. |
| 2008/0194005 A1 | 8/2008 | Emalfarb et al. |
| 2008/0220990 A1 | 9/2008 | Fox |
| 2009/0061484 A1 | 3/2009 | Scott et al. |
| 2009/0099079 A1 | 4/2009 | Emalfarb et al. |
| 2009/0209009 A1 | 8/2009 | Tolan et al. |
| 2009/0312196 A1 | 12/2009 | Colbeck et al. |
| 2010/0143971 A1 | 6/2010 | Spodsberg et al. |
| 2010/0267089 A1 | 10/2010 | Yang et al. |
| 2011/0034342 A1 | 2/2011 | Fox |
| 2011/0114744 A1 | 5/2011 | Ricciardi et al. |
| 2011/0124058 A1 | 5/2011 | Baidyaroy et al. |
| 2011/0129881 A1 | 6/2011 | Yang et al. |
| 2012/0208235 A1 | 8/2012 | Zhang et al. |
| 2012/0276594 A1 | 11/2012 | Voladri et al. |
| 2013/0323822 A1* | 12/2013 | Brevnova et al. ........ 435/254.21 |

FOREIGN PATENT DOCUMENTS

| | | |
|---|---|---|
| WO | 95/22625 A1 | 8/1995 |
| WO | 96/00787 A1 | 1/1996 |
| WO | 97/00078 A1 | 1/1997 |
| WO | 97/35966 A1 | 10/1997 |
| WO | 98/15633 A1 | 4/1998 |
| WO | 98/27230 A1 | 6/1998 |
| WO | 00/42651 A1 | 7/2000 |
| WO | 01/75767 A2 | 10/2001 |
| WO | 2005/074647 A2 | 8/2005 |
| WO | 2007/109441 A2 | 9/2007 |
| WO | 2008/073914 A2 | 6/2008 |
| WO | 2008/130603 A2 | 10/2008 |
| WO | 2009/033071 A2 | 3/2009 |
| WO | 2009/045651 A2 | 4/2009 |
| WO | 2009/152336 A1 | 12/2009 |
| WO | 2010/022511 A1 | 3/2010 |
| WO | 2010/107303 A2 | 9/2010 |
| WO | 2010/138754 A1 | 12/2010 |
| WO | 2010/148148 A2 | 12/2010 |
| WO | 2011/041594 A1 | 4/2011 |
| WO | 2011/153516 A2 | 12/2011 |
| WO | 2012/024698 A1 | 2/2012 |
| WO | 2012/044835 A1 | 4/2012 |
| WO | 2012/088159 A2 | 6/2012 |
| WO | WO 2012/125925 A2 * | 9/2012 |

OTHER PUBLICATIONS

Boel, E., et al., "Two different types of intervening sequences in the glucoamylase gene from *Aspergillus niger*," EMBO J., 3(7):1581-1585 (1984).

Botstein, D., et al., "Strategies and Applications ofin Vitro Mutagenesis," Science, 229(4719):1193-1201 [1985].

Carter, P., "Site-directed mutagenesis," Biochem. J., 237:1-7 [1986].

Christians, F.C., et al., "Directed evolution of thymidine kinase for AZT phosphorylation using DNA family shuffling," Nat. Biotechnol., 17:259-264 [1999].

(56) References Cited

OTHER PUBLICATIONS

Crameri A., et al., "DNA shuffling of a family of genes derived from diverse species accelerates directed evolution," Nature, 391:288-291 [1998].
Crameri, A., et al., "Improved green fluorescent protein by molecular evolution using DNA shuffling," Nat. Biotechnol., 14:315-319 [1996].
Crameri, A., et al., "Molecular evolution of an arsenate detoxification pathway by DNA shuffling," Nat. Biotechnol., 15:436-438 [1997].
Dale, S.J., et al., "Oligonucleotide-Directed Random Mutagenesis Using the Phosphorothioate Method," Meth. Mol. Biol., 57:369-74 [1996].
Drissen, R.E.T., et al., "Modelling ethanol production from cellulose: separate hydrolysis and fermentation versus simultaneous saccharification and fermentation," Biocat. Biotransform., 27:27-35 [2009].
Foreman, P.K., et al., "Transcriptional Regulation of Biomass-degrading Enzymes in the Filamentous Fungus *Trichoderma reesei*," J. Biol. Chem., 278(34):31988-31997 [2003].
Garg, A.K., "An addition to the genus *Chrysosporium corda*," Mycopathologia, 30(3-4):221-224 (1966).
GenBank accession No. NP_821730 dated Aug. 29, 2011.
Glenn, J.K., et al., "Mn(II) Oxidation Is the Principal Function of the Extracellular Mn-Peroxidase from *Phanerochaete chrysosporium*," Arch. Biochem. Biophys., 251(2):688-696 [1986].
Greener, A., et al., "An efficient random mutagenesis technique using an *E. coli* mutator strain," Methods Mol. Biol., 57:375-385 [1996].
Guo, Z., et al., "3'-End-Forming Signals of Yeast mRNA," Mol. Cell. Biol., 15(11):5983-5990 [1995].
Harayama, S., "Artificial evolution by DNA shuffling," Trends in Biotechnol., 16:76-82 [1998].
Harris, P.V., et al., "Stimulation of Lignocellulosic Biomass Hydrolysis by Proteins of Glycoside Hydrolase Family 61: Structure and Function of a Large, Enigmatic Family," Biochem., 49:3305-3316 [2010].
Harvey, P.J., et al., "Veratryl alcohol as a mediator and the role of radical cations in lignin biodegradation by *Phanerochaete chrysosporium*," FEBS Lett., 195(1,2):242-246 [1986].
Henriksen, A.L.S., et al., "Study of the glucoamylase promoter in *Aspergilllus niger* using green fluorescent protein," Microbiol., 145:729-34 [1999].
Jorgensen, H., "Effect of Nutrients on Fermentation of Pretreated Wheat Straw at very High Dry Matter Content by *Saccharomyces cerevisiae*," Appl. Biochem. Biotechnol., 153:44-57 [2009].
Kramer, B., et al., "Different base/base mismatches are corrected with different efficiencies by the methyl-directed DNA mismatch-repair system of *E. coli*," Cell, 38:879-887 [1984].
Li, M.Z., et al., "Harnessing homologous recombination in vitro to generate recombinant DNA via SLIC," Nature Methods, 4:251-56 (2007).
Limon, C., et al., "Primary structure and expression pattern of the 33-kDa chitinase gene from the nucoparasitic fungus *Trichocherma harzianum*," Curr. Genet., 28:478-83 [1995].
Ling, M.M., et al., "Approaches to DNA Mutagenesis: An Overview," Anal. Biochem., 254(2):157-78 [1997].
McInerney, J.O., "GCUA: general codon usage analysis," Bioinformatics, 14(4):372-73, 1998.
Minshull, J., et al., "Protein evolution by molecular breeding," Curr. Op. Chem. Biol., 3:284-290 [1999].
Nunberg, J.H., et al., "Molecular Cloning and Characterization of the Glucoamylase Gene of *Aspergillus awamori*," Mol. Cell Biol., 4(11):2306-2315 (1984).
Patten, P.A., et al., "Applications of DNA shuffling to pharmaceuticals and vaccines," Curr. Opin. Biotechnol., 8:724-733 [1997].
Park, J.B., et al., "The human glutaredoxin gene: determination of its organization, transcription start point, and promoter analysis," Gene, 197:189-93 [1997].
Romanos, M.A., et al., "Foreign gene expression in yeast: a review," Yeast 8:423-488 [1992].
Rosgaard, L., et al., "Efficiency of New Fungal Cellulase Systems in Boosting Enzymatic Degradation of Barley Straw Lignocellulose," Biotechnol. Prog., 22:493-8 [2006].
Saloheimo, M., et al., "Swollenin, a Trichoderma reesei protein with sequence similarity to the plant expansins, exhibits disruption activity on cellulosic materials," Eur. J. Biochem., 269:4202-4211 [2002].
Simonen, M., et al., "Protein Secretion in *Bacillus* Species," Microbiological Reviews, 57:109-137 (1993).
Smith, M., "In Vitro Mutagenesis," Ann. Rev. Genet., 19:423-462 [1985].
Stemmer, W.P.C., "Rapid evolution of a protein in vitro by DNA shuffling," Nature, 370:389-391 [1994].
Stemmer, W.P.C., "DNA shuffling by random fragmentation and reassembly: In vitro recombination for molecular evolution," Proc. Nat. Acad. Sci. USA, 91:10747-10751 [1994].
SwissProt Accession No. P00724 dated Feb. 22, 2012.
Taussig, R., et al., "Nucleotide sequence of the yeast SUC2 gene for invertase," Nucl. Acids Res., 11(6):1943-54 [1983].
Verduyn, C., et al., "Effect of benzoic acid on metabolic fluxes in yeasts: a continuous-culture study on the regulation of respiration and alcoholic fermentation," Yeast, 8:501-517 [1992].
Inui, M., et al., "Advanced Fermentation Technologies" in Biomass to Biofuels: Strategies for Global Industries, John Wiley & Sons, Ltd., Hoboken, NJ, pp. 311-330 (Chapter 15) [2010].
Viikari, L., et al., "Thermostable enzymes in lignocellulose hydrolysis," Adv. Biochem. Eng. Biotechnol., 108:121-45 [2007].
Weil, J., et al., "Pretreatment of Yellow Poplar Sawdust by Pressure Cooking in Water," Appl. Biochem. Biotechnol., 68(1-2): 21-40 [1997].
Wells, J.A., et al., "Cassette mutagenesis: an efficient method for generation of multiple mutations at defined sites," Gene, 34:315-323 [1985].
Wright, A., et al., "Diverse Plasmid DNA Vectors by Directed Molecular Evolution of *Cytomegalovirus* Promoters," Hum. Gene Ther., 16:881-892 [2005].
Zhang, J.-H., et al., "Directed evolution of a fucosidase from a galactosidase by DNA shuffling and screening," Proc. Nat. Acad. Sci. U.S.A., 94:4504-4509 [1997].
Zhao, X.Q., et al., "Impact of zinc supplementation on the improvement of ethanol tolerance and yield of self-flocculating yeast in continuous ethanol fermentation," J. Biotechnol., 139:55-60 [2009].
Zhu, T., et al., "Construction of two Gateway vectors for gene expression in fungi," Plasmid, 62:128-33 [2009].
UniProt Accession No. Q2GWR1 dated Mar. 21, 2006.
Lynd, L.R., et al., "Microbial Cellulose Utilization: Fundamentals and Biotechnology," Microbiology and Molecular Biology Review, 66(3):506-577 [2002].

* cited by examiner

Panel (A)

Panel B

Panel A

Panel B

Panel A

Panel B

Panel A

Panel B

```
                            SEQUENCE LISTING

<160> NUMBER OF SEQ ID NOS: 171

<210> SEQ ID NO 1
<211> LENGTH: 1029
<212> TYPE: DNA
<213> ORGANISM: Myceliophthora thermophila

<400> SEQUENCE: 1
atgtccaagg cctctgctct cctcgctggc ctgacgggcg cggccctcgt cgctgcacat      60
ggccacgtca gccacatcgt cgtcaacggc gtctactaca ggaactacga ccccacgaca     120
gactggtacc agcccaaccc gccaacagtc atcggctgga cggcagccga tcaggataat     180
ggcttcgttg aacccaacag ctttggcacg ccagatatca tctgccacaa gagcgccacc     240
cccggcggcg gccacgctac cgttgctgcc ggagacaaga tcaacatcgt ctggaccccc     300
gagtggcccg aatcccacat cggccccgtc attgactacc tagccgcctg caacggtgac     360
tgcgagaccg tcgacaagtc gtcgctgcgc tggttcaaga ttgacggcgc cggctacgac     420
aaggccgccg gccgctgggc cgccgacgct ctgcgcgcca acggcaacag ctggctcgtc     480
cagatcccgt cggatctcaa ggccggcaac tacgtcctcc gccacgagat catcgccctc     540
cacggtgctc agagccccaa cggcgcccag gcctaccgcg agtgcatcaa cctccgcgtc     600
accggcggcg gcagcaacct gcccagcggc gtcgccggca cctcgctgta caaggcgacc     660
gacccgggca tcctcttcaa cccctacgtc tcctccccgg attacaccgt ccccggcccg     720
gccctcattg ccggcgccgc cagctcgatc gcccagagca cgtcggtcgc cactgccacc     780
ggcacggcca ccgttcccgg cggcggcggc gccaacccta ccgccaccac caccgccgcc     840
acctccgccg ccccgagcac caccctgagg acgaccacta cctcggccgc gcagactacc     900
gccccgccct ccggcgatgt gcagaccaag tacggccagt gtggtggcaa cggatggacg     960
ggcccgacgg tgtgcgcccc cggctcgagc tgctccgtcc tcaacgagtg gtactcccag    1020
tgtttgtaa                                                            1029

<210> SEQ ID NO 2
<211> LENGTH: 342
<212> TYPE: PRT
<213> ORGANISM: Myceliophthora thermophila

<400> SEQUENCE: 2

Met Ser Lys Ala Ser Ala Leu Leu Ala Gly Leu Thr Gly Ala Ala Leu
1               5                  10                  15

Val Ala Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro Glu Ser His Ile Gly Pro Val Ile Asp
```

```
            100                 105                 110
Tyr Leu Ala Ala Cys Asn Gly Asp Cys Glu Thr Val Asp Lys Ser Ser
            115                 120                 125

Leu Arg Trp Phe Lys Ile Asp Gly Ala Gly Tyr Asp Lys Ala Ala Gly
130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
            165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Gly Ser Asn Leu Pro
            195                 200                 205

Ser Gly Val Ala Gly Thr Ser Leu Tyr Lys Ala Thr Asp Pro Gly Ile
            210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
            245                 250                 255

Ala Thr Ala Thr Gly Thr Ala Thr Val Pro Gly Gly Gly Ala Asn
            260                 265                 270

Pro Thr Ala Thr Thr Ala Ala Thr Ser Ala Ala Pro Ser Thr Thr
            275                 280                 285

Leu Arg Thr Thr Thr Thr Ser Ala Ala Gln Thr Thr Ala Pro Pro Ser
            290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
            325                 330                 335

Trp Tyr Ser Gln Cys Leu
            340

<210> SEQ ID NO 3
<211> LENGTH: 323
<212> TYPE: PRT
<213> ORGANISM: Myceliophthora thermophila

<400> SEQUENCE: 3

His Gly His Val Ser His Ile Val Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
            50                  55                  60

Gly His Ala Thr Val Ala Ala Gly Asp Lys Ile Asn Ile Val Trp Thr
65                  70                  75                  80

Pro Glu Trp Pro Glu Ser His Ile Gly Pro Val Ile Asp Tyr Leu Ala
            85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
            115                 120                 125
```

```
Ala Asp Ala Leu Arg Ala Asn Gly Asn Ser Trp Leu Val Gln Ile Pro
    130                 135                 140

Ser Asp Leu Lys Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Ser Asn Leu Pro Ser Gly Val
            180                 185                 190

Ala Gly Thr Ser Leu Tyr Lys Ala Thr Asp Pro Gly Ile Leu Phe Asn
            195                 200                 205

Pro Tyr Val Ser Ser Pro Asp Tyr Thr Val Pro Gly Pro Ala Leu Ile
210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
            275                 280                 285

Gln Thr Lys Tyr Gly Gln Cys Gly Gly Asn Gly Trp Thr Gly Pro Thr
290                 295                 300

Val Cys Ala Pro Gly Ser Ser Cys Ser Val Leu Asn Glu Trp Tyr Ser
305                 310                 315                 320

Gln Cys Leu

<210> SEQ ID NO 4
<211> LENGTH: 1029
<212> TYPE: DNA
<213> ORGANISM: Artificial sequence
<220> FEATURE:
<223> OTHER INFORMATION: Synthetic polynucleotide.

<400> SEQUENCE: 4
atgtccaagg cctctgctct cctcgctggc ctgacgggcg cggccctcgt cgctgcacac      60
ggccacgtca gccacatcgt cgtcaacggc gtctactaca ggggctacga ccccacgaca     120
gactggtacc agcccaaccc gccaacagtc atcggctgga cggcagccga tcaggataat     180
ggcttcgttg aacccaacag ctttggcacg ccagatatca tctgccacaa gagcgccacc     240
cccggcggcg gccacgctac cgttgctgcc ggagacaaga tcaacatcgt ctggaccccc     300
gagtggcccc actcccacat cggccccgtc attgactacc tagccgcctg caacggtgac     360
tgcgagaccg tcgacaagtc gtcgctgcgc tggttcaaga ttgacggcgc cggctacgac     420
aaggccgccg gccgctgggc cgccgacgct ctgcgcgcca acggcaacag ctggctcgtc     480
cagatcccgt cggatctcaa gcccggcaac tacgtcctcc gccacgagat catcgccctc     540
cacggtgctc agagccccaa cggcgcccag gcgtacccgc agtgcatcaa cctccgcgtc     600
accggcggcg gcagcaacct gcccagcggc gtcgccggca cctcgctgta caaggcgacc     660
gacccgggca tcctcttcaa cccctacgtc tcctccccgg attacaccgt ccccggcccg     720
gccctcattg ccggcgccgc cagctcgatc gcccagagca cgtcggtcgc cactgccacc     780
ggcacggcca ccgttcccgg cggcggcggc gccaacccta ccgccaccac caccgccgcc     840
acctccgccg cccagagcac cacgctgagg acgaccacta cctcgccgcc gcagactacc     900
gccccgccct ccggcgatgt gcagaccaag tacggccagt gtggtggcaa cggatggacg     960
```

```
ggcccgacgg tgtgcgcccc cggctcgagc tgctccgtcc tcaacgagtg gtactcccag    1020
tgtttgtaa                                                            1029
```

<210> SEQ ID NO 5
<211> LENGTH: 342
<212> TYPE: PRT
<213> ORGANISM: Artificial sequence
<220> FEATURE:
<223> OTHER INFORMATION: Synthetic polypeptides.

<400> SEQUENCE: 5

```
Met Ser Lys Ala Ser Ala Leu Leu Ala Gly Leu Thr Gly Ala Ala Leu
1               5                   10                  15

Val Ala Ala His Gly His Val Ser His Ile Val Asn Gly Val Tyr
            20                  25                  30

Tyr Arg Gly Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro His Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Lys Pro Gly Asn Tyr Val Leu Arg His Glu
                165                 170                 175

Ile Ile Ala Leu His Gly Ala Gln Ser Pro Asn Gly Ala Gln Ala Tyr
            180                 185                 190

Pro Gln Cys Ile Asn Leu Arg Val Thr Gly Gly Gly Ser Asn Leu Pro
        195                 200                 205

Ser Gly Val Ala Gly Thr Ser Leu Tyr Lys Ala Thr Asp Pro Gly Ile
    210                 215                 220

Leu Phe Asn Pro Tyr Val Ser Pro Asp Tyr Thr Val Pro Gly Pro
225                 230                 235                 240

Ala Leu Ile Ala Gly Ala Ala Ser Ser Ile Ala Gln Ser Thr Ser Val
                245                 250                 255

Ala Thr Ala Thr Gly Thr Ala Thr Val Pro Gly Gly Gly Ala Asn
            260                 265                 270

Pro Thr Ala Thr Thr Ala Ala Thr Ser Ala Ala Pro Ser Thr Thr
        275                 280                 285

Leu Arg Thr Thr Thr Thr Ser Ala Ala Gln Thr Ala Pro Pro Ser
    290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
```

<210> SEQ ID NO 6
<211> LENGTH: 323
<212> TYPE: PRT
<213> ORGANISM: Artificial sequence
<220> FEATURE:
<223> OTHER INFORMATION: Synthetic polypeptides.

<400> SEQUENCE: 6

```
His Gly His Val Ser His Ile Val Val Asn Gly Val Tyr Tyr Arg Gly
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
        35                  40                  45

Phe Gly Thr Pro Asp Ile Ile Cys His Lys Ser Ala Thr Pro Gly Gly
    50                  55                  60

Gly His Ala Thr Val Ala Ala Gly Asp Lys Ile Asn Ile Val Trp Thr
65                  70                  75                  80

Pro Glu Trp Pro His Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
        115                 120                 125

Ala Asp Ala Leu Arg Ala Asn Gly Asn Ser Trp Leu Val Gln Ile Pro
    130                 135                 140

Ser Asp Leu Lys Pro Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
                165                 170                 175

Ile Asn Leu Arg Val Thr Gly Gly Gly Ser Asn Leu Pro Ser Gly Val
            180                 185                 190

Ala Gly Thr Ser Leu Tyr Lys Ala Thr Asp Pro Gly Ile Leu Phe Asn
        195                 200                 205

Pro Tyr Val Ser Ser Pro Asp Tyr Thr Val Pro Gly Pro Ala Leu Ile
    210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
        275                 280                 285

Gln Thr Lys Tyr Gly Gln Cys Gly Gly Asn Gly Trp Thr Gly Pro Thr
    290                 295                 300

Val Cys Ala Pro Gly Ser Ser Cys Ser Val Leu Asn Glu Trp Tyr Ser
305                 310                 315                 320

Gln Cys Leu
```

<210> SEQ ID NO 7
<211> LENGTH: 1035
<212> TYPE: DNA
<213> ORGANISM: Artificial sequence

```
<220> FEATURE:
<223> OTHER INFORMATION: Synthetic polynucleotide.

<400> SEQUENCE: 7
acacaaatgt ccaaggcctc tgctctcctc gctggcctga cgggcgcggc cctcgtcgct      60
gcacacggcc acgtcagcca catcgtcgtc aacggcgtct actacaggaa ctacgacccc     120
acgacagact ggtaccagcc caacccgcca acagtcatcg gctggacggc agccgatcag     180
gataatggct tcgttgaacc caacagcttt ggcacgccag atatcatctg ccacaagagc     240
gccaccccg  gcggcggcca cgctaccgtt gctgccggag acaagatcaa catcgtatgg     300
accccgagt  ggccccactc ccacatcggc ccgtcattg  actacctagc cgcctgcaac     360
ggtgactgcg agaccgtcga caagtcgtcg ctgcgctggt tcaagattga cggcgccggc     420
tacgacaagg ccgccggccg ctgggccgcc gacgctctgc gcgccaacgg caacagctgg     480
ctcgtccaga tcccgtcgga tctcgcggcc ggcaactacg tcctccgcca cgagatcatc     540
gccctccacg gtgctcagag ccccaacggg gcccaggcgt accgcagtg  catcaacctc     600
cgcgtcaccg gcggcggcag caacctgccc agcggcgtcg ccggcacctc gctgtacaag     660
gcgaccgacc cgggcatcct cttcaacccc tacgtctcct ccccggatta caccgtcccc     720
ggcccggccc tcattgccgg cgccgccagc tcgatcgccc agagcacgtc ggtcgccact     780
gccaccggca cggccaccgt tccggcggc  ggcggcgcca accctaccgc caccaccacc     840
gccgccacct ccgccgcccc gagcaccacc ctgaggacga ccactacctc ggccgcgcag     900
actaccgccc cgccctccgg cgatgtgcag accaagtacg ccagtgtgg  tgcaacgga     960
tggacgggcc cgacggtgtg cgcccccggc tcgagctgct ccgtcctcaa cgagtggtac    1020
tcccagtgtt tgtaa                                                    1035

<210> SEQ ID NO 8
<211> LENGTH: 342
<212> TYPE: PRT
<213> ORGANISM: Artificial sequence
<220> FEATURE:
<223> OTHER INFORMATION: Synthetic polypeptides.

<400> SEQUENCE: 8

Met Ser Lys Ala Ser Ala Leu Leu Ala Gly Leu Thr Gly Ala Ala Leu
1               5                   10                  15

Val Ala Ala His Gly His Val Ser His Ile Val Val Asn Gly Val Tyr
                20                  25                  30

Tyr Arg Asn Tyr Asp Pro Thr Thr Asp Trp Tyr Gln Pro Asn Pro Pro
            35                  40                  45

Thr Val Ile Gly Trp Thr Ala Ala Asp Gln Asp Asn Gly Phe Val Glu
        50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
                85                  90                  95

Val Trp Thr Pro Glu Trp Pro His Ser His Ile Gly Pro Val Ile Asp
                100                 105                 110

Tyr Leu Ala Ala Cys Asn Gly Asp Cys Glu Thr Val Asp Lys Ser Ser
            115                 120                 125

Leu Arg Trp Phe Lys Ile Asp Gly Ala Gly Tyr Asp Lys Ala Ala Gly
        130                 135                 140

Arg Trp Ala Ala Asp Ala Leu Arg Ala Asn Gly Asn Ser Trp Leu Val
```

```
                145                 150                 155                 160
Gln Ile Pro Ser Asp Leu Ala Ala Gly Asn Tyr Val Leu Arg His Glu
                165                 170                 175

Ile Ile Ala Leu His Gly Ala Gln Ser Pro Asn Gly Ala Gln Ala Tyr
                180                 185                 190

Pro Gln Cys Ile Asn Leu Arg Val Thr Gly Gly Ser Asn Leu Pro
            195                 200                 205

Ser Gly Val Ala Gly Thr Ser Leu Tyr Lys Ala Thr Asp Pro Gly Ile
210                 215                 220

Leu Phe Asn Pro Tyr Val Ser Ser Pro Asp Tyr Thr Val Pro Gly Pro
225                 230                 235                 240

Ala Leu Ile Ala Gly Ala Ser Ser Ile Ala Gln Ser Thr Ser Val
            245                 250                 255

Ala Thr Ala Thr Gly Thr Ala Thr Val Pro Gly Gly Gly Ala Asn
            260                 265                 270

Pro Thr Ala Thr Thr Ala Ala Thr Ser Ala Ala Pro Ser Thr Thr
            275                 280                 285

Leu Arg Thr Thr Thr Thr Ser Ala Ala Gln Thr Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
                340

<210> SEQ ID NO 9
<211> LENGTH: 323
<212> TYPE: PRT
<213> ORGANISM: Artificial sequence
<220> FEATURE:
<223> OTHER INFORMATION: Synthetic polypeptides.

<400> SEQUENCE: 9

His Gly His Val Ser His Ile Val Val Asn Gly Val Tyr Tyr Arg Asn
1               5                   10                  15

Tyr Asp Pro Thr Thr Asp Trp Tyr Gln Pro Asn Pro Thr Val Ile
            20                  25                  30

Gly Trp Thr Ala Ala Asp Gln Asp Asn Gly Phe Val Glu Pro Asn Ser
            35                  40                  45

Phe Gly Thr Pro Asp Ile Ile Cys His Lys Ser Ala Thr Pro Gly Gly
        50                  55                  60

Gly His Ala Thr Val Ala Ala Gly Asp Lys Ile Asn Ile Val Trp Thr
65                  70                  75                  80

Pro Glu Trp Pro His Ser His Ile Gly Pro Val Ile Asp Tyr Leu Ala
                85                  90                  95

Ala Cys Asn Gly Asp Cys Glu Thr Val Asp Lys Ser Ser Leu Arg Trp
            100                 105                 110

Phe Lys Ile Asp Gly Ala Gly Tyr Asp Lys Ala Ala Gly Arg Trp Ala
        115                 120                 125

Ala Asp Ala Leu Arg Ala Asn Gly Asn Ser Trp Leu Val Gln Ile Pro
    130                 135                 140

Ser Asp Leu Ala Ala Gly Asn Tyr Val Leu Arg His Glu Ile Ile Ala
145                 150                 155                 160

Leu His Gly Ala Gln Ser Pro Asn Gly Ala Gln Ala Tyr Pro Gln Cys
```

```
                165                 170                 175
Ile Asn Leu Arg Val Thr Gly Gly Ser Asn Leu Pro Ser Gly Val
            180                 185                 190

Ala Gly Thr Ser Leu Tyr Lys Ala Thr Asp Pro Gly Ile Leu Phe Asn
            195                 200                 205

Pro Tyr Val Ser Ser Pro Asp Tyr Thr Val Pro Gly Pro Ala Leu Ile
210                 215                 220

Ala Gly Ala Ala Ser Ser Ile Ala Gln Ser Thr Ser Val Ala Thr Ala
225                 230                 235                 240

Thr Gly Thr Ala Thr Val Pro Gly Gly Gly Ala Asn Pro Thr Ala
                245                 250                 255

Thr Thr Thr Ala Ala Thr Ser Ala Ala Pro Ser Thr Thr Leu Arg Thr
            260                 265                 270

Thr Thr Thr Ser Ala Ala Gln Thr Thr Ala Pro Pro Ser Gly Asp Val
            275                 280                 285

Gln Thr Lys Tyr Gly Gln Cys Gly Gly Asn Gly Trp Thr Gly Pro Thr
            290                 295                 300

Val Cys Ala Pro Gly Ser Ser Cys Ser Val Leu Asn Glu Trp Tyr Ser
305                 310                 315                 320

Gln Cys Leu

<210> SEQ ID NO 10
<211> LENGTH: 1035
<212> TYPE: DNA
<213> ORGANISM: Artificial sequence
<220> FEATURE:
<223> OTHER INFORMATION: Synthetic polynucleotide.

<400> SEQUENCE: 10
acaaacatgt ccaaggcctc tgctctcctc gctggcctga cgggcgcggc cctcgtcgct      60
gcacatggcc acgtcagcca catcgtcgtc aacggcgtct actacaggaa ctacgacccc     120
acgacagact ggtaccagcc caacccgcca acagtcatcg gctggacggc agccgatcag     180
gataatggct tcgttgaacc caacagcttt ggcacgccag atatcatctg ccacaagagc     240
gccacccccg gcggcggcca cgctaccgtt gctgccggag acaagatcaa catccagtgg     300
acccccgagt ggcccgaatc ccacatcggc cccgtcattg actacctagc cgcctgcaac     360
ggtgactgcg agaccgtcga caagtcgtcg ctgcgctggt tcaagattga cggcgccggc     420
tacgacaagg ccgccggccg ctgggccgcc gacgctctgc gcgccaacgg caacagctgg     480
ctcgtccaga tcccgtcgga tctcaaggcc ggcaactacg tcctccgcca cgagatcatc     540
gccctccacg gtgctcagag ccccaacggc gcccagaact accgcagtg catcaacctc     600 cgcgtcaccg gcggcggcag caacctgccc agcggcgtcg ccggcacctc gctgtacaag     660
gcgaccgacc cgggcatcct cttcaaccc tacgtctcct ccccggatta caccgtcccc     720
ggcccggccc tcattgccgg cgccgccagc tcgatcgccc agagcacgtc ggtcgccact     780
gccaccggca cggccaccgt tccggcggc ggcggcgcca accctaccgc caccaccacc     840
gccgccacct ccgccgcccc gagcaccacc ctgaggacga ccactacctc ggccgcgcag     900
actaccgccc cgcctccgg cgatgtgcag accaagtacg gccagtgtgg tggcaacgga     960
tggacgggcc cgacggtgtg cgccccggc tcgagctgct ccgtcctcaa cgagtggtac    1020
tcccagtgtt tgtaa                                                    1035

<210> SEQ ID NO 11
```

<211> LENGTH: 342
<212> TYPE: PRT
<213> ORGANISM: Artificial sequence
<220> FEATURE:
<223> OTHER INFORMATION: Synthetic polypeptides.

<400> SEQUENCE: 11

```
Met Ser Lys Ala Ser Ala Leu Leu Ala Gly Leu Thr Gly Ala Ala Leu
1               5                   10                  15

Val Ala Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65                  70                  75                  80

Pro Gly Gly Gly His Ala Thr Val Ala Ala Gly Asp Lys Ile Asn Ile
            85                  90                  95

Gln Trp Thr Pro Glu Trp Pro Glu Ser His Ile Gly Pro Val Ile Asp
        100                 105                 110

Tyr Leu Ala Ala Cys Asn Gly Asp Cys Glu Thr Val Asp Lys Ser Ser
    115                 120                 125

Leu Arg Trp Phe Lys Ile Asp Gly Ala Gly Tyr Asp Lys Ala Ala Gly
130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
            165                 170                 175

Ile Ile Ala Leu His Gly Ala Gln Ser Pro Asn Gly Ala Gln Asn Tyr
        180                 185                 190

Pro Gln Cys Ile Asn Leu Arg Val Thr Gly Gly Gly Ser Asn Leu Pro
    195                 200                 205

Ser Gly Val Ala Gly Thr Ser Leu Tyr Lys Ala Thr Asp Pro Gly Ile
210                 215                 220

Leu Phe Asn Pro Tyr Val Ser Ser Pro Asp Tyr Thr Val Pro Gly Pro
225                 230                 235                 240

Ala Leu Ile Ala Gly Ala Ala Ser Ser Ile Ala Gln Ser Thr Ser Val
            245                 250                 255

Ala Thr Ala Thr Gly Thr Ala Thr Val Pro Gly Gly Gly Ala Asn
        260                 265                 270

Pro Thr Ala Thr Thr Ala Ala Thr Ser Ala Ala Pro Ser Thr Thr
    275                 280                 285

Leu Arg Thr Thr Thr Ser Ala Ala Gln Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
            325                 330                 335

Trp Tyr Ser Gln Cys Leu
        340
```

<210> SEQ ID NO 12
<211> LENGTH: 342
<212> TYPE: PRT
<213> ORGANISM: Artificial sequence
<220> FEATURE:
<223> OTHER INFORMATION: Synthetic polypeptides.

<400> SEQUENCE: 12

Met Ser Lys Ala Ser Ala Leu Leu Ala Gly Leu Thr Gly Ala Ala Leu
1               5                   10                  15

Val Ala Ala His Gly His Val Ser His Ile Val Val Asn Gly Val Tyr
            20                  25                  30

Tyr Arg Asn Tyr Asp Pro Thr Thr Asp Trp Tyr Gln Pro Asn Pro Pro
        35                  40                  45

Thr Val Ile Gly Trp Thr Ala Ala Asp Gln Asp Asn Gly Phe Val Glu
    50                  55                  60

Pro Asn Ser Phe Gly Thr Pro Asp Ile Ile Cys His Lys Ser Ala Thr
65              70                  75                  80

Pro Gly Gly Gly His Ala Thr Val Ala Ala Gly Asp Lys Ile Asn Ile
                85                  90                  95

Gln Trp Thr Pro Glu Trp Pro Glu Ser His Ile Gly Pro Val Ile Asp
            100                 105                 110

Tyr Leu Ala Ala Cys Asn Gly Asp Cys Glu Thr Val Asp Lys Ser Ser
        115                 120                 125

Leu Arg Trp Phe Lys Ile Asp Gly Ala Gly Tyr Asp Lys Ala Ala Gly
    130                 135                 140

Arg Trp Ala Ala Asp Ala Leu Arg Ala Asn Gly Asn Ser Trp Leu Val
145                 150                 155                 160

Gln Ile Pro Ser Asp Leu Lys Ala Gly Asn Tyr Val Leu Arg His Glu
                165                 170                 175

Ile Ile Ala Leu His Gly Ala Gln Ser Pro Asn Gly Ala Gln Asn Tyr
            180                 185                 190

Pro Gln Cys Ile Asn Leu Arg Val Thr Gly Gly Ser Asn Leu Pro
        195                 200                 205

Ser Gly Val Ala Gly Thr Ser Leu Tyr Lys Ala Thr Asp Pro Gly Ile
    210                 215                 220

Leu Phe Asn Pro Tyr Val Ser Pro Asp Tyr Thr Val Pro Gly Pro
225                 230                 235                 240

Ala Leu Ile Ala Gly Ala Ser Ser Ile Ala Gln Ser Thr Ser Val
                245                 250                 255

Ala Thr Ala Thr Gly Thr Ala Thr Val Pro Gly Gly Gly Ala Asn
            260                 265                 270

Pro Thr Ala Thr Thr Ala Thr Ser Ala Ala Pro Ser Thr Thr
        275                 280                 285

Leu Arg Thr Thr Thr Thr Ser Ala Ala Gln Thr Thr Ala Pro Pro Ser
290                 295                 300

Gly Asp Val Gln Thr Lys Tyr Gly Gln Cys Gly Gly Asn Gly Trp Thr
305                 310                 315                 320

Gly Pro Thr Val Cys Ala Pro Gly Ser Ser Cys Ser Val Leu Asn Glu
                325                 330                 335

Trp Tyr Ser Gln Cys Leu
            340

<210> SEQ ID NO 13
<211> LENGTH: 738
<212> TYPE: DNA
<213> ORGANISM: Myceliophthora thermophila

<400> SEQUENCE: 13

```
atgaagctct ccctcttttc cgtcctggcc actgccctca ccgtcgaggg gcatgccatc    60
ttccagaagg tctccgtcaa cggagcggac cagggctccc tcaccggcct ccgcgctccc   120
aacaacaaca accccgtgca gaatgtcaac agccaggaca tgatctgcgg ccagtcggga   180
tcgacgtcga acactatcat cgaggtcaag gccggcgata ggatcggtgc ctggtatcag   240
catgtcatcg gcggtgccca gttccccaac gacccagaca cccgattgca caagtcgcac   300
aagggccccg tcatggccta cctcgccaag gttgacaatg ccgcaaccgc cagcaagacg   360
ggcctgaagt ggttcaagat ttgggaggat acctttaatc ccagcaccaa gacctggggt   420
gtcgacaacc tcatcaacaa caacggctgg gtgtacttca acctcccgca gtgcatcgcc   480
gacggcaact acctcctccg cgtcgaggtc ctcgctctgc actcggccta ctcccagggc   540
caggctcagt tctaccagtc ctgcgcccag atcaacgtat ccggcggcgg ctccttcacg   600
ccggcgtcga ctgtcagctt cccgggtgcc tacagcgcca gcgaccccgg tatcctgatc   660
aacatctacg gcgccaccgg ccagcccgac aacaacggcc agccgtacac tgcccctggg   720
cccgcgccca tctcctgc                                                 738
```

<210> SEQ ID NO 14
<211> LENGTH: 246
<212> TYPE: PRT
<213> ORGANISM: Myceliophthora thermophila

<400> SEQUENCE: 14

```
Met Lys Leu Ser Leu Phe Ser Val Leu Ala Thr Ala Leu Thr Val Glu
1               5                   10                  15

Gly His Ala Ile Phe Gln Lys Val Ser Val Asn Gly Ala Asp Gln Gly
            20                  25                  30

Ser Leu Thr Gly Leu Arg Ala Pro Asn Asn Asn Pro Val Gln Asn
        35                  40                  45

Val Asn Ser Gln Asp Met Ile Cys Gly Gln Ser Gly Ser Thr Ser Asn
    50                  55                  60

Thr Ile Ile Glu Val Lys Ala Gly Asp Arg Ile Gly Ala Trp Tyr Gln
65                  70                  75                  80

His Val Ile Gly Gly Ala Gln Phe Pro Asn Asp Pro Asp Asn Pro Ile
                85                  90                  95

Ala Lys Ser His Lys Gly Pro Val Met Ala Tyr Leu Ala Lys Val Asp
            100                 105                 110

Asn Ala Ala Thr Ala Ser Lys Thr Gly Leu Lys Trp Phe Lys Ile Trp
        115                 120                 125

Glu Asp Thr Phe Asn Pro Ser Thr Lys Thr Trp Gly Val Asp Asn Leu
    130                 135                 140

Ile Asn Asn Asn Gly Trp Val Tyr Phe Asn Leu Pro Gln Cys Ile Ala
145                 150                 155                 160

Asp Gly Asn Tyr Leu Leu Arg Val Glu Val Leu Ala Leu His Ser Ala
                165                 170                 175

Tyr Ser Gln Gly Gln Ala Gln Phe Tyr Gln Ser Cys Ala Gln Ile Asn
            180                 185                 190

Val Ser Gly Gly Gly Ser Phe Thr Pro Ala Ser Thr Val Ser Phe Pro
        195                 200                 205

Gly Ala Tyr Ser Ala Ser Asp Pro Gly Ile Leu Ile Asn Ile Tyr Gly
    210                 215                 220

Ala Thr Gly Gln Pro Asp Asn Asn Gly Gln Pro Tyr Thr Ala Pro Gly
225                 230                 235                 240
```

Pro Ala Pro Ile Ser Cys
            245

<210> SEQ ID NO 15
<211> LENGTH: 227
<212> TYPE: PRT
<213> ORGANISM: Myceliophthora thermophila

<400> SEQUENCE: 15

Ile Phe Gln Lys Val Ser Val Asn Gly Ala Asp Gln Gly Ser Leu Thr
1               5                   10                  15

Gly Leu Arg Ala Pro Asn Asn Asn Pro Val Gln Asn Val Asn Ser
            20                  25                  30

Gln Asp Met Ile Cys Gly Gln Ser Gly Ser Thr Ser Asn Thr Ile Ile
        35                  40                  45

Glu Val Lys Ala Gly Asp Arg Ile Gly Ala Trp Tyr Gln His Val Ile
    50                  55                  60

Gly Gly Ala Gln Phe Pro Asn Asp Pro Asp Asn Pro Ile Ala Lys Ser
65                  70                  75                  80

His Lys Gly Pro Val Met Ala Tyr Leu Ala Lys Val Asp Asn Ala Ala
                85                  90                  95

Thr Ala Ser Lys Thr Gly Leu Lys Trp Phe Lys Ile Trp Glu Asp Thr
            100                 105                 110

Phe Asn Pro Ser Thr Lys Thr Trp Gly Val Asp Asn Leu Ile Asn Asn
        115                 120                 125

Asn Gly Trp Val Tyr Phe Asn Leu Pro Gln Cys Ile Ala Asp Gly Asn
    130                 135                 140

Tyr Leu Leu Arg Val Glu Val Leu Ala Leu His Ser Ala Tyr Ser Gln
145                 150                 155                 160

Gly Gln Ala Gln Phe Tyr Gln Ser Cys Ala Gln Ile Asn Val Ser Gly
                165                 170                 175

Gly Gly Ser Phe Thr Pro Ala Ser Thr Val Ser Phe Pro Gly Ala Tyr
            180                 185                 190

Ser Ala Ser Asp Pro Gly Ile Leu Ile Asn Ile Tyr Gly Ala Thr Gly
        195                 200                 205

Gln Pro Asp Asn Asn Gly Gln Pro Tyr Thr Ala Pro Gly Pro Ala Pro
    210                 215                 220

Ile Ser Cys
225

<210> SEQ ID NO 16
<211> LENGTH: 762
<212> TYPE: DNA
<213> ORGANISM: Myceliophthora thermophila

<400> SEQUENCE: 16
atggccctcc agctcttggc gagcttggcc ctcctctcag tgccggccct tgcccacggt      60
ggcttggcca actacaccgt cggtgatact tggtacagag gctacgaccc aaacctgccg     120
ccggagacgc agctcaacca gacctggatg atccagcggc aatgggccac catcgacccc     180
gtcttcaccg tgtcggagcc gtacctggcc tgcaacaacc cgggcgcgcc gccgccctcg     240
tacatcccca tccgcgccgg tgacaagatc acggccgtgt actggactg gctgcacgcc     300 atcgggccca tgagcgtctg gctcgcgcgg tgcgcgaca cgcccgcggc cgactgccgc     360
gacgtcgacg tcaaccgggt cggctggttc aagatctggg agggcggcct gctggagggt     420
cccaacctgg ccgaggggct ctggtaccaa aaggacttcc agcgctggga cggctccccg     480

```
tccctctggc ccgtcacgat ccccaagggg ctcaagagcg ggacctacat catccggcac    540
gagatcctgt cgcttcacgt cgccctcaag ccccagtttt acccggagtg tgcgcatctg    600
aatattactg ggggcggaga cttgctgcca cccgaagaga ctctggtgcg gtttccgggg    660
gtttacaaag aggacgatcc ctctatcttc atcgatgtct actcggagga gaacgcgaac    720
cggacagatt atacggttcc gggagggcca atctgggaag gg                       762
```

<210> SEQ ID NO 17
<211> LENGTH: 254
<212> TYPE: PRT
<213> ORGANISM: Myceliophthora thermophila

<400> SEQUENCE: 17

```
Met Ala Leu Gln Leu Leu Ala Ser Leu Ala Leu Leu Ser Val Pro Ala
1               5                   10                  15

Leu Ala His Gly Gly Leu Ala Asn Tyr Thr Val Gly Asp Thr Trp Tyr
            20                  25                  30

Arg Gly Tyr Asp Pro Asn Leu Pro Glu Thr Gln Leu Asn Gln Thr
        35                  40                  45

Trp Met Ile Gln Arg Gln Trp Ala Thr Ile Asp Pro Val Phe Thr Val
    50                  55                  60

Ser Glu Pro Tyr Leu Ala Cys Asn Asn Pro Gly Ala Pro Pro Ser
65                  70                  75                  80

Tyr Ile Pro Ile Arg Ala Gly Asp Lys Ile Thr Ala Val Tyr Trp Tyr
                85                  90                  95

Trp Leu His Ala Ile Gly Pro Met Ser Val Trp Leu Ala Arg Cys Gly
            100                 105                 110

Asp Thr Pro Ala Ala Asp Cys Arg Asp Val Asp Val Asn Arg Val Gly
        115                 120                 125

Trp Phe Lys Ile Trp Glu Gly Gly Leu Leu Glu Gly Pro Asn Leu Ala
    130                 135                 140

Glu Gly Leu Trp Tyr Gln Lys Asp Phe Gln Arg Trp Asp Gly Ser Pro
145                 150                 155                 160

Ser Leu Trp Pro Val Thr Ile Pro Lys Gly Leu Lys Ser Gly Thr Tyr
                165                 170                 175

Ile Ile Arg His Glu Ile Leu Ser Leu His Val Ala Leu Lys Pro Gln
            180                 185                 190

Phe Tyr Pro Glu Cys Ala His Leu Asn Ile Thr Gly Gly Gly Asp Leu
        195                 200                 205

Leu Pro Pro Glu Glu Thr Leu Val Arg Phe Pro Gly Val Tyr Lys Glu
    210                 215                 220

Asp Asp Pro Ser Ile Phe Ile Asp Val Tyr Ser Glu Glu Asn Ala Asn
225                 230                 235                 240

Arg Thr Asp Tyr Thr Val Pro Gly Gly Pro Ile Trp Glu Gly
                245                 250
```

<210> SEQ ID NO 18
<211> LENGTH: 231
<212> TYPE: PRT
<213> ORGANISM: Myceliophthora thermophila

<400> SEQUENCE: 18

```
Asn Tyr Thr Val Gly Asp Thr Trp Tyr Arg Gly Tyr Asp Pro Asn Leu
1               5                   10                  15

Pro Pro Glu Thr Gln Leu Asn Gln Thr Trp Met Ile Gln Arg Gln Trp
```

```
                20                  25                  30
Ala Thr Ile Asp Pro Val Phe Thr Val Ser Glu Pro Tyr Leu Ala Cys
             35                  40                  45

Asn Asn Pro Gly Ala Pro Pro Ser Tyr Ile Pro Ile Arg Ala Gly
 50                  55                  60

Asp Lys Ile Thr Ala Val Tyr Trp Tyr Trp Leu His Ala Ile Gly Pro
 65                  70                  75                  80

Met Ser Val Trp Leu Ala Arg Cys Gly Asp Thr Pro Ala Ala Asp Cys
                 85                  90                  95

Arg Asp Val Asp Val Asn Arg Val Gly Trp Phe Lys Ile Trp Glu Gly
                100                 105                 110

Gly Leu Leu Glu Gly Pro Asn Leu Ala Glu Gly Leu Trp Tyr Gln Lys
            115                 120                 125

Asp Phe Gln Arg Trp Asp Gly Ser Pro Ser Leu Trp Pro Val Thr Ile
        130                 135                 140

Pro Lys Gly Leu Lys Ser Gly Thr Tyr Ile Ile Arg His Glu Ile Leu
145                 150                 155                 160

Ser Leu His Val Ala Leu Lys Pro Gln Phe Tyr Pro Glu Cys Ala His
                165                 170                 175

Leu Asn Ile Thr Gly Gly Gly Asp Leu Leu Pro Pro Glu Glu Thr Leu
            180                 185                 190

Val Arg Phe Pro Gly Val Tyr Lys Glu Asp Asp Pro Ser Ile Phe Ile
        195                 200                 205

Asp Val Tyr Ser Glu Glu Asn Ala Asn Arg Thr Asp Tyr Thr Val Pro
    210                 215                 220

Gly Gly Pro Ile Trp Glu Gly
225                 230

<210> SEQ ID NO 19
<211> LENGTH: 705
<212> TYPE: DNA
<213> ORGANISM: Myceliophthora thermophila

<400> SEQUENCE: 19
atgaaggccc tctctctcct tgcggctgcc ggggcagtct ctgcgcatac catcttcgtc      60
cagctcgaag cagacggcac gaggtacccg gtttcgtacg ggatccggga cccaacctac     120
gacggcccca tcaccgacgt cacatccaac gacgttgctt gcaacggcgg tccgaacccg     180 acgacccccct ccagcgacgt catcaccgtc accgcgggca ccaccgtcaa ggccatctgg     240
aggcacaccc tccaatccgg cccggacgat gtcatggacg ccagccacaa gggcccgacc     300
ctggcctaca tcaagaaggt cggcgatgcc accaaggact cgggcgtcgg cggtggctgg     360
ttcaagatcc aggaggacgg ttacaacaac ggccagtggg gcaccagcac cgttatctcc     420
aacggcggcg agcactacat tgacatcccg gcctgcatcc ccgagggtca gtacctcctc     480
cgcgccgaga tgatcgccct ccacgcggcc ggtccccccg cggcgctca gctctacatg     540 gaatgtgccc agatcaacat cgtcggcggc tccggctcgg tgcccagctc gacggtcagc     600
ttccccggcg cgtatagccc caacgacccg ggtctcctca tcaacatcta ttccatgtcg     660
ccctcgagct cgtacaccat cccgggcccg ccgttttca agtgc                     705

<210> SEQ ID NO 20
<211> LENGTH: 235
<212> TYPE: PRT
<213> ORGANISM: Myceliophthora thermophila
```

```
<400> SEQUENCE: 20

Met Lys Ala Leu Ser Leu Leu Ala Ala Gly Ala Val Ser Ala His
1               5                   10                  15

Thr Ile Phe Val Gln Leu Glu Ala Asp Gly Thr Arg Tyr Pro Val Ser
                20                  25                  30

Tyr Gly Ile Arg Asp Pro Thr Tyr Asp Gly Pro Ile Thr Asp Val Thr
            35                  40                  45

Ser Asn Asp Val Ala Cys Asn Gly Gly Pro Asn Pro Thr Thr Pro Ser
    50                  55                  60

Ser Asp Val Ile Thr Val Thr Ala Gly Thr Thr Val Lys Ala Ile Trp
65                  70                  75                  80

Arg His Thr Leu Gln Ser Gly Pro Asp Asp Val Met Asp Ala Ser His
                85                  90                  95

Lys Gly Pro Thr Leu Ala Tyr Ile Lys Lys Val Gly Asp Ala Thr Lys
            100                 105                 110

Asp Ser Gly Val Gly Gly Gly Trp Phe Lys Ile Gln Glu Asp Gly Tyr
        115                 120                 125

Asn Asn Gly Gln Trp Gly Thr Ser Thr Val Ile Ser Asn Gly Gly Glu
    130                 135                 140

His Tyr Ile Asp Ile Pro Ala Cys Ile Pro Glu Gly Gln Tyr Leu Leu
145                 150                 155                 160

Arg Ala Glu Met Ile Ala Leu His Ala Ala Gly Ser Pro Gly Gly Ala
                165                 170                 175

Gln Leu Tyr Met Glu Cys Ala Gln Ile Asn Ile Val Gly Gly Ser Gly
            180                 185                 190

Ser Val Pro Ser Ser Thr Val Ser Phe Pro Gly Ala Tyr Ser Pro Asn
        195                 200                 205

Asp Pro Gly Leu Leu Ile Asn Ile Tyr Ser Met Ser Pro Ser Ser Ser
    210                 215                 220

Tyr Thr Ile Pro Gly Pro Pro Val Phe Lys Cys
225                 230                 235

<210> SEQ ID NO 21
<211> LENGTH: 220
<212> TYPE: PRT
<213> ORGANISM: Myceliophthora thermophila

<400> SEQUENCE: 21

His Thr Ile Phe Val Gln Leu Glu Ala Asp Gly Thr Arg Tyr Pro Val
1               5                   10                  15

Ser Tyr Gly Ile Arg Asp Pro Thr Tyr Asp Gly Pro Ile Thr Asp Val
                20                  25                  30

Thr Ser Asn Asp Val Ala Cys Asn Gly Gly Pro Asn Pro Thr Thr Pro
            35                  40                  45

Ser Ser Asp Val Ile Thr Val Thr Ala Gly Thr Thr Val Lys Ala Ile
    50                  55                  60

Trp Arg His Thr Leu Gln Ser Gly Pro Asp Asp Val Met Asp Ala Ser
65                  70                  75                  80

His Lys Gly Pro Thr Leu Ala Tyr Ile Lys Lys Val Gly Asp Ala Thr
                85                  90                  95

Lys Asp Ser Gly Val Gly Gly Gly Trp Phe Lys Ile Gln Glu Asp Gly
            100                 105                 110

Tyr Asn Asn Gly Gln Trp Gly Thr Ser Thr Val Ile Ser Asn Gly Gly
        115                 120                 125
```

```
Glu His Tyr Ile Asp Ile Pro Ala Cys Ile Pro Glu Gly Gln Tyr Leu
            130                 135                 140

Leu Arg Ala Glu Met Ile Ala Leu His Ala Ala Gly Ser Pro Gly Gly
145                 150                 155                 160

Ala Gln Leu Tyr Met Glu Cys Ala Gln Ile Asn Ile Val Gly Gly Ser
                165                 170                 175

Gly Ser Val Pro Ser Ser Thr Val Ser Phe Pro Gly Ala Tyr Ser Pro
            180                 185                 190

Asn Asp Pro Gly Leu Leu Ile Asn Ile Tyr Ser Met Ser Pro Ser Ser
        195                 200                 205

Ser Tyr Thr Ile Pro Gly Pro Pro Val Phe Lys Cys
    210                 215                 220

<210> SEQ ID NO 22
<211> LENGTH: 915
<212> TYPE: DNA
<213> ORGANISM: Myceliophthora thermophila

<400> SEQUENCE: 22
atgaagtcgt ctaccccggc cttgttcgcc gctgggctcc ttgctcagca tgctgcggcc    60
cactccatct tccagcaggc gagcagcggc tcgaccgact tgatacgct gtgcaccgg   120 atgccgccca caatagccc cgtcactagt gtgaccagcg gcgacatgac ctgcaaagtc   180
ggcggcacca aggggtgtc cggcttctgc gaggtgaacg ccggcgacga gttcacggtt   240
gagatgcacg cgcagcccgg cgaccgctcg tgcgccaacg aggccatcgg cgggaaccac   300
ttcggcccgg tcctcatcta catgagcaag gtcgacgacg cctccaccgc cgacgggtcc   360
ggcgactggt tcaaggtgga cgagttcggc tacgacgcaa gcaccaagac ctggggcacc   420
gacaagctca cgagaactg cggcaagcgc accttcaaca tccccagcca catccccgcg   480
ggcgactatc tcgtccgggc cgaggctatc gcgctacaca ctgccaacca gccaggcggc   540
gcgcagttct acatgagctg ctatcaagtc aggattccg gcggcgaagg gggccagctg   600
cctgccggag tcaagatccc gggcgcgtac agtgccaacg accccggcat ccttgtcgac   660
atctggggta acgatttcaa cgaccctcca ggacactcgg cccgtcacgc catcatcatc   720
atcagcagca gcagcaacaa cagcggcgcc aagatgacca agaagatcca ggagcccacc   780
atcacatcgg tcacggacct ccccaccgac gaggccaagt ggatcgcgct ccaaaagatc   840
tcgtacgtgg accagacggg cacggcgcgg acatacgagc cggcgtcgcg caagacgcgg   900
tcgccaagag tctag                                                    915

<210> SEQ ID NO 23
<211> LENGTH: 304
<212> TYPE: PRT
<213> ORGANISM: Myceliophthora thermophila

<400> SEQUENCE: 23

Met Lys Ser Ser Thr Pro Ala Leu Phe Ala Ala Gly Leu Leu Ala Gln
1               5                   10                  15

His Ala Ala Ala His Ser Ile Phe Gln Gln Ala Ser Ser Gly Ser Thr
            20                  25                  30

Asp Phe Asp Thr Leu Cys Thr Arg Met Pro Pro Asn Ser Pro Val
            35                  40                  45

Thr Ser Val Thr Ser Gly Asp Met Thr Cys Lys Val Gly Gly Thr Lys
    50                  55                  60

Gly Val Ser Gly Phe Cys Glu Val Asn Ala Gly Asp Glu Phe Thr Val
```

```
                65                  70                  75                  80
        Glu Met His Ala Gln Pro Gly Asp Arg Ser Cys Ala Asn Glu Ala Ile
                        85                  90                  95
        Gly Gly Asn His Phe Gly Pro Val Leu Ile Tyr Met Ser Lys Val Asp
                    100                 105                 110
        Asp Ala Ser Thr Ala Asp Gly Ser Gly Asp Trp Phe Lys Val Asp Glu
                    115                 120                 125
        Phe Gly Tyr Asp Ala Ser Thr Lys Thr Trp Gly Thr Asp Lys Leu Asn
                130                 135                 140
        Glu Asn Cys Gly Lys Arg Thr Phe Asn Ile Pro Ser His Ile Pro Ala
        145                 150                 155                 160
        Gly Asp Tyr Leu Val Arg Ala Glu Ala Ile Ala Leu His Thr Ala Asn
                        165                 170                 175
        Gln Pro Gly Gly Ala Gln Phe Tyr Met Ser Cys Tyr Gln Val Arg Ile
                    180                 185                 190
        Ser Gly Gly Glu Gly Gly Gln Leu Pro Ala Gly Val Lys Ile Pro Gly
                    195                 200                 205
        Ala Tyr Ser Ala Asn Asp Pro Gly Ile Leu Val Asp Ile Trp Gly Asn
                210                 215                 220
        Asp Phe Asn Asp Pro Pro Gly His Ser Ala Arg His Ala Ile Ile Ile
        225                 230                 235                 240
        Ile Ser Ser Ser Asn Asn Ser Gly Ala Lys Met Thr Lys Lys Ile
                        245                 250                 255
        Gln Glu Pro Thr Ile Thr Ser Val Thr Asp Leu Pro Thr Asp Glu Ala
                    260                 265                 270
        Lys Trp Ile Ala Leu Gln Lys Ile Ser Tyr Val Asp Gln Thr Gly Thr
                    275                 280                 285
        Ala Arg Thr Tyr Glu Pro Ala Ser Arg Lys Thr Arg Ser Pro Arg Val
                    290                 295                 300

<210> SEQ ID NO 24
        <211> LENGTH: 284
        <212> TYPE: PRT
        <213> ORGANISM: Myceliophthora thermophila

<400> SEQUENCE: 24

His Ser Ile Phe Gln Gln Ala Ser Ser Gly Ser Thr Asp Phe Asp Thr
        1               5                   10                  15
        Leu Cys Thr Arg Met Pro Pro Asn Asn Ser Pro Val Thr Ser Val Thr
                    20                  25                  30
        Ser Gly Asp Met Thr Cys Lys Val Gly Gly Thr Lys Gly Val Ser Gly
                35                  40                  45
        Phe Cys Glu Val Asn Ala Gly Asp Glu Phe Thr Val Glu Met His Ala
            50                  55                  60
        Gln Pro Gly Asp Arg Ser Cys Ala Asn Glu Ala Ile Gly Gly Asn His
        65                  70                  75                  80
        Phe Gly Pro Val Leu Ile Tyr Met Ser Lys Val Asp Asp Ala Ser Thr
                        85                  90                  95
        Ala Asp Gly Ser Gly Asp Trp Phe Lys Val Asp Glu Phe Gly Tyr Asp
                    100                 105                 110
        Ala Ser Thr Lys Thr Trp Gly Thr Asp Lys Leu Asn Glu Asn Cys Gly
                    115                 120                 125
        Lys Arg Thr Phe Asn Ile Pro Ser His Ile Pro Ala Gly Asp Tyr Leu
                130                 135                 140
```

Val Arg Ala Glu Ala Ile Ala Leu His Thr Ala Asn Gln Pro Gly Gly
145                 150                 155                 160

Ala Gln Phe Tyr Met Ser Cys Tyr Gln Val Arg Ile Ser Gly Gly Glu
            165                 170                 175

Gly Gly Gln Leu Pro Ala Gly Val Lys Ile Pro Gly Ala Tyr Ser Ala
            180                 185                 190

Asn Asp Pro Gly Ile Leu Val Asp Ile Trp Gly Asn Asp Phe Asn Asp
            195                 200                 205

Pro Pro Gly His Ser Ala Arg His Ala Ile Ile Ile Ser Ser Ser
        210                 215                 220

Ser Asn Asn Ser Gly Ala Lys Met Thr Lys Lys Ile Gln Glu Pro Thr
225                 230                 235                 240

Ile Thr Ser Val Thr Asp Leu Pro Thr Asp Glu Ala Lys Trp Ile Ala
                245                 250                 255

Leu Gln Lys Ile Ser Tyr Val Asp Gln Thr Gly Thr Ala Arg Thr Tyr
            260                 265                 270

Glu Pro Ala Ser Arg Lys Thr Arg Ser Pro Arg Val
            275                 280

<210> SEQ ID NO 25
<211> LENGTH: 726
<212> TYPE: DNA
<213> ORGANISM: Myceliophthora thermophila

<400> SEQUENCE: 25

```
atgaagtcgt ctaccccggc cttgttcgcc gctgggctcc ttgctcagca tgctgcggcc    60
cactccatct tccagcaggc gagcagcggc tcgaccgact tgatacgct gtgcacccgg    120
atgccgccca acaatagccc cgtcactagt gtgaccagcg gcgacatgac ctgcaacgtc    180
ggcggcacca aggggtgtc gggcttctgc gaggtgaacg ccggcgacga gttcacggtt    240
gagatgcacg cgcagcccgg cgaccgctcg tgcgccaacg aggccatcgg cgggaaccac    300
ttcggcccgg tcctcatcta catgagcaag gtcgacgacg cctccactgc cgacgggtcc    360
ggcgactggt tcaaggtgga cgagttcggc tacgacgcaa gcaccaagac ctggggcacc    420
gacaagctca acgagaactg cggcaagcgc accttcaaca tccccagcca catccccgcg    480
ggcgactatc tcgtccgggc cgaggctatc gcgctacaca ctgccaacca gccaggcggc    540
gcgcagttct acatgagctg ctatcaagtc aggatttccg gcggcgaagg gggccagctg    600
cctgccggag tcaagatccc gggcgcgtac agtgccaacg accccggcat ccttgtcgac    660
atctggggta cgatttcaa cgagtacgtt attccgggcc ccccggtcat cgacagcagc    720
tacttc                                                              726
```

<210> SEQ ID NO 26
<211> LENGTH: 242
<212> TYPE: PRT
<213> ORGANISM: Myceliophthora thermophila

<400> SEQUENCE: 26

Met Lys Ser Ser Thr Pro Ala Leu Phe Ala Ala Gly Leu Leu Ala Gln
1               5                   10                  15

His Ala Ala Ala His Ser Ile Phe Gln Gln Ala Ser Ser Gly Ser Thr
                20                  25                  30

Asp Phe Asp Thr Leu Cys Thr Arg Met Pro Pro Asn Asn Ser Pro Val
            35                  40                  45

Thr Ser Val Thr Ser Gly Asp Met Thr Cys Asn Val Gly Gly Thr Lys

```
            50                  55                  60
Gly Val Ser Gly Phe Cys Glu Val Asn Ala Gly Asp Glu Phe Thr Val
 65                  70                  75                  80

Glu Met His Ala Gln Pro Gly Asp Arg Ser Cys Ala Asn Glu Ala Ile
                 85                  90                  95

Gly Gly Asn His Phe Gly Pro Val Leu Ile Tyr Met Ser Lys Val Asp
                100                 105                 110

Asp Ala Ser Thr Ala Asp Gly Ser Gly Asp Trp Phe Lys Val Asp Glu
                115                 120                 125

Phe Gly Tyr Asp Ala Ser Thr Lys Thr Trp Gly Thr Asp Lys Leu Asn
130                 135                 140

Glu Asn Cys Gly Lys Arg Thr Phe Asn Ile Pro Ser His Ile Pro Ala
145                 150                 155                 160

Gly Asp Tyr Leu Val Arg Ala Glu Ala Ile Ala Leu His Thr Ala Asn
                165                 170                 175

Gln Pro Gly Gly Ala Gln Phe Tyr Met Ser Cys Tyr Gln Val Arg Ile
                180                 185                 190

Ser Gly Gly Glu Gly Gly Gln Leu Pro Ala Gly Val Lys Ile Pro Gly
                195                 200                 205

Ala Tyr Ser Ala Asn Asp Pro Gly Ile Leu Val Asp Ile Trp Gly Asn
210                 215                 220

Asp Phe Asn Glu Tyr Val Ile Pro Gly Pro Val Ile Asp Ser Ser
225                 230                 235                 240

Tyr Phe

<210> SEQ ID NO 27
<211> LENGTH: 222
<212> TYPE: PRT
<213> ORGANISM: Myceliophthora thermophila

<400> SEQUENCE: 27

His Ser Ile Phe Gln Gln Ala Ser Ser Gly Ser Thr Asp Phe Asp Thr
 1               5                  10                  15

Leu Cys Thr Arg Met Pro Pro Asn Asn Ser Pro Val Thr Ser Val Thr
                20                  25                  30

Ser Gly Asp Met Thr Cys Asn Val Gly Gly Thr Lys Gly Val Ser Gly
                35                  40                  45

Phe Cys Glu Val Asn Ala Gly Asp Glu Phe Thr Val Glu Met His Ala
 50                  55                  60

Gln Pro Gly Asp Arg Ser Cys Ala Asn Glu Ala Ile Gly Gly Asn His
 65                  70                  75                  80

Phe Gly Pro Val Leu Ile Tyr Met Ser Lys Val Asp Asp Ala Ser Thr
                85                  90                  95

Ala Asp Gly Ser Gly Asp Trp Phe Lys Val Asp Glu Phe Gly Tyr Asp
                100                 105                 110

Ala Ser Thr Lys Thr Trp Gly Thr Asp Lys Leu Asn Glu Asn Cys Gly
                115                 120                 125

Lys Arg Thr Phe Asn Ile Pro Ser His Ile Pro Ala Gly Asp Tyr Leu
130                 135                 140

Val Arg Ala Glu Ala Ile Ala Leu His Thr Ala Asn Gln Pro Gly Gly
145                 150                 155                 160

Ala Gln Phe Tyr Met Ser Cys Tyr Gln Val Arg Ile Ser Gly Gly Glu
                165                 170                 175

Gly Gly Gln Leu Pro Ala Gly Val Lys Ile Pro Gly Ala Tyr Ser Ala
```

```
                180                 185                 190
Asn Asp Pro Gly Ile Leu Val Asp Ile Trp Gly Asn Asp Phe Asn Glu
        195                 200                 205

Tyr Val Ile Pro Gly Pro Val Ile Asp Ser Ser Tyr Phe
    210                 215                 220

<210> SEQ ID NO 28
<211> LENGTH: 969
<212> TYPE: DNA
<213> ORGANISM: Myceliophthora thermophila

<400> SEQUENCE: 28
atgaagtcct tcaccctcac cactctggcc gccctggctg caacgccgc cgctcacgcg        60 accttccagg ccctctgggt cgacggcgtc gactacggcg cgcagtgtgc ccgtctgccc      120
gcgtccaact cgccggtcac cgacgtgacc tccaacgcga tccgctgcaa cgccaaccc       180 tcgcccgctc ggggcaagtg cccggtcaag gccggctcga ccgttacggt cgagatgcat      240
cagcaacccg gtgaccgctc gtgcagcagc gaggcgatcg gcggggcgca ctacggcccc      300
gtgatggtgt acatgtccaa ggtgtcggac gcggcgtcgg cggacgggtc gtcgggctgg      360
ttcaaggtgt cgaggacgg ctgggccaag aacccgtccg gcgggtcggg cgacgacgac       420
tactggggca ccaaggacct gaactcgtgc tgcgggaaga tgaacgtcaa gatccccgcc      480
gacctgccct cgggcgacta cctgctccgg gccgaggccc tcgcgctgca cggccggc       540 agcgcgggcg cgcccagtt ctacatgacc tgctaccagc tcaccgtgac cggctccggc       600
agcgccagcc cgcccaccgt ctccttcccg ggcgcctaca aggccaccga cccgggcatc      660
ctcgtcaaca tccacgcccc gctgtccggc tacaccgtgc ccggcccggc cgtctactcg      720
ggcggctcca ccaagaaggc cggcagcgcc tgcaccggct gcgagtccac ttgcgccgtc      780
ggctccggcc ccaccgccac cgtctcccag tcgcccggtt ccaccgccac ctcggccccc      840
ggcggcggcg cgggctgcac cgtccagaag taccagcagt gcggcggcca gggctacacc      900
ggctgcacca actgcgcgtc cggctccacc tgcagcgcgg tctcgccgcc ctactactcg      960
cagtgcgtc                                                              969

<210> SEQ ID NO 29
<211> LENGTH: 323
<212> TYPE: PRT
<213> ORGANISM: Myceliophthora thermophila

<400> SEQUENCE: 29

Met Lys Ser Phe Thr Leu Thr Thr Leu Ala Ala Leu Ala Gly Asn Ala
1               5                   10                  15

Ala Ala His Ala Thr Phe Gln Ala Leu Trp Val Asp Gly Val Asp Tyr
            20                  25                  30

Gly Ala Gln Cys Ala Arg Leu Pro Ala Ser Asn Ser Pro Val Thr Asp
        35                  40                  45

Val Thr Ser Asn Ala Ile Arg Cys Asn Ala Asn Pro Ser Pro Ala Arg
    50                  55                  60

Gly Lys Cys Pro Val Lys Ala Gly Ser Thr Val Thr Val Glu Met His
65                  70                  75                  80

Gln Gln Pro Gly Asp Arg Ser Cys Ser Ser Glu Ala Ile Gly Gly Ala
                85                  90                  95

His Tyr Gly Pro Val Met Val Tyr Met Ser Lys Val Ser Asp Ala Ala
            100                 105                 110
```

Ser Ala Asp Gly Ser Ser Gly Trp Phe Lys Val Phe Glu Asp Gly Trp
                115                 120                 125

Ala Lys Asn Pro Ser Gly Gly Ser Gly Asp Asp Tyr Trp Gly Thr
130                 135                 140

Lys Asp Leu Asn Ser Cys Cys Gly Lys Met Asn Val Lys Ile Pro Ala
145                 150                 155                 160

Asp Leu Pro Ser Gly Asp Tyr Leu Leu Arg Ala Glu Ala Leu Ala Leu
                165                 170                 175

His Thr Ala Gly Ser Ala Gly Gly Gln Phe Tyr Met Thr Cys Tyr
                180                 185                 190

Gln Leu Thr Val Thr Gly Ser Gly Ser Ala Ser Pro Pro Thr Val Ser
                195                 200                 205

Phe Pro Gly Ala Tyr Lys Ala Thr Asp Pro Gly Ile Leu Val Asn Ile
                210                 215                 220

His Ala Pro Leu Ser Gly Tyr Thr Val Pro Gly Pro Ala Val Tyr Ser
225                 230                 235                 240

Gly Gly Ser Thr Lys Lys Ala Gly Ser Ala Cys Thr Gly Cys Glu Ser
                245                 250                 255

Thr Cys Ala Val Gly Ser Gly Pro Thr Ala Thr Val Ser Gln Ser Pro
                260                 265                 270

Gly Ser Thr Ala Thr Ser Ala Pro Gly Gly Gly Gly Cys Thr Val
                275                 280                 285

Gln Lys Tyr Gln Gln Cys Gly Gly Gln Gly Tyr Thr Gly Cys Thr Asn
                290                 295                 300

Cys Ala Ser Gly Ser Thr Cys Ser Ala Val Ser Pro Pro Tyr Tyr Ser
305                 310                 315                 320

Gln Cys Val

<210> SEQ ID NO 30
<211> LENGTH: 305
<212> TYPE: PRT
<213> ORGANISM: Myceliophthora thermophila

<400> SEQUENCE: 30

His Ala Thr Phe Gln Ala Leu Trp Val Asp Gly Val Asp Tyr Gly Ala
1               5                   10                  15

Gln Cys Ala Arg Leu Pro Ala Ser Asn Ser Pro Val Thr Asp Val Thr
                20                  25                  30

Ser Asn Ala Ile Arg Cys Asn Ala Asn Pro Ser Pro Ala Arg Gly Lys
            35                  40                  45

Cys Pro Val Lys Ala Gly Ser Thr Val Thr Val Glu Met His Gln Gln
50                  55                  60

Pro Gly Asp Arg Ser Cys Ser Ser Glu Ala Ile Gly Gly Ala His Tyr
65                  70                  75                  80

Gly Pro Val Met Val Tyr Met Ser Lys Val Ser Asp Ala Ala Ser Ala
                85                  90                  95

Asp Gly Ser Ser Gly Trp Phe Lys Val Phe Glu Asp Gly Trp Ala Lys
                100                 105                 110

Asn Pro Ser Gly Gly Ser Gly Asp Asp Tyr Trp Gly Thr Lys Asp
            115                 120                 125

Leu Asn Ser Cys Cys Gly Lys Met Asn Val Lys Ile Pro Ala Asp Leu
            130                 135                 140

Pro Ser Gly Asp Tyr Leu Leu Arg Ala Glu Ala Leu Ala Leu His Thr
145                 150                 155                 160

Ala Gly Ser Ala Gly Gly Ala Gln Phe Tyr Met Thr Cys Tyr Gln Leu
            165                 170                 175

Thr Val Thr Gly Ser Gly Ser Ala Ser Pro Pro Thr Val Ser Phe Pro
        180                 185                 190

Gly Ala Tyr Lys Ala Thr Asp Pro Gly Ile Leu Val Asn Ile His Ala
    195                 200                 205

Pro Leu Ser Gly Tyr Thr Val Pro Gly Pro Ala Val Tyr Ser Gly Gly
    210                 215                 220

Ser Thr Lys Lys Ala Gly Ser Ala Cys Thr Gly Cys Glu Ser Thr Cys
225                 230                 235                 240

Ala Val Gly Ser Gly Pro Thr Ala Thr Val Ser Gln Ser Pro Gly Ser
            245                 250                 255

Thr Ala Thr Ser Ala Pro Gly Gly Gly Gly Cys Thr Val Gln Lys
            260                 265                 270

Tyr Gln Gln Cys Gly Gly Gln Gly Tyr Thr Gly Cys Thr Asn Cys Ala
            275                 280                 285

Ser Gly Ser Thr Cys Ser Ala Val Ser Pro Pro Tyr Tyr Ser Gln Cys
    290                 295                 300

Val
305

<210> SEQ ID NO 31
<211> LENGTH: 870
<212> TYPE: DNA
<213> ORGANISM: Myceliophthora thermophila

<400> SEQUENCE: 31 atgaaggac tcctcggcgc cgccgccctc tcgctggccg tcagcgatgt ctcggcccac     60
tacatctttc agcagctgac gacgggcggc gtcaagcacg ctgtgtacca gtacatccgc    120
aagaacacca actataactc gcccgtgacc gatctgacgt ccaacgacct ccgctgcaat    180
gtgggtgcta ccggtgcggg caccgatacc gtcacggtgc cgccggcga ttcgttcacc     240
ttcacgaccg atacgcccgt ttaccaccag gcccgacct cgatctacat gtccaaggcc     300
cccggcagcg cgtccgacta cgacggcagc ggcggctggt tcaagatcaa ggactgggct    360
gactacaccg ccacgattcc ggaatgtatt ccccccggcg actacctgct cgcatccag     420
caactcggca tccacaaccc ttggcccgcg ggcatccccc agttctacat ctcttgtgcc    480
cagatcaccg tgactggtgg cggcagtgcc aaccccggcc cgaccgtctc catcccaggc    540
gccttcaagg agaccgaccc gggctacact gtcaacatct acaacaactt ccacaactac    600
accgtccctg cccagccgt cttcacctgc aacggtagcg gcggcaacaa cggcggcggc    660
tccaacccag tcaccaccac caccaccacc accaccaggc cgtccaccag caccgcccag    720
tcccagccgt cgtcgagccc gaccagcccc tccagctgca ccgtcgcgaa gtggggccag    780
tgcggaggac agggttacag cggctgcacc gtgtgcgcgg ccgggtcgac ctgccagaag    840
accaacgact actacagcca gtgcttgtag                                     870

<210> SEQ ID NO 32
<211> LENGTH: 289
<212> TYPE: PRT
<213> ORGANISM: Myceliophthora thermophila

<400> SEQUENCE: 32

Met Lys Gly Leu Leu Gly Ala Ala Ala Leu Ser Leu Ala Val Ser Asp
1               5                   10                  15

Val Ser Ala His Tyr Ile Phe Gln Gln Leu Thr Thr Gly Gly Val Lys
            20                  25                  30

His Ala Val Tyr Gln Tyr Ile Arg Lys Asn Thr Asn Tyr Asn Ser Pro
        35                  40                  45

Val Thr Asp Leu Thr Ser Asn Asp Leu Arg Cys Asn Val Gly Ala Thr
 50                  55                  60

Gly Ala Gly Thr Asp Thr Val Thr Val Arg Ala Gly Asp Ser Phe Thr
 65                  70                  75                  80

Phe Thr Thr Asp Thr Pro Val Tyr His Gln Gly Pro Thr Ser Ile Tyr
                85                  90                  95

Met Ser Lys Ala Pro Gly Ser Ala Ser Asp Tyr Asp Gly Ser Gly Gly
            100                 105                 110

Trp Phe Lys Ile Lys Asp Trp Ala Asp Tyr Thr Ala Thr Ile Pro Glu
        115                 120                 125

Cys Ile Pro Pro Gly Asp Tyr Leu Leu Arg Ile Gln Gln Leu Gly Ile
130                 135                 140

His Asn Pro Trp Pro Ala Gly Ile Pro Gln Phe Tyr Ile Ser Cys Ala
145                 150                 155                 160

Gln Ile Thr Val Thr Gly Gly Ser Ala Asn Pro Gly Pro Thr Val
                165                 170                 175

Ser Ile Pro Gly Ala Phe Lys Glu Thr Asp Pro Gly Tyr Thr Val Asn
            180                 185                 190

Ile Tyr Asn Asn Phe His Asn Tyr Thr Val Pro Gly Pro Ala Val Phe
        195                 200                 205

Thr Cys Asn Gly Ser Gly Gly Asn Asn Gly Gly Ser Asn Pro Val
210                 215                 220

Thr Thr Thr Thr Thr Thr Thr Thr Arg Pro Ser Thr Ser Thr Ala Gln
225                 230                 235                 240

Ser Gln Pro Ser Ser Ser Pro Thr Ser Pro Ser Ser Cys Thr Val Ala
                245                 250                 255

Lys Trp Gly Gln Cys Gly Gly Gln Gly Tyr Ser Gly Cys Thr Val Cys
            260                 265                 270

Ala Ala Gly Ser Thr Cys Gln Lys Thr Asn Asp Tyr Tyr Ser Gln Cys
        275                 280                 285

Leu

<210> SEQ ID NO 33
<211> LENGTH: 270
<212> TYPE: PRT
<213> ORGANISM: Myceliophthora thermophila

<400> SEQUENCE: 33

His Tyr Ile Phe Gln Gln Leu Thr Thr Gly Gly Val Lys His Ala Val
 1               5                  10                  15

Tyr Gln Tyr Ile Arg Lys Asn Thr Asn Tyr Asn Ser Pro Val Thr Asp
            20                  25                  30

Leu Thr Ser Asn Asp Leu Arg Cys Asn Val Gly Ala Thr Gly Ala Gly
        35                  40                  45

Thr Asp Thr Val Thr Val Arg Ala Gly Asp Ser Phe Thr Phe Thr Thr
 50                  55                  60

Asp Thr Pro Val Tyr His Gln Gly Pro Thr Ser Ile Tyr Met Ser Lys
 65                  70                  75                  80

Ala Pro Gly Ser Ala Ser Asp Tyr Asp Gly Ser Gly Gly Trp Phe Lys
                85                  90                  95

```
Ile Lys Asp Trp Ala Asp Tyr Thr Ala Thr Ile Pro Glu Cys Ile Pro
            100                 105                 110

Pro Gly Asp Tyr Leu Leu Arg Ile Gln Gln Leu Gly Ile His Asn Pro
        115                 120                 125

Trp Pro Ala Gly Ile Pro Gln Phe Tyr Ile Ser Cys Ala Gln Ile Thr
    130                 135                 140

Val Thr Gly Gly Gly Ser Ala Asn Pro Gly Pro Thr Val Ser Ile Pro
145                 150                 155                 160

Gly Ala Phe Lys Glu Thr Asp Pro Gly Tyr Thr Val Asn Ile Tyr Asn
                165                 170                 175

Asn Phe His Asn Tyr Thr Val Pro Gly Pro Ala Val Phe Thr Cys Asn
            180                 185                 190

Gly Ser Gly Gly Asn Asn Gly Gly Ser Asn Pro Val Thr Thr Thr
        195                 200                 205

Thr Thr Thr Thr Thr Arg Pro Ser Thr Ser Thr Ala Gln Ser Gln Pro
    210                 215                 220

Ser Ser Ser Pro Thr Ser Pro Ser Ser Cys Thr Val Ala Lys Trp Gly
225                 230                 235                 240

Gln Cys Gly Gly Gln Gly Tyr Ser Gly Cys Thr Val Cys Ala Ala Gly
                245                 250                 255

Ser Thr Cys Gln Lys Thr Asn Asp Tyr Tyr Ser Gln Cys Leu
            260                 265                 270

<210> SEQ ID NO 34
<211> LENGTH: 834
<212> TYPE: DNA
<213> ORGANISM: Myceliophthora thermophila

<400> SEQUENCE: 34
ctgacgacgg gcggcgtcaa gcacgctgtg taccagtaca tccgcaagaa caccaactat      60
aactcgcccg tgaccgatct gacgtccaac gacctccgct gcaatgtggg tgctaccggt     120
gcgggcaccg ataccgtcac ggtgcgcgcc ggcgattcgt tcaccttcac gaccgatacg     180
cccgtttacc accagggccc gacctcgatc tacatgtcca aggcccccgg cagcgcgtcc     240
gactacgacg gcagcggcgg ctggttcaag atcaaggact ggggtgccga ctttagcagc     300
ggccaggcca cctggacctt ggcgtctgac tacaccgcca cgattccgga atgtattccc     360
cccggcgact acctgcttcg catccagcaa ctcggcatcc acaaccttg gcccgcgggc     420 atcccccagt tctacatctc ttgtgcccag atcaccgtga ctggtggcgg cagtgccaac     480
cccggcccga ccgtctccat cccaggcgcc ttcaaggaga ccgacccggg ctacactgtc     540
aacatctaca acaacttcca caactacacc gtccctggcc cagccgtctt cacctgcaac     600
ggtagcggcg gcaacaacgg cggcggctcc aacccagtca ccaccaccac caccaccacc     660
accaggccgt ccaccagcac cgcccagtcc cagccgtcgt cgagcccgac cagcccctcc     720
agctgcaccg tcgcgaagtg gggccagtgc ggaggacagg gttacagcgg ctgcaccgtg     780
tgcgcggccg ggtcgacctg ccagaagacc aacgactact acagccagtg cttg           834

<210> SEQ ID NO 35
<211> LENGTH: 303
<212> TYPE: PRT
<213> ORGANISM: Myceliophthora thermophila

<400> SEQUENCE: 35

Met Lys Gly Leu Leu Gly Ala Ala Ala Leu Ser Leu Ala Val Ser Asp
1               5                   10                  15
```

Val Ser Ala His Tyr Ile Phe Gln Gln Leu Thr Thr Gly Gly Val Lys
            20                  25                  30

His Ala Val Tyr Gln Tyr Ile Arg Lys Asn Thr Asn Tyr Asn Ser Pro
        35                  40                  45

Val Thr Asp Leu Thr Ser Asn Asp Leu Arg Cys Asn Val Gly Ala Thr
    50                  55                  60

Gly Ala Gly Thr Asp Thr Val Thr Val Arg Ala Gly Asp Ser Phe Thr
65                  70                  75                  80

Phe Thr Thr Asp Thr Pro Val Tyr His Gln Gly Pro Thr Ser Ile Tyr
                85                  90                  95

Met Ser Lys Ala Pro Gly Ser Ala Ser Asp Tyr Asp Gly Ser Gly Gly
            100                 105                 110

Trp Phe Lys Ile Lys Asp Trp Gly Ala Asp Phe Ser Ser Gly Gln Ala
        115                 120                 125

Thr Trp Thr Leu Ala Ser Asp Tyr Thr Ala Thr Ile Pro Glu Cys Ile
130                 135                 140

Pro Pro Gly Asp Tyr Leu Leu Arg Ile Gln Gln Leu Gly Ile His Asn
145                 150                 155                 160

Pro Trp Pro Ala Gly Ile Pro Gln Phe Tyr Ile Ser Cys Ala Gln Ile
                165                 170                 175

Thr Val Thr Gly Gly Ser Ala Asn Pro Gly Pro Thr Val Ser Ile
            180                 185                 190

Pro Gly Ala Phe Lys Glu Thr Asp Pro Gly Tyr Thr Val Asn Ile Tyr
        195                 200                 205

Asn Asn Phe His Asn Tyr Thr Val Pro Gly Pro Ala Val Phe Thr Cys
210                 215                 220

Asn Gly Ser Gly Gly Asn Asn Gly Gly Ser Asn Pro Val Thr Thr
225                 230                 235                 240

Thr Thr Thr Thr Thr Thr Arg Pro Ser Thr Ser Thr Ala Gln Ser Gln
                245                 250                 255

Pro Ser Ser Ser Pro Thr Ser Pro Ser Ser Cys Thr Val Ala Lys Trp
            260                 265                 270

Gly Gln Cys Gly Gly Gln Gly Tyr Ser Gly Cys Thr Val Cys Ala Ala
        275                 280                 285

Gly Ser Thr Cys Gln Lys Thr Asn Asp Tyr Tyr Ser Gln Cys Leu
    290                 295                 300

<210> SEQ ID NO 36
<211> LENGTH: 284
<212> TYPE: PRT
<213> ORGANISM: Myceliophthora thermophila

<400> SEQUENCE: 36

His Tyr Ile Phe Gln Gln Leu Thr Thr Gly Gly Val Lys His Ala Val
1               5                   10                  15

Tyr Gln Tyr Ile Arg Lys Asn Thr Asn Tyr Asn Ser Pro Val Thr Asp
            20                  25                  30

Leu Thr Ser Asn Asp Leu Arg Cys Asn Val Gly Ala Thr Gly Ala Gly
        35                  40                  45

Thr Asp Thr Val Thr Val Arg Ala Gly Asp Ser Phe Thr Phe Thr Thr
    50                  55                  60

Asp Thr Pro Val Tyr His Gln Gly Pro Thr Ser Ile Tyr Met Ser Lys
65                  70                  75                  80

Ala Pro Gly Ser Ala Ser Asp Tyr Asp Gly Ser Gly Gly Trp Phe Lys

```
                     85                  90                  95
Ile Lys Asp Trp Gly Ala Asp Phe Ser Ser Gly Gln Ala Thr Trp Thr
                100                 105                 110

Leu Ala Ser Asp Tyr Thr Ala Thr Ile Pro Glu Cys Ile Pro Pro Gly
            115                 120                 125

Asp Tyr Leu Leu Arg Ile Gln Gln Leu Gly Ile His Asn Pro Trp Pro
        130                 135                 140

Ala Gly Ile Pro Gln Phe Tyr Ile Ser Cys Ala Gln Ile Thr Val Thr
145                 150                 155                 160

Gly Gly Gly Ser Ala Asn Pro Gly Pro Thr Val Ser Ile Pro Gly Ala
                165                 170                 175

Phe Lys Glu Thr Asp Pro Gly Tyr Thr Val Asn Ile Tyr Asn Asn Phe
            180                 185                 190

His Asn Tyr Thr Val Pro Gly Pro Ala Val Phe Thr Cys Asn Gly Ser
        195                 200                 205

Gly Gly Asn Asn Gly Gly Ser Asn Pro Val Thr Thr Thr Thr
210                 215                 220

Thr Thr Thr Arg Pro Ser Thr Ser Thr Ala Gln Ser Gln Pro Ser Ser
225                 230                 235                 240

Ser Pro Thr Ser Pro Ser Ser Cys Thr Val Ala Lys Trp Gly Gln Cys
                245                 250                 255

Gly Gly Gln Gly Tyr Ser Gly Cys Thr Val Cys Ala Ala Gly Ser Thr
            260                 265                 270

Cys Gln Lys Thr Asn Asp Tyr Tyr Ser Gln Cys Leu
        275                 280

<210> SEQ ID NO 37
<211> LENGTH: 1038
<212> TYPE: DNA
<213> ORGANISM: Myceliophthora thermophila

<400> SEQUENCE: 37
atgtcttcct tcacctccaa gggtctcctt tccgccctca tgggcgcggc aacggttgcc        60
gcccacggtc acgtcaccaa catcgtcatc aacggcgtct cataccagaa cttcgaccca       120
ttcacgcacc cttatatgca gaaccctccg acggttgtcg gctggaccgc gagcaacacg       180
gacaacggct tcgtcggccc cgagtccttc tctagcccgg acatcatctg ccacaagtcc       240
gccaccaacg ctggcggcca tgccgtcgtc gcggccggcg ataaggtctt catccagtgg       300
gacacctggc ccgagtcgca ccacggtccg gtcatcgact atctcgccga ctgcggcgac       360
gcgggctgcg agaaggtcga caagaccacg ctcaagttct tcaagatcag cgagtccggc       420
ctgctcgacg gcactaacgc ccccggcaag tgggcgtccg acacgctgat cgccaacaac       480
aactcgtggc tggtccagat cccgcccaac atcgccccgg caactacgt cctgcgccac        540 gagatcatcg ccctgcacag cgccggccag cagaacggcg cccagaacta ccctcagtgc       600
ttcaacctgc aggtcaccgg ctccggcact cagaagccct ccggcgtcct cggcaccgag       660
ctctacaagg ccaccgacgc cggcatcctg gccaacatct acacctcgcc cgtcacctac       720
cagatccccg gccggccat catctcgggc gcctccgccg tccagcagac cacctcggcc       780
atcaccgcct ctgctagcgc catcaccggc tccgctaccg ccgcgcccac ggctgccacc       840
accaccgccg ccgccgccgc caccactacc accaccgctg gctccggtgc taccgccacg       900
ccctcgaccg cggctctcc ttcttccgcc cagcctgctc ctaccaccgc tgccgctacc        960
tccagccctg ctcgcccgac ccgctgcgct ggtctgaaga agcgccgtcg ccacgcccgt      1020
```
gacgtcaagg ttgccctc                                               1038

<210> SEQ ID NO 38
<211> LENGTH: 346
<212> TYPE: PRT
<213> ORGANISM: Myceliophthora thermophila

<400> SEQUENCE: 38

Met Ser Ser Phe Thr Ser Lys Gly Leu Leu Ser Ala Leu Met Gly Ala
1               5                   10                  15

Ala Thr Val Ala Ala His Gly His Val Thr Asn Ile Val Ile Asn Gly
            20                  25                  30

Val Ser Tyr Gln Asn Phe Asp Pro Phe Thr His Pro Tyr Met Gln Asn
        35                  40                  45

Pro Pro Thr Val Val Gly Trp Thr Ala Ser Asn Thr Asp Asn Gly Phe
    50                  55                  60

Val Gly Pro Glu Ser Phe Ser Ser Pro Asp Ile Ile Cys His Lys Ser
65                  70                  75                  80

Ala Thr Asn Ala Gly Gly His Ala Val Val Ala Ala Gly Asp Lys Val
                85                  90                  95

Phe Ile Gln Trp Asp Thr Trp Pro Glu Ser His His Gly Pro Val Ile
            100                 105                 110

Asp Tyr Leu Ala Asp Cys Gly Asp Ala Gly Cys Glu Lys Val Asp Lys
        115                 120                 125

Thr Thr Leu Lys Phe Phe Lys Ile Ser Glu Ser Gly Leu Leu Asp Gly
    130                 135                 140

Thr Asn Ala Pro Gly Lys Trp Ala Ser Asp Thr Leu Ile Ala Asn Asn
145                 150                 155                 160

Asn Ser Trp Leu Val Gln Ile Pro Pro Asn Ile Ala Pro Gly Asn Tyr
                165                 170                 175

Val Leu Arg His Glu Ile Ile Ala Leu His Ser Ala Gly Gln Gln Asn
            180                 185                 190

Gly Ala Gln Asn Tyr Pro Gln Cys Phe Asn Leu Gln Val Thr Gly Ser
        195                 200                 205

Gly Thr Gln Lys Pro Ser Gly Val Leu Gly Thr Glu Leu Tyr Lys Ala
    210                 215                 220

Thr Asp Ala Gly Ile Leu Ala Asn Ile Tyr Thr Ser Pro Val Thr Tyr
225                 230                 235                 240

Gln Ile Pro Gly Pro Ala Ile Ile Ser Gly Ala Ser Ala Val Gln Gln
                245                 250                 255

Thr Thr Ser Ala Ile Thr Ala Ser Ala Ser Ile Thr Gly Ser Ala
            260                 265                 270

Thr Ala Ala Pro Thr Ala Ala Thr Thr Ala Ala Ala Ala Thr
        275                 280                 285

Thr Thr Thr Thr Ala Gly Ser Gly Ala Thr Ala Thr Pro Ser Thr Gly
    290                 295                 300

Gly Ser Pro Ser Ser Ala Gln Pro Ala Pro Thr Ala Ala Ala Thr
305                 310                 315                 320

Ser Ser Pro Ala Arg Pro Thr Arg Cys Ala Gly Leu Lys Lys Arg Arg
                325                 330                 335

Arg His Ala Arg Asp Val Lys Val Ala Leu
            340                 345

<210> SEQ ID NO 39

<211> LENGTH: 326
<212> TYPE: PRT
<213> ORGANISM: Myceliophthora thermophila

<400> SEQUENCE: 39

```
Ala His Gly His Val Thr Asn Ile Val Ile Asn Gly Val Ser Tyr Gln
1               5                   10                  15

Asn Phe Asp Pro Phe Thr His Pro Tyr Met Gln Asn Pro Pro Thr Val
            20                  25                  30

Val Gly Trp Thr Ala Ser Asn Thr Asp Asn Gly Phe Val Gly Pro Glu
        35                  40                  45

Ser Phe Ser Ser Pro Asp Ile Ile Cys His Lys Ser Ala Thr Asn Ala
    50                  55                  60

Gly Gly His Ala Val Val Ala Ala Gly Asp Lys Val Phe Ile Gln Trp
65                  70                  75                  80

Asp Thr Trp Pro Glu Ser His His Gly Pro Val Ile Asp Tyr Leu Ala
                85                  90                  95

Asp Cys Gly Asp Ala Gly Cys Glu Lys Val Asp Lys Thr Thr Leu Lys
            100                 105                 110

Phe Phe Lys Ile Ser Glu Ser Gly Leu Leu Asp Gly Thr Asn Ala Pro
        115                 120                 125

Gly Lys Trp Ala Ser Asp Thr Leu Ile Ala Asn Asn Asn Ser Trp Leu
    130                 135                 140

Val Gln Ile Pro Pro Asn Ile Ala Pro Gly Asn Tyr Val Leu Arg His
145                 150                 155                 160

Glu Ile Ile Ala Leu His Ser Ala Gly Gln Gln Asn Gly Ala Gln Asn
                165                 170                 175

Tyr Pro Gln Cys Phe Asn Leu Gln Val Thr Gly Ser Gly Thr Gln Lys
            180                 185                 190

Pro Ser Gly Val Leu Gly Thr Glu Leu Tyr Lys Ala Thr Asp Ala Gly
        195                 200                 205

Ile Leu Ala Asn Ile Tyr Thr Ser Pro Val Thr Tyr Gln Ile Pro Gly
    210                 215                 220

Pro Ala Ile Ile Ser Gly Ala Ser Ala Val Gln Gln Thr Thr Ser Ala
225                 230                 235                 240

Ile Thr Ala Ser Ala Ser Ala Ile Thr Gly Ser Ala Thr Ala Ala Pro
                245                 250                 255

Thr Ala Ala Thr Thr Ala Ala Ala Ala Thr Thr Thr Thr Thr Thr Thr
            260                 265                 270

Ala Gly Ser Gly Ala Thr Ala Thr Pro Ser Thr Gly Gly Ser Pro Ser
        275                 280                 285

Ser Ala Gln Pro Ala Pro Thr Thr Ala Ala Thr Ser Ser Pro Ala
    290                 295                 300

Arg Pro Thr Arg Cys Ala Gly Leu Lys Lys Arg Arg His Ala Arg
305                 310                 315                 320

Asp Val Lys Val Ala Leu
                325
```

<210> SEQ ID NO 40
<211> LENGTH: 714
<212> TYPE: DNA
<213> ORGANISM: Myceliophthora thermophila

<400> SEQUENCE: 40
atgaagacgc tcgccgccct cgtggtctcg gccgccctcg tggccgcgca cggctatgtt    60

```
gaccacgcca cgatcggtgg caaggattat cagttctacc agccgtacca ggacccttac    120
atgggcgaca caagcccga tagggtttcc cgctccatcc cgggcaacgg ccccgtggag    180
gacgtcaact ccatcgacct ccagtgccac gccggtgccg aaccggccaa gctccacgcc    240
cccgccgccg ccggctcgac cgtgacgctc tactggaccc tctggcccga ctcccacgtc    300
ggccccgtca tcacctacat ggctcgctgc cccgacaccg gctgccagga ctggtccccg    360
ggaactaagc ccgtttggtt caagatcaag gaaggcggcc gtgagggcac ctccaatacc    420
ccgctcatga cggccccctc cgcctacacc tacacgatcc cgtcctgcct caagagcggc    480
tactacctcg tccgccacga gatcatcgcc ctgcactcgg cctggcagta ccccggcgcc    540
cagttctacc cgggctgcca ccagctccag gtcaccggcg gcggctccac cgtgccctct    600
accaacctgg tctccttccc cggcgcctac aaggggagcg accccggcat cacctacgac    660
gcttacaagg cgcaacctta caccatccct ggcccggccg tgtttacctg ctga          714
```

<210> SEQ ID NO 41
<211> LENGTH: 237
<212> TYPE: PRT
<213> ORGANISM: Myceliophthora thermophila

<400> SEQUENCE: 41

```
Met Lys Thr Leu Ala Ala Leu Val Val Ser Ala Ala Leu Val Ala Ala
1               5                  10                  15

His Gly Tyr Val Asp His Ala Thr Ile Gly Gly Lys Asp Tyr Gln Phe
            20                  25                  30

Tyr Gln Pro Tyr Gln Asp Pro Tyr Met Gly Asp Asn Lys Pro Asp Arg
        35                  40                  45

Val Ser Arg Ser Ile Pro Gly Asn Gly Pro Val Glu Asp Val Asn Ser
    50                  55                  60

Ile Asp Leu Gln Cys His Ala Gly Ala Glu Pro Ala Lys Leu His Ala
65                  70                  75                  80

Pro Ala Ala Gly Ser Thr Val Thr Leu Tyr Trp Thr Leu Trp Pro
                85                  90                  95

Asp Ser His Val Gly Pro Val Ile Thr Tyr Met Ala Arg Cys Pro Asp
            100                 105                 110

Thr Gly Cys Gln Asp Trp Ser Pro Gly Thr Lys Pro Val Trp Phe Lys
        115                 120                 125

Ile Lys Glu Gly Gly Arg Glu Gly Thr Ser Asn Thr Pro Leu Met Thr
    130                 135                 140

Ala Pro Ser Ala Tyr Thr Tyr Thr Ile Pro Ser Cys Leu Lys Ser Gly
145                 150                 155                 160

Tyr Tyr Leu Val Arg His Glu Ile Ile Ala Leu His Ser Ala Trp Gln
                165                 170                 175

Tyr Pro Gly Ala Gln Phe Tyr Pro Gly Cys His Gln Leu Gln Val Thr
            180                 185                 190

Gly Gly Gly Ser Thr Val Pro Ser Thr Asn Leu Val Ser Phe Pro Gly
        195                 200                 205

Ala Tyr Lys Gly Ser Asp Pro Gly Ile Thr Tyr Asp Ala Tyr Lys Ala
    210                 215                 220

Gln Pro Tyr Thr Ile Pro Gly Pro Ala Val Phe Thr Cys
225                 230                 235
```

<210> SEQ ID NO 42
<211> LENGTH: 219
<212> TYPE: PRT

<213> ORGANISM: Myceliophthora thermophila

<400> SEQUENCE: 42

```
Tyr Val Asp His Ala Thr Ile Gly Gly Lys Asp Tyr Gln Phe Tyr Gln
1               5                   10                  15
Pro Tyr Gln Asp Pro Tyr Met Gly Asp Asn Lys Pro Asp Arg Val Ser
            20                  25                  30
Arg Ser Ile Pro Gly Asn Gly Pro Val Glu Asp Val Asn Ser Ile Asp
        35                  40                  45
Leu Gln Cys His Ala Gly Ala Glu Pro Ala Lys Leu His Ala Pro Ala
    50                  55                  60
Ala Ala Gly Ser Thr Val Thr Leu Tyr Trp Thr Leu Trp Pro Asp Ser
65                  70                  75                  80
His Val Gly Pro Val Ile Thr Tyr Met Ala Arg Cys Pro Asp Thr Gly
                85                  90                  95
Cys Gln Asp Trp Ser Pro Gly Thr Lys Pro Val Trp Phe Lys Ile Lys
            100                 105                 110
Glu Gly Gly Arg Glu Gly Thr Ser Asn Thr Pro Leu Met Thr Ala Pro
        115                 120                 125
Ser Ala Tyr Thr Tyr Thr Ile Pro Ser Cys Leu Lys Ser Gly Tyr Tyr
    130                 135                 140
Leu Val Arg His Glu Ile Ile Ala Leu His Ser Ala Trp Gln Tyr Pro
145                 150                 155                 160
Gly Ala Gln Phe Tyr Pro Gly Cys His Gln Leu Gln Val Thr Gly Gly
                165                 170                 175
Gly Ser Thr Val Pro Ser Thr Asn Leu Val Ser Phe Pro Gly Ala Tyr
            180                 185                 190
Lys Gly Ser Asp Pro Gly Ile Thr Tyr Asp Ala Tyr Lys Ala Gln Pro
        195                 200                 205
Tyr Thr Ile Pro Gly Pro Ala Val Phe Thr Cys
    210                 215
```

<210> SEQ ID NO 43
<211> LENGTH: 723
<212> TYPE: DNA
<213> ORGANISM: Myceliophthora thermophila

<400> SEQUENCE: 43

```
atgaagacgc tcgccgccct cgtggtctcg gccgccctcg tggccgcgca cggctatgtt    60
gaccacgcca cgatcggtgg caaggattat cagttctacc agccgtacca ggacccttac   120
atgggcgaca acaagcccga tagggtttcc cgctccatcc cgggcaacgg ccccgtggag   180
gacgtcaact ccatcgacct ccagtgccac gccggtgccg aaccggccaa gctccacgcc   240
cccgccgccg ccggctcgac cgtgacgctc tactggaccc tctggcccga ctcccacgtc   300
ggccccgtca tcacctacat ggctcgctgc cccgacaccg gctgccagga ctggtccccg   360
ggaactaagc ccgtttggtt caagatcaag gaaggcggcc gtgagggcac ctccaatgtc   420
tgggctgcta ccccgctcat gacggccccc tccgcctaca cctacacgat cccgtcctgc   480
ctcaagagcg gctactacct cgtccgccac gagatcatcg ccctgcactc ggcctggcag   540
taccccggcg cccagttcta cccgggctgc caccagctcc aggtcaccgg cggcggctcc   600
accgtgccct ctaccaacct ggtctccttc cccggcgcct acaaggggag cgaccccggc   660
atcacctacg acgcttacaa ggcgcaacct tacaccatcc ctggccccgc cgtgtttacc   720
tgc                                                                 723
```

<210> SEQ ID NO 44
<211> LENGTH: 241
<212> TYPE: PRT
<213> ORGANISM: Myceliophthora thermophila

<400> SEQUENCE: 44

Met Lys Thr Leu Ala Ala Leu Val Val Ser Ala Ala Leu Val Ala Ala
1               5                   10                  15

His Gly Tyr Val Asp His Ala Thr Ile Gly Gly Lys Asp Tyr Gln Phe
                20                  25                  30

Tyr Gln Pro Tyr Gln Asp Pro Tyr Met Gly Asp Asn Lys Pro Asp Arg
            35                  40                  45

Val Ser Arg Ser Ile Pro Gly Asn Gly Pro Val Glu Asp Val Asn Ser
        50                  55                  60

Ile Asp Leu Gln Cys His Ala Gly Ala Glu Pro Ala Lys Leu His Ala
65                  70                  75                  80

Pro Ala Ala Gly Ser Thr Val Thr Leu Tyr Trp Thr Leu Trp Pro
                85                  90                  95

Asp Ser His Val Gly Pro Val Ile Thr Tyr Met Ala Arg Cys Pro Asp
                100                 105                 110

Thr Gly Cys Gln Asp Trp Ser Pro Gly Thr Lys Pro Val Trp Phe Lys
            115                 120                 125

Ile Lys Glu Gly Gly Arg Glu Gly Thr Ser Asn Val Trp Ala Ala Thr
130                 135                 140

Pro Leu Met Thr Ala Pro Ser Ala Tyr Thr Tyr Thr Ile Pro Ser Cys
145                 150                 155                 160

Leu Lys Ser Gly Tyr Tyr Leu Val Arg His Glu Ile Ile Ala Leu His
                165                 170                 175

Ser Ala Trp Gln Tyr Pro Gly Ala Gln Phe Tyr Pro Gly Cys His Gln
            180                 185                 190

Leu Gln Val Thr Gly Gly Gly Ser Thr Val Pro Ser Thr Asn Leu Val
        195                 200                 205

Ser Phe Pro Gly Ala Tyr Lys Gly Ser Asp Pro Gly Ile Thr Tyr Asp
210                 215                 220

Ala Tyr Lys Ala Gln Pro Tyr Thr Ile Pro Gly Pro Ala Val Phe Thr
225                 230                 235                 240

Cys

<210> SEQ ID NO 45
<211> LENGTH: 223
<212> TYPE: PRT
<213> ORGANISM: Myceliophthora thermophila

<400> SEQUENCE: 45

Tyr Val Asp His Ala Thr Ile Gly Gly Lys Asp Tyr Gln Phe Tyr Gln
1               5                   10                  15

Pro Tyr Gln Asp Pro Tyr Met Gly Asp Asn Lys Pro Asp Arg Val Ser
                20                  25                  30

Arg Ser Ile Pro Gly Asn Gly Pro Val Glu Asp Val Asn Ser Ile Asp
            35                  40                  45

Leu Gln Cys His Ala Gly Ala Glu Pro Ala Lys Leu His Ala Pro Ala
        50                  55                  60

Ala Ala Gly Ser Thr Val Thr Leu Tyr Trp Thr Leu Trp Pro Asp Ser
65                  70                  75                  80

His Val Gly Pro Val Ile Thr Tyr Met Ala Arg Cys Pro Asp Thr Gly
              85                  90                  95

Cys Gln Asp Trp Ser Pro Gly Thr Lys Pro Val Trp Phe Lys Ile Lys
            100                 105                 110

Glu Gly Gly Arg Glu Gly Thr Ser Asn Val Trp Ala Ala Thr Pro Leu
        115                 120                 125

Met Thr Ala Pro Ser Ala Tyr Thr Tyr Thr Ile Pro Ser Cys Leu Lys
    130                 135                 140

Ser Gly Tyr Tyr Leu Val Arg His Glu Ile Ile Ala Leu His Ser Ala
145                 150                 155                 160

Trp Gln Tyr Pro Gly Ala Gln Phe Tyr Pro Gly Cys His Gln Leu Gln
                165                 170                 175

Val Thr Gly Gly Gly Ser Thr Val Pro Ser Thr Asn Leu Val Ser Phe
            180                 185                 190

Pro Gly Ala Tyr Lys Gly Ser Asp Pro Gly Ile Thr Tyr Asp Ala Tyr
        195                 200                 205

Lys Ala Gln Pro Tyr Thr Ile Pro Gly Pro Ala Val Phe Thr Cys
    210                 215                 220

<210> SEQ ID NO 46
<211> LENGTH: 675
<212> TYPE: DNA
<213> ORGANISM: Myceliophthora thermophila

<400> SEQUENCE: 46

```
atgagatact tcctccagct cgctgcggcc gcggcctttg ccgtgaacag cgcggcgggt        60
cactacatct tccagcagtt cgcgacgggc gggtccaagt acccgccctg gaagtacatc       120
cggcgcaaca ccaacccgga ctggctgcag aacgggccgg tgacggacct gtcgtcgacc       180
gacctgcgct gcaacgtggg cggcaggtc agcaacggga ccgagaccat caccttgaac        240
gccggcgacg agttcagctt catcctcgac acgcccgtct accatgccgg ccccacctcg       300
ctctacatgt ccaaggcgcc cggagctgtg ccgactacg acggcggcgg ggcctggttc        360
aagatctacg actggggtcc gtcggggacg agctggacgt tgagtggcac gtacactcag       420
agaattccca gtgcatccc tgacggcgag tacctcctcc gcatccagca gatcgggctc        480
cacaaccccg cgccgcgcc acagttctac atcagctgcg ctcaagtcaa ggtcgtcgat       540
ggcggcagca ccaatccgac cccgaccgcc cagattccgg gagccttcca cagcaacgac       600
cctggcttga ctgtcaatat ctacaacgac cctctcacca actacgtcgt cccgggacct       660
agagtttcgc actgg                                                          675
```

<210> SEQ ID NO 47
<211> LENGTH: 225
<212> TYPE: PRT
<213> ORGANISM: Myceliophthora thermophila

<400> SEQUENCE: 47

Met Arg Tyr Phe Leu Gln Leu Ala Ala Ala Ala Phe Ala Val Asn
1               5                   10                  15

Ser Ala Ala Gly His Tyr Ile Phe Gln Gln Phe Ala Thr Gly Gly Ser
            20                  25                  30

Lys Tyr Pro Pro Trp Lys Tyr Ile Arg Arg Asn Thr Asn Pro Asp Trp
        35                  40                  45

Leu Gln Asn Gly Pro Val Thr Asp Leu Ser Ser Thr Asp Leu Arg Cys
    50                  55                  60

```
Asn Val Gly Gly Gln Val Ser Asn Gly Thr Glu Thr Ile Thr Leu Asn
 65                  70                  75                  80

Ala Gly Asp Glu Phe Ser Phe Ile Leu Asp Thr Pro Val Tyr His Ala
                 85                  90                  95

Gly Pro Thr Ser Leu Tyr Met Ser Lys Ala Pro Gly Ala Val Ala Asp
            100                 105                 110

Tyr Asp Gly Gly Ala Trp Phe Lys Ile Tyr Asp Trp Gly Pro Ser
        115                 120                 125

Gly Thr Ser Trp Thr Leu Ser Gly Tyr Thr Gln Arg Ile Pro Lys
    130                 135                 140

Cys Ile Pro Asp Gly Glu Tyr Leu Leu Arg Ile Gln Gln Ile Gly Leu
145                 150                 155                 160

His Asn Pro Gly Ala Ala Pro Gln Phe Tyr Ile Ser Cys Ala Gln Val
                165                 170                 175

Lys Val Val Asp Gly Gly Ser Thr Asn Pro Thr Pro Thr Ala Gln Ile
            180                 185                 190

Pro Gly Ala Phe His Ser Asn Asp Pro Gly Leu Thr Val Asn Ile Tyr
        195                 200                 205

Asn Asp Pro Leu Thr Asn Tyr Val Val Pro Gly Pro Arg Val Ser His
210                 215                 220

Trp
225

<210> SEQ ID NO 48
<211> LENGTH: 205
<212> TYPE: PRT
<213> ORGANISM: Myceliophthora thermophila

<400> SEQUENCE: 48

His Tyr Ile Phe Gln Gln Phe Ala Thr Gly Gly Ser Lys Tyr Pro Pro
  1               5                  10                  15

Trp Lys Tyr Ile Arg Arg Asn Thr Asn Pro Asp Trp Leu Gln Asn Gly
             20                  25                  30

Pro Val Thr Asp Leu Ser Ser Thr Asp Leu Arg Cys Asn Val Gly Gly
         35                  40                  45

Gln Val Ser Asn Gly Thr Glu Thr Ile Thr Leu Asn Ala Gly Asp Glu
     50                  55                  60

Phe Ser Phe Ile Leu Asp Thr Pro Val Tyr His Ala Gly Pro Thr Ser
 65                  70                  75                  80

Leu Tyr Met Ser Lys Ala Pro Gly Ala Val Ala Asp Tyr Asp Gly Gly
                 85                  90                  95

Gly Ala Trp Phe Lys Ile Tyr Asp Trp Gly Pro Ser Gly Thr Ser Trp
            100                 105                 110

Thr Leu Ser Gly Tyr Thr Gln Arg Ile Pro Lys Cys Ile Pro Asp
        115                 120                 125

Gly Glu Tyr Leu Leu Arg Ile Gln Gln Ile Gly Leu His Asn Pro Gly
    130                 135                 140

Ala Ala Pro Gln Phe Tyr Ile Ser Cys Ala Gln Val Lys Val Val Asp
145                 150                 155                 160

Gly Gly Ser Thr Asn Pro Thr Pro Thr Ala Gln Ile Pro Gly Ala Phe
                165                 170                 175

His Ser Asn Asp Pro Gly Leu Thr Val Asn Ile Tyr Asn Asp Pro Leu
            180                 185                 190

Thr Asn Tyr Val Val Pro Gly Pro Arg Val Ser His Trp
        195                 200                 205
```

<210> SEQ ID NO 49
<211> LENGTH: 1332
<212> TYPE: DNA
<213> ORGANISM: Myceliophthora thermophila

<400> SEQUENCE: 49

```
atgcacccct cccttctttt cacgcttggg ctggcgagcg tgcttgtccc cctctcgtct      60
gcacacacta ccttcacgac cctcttcgtc aacgatgtca accaaggtga tggtacctgc     120
attcgcatgg cgaagaaggg caatgtcgcc acccatcctc tcgcaggcgg tctcgactcc     180
gaagacatgg cctgtggtcg ggatggtcaa gaacccgtgg catttacgtg tccggcccca     240
gctggtgcca agttgactct cgagtttcgc atgtgggccg atgcttcgca gtccggatcg     300
atcgatccat cccaccttgg cgtcatggcc atctacctca agaaggtttc cgacatgaaa     360
tctgacgcgg ccgctggccc gggctggttc aagatttggg accaaggcta cgacttggcg     420
gccaagaagt gggccaccga aagctcatc gacaacaacg cctcctgag cgtcaacctt      480
ccaaccggct taccaaccgg ctactacctc gcccgccagg agatcatcac gctccaaaac     540
gttaccaatg acaggccaga gccccagttc tacgtcggct cgcacagct ctacgtcgag      600
ggcacctcgg actcacccat cccctcggac aagacggtct ccattcccgg ccacatcagc     660
gacccggccg acccgggcct gaccttcaac gtctacacgg cgacgcatc cacctacaag      720
ccgcccggcc ccgaggttta cttccccacc accaccacca cacctcctc ctcctcctcc      780
ggaagcagcg acaacaaggg agccaggcgc cagcaaaccc ccgacgacaa gcaggccgac     840
ggcctcgttc cagccgactg cctcgtcaag aacgcgaact ggtgcgccgc tgccctgccg     900
ccgtacaccg acgaggccgg ctgctgggcc gccgccgagg actgcaacaa gcagctggac     960
gcgtgctaca ccagcgcacc cccctcgggc agcaaggggt gcaaggtctg ggaggagcag    1020
gtgtgcaccg tcgtctcgca gaagtgcgag gccgggggatt caaggggcc ccgcagctc      1080
gggaaggagc tcggcgaggg gatcgatgag cctattccgg ggggaaagct gccccggcg      1140
gtcaacgcgg gagagaacgg gaatcatggc ggaggtggtg gtgatgatgg tgatgatgat    1200
aatgatgagg ccggggctgg ggcagcgtcg actccgactt ttgctgctcc tggtgcggcc    1260
aagactcccc aaccaaactc cgagagggcc cggcgccgtg aggcgcattg cggcgactg     1320
gaatctgctg ag                                                        1332
```

<210> SEQ ID NO 50
<211> LENGTH: 444
<212> TYPE: PRT
<213> ORGANISM: Myceliophthora thermophila

<400> SEQUENCE: 50

Met His Pro Ser Leu Leu Phe Thr Leu Gly Leu Ala Ser Val Leu Val
1               5                   10                  15

Pro Leu Ser Ser Ala His Thr Thr Phe Thr Thr Leu Phe Val Asn Asp
            20                  25                  30

Val Asn Gln Gly Asp Gly Thr Cys Ile Arg Met Ala Lys Lys Gly Asn
        35                  40                  45

Val Ala Thr His Pro Leu Ala Gly Gly Leu Asp Ser Glu Asp Met Ala
    50                  55                  60

Cys Gly Arg Asp Gly Gln Glu Pro Val Ala Phe Thr Cys Pro Ala Pro
65                  70                  75                  80

Ala Gly Ala Lys Leu Thr Leu Glu Phe Arg Met Trp Ala Asp Ala Ser

```
                    85                  90                  95
Gln Ser Gly Ser Ile Asp Pro Ser His Leu Gly Val Met Ala Ile Tyr
            100                 105                 110

Leu Lys Lys Val Ser Asp Met Lys Ser Asp Ala Ala Ala Gly Pro Gly
        115                 120                 125

Trp Phe Lys Ile Trp Asp Gln Gly Tyr Asp Leu Ala Ala Lys Lys Trp
    130                 135                 140

Ala Thr Glu Lys Leu Ile Asp Asn Asn Gly Leu Leu Ser Val Asn Leu
145                 150                 155                 160

Pro Thr Gly Leu Pro Thr Gly Tyr Tyr Leu Ala Arg Gln Glu Ile Ile
                165                 170                 175

Thr Leu Gln Asn Val Thr Asn Asp Arg Pro Glu Pro Gln Phe Tyr Val
            180                 185                 190

Gly Cys Ala Gln Leu Tyr Val Glu Gly Thr Ser Asp Ser Pro Ile Pro
        195                 200                 205

Ser Asp Lys Thr Val Ser Ile Pro Gly His Ile Ser Asp Pro Ala Asp
    210                 215                 220

Pro Gly Leu Thr Phe Asn Val Tyr Thr Gly Asp Ala Ser Thr Tyr Lys
225                 230                 235                 240

Pro Pro Gly Pro Glu Val Tyr Phe Pro Thr Thr Thr Thr Thr Thr Ser
                245                 250                 255

Ser Ser Ser Gly Ser Ser Asp Asn Lys Gly Ala Arg Arg Gln Gln
            260                 265                 270

Thr Pro Asp Asp Lys Gln Ala Asp Gly Leu Val Pro Ala Asp Cys Leu
        275                 280                 285

Val Lys Asn Ala Asn Trp Cys Ala Ala Ala Leu Pro Pro Tyr Thr Asp
    290                 295                 300

Glu Ala Gly Cys Trp Ala Ala Ala Glu Asp Cys Asn Lys Gln Leu Asp
305                 310                 315                 320

Ala Cys Tyr Thr Ser Ala Pro Pro Ser Gly Ser Lys Gly Cys Lys Val
                325                 330                 335

Trp Glu Glu Gln Val Cys Thr Val Val Ser Gln Lys Cys Glu Ala Gly
            340                 345                 350

Asp Phe Lys Gly Pro Pro Gln Leu Gly Lys Glu Leu Gly Glu Gly Ile
        355                 360                 365

Asp Glu Pro Ile Pro Gly Gly Lys Leu Pro Pro Ala Val Asn Ala Gly
    370                 375                 380

Glu Asn Gly Asn His Gly Gly Gly Gly Asp Asp Gly Asp Asp Asp
385                 390                 395                 400

Asn Asp Glu Ala Gly Ala Gly Ala Ala Ser Thr Pro Thr Phe Ala Ala
                405                 410                 415

Pro Gly Ala Ala Lys Thr Pro Gln Pro Asn Ser Glu Arg Ala Arg Arg
            420                 425                 430

Arg Glu Ala His Trp Arg Arg Leu Glu Ser Ala Glu
        435                 440

<210> SEQ ID NO 51
<211> LENGTH: 423
<212> TYPE: PRT
<213> ORGANISM: Myceliophthora thermophila

<400> SEQUENCE: 51

His Thr Thr Phe Thr Thr Leu Phe Val Asn Asp Val Asn Gln Gly Asp
1               5                   10                  15
```

Gly Thr Cys Ile Arg Met Ala Lys Lys Gly Asn Val Ala Thr His Pro
            20                  25                  30

Leu Ala Gly Gly Leu Asp Ser Glu Asp Met Ala Cys Gly Arg Asp Gly
        35                  40                  45

Gln Glu Pro Val Ala Phe Thr Cys Pro Ala Pro Ala Gly Ala Lys Leu
50                  55                  60

Thr Leu Glu Phe Arg Met Trp Ala Asp Ala Ser Gln Ser Gly Ser Ile
65                  70                  75                  80

Asp Pro Ser His Leu Gly Val Met Ala Ile Tyr Leu Lys Lys Val Ser
                85                  90                  95

Asp Met Lys Ser Asp Ala Ala Ala Gly Pro Gly Trp Phe Lys Ile Trp
            100                 105                 110

Asp Gln Gly Tyr Asp Leu Ala Ala Lys Lys Trp Ala Thr Glu Lys Leu
        115                 120                 125

Ile Asp Asn Asn Gly Leu Leu Ser Val Asn Leu Pro Thr Gly Leu Pro
130                 135                 140

Thr Gly Tyr Tyr Leu Ala Arg Gln Glu Ile Ile Thr Leu Gln Asn Val
145                 150                 155                 160

Thr Asn Asp Arg Pro Glu Pro Gln Phe Tyr Val Gly Cys Ala Gln Leu
                165                 170                 175

Tyr Val Glu Gly Thr Ser Asp Ser Pro Ile Pro Ser Asp Lys Thr Val
            180                 185                 190

Ser Ile Pro Gly His Ile Ser Asp Pro Ala Asp Pro Gly Leu Thr Phe
        195                 200                 205

Asn Val Tyr Thr Gly Asp Ala Ser Thr Tyr Lys Pro Pro Gly Pro Glu
210                 215                 220

Val Tyr Phe Pro Thr Thr Thr Thr Thr Ser Ser Ser Ser Ser Ser Gly
225                 230                 235                 240

Ser Ser Asp Asn Lys Gly Ala Arg Arg Gln Gln Thr Pro Asp Asp Lys
                245                 250                 255

Gln Ala Asp Gly Leu Val Pro Ala Asp Cys Leu Val Lys Asn Ala Asn
            260                 265                 270

Trp Cys Ala Ala Ala Leu Pro Pro Tyr Thr Asp Glu Ala Gly Cys Trp
        275                 280                 285

Ala Ala Ala Glu Asp Cys Asn Lys Gln Leu Asp Ala Cys Tyr Thr Ser
290                 295                 300

Ala Pro Pro Ser Gly Ser Lys Gly Cys Lys Val Trp Glu Glu Gln Val
305                 310                 315                 320

Cys Thr Val Val Ser Gln Lys Cys Glu Ala Gly Asp Phe Lys Gly Pro
                325                 330                 335

Pro Gln Leu Gly Lys Glu Leu Gly Glu Gly Ile Asp Glu Pro Ile Pro
            340                 345                 350

Gly Gly Lys Leu Pro Pro Ala Val Asn Ala Gly Glu Asn Gly Asn His
        355                 360                 365

Gly Gly Gly Gly Asp Asp Asp Asp Asn Asp Glu Ala Gly
370                 375                 380

Ala Gly Ala Ala Ser Thr Pro Thr Phe Ala Ala Pro Gly Ala Ala Lys
385                 390                 395                 400

Thr Pro Gln Pro Asn Ser Glu Arg Ala Arg Arg Glu Ala His Trp
                405                 410                 415

Arg Arg Leu Glu Ser Ala Glu
            420

<210> SEQ ID NO 52
<211> LENGTH: 834
<212> TYPE: DNA
<213> ORGANISM: Myceliophthora thermophila

<400> SEQUENCE: 52

```
atgtttctc tcaagttctt tatcttggcc ggtgggcttg ctgtcctcac cgaggctcac    60
ataagactag tgtcgcccgc ccctttacc aaccctgacc agggcccag cccactccta    120
gaggctggca gcgactatcc ctgccacaac ggcaatgggg gcggttatca gggaacgcca    180
acccagatgg caaagggttc taagcagcag ctagccttcc aggggtctgc cgttcatggg    240
ggtggctcct gccaagtgtc catcacctac gacgaaaacc cgaccgctca gagctccttc    300
aaggtcattc actcgattca aggtggctgc cccgccaggg ccgagacgat cccggattgc    360
agcgcacaaa atatcaacgc ctgcaatata aagcccgata tgcccagat ggacaccccg    420
gataagtatg agttcacgat cccggaggat ctccccagtg gcaaggccac cctcgcctgg    480
acatggatca cactatcgg caaccgcgag ttttatatgg catcgcccc ggttgagatc    540
accggcgacg gcggtagcga gtcggctctg ctgcgctgc ccgacatggt cattgccaac    600
atcccgtcca tcggaggaac ctgcgcgacc gaggagggga agtactacga atatcccaac    660
cccggtaagt cggtcgaaac catcccgggc tggaccgatt tggttcccct gcaaggcgaa    720
tgcggtgctg cctccggtgt ctcgggctcc ggcggaaacg ccagcagtgc taccctgcc    780
gcaggggccg ccccgactcc tgctgtccgc ggccgccgtc ccacctggaa cgcc          834
```

<210> SEQ ID NO 53
<211> LENGTH: 278
<212> TYPE: PRT
<213> ORGANISM: Myceliophthora thermophila

<400> SEQUENCE: 53

```
Met Phe Ser Leu Lys Phe Phe Ile Leu Ala Gly Gly Leu Ala Val Leu
1               5                   10                  15

Thr Glu Ala His Ile Arg Leu Val Ser Pro Ala Pro Phe Thr Asn Pro
            20                  25                  30

Asp Gln Gly Pro Ser Pro Leu Leu Glu Ala Gly Ser Asp Tyr Pro Cys
        35                  40                  45

His Asn Gly Asn Gly Gly Gly Tyr Gln Gly Thr Pro Thr Gln Met Ala
    50                  55                  60

Lys Gly Ser Lys Gln Gln Leu Ala Phe Gln Gly Ser Ala Val His Gly
65                  70                  75                  80

Gly Gly Ser Cys Gln Val Ser Ile Thr Tyr Asp Glu Asn Pro Thr Ala
                85                  90                  95

Gln Ser Ser Phe Lys Val Ile His Ser Ile Gln Gly Gly Cys Pro Ala
            100                 105                 110

Arg Ala Glu Thr Ile Pro Asp Cys Ser Ala Gln Asn Ile Asn Ala Cys
        115                 120                 125

Asn Ile Lys Pro Asp Asn Ala Gln Met Asp Thr Pro Asp Lys Tyr Glu
    130                 135                 140

Phe Thr Ile Pro Glu Asp Leu Pro Ser Gly Lys Ala Thr Leu Ala Trp
145                 150                 155                 160

Thr Trp Ile Asn Thr Ile Gly Asn Arg Glu Phe Tyr Met Ala Cys Ala
                165                 170                 175

Pro Val Glu Ile Thr Gly Asp Gly Gly Ser Glu Ser Ala Leu Ala Ala
            180                 185                 190
```

```
Leu Pro Asp Met Val Ile Ala Asn Ile Pro Ser Ile Gly Gly Thr Cys
            195                 200                 205

Ala Thr Glu Glu Gly Lys Tyr Tyr Glu Tyr Pro Asn Pro Gly Lys Ser
        210                 215                 220

Val Glu Thr Ile Pro Gly Trp Thr Asp Leu Val Pro Leu Gln Gly Glu
225                 230                 235                 240

Cys Gly Ala Ala Ser Gly Val Ser Gly Ser Gly Asn Ala Ser Ser
                245                 250                 255

Ala Thr Pro Ala Ala Gly Ala Ala Pro Thr Pro Ala Val Arg Gly Arg
            260                 265                 270

Arg Pro Thr Trp Asn Ala
            275

<210> SEQ ID NO 54
<211> LENGTH: 259
<212> TYPE: PRT
<213> ORGANISM: Myceliophthora thermophila

<400> SEQUENCE: 54

His Ile Arg Leu Val Ser Pro Ala Pro Phe Thr Asn Pro Asp Gln Gly
1               5                   10                  15

Pro Ser Pro Leu Leu Glu Ala Gly Ser Asp Tyr Pro Cys His Asn Gly
            20                  25                  30

Asn Gly Gly Gly Tyr Gln Gly Thr Pro Thr Gln Met Ala Lys Gly Ser
        35                  40                  45

Lys Gln Gln Leu Ala Phe Gln Gly Ser Ala Val His Gly Gly Gly Ser
    50                  55                  60

Cys Gln Val Ser Ile Thr Tyr Asp Glu Asn Pro Thr Ala Gln Ser Ser
65                  70                  75                  80

Phe Lys Val Ile His Ser Ile Gln Gly Gly Cys Pro Ala Arg Ala Glu
                85                  90                  95

Thr Ile Pro Asp Cys Ser Ala Gln Asn Ile Asn Ala Cys Asn Ile Lys
            100                 105                 110

Pro Asp Asn Ala Gln Met Asp Thr Pro Asp Lys Tyr Glu Phe Thr Ile
        115                 120                 125

Pro Glu Asp Leu Pro Ser Gly Lys Ala Thr Leu Ala Trp Thr Trp Ile
    130                 135                 140

Asn Thr Ile Gly Asn Arg Glu Phe Tyr Met Ala Cys Ala Pro Val Glu
145                 150                 155                 160

Ile Thr Gly Asp Gly Gly Ser Glu Ser Ala Leu Ala Ala Leu Pro Asp
                165                 170                 175

Met Val Ile Ala Asn Ile Pro Ser Ile Gly Gly Thr Cys Ala Thr Glu
            180                 185                 190

Glu Gly Lys Tyr Tyr Glu Tyr Pro Asn Pro Gly Lys Ser Val Glu Thr
        195                 200                 205

Ile Pro Gly Trp Thr Asp Leu Val Pro Leu Gln Gly Glu Cys Gly Ala
    210                 215                 220

Ala Ser Gly Val Ser Gly Ser Gly Asn Ala Ser Ser Ala Thr Pro
225                 230                 235                 240

Ala Ala Gly Ala Ala Pro Thr Pro Ala Val Arg Gly Arg Arg Pro Thr
                245                 250                 255

Trp Asn Ala

<210> SEQ ID NO 55
<211> LENGTH: 672
```

```
<212> TYPE: DNA
<213> ORGANISM: Myceliophthora thermophila

<400> SEQUENCE: 55
atgaagctcg ccacgctcct cgccgccctc accctcgggg tggccgacca gctcagcgtc    60
gggtccagaa agtttggcgt gtacgagcac attcgcaaga acacgaacta caactcgccc   120
gttaccgacc tgtcggacac caacctgcgc tgcaacgtcg gcggggctc gggcaccagc    180
accaccgtgc tcgacgtcaa ggccggagac tcgttcacct tcttcagcga cgttgccgtc   240
taccaccagg ggcccatctc gctgtgcgtg accggaccag tgcagagag catggatgga   300
cgggaaccgg acatgcgctg ccgaactggc tcacaagctg ctacctggc ggtgactgac    360
tacgacgggt ccggtgactg tttcaagatc tatgactggg gaccgacgtt caacggggc    420
caggcgtcgt ggccgacgag gaattcgtac gagtacagca tcctcaagtg catcagggac   480
ggcgaatacc tactgcggat tcagtccctg gccatccata acccaggtgc ccttccgcag   540
ttctacatca gctgcgccca ggtgaatgtg acgggcggag gcaccgtcac cccgagatca   600
aggcgaccga tcctgatcta tttcaacttc cactcgtata tcgtccctgg gccggcagtg   660
ttcaagtgct ag                                                      672

<210> SEQ ID NO 56
<211> LENGTH: 223
<212> TYPE: PRT
<213> ORGANISM: Myceliophthora thermophila

<400> SEQUENCE: 56

Met Lys Leu Ala Thr Leu Leu Ala Ala Leu Thr Leu Gly Val Ala Asp
 1               5                  10                  15

Gln Leu Ser Val Gly Ser Arg Lys Phe Gly Val Tyr Glu His Ile Arg
             20                  25                  30

Lys Asn Thr Asn Tyr Asn Ser Pro Val Thr Asp Leu Ser Asp Thr Asn
         35                  40                  45

Leu Arg Cys Asn Val Gly Gly Ser Gly Thr Ser Thr Val Leu
     50                  55                  60

Asp Val Lys Ala Gly Asp Ser Phe Thr Phe Ser Asp Val Ala Val
 65                  70                  75                  80

Tyr His Gln Gly Pro Ile Ser Leu Cys Val Asp Arg Thr Ser Ala Glu
                 85                  90                  95

Ser Met Asp Gly Arg Glu Pro Asp Met Arg Cys Arg Thr Gly Ser Gln
            100                 105                 110

Ala Gly Tyr Leu Ala Val Thr Asp Tyr Asp Gly Ser Gly Asp Cys Phe
        115                 120                 125

Lys Ile Tyr Asp Trp Gly Pro Thr Phe Asn Gly Gln Ala Ser Trp
    130                 135                 140

Pro Thr Arg Asn Ser Tyr Glu Tyr Ser Ile Leu Lys Cys Ile Arg Asp
145                 150                 155                 160

Gly Glu Tyr Leu Leu Arg Ile Gln Ser Leu Ala Ile His Asn Pro Gly
                165                 170                 175

Ala Leu Pro Gln Phe Tyr Ile Ser Cys Ala Gln Val Asn Val Thr Gly
            180                 185                 190

Gly Gly Thr Val Thr Pro Arg Ser Arg Arg Pro Ile Leu Ile Tyr Phe
        195                 200                 205

Asn Phe His Ser Tyr Ile Val Pro Gly Pro Ala Val Phe Lys Cys
    210                 215                 220
```

<210> SEQ ID NO 57
<211> LENGTH: 208
<212> TYPE: PRT
<213> ORGANISM: Myceliophthora thermophila

<400> SEQUENCE: 57

```
Asp Gln Leu Ser Val Gly Ser Arg Lys Phe Gly Val Tyr Glu His Ile
1               5                   10                  15
Arg Lys Asn Thr Asn Tyr Asn Ser Pro Val Thr Asp Leu Ser Asp Thr
            20                  25                  30
Asn Leu Arg Cys Asn Val Gly Gly Ser Gly Thr Ser Thr Thr Val
        35                  40                  45
Leu Asp Val Lys Ala Gly Asp Ser Phe Thr Phe Phe Ser Asp Val Ala
 50                  55                  60
Val Tyr His Gln Gly Pro Ile Ser Leu Cys Val Asp Arg Thr Ser Ala
 65                  70                  75                  80
Glu Ser Met Asp Gly Arg Glu Pro Asp Met Arg Cys Arg Thr Gly Ser
                85                  90                  95
Gln Ala Gly Tyr Leu Ala Val Thr Asp Tyr Asp Gly Ser Gly Asp Cys
            100                 105                 110
Phe Lys Ile Tyr Asp Trp Gly Pro Thr Phe Asn Gly Gly Gln Ala Ser
        115                 120                 125
Trp Pro Thr Arg Asn Ser Tyr Glu Tyr Ser Ile Leu Lys Cys Ile Arg
130                 135                 140
Asp Gly Glu Tyr Leu Leu Arg Ile Gln Ser Leu Ala Ile His Asn Pro
145                 150                 155                 160
Gly Ala Leu Pro Gln Phe Tyr Ile Ser Cys Ala Gln Val Asn Val Thr
                165                 170                 175
Gly Gly Gly Thr Val Thr Pro Arg Ser Arg Arg Pro Ile Leu Ile Tyr
            180                 185                 190
Phe Asn Phe His Ser Tyr Ile Val Pro Gly Pro Ala Val Phe Lys Cys
        195                 200                 205
```

<210> SEQ ID NO 58
<211> LENGTH: 642
<212> TYPE: DNA
<213> ORGANISM: Myceliophthora thermophila

<400> SEQUENCE: 58

```
atgaagctcg ccacgctcct cgccgccctc accctcgggc tcagcgtcgg gtccagaaag      60
tttggcgtgt acgagcacat tcgcaagaac acgaactaca actcgccgt taccgacctg     120
tcggacacca acctgcgctg caacgtcggc ggggctcgg gcaccagcac caccgtgctc     180
gacgtcaagg ccgagactc gttcaccttc ttcagcgacg ttgccgtcta ccaccagggg     240
cccatctcgc tgtgcgtgga ccggaccagt gcagagagca tggatggacg ggaaccggac     300
atgcgctgcc gaactggctc acaagctggc tacctggcgg tgactgtgat gactgtgact     360
gactacgacg ggtccggtga ctgtttcaag atctatgact ggggaccgac gttcaacggg     420
ggccaggcgt cgtggccgac gaggaattcg tacgagtaca gcatcctcaa gtgcatcagg     480
gacggcgaat acctactgcg gattcagtcc ctggccatcc ataacccagg tgcccttccg     540
cagttctaca tcagctgcgc ccaggtgaat gtgacgggcg aggcaccat ctatttcaac      600
ttccactcgt atatcgtccc tgggccggca gtgttcaagt gc                        642
```

<210> SEQ ID NO 59

```
<211> LENGTH: 214
<212> TYPE: PRT
<213> ORGANISM: Myceliophthora thermophila

<400> SEQUENCE: 59
```

| | | | | | | | | | | | | | | |
|---|---|---|---|---|---|---|---|---|---|---|---|---|---|---|
|Met|Lys|Leu|Ala|Thr|Leu|Leu|Ala|Ala|Leu|Thr|Leu|Gly|Leu|Ser|Val|
|1| | | |5| | | | |10| | | | |15| |

Met Lys Leu Ala Thr Leu Leu Ala Ala Leu Thr Leu Gly Leu Ser Val
1               5                   10                  15

Gly Ser Arg Lys Phe Gly Val Tyr Glu His Ile Arg Lys Asn Thr Asn
            20                  25                  30

Tyr Asn Ser Pro Val Thr Asp Leu Ser Asp Thr Asn Leu Arg Cys Asn
        35                  40                  45

Val Gly Gly Gly Ser Gly Thr Ser Thr Thr Val Leu Asp Val Lys Ala
    50                  55                  60

Gly Asp Ser Phe Thr Phe Phe Ser Asp Val Ala Val Tyr His Gln Gly
65                  70                  75                  80

Pro Ile Ser Leu Cys Val Asp Arg Thr Ser Ala Glu Ser Met Asp Gly
                85                  90                  95

Arg Glu Pro Asp Met Arg Cys Arg Thr Gly Ser Gln Ala Gly Tyr Leu
            100                 105                 110

Ala Val Thr Val Met Thr Val Thr Asp Tyr Asp Gly Ser Gly Asp Cys
        115                 120                 125

Phe Lys Ile Tyr Asp Trp Gly Pro Thr Phe Asn Gly Gly Gln Ala Ser
130                 135                 140

Trp Pro Thr Arg Asn Ser Tyr Glu Tyr Ser Ile Leu Lys Cys Ile Arg
145                 150                 155                 160

Asp Gly Glu Tyr Leu Leu Arg Ile Gln Ser Leu Ala Ile His Asn Pro
                165                 170                 175

Gly Ala Leu Pro Gln Phe Tyr Ile Ser Cys Ala Gln Val Asn Val Thr
            180                 185                 190

Gly Gly Gly Thr Ile Tyr Phe Asn Phe His Ser Tyr Ile Val Pro Gly
        195                 200                 205

Pro Ala Val Phe Lys Cys
        210

```
<210> SEQ ID NO 60
<211> LENGTH: 196
<212> TYPE: PRT
<213> ORGANISM: Myceliophthora thermophila

<400> SEQUENCE: 60
```

Arg Lys Phe Gly Val Tyr Glu His Ile Arg Lys Asn Thr Asn Tyr Asn
1               5                   10                  15

Ser Pro Val Thr Asp Leu Ser Asp Thr Asn Leu Arg Cys Asn Val Gly
            20                  25                  30

Gly Gly Ser Gly Thr Ser Thr Thr Val Leu Asp Val Lys Ala Gly Asp
        35                  40                  45

Ser Phe Thr Phe Phe Ser Asp Val Ala Val Tyr His Gln Gly Pro Ile
    50                  55                  60

Ser Leu Cys Val Asp Arg Thr Ser Ala Glu Ser Met Asp Gly Arg Glu
65                  70                  75                  80

Pro Asp Met Arg Cys Arg Thr Gly Ser Gln Ala Gly Tyr Leu Ala Val
                85                  90                  95

Thr Val Met Thr Val Thr Asp Tyr Asp Gly Ser Gly Asp Cys Phe Lys
            100                 105                 110

Ile Tyr Asp Trp Gly Pro Thr Phe Asn Gly Gly Gln Ala Ser Trp Pro
        115                 120                 125

Thr Arg Asn Ser Tyr Glu Tyr Ser Ile Leu Lys Cys Ile Arg Asp Gly
        130                 135                 140

Glu Tyr Leu Leu Arg Ile Gln Ser Leu Ala Ile His Asn Pro Gly Ala
145                 150                 155                 160

Leu Pro Gln Phe Tyr Ile Ser Cys Ala Gln Val Asn Val Thr Gly Gly
                165                 170                 175

Gly Thr Ile Tyr Phe Asn Phe His Ser Tyr Ile Val Pro Gly Pro Ala
            180                 185                 190

Val Phe Lys Cys
        195

<210> SEQ ID NO 61
<211> LENGTH: 579
<212> TYPE: DNA
<213> ORGANISM: Myceliophthora thermophila

<400> SEQUENCE: 61
atgaccaaga atgcgcagag caagcagggc gttgagaacc caacaagcgg cgacatccgc    60
tgctacacct cgcagacggc ggccaacgtc gtgaccgtgc cggccggctc gaccattcac   120
tacatctcga cccagcagat caaccacccc ggcccgactc agtactacct ggccaaggta   180 cccccccggct cgtcggccaa gacctttgac gggtccggcg ccgtctggtt caagatctcg   240
accacgatgc ctaccgtgga cagcaacaag cagatgttct ggccagggca aaacacttat   300
gagacctcaa acaccaccat tcccgccaac accccggacg gcgagtacct ccttcgcgtc   360
aagcagatcg ccctccacat ggcgtctcag cccaacaagg tccagttcta cctcgcctgc   420
acccagatca agatcaccgg tggtcgcaac ggcacccccca gcccgctggt cgcgctgccc   480
ggagcctaca gagcaccga ccccggcatc ctggtcgaca tctactccat gaagcccgaa   540
tcgtaccagc ctccccgggcc gcccgtctgg cgcggctaa                         579

<210> SEQ ID NO 62
<211> LENGTH: 192
<212> TYPE: PRT
<213> ORGANISM: Myceliophthora thermophila

<400> SEQUENCE: 62

Met Thr Lys Asn Ala Gln Ser Lys Gln Gly Val Glu Asn Pro Thr Ser
1               5                   10                  15

Gly Asp Ile Arg Cys Tyr Thr Ser Gln Thr Ala Ala Asn Val Val Thr
            20                  25                  30

Val Pro Ala Gly Ser Thr Ile His Tyr Ile Ser Thr Gln Gln Ile Asn
        35                  40                  45

His Pro Gly Pro Thr Gln Tyr Tyr Leu Ala Lys Val Pro Pro Gly Ser
    50                  55                  60

Ser Ala Lys Thr Phe Asp Gly Ser Gly Ala Val Trp Phe Lys Ile Ser
65                  70                  75                  80

Thr Thr Met Pro Thr Val Asp Ser Asn Lys Gln Met Phe Trp Pro Gly
                85                  90                  95

Gln Asn Thr Tyr Glu Thr Ser Asn Thr Thr Ile Pro Ala Asn Thr Pro
            100                 105                 110

Asp Gly Glu Tyr Leu Leu Arg Val Lys Gln Ile Ala Leu His Met Ala
        115                 120                 125

Ser Gln Pro Asn Lys Val Gln Phe Tyr Leu Ala Cys Thr Gln Ile Lys
    130                 135                 140

```
Ile Thr Gly Gly Arg Asn Gly Thr Pro Ser Pro Leu Val Ala Leu Pro
145                 150                 155                 160

Gly Ala Tyr Lys Ser Thr Asp Pro Gly Ile Leu Val Asp Ile Tyr Ser
                165                 170                 175

Met Lys Pro Glu Ser Tyr Gln Pro Pro Gly Pro Pro Val Trp Arg Gly
            180                 185                 190

<210> SEQ ID NO 63
<211> LENGTH: 672
<212> TYPE: DNA
<213> ORGANISM: Myceliophthora thermophila

<400> SEQUENCE: 63
atgaggcttc tcgcaagctt gttgctcgca gctacggctg ttcaagctca ctttgttaac    60
ggacagcccg aagagagtga ctggtcagcc acgcgcatga ccaagaatgc gcagagcaag   120
cagggcgttg agaacccaac aagcggcgac atccgctgct acacctcgca gacggcggcc   180
aacgtcgtga ccgtgccggc cggctcgacc attcactaca tctcgaccca gcagatcaac   240
cacccggcc cgactcagta ctacctggcc aaggtacccc ccggctcgtc ggccaagacc   300
tttgacgggt ccgcgccgt ctggttcaag atctcgacca cgatgcctac cgtggacagc   360
aacaagcaga tgttctggcc agggcagaac acttatgaga cctcaaacac caccattccc   420
gccaacaccc cggacggcga gtacctcctt cgcgtcaagc agatcgccct ccacatggcg   480
tctcagccca caaggtcca gttctacctc gcctgcaccc agatcaagat caccggtggt   540
cgcaacggca ccccagccc gctggtcgcg ctgcccggag cctacaagag caccgacccc   600
ggcatcctgg tcgacatcta ctccatgaag cccgaatcgt accagcctcc cgggccgccc   660
gtctggcgcg gc                                                      672

<210> SEQ ID NO 64
<211> LENGTH: 224
<212> TYPE: PRT
<213> ORGANISM: Myceliophthora thermophila

<400> SEQUENCE: 64

Met Arg Leu Leu Ala Ser Leu Leu Leu Ala Ala Thr Ala Val Gln Ala
1               5                   10                  15

His Phe Val Asn Gly Gln Pro Glu Glu Ser Asp Trp Ser Ala Thr Arg
            20                  25                  30

Met Thr Lys Asn Ala Gln Ser Lys Gln Gly Val Glu Asn Pro Thr Ser
        35                  40                  45

Gly Asp Ile Arg Cys Tyr Thr Ser Gln Thr Ala Ala Asn Val Val Thr
    50                  55                  60

Val Pro Ala Gly Ser Thr Ile His Tyr Ile Ser Thr Gln Gln Ile Asn
65                  70                  75                  80

His Pro Gly Pro Thr Gln Tyr Tyr Leu Ala Lys Val Pro Pro Gly Ser
                85                  90                  95

Ser Ala Lys Thr Phe Asp Gly Ser Gly Ala Val Trp Phe Lys Ile Ser
            100                 105                 110

Thr Thr Met Pro Thr Val Asp Ser Asn Lys Gln Met Phe Trp Pro Gly
        115                 120                 125

Gln Asn Thr Tyr Glu Thr Ser Asn Thr Thr Ile Pro Ala Asn Thr Pro
    130                 135                 140

Asp Gly Glu Tyr Leu Leu Arg Val Lys Gln Ile Ala Leu His Met Ala
145                 150                 155                 160
```

Ser Gln Pro Asn Lys Val Gln Phe Tyr Leu Ala Cys Thr Gln Ile Lys
            165                 170                 175

Ile Thr Gly Gly Arg Asn Gly Thr Pro Ser Pro Leu Val Ala Leu Pro
        180                 185                 190

Gly Ala Tyr Lys Ser Thr Asp Pro Gly Ile Leu Val Asp Ile Tyr Ser
    195                 200                 205

Met Lys Pro Glu Ser Tyr Gln Pro Pro Gly Pro Val Trp Arg Gly
210                 215                 220

<210> SEQ ID NO 65
<211> LENGTH: 208
<212> TYPE: PRT
<213> ORGANISM: Myceliophthora thermophila

<400> SEQUENCE: 65

His Phe Val Asn Gly Gln Pro Glu Glu Ser Asp Trp Ser Ala Thr Arg
1               5                   10                  15

Met Thr Lys Asn Ala Gln Ser Lys Gln Gly Val Glu Asn Pro Thr Ser
            20                  25                  30

Gly Asp Ile Arg Cys Tyr Thr Ser Gln Thr Ala Ala Asn Val Val Thr
        35                  40                  45

Val Pro Ala Gly Ser Thr Ile His Tyr Ile Ser Thr Gln Gln Ile Asn
    50                  55                  60

His Pro Gly Pro Thr Gln Tyr Tyr Leu Ala Lys Val Pro Pro Gly Ser
65                  70                  75                  80

Ser Ala Lys Thr Phe Asp Gly Ser Gly Ala Val Trp Phe Lys Ile Ser
                85                  90                  95

Thr Thr Met Pro Thr Val Asp Ser Asn Lys Gln Met Phe Trp Pro Gly
            100                 105                 110

Gln Asn Thr Tyr Glu Thr Ser Asn Thr Thr Ile Pro Ala Asn Thr Pro
        115                 120                 125

Asp Gly Glu Tyr Leu Leu Arg Val Lys Gln Ile Ala Leu His Met Ala
    130                 135                 140

Ser Gln Pro Asn Lys Val Gln Phe Tyr Leu Ala Cys Thr Gln Ile Lys
145                 150                 155                 160

Ile Thr Gly Gly Arg Asn Gly Thr Pro Ser Pro Leu Val Ala Leu Pro
                165                 170                 175

Gly Ala Tyr Lys Ser Thr Asp Pro Gly Ile Leu Val Asp Ile Tyr Ser
            180                 185                 190

Met Lys Pro Glu Ser Tyr Gln Pro Pro Gly Pro Val Trp Arg Gly
        195                 200                 205

<210> SEQ ID NO 66
<211> LENGTH: 849
<212> TYPE: DNA
<213> ORGANISM: Myceliophthora thermophila

<400> SEQUENCE: 66
atgaagccct ttagcctcgt cgccctggcg actgccgtga gcggccatgc catcttccag        60
cgggtgtcgg tcaacgggca ggaccagggc cagctcaagg gggtgcgggc gccgtcgagc       120
aactccccga tccagaacgt caacgatgcc aacatggcct gcaacgccaa cattgtgtac       180
cacgacaaca ccatcatcaa ggtgcccgcg ggagcccgcg tcggcgcgtg gtggcagcac       240
gtcatcggcg gccgcagggg cgccaacgac ccggacaacc cgatcgccgc ctcccacaag       300
ggccccatcc aggtctacct ggccaaggtg acaacgcggg cgacggcgtc gccgtcgggc       360

-continued

```
ctcaagtggt tcaaggtggc cgagcgcggc ctgaacaacg gcgtgtgggc ctacctgatg    420
cgcgtcgagc tgctcgccct gcacagcgcc tcgagcccg gcggcgccca gttctacatg    480
ggctgtgcac agatcgaagt cactggctcc ggcaccaact cgggctccga ctttgtctcg    540
ttccccggcg cctactcggc caacgacccg ggcatcttgc tgagcatcta cgacagctcg    600
ggcaagccca caatggcgg gcgctcgtac ccgatccccg gcccgcgccc catctcctgc    660
tccggcagcg gcggcggcgg caacaacggc ggcgacggcg gcgacgacaa caacggtggt    720
ggcaacaaca acggcggcgg cagcgtcccc ctgtacgggc agtgcggcgg catcggctac    780
acgggcccga ccacctgtgc ccagggaact tgcaaggtgt cgaacgaata ctacagccag    840
tgcctcccc                                                            849
```

<210> SEQ ID NO 67
<211> LENGTH: 283
<212> TYPE: PRT
<213> ORGANISM: Myceliophthora thermophila

<400> SEQUENCE: 67

```
Met Lys Pro Phe Ser Leu Val Ala Leu Ala Thr Ala Val Ser Gly His
1               5                   10                  15

Ala Ile Phe Gln Arg Val Ser Val Asn Gly Gln Asp Gln Gly Gln Leu
            20                  25                  30

Lys Gly Val Arg Ala Pro Ser Ser Asn Ser Pro Ile Gln Asn Val Asn
        35                  40                  45

Asp Ala Asn Met Ala Cys Asn Ala Asn Ile Val Tyr His Asp Asn Thr
    50                  55                  60

Ile Ile Lys Val Pro Ala Gly Ala Arg Val Gly Ala Trp Trp Gln His
65                  70                  75                  80

Val Ile Gly Gly Pro Gln Gly Ala Asn Asp Pro Asp Asn Pro Ile Ala
                85                  90                  95

Ala Ser His Lys Gly Pro Ile Gln Val Tyr Leu Ala Lys Val Asp Asn
            100                 105                 110

Ala Thr Ala Ser Pro Ser Gly Leu Lys Trp Phe Lys Val Ala Glu
        115                 120                 125

Arg Gly Leu Asn Asn Gly Val Trp Ala Tyr Leu Met Arg Val Glu Leu
    130                 135                 140

Leu Ala Leu His Ser Ala Ser Pro Gly Gly Ala Gln Phe Tyr Met
145                 150                 155                 160

Gly Cys Ala Gln Ile Glu Val Thr Gly Ser Gly Thr Asn Ser Gly Ser
                165                 170                 175

Asp Phe Val Ser Phe Pro Gly Ala Tyr Ser Ala Asn Asp Pro Gly Ile
            180                 185                 190

Leu Leu Ser Ile Tyr Asp Ser Ser Gly Lys Pro Asn Gly Gly Arg
        195                 200                 205

Ser Tyr Pro Ile Pro Gly Pro Arg Pro Ile Ser Cys Ser Gly Ser Gly
    210                 215                 220

Gly Gly Gly Asn Asn Gly Gly Asp Gly Gly Asp Asp Asn Asn Gly Gly
225                 230                 235                 240

Gly Asn Asn Asn Gly Gly Ser Val Pro Leu Tyr Gly Gln Cys Gly
                245                 250                 255

Gly Ile Gly Tyr Thr Gly Pro Thr Thr Cys Ala Gln Gly Thr Cys Lys
            260                 265                 270

Val Ser Asn Glu Tyr Tyr Ser Gln Cys Leu Pro
        275                 280
```

<210> SEQ ID NO 68
<211> LENGTH: 268
<212> TYPE: PRT
<213> ORGANISM: Myceliophthora thermophila

<400> SEQUENCE: 68

```
His Ala Ile Phe Gln Arg Val Ser Val Asn Gly Gln Asp Gln Gly Gln
1               5                   10                  15
Leu Lys Gly Val Arg Ala Pro Ser Ser Asn Ser Pro Ile Gln Asn Val
            20                  25                  30
Asn Asp Ala Asn Met Ala Cys Asn Ala Asn Ile Val Tyr His Asp Asn
        35                  40                  45
Thr Ile Ile Lys Val Pro Ala Gly Ala Arg Val Gly Ala Trp Trp Gln
    50                  55                  60
His Val Ile Gly Gly Pro Gln Gly Ala Asn Asp Pro Asp Asn Pro Ile
65                  70                  75                  80
Ala Ala Ser His Lys Gly Pro Ile Gln Val Tyr Leu Ala Lys Val Asp
                85                  90                  95
Asn Ala Ala Thr Ala Ser Pro Ser Gly Leu Lys Trp Phe Lys Val Ala
            100                 105                 110
Glu Arg Gly Leu Asn Asn Gly Val Trp Ala Tyr Leu Met Arg Val Glu
        115                 120                 125
Leu Leu Ala Leu His Ser Ala Ser Ser Pro Gly Gly Ala Gln Phe Tyr
    130                 135                 140
Met Gly Cys Ala Gln Ile Glu Val Thr Gly Ser Gly Thr Asn Ser Gly
145                 150                 155                 160
Ser Asp Phe Val Ser Phe Pro Gly Ala Tyr Ser Ala Asn Asp Pro Gly
                165                 170                 175
Ile Leu Leu Ser Ile Tyr Asp Ser Ser Gly Lys Pro Asn Asn Gly Gly
            180                 185                 190
Arg Ser Tyr Pro Ile Pro Gly Pro Arg Pro Ile Ser Cys Ser Gly Ser
        195                 200                 205
Gly Gly Gly Gly Asn Asn Gly Gly Asp Gly Gly Asp Asp Asn Asn Gly
    210                 215                 220
Gly Gly Asn Asn Asn Gly Gly Gly Ser Val Pro Leu Tyr Gly Gln Cys
225                 230                 235                 240
Gly Gly Ile Gly Tyr Thr Gly Pro Thr Thr Cys Ala Gln Gly Thr Cys
                245                 250                 255
Lys Val Ser Asn Glu Tyr Tyr Ser Gln Cys Leu Pro
            260                 265
```

<210> SEQ ID NO 69
<211> LENGTH: 639
<212> TYPE: DNA
<213> ORGANISM: Myceliophthora thermophila

<400> SEQUENCE: 69

```
atgaagctca cctcgtccct cgctgtcctg ccgctgccg cgcccaggc tcactatacc      60 ttccctaggg ccggcactgg tggttcgctc tctggcgagt gggaggtggt ccgcatgacc     120
gagaaccatt actcgcacgg cccggtcacc gatgtcacca gccccgagat gacctgctat     180
cagtccggcg tgcagggtgc gccccagacc gtccaggtca aggcgggctc ccaattcacc     240
ttcagcgtgg atccctccat cggccacccc ggccctctcc agttctacat ggctaaggtg     300
ccgtcgggcc agacggccgc cacctttgac ggcacgggag ccgtgtggtt caagatctac     360
```

```
caagacggcc cgaacggcct cggcaccgac agcattacct ggcccagcgc cggcaaaacc    420
gaggtctcgg tcaccatccc cagctgcatc gaggatggcg agtacctgct ccgggtcgag    480
cacacccccc tccctacagc gccagcagcg caaaaccgag ctcgctcgtc accatcccca    540
gctgcataca aggccaccga cccgggcatc ctcttccagc tctactggcc catcccgacc    600
gagtacatca accccggccc ggccccgtc tcttgctaa                            639
```

<210> SEQ ID NO 70
<211> LENGTH: 212
<212> TYPE: PRT
<213> ORGANISM: Myceliophthora thermophila

<400> SEQUENCE: 70

```
Met Lys Leu Thr Ser Ser Leu Ala Val Leu Ala Ala Gly Ala Gln
1               5                   10                  15

Ala His Tyr Thr Phe Pro Arg Ala Gly Thr Gly Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
    50                  55                  60

Gln Gly Ala Pro Gln Thr Val Gln Val Lys Ala Gly Ser Gln Phe Thr
65                  70                  75                  80

Phe Ser Val Asp Pro Ser Ile Gly His Pro Gly Pro Leu Gln Phe Tyr
                85                  90                  95

Met Ala Lys Val Pro Ser Gly Gln Thr Ala Ala Thr Phe Asp Gly Thr
            100                 105                 110

Gly Ala Val Trp Phe Lys Ile Tyr Gln Asp Gly Pro Asn Gly Leu Gly
        115                 120                 125

Thr Asp Ser Ile Thr Trp Pro Ser Ala Gly Lys Thr Glu Val Ser Val
130                 135                 140

Thr Ile Pro Ser Cys Ile Glu Asp Gly Glu Tyr Leu Leu Arg Val Glu
145                 150                 155                 160

His Thr Pro Leu Pro Thr Ala Pro Ala Ala Gln Asn Arg Ala Arg Ser
                165                 170                 175

Ser Pro Ser Pro Ala Ala Tyr Lys Ala Thr Asp Pro Gly Ile Leu Phe
            180                 185                 190

Gln Leu Tyr Trp Pro Ile Pro Thr Glu Tyr Ile Asn Pro Gly Pro Ala
        195                 200                 205

Pro Val Ser Cys
    210
```

<210> SEQ ID NO 71
<211> LENGTH: 195
<212> TYPE: PRT
<213> ORGANISM: Myceliophthora thermophila

<400> SEQUENCE: 71

```
His Tyr Thr Phe Pro Arg Ala Gly Thr Gly Gly Ser Leu Ser Gly Glu
1               5                   10                  15

Trp Glu Val Val Arg Met Thr Glu Asn His Tyr Ser His Gly Pro Val
                20                  25                  30

Thr Asp Val Thr Ser Pro Glu Met Thr Cys Tyr Gln Ser Gly Val Gln
            35                  40                  45

Gly Ala Pro Gln Thr Val Gln Val Lys Ala Gly Ser Gln Phe Thr Phe
```

```
                 50                  55                  60
Ser Val Asp Pro Ser Ile Gly His Pro Gly Pro Leu Gln Phe Tyr Met
 65                  70                  75                  80

Ala Lys Val Pro Ser Gly Gln Thr Ala Ala Thr Phe Asp Gly Thr Gly
                 85                  90                  95

Ala Val Trp Phe Lys Ile Tyr Gln Asp Gly Pro Asn Gly Leu Gly Thr
                100                 105                 110

Asp Ser Ile Thr Trp Pro Ser Ala Gly Lys Thr Glu Val Ser Val Thr
                115                 120                 125

Ile Pro Ser Cys Ile Glu Asp Gly Glu Tyr Leu Leu Arg Val Glu His
                130                 135                 140

Thr Pro Leu Pro Thr Ala Pro Ala Ala Gln Asn Arg Ala Arg Ser Ser
145                 150                 155                 160

Pro Ser Pro Ala Ala Tyr Lys Ala Thr Asp Pro Gly Ile Leu Phe Gln
                165                 170                 175

Leu Tyr Trp Pro Ile Pro Thr Glu Tyr Ile Asn Pro Gly Pro Ala Pro
                180                 185                 190

Val Ser Cys
        195

<210> SEQ ID NO 72
<211> LENGTH: 695
<212> TYPE: DNA
<213> ORGANISM: Myceliophthora thermophila

<400> SEQUENCE: 72
atgaagctca cctcgtccct cgctgtcctg gccgctgccg gcgcccaggc tcactatacc      60
ttccctaggg ccggcactgg tggttcgctc tctggcgagt gggaggtggt ccgcatgacc     120
gagaccatta ctcgcacggc ccggtcaccg atgtcaccag ccccgagatg acctgctatc     180
agtccggcgt gcagggtgcg ccccagaccg tccaggtcaa ggcgggctcc caattcacct     240
tcagcgtgga tccctccatc ggccaccccg gccctctcca gttctacatg gctaaggtgc     300
cgtcgggcca gacggccgcc acctttgacg gcacgggagc cgtgtggttc aagatctacc     360
aagacggccc gaacggcctc ggcaccgaca gcattacctg gcccagcgcc ggcaaaaccg     420
aggtctcggt caccatcccc agctgcatcg aggatggcga gtacctgctc cgggtcgagc     480
acatcgcgct ccagagcgcc agcagcgtgg gcggcgccca gttctacatc gcctgcgccc     540
agctctccgt caccggcggc tccggcaccc tcaacacggg ctcgctcgtc ccctgcccg      600 gcgcctacaa ggccaccgac ccgggcatcc tcttccagct ctactggccc atcccgaccg     660
agtacatcaa ccccggcccg gccccgtct cttgc                                 695

<210> SEQ ID NO 73
<211> LENGTH: 232
<212> TYPE: PRT
<213> ORGANISM: Myceliophthora thermophila

<400> SEQUENCE: 73

Met Lys Leu Thr Ser Ser Leu Ala Val Leu Ala Ala Gly Ala Gln
 1               5                  10                  15

Ala His Tyr Thr Phe Pro Arg Ala Gly Thr Gly Gly Ser Leu Ser Gly
                20                  25                  30

Glu Trp Glu Val Val Arg Met Thr Glu Asn His Tyr Ser His Gly Pro
            35                  40                  45

Val Thr Asp Val Thr Ser Pro Glu Met Thr Cys Tyr Gln Ser Gly Val
```

```
                    50                  55                  60
Gln Gly Ala Pro Gln Thr Val Gln Val Lys Ala Gly Ser Gln Phe Thr
 65                  70                  75                  80

Phe Ser Val Asp Pro Ser Ile Gly His Pro Gly Pro Leu Gln Phe Tyr
                     85                  90                  95

Met Ala Lys Val Pro Ser Gly Gln Thr Ala Ala Thr Phe Asp Gly Thr
                    100                 105                 110

Gly Ala Val Trp Phe Lys Ile Tyr Gln Asp Gly Pro Asn Gly Leu Gly
                115                 120                 125

Thr Asp Ser Ile Thr Trp Pro Ser Ala Gly Lys Thr Glu Val Ser Val
130                 135                 140

Thr Ile Pro Ser Cys Ile Glu Asp Gly Glu Tyr Leu Leu Arg Val Glu
145                 150                 155                 160

His Ile Ala Leu His Ser Ala Ser Ser Val Gly Gly Ala Gln Phe Tyr
                165                 170                 175

Ile Ala Cys Ala Gln Leu Ser Val Thr Gly Gly Ser Gly Thr Leu Asn
                180                 185                 190

Thr Gly Ser Leu Val Ser Leu Pro Gly Ala Tyr Lys Ala Thr Asp Pro
                195                 200                 205

Gly Ile Leu Phe Gln Leu Tyr Trp Pro Ile Pro Thr Glu Tyr Ile Asn
                210                 215                 220

Pro Gly Pro Ala Pro Val Ser Cys
225                 230

<210> SEQ ID NO 74
<211> LENGTH: 215
<212> TYPE: PRT
<213> ORGANISM: Myceliophthora thermophila

<400> SEQUENCE: 74

His Tyr Thr Phe Pro Arg Ala Gly Thr Gly Gly Ser Leu Ser Gly Glu
 1               5                  10                  15

Trp Glu Val Val Arg Met Thr Glu Asn His Tyr Ser His Gly Pro Val
                 20                  25                  30

Thr Asp Val Thr Ser Pro Glu Met Thr Cys Tyr Gln Ser Gly Val Gln
             35                  40                  45

Gly Ala Pro Gln Thr Val Gln Val Lys Ala Gly Ser Gln Phe Thr Phe
 50                  55                  60

Ser Val Asp Pro Ser Ile Gly His Pro Gly Pro Leu Gln Phe Tyr Met
 65                  70                  75                  80

Ala Lys Val Pro Ser Gly Gln Thr Ala Ala Thr Phe Asp Gly Thr Gly
                 85                  90                  95

Ala Val Trp Phe Lys Ile Tyr Gln Asp Gly Pro Asn Gly Leu Gly Thr
                100                 105                 110

Asp Ser Ile Thr Trp Pro Ser Ala Gly Lys Thr Glu Val Ser Val Thr
            115                 120                 125

Ile Pro Ser Cys Ile Glu Asp Gly Glu Tyr Leu Leu Arg Val Glu His
130                 135                 140

Ile Ala Leu His Ser Ala Ser Ser Val Gly Gly Ala Gln Phe Tyr Ile
145                 150                 155                 160

Ala Cys Ala Gln Leu Ser Val Thr Gly Gly Ser Gly Thr Leu Asn Thr
                165                 170                 175

Gly Ser Leu Val Ser Leu Pro Gly Ala Tyr Lys Ala Thr Asp Pro Gly
            180                 185                 190
```

Ile Leu Phe Gln Leu Tyr Trp Pro Ile Pro Thr Glu Tyr Ile Asn Pro
        195                 200                 205

Gly Pro Ala Pro Val Ser Cys
    210                 215

<210> SEQ ID NO 75
<211> LENGTH: 447
<212> TYPE: DNA
<213> ORGANISM: Myceliophthora thermophila

<400> SEQUENCE: 75
atgccgccac cacgactgag caccctcctt cccctcctag ccttaatagc ccccaccgcc    60
ctggggcact cccacctcgg gtacatcatc atcaacggcg aggtatacca aggattcgac   120
ccgcggccgg agcaggcgaa ctcgccgttg cgcgtgggct ggtcgacggg ggcaatcgac   180
gacgggttcg tggcgccggc caactactcg tcgcccgaca tcatctgcca catcgagggg   240
gccagcccgc cggcgcacgc gcccgtccgg gcgggcgacc gggtgcacgt gcaatggaac   300
ggctggccgc tcggacacgt ggggccggtg ctgtcgtacc tggcgccctg cggcgggctg   360
gaggggtccg agagcgggtg cgccggggtg gacaagcggc agctgcggtg gaccaaggtg   420
gacgactcgc tgccggcgat ggagctg                                      447

<210> SEQ ID NO 76
<211> LENGTH: 149
<212> TYPE: PRT
<213> ORGANISM: Myceliophthora thermophila

<400> SEQUENCE: 76

Met Pro Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Ile Asn
            20                  25                  30

Gly Glu Val Tyr Gln Gly Phe Asp Pro Arg Pro Glu Gln Ala Asn Ser
        35                  40                  45

Pro Leu Arg Val Gly Trp Ser Thr Gly Ala Ile Asp Asp Gly Phe Val
    50                  55                  60

Ala Pro Ala Asn Tyr Ser Ser Pro Asp Ile Ile Cys His Ile Glu Gly
65                  70                  75                  80

Ala Ser Pro Pro Ala His Ala Pro Val Arg Ala Gly Asp Arg Val His
                85                  90                  95

Val Gln Trp Asn Gly Trp Pro Leu Gly His Val Gly Pro Val Leu Ser
            100                 105                 110

Tyr Leu Ala Pro Cys Gly Gly Leu Glu Gly Ser Glu Ser Gly Cys Ala
        115                 120                 125

Gly Val Asp Lys Arg Gln Leu Arg Trp Thr Lys Val Asp Asp Ser Leu
    130                 135                 140

Pro Ala Met Glu Leu
145

<210> SEQ ID NO 77
<211> LENGTH: 127
<212> TYPE: PRT
<213> ORGANISM: Myceliophthora thermophila

<400> SEQUENCE: 77

His Ser His Leu Gly Tyr Ile Ile Ile Asn Gly Glu Val Tyr Gln Gly
1               5                   10                  15

Phe Asp Pro Arg Pro Glu Gln Ala Asn Ser Pro Leu Arg Val Gly Trp
            20                  25                  30

Ser Thr Gly Ala Ile Asp Asp Gly Phe Val Ala Pro Ala Asn Tyr Ser
        35                  40                  45

Ser Pro Asp Ile Ile Cys His Ile Glu Gly Ala Ser Pro Pro Ala His
    50                  55                  60

Ala Pro Val Arg Ala Gly Asp Arg Val His Val Gln Trp Asn Gly Trp
65                  70                  75                  80

Pro Leu Gly His Val Gly Pro Val Leu Ser Tyr Leu Ala Pro Cys Gly
                85                  90                  95

Gly Leu Glu Gly Ser Glu Ser Gly Cys Ala Gly Val Asp Lys Arg Gln
            100                 105                 110

Leu Arg Trp Thr Lys Val Asp Asp Ser Leu Pro Ala Met Glu Leu
        115                 120                 125

<210> SEQ ID NO 78
<211> LENGTH: 1176
<212> TYPE: DNA
<213> ORGANISM: Myceliophthora thermophila

<400> SEQUENCE: 78
atgccgccac cacgactgag caccctcctt cccctcctag ccttaatagc ccccaccgcc    60
ctggggcact cccacctcgg gtacatcatc atcaacggcg aggtatacca aggattcgac   120
ccgcggccgg agcaggcgaa ctcgccgttg cgcgtgggct ggtcgacggg ggcaatcgac   180
gacgggttcg tggcgccggc caactactcg tcgcccgaca tcatctgcca catcgagggg   240
gccagcccgc cggcgcacgc gcccgtccgg gcgggcgacc gggtgcacgt gcaatggaaa   300
cggctggccg ctcggacacg tggggccggt gctgtcgtac ctggcgccct gcggcgggct   360
ggaggggtcc gagagcgggt ggacgactcg ctgccggcga tggagctggt cggggccgcg   420
gggggcgcgg ggggcgagga cgacggcagc ggcagcgacg gcagcggcag cggcggcagc   480
ggacgcgtcg gcgtgcccgg gcagcgctgg gccaccgacg tgttgatcgc ggccaacaac   540
agctggcagg tcgagatccc gcgcgggctg cgggacgggc gtacgtgct  gcgccacgag   600
atcgtcgcgc tgcactacgc ggccgagccc ggcggcgcgc agaactaccc gctctgcgtc   660
aacctgtggg tcgagggcgg cgacggcagc atggagctgg accacttcga cgccacccag   720
ttctaccggc ccgacgaccc gggcatcctg ctcaacgtga cggccggcct gcgctcatac   780
gccgtgccgg ccccgacgct ggccgcgggg gcgacgccgg tgccgtacgc gcagcagaac   840
atcagctcgg cgagggcgga tggaaccccc gtgattgtca ccaggagcac ggagacggtg   900
cccttcaccg cggcacccac gccagccgag acggcagaag ccaaaggggg gaggtatgat   960
gaccaaaccc gaactaaaga cctaaatgaa cgcttctttt atagtagccg ccagaacag   1020
aagaggctga cagcgacctc aagaagggaa ctagttgatc atcgtacccg gtacctctcc   1080
gtagctgtct gcgcagattt cggcgctcat aaggcagcag aaaccaacca cgaagctttg   1140
agaggcggca ataagcacca tggcggtgtt tcagag                            1176

<210> SEQ ID NO 79
<211> LENGTH: 392
<212> TYPE: PRT
<213> ORGANISM: Myceliophthora thermophila

<400> SEQUENCE: 79

Met Pro Pro Pro Arg Leu Ser Thr Leu Leu Pro Leu Leu Ala Leu Ile
1               5                   10                  15

Ala Pro Thr Ala Leu Gly His Ser His Leu Gly Tyr Ile Ile Ile Asn
            20                  25                  30

Gly Glu Val Tyr Gln Gly Phe Asp Pro Arg Pro Glu Gln Ala Asn Ser
        35                  40                  45

Pro Leu Arg Val Gly Trp Ser Thr Gly Ala Ile Asp Asp Gly Phe Val
 50                  55                  60

Ala Pro Ala Asn Tyr Ser Ser Pro Asp Ile Ile Cys His Ile Glu Gly
 65                  70                  75                  80

Ala Ser Pro Pro Ala His Ala Pro Val Arg Ala Gly Asp Arg Val His
                 85                  90                  95

Val Gln Trp Lys Arg Leu Ala Ala Arg Thr Arg Gly Ala Gly Ala Val
            100                 105                 110

Val Pro Gly Ala Leu Arg Arg Ala Gly Val Arg Glu Arg Val Asp
            115                 120                 125

Asp Ser Leu Pro Ala Met Glu Leu Val Gly Ala Gly Gly Ala Gly
 130                 135                 140

Gly Glu Asp Asp Gly Ser Gly Ser Asp Gly Ser Gly Ser Gly Gly Ser
145                 150                 155                 160

Gly Arg Val Gly Val Pro Gly Gln Arg Trp Ala Thr Asp Val Leu Ile
                165                 170                 175

Ala Ala Asn Asn Ser Trp Gln Val Glu Ile Pro Arg Gly Leu Arg Asp
            180                 185                 190

Gly Pro Tyr Val Leu Arg His Glu Ile Val Ala Leu His Tyr Ala Ala
        195                 200                 205

Glu Pro Gly Gly Ala Gln Asn Tyr Pro Leu Cys Val Asn Leu Trp Val
210                 215                 220

Glu Gly Gly Asp Gly Ser Met Glu Leu Asp His Phe Asp Ala Thr Gln
225                 230                 235                 240

Phe Tyr Arg Pro Asp Asp Pro Gly Ile Leu Leu Asn Val Thr Ala Gly
            245                 250                 255

Leu Arg Ser Tyr Ala Val Pro Gly Pro Thr Leu Ala Ala Gly Ala Thr
            260                 265                 270

Pro Val Pro Tyr Ala Gln Gln Asn Ile Ser Ser Ala Arg Ala Asp Gly
            275                 280                 285

Thr Pro Val Ile Val Thr Arg Ser Thr Glu Thr Val Pro Phe Thr Ala
 290                 295                 300

Ala Pro Thr Pro Ala Glu Thr Ala Glu Ala Lys Gly Gly Arg Tyr Asp
305                 310                 315                 320

Asp Gln Thr Arg Thr Lys Asp Leu Asn Glu Arg Phe Phe Tyr Ser Ser
            325                 330                 335

Arg Pro Glu Gln Lys Arg Leu Thr Ala Thr Ser Arg Arg Glu Leu Val
            340                 345                 350

Asp His Arg Thr Arg Tyr Leu Ser Val Ala Val Cys Ala Asp Phe Gly
            355                 360                 365

Ala His Lys Ala Ala Glu Thr Asn His Glu Ala Leu Arg Gly Gly Asn
 370                 375                 380

Lys His His Gly Gly Val Ser Glu
385                 390

<210> SEQ ID NO 80
<211> LENGTH: 370
<212> TYPE: PRT
<213> ORGANISM: Myceliophthora thermophila

<400> SEQUENCE: 80

```
His Ser His Leu Gly Tyr Ile Ile Asn Gly Glu Val Tyr Gln Gly
1               5                   10                  15

Phe Asp Pro Arg Pro Glu Gln Ala Asn Ser Pro Leu Arg Val Gly Trp
            20                  25                  30

Ser Thr Gly Ala Ile Asp Asp Gly Phe Val Ala Pro Ala Asn Tyr Ser
        35                  40                  45

Ser Pro Asp Ile Ile Cys His Ile Glu Gly Ala Ser Pro Pro Ala His
50                  55                  60

Ala Pro Val Arg Ala Gly Asp Arg Val His Val Gln Trp Lys Arg Leu
65                  70                  75                  80

Ala Ala Arg Thr Arg Gly Ala Gly Ala Val Val Pro Gly Ala Leu Arg
                85                  90                  95

Arg Ala Gly Gly Val Arg Glu Arg Val Asp Asp Ser Leu Pro Ala Met
            100                 105                 110

Glu Leu Val Gly Ala Ala Gly Ala Gly Gly Glu Asp Asp Gly Ser
        115                 120                 125

Gly Ser Asp Gly Ser Gly Ser Gly Gly Ser Gly Arg Val Gly Val Pro
130                 135                 140

Gly Gln Arg Trp Ala Thr Asp Val Leu Ile Ala Ala Asn Asn Ser Trp
145                 150                 155                 160

Gln Val Glu Ile Pro Arg Gly Leu Arg Asp Gly Pro Tyr Val Leu Arg
                165                 170                 175

His Glu Ile Val Ala Leu His Tyr Ala Ala Glu Pro Gly Gly Ala Gln
            180                 185                 190

Asn Tyr Pro Leu Cys Val Asn Leu Trp Val Glu Gly Gly Asp Gly Ser
        195                 200                 205

Met Glu Leu Asp His Phe Asp Ala Thr Gln Phe Tyr Arg Pro Asp Asp
210                 215                 220

Pro Gly Ile Leu Leu Asn Val Thr Ala Gly Leu Arg Ser Tyr Ala Val
225                 230                 235                 240

Pro Gly Pro Thr Leu Ala Ala Gly Ala Thr Pro Val Pro Tyr Ala Gln
                245                 250                 255

Gln Asn Ile Ser Ser Ala Arg Ala Asp Gly Thr Pro Val Ile Val Thr
            260                 265                 270

Arg Ser Thr Glu Thr Val Pro Phe Thr Ala Ala Pro Thr Pro Ala Glu
        275                 280                 285

Thr Ala Glu Ala Lys Gly Gly Arg Tyr Asp Asp Gln Thr Arg Thr Lys
290                 295                 300

Asp Leu Asn Glu Arg Phe Phe Tyr Ser Ser Arg Pro Glu Gln Lys Arg
305                 310                 315                 320

Leu Thr Ala Thr Ser Arg Arg Glu Leu Val Asp His Arg Thr Arg Tyr
                325                 330                 335

Leu Ser Val Ala Val Cys Ala Asp Phe Gly Ala His Lys Ala Ala Glu
            340                 345                 350

Thr Asn His Glu Ala Leu Arg Gly Gly Asn Lys His His Gly Gly Val
        355                 360                 365

Ser Glu
    370
```

<210> SEQ ID NO 81
<211> LENGTH: 453
<212> TYPE: DNA
<213> ORGANISM: Myceliophthora thermophila

<400> SEQUENCE: 81

```
atgaggtcga cattggccgg tgccctggca gccatcgctg ctcagaaagt agccggccac    60
gccacgtttc agcagctctg gcacggctcc tcctgtgtcc gccttccggc tagcaactca   120
cccgtcacca atgtgggaag cagagacttc gtctgcaacg ctggcacccg ccccgtcagt   180
ggcaagtgcc ccgtgaaggc tggcggcacc gtcaccatcg agatgcacca gcaacccggc   240
gaccgcagct gcaacaacga agccatcgga ggggcgcatt ggggcccgt ccaggtgtac    300
ctgaccaagg ttcaggacgc cgcgacggcc gacggctcga cgggctggtt caagatcttc   360
tccgactcgt ggtccaagaa gcccgggggc aacttgggcg acgacgacaa ctggggcacg   420
cgcgacctga acgcctgctg cgggaagatg gac                                453
```

<210> SEQ ID NO 82
<211> LENGTH: 151
<212> TYPE: PRT
<213> ORGANISM: Myceliophthora thermophila

<400> SEQUENCE: 82

```
Met Arg Ser Thr Leu Ala Gly Ala Leu Ala Ala Ile Ala Ala Gln Lys
1               5                   10                  15
Val Ala Gly His Ala Thr Phe Gln Gln Leu Trp His Gly Ser Ser Cys
                20                  25                  30
Val Arg Leu Pro Ala Ser Asn Ser Pro Val Thr Asn Val Gly Ser Arg
            35                  40                  45
Asp Phe Val Cys Asn Ala Gly Thr Arg Pro Val Ser Gly Lys Cys Pro
        50                  55                  60
Val Lys Ala Gly Gly Thr Val Thr Ile Glu Met His Gln Gln Pro Gly
65                  70                  75                  80
Asp Arg Ser Cys Asn Asn Glu Ala Ile Gly Gly Ala His Trp Gly Pro
                85                  90                  95
Val Gln Val Tyr Leu Thr Lys Val Gln Asp Ala Ala Thr Ala Asp Gly
            100                 105                 110
Ser Thr Gly Trp Phe Lys Ile Phe Ser Asp Ser Trp Ser Lys Lys Pro
        115                 120                 125
Gly Gly Asn Leu Gly Asp Asp Asp Asn Trp Gly Thr Arg Asp Leu Asn
    130                 135                 140
Ala Cys Cys Gly Lys Met Asp
145                 150
```

<210> SEQ ID NO 83
<211> LENGTH: 132
<212> TYPE: PRT
<213> ORGANISM: Myceliophthora thermophila

<400> SEQUENCE: 83

```
His Ala Thr Phe Gln Gln Leu Trp His Gly Ser Ser Cys Val Arg Leu
1               5                   10                  15
Pro Ala Ser Asn Ser Pro Val Thr Asn Val Gly Ser Arg Asp Phe Val
                20                  25                  30
Cys Asn Ala Gly Thr Arg Pro Val Ser Gly Lys Cys Pro Val Lys Ala
            35                  40                  45
Gly Gly Thr Val Thr Ile Glu Met His Gln Gln Pro Gly Asp Arg Ser
        50                  55                  60
Cys Asn Asn Glu Ala Ile Gly Gly Ala His Trp Gly Pro Val Gln Val
65                  70                  75                  80
```

Tyr Leu Thr Lys Val Gln Asp Ala Ala Thr Ala Asp Gly Ser Thr Gly
            85                  90                  95

Trp Phe Lys Ile Phe Ser Asp Ser Trp Ser Lys Lys Pro Gly Gly Asn
            100                 105                 110

Leu Gly Asp Asp Asn Trp Gly Thr Arg Asp Leu Asn Ala Cys Cys
            115                 120                 125

Gly Lys Met Asp
        130

<210> SEQ ID NO 84
<211> LENGTH: 837
<212> TYPE: DNA
<213> ORGANISM: Myceliophthora thermophila

<400> SEQUENCE: 84

```
atgaggtcga cattggccgg tgccctggca gccatcgctg ctcagaaagt agccggccac      60
gccacgtttc agcagctctg gcacggctcc tcctgtgtcc gccttccggc tagcaactca     120
cccgtcacca atgtgggaag cagagacttc gtctgcaacg ctggcacccg ccccgtcagt     180
ggcaagtgcc ccgtgaaggc tggcggcacc gtcaccatcg agatgcacca gcaacccggc     240
gaccgcagct gcaacaacga agccatcgga ggggcgcatt ggggccccgt ccaggtgtac     300
ctgaccaagg ttcaggacgc cgcgacggcc gacggctcga cgggctggtt caagatcttc     360
tccgactcgt ggtccaagaa gcccgggggc aactcgggcg acgacgacaa ctggggcacg     420
cgcgacctga acgcctgctg cgggaagatg gacgtggcca tcccggccga catcgcgtcg     480
ggcgactacc tgctgcgggc cgaggcgctg gccctgcaca cggccggaca ggccggcggc     540
gcccagttct acatgagctg ctaccagatg acggtcgagg cggctccgg accgccaac     600
ccgcccaccg tcaagttccc gggcgcctac agcgccaaca cccgggcat cctcgtcaac     660
atccacgccc cccttttccag ctacaccgcg cccggcccgg ccgtctacgc gggcggcacc     720
atccgcgagg ccggctccgc ctgcaccggc tgcgcgcaga cctgcaaggt cgggtcgtcc     780
ccgagcgccg ttgccccccgg cagcggcgcg ggcaacggcg cgggttcca accccga       837
```

<210> SEQ ID NO 85
<211> LENGTH: 279
<212> TYPE: PRT
<213> ORGANISM: Myceliophthora thermophila

<400> SEQUENCE: 85

Met Arg Ser Thr Leu Ala Gly Ala Leu Ala Ala Ile Ala Ala Gln Lys
1               5                   10                  15

Val Ala Gly His Ala Thr Phe Gln Gln Leu Trp His Gly Ser Ser Cys
            20                  25                  30

Val Arg Leu Pro Ala Ser Asn Ser Pro Val Thr Asn Val Gly Ser Arg
        35                  40                  45

Asp Phe Val Cys Asn Ala Gly Thr Arg Pro Val Ser Gly Lys Cys Pro
    50                  55                  60

Val Lys Ala Gly Gly Thr Val Thr Ile Glu Met His Gln Gln Pro Gly
65                  70                  75                  80

Asp Arg Ser Cys Asn Asn Glu Ala Ile Gly Gly Ala His Trp Gly Pro
            85                  90                  95

Val Gln Val Tyr Leu Thr Lys Val Gln Asp Ala Ala Thr Ala Asp Gly
            100                 105                 110

Ser Thr Gly Trp Phe Lys Ile Phe Ser Asp Ser Trp Ser Lys Lys Pro

```
            115                 120                 125
Gly Gly Asn Ser Gly Asp Asp Asn Trp Gly Thr Arg Asp Leu Asn
    130                 135                 140

Ala Cys Cys Gly Lys Met Asp Val Ala Ile Pro Ala Asp Ile Ala Ser
145                 150                 155                 160

Gly Asp Tyr Leu Leu Arg Ala Glu Ala Leu Ala Leu His Thr Ala Gly
                165                 170                 175

Gln Ala Gly Gly Ala Gln Phe Tyr Met Ser Cys Tyr Gln Met Thr Val
            180                 185                 190

Glu Gly Gly Ser Gly Thr Ala Asn Pro Pro Thr Val Lys Phe Pro Gly
                195                 200                 205

Ala Tyr Ser Ala Asn Asp Pro Gly Ile Leu Val Asn Ile His Ala Pro
            210                 215                 220

Leu Ser Ser Tyr Thr Ala Pro Gly Pro Ala Val Tyr Ala Gly Gly Thr
225                 230                 235                 240

Ile Arg Glu Ala Gly Ser Ala Cys Thr Gly Cys Ala Gln Thr Cys Lys
                245                 250                 255

Val Gly Ser Ser Pro Ser Ala Val Ala Pro Gly Ser Gly Ala Gly Asn
            260                 265                 270

Gly Gly Gly Phe Gln Pro Arg
            275

<210> SEQ ID NO 86
<211> LENGTH: 260
<212> TYPE: PRT
<213> ORGANISM: Myceliophthora thermophila

<400> SEQUENCE: 86

His Ala Thr Phe Gln Gln Leu Trp His Gly Ser Ser Cys Val Arg Leu
1               5                   10                  15

Pro Ala Ser Asn Ser Pro Val Thr Asn Val Gly Ser Arg Asp Phe Val
            20                  25                  30

Cys Asn Ala Gly Thr Arg Pro Val Ser Gly Lys Cys Pro Val Lys Ala
        35                  40                  45

Gly Gly Thr Val Thr Ile Glu Met His Gln Gln Pro Gly Asp Arg Ser
    50                  55                  60

Cys Asn Asn Glu Ala Ile Gly Gly Ala His Trp Gly Pro Val Gln Val
65                  70                  75                  80

Tyr Leu Thr Lys Val Gln Asp Ala Ala Thr Ala Asp Gly Ser Thr Gly
                85                  90                  95

Trp Phe Lys Ile Phe Ser Asp Ser Trp Ser Lys Pro Gly Gly Asn
            100                 105                 110

Ser Gly Asp Asp Asp Asn Trp Gly Thr Arg Asp Leu Asn Ala Cys Cys
            115                 120                 125

Gly Lys Met Asp Val Ala Ile Pro Ala Asp Ile Ala Ser Gly Asp Tyr
    130                 135                 140

Leu Leu Arg Ala Glu Ala Leu Ala Leu His Thr Ala Gly Gln Ala Gly
145                 150                 155                 160

Gly Ala Gln Phe Tyr Met Ser Cys Tyr Gln Met Thr Val Glu Gly Gly
                165                 170                 175

Ser Gly Thr Ala Asn Pro Pro Thr Val Lys Phe Pro Gly Ala Tyr Ser
            180                 185                 190

Ala Asn Asp Pro Gly Ile Leu Val Asn Ile His Ala Pro Leu Ser Ser
        195                 200                 205
```

Tyr Thr Ala Pro Gly Pro Ala Val Tyr Ala Gly Gly Thr Ile Arg Glu
210                 215                 220

Ala Gly Ser Ala Cys Thr Gly Cys Ala Gln Thr Cys Lys Val Gly Ser
225                 230                 235                 240

Ser Pro Ser Ala Val Ala Pro Gly Ser Gly Ala Gly Asn Gly Gly Gly
            245                 250                 255

Phe Gln Pro Arg
            260

<210> SEQ ID NO 87
<211> LENGTH: 735
<212> TYPE: DNA
<213> ORGANISM: Myceliophthora thermophila

<400> SEQUENCE: 87
atgctcctcc tcaccctagc cacactcgtc accctcctgg cgcgccacgt ctcggctcac      60
gcccggctgt tccgcgtctc tgtcgacggg aaagaccagg gcgacgggct gaacaagtac     120
atccgctcgc cggcgaccaa cgaccccgtg cgcgacctct cgagcgccgc catcgtgtgc     180
aacacccagg ggtccaaggc cgccccggac ttcgtcaggg ccgcggccgg cgacaagctg     240
accttcctct gggcgcacga caacccggac gacccggtcg actacgtcct cgacccgtcc     300
cacaagggcg ccatcctgac ctacgtcgcc gcctacccct ccggggaccc gaccggcccc     360
atctggagca agcttgccga ggaaggattc accggcgggc agtgggcgac catcaagatg     420
atcgacaacg gcggcaaggt cgacgtgacg ctgcccgagg cccttgcgcc gggaaagtac     480
ctgatccgcc aggagctgct ggccctgcac cgggccgact tgcctgcga cgaccccggcc     540 caccccaacc gcggcgccga gtcgtacccc aactgcgtcc aggtggaggt gtcgggcagc     600
ggcgacaaga agccggacca gaactttgac ttcaacaagg gctatacctg cgataacaaa     660
ggactccact ttaagatcta catcggtcag gacagccagt atgtggcccc ggggccgcgg     720
ccttggaatg ggagc                                                      735

<210> SEQ ID NO 88
<211> LENGTH: 245
<212> TYPE: PRT
<213> ORGANISM: Myceliophthora thermophila

<400> SEQUENCE: 88

Met Leu Leu Leu Thr Leu Ala Thr Leu Val Thr Leu Leu Ala Arg His
1               5                   10                  15

Val Ser Ala His Ala Arg Leu Phe Arg Val Ser Val Asp Gly Lys Asp
            20                  25                  30

Gln Gly Asp Gly Leu Asn Lys Tyr Ile Arg Ser Pro Ala Thr Asn Asp
        35                  40                  45

Pro Val Arg Asp Leu Ser Ser Ala Ile Val Cys Asn Thr Gln Gly
    50                  55                  60

Ser Lys Ala Ala Pro Asp Phe Val Arg Ala Ala Gly Asp Lys Leu
65                  70                  75                  80

Thr Phe Leu Trp Ala His Asp Asn Pro Asp Pro Val Asp Tyr Val
                85                  90                  95

Leu Asp Pro Ser His Lys Gly Ala Ile Leu Thr Tyr Val Ala Ala Tyr
            100                 105                 110

Pro Ser Gly Asp Pro Thr Gly Pro Ile Trp Ser Lys Leu Ala Glu Glu
        115                 120                 125

Gly Phe Thr Gly Gly Gln Trp Ala Thr Ile Lys Met Ile Asp Asn Gly

```
                130              135              140
Gly Lys Val Asp Val Thr Leu Pro Glu Ala Leu Ala Pro Gly Lys Tyr
145                 150                 155                 160

Leu Ile Arg Gln Glu Leu Leu Ala Leu His Arg Ala Asp Phe Ala Cys
                165                 170                 175

Asp Asp Pro Ala His Pro Asn Arg Gly Ala Glu Ser Tyr Pro Asn Cys
                180                 185                 190

Val Gln Val Glu Val Ser Gly Ser Gly Asp Lys Lys Pro Asp Gln Asn
                195                 200                 205

Phe Asp Phe Asn Lys Gly Tyr Thr Cys Asp Asn Lys Gly Leu His Phe
                210                 215                 220

Lys Ile Tyr Ile Gly Gln Asp Ser Gln Tyr Val Ala Pro Gly Pro Arg
225                 230                 235                 240

Pro Trp Asn Gly Ser
                245

<210> SEQ ID NO 89
<211> LENGTH: 226
<212> TYPE: PRT
<213> ORGANISM: Myceliophthora thermophila

<400> SEQUENCE: 89

His Ala Arg Leu Phe Arg Val Ser Val Asp Gly Lys Asp Gln Gly Asp
1               5                   10                  15

Gly Leu Asn Lys Tyr Ile Arg Ser Pro Ala Thr Asn Asp Pro Val Arg
                20                  25                  30

Asp Leu Ser Ser Ala Ala Ile Val Cys Asn Thr Gln Gly Ser Lys Ala
                35                  40                  45

Ala Pro Asp Phe Val Arg Ala Ala Gly Asp Lys Leu Thr Phe Leu
                50                  55                  60

Trp Ala His Asp Asn Pro Asp Asp Pro Val Asp Tyr Val Leu Asp Pro
65                  70                  75                  80

Ser His Lys Gly Ala Ile Leu Thr Tyr Val Ala Ala Tyr Pro Ser Gly
                85                  90                  95

Asp Pro Thr Gly Pro Ile Trp Ser Lys Leu Ala Glu Glu Gly Phe Thr
                100                 105                 110

Gly Gly Gln Trp Ala Thr Ile Lys Met Ile Asp Asn Gly Gly Lys Val
                115                 120                 125

Asp Val Thr Leu Pro Glu Ala Leu Ala Pro Gly Lys Tyr Leu Ile Arg
                130                 135                 140

Gln Glu Leu Leu Ala Leu His Arg Ala Asp Phe Ala Cys Asp Asp Pro
145                 150                 155                 160

Ala His Pro Asn Arg Gly Ala Glu Ser Tyr Pro Asn Cys Val Gln Val
                165                 170                 175

Glu Val Ser Gly Ser Gly Asp Lys Lys Pro Asp Gln Asn Phe Asp Phe
                180                 185                 190

Asn Lys Gly Tyr Thr Cys Asp Asn Lys Gly Leu His Phe Lys Ile Tyr
                195                 200                 205

Ile Gly Gln Asp Ser Gln Tyr Val Ala Pro Gly Pro Arg Pro Trp Asn
                210                 215                 220

Gly Ser
225

<210> SEQ ID NO 90
<211> LENGTH: 600
```

<212> TYPE: DNA
<213> ORGANISM: Myceliophthora thermophila

<400> SEQUENCE: 90

```
atgttcactt cgctttgcat cacagatcat tggaggactc ttagcagcca ctctgggcca      60
gtcatgaact atctcgccca ttgcaccaat gacgactgca agtctttcaa gggcgacagc     120
ggcaacgtct gggtcaagat cgagcagctc gcgtacaacc cgtcagccaa ccccccctgg     180
gcgtctgacc tcctccgtga gcacggtgcc aagtggaagg tgacgatccc gcccagtctt     240
gtccccggcg aatatctgct gcggcacgag atcctggggt tgcacgtcgc aggaaccgtg     300
atgggcgccc agttctaccc cggctgcacc cagatcaggg tcaccgaagg cgggagcacg     360
cagctgccct cgggtattgc gctcccaggc gcttacggcc acaagacga gggtatcttg      420
gtcgacttgt ggagggttaa ccagggccag gtcaactaca cggcgcctgg aggacccgtt     480
tggagcgaag cgtgggacac cgagtttggc gggtccaaca cgaccgagtg cgccaccatg     540
ctcgacgacc tgctcgacta catggcggcc aacgacgagt ggatcggctg gacggcctag     600
```

<210> SEQ ID NO 91
<211> LENGTH: 199
<212> TYPE: PRT
<213> ORGANISM: Myceliophthora thermophila

<400> SEQUENCE: 91

```
Met Phe Thr Ser Leu Cys Ile Thr Asp His Trp Arg Thr Leu Ser Ser
1               5                   10                  15

His Ser Gly Pro Val Met Asn Tyr Leu Ala His Cys Thr Asn Asp Asp
            20                  25                  30

Cys Lys Ser Phe Lys Gly Asp Ser Gly Asn Val Trp Val Lys Ile Glu
        35                  40                  45

Gln Leu Ala Tyr Asn Pro Ser Ala Asn Pro Pro Trp Ala Ser Asp Leu
    50                  55                  60

Leu Arg Glu His Gly Ala Lys Trp Lys Val Thr Ile Pro Pro Ser Leu
65                  70                  75                  80

Val Pro Gly Glu Tyr Leu Leu Arg His Glu Ile Leu Gly Leu His Val
                85                  90                  95

Ala Gly Thr Val Met Gly Ala Gln Phe Tyr Pro Gly Cys Thr Gln Ile
            100                 105                 110

Arg Val Thr Glu Gly Gly Ser Thr Gln Leu Pro Ser Gly Ile Ala Leu
        115                 120                 125

Pro Gly Ala Tyr Gly Pro Gln Asp Glu Gly Ile Leu Val Asp Leu Trp
    130                 135                 140

Arg Val Asn Gln Gly Gln Val Asn Tyr Thr Ala Pro Gly Gly Pro Val
145                 150                 155                 160

Trp Ser Glu Ala Trp Asp Thr Glu Phe Gly Gly Ser Asn Thr Thr Glu
                165                 170                 175

Cys Ala Thr Met Leu Asp Asp Leu Leu Asp Tyr Met Ala Ala Asn Asp
            180                 185                 190

Glu Trp Ile Gly Trp Thr Ala
        195
```

<210> SEQ ID NO 92
<211> LENGTH: 693
<212> TYPE: DNA
<213> ORGANISM: Myceliophthora thermophila

<400> SEQUENCE: 92

```
atgaactatc tcgcccattg caccaatgac gactgcaagt ctttcaaggg cgacagcggc      60
aacgtctggg tcaagatcga gcagctcgcg tacaacccgt cagccaaccc ccctgggcg     120 tctgacctcc tccgtgagca cggtgccaag tggaaggtga cgatcccgcc cagtcttgtc     180
cccggcgaat atctgctgcg gcacgagatc ctggggttgc acgtcgcagg aaccgtgatg     240
ggcgcccagt tctaccccgg ctgcacccag atcagggtca ccgaaggcgg gagcacgcag     300
ctgccctcgg gtattgcgct cccaggcgct tacggcccac aagacgaggg tatcttggtc     360
gacttgtgga gggttaacca gggccaggtc aactacacgg cgcctggagg acccgtttgg     420
agcgaagcgt gggacaccga gtttggcggg tccaacacga ccgagtgcgc caccatgctc     480
gacgacctgc tcgactacat ggcggccaac gacgacccat gctgcaccga ccagaaccag     540 ttcggggagtc tcgagccggg gagcaaggcg gccggcggct cgccgagcct gtacgatacc     600
gtcttggtcc ccgttctcca gaagaaagtg ccgacaaagc tgcagtggag cggaccggcg     660
agcgtcaacg gggatgagtt gacagagagg ccc                                  693
```

<210> SEQ ID NO 93
<211> LENGTH: 231
<212> TYPE: PRT
<213> ORGANISM: Myceliophthora thermophila

<400> SEQUENCE: 93

```
Met Asn Tyr Leu Ala His Cys Thr Asn Asp Asp Cys Lys Ser Phe Lys
1               5                   10                  15

Gly Asp Ser Gly Asn Val Trp Val Lys Ile Glu Gln Leu Ala Tyr Asn
            20                  25                  30

Pro Ser Ala Asn Pro Pro Trp Ala Ser Asp Leu Leu Arg Glu His Gly
        35                  40                  45

Ala Lys Trp Lys Val Thr Ile Pro Pro Ser Leu Val Pro Gly Glu Tyr
    50                  55                  60

Leu Leu Arg His Glu Ile Leu Gly Leu His Val Ala Gly Thr Val Met
65                  70                  75                  80

Gly Ala Gln Phe Tyr Pro Gly Cys Thr Gln Ile Arg Val Thr Glu Gly
                85                  90                  95

Gly Ser Thr Gln Leu Pro Ser Gly Ile Ala Leu Pro Gly Ala Tyr Gly
            100                 105                 110

Pro Gln Asp Glu Gly Ile Leu Val Asp Leu Trp Arg Val Asn Gln Gly
        115                 120                 125

Gln Val Asn Tyr Thr Ala Pro Gly Gly Pro Val Trp Ser Glu Ala Trp
    130                 135                 140

Asp Thr Glu Phe Gly Gly Ser Asn Thr Thr Glu Cys Ala Thr Met Leu
145                 150                 155                 160

Asp Asp Leu Leu Asp Tyr Met Ala Ala Asn Asp Asp Pro Cys Cys Thr
                165                 170                 175

Asp Gln Asn Gln Phe Gly Ser Leu Glu Pro Gly Ser Lys Ala Ala Gly
            180                 185                 190

Gly Ser Pro Ser Leu Tyr Asp Thr Val Leu Val Pro Val Leu Gln Lys
        195                 200                 205

Lys Val Pro Thr Lys Leu Gln Trp Ser Gly Pro Ala Ser Val Asn Gly
    210                 215                 220

Asp Glu Leu Thr Glu Arg Pro
225                 230
```

<210> SEQ ID NO 94
<211> LENGTH: 681
<212> TYPE: DNA
<213> ORGANISM: Myceliophthora thermophila

<400> SEQUENCE: 94

```
atgaagctga cgctgccat cgccgtgctc gcggccgccc ttgccgaggg gcactatacc      60
ttccccagca tcgccaacac ggccgactgg caatatgtgc gcatcacgac caacttccag    120
agcaacggcc ccgtgacgga cgtcaactcg gaccagatcc ggtgctacga gcgcaacccg    180
ggcaccggcg cccccggcat ctacaacgtc acggccggca aaccatcaa ctacaacgcc     240
aagtcgtcca tctcccaccc gggacccatg gccttctaca ttgccaaggt tcccgccggc    300
cagtcggccg ccacctggga cggtaagggc gccgtctggt ccaagatcca ccaggagatg    360
ccgcactttg gcaccagcct cacctgggac tccaacggcc gcacctccat gcccgtcacc    420
atccccgct gtctgcagga cggcgagtat ctgctgcgtg cagagcacat tgccctccac     480
agcgccggca ccccggcgg cgcccagttc tacatttctt gtgccagct ctcagtcacc     540
ggcggcagcg ggacctggaa ccccaggaac aaggtgtcgt tccccggcgc ctacaaggcc    600
actgaccccgg catcctgat caacatctac taccccgtcc cgactagcta cactcccgct    660
ggtcccccg tcgacacctg c                                               681
```

<210> SEQ ID NO 95
<211> LENGTH: 227
<212> TYPE: PRT
<213> ORGANISM: Myceliophthora thermophila

<400> SEQUENCE: 95

```
Met Lys Leu Ser Ala Ala Ile Ala Val Leu Ala Ala Leu Ala Glu
1               5                   10                  15

Gly His Tyr Thr Phe Pro Ser Ile Ala Asn Thr Ala Asp Trp Gln Tyr
            20                  25                  30

Val Arg Ile Thr Thr Asn Phe Gln Ser Asn Gly Pro Val Thr Asp Val
        35                  40                  45

Asn Ser Asp Gln Ile Arg Cys Tyr Glu Arg Asn Pro Gly Thr Gly Ala
50                  55                  60

Pro Gly Ile Tyr Asn Val Thr Ala Gly Thr Thr Ile Asn Tyr Asn Ala
65                  70                  75                  80

Lys Ser Ser Ile Ser His Pro Gly Pro Met Ala Phe Tyr Ile Ala Lys
                85                  90                  95

Val Pro Ala Gly Gln Ser Ala Ala Thr Trp Asp Gly Lys Gly Ala Val
            100                 105                 110

Trp Ser Lys Ile His Gln Glu Met Pro His Phe Gly Thr Ser Leu Thr
        115                 120                 125

Trp Asp Ser Asn Gly Arg Thr Ser Met Pro Val Thr Ile Pro Arg Cys
130                 135                 140

Leu Gln Asp Gly Glu Tyr Leu Leu Arg Ala Glu His Ile Ala Leu His
145                 150                 155                 160

Ser Ala Gly Ser Pro Gly Gly Ala Gln Phe Tyr Ile Ser Cys Ala Gln
                165                 170                 175

Leu Ser Val Thr Gly Gly Ser Gly Thr Trp Asn Pro Arg Asn Lys Val
            180                 185                 190

Ser Phe Pro Gly Ala Tyr Lys Ala Thr Asp Pro Gly Ile Leu Ile Asn
        195                 200                 205

Ile Tyr Tyr Pro Val Pro Thr Ser Tyr Thr Pro Ala Gly Pro Pro Val
```

Asp Thr Cys
225

<210> SEQ ID NO 96
<211> LENGTH: 210
<212> TYPE: PRT
<213> ORGANISM: Myceliophthora thermophila

<400> SEQUENCE: 96

His Tyr Thr Phe Pro Ser Ile Ala Asn Thr Ala Asp Trp Gln Tyr Val
1               5                   10                  15

Arg Ile Thr Thr Asn Phe Gln Ser Asn Gly Pro Val Thr Asp Val Asn
            20                  25                  30

Ser Asp Gln Ile Arg Cys Tyr Glu Arg Asn Pro Gly Thr Gly Ala Pro
        35                  40                  45

Gly Ile Tyr Asn Val Thr Ala Gly Thr Thr Ile Asn Tyr Asn Ala Lys
    50                  55                  60

Ser Ser Ile Ser His Pro Gly Pro Met Ala Phe Tyr Ile Ala Lys Val
65                  70                  75                  80

Pro Ala Gly Gln Ser Ala Ala Thr Trp Asp Gly Lys Gly Ala Val Trp
                85                  90                  95

Ser Lys Ile His Gln Glu Met Pro His Phe Gly Thr Ser Leu Thr Trp
            100                 105                 110

Asp Ser Asn Gly Arg Thr Ser Met Pro Val Thr Ile Pro Arg Cys Leu
        115                 120                 125

Gln Asp Gly Glu Tyr Leu Leu Arg Ala Glu His Ile Ala Leu His Ser
    130                 135                 140

Ala Gly Ser Pro Gly Gly Ala Gln Phe Tyr Ile Ser Cys Ala Gln Leu
145                 150                 155                 160

Ser Val Thr Gly Gly Ser Gly Thr Trp Asn Pro Arg Asn Lys Val Ser
                165                 170                 175

Phe Pro Gly Ala Tyr Lys Ala Thr Asp Pro Gly Ile Leu Ile Asn Ile
            180                 185                 190

Tyr Tyr Pro Val Pro Thr Ser Tyr Thr Pro Ala Gly Pro Pro Val Asp
        195                 200                 205

Thr Cys
    210

<210> SEQ ID NO 97
<211> LENGTH: 765
<212> TYPE: DNA
<213> ORGANISM: Myceliophthora thermophila

<400> SEQUENCE: 97
atgtaccgca cgctcggttc cattgccctg ctcgcggggg gcgctgccgc ccacggcgcc      60
gtgaccagct acaacattgc gggcaaggac taccctggat actcgggctt cgcccctacc     120
ggccaggatg tcatccagtg gcaatggccc gactataacc ccgtgctgtc cgccagcgac     180
cccaagctcc gctgcaacgg cggcaccggg gcggcgctgt atgccgaggc ggcccccggc     240
gacaccatca cggccaccctg ggcccagtgg acgcactccc agggcccgat cctggtgtgg     300
atgtacaagt gccccggcga cttcagctcc tgcgacggct ccggcgcggg ttggttcaag     360
atcgacgagg ccggcttcca cggcgacggc acgaccgtct tcctcgacac cgagaccccc     420
tcgggctggg acattgccaa gctggtcggc ggcaacaagt cgtggagcag caagatccct     480

```
gacggcctcg ccccgggcaa ttacctggtc cgccacgagc tcatcgccct gcaccaggcc    540
aacaacccgc aattctaccc cgagtgcgcc cagatcaagg tcaccggctc tggcaccgcc    600
gagcccgccg cctcctacaa ggccgccatc cccggctact gccagcagag cgaccccaac    660
atttcgttca acatcaacga ccactccctc ccgcaggagt acaagatccc cggtcccccg    720
gtcttcaagg gcaccgcctc cgccaaggct cgcgctttcc aggcc                    765
```

<210> SEQ ID NO 98
<211> LENGTH: 255
<212> TYPE: PRT
<213> ORGANISM: Myceliophthora thermophila

<400> SEQUENCE: 98

```
Met Tyr Arg Thr Leu Gly Ser Ile Ala Leu Leu Ala Gly Gly Ala Ala
1               5                   10                  15

Ala His Gly Ala Val Thr Ser Tyr Asn Ile Ala Gly Lys Asp Tyr Pro
                20                  25                  30

Gly Tyr Ser Gly Phe Ala Pro Thr Gly Gln Asp Val Ile Gln Trp Gln
            35                  40                  45

Trp Pro Asp Tyr Asn Pro Val Leu Ser Ala Ser Asp Pro Lys Leu Arg
50                  55                  60

Cys Asn Gly Gly Thr Gly Ala Ala Leu Tyr Ala Glu Ala Ala Pro Gly
65                  70                  75                  80

Asp Thr Ile Thr Ala Thr Trp Ala Gln Trp Thr His Ser Gln Gly Pro
                85                  90                  95

Ile Leu Val Trp Met Tyr Lys Cys Pro Gly Asp Phe Ser Ser Cys Asp
            100                 105                 110

Gly Ser Gly Ala Gly Trp Phe Lys Ile Asp Glu Ala Gly Phe His Gly
        115                 120                 125

Asp Gly Thr Thr Val Phe Leu Asp Thr Glu Thr Pro Ser Gly Trp Asp
    130                 135                 140

Ile Ala Lys Leu Val Gly Gly Asn Lys Ser Trp Ser Ser Lys Ile Pro
145                 150                 155                 160

Asp Gly Leu Ala Pro Gly Asn Tyr Leu Val Arg His Glu Leu Ile Ala
                165                 170                 175

Leu His Gln Ala Asn Asn Pro Gln Phe Tyr Pro Glu Cys Ala Gln Ile
            180                 185                 190

Lys Val Thr Gly Ser Gly Thr Ala Glu Pro Ala Ala Ser Tyr Lys Ala
        195                 200                 205

Ala Ile Pro Gly Tyr Cys Gln Gln Ser Asp Pro Asn Ile Ser Phe Asn
    210                 215                 220

Ile Asn Asp His Ser Leu Pro Gln Glu Tyr Lys Ile Pro Gly Pro Pro
225                 230                 235                 240

Val Phe Lys Gly Thr Ala Ser Ala Lys Ala Arg Ala Phe Gln Ala
                245                 250                 255
```

<210> SEQ ID NO 99
<211> LENGTH: 236
<212> TYPE: PRT
<213> ORGANISM: Myceliophthora thermophila

<400> SEQUENCE: 99

```
Ala Val Thr Ser Tyr Asn Ile Ala Gly Lys Asp Tyr Pro Gly Tyr Ser
1               5                   10                  15

Gly Phe Ala Pro Thr Gly Gln Asp Val Ile Gln Trp Gln Trp Pro Asp
                20                  25                  30
```

Tyr Asn Pro Val Leu Ser Ala Ser Asp Pro Lys Leu Arg Cys Asn Gly
        35                  40                  45

Gly Thr Gly Ala Ala Leu Tyr Ala Glu Ala Ala Pro Gly Asp Thr Ile
 50                  55                  60

Thr Ala Thr Trp Ala Gln Trp Thr His Ser Gln Gly Pro Ile Leu Val
 65                  70                  75                  80

Trp Met Tyr Lys Cys Pro Gly Asp Phe Ser Ser Cys Asp Gly Ser Gly
                 85                  90                  95

Ala Gly Trp Phe Lys Ile Asp Glu Ala Gly Phe His Gly Asp Gly Thr
            100                 105                 110

Thr Val Phe Leu Asp Thr Glu Thr Pro Ser Gly Trp Asp Ile Ala Lys
        115                 120                 125

Leu Val Gly Gly Asn Lys Ser Trp Ser Ser Lys Ile Pro Asp Gly Leu
130                 135                 140

Ala Pro Gly Asn Tyr Leu Val Arg His Glu Leu Ile Ala Leu His Gln
145                 150                 155                 160

Ala Asn Asn Pro Gln Phe Tyr Pro Glu Cys Ala Gln Ile Lys Val Thr
                165                 170                 175

Gly Ser Gly Thr Ala Glu Pro Ala Ala Ser Tyr Lys Ala Ala Ile Pro
            180                 185                 190

Gly Tyr Cys Gln Gln Ser Asp Pro Asn Ile Ser Phe Asn Ile Asn Asp
        195                 200                 205

His Ser Leu Pro Gln Glu Tyr Lys Ile Pro Gly Pro Pro Val Phe Lys
    210                 215                 220

Gly Thr Ala Ser Ala Lys Ala Arg Ala Phe Gln Ala
225                 230                 235

<210> SEQ ID NO 100
<211> LENGTH: 675
<212> TYPE: DNA
<213> ORGANISM: Myceliophthora thermophila

<400> SEQUENCE: 100
atgctgacaa caaccttcgc cctcctgacg gccgctctcg gcgtcagcgc ccattatacc      60
ctccccaggg tcgggaccgg ttccgactgg cagcacgtgc ggcgggctga caactggcaa     120
aacaacggct tcgtcggcga cgtcaactcg gagcagatca ggtgcttcca ggcgaccccT     180
gccggcgccc aagacgtcta cactgttcag gcgggatcga ccgtgaccta ccacgccaac     240
cccagtatct accaccccgg ccccatgcag ttctacctgg cccgcgttcc ggacggacag     300
gacgtcaagt cgtggaccgg cgagggtgcc gtgtggttca aggtgtacga ggagcagcct     360
caatttggcg cccagctgac ctggcctagc aacggcaaga gctcgttcga ggttcctatc     420
cccagctgca ttcgggcggg caactacctc ctccgcgctg agcacatcgc cctgcacgtt     480
gcccaaagcc agggcggcgc ccagttctac atctcgtgcg cccagctcca ggtcactggt     540
ggcggcagca ccgagccttc tcagaaggtt tccttcccgg gtgcctacaa gtccaccgac     600
cccggcattc ttatcaacat caactacccc gtccctacct cgtaccagaa tccgggtccg     660
gctgtcttcc gttgc                                                     675

<210> SEQ ID NO 101
<211> LENGTH: 225
<212> TYPE: PRT
<213> ORGANISM: Myceliophthora thermophila

<400> SEQUENCE: 101

Met Leu Thr Thr Thr Phe Ala Leu Leu Thr Ala Ala Leu Gly Val Ser
1               5                   10                  15

Ala His Tyr Thr Leu Pro Arg Val Gly Thr Gly Ser Asp Trp Gln His
            20                  25                  30

Val Arg Arg Ala Asp Asn Trp Gln Asn Asn Gly Phe Val Gly Asp Val
        35                  40                  45

Asn Ser Glu Gln Ile Arg Cys Phe Gln Ala Thr Pro Ala Gly Ala Gln
50                  55                  60

Asp Val Tyr Thr Val Gln Ala Gly Ser Thr Val Thr Tyr His Ala Asn
65                  70                  75                  80

Pro Ser Ile Tyr His Pro Gly Pro Met Gln Phe Tyr Leu Ala Arg Val
                85                  90                  95

Pro Asp Gly Gln Asp Val Lys Ser Trp Thr Gly Glu Gly Ala Val Trp
            100                 105                 110

Phe Lys Val Tyr Glu Glu Gln Pro Gln Phe Gly Ala Gln Leu Thr Trp
        115                 120                 125

Pro Ser Asn Gly Lys Ser Ser Phe Glu Val Pro Ile Pro Ser Cys Ile
130                 135                 140

Arg Ala Gly Asn Tyr Leu Leu Arg Ala Glu His Ile Ala Leu His Val
145                 150                 155                 160

Ala Gln Ser Gln Gly Gly Ala Gln Phe Tyr Ile Ser Cys Ala Gln Leu
                165                 170                 175

Gln Val Thr Gly Gly Gly Ser Thr Glu Pro Ser Gln Lys Val Ser Phe
            180                 185                 190

Pro Gly Ala Tyr Lys Ser Thr Asp Pro Gly Ile Leu Ile Asn Ile Asn
        195                 200                 205

Tyr Pro Val Pro Thr Ser Tyr Gln Asn Pro Gly Pro Ala Val Phe Arg
210                 215                 220

Cys
225

<210> SEQ ID NO 102
<211> LENGTH: 208
<212> TYPE: PRT
<213> ORGANISM: Myceliophthora thermophila

<400> SEQUENCE: 102

His Tyr Thr Leu Pro Arg Val Gly Thr Gly Ser Asp Trp Gln His Val
1               5                   10                  15

Arg Arg Ala Asp Asn Trp Gln Asn Asn Gly Phe Val Gly Asp Val Asn
            20                  25                  30

Ser Glu Gln Ile Arg Cys Phe Gln Ala Thr Pro Ala Gly Ala Gln Asp
        35                  40                  45

Val Tyr Thr Val Gln Ala Gly Ser Thr Val Thr Tyr His Ala Asn Pro
50                  55                  60

Ser Ile Tyr His Pro Gly Pro Met Gln Phe Tyr Leu Ala Arg Val Pro
65                  70                  75                  80

Asp Gly Gln Asp Val Lys Ser Trp Thr Gly Glu Gly Ala Val Trp Phe
                85                  90                  95

Lys Val Tyr Glu Glu Gln Pro Gln Phe Gly Ala Gln Leu Thr Trp Pro
            100                 105                 110

Ser Asn Gly Lys Ser Ser Phe Glu Val Pro Ile Pro Ser Cys Ile Arg
        115                 120                 125

Ala Gly Asn Tyr Leu Leu Arg Ala Glu His Ile Ala Leu His Val Ala

```
                    130                 135                 140
Gln Ser Gln Gly Gly Ala Gln Phe Tyr Ile Ser Cys Ala Gln Leu Gln
145                 150                 155                 160

Val Thr Gly Gly Gly Ser Thr Glu Pro Ser Gln Lys Val Ser Phe Pro
                165                 170                 175

Gly Ala Tyr Lys Ser Thr Asp Pro Gly Ile Leu Ile Asn Ile Asn Tyr
            180                 185                 190

Pro Val Pro Thr Ser Tyr Gln Asn Pro Gly Pro Ala Val Phe Arg Cys
        195                 200                 205

<210> SEQ ID NO 103
<211> LENGTH: 711
<212> TYPE: DNA
<213> ORGANISM: Myceliophthora thermophila

<400> SEQUENCE: 103
atgaaggttc tcgcgcccct gattctggcc ggtgccgcca gcgcccacac catcttctca      60
tccctcgagg tgggcggcgt caaccagggc atcgggcagg gtgtccgcgt gccgtcgtac     120
aacggtccga tcgaggacgt gacgtccaac tcgatcgcct gcaacgggcc ccccaacccg     180
acgacgccga ccaacaaggt catcacggtc cgggccggcg agacggtgac ggccgtctgg     240
cggtacatgc tgagcaccac cggctcggcc cccaacgaca tcatggacag cagccacaag     300
ggcccgacca tggcctacct caagaaggtc gacaacgcca ccaccgactc gggcgtcggc     360
ggcggctggt tcaagatcca ggaggacggc cttaccaacg gcgtctgggg caccgagcgc     420
gtcatcaacg gccagggccg ccacaacatc aagatccccg agtgcatcgc ccccggccag     480
tacctcctcc gcgccgagat gcttgccctg cacggagctt ccaactaccc cggcgctcag     540
ttctacatgg agtgcgccca gctcaatatc gtcggcggca ccggcagcaa gacgccgtcc     600
accgtcagct ccccgggcgc ttacaagggt accgaccccg gagtcaagat caacatctac     660 tggcccccccg tcaccagcta ccagattccc ggccccggcg tgttcacctg c             711

<210> SEQ ID NO 104
<211> LENGTH: 237
<212> TYPE: PRT
<213> ORGANISM: Myceliophthora thermophila

<400> SEQUENCE: 104

Met Lys Val Leu Ala Pro Leu Ile Leu Ala Gly Ala Ala Ser Ala His
1                   5                   10                  15

Thr Ile Phe Ser Ser Leu Glu Val Gly Gly Val Asn Gln Gly Ile Gly
                20                  25                  30

Gln Gly Val Arg Val Pro Ser Tyr Asn Gly Pro Ile Glu Asp Val Thr
            35                  40                  45

Ser Asn Ser Ile Ala Cys Asn Gly Pro Pro Asn Pro Thr Thr Pro Thr
        50                  55                  60

Asn Lys Val Ile Thr Val Arg Ala Gly Glu Thr Val Thr Ala Val Trp
65                  70                  75                  80

Arg Tyr Met Leu Ser Thr Thr Gly Ser Ala Pro Asn Asp Ile Met Asp
                85                  90                  95

Ser Ser His Lys Gly Pro Thr Met Ala Tyr Leu Lys Lys Val Asp Asn
                100                 105                 110

Ala Thr Thr Asp Ser Gly Val Gly Gly Trp Phe Lys Ile Gln Glu
            115                 120                 125

Asp Gly Leu Thr Asn Gly Val Trp Gly Thr Glu Arg Val Ile Asn Gly
```

```
                130                 135                 140
Gln Gly Arg His Asn Ile Lys Ile Pro Glu Cys Ile Ala Pro Gly Gln
145                 150                 155                 160

Tyr Leu Leu Arg Ala Glu Met Leu Ala Leu His Gly Ala Ser Asn Tyr
                165                 170                 175

Pro Gly Ala Gln Phe Tyr Met Glu Cys Ala Gln Leu Asn Ile Val Gly
                180                 185                 190

Gly Thr Gly Ser Lys Thr Pro Ser Thr Val Ser Phe Pro Gly Ala Tyr
                195                 200                 205

Lys Gly Thr Asp Pro Gly Val Lys Ile Asn Ile Tyr Trp Pro Pro Val
                210                 215                 220

Thr Ser Tyr Gln Ile Pro Gly Pro Gly Val Phe Thr Cys
225                 230                 235

<210> SEQ ID NO 105
<211> LENGTH: 222
<212> TYPE: PRT
<213> ORGANISM: Myceliophthora thermophila

<400> SEQUENCE: 105

His Thr Ile Phe Ser Ser Leu Glu Val Gly Val Asn Gln Gly Ile
1               5                   10                  15

Gly Gln Gly Val Arg Val Pro Ser Tyr Asn Gly Pro Ile Glu Asp Val
                20                  25                  30

Thr Ser Asn Ser Ile Ala Cys Asn Gly Pro Pro Asn Pro Thr Thr Pro
                35                  40                  45

Thr Asn Lys Val Ile Thr Val Arg Ala Gly Glu Thr Val Thr Ala Val
                50                  55                  60

Trp Arg Tyr Met Leu Ser Thr Thr Gly Ser Ala Pro Asn Asp Ile Met
65                  70                  75                  80

Asp Ser Ser His Lys Gly Pro Thr Met Ala Tyr Leu Lys Lys Val Asp
                85                  90                  95

Asn Ala Thr Thr Asp Ser Gly Val Gly Gly Trp Phe Lys Ile Gln
                100                 105                 110

Glu Asp Gly Leu Thr Asn Gly Val Trp Gly Thr Glu Arg Val Ile Asn
                115                 120                 125

Gly Gln Gly Arg His Asn Ile Lys Ile Pro Glu Cys Ile Ala Pro Gly
                130                 135                 140

Gln Tyr Leu Leu Arg Ala Glu Met Leu Ala Leu His Gly Ala Ser Asn
145                 150                 155                 160

Tyr Pro Gly Ala Gln Phe Tyr Met Glu Cys Ala Gln Leu Asn Ile Val
                165                 170                 175

Gly Gly Thr Gly Ser Lys Thr Pro Ser Thr Val Ser Phe Pro Gly Ala
                180                 185                 190

Tyr Lys Gly Thr Asp Pro Gly Val Lys Ile Asn Ile Tyr Trp Pro Pro
                195                 200                 205

Val Thr Ser Tyr Gln Ile Pro Gly Pro Gly Val Phe Thr Cys
                210                 215                 220

<210> SEQ ID NO 106
<211> LENGTH: 225
<212> TYPE: DNA
<213> ORGANISM: Myceliophthora thermophila

<400> SEQUENCE: 106
atgatcgaca acctccctga tgactcccta caacccgcct gcctccgccc gggccactac      60
```

```
ctcgtccgcc acgagatcat cgcgctgcac tcggcctggg ccgagggcga ggcccagttc      120
tacccctccc cccttttcc ttttttccc tcccttctt tgtccggtaa ctacacgatt      180
cccggtcccg cgatctggaa gtgcccagag gcacagcaga acgag                    225

<210> SEQ ID NO 107
<211> LENGTH: 75
<212> TYPE: PRT
<213> ORGANISM: Myceliophthora thermophila

<400> SEQUENCE: 107

Met Ile Asp Asn Leu Pro Asp Asp Ser Leu Gln Pro Ala Cys Leu Arg
1               5                   10                  15

Pro Gly His Tyr Leu Val Arg His Glu Ile Ile Ala Leu His Ser Ala
            20                  25                  30

Trp Ala Glu Gly Glu Ala Gln Phe Tyr Pro Phe Pro Leu Phe Pro Phe
        35                  40                  45

Phe Pro Ser Leu Leu Leu Ser Gly Asn Tyr Thr Ile Pro Gly Pro Ala
    50                  55                  60

Ile Trp Lys Cys Pro Glu Ala Gln Gln Asn Glu
65                  70                  75

<210> SEQ ID NO 108
<211> LENGTH: 57
<212> TYPE: PRT
<213> ORGANISM: Myceliophthora thermophila

<400> SEQUENCE: 108

His Tyr Leu Val Arg His Glu Ile Ile Ala Leu His Ser Ala Trp Ala
1               5                   10                  15

Glu Gly Glu Ala Gln Phe Tyr Pro Phe Pro Leu Phe Pro Phe Phe Pro
            20                  25                  30

Ser Leu Leu Leu Ser Gly Asn Tyr Thr Ile Pro Gly Pro Ala Ile Trp
        35                  40                  45

Lys Cys Pro Glu Ala Gln Gln Asn Glu
    50                  55

<210> SEQ ID NO 109
<211> LENGTH: 1395
<212> TYPE: DNA
<213> ORGANISM: Myceliophthora thermophila

<400> SEQUENCE: 109
atggggcaga agactctcca ggggctggtg gcggcggcgg cactggcagc ctcggtggcg       60
aacgcgcagc aaccgggcac cttcacgccc gaggtgcatc cgacgctgcc gacgtggaag     120
tgcacgacga gcggcgggtg cgtccagcag gacacgtcgg tggtgctcga ctggaactac     180
cgctggttcc acaccgagga cggtagcaag tcgtgcatca cctctagcgg cgtcgaccgg     240
acctgtgcc cggacgaggc gacgtgcgcc aagaactgct tcgtcgaggg cgtcaactac      300
acgagcagcg gggtcgagac gtccggcagc tccctcaccc tccgccagtt cttcaagggc     360
tccgacggcg ccatcaacag cgtctccccg cgcgtctacc tgctcggggg agacggcaac     420
tatgtcgtgc tcaagctcct cggccaggag ctgagcttcg acgtggacgt atcgtcgctc     480
ccgtgcggcg agaacgcggc cctgtacctg tccgagatgg acgcgacggg aggacggaac     540
gagtacaaca cgggcggggc cgagtacggg tcgggctact gtgacgccca gtgccccgtg     600
cagaactgga acaacgggac gctcaacacg ggccgggtgg gctcgtgctg caacgagatg     660
```

-continued

```
gacatcctcg aggccaactc caaggccgag gccttcacgc cgcacccctg catcggcaac    720
tcgtgcgaca agagcgggtg cggcttcaac gcgtacgcgc gcggttacca caactactgg    780
gcccccggcg gcacgctcga cacgtcccgg cctttcacca tgatcacccg cttcgtcacc    840
gacgacggca ccacctcggg caagctcgcc cgcatcgagc gcgtctacgt ccaggacggc    900
aagaaggtgc ccagcgcggc gcccgggggg gacgtcatca cggccgacgg gtgcacctcc    960
gcgcagccct acggcggcct ttccggcatg ggcgacgccc tcggccgcgg catggtcctg   1020
gccctgagca tctggaacga cgcgtccggg tacatgaact ggctcgacgc cggcagcaac   1080
ggcccctgca gcgacaccga gggtaacccg tccaacatcc tggccaacca cccggacgcc   1140
cacgtcgtgc tctccaacat ccgctggggc gacatcggct ccaccgtcga caccggcgat   1200
ggcgacaaca acggcggcgg ccccaacccg tcatccacca ccaccgctac cgctaccacc   1260
acctcctccg gcccggccga gcctacccag acccactacg gccagtgtgg agggaaagga   1320
tggacgggcc ctacccgctg cgagacgccc tacacctgca agtaccagaa cgactggtac   1380
tcgcagtgcc tgtag                                                    1395

<210> SEQ ID NO 110
<211> LENGTH: 464
<212> TYPE: PRT
<213> ORGANISM: Myceliophthora thermophila

<400> SEQUENCE: 110

Met Gly Gln Lys Thr Leu Gln Gly Leu Val Ala Ala Ala Leu Ala
1               5                   10                  15

Ala Ser Val Ala Asn Ala Gln Gln Pro Gly Thr Phe Thr Pro Glu Val
                20                  25                  30

His Pro Thr Leu Pro Thr Trp Lys Cys Thr Thr Ser Gly Gly Cys Val
            35                  40                  45

Gln Gln Asp Thr Ser Val Val Leu Asp Trp Asn Tyr Arg Trp Phe His
        50                  55                  60

Thr Glu Asp Gly Ser Lys Ser Cys Ile Thr Ser Ser Gly Val Asp Arg
65                  70                  75                  80

Thr Leu Cys Pro Asp Glu Ala Thr Cys Ala Lys Asn Cys Phe Val Glu
                85                  90                  95

Gly Val Asn Tyr Thr Ser Ser Gly Val Glu Thr Ser Gly Ser Ser Leu
            100                 105                 110

Thr Leu Arg Gln Phe Phe Lys Gly Ser Asp Gly Ala Ile Asn Ser Val
        115                 120                 125

Ser Pro Arg Val Tyr Leu Leu Gly Gly Asp Gly Asn Tyr Val Val Leu
    130                 135                 140

Lys Leu Leu Gly Gln Glu Leu Ser Phe Asp Val Asp Val Ser Ser Leu
145                 150                 155                 160

Pro Cys Gly Glu Asn Ala Ala Leu Tyr Leu Ser Glu Met Asp Ala Thr
                165                 170                 175

Gly Gly Arg Asn Glu Tyr Asn Thr Gly Gly Ala Glu Tyr Gly Ser Gly
            180                 185                 190

Tyr Cys Asp Ala Gln Cys Pro Val Gln Asn Trp Asn Asn Gly Thr Leu
        195                 200                 205

Asn Thr Gly Arg Val Gly Ser Cys Cys Asn Glu Met Asp Ile Leu Glu
    210                 215                 220

Ala Asn Ser Lys Ala Glu Ala Phe Thr Pro His Pro Cys Ile Gly Asn
225                 230                 235                 240
```

```
Ser Cys Asp Lys Ser Gly Cys Gly Phe Asn Ala Tyr Ala Arg Gly Tyr
            245                 250                 255

His Asn Tyr Trp Ala Pro Gly Gly Thr Leu Asp Thr Ser Arg Pro Phe
            260                 265                 270

Thr Met Ile Thr Arg Phe Val Thr Asp Asp Gly Thr Thr Ser Gly Lys
            275                 280                 285

Leu Ala Arg Ile Glu Arg Val Tyr Val Gln Asp Gly Lys Lys Val Pro
            290                 295                 300

Ser Ala Ala Pro Gly Gly Asp Val Ile Thr Ala Asp Gly Cys Thr Ser
305                 310                 315                 320

Ala Gln Pro Tyr Gly Gly Leu Ser Gly Met Gly Asp Ala Leu Gly Arg
                325                 330                 335

Gly Met Val Leu Ala Leu Ser Ile Trp Asn Asp Ala Ser Gly Tyr Met
            340                 345                 350

Asn Trp Leu Asp Ala Gly Ser Asn Gly Pro Cys Ser Asp Thr Glu Gly
            355                 360                 365

Asn Pro Ser Asn Ile Leu Ala Asn His Pro Asp Ala His Val Val Leu
            370                 375                 380

Ser Asn Ile Arg Trp Gly Asp Ile Gly Ser Thr Val Asp Thr Gly Asp
385                 390                 395                 400

Gly Asp Asn Asn Gly Gly Gly Pro Asn Pro Ser Ser Thr Thr Thr Ala
                405                 410                 415

Thr Ala Thr Thr Thr Ser Ser Gly Pro Ala Glu Pro Thr Gln Thr His
            420                 425                 430

Tyr Gly Gln Cys Gly Gly Lys Gly Trp Thr Gly Pro Thr Arg Cys Glu
            435                 440                 445

Thr Pro Tyr Thr Cys Lys Tyr Gln Asn Asp Trp Tyr Ser Gln Cys Leu
            450                 455                 460

<210> SEQ ID NO 111
<211> LENGTH: 442
<212> TYPE: PRT
<213> ORGANISM: Myceliophthora thermophila

<400> SEQUENCE: 111

Gln Gln Pro Gly Thr Phe Thr Pro Glu Val His Pro Thr Leu Pro Thr
1               5                   10                  15

Trp Lys Cys Thr Thr Ser Gly Gly Cys Val Gln Gln Asp Thr Ser Val
            20                  25                  30

Val Leu Asp Trp Asn Tyr Arg Trp Phe His Thr Glu Asp Gly Ser Lys
        35                  40                  45

Ser Cys Ile Thr Ser Ser Gly Val Asp Arg Thr Leu Cys Pro Asp Glu
    50                  55                  60

Ala Thr Cys Ala Lys Asn Cys Phe Val Glu Gly Val Asn Tyr Thr Ser
65                  70                  75                  80

Ser Gly Val Glu Thr Ser Gly Ser Ser Leu Thr Leu Arg Gln Phe Phe
                85                  90                  95

Lys Gly Ser Asp Gly Ala Ile Asn Ser Val Ser Pro Arg Val Tyr Leu
            100                 105                 110

Leu Gly Gly Asp Gly Asn Tyr Val Val Leu Lys Leu Leu Gly Gln Glu
            115                 120                 125

Leu Ser Phe Asp Val Asp Val Ser Ser Leu Pro Cys Gly Glu Asn Ala
            130                 135                 140

Ala Leu Tyr Leu Ser Glu Met Asp Ala Thr Gly Gly Arg Asn Glu Tyr
```

```
                145                 150                 155                 160
Asn Thr Gly Gly Ala Glu Tyr Gly Ser Gly Tyr Cys Asp Ala Gln Cys
                    165                 170                 175
Pro Val Gln Asn Trp Asn Asn Gly Thr Leu Asn Thr Gly Arg Val Gly
                    180                 185                 190
Ser Cys Cys Asn Glu Met Asp Ile Leu Glu Ala Asn Ser Lys Ala Glu
                    195                 200                 205
Ala Phe Thr Pro His Pro Cys Ile Gly Asn Ser Cys Asp Lys Ser Gly
                    210                 215                 220
Cys Gly Phe Asn Ala Tyr Ala Arg Gly Tyr His Asn Tyr Trp Ala Pro
225                 230                 235                 240
Gly Gly Thr Leu Asp Thr Ser Arg Pro Phe Thr Met Ile Thr Arg Phe
                    245                 250                 255
Val Thr Asp Asp Gly Thr Thr Ser Gly Lys Leu Ala Arg Ile Glu Arg
                    260                 265                 270
Val Tyr Val Gln Asp Gly Lys Lys Val Pro Ser Ala Ala Pro Gly Gly
                    275                 280                 285
Asp Val Ile Thr Ala Asp Gly Cys Thr Ser Ala Gln Pro Tyr Gly Gly
                    290                 295                 300
Leu Ser Gly Met Gly Asp Ala Leu Gly Arg Gly Met Val Leu Ala Leu
305                 310                 315                 320
Ser Ile Trp Asn Asp Ala Ser Gly Tyr Met Asn Trp Leu Asp Ala Gly
                    325                 330                 335
Ser Asn Gly Pro Cys Ser Asp Thr Glu Gly Asn Pro Ser Asn Ile Leu
                    340                 345                 350
Ala Asn His Pro Asp Ala His Val Val Leu Ser Asn Ile Arg Trp Gly
                    355                 360                 365
Asp Ile Gly Ser Thr Val Asp Thr Gly Asp Gly Asp Asn Asn Gly Gly
                    370                 375                 380
Gly Pro Asn Pro Ser Ser Thr Thr Thr Ala Thr Ala Thr Thr Thr Ser
385                 390                 395                 400
Ser Gly Pro Ala Glu Pro Thr Gln Thr His Tyr Gly Gln Cys Gly Gly
                    405                 410                 415
Lys Gly Trp Thr Gly Pro Thr Arg Cys Glu Thr Pro Tyr Thr Cys Lys
                    420                 425                 430
Tyr Gln Asn Asp Trp Tyr Ser Gln Cys Leu
                    435                 440

<210> SEQ ID NO 112
<211> LENGTH: 1170
<212> TYPE: DNA
<213> ORGANISM: Myceliophthora thermophila

<400> SEQUENCE: 112
atgaagtcct ccatcctcgc cagcgtcttc gccacgggcg ccgtggctca aagtggtccg      60
tggcagcaat gtggtggcat cggatggcaa ggatcgaccg actgtgtgtc gggttaccac     120
tgcgtctacc agaacgattg gtacagccag tgcgtgcctg gcgcggcgtc gacaacgctc     180
cagacatcta ccacgtccag gcccaccgcc accagcaccg ccctccgtc gtccaccacc      240 tcgcctagca agggcaagct caagtggctc ggcagcaacg agtcgggcgc cgagttcggg     300
gagggcaact accccggcct ctggggcaag cacttcatct cccgtcgac ttcggcgatt      360 cagacgctca tcaatgatgg atacaacatc ttccggatcg acttctcgat ggagcgtctg     420
gtgcccaacc agttgacgtc gtccttcgac gagggctacc tccgcaacct gaccgaggtg     480
```

```
gtcaacttcg tgacgaacgc gggcaagtac gccgtcctgg acccgcacaa ctacggccgg      540
tactacggca acgtcatcac ggacacgaac gcgttccgga ccttctggac caacctggcc      600
aagcagttcg cctccaactc gctcgtcatc ttcgacacca caacgagta caacacgatg      660 gaccagaccc tggtgctcaa cctcaaccag gccgccatcg acggcatccg ggccgccggc      720
gcgacctcgc agtacatctt cgtcgagggc aacgcgtgga gcggggcctg gagctggaac      780
acgaccaaca ccaacatggc cgccctgacg acccgcaga acaagatcgt gtacgagatg      840
caccagtacc tcgactcgga cagctcgggc acccacgccg agtgcgtcag cagcaacatc      900
ggcgcccagc gcgtcgtcgg agccacccag tggctccgcg ccaacggcaa gctcggcgtc      960
ctcggcgagt cgccggcgg cgccaacgcc gtctgccagc aggccgtcac cggcctcctc     1020
gaccacctcc aggacaacag cgacgtctgg ctgggtgccc tctggtgggc cgccggtccc     1080
tggtggggcg actacatgta ctcgttcgag cctccttcgg gcaccggcta tgtcaactac     1140
aactcgatcc taaagaagta cttgccgtaa                                     1170
```

<210> SEQ ID NO 113
<211> LENGTH: 389
<212> TYPE: PRT
<213> ORGANISM: Myceliophthora thermophila

<400> SEQUENCE: 113

```
Met Lys Ser Ser Ile Leu Ala Ser Val Phe Ala Thr Gly Ala Val Ala
1               5                   10                  15

Gln Ser Gly Pro Trp Gln Gln Cys Gly Gly Ile Gly Trp Gln Gly Ser
            20                  25                  30

Thr Asp Cys Val Ser Gly Tyr His Cys Val Tyr Gln Asn Asp Trp Tyr
        35                  40                  45

Ser Gln Cys Val Pro Gly Ala Ala Ser Thr Thr Leu Gln Thr Ser Thr
    50                  55                  60

Thr Ser Arg Pro Thr Ala Thr Ser Thr Ala Pro Pro Ser Ser Thr Thr
65                  70                  75                  80

Ser Pro Ser Lys Gly Lys Leu Lys Trp Leu Gly Ser Asn Glu Ser Gly
                85                  90                  95

Ala Glu Phe Gly Glu Gly Asn Tyr Pro Gly Leu Trp Gly Lys His Phe
            100                 105                 110

Ile Phe Pro Ser Thr Ser Ala Ile Gln Thr Leu Ile Asn Asp Gly Tyr
        115                 120                 125

Asn Ile Phe Arg Ile Asp Phe Ser Met Glu Arg Leu Val Pro Asn Gln
    130                 135                 140

Leu Thr Ser Ser Phe Asp Glu Gly Tyr Leu Arg Asn Leu Thr Glu Val
145                 150                 155                 160

Val Asn Phe Val Thr Asn Ala Gly Lys Tyr Ala Val Leu Asp Pro His
                165                 170                 175

Asn Tyr Gly Arg Tyr Tyr Gly Asn Val Ile Thr Asp Thr Asn Ala Phe
            180                 185                 190

Arg Thr Phe Trp Thr Asn Leu Ala Lys Gln Phe Ala Ser Asn Ser Leu
        195                 200                 205

Val Ile Phe Asp Thr Asn Asn Glu Tyr Asn Thr Met Asp Gln Thr Leu
    210                 215                 220

Val Leu Asn Leu Asn Gln Ala Ala Ile Asp Gly Ile Arg Ala Ala Gly
225                 230                 235                 240

Ala Thr Ser Gln Tyr Ile Phe Val Glu Gly Asn Ala Trp Ser Gly Ala
```

```
                245                 250                 255
Trp Ser Trp Asn Thr Thr Asn Thr Asn Met Ala Ala Leu Thr Asp Pro
            260                 265                 270

Gln Asn Lys Ile Val Tyr Glu Met His Gln Tyr Leu Asp Ser Asp Ser
        275                 280                 285

Ser Gly Thr His Ala Glu Cys Val Ser Ser Asn Ile Gly Ala Gln Arg
    290                 295                 300

Val Val Gly Ala Thr Gln Trp Leu Arg Ala Asn Gly Lys Leu Gly Val
305                 310                 315                 320

Leu Gly Glu Phe Ala Gly Ala Asn Ala Val Cys Gln Gln Ala Val
                325                 330                 335

Thr Gly Leu Leu Asp His Leu Gln Asp Asn Ser Glu Val Trp Leu Gly
                340                 345                 350

Ala Leu Trp Trp Ala Ala Gly Pro Trp Trp Gly Asp Tyr Met Tyr Ser
                355                 360                 365

Phe Glu Pro Pro Ser Gly Thr Gly Tyr Val Asn Tyr Asn Ser Ile Leu
            370                 375                 380

Lys Lys Tyr Leu Pro
385

<210> SEQ ID NO 114
<211> LENGTH: 373
<212> TYPE: PRT
<213> ORGANISM: Myceliophthora thermophila

<400> SEQUENCE: 114

Gln Ser Gly Pro Trp Gln Gln Cys Gly Gly Ile Gly Trp Gln Gly Ser
1               5                   10                  15

Thr Asp Cys Val Ser Gly Tyr His Cys Val Tyr Gln Asn Asp Trp Tyr
            20                  25                  30

Ser Gln Cys Val Pro Gly Ala Ala Ser Thr Thr Leu Gln Thr Ser Thr
        35                  40                  45

Thr Ser Arg Pro Thr Ala Thr Ser Thr Ala Pro Pro Ser Ser Thr Thr
    50                  55                  60

Ser Pro Ser Lys Gly Lys Leu Lys Trp Leu Gly Ser Asn Glu Ser Gly
65                  70                  75                  80

Ala Glu Phe Gly Glu Gly Asn Tyr Pro Gly Leu Trp Gly Lys His Phe
                85                  90                  95

Ile Phe Pro Ser Thr Ser Ala Ile Gln Thr Leu Ile Asn Asp Gly Tyr
            100                 105                 110

Asn Ile Phe Arg Ile Asp Phe Ser Met Glu Arg Leu Val Pro Asn Gln
        115                 120                 125

Leu Thr Ser Ser Phe Asp Glu Gly Tyr Leu Arg Asn Leu Thr Glu Val
    130                 135                 140

Val Asn Phe Val Thr Asn Ala Gly Lys Tyr Ala Val Leu Asp Pro His
145                 150                 155                 160

Asn Tyr Gly Arg Tyr Tyr Gly Asn Val Ile Thr Asp Thr Asn Ala Phe
                165                 170                 175

Arg Thr Phe Trp Thr Asn Leu Ala Lys Gln Phe Ala Ser Asn Ser Leu
            180                 185                 190

Val Ile Phe Asp Thr Asn Asn Glu Tyr Asn Thr Met Asp Gln Thr Leu
        195                 200                 205

Val Leu Asn Leu Asn Gln Ala Ala Ile Asp Gly Ile Arg Ala Ala Gly
    210                 215                 220
```

```
Ala Thr Ser Gln Tyr Ile Phe Val Glu Gly Asn Ala Trp Ser Gly Ala
225                 230                 235                 240

Trp Ser Trp Asn Thr Thr Asn Thr Asn Met Ala Ala Leu Thr Asp Pro
                245                 250                 255

Gln Asn Lys Ile Val Tyr Glu Met His Gln Tyr Leu Asp Ser Asp Ser
            260                 265                 270

Ser Gly Thr His Ala Glu Cys Val Ser Ser Asn Ile Gly Ala Gln Arg
        275                 280                 285

Val Val Gly Ala Thr Gln Trp Leu Arg Ala Asn Gly Lys Leu Gly Val
    290                 295                 300

Leu Gly Glu Phe Ala Gly Gly Ala Asn Ala Val Cys Gln Gln Ala Val
305                 310                 315                 320

Thr Gly Leu Leu Asp His Leu Gln Asp Asn Ser Glu Val Trp Leu Gly
                325                 330                 335

Ala Leu Trp Trp Ala Ala Gly Pro Trp Trp Gly Asp Tyr Met Tyr Ser
                340                 345                 350

Phe Glu Pro Pro Ser Gly Thr Gly Tyr Val Asn Tyr Asn Ser Ile Leu
            355                 360                 365

Lys Lys Tyr Leu Pro
    370

<210> SEQ ID NO 115
<211> LENGTH: 2613
<212> TYPE: DNA
<213> ORGANISM: Myceliophthora thermophila

<400> SEQUENCE: 115
atgaaggctg ctgcgctttc ctgcctcttc ggcagtaccc ttgccgttgc aggcgccatt    60
gaatcgagaa aggttcacca gaagcccctc gcgagatctg aacctttta cccgtcgcca   120 tggatgaatc ccaacgccga cggctgggcg gaggcctatg cccaggccaa gtcctttgtc   180
tcccaaatga ctctgctaga aaggtcaact tgaccacgg gagtcggctg ggggctgag    240 cagtgcgtcg gccaagtggg cgcgatccct cgccttggac ttcgcagtct gtgcatgcat   300 gactccctc tcggcatccg aggagccgac tacaactcag cgttccctc tggccagacc    360 gttgctgcta cctgggatcg cggtctgatg taccgtcgcg gctacgcaat gggccaggag   420
gccaaaggca agggcatcaa tgtccttctc ggaccagtcg ccggcccct tggccgcatg   480 cccgagggcg gtcgtaactg ggaaggcttc gctccggatc ccgtccttac cggcatcggc   540
atgtccgaga cgatcaaggg cattcaggat gctggcgtca tcgcttgtgc gaagcacttt   600
attggaaacg agcaggagca cttcagacag gtgccagaag cccagggata cggttacaac   660
atcagcgaaa ccctctcctc caacattgac gacaagacca tgcacgagct ctacctttgg   720
ccgtttgccg atgccgtccg gccggcgtc ggctctgtca tgtgctcgta ccagcaggtc   780
aacaactcgt acgcctgcca gaactcgaag ctgctgaacg acctcctcaa gaacgagctt   840
gggtttcagg gcttcgtcat gagcgactgg caggcacagc acactggcgc agcaagcgcc   900
gtggctggtc tcgatatgtc catgccgggc gacacccagt tcaacactgg cgtcagtttc   960
tggggcgcca atctcaccct cgccgtcctc aacggcacag tccctgccta ccgtctcgac   1020
gacatggcca tgcgcatcat ggccgccctc ttcaaggtca ccaagaccac cgacctggaa   1080
ccgatcaact tctccttctg gaccgacgac acttatggcc cgatccactg ggccgccaag   1140
cagggctacc aggagattaa ttcccacgtt gacgtccgcg ccgaccacgg caacctcatc   1200
cgggagattg ccgccaaggg tacggtgctg ctgaagaata ccggctctct accccctgaac   1260
```

```
aagccaaagt tcgtggccgt catcggcgag gatgctgggt cgagcccaa cgggcccaac    1320
ggctgcagcg accgcggctg taacgaaggc acgctcgcca tgggctgggg atccggcaca    1380
gccaactatc cgtacctcgt ttcccccgac gccgcgctcc aggcccgggc catccaggac    1440
ggcacgaggt acgagagcgt cctgtccaac tacgccgagg aaaagacaaa ggctctggtc    1500
tcgcaggcca atgcaaccgc catcgtcttc gtcaatgccg actcaggcga gggctacatc    1560
aacgtggacg gtaacgaggg cgaccgtaag aacctgactc tctggaacaa cggtgatact    1620
ctggtcaaga cgtctcgag ctggtgcagc aacaccatcg tcgtcatcca ctcggtcggc    1680
ccggtcctcc tgaccgattg gtacgacaac cccaacatca cggccattct ctgggctggt    1740
cttccgggcc aggagtcggg caactccatc accgacgtgc tttacggcaa ggtcaacccc    1800
gccgcccgct cgcccttcac ttggggcaag acccgcgaaa gctatggcgc ggacgtcctg    1860
tacaagccga ataatggcaa tggtgcgccc caacaggact tcaccgaggg cgtcttcatc    1920
gactaccgct acttcgacaa ggttgacgat gactcggtca tctacgagtt cggccacggc    1980
ctgagctaca ccaccttcga gtacagcaac atccgcgtcg tcaagtccaa cgtcagcgag    2040
taccggccca cgacgggcac cacggcccag gccccgacgt ttggcaactt ctccaccgac    2100
ctcgaggact atctcttccc caaggacgag ttccctaca tctaccagta catctacccg    2160
tacctcaaca cgaccgaccc ccggagggcc tcggccgatc cccactacgg ccagaccgcc    2220
gaggagttcc tcccgcccca cgccaccgat gacgaccccc agccgctcct ccggtcctcg    2280
ggcgaaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                2613
```

<210> SEQ ID NO 116
<211> LENGTH: 870
<212> TYPE: PRT
<213> ORGANISM: Myceliophthora thermophila

<400> SEQUENCE: 116

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

```
Leu Met Tyr Arg Arg Gly Tyr Ala Met Gly Gln Glu Ala Lys Gly Lys
130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Gln Ala Gln His Thr Gly Ala Ala Ser Ala Val Ala Gly Leu
    290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Asp Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Ser Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
    530                 535                 540

Val Ser Ser Trp Cys Ser Asn Thr Ile Val Val Ile His Ser Val Gly
```

```
              545                 550                 555                 560
        Pro Val Leu Leu Thr Asp Trp Tyr Asp Asn Pro Asn Ile Thr Ala Ile
                        565                 570                 575

Leu Trp Ala Gly Leu Pro Gly Gln Glu Ser Gly Asn Ser Ile Thr Asp
                        580                 585                 590

Val Leu Tyr Gly Lys Val Asn Pro Ala Ala Arg Ser Pro Phe Thr Trp
                        595                 600                 605

Gly Lys Thr Arg Glu Ser Tyr Gly Ala Asp Val Leu Tyr Lys Pro Asn
                        610                 615                 620

Asn Gly Asn Gly Ala Pro Gln Gln Asp Phe Thr Glu Gly Val Phe Ile
        625                 630                 635                 640

Asp Tyr Arg Tyr Phe Asp Lys Val Asp Asp Ser Val Ile Tyr Glu
                        645                 650                 655

Phe Gly His Gly Leu Ser Tyr Thr Thr Phe Glu Tyr Ser Asn Ile Arg
                        660                 665                 670

Val Val Lys Ser Asn Val Ser Glu Tyr Arg Pro Thr Thr Gly Thr Thr
                        675                 680                 685

Ala Gln Ala Pro Thr Phe Gly Asn Phe Ser Thr Asp Leu Glu Asp Tyr
                        690                 695                 700

Leu Phe Pro Lys Asp Glu Phe Pro Tyr Ile Tyr Gln Tyr Ile Tyr Pro
        705                 710                 715                 720

Tyr Leu Asn Thr Thr Asp Pro Arg Arg Ala Ser Ala Asp Pro His Tyr
                        725                 730                 735

Gly Gln Thr Ala Glu Glu Phe Leu Pro Pro His Ala Thr Asp Asp Asp
                        740                 745                 750

Pro Gln Pro Leu Leu Arg Ser Ser Gly Gly Asn Ser Pro Gly Gly Asn
                        755                 760                 765

Arg Gln Leu Tyr Asp Ile Val Tyr Thr Ile Thr Ala Asp Ile Thr Asn
                        770                 775                 780

Thr Gly Ser Val Val Gly Glu Glu Val Pro Gln Leu Tyr Val Ser Leu
        785                 790                 795                 800

Gly Gly Pro Glu Asp Pro Lys Val Gln Leu Arg Asp Phe Asp Arg Met
                        805                 810                 815

Arg Ile Glu Pro Gly Glu Thr Arg Gln Phe Thr Gly Arg Leu Thr Arg
                        820                 825                 830

Arg Asp Leu Ser Asn Trp Asp Val Thr Val Gln Asp Trp Val Ile Ser
                        835                 840                 845

Arg Tyr Pro Lys Thr Ala Tyr Val Gly Arg Ser Ser Arg Lys Leu Asp
                        850                 855                 860

Leu Lys Ile Glu Leu Pro
        865                 870

<210> SEQ ID NO 117
<211> LENGTH: 851
<212> TYPE: PRT
<213> ORGANISM: Myceliophthora thermophila

<400> SEQUENCE: 117

Ile Glu Ser Arg Lys Val His Gln Lys Pro Leu Ala Arg Ser Glu Pro
        1               5                   10                  15

Phe Tyr Pro Ser Pro Trp Met Asn Pro Asn Ala Asp Gly Trp Ala Glu
                        20                  25                  30

Ala Tyr Ala Gln Ala Lys Ser Phe Val Ser Gln Met Thr Leu Leu Glu
                        35                  40                  45
```

-continued

```
Lys Val Asn Leu Thr Thr Gly Val Gly Trp Gly Ala Glu Gln Cys Val
 50                  55                  60

Gly Gln Val Gly Ala Ile Pro Arg Leu Gly Leu Arg Ser Leu Cys Met
 65                  70                  75                  80

His Asp Ser Pro Leu Gly Ile Arg Gly Ala Asp Tyr Asn Ser Ala Phe
                 85                  90                  95

Pro Ser Gly Gln Thr Val Ala Ala Thr Trp Asp Arg Gly Leu Met Tyr
                100                 105                 110

Arg Arg Gly Tyr Ala Met Gly Gln Glu Ala Lys Gly Lys Gly Ile Asn
                115                 120                 125

Val Leu Leu Gly Pro Val Ala Gly Pro Leu Gly Arg Met Pro Glu Gly
130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
                180                 185                 190

Pro Glu Ala Gln Gly Tyr Gly Tyr Asn Ile Ser Glu Thr Leu Ser Ser
                195                 200                 205

Asn Ile Asp Asp Lys Thr Met His Glu Leu Tyr Leu Trp Pro Phe Ala
210                 215                 220

Asp Ala Val Arg Ala Gly Val Gly Ser Val Met Cys Ser Tyr Gln Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Gln
                260                 265                 270

Ala Gln His Thr Gly Ala Ala Ser Ala Val Ala Gly Leu Asp Met Ser
                275                 280                 285

Met Pro Gly Asp Thr Gln Phe Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Asp Asp Thr
                340                 345                 350

Tyr Gly Pro Ile His Trp Ala Ala Lys Gln Gly Tyr Gln Glu Ile Asn
                355                 360                 365

Ser His Val Asp Val Arg Ala Asp His Gly Asn Leu Ile Arg Glu Ile
370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Ser Ser
                405                 410                 415

Pro Asn Gly Pro Asn Gly Cys Ser Asp Arg Gly Cys Asn Glu Gly Thr
                420                 425                 430

Leu Ala Met Gly Trp Gly Ser Gly Thr Ala Asn Tyr Pro Tyr Leu Val
                435                 440                 445

Ser Pro Asp Ala Ala Leu Gln Ala Arg Ala Ile Gln Asp Gly Thr Arg
450                 455                 460

Tyr Glu Ser Val Leu Ser Asn Tyr Ala Glu Glu Lys Thr Lys Ala Leu
```

```
            465                 470                 475                 480
        Val Ser Gln Ala Asn Ala Thr Ala Ile Val Phe Val Asn Ala Asp Ser
                        485                 490                 495
        Gly Glu Gly Tyr Ile Asn Val Asp Gly Asn Glu Gly Asp Arg Lys Asn
                        500                 505                 510
        Leu Thr Leu Trp Asn Asn Gly Asp Thr Leu Val Lys Asn Val Ser Ser
                        515                 520                 525
        Trp Cys Ser Asn Thr Ile Val Val Ile His Ser Val Gly Pro Val Leu
                        530                 535                 540
        Leu Thr Asp Trp Tyr Asp Asn Pro Asn Ile Thr Ala Ile Leu Trp Ala
        545                 550                 555                 560
        Gly Leu Pro Gly Gln Glu Ser Gly Asn Ser Ile Thr Asp Val Leu Tyr
                        565                 570                 575
        Gly Lys Val Asn Pro Ala Ala Arg Ser Pro Phe Thr Trp Gly Lys Thr
                        580                 585                 590
        Arg Glu Ser Tyr Gly Ala Asp Val Leu Tyr Lys Pro Asn Asn Gly Asn
                        595                 600                 605
        Gly Ala Pro Gln Gln Asp Phe Thr Glu Gly Val Phe Ile Asp Tyr Arg
                        610                 615                 620
        Tyr Phe Asp Lys Val Asp Asp Ser Val Ile Tyr Glu Phe Gly His
        625                 630                 635                 640
        Gly Leu Ser Tyr Thr Thr Phe Glu Tyr Ser Asn Ile Arg Val Val Lys
                        645                 650                 655
        Ser Asn Val Ser Glu Tyr Arg Pro Thr Thr Gly Thr Thr Ala Gln Ala
                        660                 665                 670
        Pro Thr Phe Gly Asn Phe Ser Thr Asp Leu Glu Asp Tyr Leu Phe Pro
                        675                 680                 685
        Lys Asp Glu Phe Pro Tyr Ile Tyr Gln Tyr Ile Tyr Pro Tyr Leu Asn
                        690                 695                 700
        Thr Thr Asp Pro Arg Arg Ala Ser Ala Asp Pro His Tyr Gly Gln Thr
        705                 710                 715                 720
        Ala Glu Glu Phe Leu Pro Pro His Ala Thr Asp Asp Pro Gln Pro
                        725                 730                 735
        Leu Leu Arg Ser Ser Gly Gly Asn Ser Pro Gly Gly Asn Arg Gln Leu
                        740                 745                 750
        Tyr Asp Ile Val Tyr Thr Ile Thr Ala Asp Ile Thr Asn Thr Gly Ser
                        755                 760                 765
        Val Val Gly Glu Glu Val Pro Gln Leu Tyr Val Ser Leu Gly Gly Pro
                        770                 775                 780
        Glu Asp Pro Lys Val Gln Leu Arg Asp Phe Asp Arg Met Arg Ile Glu
        785                 790                 795                 800
        Pro Gly Glu Thr Arg Gln Phe Thr Gly Arg Leu Thr Arg Arg Asp Leu
                        805                 810                 815
        Ser Asn Trp Asp Val Thr Val Gln Asp Trp Val Ile Ser Arg Tyr Pro
                        820                 825                 830
        Lys Thr Ala Tyr Val Gly Arg Ser Ser Arg Lys Leu Asp Leu Lys Ile
                        835                 840                 845
        Glu Leu Pro
            850

<210> SEQ ID NO 118
<211> LENGTH: 2613
<212> TYPE: DNA
<213> ORGANISM: Artificial Sequence
```

<220> FEATURE:
<223> OTHER INFORMATION: Synthetic polynucleotide.

<400> SEQUENCE: 118

| | | | | | |
|---|---|---|---|---|---|
| atgaaggctg | ctgcgctttc | ctgcctcttc | ggcagtaccc | ttgccgttgc | aggcgccatt | 60 |
| gaatcgagaa | aggttcacca | gaagcccctc | gcgagatctg | aaccttttta | cccgtcgcca | 120 |
| tggatgaatc | ccaacgccga | cggctgggcg | gaggcctatg | cccaggccaa | gtcctttgtc | 180 |
| tcccaaatga | ctctgctaga | aaggtcaact | tgaccacgg | gagtcggctg | ggggctgag | 240 |
| cagtgcgtcg | gccaagtggg | cgcgatccct | cgccttggac | ttcgcagtct | gtgcatgcat | 300 |
| gactcccctc | tcggcatccg | aggagccgac | tacaactcag | cgttcccctc | tggccagacc | 360 |
| gttgctgcta | cctgggatcg | cggtctgatg | taccgtcgcg | gctacgcaat | gggccaggag | 420 |
| gccaaaggca | agggcatcaa | tgtccttctc | ggaccagtcg | ccggccccct | tggccgcatg | 480 |
| cccgagggcg | gtcgtaactg | ggaaggcttc | gctccggatc | ccgtccttac | cggcatcggc | 540 |
| atgtccgaga | cgatcaaggg | cattcaggat | gctggcgtca | tcgcttgtgc | gaagcacttt | 600 |
| attggaaacg | agcaggagca | cttcagacag | gtgccagaag | cccagggata | cggttacaac | 660 |
| atcagcgaaa | ccctctcctc | caacattgac | gacaagacca | tgcacgagct | ctacctttgg | 720 |
| ccgtttgccg | atgccgtccg | ggccggcgtc | ggctctgtca | tgtgctcgta | caaccaggtc | 780 |
| aacaactcgt | acgcctgcca | gaactcgaag | ctgctgaacg | acctcctcaa | gaacgagctt | 840 |
| gggtttcagg | gcttcgtcat | gagcgactgg | tgggcacagc | acactggcgc | agcaagcgcc | 900 |
| gtggctggtc | tcgatatgtc | catgccgggc | gacaccatgt | tcaacactgg | cgtcagtttc | 960 |
| tggggcgcca | atctcaccct | cgccgtcctc | aacggcacag | tccctgccta | ccgtctcgac | 1020 |
| gacatggcca | tgcgcatcat | ggccgccctc | ttcaaggtca | ccaagaccac | cgacctggaa | 1080 |
| ccgatcaact | tctccttctg | gacccgcgac | acttatggcc | cgatccactg | ggccgccaag | 1140 |
| cagggctacc | aggagattaa | ttcccacgtt | gacgtccgcg | ccgaccacgg | caacctcatc | 1200 |
| cggaacattg | ccgccaaggg | tacggtgctg | ctgaagaata | ccggctctct | acccctgaac | 1260 |
| aagccaaagt | tcgtggccgt | catcggcgag | gatgctgggc | cgagcccaa | cgggcccaac | 1320 |
| ggctgcagcg | accgcggctg | taacgaaggc | acgctcgcca | tgggctgggg | atccggcaca | 1380 |
| gccaactatc | cgtacctcgt | ttcccccgac | gccgcgctcc | agttgcgggc | catccaggac | 1440 |
| ggcacgaggt | acgagagcgt | cctgtccaac | tacgccgagg | aaaatacaaa | ggctctggtc | 1500 |
| tcgcaggcca | atgcaaccgc | catcgtcttc | gtcaatgccg | actcaggcga | gggctacatc | 1560 |
| aacgtggacg | gtaacgaggg | cgaccgtaag | aacctgactc | tctggaacaa | cggtgatact | 1620 |
| ctggtcaaga | acgtctcgag | ctggtgcagc | aacaccatcg | tcgtcatcca | ctcggtcggc | 1680 |
| ccggtcctcc | tgaccgattg | gtacgacaac | cccaacatca | cggccattct | ctgggctggt | 1740 |
| cttccgggcc | aggagtcggg | caactccatc | accgacgtgc | tttacggcaa | ggtcaacccc | 1800 |
| gccgcccgct | cgcccttcac | ttggggcaag | acccgcgaaa | gctatggcgc | ggacgtcctg | 1860 |
| tacaagccga | ataatggcaa | ttgggcgccc | caacaggact | tcaccgaggg | cgtcttcatc | 1920 |
| gactaccgct | acttcgacaa | ggttgacgat | gactcggtca | tctacgagtt | cggccacggc | 1980 |
| ctgagctaca | ccaccttcga | gtacagcaac | atccgcgtcg | tcaagtccaa | cgtcagcgag | 2040 |
| taccggccca | cgacgggcac | cacgattcag | gccccgacgt | ttggcaactt | ctccaccgac | 2100 |
| ctcgaggact | atctcttccc | caaggacgag | ttccctaca | tcccgcagta | catctacccg | 2160 |
| tacctcaaca | cgaccgaccc | ccggagggcc | tcggccgatc | cccactacgg | ccagaccgcc | 2220 |

```
gaggagttcc tcccgcccca cgccaccgat gacgacccccc agccgctcct ccggtcctcg    2280
ggcggaaact cccccggcgg caaccgccag ctgtacgaca ttgtctacac aatcacggcc    2340
gacatcacga atacgggctc cgttgtaggc gaggaggtac cgcagctcta cgtctcgctg    2400
ggcggtcccg aggatcccaa ggtgcagctg cgcgactttg acaggatgcg gatcgaaccc    2460
ggcgagacga ggcagttcac cggccgcctg acgcgcagag atctgagcaa ctgggacgtc    2520
acggtgcagg actgggtcat cagcaggtat cccaagacgg catatgttgg gaggagcagc    2580
cggaagttgg atctcaagat tgagcttcct tga                                 2613
```

<210> SEQ ID NO 119
<211> LENGTH: 870
<212> TYPE: PRT
<213> ORGANISM: Artificial Sequence
<220> FEATURE:
<223> OTHER INFORMATION: Synthetic polypeptides.

<400> SEQUENCE: 119

```
Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
```

```
                   290                 295                 300
Asp Met Ser Met Pro Gly Asp Thr Met Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Leu Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
    530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
        675                 680                 685

Ile Gln Ala Pro Thr Phe Gly Asn Phe Ser Thr Asp Leu Glu Asp Tyr
    690                 695                 700

Leu Phe Pro Lys Asp Glu Phe Pro Tyr Ile Pro Gln Tyr Ile Tyr Pro
705                 710                 715                 720
```

```
Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
    770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
    850                 855                 860

Leu Lys Ile Glu Leu Pro
865                 870

<210> SEQ ID NO 120
<211> LENGTH: 851
<212> TYPE: PRT
<213> ORGANISM: Artificial Sequence
<220> FEATURE:
<223> OTHER INFORMATION: Synthetic polypeptides.

<400> SEQUENCE: 120

Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Asp Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Gly Ala Glu Gln Cys Val
    50                  55                  60

Gly Gln Val Gly Ala Ile Pro Arg Leu Gly Leu Arg Ser Leu Cys Met
65                  70                  75                  80

His Asp Ser Pro Leu Gly Ile Arg Gly Ala Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
        115                 120                 125

Val Leu Leu Gly Pro Val Ala Gly Pro Leu Gly Arg Met Pro Glu Gly
    130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
        195                 200                 205
```

```
Asn Ile Asp Asp Lys Thr Met His Glu Leu Tyr Leu Trp Pro Phe Ala
            210                 215                 220

Asp Ala Val Arg Ala Gly Val Gly Ser Val Met Cys Ser Tyr Asn Gln
225                 230                 235                 240

Val Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Trp
            260                 265                 270

Ala Gln His Thr Gly Ala Ala Ser Ala Val Ala Gly Leu Asp Met Ser
        275                 280                 285

Met Pro Gly Asp Thr Met Phe Asn Thr Gly Val Ser Phe Trp Gly Ala
290                 295                 300

Asn Leu Thr Leu Ala Val Leu Asn Gly Thr Val Pro Ala Tyr Arg Leu
305                 310                 315                 320

Asp Asp Met Ala Met Arg Ile Met Ala Ala Leu Phe Lys Val Thr Lys
                325                 330                 335

Thr Thr Asp Leu Glu Pro Ile Asn Phe Ser Phe Trp Thr Arg Asp Thr
            340                 345                 350

Tyr Gly Pro Ile His Trp Ala Ala Lys Gln Gly Tyr Gln Glu Ile Asn
        355                 360                 365

Ser His Val Asp Val Arg Ala Asp His Gly Asn Leu Ile Arg Asn Ile
370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Pro Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
        435                 440                 445

Ser Pro Asp Ala Ala Leu Gln Leu Arg Ala Ile Gln Asp Gly Thr Arg
450                 455                 460

Tyr Glu Ser Val Leu Ser Asn Tyr Ala Glu Asn Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Val Ile His Ser Val Gly Pro Val Leu
530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Trp Ala Pro Gln Gln Asp Phe Thr Glu Gly Val Phe Ile Asp Tyr Arg
610                 615                 620
```

| | | | | | | | | | | | |
|---|---|---|---|---|---|---|---|---|---|---|---|
|Tyr|Phe|Asp|Lys|Val|Asp|Asp|Ser|Val|Ile|Tyr|Glu|Phe|Gly|His|
|625| | | | |630| | | |635| | | | |640|

Gly Leu Ser Tyr Thr Thr Phe Glu Tyr Ser Asn Ile Arg Val Val Lys
                    645                 650                 655

Ser Asn Val Ser Glu Tyr Arg Pro Thr Thr Gly Thr Thr Ile Gln Ala
                660                 665                 670

Pro Thr Phe Gly Asn Phe Ser Thr Asp Leu Glu Asp Tyr Leu Phe Pro
            675                 680                 685

Lys Asp Glu Phe Pro Tyr Ile Pro Gln Tyr Ile Tyr Pro Tyr Leu Asn
        690                 695                 700

Thr Thr Asp Pro Arg Arg Ala Ser Ala Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
                740                 745                 750

Tyr Asp Ile Val Tyr Thr Ile Thr Ala Asp Ile Thr Asn Thr Gly Ser
            755                 760                 765

Val Val Gly Glu Glu Val Pro Gln Leu Tyr Val Ser Leu Gly Gly Pro
770                 775                 780

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Arg Asp Leu
                805                 810                 815

Ser Asn Trp Asp Val Thr Val Gln Asp Trp Val Ile Ser Arg Tyr Pro
                820                 825                 830

Lys Thr Ala Tyr Val Gly Arg Ser Ser Arg Lys Leu Asp Leu Lys Ile
            835                 840                 845

Glu Leu Pro
850

<210> SEQ ID NO 121
<211> LENGTH: 2613
<212> TYPE: DNA
<213> ORGANISM: Artificial Sequence
<220> FEATURE:
<223> OTHER INFORMATION: Synthetic polynucleotide.

<400> SEQUENCE: 121

```
atgaaggctg ctgcgctttc ctgcctcttc ggcagtaccc ttgccgttgc aggcgccatt    60
gaatcgagaa aggttcacca gaagcccctc gcgagatctg aaccttttta cccgtcgcca   120
tggatgaatc ccaacgccat cggctgggcg gaggcctatg cccaggccaa gtcctttgtc   180
tcccaaatga ctctgctaga aaggtcaac ttgaccacgg gagtcggctg ggggaggag    240
cagtgcgtcg gcaacgtggg cgcgatccct cgccttggac ttcgcagtct gtgcatgcat   300
gactcccctc tcggcgtgcg aggaaccgac tacaactcag cgttcccctc tggccagacc   360
gttgctgcta cctgggatcg cggtctgatg taccgtcgcg gctacgcaat gggccaggag   420
gccaaaggca agggcatcaa tgtccttctc ggaccagtcg ccggccccct tggccgcatg   480
cccgagggcg gtcgtaactg ggaaggcttc gctccggatc ccgtccttac cggcatcggc   540
atgtccgaga cgatcaaggg cattcaggat gctggcgtca tcgcttgtgc gaagcacttt   600
attggaaacg agcaggagca cttcagacag gtgccagaag cccagggata cggttacaac   660
atcagcgaaa ccctctcctc caacattgac gacaagacca tgcacgagct ctaccttgg   720
```

```
ccgtttgccg atgccgtccg ggccggcgtc ggctctgtca tgtgctcgta caaccagggc    780
aacaactcgt acgcctgcca gaactcgaag ctgctgaacg acctcctcaa gaacgagctt    840
gggtttcagg gcttcgtcat gagcgactgg tgggcacagc acactggcgc agcaagcgcc    900
gtggctggtc tcgatatgtc catgccgggc gacaccatgg tcaacactgg cgtcagtttc    960
tggggcgcca atctcaccct cgccgtcctc aacggcacag tccctgccta ccgtctcgac   1020
gacatgtgca tgcgcatcat ggccgccctc ttcaaggtca ccaagaccac cgacctggaa   1080
ccgatcaact tctccttctg gacccgcgac acttatggcc cgatccactg gccgccaag    1140
cagggctacc aggagattaa ttcccacgtt gacgtccgcg ccgaccacgg caacctcatc   1200
cggaacattg ccgccaaggg tacggtgctg ctgaagaata ccggctctct accccctgaac   1260
aagccaaagt tcgtggccgt catcggcgag gatgctgggc cgagcccaa cgggcccaac    1320
ggctgcagcg accgcggctg taacgaaggc acgctcgcca tgggctgggg atccggcaca   1380
gccaactatc cgtacctcgt ttccccgac gccgcgctcc aggcgcgggc catccaggac    1440
ggcacgaggt acgagagcgt cctgtccaac tacgccgagg aaaatacaaa ggctctggtc   1500
tcgcaggcca atgcaaccgc catcgtcttc gtcaatgccg actcaggcga gggctacatc   1560
aacgtggacg taacgagggc cgaccgtaag aacctgactc tctggaacaa cggtgatact   1620
ctggtcaaga cgtctcgag ctggtgcagc aacaccatcg tcgtcatcca ctcggtcggc    1680
ccggtcctcc tgaccgattg gtacgacaac cccaacatca cggccattct ctgggctggt   1740
cttccgggcc aggagtcggg caactccatc accgacgtgc tttacggcaa ggtcaacccc   1800
gccgcccgct cgcccttcac ttggggcaag acccgcgaaa gctatggcgc ggacgtcctg   1860
tacaagccga ataatggcaa ttgggcgccc caacaggact tcaccgaggg cgtcttcatc   1920
gactaccgct acttcgacaa ggttgacgat gactcggtca tctacgagtt cggccacggc   1980
ctgagctaca ccaccttcga gtacagcaac atccgcgtcg tcaagtccaa cgtcagcgag   2040
taccggccca cgacgggcac cacgattcag gccccgacgt ttggcaactt ctccaccgac   2100
ctcgaggact atctcttccc caaggacgag ttccctaca tcccgcagta catctacccg    2160
tacctcaaca cgaccgaccc ccggagggcc tcgggcgatc cccactacgg ccagaccgcc   2220
gaggagttcc tcccgcccca cgccaccgat gacgaccccc agccgctcct ccggtcctcg   2280
ggcgaaaact cccccggcgg caaccgccag ctgtacgaca ttgtctacac aatcacggcc   2340
gacatcacga atacgggctc cgttgtaggc gaggaggtac cgcagctcta cgtctcgctg   2400
ggcggtcccg aggatcccaa ggtgcagctg cgcgactttg acaggatgcg gatcgaaccc   2460
ggcgagacga ggcagttcac cggccgcctg acgcgcagag atctgagcaa ctgggacgtc   2520
acggtgcagg actgggtcat cagcaggtat cccaagacgg catatgttgg gaggagcagc   2580
cggaagttgg atctcaagat tgagcttcct tga                                2613
```

<210> SEQ ID NO 122
<211> LENGTH: 870
<212> TYPE: PRT
<213> ORGANISM: Artificial Sequence
<220> FEATURE:
<223> OTHER INFORMATION: Synthetic polypeptides.

<400> SEQUENCE: 122

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

```
Ser Glu Pro Phe Tyr Pro Ser Pro Trp Met Asn Pro Asn Ala Ile Gly
        35                  40                  45

Trp Ala Glu Ala Tyr Ala Gln Ala Lys Ser Phe Val Ser Gln Met Thr
 50                  55                  60

Leu Leu Glu Lys Val Asn Leu Thr Thr Gly Val Gly Trp Gly Glu Glu
 65                  70                  75                  80

Gln Cys Val Gly Asn Val Gly Ala Ile Pro Arg Leu Gly Leu Arg Ser
                 85                  90                  95

Leu Cys Met His Asp Ser Pro Leu Gly Val Arg Gly Thr Asp Tyr Asn
                100                 105                 110

Ser Ala Phe Pro Ser Gly Gln Thr Val Ala Ala Thr Trp Asp Arg Gly
            115                 120                 125

Leu Met Tyr Arg Arg Gly Tyr Ala Met Gly Gln Glu Ala Lys Gly Lys
        130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Asn Gln Gly Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Trp Ala Gln His Thr Gly Ala Ala Ser Ala Val Ala Gly Leu
290                 295                 300

Asp Met Ser Met Pro Gly Asp Thr Met Val Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Cys Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Arg Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Asn Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Pro Ser Pro Asn Gly Pro Asn Gly Cys Ser Asp Arg Gly Cys Asn
        435                 440                 445
```

```
Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Asn Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
        515                 520                 525

Arg Lys Asn Leu Thr Leu Trp Asn Asn Gly Asp Thr Leu Val Lys Asn
    530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590

Val Leu Tyr Gly Lys Val Asn Pro Ala Ala Arg Ser Pro Phe Thr Trp
        595                 600                 605

Gly Lys Thr Arg Glu Ser Tyr Gly Ala Asp Val Leu Tyr Lys Pro Asn
    610                 615                 620

Asn Gly Asn Trp Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
            660                 665                 670

Val Val Lys Ser Asn Val Ser Glu Tyr Arg Pro Thr Thr Gly Thr Thr
        675                 680                 685

Ile Gln Ala Pro Thr Phe Gly Asn Phe Ser Thr Asp Leu Glu Asp Tyr
    690                 695                 700

Leu Phe Pro Lys Asp Glu Phe Pro Tyr Ile Pro Gln Tyr Ile Tyr Pro
705                 710                 715                 720

Tyr Leu Asn Thr Thr Asp Pro Arg Arg Ala Ser Gly Asp Pro His Tyr
                725                 730                 735

Gly Gln Thr Ala Glu Glu Phe Leu Pro Pro His Ala Thr Asp Asp Asp
            740                 745                 750

Pro Gln Pro Leu Leu Arg Ser Ser Gly Asn Ser Pro Gly Gly Asn
        755                 760                 765

Arg Gln Leu Tyr Asp Ile Val Tyr Thr Ile Thr Ala Asp Ile Thr Asn
    770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
        835                 840                 845

Arg Tyr Pro Lys Thr Ala Tyr Val Gly Arg Ser Ser Arg Lys Leu Asp
    850                 855                 860

Leu Lys Ile Glu Leu Pro
```

-continued

<210> SEQ ID NO 123
<211> LENGTH: 851
<212> TYPE: PRT
<213> ORGANISM: Artificial Sequence
<220> FEATURE:
<223> OTHER INFORMATION: Synthetic polypeptides.

<400> SEQUENCE: 123

```
Ile Glu Ser Arg Lys Val His Gln Lys Pro Leu Ala Arg Ser Glu Pro
1               5                   10                  15

Phe Tyr Pro Ser Pro Trp Met Asn Pro Asn Ala Ile Gly Trp Ala Glu
            20                  25                  30

Ala Tyr Ala Gln Ala Lys Ser Phe Val Ser Gln Met Thr Leu Leu Glu
        35                  40                  45

Lys Val Asn Leu Thr Thr Gly Val Gly Trp Gly Glu Glu Gln Cys Val
    50                  55                  60

Gly Asn Val Gly Ala Ile Pro Arg Leu Gly Leu Arg Ser Leu Cys Met
65                  70                  75                  80

His Asp Ser Pro Leu Gly Val Arg Gly Thr Asp Tyr Asn Ser Ala Phe
                85                  90                  95

Pro Ser Gly Gln Thr Val Ala Ala Thr Trp Asp Arg Gly Leu Met Tyr
            100                 105                 110

Arg Arg Gly Tyr Ala Met Gly Gln Glu Ala Lys Gly Lys Gly Ile Asn
        115                 120                 125

Val Leu Leu Gly Pro Val Ala Gly Pro Leu Gly Arg Met Pro Glu Gly
    130                 135                 140

Gly Arg Asn Trp Glu Gly Phe Ala Pro Asp Pro Val Leu Thr Gly Ile
145                 150                 155                 160

Gly Met Ser Glu Thr Ile Lys Gly Ile Gln Asp Ala Gly Val Ile Ala
                165                 170                 175

Cys Ala Lys His Phe Ile Gly Asn Glu Gln Glu His Phe Arg Gln Val
            180                 185                 190

Pro Glu Ala Gln Gly Tyr Gly Tyr Asn Ile Ser Glu Thr Leu Ser Ser
        195                 200                 205

Asn Ile Asp Asp Lys Thr Met His Glu Leu Tyr Leu Trp Pro Phe Ala
    210                 215                 220

Asp Ala Val Arg Ala Gly Val Gly Ser Val Met Cys Ser Tyr Asn Gln
225                 230                 235                 240

Gly Asn Asn Ser Tyr Ala Cys Gln Asn Ser Lys Leu Leu Asn Asp Leu
                245                 250                 255

Leu Lys Asn Glu Leu Gly Phe Gln Gly Phe Val Met Ser Asp Trp Trp
            260                 265                 270

Ala Gln His Thr Gly Ala Ala Ser Ala Val Ala Gly Leu Asp Met Ser
        275                 280                 285

Met Pro Gly Asp Thr Met Val Asn Thr Gly Val Ser Phe Trp Gly Ala
    290                 295                 300

Asn Leu Thr Leu Ala Val Leu Asn Gly Thr Val Pro Ala Tyr Arg Leu
305                 310                 315                 320

Asp Asp Met Cys Met Arg Ile Met Ala Ala Leu Phe Lys Val Thr Lys
                325                 330                 335

Thr Thr Asp Leu Glu Pro Ile Asn Phe Ser Phe Trp Thr Arg Asp Thr
            340                 345                 350

Tyr Gly Pro Ile His Trp Ala Ala Lys Gln Gly Tyr Gln Glu Ile Asn
```

```
              355                 360                 365
Ser His Val Asp Val Arg Ala Asp His Gly Asn Leu Ile Arg Asn Ile
370                 375                 380

Ala Ala Lys Gly Thr Val Leu Leu Lys Asn Thr Gly Ser Leu Pro Leu
385                 390                 395                 400

Asn Lys Pro Lys Phe Val Ala Val Ile Gly Glu Asp Ala Gly Pro Ser
                405                 410                 415

Pro Asn Gly Pro Asn Gly Cys Ser Asp Arg Gly Cys Asn Glu Gly Thr
            420                 425                 430

Leu Ala Met Gly Trp Gly Ser Gly Thr Ala Asn Tyr Pro Tyr Leu Val
        435                 440                 445

Ser Pro Asp Ala Ala Leu Gln Ala Arg Ala Ile Gln Asp Gly Thr Arg
    450                 455                 460

Tyr Glu Ser Val Leu Ser Asn Tyr Ala Glu Asn Thr Lys Ala Leu
465                 470                 475                 480

Val Ser Gln Ala Asn Ala Thr Ala Ile Val Phe Val Asn Ala Asp Ser
                485                 490                 495

Gly Glu Gly Tyr Ile Asn Val Asp Gly Asn Glu Gly Asp Arg Lys Asn
            500                 505                 510

Leu Thr Leu Trp Asn Asn Gly Asp Thr Leu Val Lys Asn Val Ser Ser
        515                 520                 525

Trp Cys Ser Asn Thr Ile Val Val Ile His Ser Val Gly Pro Val Leu
    530                 535                 540

Leu Thr Asp Trp Tyr Asp Asn Pro Asn Ile Thr Ala Ile Leu Trp Ala
545                 550                 555                 560

Gly Leu Pro Gly Gln Glu Ser Gly Asn Ser Ile Thr Asp Val Leu Tyr
                565                 570                 575

Gly Lys Val Asn Pro Ala Ala Arg Ser Pro Phe Thr Trp Gly Lys Thr
            580                 585                 590

Arg Glu Ser Tyr Gly Ala Asp Val Leu Tyr Lys Pro Asn Asn Gly Asn
        595                 600                 605

Trp Ala Pro Gln Gln Asp Phe Thr Glu Gly Val Phe Ile Asp Tyr Arg
    610                 615                 620

Tyr Phe Asp Lys Val Asp Asp Ser Val Ile Tyr Glu Phe Gly His
625                 630                 635                 640

Gly Leu Ser Tyr Thr Thr Phe Glu Tyr Ser Asn Ile Arg Val Val Lys
                645                 650                 655

Ser Asn Val Ser Glu Tyr Arg Pro Thr Thr Gly Thr Thr Ile Gln Ala
            660                 665                 670

Pro Thr Phe Gly Asn Phe Ser Thr Asp Leu Glu Asp Tyr Leu Phe Pro
        675                 680                 685

Lys Asp Glu Phe Pro Tyr Ile Pro Gln Tyr Ile Tyr Pro Tyr Leu Asn
    690                 695                 700

Thr Thr Asp Pro Arg Arg Ala Ser Gly Asp Pro His Tyr Gly Gln Thr
705                 710                 715                 720

Ala Glu Glu Phe Leu Pro Pro His Ala Thr Asp Asp Pro Gln Pro
                725                 730                 735

Leu Leu Arg Ser Ser Gly Gly Asn Ser Pro Gly Gly Asn Arg Gln Leu
            740                 745                 750

Tyr Asp Ile Val Tyr Thr Ile Thr Ala Asp Ile Thr Asn Thr Gly Ser
        755                 760                 765

Val Val Gly Glu Glu Val Pro Gln Leu Tyr Val Ser Leu Gly Gly Pro
    770                 775                 780
```

Glu Asp Pro Lys Val Gln Leu Arg Asp Phe Asp Arg Met Arg Ile Glu
785                 790                 795                 800

Pro Gly Glu Thr Arg Gln Phe Thr Gly Arg Leu Thr Arg Asp Leu
            805                 810                 815

Ser Asn Trp Asp Val Thr Val Gln Asp Trp Val Ile Ser Arg Tyr Pro
        820                 825                 830

Lys Thr Ala Tyr Val Gly Arg Ser Ser Arg Lys Leu Asp Leu Lys Ile
        835                 840                 845

Glu Leu Pro
    850

<210> SEQ ID NO 124
<211> LENGTH: 1368
<212> TYPE: DNA
<213> ORGANISM: Talaromyces emersonii

<400> SEQUENCE: 124

```
atgcttcgac gggctcttct tctatcctct tccgccatcc ttgctgtcaa ggcacagcag      60
gccggcacgg cgacggcaga gaaccacccg cccctgacat ggcaggaatg caccgcccct     120
gggagctgca ccacccagaa cggggcggtc gttcttgatg cgaactggcg ttgggtgcac     180
gatgtgaacg gatacaccaa ctgctacacg gcaatacct gggaccccac gtactgccct      240
gacgacgaaa cctgcgccca gaactgtgcg ctggacggcg cggattacga gggcacctac     300
ggcgtgactt cgtcgggcag ctccttgaaa ctcaatttcg tcaccgggtc gaacgtcgga     360
tcccgtctct acctgctgca ggacgactcg acctatcaga tcttcaagct tctgaaccgc     420
gagttcagct ttgacgtcga tgtctccaat cttccgtgcg gattgaacgg cgctctgtac     480
tttgtcgcca tggacgccga cggcggcgtg tccaagtacc cgaacaacaa ggctggtgcc     540
aagtacggaa ccgggtattg cgactcccaa tgcccacggg acctcaagtt catcgacggc     600
gaggccaacg tcgagggctg gcagccgtct cgaacaacg ccaacaccgg aattggcgac      660
cacggctcct gctgtgcgga gatggatgtc tgggaagcaa acagcatctc caatgcggtc     720
actccgcacc cgtgcgacac gccaggccag acgatgtgct ctggagatga ctgcggtggc     780
acatactcta acgatcgcta cgcgggaacc tgcgatcctg acggctgtga cttcaacct      840
taccgcatgg gcaacacttc tttctacggg cctggcaaga tcatcgatac caccaagccc     900
ttcactgtcg tgacgcagtt cctcactgat gatggtacgg atactggaac tctcagcgag     960
atcaagcgct tctacatcca gaacagcaac gtcattccgc agcccaactc ggacatcagt    1020
ggcgtgaccg gcaactcgat cacgacggag ttctgcactg ctcagaagca ggcctttggc    1080
gacacggacg acttctctca gcacggtggc ctggccaaga tgggagcggc catgcagcag    1140
ggtatggtcc tggtgatgag tttgtgggac gactacgccg cgcagatgct gtggttggat    1200
tccgactacc cgacggatgc ggaccccacg acccctggta ttgcccgtgg aacgtgtccg    1260
acggactcgg gcgtcccatc ggatgtcgag tcgcagagcc ccaactccta cgtgacctac    1320
tcgaacatta gtttggtcc gatcaactcg accttcaccg cttcgtga              1368
```

<210> SEQ ID NO 125
<211> LENGTH: 455
<212> TYPE: PRT
<213> ORGANISM: Talaromyces emersonii

<400> SEQUENCE: 125

Met Leu Arg Arg Ala Leu Leu Leu Ser Ser Ser Ala Ile Leu Ala Val

-continued

```
1               5                   10                  15
Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
                35                  40                  45

Ala Val Val Leu Asp Ala Asn Trp Arg Trp Val His Asp Val Asn Gly
 50                  55                  60

Tyr Thr Asn Cys Tyr Thr Gly Asn Thr Trp Asp Pro Thr Tyr Cys Pro
 65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
                100                 105                 110

Phe Val Thr Gly Ser Asn Val Gly Ser Arg Leu Tyr Leu Leu Gln Asp
                115                 120                 125

Asp Ser Thr Tyr Gln Ile Phe Lys Leu Leu Asn Arg Glu Phe Ser Phe
130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
                180                 185                 190

Arg Asp Leu Lys Phe Ile Asp Gly Glu Ala Asn Val Glu Gly Trp Gln
                195                 200                 205

Pro Ser Ser Asn Asn Ala Asn Thr Gly Ile Gly Asp His Gly Ser Cys
210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
                260                 265                 270

Pro Asp Gly Cys Asp Phe Asn Pro Tyr Arg Met Gly Asn Thr Ser Phe
                275                 280                 285

Tyr Gly Pro Gly Lys Ile Ile Asp Thr Thr Lys Pro Phe Thr Val Val
                290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
                340                 345                 350

Thr Ala Gln Lys Gln Ala Phe Gly Asp Thr Asp Phe Ser Gln His
                355                 360                 365

Gly Gly Leu Ala Lys Met Gly Ala Ala Met Gln Gln Gly Met Val Leu
                370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
                420                 425                 430
```

Ser Pro Asn Ser Tyr Val Thr Tyr Ser Asn Ile Lys Phe Gly Pro Ile
        435                 440                 445

Asn Ser Thr Phe Thr Ala Ser
    450                 455

<210> SEQ ID NO 126
<211> LENGTH: 437
<212> TYPE: PRT
<213> ORGANISM: Talaromyces emersonii

<400> SEQUENCE: 126

Gln Gln Ala Gly Thr Ala Thr Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Ala Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
            180                 185                 190

Ser Asn Asn Ala Asn Thr Gly Ile Gly Asp His Gly Ser Cys Cys Ala
        195                 200                 205

Glu Met Asp Val Trp Glu Ala Asn Ser Ile Ser Asn Ala Val Thr Pro
    210                 215                 220

His Pro Cys Asp Thr Pro Gly Gln Thr Met Cys Ser Gly Asp Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly

```
                340             345             350
Leu Ala Lys Met Gly Ala Ala Met Gln Gln Gly Met Val Leu Val Met
            355                 360                 365

Ser Leu Trp Asp Asp Tyr Ala Ala Gln Met Leu Trp Leu Asp Ser Asp
        370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Asn Ser
                420                 425                 430

Thr Phe Thr Ala Ser
        435

<210> SEQ ID NO 127
<211> LENGTH: 1581
<212> TYPE: DNA
<213> ORGANISM: Myceliophthora thermophila

<400> SEQUENCE: 127
atgtacgcca agttcgcgac cctcgccgcc cttgtggctg gcgccgctgc tcagaacgcc      60
tgcactctga ccgctgagaa ccaccccctcg ctgacgtggt ccaagtgcac gtctggcggc    120
agctgcacca gcgtccaggg ttccatcacc atcgacgcca actggcggtg gactcaccgg    180
accgatagcg ccaccaactg ctacgagggc aacaagtggg atacttcgta ctgcagcgat    240
ggtccttctt gcgcctccaa gtgctgcatc gacggcgctg actactcgag cacctatggc    300
atcaccacga gcggtaactc cctgaacctc aagttcgtca ccaagggcca gtactcgacc    360
aacatcggct cgcgtaccta cctgatggag agcgacacca gtaccagat gttccagctc    420
ctcggcaacg agttcacctt cgatgtcgac gtctccaacc tcggctgcgg cctcaatggc    480
gccctctact tcgtgtccat ggatgccgat ggtggcatgt ccaagtactc gggcaacaag    540
gcaggtgcca agtacggtac cggctactgt gattctcagt gccccgcgga cctcaagttc    600
atcaacggcg aggccaacgt agagaactgg cagagctcga ccaacgatgc caacgccggc    660
acgggcaagt acggcagctg ctgctccgag atggacgtct gggaggccaa caacatggcc    720
gccgccttca ctccccaccc ttgcaccgtg atcggccagt cgcgctgcga gggcgactcg    780
tgcggcggta cctacagcac cgaccgctat gccggcatct gcgaccccga cggatgcgac    840
ttcaactcgt accgccaggg caacaagacc ttctacggca agggcatgac ggtcgacacg    900
accaagaaga tcacggtcgt cacccagttc ctcaagaact cggccggcga gctctccgag    960
atcaagcggt tctacgtcca gaacggcaag gtcatcccca ctccgagtc caccatcccg   1020
ggcgtcgagg gcaactccat cacccaggac tggtgcgacc gccagaaggc cgccttcggc   1080
gacgtgaccg acttccagga caagggcggc atggtccaga tgggcaaggc cctcgcgggg   1140
cccatggtcc tcgtcatgtc catctgggac gaccacgccg tcaacatgct ctggctcgac   1200
tccacctggc ccatcgacgg cgccggcaag ccgggcgccg agcgcggtgc ctgccccacc   1260
acctcgggcg tccccgctga ggtcgaggcc gaggcccca actccaacgt catcttctcc   1320
aacatccgct tcggccccat cggctccacc gtctccggcc tgcccgacgg cggcagcggc   1380
aaccccaacc cgcccgtcag ctcgtccacc ccggtcccct cctcgtccac cacatcctcc   1440
ggttcctccg gcccgactgg cggcacgggt gtcgctaagc actatgagca atgcggagga   1500
atcgggttca ctggccctac ccagtgcgag agcccctaca cttgcaccaa gctgaatgac   1560
```

```
tggtactcgc agtgcctgta a                                              1581
```

<210> SEQ ID NO 128
<211> LENGTH: 526
<212> TYPE: PRT
<213> ORGANISM: Myceliophthora thermophila

<400> SEQUENCE: 128

| | | | | | | | | | | | | | | |
|---|---|---|---|---|---|---|---|---|---|---|---|---|---|---|
| Met | Tyr | Ala | Lys | Phe | Ala | Thr | Leu | Ala | Ala | Leu | Val | Ala | Gly | Ala |
| 1 | | | | 5 | | | | | 10 | | | | | 15 |
| Ala | Gln | Asn | Ala | Cys | Thr | Leu | Thr | Ala | Glu | Asn | His | Pro | Ser | Leu | Thr |
| | | | 20 | | | | | 25 | | | | | 30 | | |
| Tyr | Ser | Lys | Cys | Thr | Ser | Gly | Gly | Ser | Cys | Thr | Ser | Val | Gln | Gly | Ser |
| | | | 35 | | | | 40 | | | | | 45 | | | |
| Ile | Thr | Ile | Asp | Ala | Asn | Trp | Arg | Trp | Thr | His | Arg | Thr | Asp | Ser | Ala |
| | 50 | | | | | 55 | | | | | 60 | | | | |
| Thr | Asn | Cys | Tyr | Glu | Gly | Asn | Lys | Trp | Asp | Thr | Ser | Trp | Cys | Ser | Asp |
| 65 | | | | | 70 | | | | | 75 | | | | | 80 |
| Gly | Pro | Ser | Cys | Ala | Ser | Lys | Cys | Cys | Ile | Asp | Gly | Ala | Asp | Tyr | Ser |
| | | | | 85 | | | | | 90 | | | | | 95 | |
| Ser | Thr | Tyr | Gly | Ile | Thr | Thr | Ser | Gly | Asn | Ser | Leu | Asn | Leu | Lys | Phe |
| | | | 100 | | | | | 105 | | | | | 110 | | |
| Val | Thr | Lys | Gly | Gln | Tyr | Ser | Thr | Asn | Ile | Gly | Ser | Arg | Thr | Tyr | Leu |
| | | | 115 | | | | | 120 | | | | | 125 | | |
| Met | Glu | Ser | Asp | Thr | Lys | Tyr | Gln | Met | Phe | Gln | Leu | Leu | Gly | Asn | Glu |
| | 130 | | | | | 135 | | | | | 140 | | | | |
| Phe | Thr | Phe | Asp | Val | Asp | Val | Ser | Asn | Leu | Gly | Cys | Gly | Leu | Asn | Gly |
| 145 | | | | | 150 | | | | | 155 | | | | | 160 |
| Ala | Leu | Tyr | Phe | Val | Ser | Met | Asp | Ala | Asp | Gly | Gly | Met | Ser | Lys | Tyr |
| | | | | 165 | | | | | 170 | | | | | 175 | |
| Ser | Gly | Asn | Lys | Ala | Gly | Ala | Lys | Tyr | Gly | Thr | Gly | Tyr | Cys | Asp | Ser |
| | | | 180 | | | | | 185 | | | | | 190 | | |
| Gln | Cys | Pro | Arg | Asp | Leu | Lys | Phe | Ile | Asn | Gly | Glu | Ala | Asn | Val | Glu |
| | | | 195 | | | | | 200 | | | | | 205 | | |
| Asn | Trp | Gln | Ser | Ser | Thr | Asn | Asp | Ala | Asn | Ala | Gly | Thr | Gly | Lys | Tyr |
| | 210 | | | | | 215 | | | | | 220 | | | | |
| Gly | Ser | Cys | Cys | Ser | Glu | Met | Asp | Val | Trp | Glu | Ala | Asn | Asn | Met | Ala |
| 225 | | | | | 230 | | | | | 235 | | | | | 240 |
| Ala | Ala | Phe | Thr | Pro | His | Pro | Cys | Thr | Val | Ile | Gly | Gln | Ser | Arg | Cys |
| | | | | 245 | | | | | 250 | | | | | 255 | |
| Glu | Gly | Asp | Ser | Cys | Gly | Gly | Thr | Tyr | Ser | Thr | Asp | Arg | Tyr | Ala | Gly |
| | | | 260 | | | | | 265 | | | | | 270 | | |
| Ile | Cys | Asp | Pro | Asp | Gly | Cys | Asp | Phe | Asn | Ser | Tyr | Arg | Gln | Gly | Asn |
| | | | 275 | | | | | 280 | | | | | 285 | | |
| Lys | Thr | Phe | Tyr | Gly | Lys | Gly | Met | Thr | Val | Asp | Thr | Thr | Lys | Lys | Ile |
| | 290 | | | | | 295 | | | | | 300 | | | | |
| Thr | Val | Val | Thr | Gln | Phe | Leu | Lys | Asn | Ser | Ala | Gly | Glu | Leu | Ser | Glu |
| 305 | | | | | 310 | | | | | 315 | | | | | 320 |
| Ile | Lys | Arg | Phe | Tyr | Val | Gln | Asn | Gly | Lys | Val | Ile | Pro | Asn | Ser | Glu |
| | | | | 325 | | | | | 330 | | | | | 335 | |
| Ser | Thr | Ile | Pro | Gly | Val | Glu | Gly | Asn | Ser | Ile | Thr | Gln | Asp | Trp | Cys |
| | | | 340 | | | | | 345 | | | | | 350 | | |
| Asp | Arg | Gln | Lys | Ala | Ala | Phe | Gly | Asp | Val | Thr | Asp | Phe | Gln | Asp | Lys |
| | | | 355 | | | | | 360 | | | | | 365 | | |

Gly Gly Met Val Gln Met Gly Lys Ala Leu Ala Gly Pro Met Val Leu
        370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                    405                 410                 415

Ala Cys Pro Thr Thr Ser Gly Val Pro Ala Glu Val Glu Ala Glu Ala
                420                 425                 430

Pro Asn Ser Asn Val Ile Phe Ser Asn Ile Arg Phe Gly Pro Ile Gly
            435                 440                 445

Ser Thr Val Ser Gly Leu Pro Asp Gly Ser Gly Asn Pro Asn Pro
        450                 455                 460

Pro Val Ser Ser Thr Pro Val Pro Ser Ser Thr Thr Ser Ser
465                 470                 475                 480

Gly Ser Ser Gly Pro Thr Gly Thr Gly Val Ala Lys His Tyr Glu
                    485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
        515                 520                 525

<210> SEQ ID NO 129
<211> LENGTH: 509
<212> TYPE: PRT
<213> ORGANISM: Myceliophthora thermophila

<400> SEQUENCE: 129

Gln Asn Ala Cys Thr Leu Thr Ala Glu Asn His Pro Ser Leu Thr Tyr
1               5                   10                  15

Ser Lys Cys Thr Ser Gly Gly Ser Cys Thr Ser Val Gln Gly Ser Ile
                20                  25                  30

Thr Ile Asp Ala Asn Trp Arg Trp Thr His Arg Thr Asp Ser Ala Thr
            35                  40                  45

Asn Cys Tyr Glu Gly Asn Lys Trp Asp Thr Ser Trp Cys Ser Asp Gly
        50                  55                  60

Pro Ser Cys Ala Ser Lys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala

```
                210              215                 220
Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
                260                 265                 270

Thr Phe Tyr Gly Lys Gly Met Thr Val Asp Thr Thr Lys Lys Ile Thr
            275                 280                 285

Val Val Thr Gln Phe Leu Lys Asn Ser Ala Gly Glu Leu Ser Glu Ile
        290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
                340                 345                 350

Gly Met Val Gln Met Gly Lys Ala Leu Ala Gly Pro Met Val Leu Val
            355                 360                 365

Met Ser Ile Trp Asp Asp His Ala Val Asn Met Leu Trp Leu Asp Ser
        370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
                420                 425                 430

Thr Val Ser Gly Leu Pro Asp Gly Gly Ser Gly Asn Pro Asn Pro Pro
            435                 440                 445

Val Ser Ser Ser Thr Pro Val Pro Ser Ser Ser Thr Thr Ser Ser Gly
        450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
                500                 505
```

<210> SEQ ID NO 130
<211> LENGTH: 1581
<212> TYPE: DNA
<213> ORGANISM: Artificial Sequence
<220> FEATURE:
<223> OTHER INFORMATION: Synthetic polynucleotide.

<400> SEQUENCE: 130

```
atgtacgcca agttcgcgac cctcgccgcc cttgtggctg gcgccgctgc tcagaacgcc    60
tgcactctga ccgctgagaa ccacccctcg ctgacgtggt ccaagtgcac gtctggcggc   120
agctgcacca gcgtccaggg ttccatcacc atcgacgcca actggcggtg gactcaccgg   180
accgatagcg ccaccaactg ctacgagggc aacaagtggg atacttcgtg gtgcagcgat   240
ggtccttctt gcgcctccaa gtgctgcatc gacggcgctg actactcgag cacctatggc   300
atcaccacga gcgtaactc cctgaacctc aagttcgtca ccagggca gtactcgacc   360 aacatcggct cgcgtaccta cctgatggag agcgacacca gtaccagat gttccagctc   420
```

```
ctcggcaacg agttcacctt cgatgtcgac gtctccaacc tcggctgcgg cctcaatggc    480
gccctctact tcgtgtccat ggatgccgat ggtggcatgt ccaagtactc gggcaacaag    540
gcaggtgcca agtacggtac cggctactgt gattctcagt gccccgcga cctcaagttc    600
atcaacggcg aggccaacgt agagaactgg cagagctcga ccaacgatgc caacgccggc    660
acgggcaagt acggcagctg ctgctccgag atggacgtct gggaggccaa caacatggcc    720
gccgccttca ctccccaccc ttgcaccgtg atcggccagt cgcgctgcga gggcgactcg    780
tgcggcggta cctacagcac cgaccgctat gccggcatct gcgaccccga cggatgcgac    840
ttcaactcgt accgccaggg caacaagacc ttctacggca agggcatgac ggtcgacacg    900
accaagaaga tcacggtcgt cacccagttc ctcaagaact cggccggcga gctctccgag    960
atcaagcggt tctacgtcca gaacggcaag gtcatcccca actccgagtc caccatcccg   1020
ggcgtcgagg gcaactccat cacccaggac tggtgcgacc gccagaaggc cgccttcggc   1080
gacgtgaccg acttccagga caagggcggc atggtccaga tgggcaaggc cctcgcgggg   1140
cccatggtcc tcgtcatgtc catctgggac gaccacgccg tcaacatgct ctggctcgac   1200
tccacctggc ccatcgacgg cgccggcaag ccgggcgccg agcgcggtgc ctgccccacc   1260
acctcgggcg tccccgctga ggtcgaggcc gaggccccca actccaacgt catcttctcc   1320
aacatccgct tcgccccat cggctccacc gtctccggcc tgcccgacgg cggcagcggc   1380
aaccccaacc cgcccgtcag ctcgtccacc ccggtccccc tcgtccac cacatcctcc    1440
ggttcctccg gcccgactgg cggcacgggt gtcgctaagc actatgagca atgcggagga   1500
atcgggttca ctggccctac ccagtgcgag agcccctaca cttgcaccaa gctgaatgac   1560
tggtactcgc agtgcctgta a                                             1581
```

<210> SEQ ID NO 131
<211> LENGTH: 526
<212> TYPE: PRT
<213> ORGANISM: Artificial Sequence
<220> FEATURE:
<223> OTHER INFORMATION: Synthetic polypeptides.

<400> SEQUENCE: 131

```
Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Trp Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
```

```
            145                 150                 155                 160
Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
                180                 185                 190

Gln Cys Pro Arg Asp Leu Lys Phe Ile Asn Gly Glu Ala Asn Val Glu
                195                 200                 205

Asn Trp Gln Ser Ser Thr Asn Asp Ala Asn Ala Gly Thr Gly Lys Tyr
210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
                260                 265                 270

Ile Cys Asp Pro Asp Gly Cys Asp Phe Asn Ser Tyr Arg Gln Gly Asn
                275                 280                 285

Lys Thr Phe Tyr Gly Lys Gly Met Thr Val Asp Thr Lys Lys Ile
                290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
                340                 345                 350

Asp Arg Gln Lys Ala Ala Phe Gly Asp Val Thr Asp Phe Gln Asp Lys
                355                 360                 365

Gly Gly Met Val Gln Met Gly Lys Ala Leu Ala Gly Pro Met Val Leu
                370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
                420                 425                 430

Pro Asn Ser Asn Val Ile Phe Ser Asn Ile Arg Phe Gly Pro Ile Gly
                435                 440                 445

Ser Thr Val Ser Gly Leu Pro Asp Gly Ser Gly Asn Pro Asn Pro
450                 455                 460

Pro Val Ser Ser Ser Thr Pro Val Pro Ser Ser Ser Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
                515                 520                 525
```

<210> SEQ ID NO 132
<211> LENGTH: 509
<212> TYPE: PRT
<213> ORGANISM: Artificial Sequence
<220> FEATURE:
<223> OTHER INFORMATION: Synthetic polypeptides.

```
<400> SEQUENCE: 132

Gln Asn Ala Cys Thr Leu Thr Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Trp Cys Ser Asp Gly
    50                  55                  60

Pro Ser Cys Ala Ser Lys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190

Trp Gln Ser Ser Thr Asn Asp Ala Asn Ala Gly Thr Gly Lys Tyr Gly
        195                 200                 205

Ser Cys Cys Ser Glu Met Asp Val Trp Glu Ala Asn Asn Met Ala Ala
    210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Thr Lys Lys Ile Thr
        275                 280                 285

Val Val Thr Gln Phe Leu Lys Asn Ser Ala Gly Glu Leu Ser Glu Ile
    290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Asp Trp Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Val Asn Met Leu Trp Leu Asp Ser
    370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415
```

```
Asn Ser Asn Val Ile Phe Ser Asn Ile Arg Phe Gly Pro Ile Gly Ser
                420                 425                 430

Thr Val Ser Gly Leu Pro Asp Gly Ser Gly Asn Pro Asn Pro Pro
            435                 440                 445

Val Ser Ser Thr Pro Val Pro Ser Ser Thr Thr Ser Ser Gly
450                 455                 460

Ser Ser Gly Pro Thr Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 133
<211> LENGTH: 1581
<212> TYPE: DNA
<213> ORGANISM: Artificial Sequence
<220> FEATURE:
<223> OTHER INFORMATION: Synthetic polynucleotide.

<400> SEQUENCE: 133
```

| | | | | | |
|---|---|---|---|---|---|
| atgtacgcca | agttcgcgac | cctcgccgcc | cttgtggctg | gcgccgctgc | tcagaacgcc | 60 |
| tgcactctga | cgctgagaa | ccaccctcg | ctgacgtggt | ccaagtgcac | gtctggcggc | 120 |
| agctgcacca | gcgtccaggg | ttccatcacc | atcgacgcca | actggcggtg | gactcaccgg | 180 |
| accgatagcg | ccaccaactg | ctacgagggc | aacaagtggg | atacttcgta | ctgcagcgat | 240 |
| ggtccttctt | gcgcctccaa | gtgctgcatc | gacggcgctg | actactcgag | cacctatggc | 300 |
| atcaccacga | gcgttaactc | cctgaacctc | aagttcgtca | ccaagggcca | gtactcgacc | 360 |
| aacatcggct | cgcgtaccta | cctgatggag | agcgacacca | gtaccagat | gttccagctc | 420 |
| ctcggcaacg | agttcacctt | cgatgtcgac | gtctccaacc | tcggctgcgg | cctcaatggc | 480 |
| gccctctact | tcgtgtccat | ggatgccgat | ggtggcatgt | ccaagtactc | gggcaacaag | 540 |
| gcaggtgcca | gtacggtac | cggctactgt | gattctcagt | gccccgcga | cctcaagttc | 600 |
| atcaacggcg | aggccaacgt | agagaactgg | cagagctcga | ccaacgatgc | caacgccggc | 660 |
| acgggcaagt | acggcagctg | ctgctccgag | atgacgtct | gggaggccaa | caacatggcc | 720 |
| gccgccttca | ctccccaccc | ttgcaccgtg | atcggccagt | cgcgctgcga | gggcgactcg | 780 |
| tgcggcggta | cctacagcac | cgaccgctat | gccggcatct | gcgaccccga | cggatgcgac | 840 |
| ttcaactcgt | accgccaggg | caacaagacc | ttctacggca | agggcatgac | ggtcgacacg | 900 |
| accaagaaga | tcacggtcgt | cacccagttc | ctcaagaact | cggccggcga | gctctccgag | 960 |
| atcaagcggt | tctacgtcca | gaacggcaag | gtcatcccca | ctccgagtc | caccatcccg | 1020 |
| ggcgtcgagg | gcaactccat | cacccaggag | tactgcgacc | gccagaaggc | cgccttcggc | 1080 |
| gacgtgaccg | acttccagga | caagggcggc | atggtccaga | tgggcaaggc | cctcgcgggg | 1140 |
| cccatggtcc | tcgtcatgtc | catctgggac | gaccacgccg | acaacatgct | ctggctcgac | 1200 |
| tccacctggc | ccatcgacgg | cgccggcaag | ccgggcgccg | agcgcggtgc | ctgccccacc | 1260 |
| acctcgggcg | tccccgctga | ggtcgaggcc | gaggcccca | actccaacgt | catcttctcc | 1320 |
| aacatccgct | tcggccccat | cggctccacc | gtctccggcc | tgcccgacgg | cggcagcggc | 1380 |
| aaccccaacc | cgcccgtcag | ctcgtccacc | ccggtcccct | cctcgtccac | cacatcctcc | 1440 |
| ggttcctccg | gcccgactgg | cggcacgggt | gtcgctaagc | actatgagca | atgcggagga | 1500 |

```
atcgggttca ctggccctac ccagtgcgag agcccctaca cttgcaccaa gctgaatgac   1560
tggtactcgc agtgcctgta a                                              1581
```

<210> SEQ ID NO 134
<211> LENGTH: 526
<212> TYPE: PRT
<213> ORGANISM: Artificial Sequence
<220> FEATURE:
<223> OTHER INFORMATION: Synthetic polypeptides.

<400> SEQUENCE: 134

```
Met Tyr Ala Lys Phe Ala Thr Leu Ala Ala Leu Val Ala Gly Ala Ala
1               5                   10                  15

Ala Gln Asn Ala Cys Thr Leu Asn Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Thr Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285

Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Glu Tyr Cys
            340                 345                 350
```

-continued

```
Asp Arg Gln Lys Ala Ala Phe Gly Asp Val Thr Asp Phe Gln Asp Lys
            355                 360                 365

Gly Gly Met Val Gln Met Gly Lys Ala Leu Ala Gly Pro Met Val Leu
        370                 375                 380

Val Met Ser Ile Trp Asp Asp His Ala Asp Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
                420                 425                 430

Pro Asn Ser Asn Val Ile Phe Ser Asn Ile Arg Phe Gly Pro Ile Gly
            435                 440                 445

Ser Thr Val Ser Gly Leu Pro Asp Gly Ser Gly Asn Pro Asn Pro
            450                 455                 460

Pro Val Ser Ser Thr Pro Val Pro Ser Ser Thr Thr Ser Ser
465                 470                 475                 480

Gly Ser Ser Gly Pro Thr Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
            515                 520                 525

<210> SEQ ID NO 135
<211> LENGTH: 509
<212> TYPE: PRT
<213> ORGANISM: Artificial Sequence
<220> FEATURE:
<223> OTHER INFORMATION: Synthetic polypeptides.

<400> SEQUENCE: 135

Gln Asn Ala Cys Thr Leu Asn Ala Glu Asn His Pro Ser Leu Thr Trp
1               5                   10                  15

Ser Lys Cys Thr Ser Gly Gly Ser Cys Thr Ser Val Gln Gly Ser Ile
            20                  25                  30

Thr Ile Asp Ala Asn Trp Arg Trp Thr His Arg Thr Asp Ser Ala Thr
        35                  40                  45

Asn Cys Tyr Glu Gly Asn Lys Trp Asp Thr Ser Tyr Cys Ser Asp Gly
    50                  55                  60

Pro Ser Cys Ala Ser Lys Cys Cys Ile Asp Gly Ala Asp Tyr Ser Ser
65                  70                  75                  80

Thr Tyr Gly Ile Thr Thr Ser Gly Asn Ser Leu Asn Leu Lys Phe Val
                85                  90                  95

Thr Lys Gly Gln Tyr Ser Thr Asn Ile Gly Ser Arg Thr Tyr Leu Met
            100                 105                 110

Glu Ser Asp Thr Lys Tyr Gln Met Phe Gln Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Glu Ala Asn Val Glu Asn
            180                 185                 190
```

Trp Gln Ser Ser Thr Asn Asp Ala Asn Ala Gly Thr Gly Lys Tyr Gly
            195                 200                 205

Ser Cys Cys Ser Glu Met Asp Val Trp Glu Ala Asn Asn Met Ala Ala
    210                 215                 220

Ala Phe Thr Pro His Pro Cys Thr Val Ile Gly Gln Ser Arg Cys Glu
225                 230                 235                 240

Gly Asp Ser Cys Gly Gly Thr Tyr Ser Thr Asp Arg Tyr Ala Gly Ile
                245                 250                 255

Cys Asp Pro Asp Gly Cys Asp Phe Asn Ser Tyr Arg Gln Gly Asn Lys
            260                 265                 270

Thr Phe Tyr Gly Lys Gly Met Thr Val Asp Thr Lys Lys Ile Thr
        275                 280                 285

Val Val Thr Gln Phe Leu Lys Asn Ser Ala Gly Glu Leu Ser Glu Ile
    290                 295                 300

Lys Arg Phe Tyr Val Gln Asn Gly Lys Val Ile Pro Asn Ser Glu Ser
305                 310                 315                 320

Thr Ile Pro Gly Val Glu Gly Asn Ser Ile Thr Gln Glu Tyr Cys Asp
                325                 330                 335

Arg Gln Lys Ala Ala Phe Gly Asp Val Thr Asp Phe Gln Asp Lys Gly
            340                 345                 350

Gly Met Val Gln Met Gly Lys Ala Leu Ala Gly Pro Met Val Leu Val
        355                 360                 365

Met Ser Ile Trp Asp Asp His Ala Asp Asn Met Leu Trp Leu Asp Ser
    370                 375                 380

Thr Trp Pro Ile Asp Gly Ala Gly Lys Pro Gly Ala Glu Arg Gly Ala
385                 390                 395                 400

Cys Pro Thr Thr Ser Gly Val Pro Ala Glu Val Glu Ala Glu Ala Pro
                405                 410                 415

Asn Ser Asn Val Ile Phe Ser Asn Ile Arg Phe Gly Pro Ile Gly Ser
            420                 425                 430

Thr Val Ser Gly Leu Pro Asp Gly Gly Ser Gly Asn Pro Asn Pro Pro
        435                 440                 445

Val Ser Ser Ser Thr Pro Val Pro Ser Ser Ser Thr Thr Ser Ser Gly
    450                 455                 460

Ser Ser Gly Pro Thr Gly Gly Thr Gly Val Ala Lys His Tyr Glu Gln
465                 470                 475                 480

Cys Gly Gly Ile Gly Phe Thr Gly Pro Thr Gln Cys Glu Ser Pro Tyr
                485                 490                 495

Thr Cys Thr Lys Leu Asn Asp Trp Tyr Ser Gln Cys Leu
            500                 505

<210> SEQ ID NO 136
<211> LENGTH: 1449
<212> TYPE: DNA
<213> ORGANISM: Myceliophthora thermophila

<400> SEQUENCE: 136
atggccaaga agcttttcat caccgccgcg cttgcggctg ccgtgttggc ggccccgtc      60 attgaggagc gccagaactg cggcgctgtg tggactcaat gcggcggtaa cgggtggcaa     120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300

```
acgcccccgc ccgtctccag ccccgtgacc agcattcccg gcggtgcgac ctccacggcg    360
agctactctg gcaaccccTT ctcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtccagactc tgtcccaggt ccgggctctc aataaggccg gtgccaatcc tccctatgct    600
gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca ttgagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc    1020
gccaactaca acgcctggag catcgcttcg gccccgtcgt acacgtcgcc taaccctaac    1080
tacgacgaga agcactacat cgaggccttc agcccgctct tgaactcggc cggcttcccc    1140
gcacgcttca ttgtcgacac tggccgcaac ggcaaacaac ctaccggcca acaacagtgg    1200
ggtgactggt gcaatgtcaa gggcaccggc tttggcgtgc ccccgacggc caacacgggc    1260
cacgagctgg tcgatgcctt tgtctgggtc aagcccggcg gcgagtccga cggcacaagc    1320
gacaccagcg ccgcccgcta cgactaccac tgcggcctgt ccgatgccct gcagcctgcc    1380
cccgaggctg acagtggtt ccaggcctac ttcgagcagc tgctcaccaa cgccaacccg    1440
cccttctaa                                                            1449

<210> SEQ ID NO 137
<211> LENGTH: 482
<212> TYPE: PRT
<213> ORGANISM: Myceliophthora thermophila

<400> SEQUENCE: 137

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
                20                  25                  30

Gln Cys Gly Gly Asn Gly Trp Gln Gly Pro Thr Cys Cys Ala Ser Gly
            35                  40                  45

Ser Thr Cys Val Ala Gln Asn Glu Trp Tyr Ser Gln Cys Leu Pro Asn
        50                  55                  60

Ser Gln Val Thr Ser Ser Thr Thr Pro Ser Ser Thr Ser Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
```

```
                165                 170                 175
Asp Thr Leu Met Val Gln Thr Leu Ser Gln Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 138
<211> LENGTH: 465
<212> TYPE: PRT
<213> ORGANISM: Myceliophthora thermophila

<400> SEQUENCE: 138

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
                20                  25                  30

Thr Cys Val Ala Gln Asn Glu Trp Tyr Ser Gln Cys Leu Pro Asn Ser
            35                  40                  45

Gln Val Thr Ser Ser Thr Thr Pro Ser Ser Thr Ser Thr Ser Gln Arg
```

```
            50                  55                  60
Ser Thr Ser Thr Ser Ser Thr Thr Arg Ser Gly Ser Ser Ser Ser
 65                  70                  75                  80

Ser Ser Thr Thr Pro Pro Val Ser Ser Pro Val Thr Ser Ile Pro
                     85                  90                  95

Gly Gly Ala Thr Ser Thr Ala Ser Tyr Ser Gly Asn Pro Phe Ser Gly
                100                 105                 110

Val Arg Leu Phe Ala Asn Asp Tyr Tyr Arg Ser Glu Val His Asn Leu
            115                 120                 125

Ala Ile Pro Ser Met Thr Gly Thr Leu Ala Ala Lys Ala Ser Ala Val
        130                 135                 140

Ala Glu Val Pro Ser Phe Gln Trp Leu Asp Arg Asn Val Thr Ile Asp
145                 150                 155                 160

Thr Leu Met Val Gln Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
        210                 215                 220

His Ile Glu Tyr Ser Asp Ile Arg Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
    290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Ser Ala Gly Phe Pro Ala Arg Phe Ile Val
        355                 360                 365

Asp Thr Gly Arg Asn Gly Lys Gln Pro Thr Gly Gln Gln Gln Trp Gly
    370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465
```

<210> SEQ ID NO 139
<211> LENGTH: 1449
<212> TYPE: DNA
<213> ORGANISM: Artificial Sequence
<220> FEATURE:
<223> OTHER INFORMATION: Synthetic polynucleotide.

<400> SEQUENCE: 139

```
atggccaaga agcttttcat caccgccgcg cttgcggctg ccgtgttggc ggccccgtc      60
attgaggagc gccagaactg cggcgctgtg tggactcaat gcggcggtaa cgggtggcaa    120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300
acgcccaccc ccgtctccag ccccgtgacc agcattcccg gcggtgcgac ctccacggcg    360
agctactctg caaccccctt ctcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtcccgactc tgtcccgcgt ccgggctctc aataaggccg gtgccaatcc tccctatgct    600
gcccaactcg tcgtctacga cctccccgac cgtgactgtg ccgccgctgc gtccaacggc    660
gagttttcga ttgcaaacgg cggcgccgcc aactacagga gctacatcga cgctatccgc    720
aagcacatca ttgagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgtcgcc taaccctaac   1080
tacgacgaga agcactacat cgaggccttc agcccgctct gaactcggc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc ccccgacggc caacacgggc   1260
cacgagctgg tcgatgcctt tgtctgggtc aagcccggcg cgagtccga cggcacaagc   1320
gacaccagcg ccgcccgcta cgactaccac tgcggcctgt ccgatgccct gcagcctgcc   1380
cccgaggctg acagtggttc caggcctac ttcgagcagc tgctcaccaa cgccaacccg   1440
cccttctaa                                                          1449
```

<210> SEQ ID NO 140
<211> LENGTH: 482
<212> TYPE: PRT
<213> ORGANISM: Artificial Sequence
<220> FEATURE:
<223> OTHER INFORMATION: Synthetic polypeptides.

<400> SEQUENCE: 140

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45
```

```
Ser Thr Cys Val Ala Gln Asn Glu Trp Tyr Ser Gln Cys Leu Pro Asn
 50                  55                  60

Ser Gln Val Thr Ser Thr Thr Pro Ser Ser Thr Ser Thr Ser Gln
 65              70                  75                  80

Arg Ser Thr Ser Thr Ser Ser Thr Thr Arg Ser Gly Ser Ser Ser
                 85                  90                  95

Ser Ser Ser Thr Thr Pro Thr Pro Val Ser Ser Pro Val Thr Ser Ile
                100                 105                 110

Pro Gly Gly Ala Thr Ser Thr Ala Ser Tyr Ser Gly Asn Pro Phe Ser
            115                 120                 125

Gly Val Arg Leu Phe Ala Asn Asp Tyr Arg Ser Glu Val His Asn
130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Pro Thr Leu Ser Arg Val Arg Ala Leu Asn Lys
            180                 185                 190

Ala Gly Ala Asn Pro Pro Tyr Ala Ala Gln Leu Val Val Tyr Asp Leu
            195                 200                 205

Pro Asp Arg Asp Cys Ala Ala Ala Ala Ser Asn Gly Glu Phe Ser Ile
210                 215                 220

Ala Asn Gly Gly Ala Ala Asn Tyr Arg Ser Tyr Ile Asp Ala Ile Arg
225                 230                 235                 240

Lys His Ile Ile Glu Tyr Ser Asp Ile Arg Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
            275                 280                 285

Gln Leu Asn Leu Pro Asn Val Ala Met Tyr Leu Asp Ala Gly His Ala
        290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
            435                 440                 445

Tyr His Cys Gly Leu Ser Asp Ala Leu Gln Pro Ala Pro Glu Ala Gly
    450                 455                 460
```

-continued

Gln Trp Phe Gln Ala Tyr Phe Glu Gln Leu Leu Thr Asn Ala Asn Pro
465                 470                 475                 480

Pro Phe

<210> SEQ ID NO 141
<211> LENGTH: 465
<212> TYPE: PRT
<213> ORGANISM: Artificial Sequence
<220> FEATURE:
<223> OTHER INFORMATION: Synthetic polypeptides.

<400> SEQUENCE: 141

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
                20                  25                  30

Thr Cys Val Ala Gln Asn Glu Trp Tyr Ser Gln Cys Leu Pro Asn Ser
            35                  40                  45

Gln Val Thr Ser Ser Thr Pro Ser Ser Thr Ser Thr Ser Gln Arg
    50                  55                  60

Ser Thr Ser Thr Ser Ser Ser Thr Thr Arg Ser Gly Ser Ser Ser Ser
65                  70                  75                  80

Ser Ser Thr Thr Pro Thr Pro Val Ser Ser Pro Val Thr Ser Ile Pro
                85                  90                  95

Gly Gly Ala Thr Ser Thr Ala Ser Tyr Ser Gly Asn Pro Phe Ser Gly
                100                 105                 110

Val Arg Leu Phe Ala Asn Asp Tyr Tyr Arg Ser Glu Val His Asn Leu
            115                 120                 125

Ala Ile Pro Ser Met Thr Gly Thr Leu Ala Ala Lys Ala Ser Ala Val
130                 135                 140

Ala Glu Val Pro Ser Phe Gln Trp Leu Asp Arg Asn Val Thr Ile Asp
145                 150                 155                 160

Thr Leu Met Val Pro Thr Leu Ser Arg Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

Asn Gly Gly Ala Ala Asn Tyr Arg Ser Tyr Ile Asp Ala Ile Arg Lys
    210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
    290                 295                 300

Gly Ile Tyr Asn Asp Ala Gly Lys Pro Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala

```
                    340                 345                 350
Phe Ser Pro Leu Leu Asn Ser Ala Gly Phe Pro Ala Arg Phe Ile Val
            355                 360                 365

Asp Thr Gly Arg Asn Gly Lys Gln Pro Thr Gly Gln Gln Gln Trp Gly
        370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465

<210> SEQ ID NO 142
<211> LENGTH: 1449
<212> TYPE: DNA
<213> ORGANISM: Artificial Sequence
<220> FEATURE:
<223> OTHER INFORMATION: Synthetic polynucleotide.

<400> SEQUENCE: 142
atggccaaga agcttttcat caccgccgcg cttgcggctg ccgtgttggc ggccccgtc      60
attgaggagc gccagaactg cggcgctgtg tggactcaat gcggcggtaa cgggtggcaa    120
ggtcccacat gctgcgcctc gggctcgacc tgcgttgcgc agaacgagtg gtactctcag    180
tgcctgccca acagccaggt gacgagttcc accactccgt cgtcgacttc cacctcgcag    240
cgcagcacca gcacctccag cagcaccacc aggagcggca gctcctcctc ctcctccacc    300
acgcccccgc ccgtctccag ccccgtgacc agcattcccg gcggtgcgac tccacggcg    360
agctactctg gcaaccccct tcgggcgtc cggctcttcg ccaacgacta ctacaggtcc    420
gaggtccaca atctcgccat tcctagcatg actggtactc tggcggccaa ggcttccgcc    480
gtcgccgaag tccctagctt ccagtggctc gaccggaacg tcaccatcga caccctgatg    540
gtcccgactc tgtcccgcgt ccgggctctc aataaggccg gtgccaatcc tccctatgct    600
gcccaactcg tcgtctacga cctccccgac cgtgactgtg ccgccgctgc gtccaacggc    660
gagtttcga ttgcaaacgg cggcgccgcc aactacagga gctacatcga cgctatccgc    720
aagcacatca aggagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gcccgtcgt acacgtcgcc taacccctaac   1080
tacgacgaga agcactacat cgaggccttc agcccgctct gaacgacgc cggcttcccc   1140
gcacgcttca ttgtcgacac tggccgcaac ggcaaacaac ctaccggcca caacagtgg   1200
ggtgactggt gcaatgtcaa gggcaccggc tttggcgtgc cccgacggc caacacgggc   1260
cacgagctgg tcgatgcctt tgtctgggtc aagcccggcg gcgagtccga cggcacaagc   1320
```

```
gacaccagcg ccgcccgcta cgactaccac tgcggcctgt ccgatgccct gcagcctgcc    1380
cccgaggctg acagtggttc ccaggcctac ttcgagcagc tgctcaccaa cgccaacccg    1440
cccttctaa                                                            1449
```

<210> SEQ ID NO 143
<211> LENGTH: 482
<212> TYPE: PRT
<213> ORGANISM: Artificial Sequence
<220> FEATURE:
<223> OTHER INFORMATION: Synthetic polypeptides.

<400> SEQUENCE: 143

```
Met Ala Lys Lys Leu Phe Ile Thr Ala Ala Leu Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Ser Thr Thr Arg Ser Gly Ser Ser Ser
                85                  90                  95

Ser Ser Ser Thr Thr Pro Pro Val Ser Ser Pro Val Thr Ser Ile
            100                 105                 110

Pro Gly Gly Ala Thr Ser Thr Ala Ser Tyr Ser Gly Asn Pro Phe Ser
        115                 120                 125

Gly Val Arg Leu Phe Ala Asn Asp Tyr Tyr Arg Ser Glu Val His Asn
    130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Pro Thr Leu Ser Arg Val Arg Ala Leu Asn Lys
            180                 185                 190

Ala Gly Ala Asn Pro Pro Tyr Ala Ala Gln Leu Val Val Tyr Asp Leu
        195                 200                 205

Pro Asp Arg Asp Cys Ala Ala Ala Ala Ser Asn Gly Glu Phe Ser Ile
    210                 215                 220

Ala Asn Gly Gly Ala Ala Asn Tyr Arg Ser Tyr Ile Asp Ala Ile Arg
225                 230                 235                 240

Lys His Ile Lys Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335
```

```
Ala Thr Asn Val Ala Asn Tyr Asn Ala Trp Ser Ile Ala Ser Ala Pro
            340                 345                 350

Ser Tyr Thr Ser Pro Asn Pro Asn Tyr Asp Glu Lys His Tyr Ile Glu
            355                 360                 365

Ala Phe Ser Pro Leu Leu Asn Asp Ala Gly Phe Pro Ala Arg Phe Ile
370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
            435                 440                 445

Tyr His Cys Gly Leu Ser Asp Ala Leu Gln Pro Ala Pro Glu Ala Gly
            450                 455                 460

Gln Trp Phe Gln Ala Tyr Phe Glu Gln Leu Leu Thr Asn Ala Asn Pro
465                 470                 475                 480

Pro Phe

<210> SEQ ID NO 144
<211> LENGTH: 465
<212> TYPE: PRT
<213> ORGANISM: Artificial Sequence
<220> FEATURE:
<223> OTHER INFORMATION: Synthetic polypeptides.

<400> SEQUENCE: 144

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
            20                  25                  30

Thr Cys Val Ala Gln Asn Glu Trp Tyr Ser Gln Cys Leu Pro Asn Ser
        35                  40                  45

Gln Val Thr Ser Ser Thr Pro Ser Ser Thr Ser Thr Ser Gln Arg
    50                  55                  60

Ser Thr Ser Thr Ser Ser Thr Thr Arg Ser Gly Ser Ser Ser Ser
65                  70                  75                  80

Ser Ser Thr Thr Pro Pro Pro Val Ser Ser Pro Val Thr Ser Ile Pro
                85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val His Asn Leu
        115                 120                 125

Ala Ile Pro Ser Met Thr Gly Thr Leu Ala Ala Lys Ala Ser Ala Val
    130                 135                 140

Ala Glu Val Pro Ser Phe Gln Trp Leu Asp Arg Asn Val Thr Ile Asp
145                 150                 155                 160

Thr Leu Met Val Pro Thr Leu Ser Arg Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205
```

Asn Gly Gly Ala Ala Asn Tyr Arg Ser Tyr Ile Asp Ala Ile Arg Lys
    210                 215                 220

His Ile Lys Glu Tyr Ser Asp Ile Arg Ile Leu Val Ile Glu Pro
225                 230                 235                 240

Asp Ser Met Ala Asn Met Val Thr Asn Met Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Glu Leu Phe Ala
    290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Ser Pro Asn Pro Asn Tyr Asp Glu Lys His Tyr Ile Glu Ala
            340                 345                 350

Phe Ser Pro Leu Leu Asn Asp Ala Gly Phe Pro Ala Arg Phe Ile Val
        355                 360                 365

Asp Thr Gly Arg Asn Gly Lys Gln Pro Thr Gly Gln Gln Gln Trp Gly
    370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
    450                 455                 460

Phe
465

<210> SEQ ID NO 145
<211> LENGTH: 1449
<212> TYPE: DNA
<213> ORGANISM: Artificial Sequence
<220> FEATURE:
<223> OTHER INFORMATION: Synthetic polynucleotide.

<400> SEQUENCE: 145
atggccaaga agcttttcat caccgccgcg cttgcggctg ccgtgttggc ggccccgtc       60 attgaggagc gccagaactg cggcgctgtg tggactcaat gcggcggtaa cgggtggcaa     120
ggtcccacat gctgcgcctc gggctcgacc tgcgttgcgc agaacgagtg gtactctcag     180
tgcctgccca acagccaggt gacgagttcc accactccgt cgtcgacttc cacctcgcag     240
cgcagcacca gcacctccag cagcaccacc aggagcggca gctcctcctc ctcctccacc     300
acgcccaccc ccgtctccag ccccgtgacc agcattcccg gcggtgcgac tccacggcg      360 agctactctg caaccccctt ctcgggcgtc cggctcttcg ccaacgacta ctacaggtcc     420
gaggtcatga atctcgccat tcctagcatg actggtactc tggcggccaa ggcttccgcc     480
gtcgccgaag tccctagctt ccagtggctc gaccggaacg tcaccatcga caccctgatg     540

```
gtcaccactc tgtcccaggt ccgggctctc aataaggccg gtgccaatcc tccctatgct    600
gcccaactcg tcgtctacga cctccccgac cgtgactgtg ccgccgctgc gtccaacggc    660
gagttttcga ttgcaaacgg cggcagcgcc aactacagga gctacatcga cgctatccgc    720
aagcacatca ttgagtactc ggacatccgg atcatcctgg ttatcgagcc cgactcgatg    780
gccaacatgg tgaccaacat gaacgtggcc aagtgcagca acgccgcgtc gacgtaccac    840
gagttgaccg tgtacgcgct caagcagctg aacctgccca acgtcgccat gtatctcgac    900
gccggccacg ccggctggct cggctggccc gccaacatcc agcccgccgc cgagctgttt    960
gccggcatct acaatgatgc cggcaagccg gctgccgtcc gcggcctggc cactaacgtc   1020
gccaactaca acgcctggag catcgcttcg gccccgtcgt acacgcagcc taaccctaac   1080
tacgacgaga agcactacat cgaggccttc agcccgctct tgaactcggc cggcttcccc   1140
gcacgcttca ttgtcgacac tggccgcaac ggcaaacaac ctaccggcca acaacagtgg   1200
ggtgactggt gcaatgtcaa gggcaccggc tttggcgtgc cccgacggc caacacgggc    1260 cacgagctgg tcgatgcctt tgtctgggtc aagcccggcg cgagtccga cggcacaagc    1320 gacaccagcg ccgcccgcta cgactaccac tgcggcctgt ccgatgccct gcagcctgcc   1380
cccgaggctg acagtggtt ccaggcctac ttcgagcagc tgctcaccaa cgccaacccg    1440
cccttctaa                                                           1449
```

<210> SEQ ID NO 146
<211> LENGTH: 482
<212> TYPE: PRT
<213> ORGANISM: Artificial Sequence
<220> FEATURE:
<223> OTHER INFORMATION: Synthetic polypeptides.

<400> SEQUENCE: 146

Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Trp Thr
            20                  25                  30

Gln Cys Gly Gly Asn Gly Trp Gln Gly Pro Thr Cys Cys Ala Ser Gly
        35                  40                  45

Ser Thr Cys Val Ala Gln Asn Glu Trp Tyr Ser Gln Cys Leu Pro Asn
    50                  55                  60

Ser Gln Val Thr Ser Ser Thr Thr Pro Ser Ser Thr Ser Thr Ser Gln
65                  70                  75                  80

Arg Ser Thr Ser Thr Ser Ser Thr Thr Arg Ser Gly Ser Ser Ser
                85                  90                  95

Ser Ser Ser Thr Thr Pro Thr Pro Val Ser Ser Pro Val Thr Ser Ile
                100                 105                 110

Pro Gly Gly Ala Thr Ser Thr Ala Ser Tyr Ser Gly Asn Pro Phe Ser
            115                 120                 125

Gly Val Arg Leu Phe Ala Asn Asp Tyr Tyr Arg Ser Glu Val Met Asn
        130                 135                 140

Leu Ala Ile Pro Ser Met Thr Gly Thr Leu Ala Ala Lys Ala Ser Ala
145                 150                 155                 160

Val Ala Glu Val Pro Ser Phe Gln Trp Leu Asp Arg Asn Val Thr Ile
                165                 170                 175

Asp Thr Leu Met Val Thr Thr Leu Ser Gln Val Arg Ala Leu Asn Lys
            180                 185                 190

Ala Gly Ala Asn Pro Pro Tyr Ala Ala Gln Leu Val Val Tyr Asp Leu

-continued

```
                195                 200                 205
Pro Asp Arg Asp Cys Ala Ala Ala Ser Asn Gly Glu Phe Ser Ile
    210                 215                 220

Ala Asn Gly Gly Ser Ala Asn Tyr Arg Ser Tyr Ile Asp Ala Ile Arg
225                 230                 235                 240

Lys His Ile Ile Glu Tyr Ser Asp Ile Arg Ile Ile Leu Val Ile Glu
                245                 250                 255

Pro Asp Ser Met Ala Asn Met Val Thr Asn Met Asn Val Ala Lys Cys
            260                 265                 270

Ser Asn Ala Ala Ser Thr Tyr His Glu Leu Thr Val Tyr Ala Leu Lys
        275                 280                 285

Gln Leu Asn Leu Pro Asn Val Ala Met Tyr Leu Asp Ala Gly His Ala
    290                 295                 300

Gly Trp Leu Gly Trp Pro Ala Asn Ile Gln Pro Ala Ala Glu Leu Phe
305                 310                 315                 320

Ala Gly Ile Tyr Asn Asp Ala Gly Lys Pro Ala Ala Val Arg Gly Leu
                325                 330                 335

Ala Thr Asn Val Ala Asn Tyr Asn Ala Trp Ser Ile Ala Ser Ala Pro
            340                 345                 350

Ser Tyr Thr Gln Pro Asn Pro Asn Tyr Asp Glu Lys His Tyr Ile Glu
        355                 360                 365

Ala Phe Ser Pro Leu Leu Asn Ser Ala Gly Phe Pro Ala Arg Phe Ile
    370                 375                 380

Val Asp Thr Gly Arg Asn Gly Lys Gln Pro Thr Gly Gln Gln Gln Trp
385                 390                 395                 400

Gly Asp Trp Cys Asn Val Lys Gly Thr Gly Phe Gly Val Arg Pro Thr
                405                 410                 415

Ala Asn Thr Gly His Glu Leu Val Asp Ala Phe Val Trp Val Lys Pro
            420                 425                 430

Gly Gly Glu Ser Asp Gly Thr Ser Asp Thr Ser Ala Ala Arg Tyr Asp
        435                 440                 445

Tyr His Cys Gly Leu Ser Asp Ala Leu Gln Pro Ala Pro Glu Ala Gly
    450                 455                 460

Gln Trp Phe Gln Ala Tyr Phe Glu Gln Leu Leu Thr Asn Ala Asn Pro
465                 470                 475                 480

Pro Phe

<210> SEQ ID NO 147
<211> LENGTH: 465
<212> TYPE: PRT
<213> ORGANISM: Artificial Sequence
<220> FEATURE:
<223> OTHER INFORMATION: Synthetic polypeptides.

<400> SEQUENCE: 147

Ala Pro Val Ile Glu Glu Arg Gln Asn Cys Gly Ala Val Trp Thr Gln
1               5                   10                  15

Cys Gly Gly Asn Gly Trp Gln Gly Pro Thr Cys Cys Ala Ser Gly Ser
                20                  25                  30

Thr Cys Val Ala Gln Asn Glu Trp Tyr Ser Gln Cys Leu Pro Asn Ser
            35                  40                  45

Gln Val Thr Ser Ser Thr Thr Pro Ser Ser Thr Ser Gln Arg
        50                  55                  60

Ser Thr Ser Thr Ser Ser Ser Thr Arg Ser Gly Ser Ser Ser
65                  70                  75                  80
```

Ser Ser Thr Thr Pro Thr Pro Val Ser Ser Pro Val Thr Ser Ile Pro
             85                  90                  95

Gly Gly Ala Thr Ser Thr Ala Ser Tyr Ser Gly Asn Pro Phe Ser Gly
            100                 105                 110

Val Arg Leu Phe Ala Asn Asp Tyr Tyr Arg Ser Glu Val Met Asn Leu
            115                 120                 125

Ala Ile Pro Ser Met Thr Gly Thr Leu Ala Ala Lys Ala Ser Ala Val
        130                 135                 140

Ala Glu Val Pro Ser Phe Gln Trp Leu Asp Arg Asn Val Thr Ile Asp
145                 150                 155                 160

Thr Leu Met Val Thr Thr Leu Ser Gln Val Arg Ala Leu Asn Lys Ala
                165                 170                 175

Gly Ala Asn Pro Pro Tyr Ala Ala Gln Leu Val Val Tyr Asp Leu Pro
            180                 185                 190

Asp Arg Asp Cys Ala Ala Ala Ser Asn Gly Glu Phe Ser Ile Ala
        195                 200                 205

Asn Gly Gly Ser Ala Asn Tyr Arg Ser Tyr Ile Asp Ala Ile Arg Lys
        210                 215                 220

His Ile Ile Glu Tyr Ser Asp Ile Arg Ile Ile Leu Val Ile Glu Pro
225                 230                 235                 240

Asp Ser Met Ala Asn Met Val Thr Asn Met Asn Val Ala Lys Cys Ser
                245                 250                 255

Asn Ala Ala Ser Thr Tyr His Glu Leu Thr Val Tyr Ala Leu Lys Gln
            260                 265                 270

Leu Asn Leu Pro Asn Val Ala Met Tyr Leu Asp Ala Gly His Ala Gly
        275                 280                 285

Trp Leu Gly Trp Pro Ala Asn Ile Gln Pro Ala Ala Glu Leu Phe Ala
290                 295                 300

Gly Ile Tyr Asn Asp Ala Gly Lys Pro Ala Ala Val Arg Gly Leu Ala
305                 310                 315                 320

Thr Asn Val Ala Asn Tyr Asn Ala Trp Ser Ile Ala Ser Ala Pro Ser
                325                 330                 335

Tyr Thr Gln Pro Asn Pro Asn Tyr Asp Glu Lys His Tyr Ile Glu Ala
            340                 345                 350

Phe Ser Pro Leu Leu Asn Ser Ala Gly Phe Pro Ala Arg Phe Ile Val
        355                 360                 365

Asp Thr Gly Arg Asn Gly Lys Gln Pro Thr Gly Gln Gln Gln Trp Gly
        370                 375                 380

Asp Trp Cys Asn Val Lys Gly Thr Gly Phe Gly Val Arg Pro Thr Ala
385                 390                 395                 400

Asn Thr Gly His Glu Leu Val Asp Ala Phe Val Trp Val Lys Pro Gly
                405                 410                 415

Gly Glu Ser Asp Gly Thr Ser Asp Thr Ser Ala Ala Arg Tyr Asp Tyr
            420                 425                 430

His Cys Gly Leu Ser Asp Ala Leu Gln Pro Ala Pro Glu Ala Gly Gln
        435                 440                 445

Trp Phe Gln Ala Tyr Phe Glu Gln Leu Leu Thr Asn Ala Asn Pro Pro
450                 455                 460

Phe
465

<210> SEQ ID NO 148
<211> LENGTH: 1239

```
<212> TYPE: DNA
<213> ORGANISM: Myceliophthora thermophila

<400> SEQUENCE: 148
atgcactcca aagctttctt ggcagcgctt cttgcgcctg ccgtctcagg gcaactgaac      60
gacctcgccg tcagggctgg actcaagtac tttggtactg ctcttagcga gagcgtcatc     120
aacagtgata ctcggtatgc tgccatcctc agcgacaaga gcatgttcgg ccagctcgtc     180
cccgagaatg gcatgaagtg ggatgctact gagccgtccc gtggccagtt caactacgcc     240
tcgggcgaca tcacggccaa cacggccaag aagaatggcc agggcatgcg ttgccacacc     300
atggtctggt acagccagct cccgagctgg gtctcctcgg gctcgtggac cagggactcg     360
ctcacctcgg tcatcgagac gcacatgaac aacgtcatgg ccactacaa gggccaatgc     420
tacgcctggg atgtcatcaa cgaggccatc aatgacgacg caactcctg gcgcgacaac     480
gtctttctcc ggacctttgg gaccgactac ttcgccctgt ccttcaacct agccaagaag     540
gccgatcccg ataccaagct gtactacaac gactacaacc tcgagtacaa ccaggccaag     600
acggaccgcg ctgttgagct cgtcaagatg gtccaggccg ccggcgcgcc catcgacggt     660
gtcggcttcc agggccacct cattgtcggc tcgaccccga cgcgctcgca gctggccacc     720
gccctccagc gcttcaccgc gctcggcctc gaggtcgcct acaccgagct cgacatccgc     780
cactcgagcc tgccggcctc ttcgtcggcg ctcgcgaccc agggcaacga cttcgccaac     840
gtggtcggct cttgcctcga caccgccggc tgcgtcggcg tcaccgtctg gggcttcacc     900
gatgcgcact cgtggatccc gaacacgttc cccggccagg cgacgccct gatctacgac     960
agcaactaca caagaagcc cgcgtggacc tcgatctcgt ccgtcctggc cgccaaggcc    1020
accggcgccc cgcccgcctc gtcctccacc accctcgtca ccatcaccac ccctccgccg    1080
gcatccacca ccgcctcctc ctcctccagt gccacgccca cgagcgtccc gacgcagacg    1140
aggtggggac agtgcggcgg catcggatgg acggggccga cccagtgcga gagcccatgg    1200
acctgccaga agctgaacga ctggtactgg cagtgcctg                           1239

<210> SEQ ID NO 149
<211> LENGTH: 413
<212> TYPE: PRT
<213> ORGANISM: Myceliophthora thermophila

<400> SEQUENCE: 149

Met His Ser Lys Ala Phe Leu Ala Ala Leu Leu Ala Pro Ala Val Ser
1               5                   10                  15

Gly Gln Leu Asn Asp Leu Ala Val Arg Ala Gly Leu Lys Tyr Phe Gly
            20                  25                  30

Thr Ala Leu Ser Glu Ser Val Ile Asn Ser Asp Thr Arg Tyr Ala Ala
        35                  40                  45

Ile Leu Ser Asp Lys Ser Met Phe Gly Gln Leu Val Pro Glu Asn Gly
    50                  55                  60

Met Lys Trp Asp Ala Thr Glu Pro Ser Arg Gly Gln Phe Asn Tyr Ala
65                  70                  75                  80

Ser Gly Asp Ile Thr Ala Asn Thr Ala Lys Lys Asn Gly Gln Gly Met
                85                  90                  95

Arg Cys His Thr Met Val Trp Tyr Ser Gln Leu Pro Ser Trp Val Ser
            100                 105                 110

Ser Gly Ser Trp Thr Arg Asp Ser Leu Thr Ser Val Ile Glu Thr His
        115                 120                 125
```

```
Met Asn Asn Val Met Gly His Tyr Lys Gly Gln Cys Tyr Ala Trp Asp
130                 135                 140

Val Ile Asn Glu Ala Ile Asn Asp Asp Gly Asn Ser Trp Arg Asp Asn
145                 150                 155                 160

Val Phe Leu Arg Thr Phe Gly Thr Asp Tyr Phe Ala Leu Ser Phe Asn
                165                 170                 175

Leu Ala Lys Lys Ala Asp Pro Asp Thr Lys Leu Tyr Tyr Asn Asp Tyr
                180                 185                 190

Asn Leu Glu Tyr Asn Gln Ala Lys Thr Asp Arg Ala Val Glu Leu Val
                195                 200                 205

Lys Met Val Gln Ala Ala Gly Ala Pro Ile Asp Gly Val Gly Phe Gln
210                 215                 220

Gly His Leu Ile Val Gly Ser Thr Pro Thr Arg Ser Gln Leu Ala Thr
225                 230                 235                 240

Ala Leu Gln Arg Phe Thr Ala Leu Gly Leu Glu Val Ala Tyr Thr Glu
                245                 250                 255

Leu Asp Ile Arg His Ser Ser Leu Pro Ala Ser Ser Ala Leu Ala
                260                 265                 270

Thr Gln Gly Asn Asp Phe Ala Asn Val Val Gly Ser Cys Leu Asp Thr
                275                 280                 285

Ala Gly Cys Val Gly Val Thr Val Trp Gly Phe Thr Asp Ala His Ser
290                 295                 300

Trp Ile Pro Asn Thr Phe Pro Gly Gln Gly Asp Ala Leu Ile Tyr Asp
305                 310                 315                 320

Ser Asn Tyr Asn Lys Lys Pro Ala Trp Thr Ser Ile Ser Ser Val Leu
                325                 330                 335

Ala Ala Lys Ala Thr Gly Ala Pro Pro Ala Ser Ser Thr Thr Leu
                340                 345                 350

Val Thr Ile Thr Thr Pro Pro Ala Ser Thr Thr Ala Ser Ser Ser
                355                 360                 365

Ser Ser Ala Thr Pro Thr Ser Val Pro Thr Gln Thr Arg Trp Gly Gln
370                 375                 380

Cys Gly Gly Ile Gly Trp Thr Gly Pro Thr Gln Cys Glu Ser Pro Trp
385                 390                 395                 400

Thr Cys Gln Lys Leu Asn Asp Trp Tyr Trp Gln Cys Leu
                405                 410

<210> SEQ ID NO 150
<211> LENGTH: 396
<212> TYPE: PRT
<213> ORGANISM: Myceliophthora thermophila

<400> SEQUENCE: 150

Gln Leu Asn Asp Leu Ala Val Arg Ala Gly Leu Lys Tyr Phe Gly Thr
1               5                   10                  15

Ala Leu Ser Glu Ser Val Ile Asn Ser Asp Thr Arg Tyr Ala Ala Ile
                20                  25                  30

Leu Ser Asp Lys Ser Met Phe Gly Gln Leu Val Pro Glu Asn Gly Met
                35                  40                  45

Lys Trp Asp Ala Thr Glu Pro Ser Arg Gly Gln Phe Asn Tyr Ala Ser
                50                  55                  60

Gly Asp Ile Thr Ala Asn Thr Ala Lys Lys Asn Gly Gln Gly Met Arg
65                  70                  75                  80

Cys His Thr Met Val Trp Tyr Ser Gln Leu Pro Ser Trp Val Ser Ser
                85                  90                  95
```

```
Gly Ser Trp Thr Arg Asp Ser Leu Thr Ser Val Ile Glu Thr His Met
            100                 105                 110

Asn Asn Val Met Gly His Tyr Lys Gly Gln Cys Tyr Ala Trp Asp Val
            115                 120                 125

Ile Asn Glu Ala Ile Asn Asp Asp Gly Asn Ser Trp Arg Asp Asn Val
130                 135                 140

Phe Leu Arg Thr Phe Gly Thr Asp Tyr Phe Ala Leu Ser Phe Asn Leu
145                 150                 155                 160

Ala Lys Lys Ala Asp Pro Asp Thr Lys Leu Tyr Tyr Asn Asp Tyr Asn
                165                 170                 175

Leu Glu Tyr Asn Gln Ala Lys Thr Asp Arg Ala Val Glu Leu Val Lys
            180                 185                 190

Met Val Gln Ala Ala Gly Ala Pro Ile Asp Gly Val Gly Phe Gln Gly
            195                 200                 205

His Leu Ile Val Gly Ser Thr Pro Thr Arg Ser Gln Leu Ala Thr Ala
210                 215                 220

Leu Gln Arg Phe Thr Ala Leu Gly Leu Glu Val Ala Tyr Thr Glu Leu
225                 230                 235                 240

Asp Ile Arg His Ser Ser Leu Pro Ala Ser Ser Ala Leu Ala Thr
                245                 250                 255

Gln Gly Asn Asp Phe Ala Asn Val Val Gly Ser Cys Leu Asp Thr Ala
            260                 265                 270

Gly Cys Val Gly Val Thr Val Trp Gly Phe Thr Asp Ala His Ser Trp
            275                 280                 285

Ile Pro Asn Thr Phe Pro Gly Gln Gly Asp Ala Leu Ile Tyr Asp Ser
290                 295                 300

Asn Tyr Asn Lys Lys Pro Ala Trp Thr Ser Ile Ser Ser Val Leu Ala
305                 310                 315                 320

Ala Lys Ala Thr Gly Ala Pro Pro Ala Ser Ser Thr Thr Leu Val
                325                 330                 335

Thr Ile Thr Thr Pro Pro Pro Ala Ser Thr Thr Ala Ser Ser Ser Ser
            340                 345                 350

Ser Ala Thr Pro Thr Ser Val Pro Thr Gln Thr Arg Trp Gly Gln Cys
            355                 360                 365

Gly Gly Ile Gly Trp Thr Gly Pro Thr Gln Cys Glu Ser Pro Trp Thr
370                 375                 380

Cys Gln Lys Leu Asn Asp Trp Tyr Trp Gln Cys Leu
385                 390                 395

<210> SEQ ID NO 151
<211> LENGTH: 654
<212> TYPE: DNA
<213> ORGANISM: Myceliophthora thermophila

<400> SEQUENCE: 151
atggtctcgt tcactctcct cctcacggtc atcgccgctg cggtgacgac ggccagccct    60
ctcgaggtgg tcaagcgcgg catccagccg ggcacgggca cccacgaggg gtacttctac   120
tcgttctgga ccgacggccg tggctcggtc gacttcaacc ccgggccccg cggctcgtac   180
agcgtcacct ggaacaacgt caacaactgg gttggcggca agggctggaa cccgggcccg   240
ccgcgcaaga ttgcgtacaa cggcacctgg aacaactaca acgtgaacag ctacctcgcc   300
ctgtacggct ggactcgcaa cccgctggtc gagtattaca tcgtggaggc ataccggcacg   360 tacaaccct cgtcgggcac ggcgcggctg ggcaccatcg aggacgacgg cggcgtgtac   420
```

```
gacatctaca agacgacgcg gtacaaccag ccgtccatcg aggggacctc caccttcgac    480
cagtactggt ccgtccgccg ccagaagcgc gtcggcggca ctatcgacac gggcaagcac    540
tttgacgagt ggaagcgcca gggcaacctc cagctcggca cctggaacta catgatcatg    600
gccaccgagg ctaccagag ctctggttcg gccactatcg aggtccggga ggcc           654
```

<210> SEQ ID NO 152
<211> LENGTH: 218
<212> TYPE: PRT
<213> ORGANISM: Myceliophthora thermophila

<400> SEQUENCE: 152

```
Met Val Ser Phe Thr Leu Leu Thr Val Ile Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60

Asn Asn Val Asn Asn Trp Val Gly Gly Lys Gly Trp Asn Pro Gly Pro
65                  70                  75                  80

Pro Arg Lys Ile Ala Tyr Asn Gly Thr Trp Asn Asn Tyr Asn Val Asn
                85                  90                  95

Ser Tyr Leu Ala Leu Tyr Gly Trp Thr Arg Asn Pro Leu Val Glu Tyr
            100                 105                 110

Tyr Ile Val Glu Ala Tyr Gly Thr Tyr Asn Pro Ser Ser Gly Thr Ala
        115                 120                 125

Arg Leu Gly Thr Ile Glu Asp Asp Gly Gly Val Tyr Asp Ile Tyr Lys
    130                 135                 140

Thr Thr Arg Tyr Asn Gln Pro Ser Ile Glu Gly Thr Ser Thr Phe Asp
145                 150                 155                 160

Gln Tyr Trp Ser Val Arg Arg Gln Lys Arg Val Gly Gly Thr Ile Asp
                165                 170                 175

Thr Gly Lys His Phe Asp Glu Trp Lys Arg Gln Gly Asn Leu Gln Leu
            180                 185                 190

Gly Thr Trp Asn Tyr Met Ile Met Ala Thr Glu Gly Tyr Gln Ser Ser
        195                 200                 205

Gly Ser Ala Thr Ile Glu Val Arg Glu Ala
    210                 215
```

<210> SEQ ID NO 153
<211> LENGTH: 218
<212> TYPE: PRT
<213> ORGANISM: Myceliophthora thermophila

<400> SEQUENCE: 153

```
Met Val Ser Phe Thr Leu Leu Thr Val Ile Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60
```

```
Asn Asn Val Asn Asn Trp Val Gly Gly Lys Gly Trp Asn Pro Gly Pro
 65                  70                  75                  80

Pro Arg Lys Ile Ala Tyr Asn Gly Thr Trp Asn Asn Tyr Asn Val Asn
                 85                  90                  95

Ser Tyr Leu Ala Leu Tyr Gly Trp Thr Arg Asn Pro Leu Val Glu Tyr
            100                 105                 110

Tyr Ile Val Glu Ala Tyr Gly Thr Tyr Asn Pro Ser Ser Gly Thr Ala
        115                 120                 125

Arg Leu Gly Thr Ile Glu Asp Asp Gly Val Tyr Asp Ile Tyr Lys
    130                 135                 140

Thr Thr Arg Tyr Asn Gln Pro Ser Ile Glu Gly Thr Ser Thr Phe Asp
145                 150                 155                 160

Gln Tyr Trp Ser Val Arg Arg Gln Lys Arg Val Gly Gly Thr Ile Asp
                165                 170                 175

Thr Gly Lys His Phe Asp Glu Trp Lys Arg Gln Gly Asn Leu Gln Leu
            180                 185                 190

Gly Thr Trp Asn Tyr Met Ile Met Ala Thr Glu Gly Tyr Gln Ser Ser
        195                 200                 205

Gly Ser Ala Thr Ile Glu Val Arg Glu Ala
    210                 215
```

<210> SEQ ID NO 154
<211> LENGTH: 1155
<212> TYPE: DNA
<213> ORGANISM: Myceliophthora thermophila

<400> SEQUENCE: 154

```
atgcgtactc ttacgttcgt gctggcagcc gccccggtgg ctgtgcttgc ccaatctcct     60
ctgtggggcc agtgcggcgg tcaaggctgg acaggtccca cgacctgcgt ttctggcgca    120
gtatgccaat cgtcaatga ctggtactcc caatgcgtgc ccggatcgag caaccctcct    180
acgggcacca ccagcagcac cactggaagc accccggctc ctactggcgg cggcggcagc    240
ggaaccggcc tccacgacaa attcaaggcc aagggcaagc tctacttcgg aaccgagatc    300
gatcactacc atctcaacaa caatgccttg accaacattg tcaagaaaga ctttggtcaa    360
gtcactcacg agaacagctt gaagtgggat gctactgagc cgagccgcaa tcaattcaac    420
tttgccaacg ccgacgcggt tgtcaacttt gcccaggcca acggcaagct catccgcggc    480
cacaccctcc tctggcactc tcagctgccg cagtgggtgc agaacatcaa cgaccgcaac    540
accttgaccc aggtcatcga gaaccacgtc accaccttg tcactcgcta aagggcaag    600
atcctccact gggacgtcgt taacgagatc tttgccgagg acggctcgct ccgcgacagc    660
gtcttcagcc gcgtcctcgg cgaggacttt gtcggcatcg ccttccgcgc cgcccgcgcc    720
gccgatccca cgccaagct ctacatcaac gactacaacc tcgacattgc caactacgcc    780
aaggtgaccc ggggcatggt cgagaaggtc aacaagtgga tcgcccaggg catcccgatc    840
gacggcatcg gcacccagtg ccacctggcc gggcccggcg gtggaacac ggccgccggc    900
gtccccgacg ccctcaaggc cctcgccgcg gccaacgtca aggagatcgc catcaccgag    960
ctcgacatcg ccggcgcctc cgccaacgac tacctcaccg tcatgaacgc ctgcctccag   1020
gtctccaagt gcgtcggcat caccgtctgg ggcgtctctg acaaggacag ctggaggtcg   1080
agcagcaacc cgctcctctt cgacagcaac taccagccaa aggcggcata caatgctctg   1140
attaatgcct gtaa                                                      1155
```

<210> SEQ ID NO 155
<211> LENGTH: 384
<212> TYPE: PRT
<213> ORGANISM: Myceliophthora thermophila

<400> SEQUENCE: 155

Met Arg Thr Leu Thr Phe Val Leu Ala Ala Pro Val Ala Val Leu
1               5                   10                  15

Ala Gln Ser Pro Leu Trp Gly Gln Cys Gly Gly Gln Gly Trp Thr Gly
            20                  25                  30

Pro Thr Thr Cys Val Ser Gly Ala Val Cys Gln Phe Val Asn Asp Trp
        35                  40                  45

Tyr Ser Gln Cys Val Pro Gly Ser Ser Asn Pro Thr Gly Thr Thr
    50                  55                  60

Ser Ser Thr Thr Gly Ser Thr Pro Ala Pro Thr Gly Gly Gly Ser
65                  70                  75                  80

Gly Thr Gly Leu His Asp Lys Phe Lys Ala Lys Gly Lys Leu Tyr Phe
                85                  90                  95

Gly Thr Glu Ile Asp His Tyr His Leu Asn Asn Asn Ala Leu Thr Asn
                100                 105                 110

Ile Val Lys Lys Asp Phe Gly Gln Val Thr His Glu Asn Ser Leu Lys
            115                 120                 125

Trp Asp Ala Thr Glu Pro Ser Arg Asn Gln Phe Asn Phe Ala Asn Ala
    130                 135                 140

Asp Ala Val Val Asn Phe Ala Gln Ala Asn Gly Lys Leu Ile Arg Gly
145                 150                 155                 160

His Thr Leu Leu Trp His Ser Gln Leu Pro Gln Trp Val Gln Asn Ile
                165                 170                 175

Asn Asp Arg Asn Thr Leu Thr Gln Val Ile Glu Asn His Val Thr Thr
            180                 185                 190

Leu Val Thr Arg Tyr Lys Gly Lys Ile Leu His Trp Asp Val Val Asn
        195                 200                 205

Glu Ile Phe Ala Glu Asp Gly Ser Leu Arg Asp Ser Val Phe Ser Arg
    210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Arg Gly Met Val Glu Lys Val Asn Lys
            260                 265                 270

Trp Ile Ala Gln Gly Ile Pro Ile Asp Gly Ile Gly Thr Gln Cys His
        275                 280                 285

Leu Ala Gly Pro Gly Gly Trp Asn Thr Ala Ala Gly Val Pro Asp Ala
    290                 295                 300

Leu Lys Ala Leu Ala Ala Asn Val Lys Glu Ile Ala Ile Thr Glu
305                 310                 315                 320

Leu Asp Ile Ala Gly Ala Ser Ala Asn Asp Tyr Leu Thr Val Met Asn
                325                 330                 335

Ala Cys Leu Gln Val Ser Lys Cys Val Gly Ile Thr Val Trp Gly Val
            340                 345                 350

Ser Asp Lys Asp Ser Trp Arg Ser Ser Asn Pro Leu Leu Phe Asp
        355                 360                 365

Ser Asn Tyr Gln Pro Lys Ala Ala Tyr Asn Ala Leu Ile Asn Ala Leu
    370                 375                 380

<210> SEQ ID NO 156
<211> LENGTH: 367
<212> TYPE: PRT
<213> ORGANISM: Myceliophthora thermophila

<400> SEQUENCE: 156

Gln Ser Pro Leu Trp Gly Gln Cys Gly Gly Gln Gly Trp Thr Gly Pro
1               5                   10                  15

Thr Thr Cys Val Ser Gly Ala Val Cys Gln Phe Val Asn Asp Trp Tyr
            20                  25                  30

Ser Gln Cys Val Pro Gly Ser Ser Asn Pro Pro Thr Gly Thr Thr Ser
        35                  40                  45

Ser Thr Thr Gly Ser Thr Pro Ala Pro Thr Gly Gly Gly Ser Gly
    50                  55                  60

Thr Gly Leu His Asp Lys Phe Lys Ala Lys Gly Lys Leu Tyr Phe Gly
65                  70                  75                  80

Thr Glu Ile Asp His Tyr His Leu Asn Asn Ala Leu Thr Asn Ile
                85                  90                  95

Val Lys Lys Asp Phe Gly Gln Val Thr His Glu Asn Ser Leu Lys Trp
            100                 105                 110

Asp Ala Thr Glu Pro Ser Arg Asn Gln Phe Asn Phe Ala Asn Ala Asp
        115                 120                 125

Ala Val Val Asn Phe Ala Gln Ala Asn Gly Lys Leu Ile Arg Gly His
    130                 135                 140

Thr Leu Leu Trp His Ser Gln Leu Pro Gln Trp Val Gln Asn Ile Asn
145                 150                 155                 160

Asp Arg Asn Thr Leu Thr Gln Val Ile Glu Asn His Val Thr Thr Leu
                165                 170                 175

Val Thr Arg Tyr Lys Gly Lys Ile Leu His Trp Asp Val Val Asn Glu
            180                 185                 190

Ile Phe Ala Glu Asp Gly Ser Leu Arg Asp Ser Val Phe Ser Arg Val
        195                 200                 205

Leu Gly Glu Asp Phe Val Gly Ile Ala Phe Arg Ala Ala Arg Ala Ala
    210                 215                 220

Asp Pro Asn Ala Lys Leu Tyr Ile Asn Asp Tyr Asn Leu Asp Ile Ala
225                 230                 235                 240

Asn Tyr Ala Lys Val Thr Arg Gly Met Val Glu Lys Val Asn Lys Trp
                245                 250                 255

Ile Ala Gln Gly Ile Pro Ile Asp Gly Ile Gly Thr Gln Cys His Leu
            260                 265                 270

Ala Gly Pro Gly Gly Trp Asn Thr Ala Ala Gly Val Pro Asp Ala Leu
        275                 280                 285

Lys Ala Leu Ala Ala Ala Asn Val Lys Glu Ile Ala Ile Thr Glu Leu
    290                 295                 300

Asp Ile Ala Gly Ala Ser Ala Asn Asp Tyr Leu Thr Val Met Asn Ala
305                 310                 315                 320

Cys Leu Gln Val Ser Lys Cys Val Gly Ile Thr Val Trp Gly Val Ser
                325                 330                 335

Asp Lys Asp Ser Trp Arg Ser Ser Asn Pro Leu Leu Phe Asp Ser
        340                 345                 350

Asn Tyr Gln Pro Lys Ala Ala Tyr Asn Ala Leu Ile Asn Ala Leu
    355                 360                 365

<210> SEQ ID NO 157

```
<211> LENGTH: 687
<212> TYPE: DNA
<213> ORGANISM: Myceliophthora thermophila

<400> SEQUENCE: 157
atggtctcgc tcaagtccct cctcctcgcc gcggcggcga cgttgacggc ggtgacggcg      60
cgcccgttcg actttgacga cggcaactcg accgaggcgc tggccaagcg ccaggtcacg     120
cccaacgcgc agggctacca ctcgggctac ttctactcgt ggtggtccga cggcggcggc     180
caggccacct tcaccctgct cgagggcagc cactaccagg tcaactggag gaacacgggc     240
aactttgtcg gtggcaaggg ctggaacccg gtaccggcc ggaccatcaa ctacggcggc      300
tcgttcaacc cgagcggcaa cggctacctg gccgtctacg gctggacgca caacccgctg     360
atcgagtact acgtggtcga gtcgtacggg acctacaacc cgggcagcca ggcccagtac     420
aagggcagct tccagagcga cggcggcacc tacaacatct acgtctcgac ccgctacaac     480
gcgccctcga tcgagggcac ccgcaccttc cagcagtact ggtccatccg cacctccaag     540
cgcgtcggcg gctccgtcac catgcagaac cacttcaacg cctgggccca gcacggcatg     600 ccctcggct cccacgacta ccagatcgtc gccaccgagg gctaccagag cagcggctcc      660
tccgacatct acgtccagac tcactag                                         687

<210> SEQ ID NO 158
<211> LENGTH: 228
<212> TYPE: PRT
<213> ORGANISM: Myceliophthora thermophila

<400> SEQUENCE: 158

Met Val Ser Leu Lys Ser Leu Leu Leu Ala Ala Ala Thr Leu Thr
1               5                   10                  15

Ala Val Thr Ala Arg Pro Phe Asp Phe Asp Asp Gly Asn Ser Thr Glu
            20                  25                  30

Ala Leu Ala Lys Arg Gln Val Thr Pro Asn Ala Gln Gly Tyr His Ser
        35                  40                  45

Gly Tyr Phe Tyr Ser Trp Trp Ser Asp Gly Gly Gln Ala Thr Phe
    50                  55                  60

Thr Leu Leu Glu Gly Ser His Tyr Gln Val Asn Trp Arg Asn Thr Gly
65                  70                  75                  80

Asn Phe Val Gly Gly Lys Gly Trp Asn Pro Gly Thr Gly Arg Thr Ile
                85                  90                  95

Asn Tyr Gly Gly Ser Phe Asn Pro Ser Gly Asn Gly Tyr Leu Ala Val
            100                 105                 110

Tyr Gly Trp Thr His Asn Pro Leu Ile Glu Tyr Tyr Val Val Glu Ser
        115                 120                 125

Tyr Gly Thr Tyr Asn Pro Gly Ser Gln Ala Gln Tyr Lys Gly Ser Phe
    130                 135                 140

Gln Ser Asp Gly Gly Thr Tyr Asn Ile Tyr Val Ser Thr Arg Tyr Asn
145                 150                 155                 160

Ala Pro Ser Ile Glu Gly Thr Arg Thr Phe Gln Gln Tyr Trp Ser Ile
                165                 170                 175

Arg Thr Ser Lys Arg Val Gly Gly Ser Val Thr Met Gln Asn His Phe
            180                 185                 190

Asn Ala Trp Ala Gln His Gly Met Pro Leu Gly Ser His Asp Tyr Gln
        195                 200                 205

Ile Val Ala Thr Glu Gly Tyr Gln Ser Ser Gly Ser Ser Asp Ile Tyr
    210                 215                 220
```

Val Gln Thr His
225

<210> SEQ ID NO 159
<211> LENGTH: 208
<212> TYPE: PRT
<213> ORGANISM: Myceliophthora thermophila

<400> SEQUENCE: 159

Arg Pro Phe Asp Phe Asp Asp Gly Asn Ser Thr Glu Ala Leu Ala Lys
1               5                   10                  15

Arg Gln Val Thr Pro Asn Ala Gln Gly Tyr His Ser Gly Tyr Phe Tyr
            20                  25                  30

Ser Trp Trp Ser Asp Gly Gly Gln Ala Thr Phe Thr Leu Leu Glu
        35                  40                  45

Gly Ser His Tyr Gln Val Asn Trp Arg Asn Thr Gly Asn Phe Val Gly
    50                  55                  60

Gly Lys Gly Trp Asn Pro Gly Thr Gly Arg Thr Ile Asn Tyr Gly Gly
65                  70                  75                  80

Ser Phe Asn Pro Ser Gly Asn Gly Tyr Leu Ala Val Tyr Gly Trp Thr
                85                  90                  95

His Asn Pro Leu Ile Glu Tyr Tyr Val Val Glu Ser Tyr Gly Thr Tyr
            100                 105                 110

Asn Pro Gly Ser Gln Ala Gln Tyr Lys Gly Ser Phe Gln Ser Asp Gly
        115                 120                 125

Gly Thr Tyr Asn Ile Tyr Val Ser Thr Arg Tyr Asn Ala Pro Ser Ile
    130                 135                 140

Glu Gly Thr Arg Thr Phe Gln Gln Tyr Trp Ser Ile Arg Thr Ser Lys
145                 150                 155                 160

Arg Val Gly Gly Ser Val Thr Met Gln Asn His Phe Asn Ala Trp Ala
                165                 170                 175

Gln His Gly Met Pro Leu Gly Ser His Asp Tyr Gln Ile Val Ala Thr
            180                 185                 190

Glu Gly Tyr Gln Ser Ser Gly Ser Ser Asp Ile Tyr Val Gln Thr His
        195                 200                 205

<210> SEQ ID NO 160
<211> LENGTH: 681
<212> TYPE: DNA
<213> ORGANISM: Myceliophthora thermophila

<400> SEQUENCE: 160
atggttaccc tcactcgcct ggcggtcgcc gcggcggcca tgatctccag cactggcctg    60
gctgccccga cgcccgaagc tggccccgac cttcccgact tgagctcgg ggtcaacaac   120 ctcgcccgcc gcgcgctgga ctacaaccag aactacagga ccagcggcaa cgtcaactac   180
tcgcccaccg acaacggcta ctcggtcagc ttctccaacg cgggagattt tgtcgtcggg   240
aagggctgga ggacgggagc caccagaaac atcaccttct cgggatcgac acagcatacc   300
tcgggcaccg tgctcgtctc cgtctacggc tggacccgga accgctgat cgagtactac   360 gtgcaggagt acacgtccaa cggggccggc tccgctcagg gcgagaagct gggcacggtc   420
gagagcgacg ggggcacgta cgagatctgg cggcaccagc aggtcaacca gccgtcgatc   480
gagggcacct cgaccttctg gcagtacatc tcgaaccgcg tgtccggcca gcggcccaac   540
ggcggcaccg tcaccctcgc caaccacttc gccgcctggc agaagctcgg cctgaacctg   600

```
ggccagcacg actaccaggt cctggccacc gagggctggg gcaacgccgg cggcagctcc      660
cagtacaccg tcagcggctg a                                                681
```

<210> SEQ ID NO 161
<211> LENGTH: 226
<212> TYPE: PRT
<213> ORGANISM: Myceliophthora thermophila

<400> SEQUENCE: 161

| Met | Val | Thr | Leu | Thr | Arg | Leu | Ala | Val | Ala | Ala | Ala | Met | Ile | Ser |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Thr Gly Leu Ala Ala Pro Thr Pro Glu Ala Gly Pro Asp Leu Pro
          20                  25                  30

Asp Phe Glu Leu Gly Val Asn Asn Leu Ala Arg Arg Ala Leu Asp Tyr
             35                  40                  45

Asn Gln Asn Tyr Arg Thr Ser Gly Asn Val Asn Tyr Ser Pro Thr Asp
     50                  55                  60

Asn Gly Tyr Ser Val Ser Phe Ser Asn Ala Gly Asp Phe Val Val Gly
65                  70                  75                  80

Lys Gly Trp Arg Thr Gly Ala Thr Arg Asn Ile Thr Phe Ser Gly Ser
                 85                  90                  95

Thr Gln His Thr Ser Gly Thr Val Leu Val Ser Val Tyr Gly Trp Thr
             100                 105                 110

Arg Asn Pro Leu Ile Glu Tyr Tyr Val Gln Glu Tyr Thr Ser Asn Gly
         115                 120                 125

Ala Gly Ser Ala Gln Gly Glu Lys Leu Gly Thr Val Glu Ser Asp Gly
     130                 135                 140

Gly Thr Tyr Glu Ile Trp Arg His Gln Gln Val Asn Gln Pro Ser Ile
145                 150                 155                 160

Glu Gly Thr Ser Thr Phe Trp Gln Tyr Ile Ser Asn Arg Val Ser Gly
                 165                 170                 175

Gln Arg Pro Asn Gly Gly Thr Val Thr Leu Ala Asn His Phe Ala Ala
             180                 185                 190

Trp Gln Lys Leu Gly Leu Asn Leu Gly Gln His Asp Tyr Gln Val Leu
         195                 200                 205

Ala Thr Glu Gly Trp Gly Asn Ala Gly Gly Ser Ser Gln Tyr Thr Val
     210                 215                 220

Ser Gly
225

<210> SEQ ID NO 162
<211> LENGTH: 205
<212> TYPE: PRT
<213> ORGANISM: Myceliophthora thermophila

<400> SEQUENCE: 162

Ala Pro Thr Pro Glu Ala Gly Pro Asp Leu Pro Asp Phe Glu Leu Gly
1               5                   10                  15

Val Asn Asn Leu Ala Arg Arg Ala Leu Asp Tyr Asn Gln Asn Tyr Arg
             20                  25                  30

Thr Ser Gly Asn Val Asn Tyr Ser Pro Thr Asp Asn Gly Tyr Ser Val
         35                  40                  45

Ser Phe Ser Asn Ala Gly Asp Phe Val Val Gly Lys Gly Trp Arg Thr
     50                  55                  60

Gly Ala Thr Arg Asn Ile Thr Phe Ser Gly Ser Thr Gln His Thr Ser
65                  70                  75                  80

```
Gly Thr Val Leu Val Ser Val Tyr Gly Trp Thr Arg Asn Pro Leu Ile
                85                  90                  95

Glu Tyr Tyr Val Gln Glu Tyr Thr Ser Asn Gly Ala Gly Ser Ala Gln
            100                 105                 110

Gly Glu Lys Leu Gly Thr Val Glu Ser Asp Gly Thr Tyr Glu Ile
        115                 120                 125

Trp Arg His Gln Gln Val Asn Gln Pro Ser Ile Glu Gly Thr Ser Thr
    130                 135                 140

Phe Trp Gln Tyr Ile Ser Asn Arg Val Ser Gly Gln Arg Pro Asn Gly
145                 150                 155                 160

Gly Thr Val Thr Leu Ala Asn His Phe Ala Ala Trp Gln Lys Leu Gly
                165                 170                 175

Leu Asn Leu Gly Gln His Asp Tyr Gln Val Leu Ala Thr Glu Gly Trp
            180                 185                 190

Gly Asn Ala Gly Gly Ser Ser Gln Tyr Thr Val Ser Gly
        195                 200                 205

<210> SEQ ID NO 163
<211> LENGTH: 1833
<212> TYPE: DNA
<213> ORGANISM: Myceliophthora thermophila

<400> SEQUENCE: 163
atgttcttcg cttctctgct gctcggtctc ctggcgggcg tgtccgcttc accgggacac     60
gggcggaatt ccaccttcta caaccccatc ttccccggct tctacccga tccgagctgc    120 atctacgtgc ccgagcgtga ccacaccttc ttctgtgcct cgtcgagctt caacgccttc    180
ccgggcatcc cgattcatgc cagcaaggac ctgcagaact ggaagttgat cggccatgtg    240
ctgaatcgca aggaacagct tccccggctc gctgagacca ccggtcgac cagcggcatc     300 tgggcaccca ccctccggtt ccatgacgac accttctggt tggtcaccac actagtggac    360
gacgaccggc cgcaggagga cgcttccaga tgggacaata ttatcttcaa ggcaaagaat    420
ccgtatgatc cgaggtcctg gtccaaggcc gtccacttca acttcactgg ctacgacacg    480
gagcctttct gggacgaaga tggaaaggtg tacatcaccg cgcccatgc ttggcatgtt     540 ggcccataca tccagcaggc cgaagtcgat ctcgacacgg gggccgtcgg cgagtggcgc    600
atcatctgga acggaacggg cggcatggct cctgaaggc gcacatcta ccgcaaagat     660 gggtggtact acttgctggc tgctgaaggg gggaccggca tcgaccatat ggtgaccatg    720
gcccggtcga gaaaaatctc cagtccttac gagtccaacc caaacaaccc cgtgttgacc    780
aacgccaaca cgaccagtta ctttcaaacc gtcgggcatt cagacctgtt ccatgacaga    840
catgggaact ggtgggcagt cgccctctcc acccgctccg gtccagaata tcttcactac    900
cccatgggcc gcgagaccgt catgacagcc gtgagctggc cgaaggacga gtggccaacc    960
ttcaccccca tatctggcaa gatgagcggc tggccgatgc ctccttcgca gaaggacatt   1020
cgcggagtcg gcccctacgt caactccccc gacccggaac cctgaccttt ccccgctcg   1080 gcgcccctgc cggcccacct cacctactgg cgataccga ccgtcctc ctacacgccg     1140 tccccgcccg gcaccccaa cccctccgc ctgaccccgt cccgcctgaa cctgaccgcc    1200
ctcaacggca actacgcggg ggccgaccag accttcgtct cgcgccggca gcagcacacc   1260
ctcttcacct acagcgtcac gctcgactac gcgccgcgga ccgccgggga ggaggccggc   1320
gtgaccgcct tcctgacgca gaaccaccac ctcgacctgg gcgtcgtcct gctccctcgc   1380
```

-continued

```
ggctccgcca ccgcgccctc gctgccgggc ctgagtagta gtacaactac tactagtagt    1440
agtagtagtc gtccggacga ggaggaggag cgcgaggcgg gcgaagagga agaagagggc    1500
ggacaagact tgatgatccc gcatgtgcgg ttcagggcg agtcgtacgt gcccgtcccg     1560
gcgcccgtcg tgtacccgat accccgggcc tggagaggcg ggaagcttgt gttagagatc    1620
cgggcttgta attcgactca cttctcgttc cgtgtcgggc cggacgggag acggtctgag    1680
cggacggtgg tcatggaggc ttcgaacgag gccgttagct ggggctttac tggaacgctg    1740
ctgggcatct atgcgaccag taatggtggc aacggaacca cgccggcgta tttttcggat    1800
tggaggtaca caccattgga gcagtttagg gat                                 1833
```

<210> SEQ ID NO 164
<211> LENGTH: 611
<212> TYPE: PRT
<213> ORGANISM: Myceliophthora thermophila

<400> SEQUENCE: 164

```
Met Phe Phe Ala Ser Leu Leu Gly Leu Ala Gly Val Ser Ala
1               5                   10                  15

Ser Pro Gly His Gly Arg Asn Ser Thr Phe Tyr Asn Pro Ile Phe Pro
            20                  25                  30

Gly Phe Tyr Pro Asp Pro Ser Cys Ile Tyr Val Pro Glu Arg Asp His
        35                  40                  45

Thr Phe Phe Cys Ala Ser Ser Phe Asn Ala Phe Pro Gly Ile Pro
    50                  55                  60

Ile His Ala Ser Lys Asp Leu Gln Asn Trp Lys Leu Ile Gly His Val
65                  70                  75                  80

Leu Asn Arg Lys Glu Gln Leu Pro Arg Leu Ala Glu Thr Asn Arg Ser
                85                  90                  95

Thr Ser Gly Ile Trp Ala Pro Thr Leu Arg Phe His Asp Asp Thr Phe
            100                 105                 110

Trp Leu Val Thr Thr Leu Val Asp Asp Arg Pro Gln Glu Asp Ala
        115                 120                 125

Ser Arg Trp Asp Asn Ile Ile Phe Lys Ala Lys Asn Pro Tyr Asp Pro
    130                 135                 140

Arg Ser Trp Ser Lys Ala Val His Phe Asn Phe Thr Gly Tyr Asp Thr
145                 150                 155                 160

Glu Pro Phe Trp Asp Glu Asp Gly Lys Val Tyr Ile Thr Gly Ala His
                165                 170                 175

Ala Trp His Val Gly Pro Tyr Ile Gln Gln Ala Glu Val Asp Leu Asp
            180                 185                 190

Thr Gly Ala Val Gly Glu Trp Arg Ile Ile Trp Asn Gly Thr Gly Gly
        195                 200                 205

Met Ala Pro Glu Gly Pro His Ile Tyr Arg Lys Asp Gly Trp Tyr Tyr
    210                 215                 220

Leu Leu Ala Ala Glu Gly Gly Thr Gly Ile Asp His Met Val Thr Met
225                 230                 235                 240

Ala Arg Ser Arg Lys Ile Ser Ser Pro Tyr Glu Ser Asn Pro Asn Asn
                245                 250                 255

Pro Val Leu Thr Asn Ala Asn Thr Thr Ser Tyr Phe Gln Thr Val Gly
            260                 265                 270

His Ser Asp Leu Phe His Asp Arg His Gly Asn Trp Trp Ala Val Ala
        275                 280                 285

Leu Ser Thr Arg Ser Gly Pro Glu Tyr Leu His Tyr Pro Met Gly Arg
```

```
                    290                 295                 300
Glu Thr Val Met Thr Ala Val Ser Trp Pro Lys Asp Glu Trp Pro Thr
305                 310                 315                 320

Phe Thr Pro Ile Ser Gly Lys Met Ser Gly Trp Pro Met Pro Pro Ser
                325                 330                 335

Gln Lys Asp Ile Arg Gly Val Gly Pro Tyr Val Asn Ser Pro Asp Pro
                340                 345                 350

Glu His Leu Thr Phe Pro Arg Ser Ala Pro Leu Pro Ala His Leu Thr
            355                 360                 365

Tyr Trp Arg Tyr Pro Asn Pro Ser Ser Tyr Thr Pro Ser Pro Pro Gly
        370                 375                 380

His Pro Asn Thr Leu Arg Leu Thr Pro Ser Arg Leu Asn Leu Thr Ala
385                 390                 395                 400

Leu Asn Gly Asn Tyr Ala Gly Ala Asp Gln Thr Phe Val Ser Arg Arg
                405                 410                 415

Gln Gln His Thr Leu Phe Thr Tyr Ser Val Thr Leu Asp Tyr Ala Pro
                420                 425                 430

Arg Thr Ala Gly Glu Glu Ala Gly Val Thr Ala Phe Leu Thr Gln Asn
            435                 440                 445

His His Leu Asp Leu Gly Val Val Leu Leu Pro Arg Gly Ser Ala Thr
        450                 455                 460

Ala Pro Ser Leu Pro Gly Leu Ser Ser Ser Thr Thr Thr Thr Ser Ser
465                 470                 475                 480

Ser Ser Ser Arg Pro Asp Glu Glu Glu Arg Glu Ala Gly Glu Glu
                485                 490                 495

Glu Glu Glu Gly Gly Gln Asp Leu Met Ile Pro His Val Arg Phe Arg
            500                 505                 510

Gly Glu Ser Tyr Val Pro Val Pro Ala Pro Val Tyr Pro Ile Pro
        515                 520                 525

Arg Ala Trp Arg Gly Gly Lys Leu Val Leu Glu Ile Arg Ala Cys Asn
530                 535                 540

Ser Thr His Phe Ser Phe Arg Val Gly Pro Asp Gly Arg Arg Ser Glu
545                 550                 555                 560

Arg Thr Val Val Met Glu Ala Ser Asn Glu Ala Val Ser Trp Gly Phe
                565                 570                 575

Thr Gly Thr Leu Leu Gly Ile Tyr Ala Thr Ser Asn Gly Gly Asn Gly
                580                 585                 590

Thr Thr Pro Ala Tyr Phe Ser Asp Trp Arg Tyr Thr Pro Leu Glu Gln
                595                 600                 605

Phe Arg Asp
        610

<210> SEQ ID NO 165
<211> LENGTH: 595
<212> TYPE: PRT
<213> ORGANISM: Myceliophthora thermophila

<400> SEQUENCE: 165

Ser Pro Gly His Gly Arg Asn Ser Thr Phe Tyr Asn Pro Ile Phe Pro
1               5                   10                  15

Gly Phe Tyr Pro Asp Pro Ser Cys Ile Tyr Val Pro Glu Arg Asp His
                20                  25                  30

Thr Phe Phe Cys Ala Ser Ser Phe Asn Ala Phe Pro Gly Ile Pro
            35                  40                  45
```

```
Ile His Ala Ser Lys Asp Leu Gln Asn Trp Lys Leu Ile Gly His Val
 50                  55                  60
Leu Asn Arg Lys Glu Gln Leu Pro Arg Leu Ala Glu Thr Asn Arg Ser
 65                  70                  75                  80
Thr Ser Gly Ile Trp Ala Pro Thr Leu Arg Phe His Asp Asp Thr Phe
                 85                  90                  95
Trp Leu Val Thr Thr Leu Val Asp Asp Asp Arg Pro Gln Glu Asp Ala
                100                 105                 110
Ser Arg Trp Asp Asn Ile Ile Phe Lys Ala Lys Asn Pro Tyr Asp Pro
                115                 120                 125
Arg Ser Trp Ser Lys Ala Val His Phe Asn Phe Thr Gly Tyr Asp Thr
                130                 135                 140
Glu Pro Phe Trp Asp Glu Asp Gly Lys Val Tyr Ile Thr Gly Ala His
145                 150                 155                 160
Ala Trp His Val Gly Pro Tyr Ile Gln Gln Ala Glu Val Asp Leu Asp
                165                 170                 175
Thr Gly Ala Val Gly Glu Trp Arg Ile Ile Trp Asn Gly Thr Gly Gly
                180                 185                 190
Met Ala Pro Glu Gly Pro His Ile Tyr Arg Lys Asp Gly Trp Tyr Tyr
                195                 200                 205
Leu Leu Ala Ala Glu Gly Gly Thr Gly Ile Asp His Met Val Thr Met
            210                 215                 220
Ala Arg Ser Arg Lys Ile Ser Ser Pro Tyr Glu Ser Asn Pro Asn Asn
225                 230                 235                 240
Pro Val Leu Thr Asn Ala Asn Thr Thr Ser Tyr Phe Gln Thr Val Gly
                245                 250                 255
His Ser Asp Leu Phe His Asp Arg His Gly Asn Trp Trp Ala Val Ala
                260                 265                 270
Leu Ser Thr Arg Ser Gly Pro Glu Tyr Leu His Tyr Pro Met Gly Arg
            275                 280                 285
Glu Thr Val Met Thr Ala Val Ser Trp Pro Lys Asp Glu Trp Pro Thr
            290                 295                 300
Phe Thr Pro Ile Ser Gly Lys Met Ser Gly Trp Pro Met Pro Pro Ser
305                 310                 315                 320
Gln Lys Asp Ile Arg Gly Val Gly Pro Tyr Val Asn Ser Pro Asp Pro
                325                 330                 335
Glu His Leu Thr Phe Pro Arg Ser Ala Pro Leu Pro Ala His Leu Thr
                340                 345                 350
Tyr Trp Arg Tyr Pro Asn Pro Ser Ser Tyr Thr Pro Ser Pro Pro Gly
            355                 360                 365
His Pro Asn Thr Leu Arg Leu Thr Pro Ser Arg Leu Asn Leu Thr Ala
            370                 375                 380
Leu Asn Gly Asn Tyr Ala Gly Ala Asp Gln Thr Phe Val Ser Arg Arg
385                 390                 395                 400
Gln Gln His Thr Leu Phe Thr Tyr Ser Val Thr Leu Asp Tyr Ala Pro
                405                 410                 415
Arg Thr Ala Gly Glu Glu Ala Gly Val Thr Ala Phe Leu Thr Gln Asn
                420                 425                 430
His His Leu Asp Leu Gly Val Val Leu Leu Pro Arg Gly Ser Ala Thr
            435                 440                 445
Ala Pro Ser Leu Pro Gly Leu Ser Ser Thr Thr Thr Thr Ser Ser
450                 455                 460

Ser Ser Ser Arg Pro Asp Glu Glu Glu Glu Arg Glu Ala Gly Glu Glu
```

Glu Glu Glu Gly Gly Gln Asp Leu Met Ile Pro His Val Arg Phe Arg
                485                 490                 495

Gly Glu Ser Tyr Val Pro Val Pro Ala Pro Val Tyr Pro Ile Pro
                500                 505                 510

Arg Ala Trp Arg Gly Gly Lys Leu Val Leu Glu Ile Arg Ala Cys Asn
                515                 520                 525

Ser Thr His Phe Ser Phe Arg Val Gly Pro Asp Gly Arg Arg Ser Glu
                530                 535                 540

Arg Thr Val Val Met Glu Ala Ser Asn Glu Ala Val Ser Trp Gly Phe
545                 550                 555                 560

Thr Gly Thr Leu Leu Gly Ile Tyr Ala Thr Ser Asn Gly Gly Asn Gly
                565                 570                 575

Thr Thr Pro Ala Tyr Phe Ser Asp Trp Arg Tyr Thr Pro Leu Glu Gln
                580                 585                 590

Phe Arg Asp
        595

<210> SEQ ID NO 166
<211> LENGTH: 942
<212> TYPE: DNA
<213> ORGANISM: Myceliophthora thermophila

<400> SEQUENCE: 166
atgaagctcc tgggcaaact ctcggcggca ctcgccctcg cgggcagcag gctggctgcc      60
gcgcacccgg tcttcgacga gctgatgcgg ccgacggcgc cgctggtgcg cccgcgggcg     120
gccctgcagc aggtgaccaa ctttggcagc aacccgtcca acacgaagat gttcatctac     180
gtgcccgaca gctggccccc caacccgccc atcatagtgg ccatccacta ctgcaccggc     240
accgcccagg cctactactc gggctcccct tacgcccgcc tcgccgacca aagggcttc      300
atcgtcatct acccggagtc ccctacagc ggcacctgtt gggacgtctc gtcgcgcgcc     360
gccctgaccc acaacggcgg cggcgacagc aactcgatcg ccaacatggt cacctacacc     420
ctcgaaaagt acaatggcga cgccagcaag gtctttgtca ccggctcctc gtccggcgcc     480
atgatgacga acgtgatggc cgccgcgtac ccggaactgt tcgcggcagg aatcgcctac     540
tcgggcgtgc cgccggctg cttctacagc cagtccggag caccaacgc gtggaacagc      600
tcgtgcgcca acgggcagat caactcgacg ccccaggtgt gggccaagat ggtcttcgac     660
atgtacccgg aatacgacgg cccgcgcccc aagatgcaga tctaccacgg ctcggccgac     720
ggcacgctca gacccagcaa ctacaacgag accatcaagc agtggtgcgg cgtcttcggc     780
ttcgactaca cccgccccga caccacccag gccaactccc gcaggccgg ctacaccacc      840
tacacctggg gcgagcagca gctcgtcggc atctacgccc agggcgtcgg acacacggtc     900
cccatccgcg gcagcgacga catggccttc tttggcctgt ga                        942

<210> SEQ ID NO 167
<211> LENGTH: 313
<212> TYPE: PRT
<213> ORGANISM: Myceliophthora thermophila

<400> SEQUENCE: 167

Met Lys Leu Leu Gly Lys Leu Ser Ala Ala Leu Ala Leu Ala Gly Ser
1               5                   10                  15

Arg Leu Ala Ala Ala His Pro Val Phe Asp Glu Leu Met Arg Pro Thr
                20                  25                  30

Ala Pro Leu Val Arg Pro Arg Ala Ala Leu Gln Gln Val Thr Asn Phe
         35                  40                  45

Gly Ser Asn Pro Ser Asn Thr Lys Met Phe Ile Tyr Val Pro Asp Lys
 50                  55                  60

Leu Ala Pro Asn Pro Pro Ile Ile Val Ala Ile His Tyr Cys Thr Gly
65                  70                  75                  80

Thr Ala Gln Ala Tyr Tyr Ser Gly Ser Pro Tyr Ala Arg Leu Ala Asp
             85                  90                  95

Gln Lys Gly Phe Ile Val Ile Tyr Pro Glu Ser Pro Tyr Ser Gly Thr
                100                 105                 110

Cys Trp Asp Val Ser Ser Arg Ala Ala Leu Thr His Asn Gly Gly Gly
            115                 120                 125

Asp Ser Asn Ser Ile Ala Asn Met Val Thr Tyr Thr Leu Glu Lys Tyr
        130                 135                 140

Asn Gly Asp Ala Ser Lys Val Phe Val Thr Gly Ser Ser Ser Gly Ala
145                 150                 155                 160

Met Met Thr Asn Val Met Ala Ala Tyr Pro Glu Leu Phe Ala Ala
                165                 170                 175

Gly Ile Ala Tyr Ser Gly Val Pro Ala Gly Cys Phe Tyr Ser Gln Ser
            180                 185                 190

Gly Gly Thr Asn Ala Trp Asn Ser Ser Cys Ala Asn Gly Gln Ile Asn
        195                 200                 205

Ser Thr Pro Gln Val Trp Ala Lys Met Val Phe Asp Met Tyr Pro Glu
    210                 215                 220

Tyr Asp Gly Pro Arg Pro Lys Met Gln Ile Tyr His Gly Ser Ala Asp
225                 230                 235                 240

Gly Thr Leu Arg Pro Ser Asn Tyr Asn Glu Thr Ile Lys Gln Trp Cys
                245                 250                 255

Gly Val Phe Gly Phe Asp Tyr Thr Arg Pro Asp Thr Thr Gln Ala Asn
            260                 265                 270

Ser Pro Gln Ala Gly Tyr Thr Thr Tyr Thr Trp Gly Glu Gln Gln Leu
        275                 280                 285

Val Gly Ile Tyr Ala Gln Gly Val Gly His Thr Val Pro Ile Arg Gly
    290                 295                 300

Ser Asp Asp Met Ala Phe Phe Gly Leu
305                 310

<210> SEQ ID NO 168
<211> LENGTH: 292
<212> TYPE: PRT
<213> ORGANISM: Myceliophthora thermophila

<400> SEQUENCE: 168

His Pro Val Phe Asp Glu Leu Met Arg Pro Thr Ala Pro Leu Val Arg
1               5                   10                  15

Pro Arg Ala Ala Leu Gln Gln Val Thr Asn Phe Gly Ser Asn Pro Ser
            20                  25                  30

Asn Thr Lys Met Phe Ile Tyr Val Pro Asp Lys Leu Ala Pro Asn Pro
        35                  40                  45

Pro Ile Ile Val Ala Ile His Tyr Cys Thr Gly Thr Ala Gln Ala Tyr
    50                  55                  60

Tyr Ser Gly Ser Pro Tyr Ala Arg Leu Ala Asp Gln Lys Gly Phe Ile
65                  70                  75                  80

Val Ile Tyr Pro Glu Ser Pro Tyr Ser Gly Thr Cys Trp Asp Val Ser 85                  90                  95
Ser Arg Ala Ala Leu Thr His Asn Gly Gly Gly Asp Ser Asn Ser Ile
                100                 105                 110

Ala Asn Met Val Thr Tyr Thr Leu Glu Lys Tyr Asn Gly Asp Ala Ser
            115                 120                 125

Lys Val Phe Val Thr Gly Ser Ser Gly Ala Met Met Thr Asn Val
        130                 135                 140

Met Ala Ala Ala Tyr Pro Glu Leu Phe Ala Ala Gly Ile Ala Tyr Ser
145                 150                 155                 160

Gly Val Pro Ala Gly Cys Phe Tyr Ser Gln Ser Gly Gly Thr Asn Ala
                165                 170                 175

Trp Asn Ser Ser Cys Ala Asn Gly Gln Ile Asn Ser Thr Pro Gln Val
            180                 185                 190

Trp Ala Lys Met Val Phe Asp Met Tyr Pro Glu Tyr Asp Gly Pro Arg
        195                 200                 205

Pro Lys Met Gln Ile Tyr His Gly Ser Ala Asp Gly Thr Leu Arg Pro
    210                 215                 220

Ser Asn Tyr Asn Glu Thr Ile Lys Gln Trp Cys Gly Val Phe Gly Phe
225                 230                 235                 240

Asp Tyr Thr Arg Pro Asp Thr Thr Gln Ala Asn Ser Pro Gln Ala Gly
                245                 250                 255

Tyr Thr Tyr Thr Trp Gly Glu Gln Gln Leu Val Gly Ile Tyr Ala
            260                 265                 270

Gln Gly Val Gly His Thr Val Pro Ile Arg Gly Ser Asp Asp Met Ala
        275                 280                 285

Phe Phe Gly Leu
    290

<210> SEQ ID NO 169
<211> LENGTH: 840
<212> TYPE: DNA
<213> ORGANISM: Myceliophthora thermophila

<400> SEQUENCE: 169

```
atgatctcgg ttcctgctct cgctctggcc cttctggccg ccgtccaggt cgtcgagtct    60
gcctcggctg ctgtggcaa ggcgccccct tcctcgggca ccaagtcgat gacggtcaac   120
ggcaagcagc gccagtacat tctccagctg cccaacaact acgacgccaa caaggcccac   180
agggtggtga tcgggtacca ctggcgcgac ggatccatga cgacgtggc caacggcggc   240 ttctacgatc tgcggtcccg ggcgggcgac agcaccatcc tcgttgcccc caacggcctc   300
aatgccggat gggccaacgt gggcggcgag gacatcacct tacggacca gatcgtagac   360 atgctcaaga cgacctctg cgtggacgag acccagttct tgctacgggc tggagctat   420 ggcggtgcca tgagccatag cgtggcttgt tctcggccag acgtcttcaa ggccgtcgcg   480
gtcatcgccg gggcccagct gtccggctgc gccggcggca cgacgcccgt ggcgtaccta   540
ggcatccacg gagccgccga caacgtcctg cccatcgacc tcggccgcca gctgcgcgac   600
aagtggctgc agaccaacgg ctgcaactac cagggcgccc aggacccgc gccgggccag   660 caggcccaca tcaagaccac ctacagctgc tcccgcgcgc ccgtcacctg gatcggccac   720 ggggcggcc acgtccccga ccccacgggc aacaacggcg tcaagtttgc gccccaggag   780
acctgggact tctttgatgc cgccgtcgga gcggccggcg cgcagagccc gatgacataa   840
```

<210> SEQ ID NO 170

<211> LENGTH: 279
<212> TYPE: PRT
<213> ORGANISM: Myceliophthora thermophila

<400> SEQUENCE: 170

```
Met Ile Ser Val Pro Ala Leu Ala Leu Leu Ala Ala Val Gln
1               5                   10                  15

Val Val Glu Ser Ala Ser Ala Gly Cys Gly Lys Ala Pro Ser Ser
            20                  25                  30

Gly Thr Lys Ser Met Thr Val Asn Gly Lys Gln Arg Gln Tyr Ile Leu
            35                  40                  45

Gln Leu Pro Asn Asn Tyr Asp Ala Asn Lys Ala His Arg Val Val Ile
        50                  55                  60

Gly Tyr His Trp Arg Asp Gly Ser Met Asn Asp Val Ala Asn Gly Gly
65                  70                  75                  80

Phe Tyr Asp Leu Arg Ser Arg Ala Gly Asp Ser Thr Ile Phe Val Ala
                85                  90                  95

Pro Asn Gly Leu Asn Ala Gly Trp Ala Asn Val Gly Gly Glu Asp Ile
            100                 105                 110

Thr Phe Thr Asp Gln Ile Val Asp Met Leu Lys Asn Asp Leu Cys Val
        115                 120                 125

Asp Glu Thr Gln Phe Phe Ala Thr Gly Trp Ser Tyr Gly Gly Ala Met
    130                 135                 140

Ser His Ser Val Ala Cys Ser Arg Pro Asp Val Phe Lys Ala Val Ala
145                 150                 155                 160

Val Ile Ala Gly Ala Gln Leu Ser Gly Cys Ala Gly Gly Thr Thr Pro
                165                 170                 175

Val Ala Tyr Leu Gly Ile His Gly Ala Ala Asp Asn Val Leu Pro Ile
            180                 185                 190

Asp Leu Gly Arg Gln Leu Arg Asp Lys Trp Leu Gln Thr Asn Gly Cys
        195                 200                 205

Asn Tyr Gln Gly Ala Gln Asp Pro Ala Pro Gly Gln Gln Ala His Ile
    210                 215                 220

Lys Thr Thr Tyr Ser Cys Ser Arg Ala Pro Val Thr Trp Ile Gly His
225                 230                 235                 240

Gly Gly Gly His Val Pro Asp Pro Thr Gly Asn Asn Gly Val Lys Phe
                245                 250                 255

Ala Pro Gln Glu Thr Trp Asp Phe Phe Asp Ala Ala Val Gly Ala Ala
            260                 265                 270

Gly Ala Gln Ser Pro Met Thr
        275
```

<210> SEQ ID NO 171
<211> LENGTH: 259
<212> TYPE: PRT
<213> ORGANISM: Myceliophthora thermophila

<400> SEQUENCE: 171

```
Ala Ser Ala Gly Cys Gly Lys Ala Pro Pro Ser Ser Gly Thr Lys Ser
1               5                   10                  15

Met Thr Val Asn Gly Lys Gln Arg Gln Tyr Ile Leu Gln Leu Pro Asn
            20                  25                  30

Asn Tyr Asp Ala Asn Lys Ala His Arg Val Val Ile Gly Tyr His Trp
        35                  40                  45

Arg Asp Gly Ser Met Asn Asp Val Ala Asn Gly Gly Phe Tyr Asp Leu
    50                  55                  60
```

-continued

```
Arg Ser Arg Ala Gly Asp Ser Thr Ile Phe Val Ala Pro Asn Gly Leu
65              70              75              80

Asn Ala Gly Trp Ala Asn Val Gly Gly Glu Asp Ile Thr Phe Thr Asp
            85              90              95

Gln Ile Val Asp Met Leu Lys Asn Asp Leu Cys Val Asp Glu Thr Gln
            100             105             110

Phe Phe Ala Thr Gly Trp Ser Tyr Gly Gly Ala Met Ser His Ser Val
            115             120             125

Ala Cys Ser Arg Pro Asp Val Phe Lys Ala Val Ala Val Ile Ala Gly
    130             135             140

Ala Gln Leu Ser Gly Cys Ala Gly Gly Thr Thr Pro Val Ala Tyr Leu
145             150             155             160

Gly Ile His Gly Ala Ala Asp Asn Val Leu Pro Ile Asp Leu Gly Arg
                165             170             175

Gln Leu Arg Asp Lys Trp Leu Gln Thr Asn Gly Cys Asn Tyr Gln Gly
            180             185             190

Ala Gln Asp Pro Ala Pro Gly Gln Gln Ala His Ile Lys Thr Thr Tyr
        195             200             205

Ser Cys Ser Arg Ala Pro Val Thr Trp Ile Gly His Gly Gly Gly His
    210             215             220

Val Pro Asp Pro Thr Gly Asn Asn Gly Val Lys Phe Ala Pro Gln Glu
225             230             235             240

Thr Trp Asp Phe Phe Asp Ala Ala Val Gly Ala Ala Gly Ala Gln Ser
                245             250             255

Pro Met Thr
```

GH61 GLYCOSIDE HYDROLASE PROTEIN VARIANTS AND COFACTORS THAT ENHANCE GH61 ACTIVITY

The present application is a continuation-in-part of U.S. patent application. Ser. No. 13/215,193, filed Aug. 22, 2011, now U.S. Pat. No. 8,298,795, which claims priority to U.S. Prov. Appln. Ser. No. 61/375,788, filed Aug. 20, 2010. This application also claims the priority of U.S. Prov. Appln. Ser. No. 61/526,224, filed Aug. 22, 2011, and U.S. Prov. Appln. Ser. No. 61/601,997, filed Feb. 22, 2012, all of which are hereby incorporated in their entireties for all purposes.

REFERENCE TO A "SEQUENCE LISTING", A TABLE, OR A COMPUTER PROGRAM LISTING APPENDIX SUBMITTED AS AN ASCII TEXT FILE

The Sequence Listing written in file CX35-101US2A_ST25.TXT, created on Aug. 20, 2012, 416,766 bytes, machine format IBM-PC, MS-Windows operating system, is hereby incorporated by reference.

FIELD OF THE INVENTION

The invention relates generally to the field of glycolytic enzymes and their use, and to the field of directed enzyme evolution or modification. More specifically, the present invention provides GH61 protein variants, and methods for the use of such protein variants in production of fermentable sugars and ethanol from cellulosic biomass.

BACKGROUND

Cellulosic biomass is a significant renewable resource for the generation of fermentable sugars. These sugars can be used as substrates for fermentation and other metabolic processes to produce biofuels, chemical compounds and other commercially valuable end-products.

The conversion of cellulosic biomass to fermentable sugars may begin with chemical, mechanical, enzymatic or other pretreatments to increase the susceptibility of cellulose to hydrolysis. Such pretreatment may be followed by the enzymatic conversion of cellulose to cellobiose, cello-oligosaccharides, glucose, and other sugars and sugar polymers, using enzymes that break down cellulose. These enzymes are collectively referred to as "cellulases" and include endoglucanases, beta-glucosidases and cellobiohydrolases.

SUMMARY OF THE INVENTION

The invention provides numerous variants of GH61 proteins. In some embodiments, these variants comprise amino acid substitutions as set forth herein. In some embodiments, these variants exhibit an improved ability to synergize with cellulase enzymes, thereby increasing the yield of fermentable sugars obtained by saccharification of cellulose-containing biomass. Sugars obtained from saccharification can be fermented to produce alcohol and other end-products. Thus, the GH61 variant proteins of this invention have important commercial applicability in the production of biofuels and other end-products. In some embodiments, the present invention provides GH61 variant proteins comprising an amino acid sequence that is substantially identical (for example, at least about 70%, about 75%, about 80%, about 85%, about 90%, about 91%, about 92%, about 93%, about 94%, about 95%, about 96%, about 97%, about 98%, about 99%, or about 100% identical) to SEQ ID NO:2 or a fragment of SEQ ID NO:2 having GH61 activity as defined below. In some embodiments, the variant protein has one or more amino acid substitutions with respect to SEQ ID NO:2 or a fragment of SEQ ID NO:2. In some embodiments, the GH61 is at least 95% identical to SEQ ID NO:2 or a fragment of SEQ ID NO:2 having GH61 activity. In some embodiments, the GH61 variant proteins have increased thermoactivity compared with the GH61 wild-type protein of SEQ ID NO:2. In some further embodiments, the GH61 variant proteins have increased thermostability compared with the GH61 wild-type protein of SEQ ID NO:2.

In some embodiments, the present invention provides GH61 variants comprising substitution(s) in at least one of the positions as indicated herein. In some embodiments, the substitution(s) provide GH61 variants that have increased activity as compared to wild-type GH61. In some embodiments, the GH61 variants comprise at least one substitution selected from those listed in Table 1 and/or Table 2 in any combination, wherein the positions are numbered with reference to SEQ ID NO:2.

In some further embodiments, the GH61 variants provided herein comprise the any one or more of the mutations listed in Table 1 and/or Table 2 in any combination. It is not intended that the present invention be limited to the specific substitutions. Any two, three, four, or more than four substitutions find use in any combination that improves GH61 activity. Non-limiting illustrations of effective combinations are provided herein.

In some embodiments, a substitution or combination of substitutions in the amino acid sequence as provided herein results in the variant protein having increased GH61 activity in a saccharification reaction. In some embodiments, crystalline cellulose undergoes saccharification by cellulase enzymes that are contained in culture broth from *M. thermophila* cells. When measured in this manner, a GH61 variant protein of this invention causes increase in yield of fermentable sugars (e.g., glucose) to a degree that is about 1.5-fold, about 2-fold, about 3-fold, about 5-fold, about 8-fold, about 10-fold or more compared with the parental GH61 sequence (SEQ ID NO:2) or biologically active fragment, compared with a reference protein comprising SEQ ID NO:2 or the fragment, without any substitutions. It is not intended that the present invention be limited to the production of any particular fermentable sugar(s). It is also not intended that the present invention be limited to any specific level of improvement in the yield of fermentable sugar using at least one of the variants provided herein.

This invention also provides GH61 protein variants that are more resistant to the presence of enzyme inhibitors that may be present in commercial sources of biomass, or be generated as a result of pretreatment of the biomass substrate.

In some embodiments, the present invention provides GH61 variant proteins comprising amino acid sequences that are at least about at least about 60%, at least about 65%, at least about 70%, 75%, at least 80%, at least about 85%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:2 or a fragment of SEQ ID NO:2 having GH61 activity, wherein the amino acid sequence of the variant protein has one or more amino acid substitutions with respect to SEQ ID NO:2 or the fragment.

In some embodiments, the present invention provides GH61 variant proteins comprising amino acid sequences that are at least about at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:2 or a fragment of SEQ ID NO:2 having GH61 activity, wherein the amino acid sequence of the variant protein has one or more amino acid substitutions with respect to SEQ ID NO:2 or the fragment, and wherein the substitution(s) in the amino acid sequence result in the variant protein having increased GH61 activity in a reaction where crystalline cellulose undergoes saccharification by cellulase enzymes that are contained in culture broth from *M. thermophila* cells, compared with a reference protein comprising SEQ ID NO:2 or the fragment, without any substitutions.

In some embodiments, the present invention provides GH61 variant proteins comprising amino acid sequences that are at least about 60%, at least about 65%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% identical to SEQ ID NO:2 or a fragment of SEQ ID NO:2 having GH61 activity, wherein the amino acid sequence of the variant protein has one or more amino acid substitutions with respect to SEQ ID NO:2 or the fragment, and wherein the polynucleotide encoding the GH61 variant protein comprises at least one mutation and/or mutation set selected from those listed in Table 1 and/or Table 2 in any combination, wherein the nucleotide positions of the substitutions are determined by alignment with SEQ ID NO:1.

In some embodiments, the present invention provides enzyme compositions comprising at least one GH61 variant of the present invention and/or at least one wild-type GH61 protein. In some embodiments, the present invention provides enzyme compositions comprising at least one GH61 variant protein of this invention is combined with one or more cellulase enzyme(s), including but not limited to endoglucanases (EG), beta-glucosidases (BGL), cellobiohydrolases (e.g., CBH1 and/or CBH2), and/or at least one wild-type GH61 protein. In some embodiments, the enzyme compositions further comprise one or more enzymes selected from cellulases, hemicellulases, xylanases, amylases, glucoamylases, proteases, esterases xylosidases, and lipases.

The invention also includes polynucleotides encoding GH61 variant proteins, recombinant cells expressing such polynucleotides and optionally one or more cellulase enzymes, and methods for increasing yield of fermentable sugars in a saccharification reaction by conducting the reaction in the presence of at least one GH61 protein of this invention.

In some embodiments, the present invention provides at least one polynucleotide comprising at least one nucleic acid sequence encoding at least one GH61 variant protein; at least one polynucleotide that hybridizes under stringent hybridization conditions to at least one polynucleotide encoding at least one GH61 variant protein; and/or at least one polynucleotide that hybridizes under stringent hybridization conditions to the complement of at least one polynucleotide encoding at least one polypeptide comprising at least one GH61 variant protein.

The present invention also provides recombinant nucleic acid constructs comprising at least one polynucleotide sequence encoding at least one GH61 protein, wherein the polynucleotide is selected from: (a) a polynucleotide that encodes a polypeptide comprising an amino acid sequence having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% identity to SEQ ID NO:2, wherein the amino acid sequence comprises at least one substitution and/or substitution set provided herein; (b) a polynucleotide that hybridizes under stringent hybridization conditions to at least a fragment of a polynucleotide that encodes a polypeptide having the amino acid sequence of SEQ ID NO:2, and wherein the amino acid sequence comprises at least one substitution and/or at least one substitution set provided herein; and/or (c) a polynucleotide that hybridizes under stringent hybridization conditions to the complement of at least a fragment of a polynucleotide that encodes a polypeptide having the amino acid sequence of SEQ ID NO:2, and wherein the amino acid sequence comprises at least one substitution and/or at least one substitution set provided herein.

The present invention further provides recombinant nucleic acid constructs comprising at least one polynucleotide sequence encoding at least one GH61 protein, wherein the polynucleotide is selected from: (a) a polynucleotide that encodes a polypeptide comprising an amino acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:2, wherein the amino acid sequence comprises at least one substitution and/or substitution set provided herein; (b) a polynucleotide that hybridizes under stringent hybridization conditions to a polynucleotide that encodes a polypeptide having the amino acid sequence of SEQ ID NO:2, and wherein the amino acid sequence comprises at least one substitution and/or at least one substitution set provided herein; and/or (c) a polynucleotide that hybridizes under stringent hybridization conditions to the complement of a polynucleotide that encodes a polypeptide having the amino acid sequence of SEQ ID NO:2, and wherein the amino acid sequence comprises at least one substitution and/or at least one substitution set provided herein. In some embodiments of the nucleic acid constructs, the polynucleotide sequence is at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:1, and wherein the polynucleotide sequence comprises at least one mutation and/or at least one mutation set provided herein. Exemplary are those shown in Table 1 and Table 2, which may be incorporated into the polynucleotide in any combination.

In some embodiments, the present invention provides polynucleotides and nucleic acid constructs comprising polynucleotides encoding at least one GH61 variant and/or wild-type protein (e.g., any of SEQ ID NOS:2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 64, 65, 67, 68, 70, 71, 73, 74, 76, 77, 79, 80, 82, 83, 85, 86, 88, 89, 91, 93, 95, 96, 98, 99, 101, 102, 104, 105, 107, 108), operably linked to promoters. In some embodiments, the promoters are heterologous promoters. In some embodiments, the present invention provides expression constructs comprising polynucleotides and/or nucleic acid constructs that comprise polynucleotides encoding at least one GH61 variant and/or wild-type protein. In some embodiments, the expression constructs comprise at least one nucleic acid sequence operably linked to at least one additional regulatory sequence.

The present invention also provides recombinant host cells that express at least one polynucleotide sequence encoding at least one GH61 variant protein. In some embodiments, the host cell also expresses at least one polynucleotide sequence encoding at least one GH61 wild-type protein. In some embodiments, the expressed GH61 variant and/or wild-type protein is secreted from the host cell. In some embodiments, the host cell also produces at least one cellulase enzyme selected from endoglucanases (EG), beta-glucosidases (BGL), cellobiohydrolases (e.g., CBH1 and/or CBH2), xylanases, xylosidases, etc. In some embodiments, the host cell is a yeast, while in some other embodiments, the host cell is a filamentous fungal cell. In some further embodiments, the filamentous fungal cell is a *Myceliophthora*, a *Thielavia*, a *Trichoderma*, or an *Aspergillus* cell. In some embodiments, the filamentous fungal cell is *Myceliophthora thermophila*. In some additional embodiments, the host cell also produces at least one additional enzyme (e.g., esterase, protease, amylase, laccase, etc.).

In some additional embodiments, the present invention provides methods for producing at least one end-product from at least one cellulosic substrate. The substrate is contacted with at least one GH61 variant protein of the invention, and one or more cellulase enzymes. The fermentable sugars that are produced as a result are contacted with a microorganism in a fermentation to produce an end-product (e.g., an alcohol such as ethanol). The fermentation may be simultaneous with the saccharification, or may occur subsequently. It is not intended that the fermentation end-product be limited to any specific composition, as various end-products may be obtained from the fermentation reaction, including but not limited to alcohols.

The present invention also provides methods for producing fermentable sugars from cellulosic substrates, comprising contacting at the cellulosic substrate with at least one enzyme composition provided herein, under culture conditions whereby fermentable sugars are produced. In some embodiments the enzyme composition comprises a plurality of enzymes selected from at least one GH61 variant, at least one wild-type GH61, at least one endoglucanase (EG), at least one beta-glucosidase (BGL), at least one cellobiohydrolase (e.g., CBH1 and/or CBH2), at least one xylanase, at least one xylosidase, and/or at least one esterase. In some embodiments, the CBH1 is CBH1a. In further embodiments, the CBH2 is CHB2b. In some embodiments, the methods further comprise the step of pretreating the cellulosic substrate prior to the contacting step. In some embodiments, the enzyme composition is added concurrently with the pretreating step.

In some embodiments, the cellulosic substrate comprises wheat grass, wheat straw, barley straw, sorghum, rice grass, sugarcane, sugarcane straw, bagasse, switchgrass, corn stover, corn fiber, grains, or a combination thereof. In further embodiments, the fermentable sugars comprise glucose and/or xylose. In some embodiments, the methods further comprise the step of recovering the fermentable sugars. In some embodiments, the methods further comprise the step of contacting the fermentable sugars with a microorganism under conditions such that the microorganism produces at least one fermentation end product. In further embodiments, the fermentation end product is selected from alcohols, fatty alcohols, fatty acids, lactic acid, acetic acid, 3-hydroxypropionic acid, acrylic acid, succinic acid, citric acid, malic acid, fumaric acid, amino acids, 1,3-propanediol, ethylene, glycerol, butadiene, and/or beta-lactams. In some still further embodiments, the fermentation end product is an alcohol selected from ethanol and butanol. In some embodiments, the alcohol is ethanol. It is not intended that the fermentation end-product be limited to any specific composition(s), as various end-products can be produced using the present invention.

The present invention also provides methods for producing an end product from a cellulosic substrate, comprising: contacting the cellulosic substrate with at any enzyme composition provided herein, under conditions whereby fermentable sugars are produced from the substrate; and contacting the fermentable sugars with a microorganism in a fermentation to produce an end-product. In some embodiments, the methods comprise simultaneous saccharification and fermentation reactions (SSF). In some alternative embodiments, the methods comprise saccharification of the cellulosic substrate and fermentation in separate reactions (SHF). In some additional embodiments, the methods comprise production of at least one enzyme simultaneously with hydrolysis and/or fermentation (e.g., "consolidated bioprocessing").

The present invention also provides methods for producing a fermentation end product from a cellulosic substrate, comprising obtaining fermentable sugars produced according to any method provided herein, and contacting the fermentable sugars with a microorganism in a fermentation to produce a fermentation end product. In some embodiments, the fermentation end product is selected from alcohols, fatty alcohols, fatty acids, lactic acid, acetic acid, 3-hydroxypropionic acid, acrylic acid, citric acid, malic acid, fumaric acid, succinic acid, amino acids, 1,3-propanediol, ethylene, glycerol, butadiene, and/or beta-lactams. In some embodiments, the fermentation end product is at least one alcohol selected from ethanol and butanol. In further embodiments, the alcohol is ethanol. In some still further embodiments, the microorganism is a yeast. In some embodiments, the methods further comprise the step of recovering the fermentation end product. It is not intended that the fermentation end-product be limited to any specific composition(s), as various end-products can be produced using the present invention. It is also not intended that the present invention be limited to any particular microorganism. It is further not intended that the present invention be limited to any particular yeast, as any suitable yeast finds use in the present invention.

The present invention also provides for use of at least one GH61 variant protein as provided herein to produce at least one fermentation end product. The present invention also provides for use of at least one GH61 variant protein provided herein to produce at least one fermentation end product selected from alcohols, fatty alcohols, fatty acids, lactic acid, acetic acid, 3-hydroxypropionic acid, acrylic acid, citric acid, malic acid, fumaric acid, succinic acid, amino acids, 1,3-propanediol, ethylene, glycerol, butadiene, and/or beta-lactams. In some embodiments, the fermentation end product is an alcohol selected from ethanol and butanol. In some embodiments, the alcohol is ethanol. It is not intended that the fermentation end-product be limited to any specific composition(s), as various end-products can be produced using the present invention.

A further embodiment of the invention is a composition comprising a GH61 protein, one or more cellulase enzymes, a cellulosic substrate, and an effective concentration of $Cu^{++}$ and/or gallic acid, as further described and illustrated below. The GH61 protein may be any GH61 protein disclosed herein, such as a protein comprising an amino acid sequence at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% identical to SEQ ID NO:2, or a fragment thereof with GH61 activity. In some embodiments, the GH61 protein is a variant protein comprising all or part of SEQ ID NO:2 having GH61 activity, wherein the variant comprises one or more of the amino acid substitutions provided herein. In some embodiments, the cellulase enzyme(s) are selected from endoglucanases (EG), beta-glucosidases (BGL), cellobiohydrolases (e.g., CBH1 and/or CBH2), xylanases, xylosidases, etc. In some embodiments, the presence of $Cu^{++}$, gallic acid, or both enhances activity of the GH61 protein, thereby increasing the rate of glucose production or reducing the amount of GH61 protein needed to supply GH61 activity in a saccharification reaction.

In another embodiment, the present invention provides methods for producing fermentable sugars from cellulosic substrate(s), in which a composition comprising at least one GH61, at least one cofactor, at least one additional cellulase enzyme, and at least one cellulosic substrate is cultured or maintained under conditions whereby fermentable sugars are produced from the substrate(s). The fermentable sugars can then be contacted with a microorganism under conditions such that the microorganism produces at least one fermentation end product, such as ethanol. A further embodiment of the invention is use of $Cu^{++}$ to increase production of fermentable sugars from a saccharification reaction where cellulase activity is enhanced in the presence of a protein or protein variant with GH61 activity.

The present invention provides GH61 variant proteins comprising amino acid sequences that are at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to SEQ ID NO:2 or a fragment of SEQ ID NO:2 having GH61 activity, wherein the amino acid sequence of the variant protein has one or more amino acid substitutions with respect to SEQ ID NO:2 or the fragment. In some embodiments, the GH61 variant proteins comprise an amino acid sequence that is at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to SEQ ID NO:2 or a fragment of SEQ ID NO:2 having GH61 activity, wherein the amino acid sequence of the variant protein has one or more amino acid substitutions with respect to SEQ ID NO:2 or the fragment. In some embodiments, the GH61 variant proteins are at least 95% identical to SEQ ID NO:2 or a fragment of SEQ ID NO:2 having GH61 activity. In some embodiments, the GH61 variant proteins have increased thermoactivity, thermostability, and/or activity, as compared to the GH61 wild-type protein of SEQ ID NO:2. In some further embodiments, the GH61 variant proteins comprise at least one substitution(s) at one or more of the following amino acid positions: 20, 35, 42, 44, 45, 68, 87, 97, 103, 104, 127, 131, 132, 133, 134, 137, 139, 142, 143, 162, 163, 164, 165, 166, 167, 168, 169, 170, 171, 172, 173, 174, 175, 176, 177, 178, 179, 180, 181, 190, 191, 192, 192, 205, 212, 215, 218, 232, 236, 239, 244, 246, 258, 270, 273, 317, 322, 323, 328, 330, and/or 341, wherein the amino acid positions are numbered with reference to SEQ ID NO:2. In some embodiments, the GH61 variant proteins comprise at least one substitution(s) at one or more of the following amino acid positions: H20, N35, W42, Q44, P45, F68, T87, V97, P103, E104, S127, W131, F132, K133, I134. A137, Y139, A142, A143, I162, P163, S164, D165, L166, K167, A168, G169, N170, Y171, V172, L173, R174, H175, E176, I177, I178, A179, L180, H181, Q190, A191, Y192, Y192, S205, A212, S215, K218, S232, T236, G239, A244, A246, T258, G270, P273, N317, P322, T323, G328, S330, and/or C341, wherein the amino acid positions are numbered with reference to SEQ ID NO:2. In some further embodiments, the GH61 variant proteins comprise at least one substitution(s) at one or more of the following amino acid positions: H20, N35, W42, E104, I134, S164, K167, A168, V172, I177, A179, and/or A191, wherein the amino acid positions are numbered with reference to SEQ ID NO:2. In some additional embodiments, the GH61 variant proteins comprise at least two amino acid substitutions. In still some further embodiments, the GH61 variant proteins comprise at least one substitution set selected from: N35/E104/A168; W42/E104/K167; N35/W42/V97/A191; W42/E104; E104/K167; W42/A191; N35/W42/A191; V97/A191; and N35/E104/A191, wherein the amino acid positions are numbered with reference to SEQ ID NO:2. In some embodiments, the GH61 variant proteins comprise at least one amino acid substitution comprising one or more of the following substitutions numbered with reference to SEQ ID NO:2: H20C/D, N35G, W42P, Q44V, P45T, F68Y, T87P, V97Q, P103E/H, E104C/D/H/Q, S127T, W131X, F132X, K133X, 134X, A137P, Y139L, A142W, A143P, I162X, P163X, S164X, D165X, L166X, K167A/X, A168P/X, G169X, N170X, Y171A/R, V172X, L173X, R174X, H175X, E176X, I177X, I178X, A179X, L180M/W, H181X, Q190E/H, A191N/T, Y192H, Y192Q, S205N, A212P, S215W, K218T, S232A, T236P, G239D, A244D, A246T, T258I, G270S, P273S, N317K, P322L, T323P, G328A, S330R, and/or C341R, wherein the amino acid positions are numbered with reference to SEQ ID NO:2. In some additional embodiments, the GH61 variant proteins comprise one or more of the following substitutions: N35G, W42P, V97Q, E104H, K167A, A168P, and/or A191N, wherein the amino acid positions are numbered with reference to SEQ ID NO:2. In some embodiments, the GH61 variant proteins comprise one or more of the following substitution sets: N35G/E104H/A168P; W42P/E104H/K167A; N35G/W42P/V97Q/A191N; W42P/E104H; E104H/K167A; W42P/A191N; N35G/W42P/A191N; V97Q/A191N; and/or N35G/E104H/A191N, wherein the amino acid positions are numbered with reference to SEQ ID NO:2. In some additional embodiments, the GH61 variant proteins comprise the substitutions N35G/E104H/A168P, wherein the amino acid positions are numbered with reference to SEQ ID NO:2. In some further embodiments, the GH61 variant proteins comprise the sequence set forth in any of SEQ ID NOS:4, 6, and/or 8. In some additional further embodiments, the GH61 variant proteins are encoded by at least one polynucleotide sequence set forth in SEQ ID NOS:3, 5, and/or 7. In some embodiments, the GH61 variant proteins comprise at least one substitution(s) at one or more of the following amino acid positions: 24, 28, 32, 34, 35, 40, 44, 45, 46, 49, 51, 54, 55, 56, 58, 64, 66, 67, 69, 70, 71, 78, 80, 82, 83, 88, 93, 95, 101, 104, 116, 118, 128, 130, 136, 137, 141, 142, 144, 145, 150, 155, 161, 164, 168, 184, 187, 199, 203, 205, 212, 218, 219, 230, 231, 232, 233, 234, 236, 237, 245, 253, 263, 266, 267, 268, 269, 270, 271, 280, 281, 282, 290, 295, 297, 303, 305, 310, 317, 320, 324, 326, 327, 329, 330, 332, 333, 336, 337, and/or 339, wherein the amino acid positions are numbered with reference to SEQ ID NO:2. In some further embodiments, the GH61 variant proteins, comprise at least one substitution(s) at one or more of the following amino acid positions: S24, V28, Y32, R34, N35, T40, Q44, P45, N46, T49, I51, T54, A55, A56, Q58, E64, N66, S67, G69, T70, P71, S78, T80, G82, G83, V88, K93, N95, E101, E104, A116, N118, S128, R130, G136, A137, K141, A142, G144, R145, A150, G155, Q161, S164, A168, Q184, N187, R199, G203, S205, A212, K218, A219, V230, S231, S232, P233, D234, T236, V237, G245, S253, A263, P266, G267, G268, G269, G270, A271, A280, T281, S282, R290, S295, A297, P303, G305, K310, N317, T320, V324, A326, P327, S329, S330, S332, V333, E336, W337, and/or S339, wherein the amino acid positions are numbered with reference to SEQ ID NO:2. In some further embodiments, the GH61 variant proteins comprise a plurality of amino acid substitutions as set forth herein. In some embodiments, the GH61 variant proteins comprise at least one substitution set selected from: N35/T40/E104/A168/P327; N35/P45/E104/A168/N317; N35/E104/A168/N317; N35/E104/A168/N317/S329; N35/E104/A137/A168/S232; N35/E104/A168/N317/T320; N35/E104/A168/D234; N35/T40/E104/A142/A168; N35/E104/R145/A168; N35/T40/S78/V88/E104/S128K/A168/D234; N35/E104/A168/S330; N35/E104/A168/G203/P266; N35/E104/A168/D234; N35/E104/A168/S330; N35/E104/A168/W337; R34/N35/E104/R145/A168; Y32/N35/E64/E104/A168; V28/N35/P45/E104/A168; N35/E104/G144/A168/V333; N35/N66/E104/A168; N35/E104/A168/P327; N35/E104/A168/G203; N35/E104/A168/S339; N35/P45/N46/E104/A150/A168; N35/E104/A168/S231; N35/T40/E104/A168/D234/P327; N35/E104/A168/S231; N35/E104/A168/N317; N35/E104/A168/S330; N35/E104/A168/S329; N35/E104/A168/P327; N35/P45/E104/A168; N35/E104/A116/A168; N35/T40/E104/A168/V230/P327; N35/E104/A168/S332; N35/E104/A168/G203; N35/E104/R145/A168/S329; N35/T40/T49/E104/A168/D234; /P327; N35/A56/E104/A168; N35/E104/Q161/A168; N35/E104/A168/S332; N35/P45/T49/E104/A168/N317/T320; N35/E104/A168/V237; N35/E104/A168/E336; N35/E104/A168/P233; N35/E104/R130/A168; N35/E104/A168/P327; N35/E104/A168/N317; N35/Q44/E104/A168; N35/E104/A168/A326; N35/E104/A168/N317; N35/T40/E104/S128/A168; N35/T80/E104/A168/P303; N35/E104/A116/A168; N35/E104/A168/S231/S295; N35/T40/E101/E104/A168/P327; N35/P45/E104/A168/A219/S232; N35/N46/E104/A168; N35/E104/A168/A326; N35/E104/A168/G203/T281; N35/E104/A168/E336; N35/T40/E104/S128/A142/A168; N35/E104/N118/A168; N35/E104/G155/A168; S24/N35/E104/A168/V237/P303; N35/E104/Q161/A168; N35/Q44/S67/E104/A168; V28/N35/E104/A168; N35/E104/A168/Q184; N35/T54/E104/A168; N35/N66/E104/A168; N35/E64/E104/A168; N35/E104/S164/A168/A271; N35/N66/E104/A168; N35/G83/E104/A168; N35/E104/K141/A168; N35/E104/A168/N317/T320; N35/E104/R130/A168; N35/E104/R145/A168; N35/T70/E104/A168; N35/E104/R130/A168; N35/E104/A168/Q184; N35/E104/A168/S329; N35/T49/E104/A168; Y32/N35/E104/A168; N35/E104/A168/S330; N35/Q58/E104/A168; Y32/N35/P71/E104/A168; N35/E104/A168/S330; N35/T80/E104/A168; N35/G82/E104/A168; N35/E104/A168/S295; N35/N66/E104/A168; N35/T54/E104/A168; N35/P45/E104/A168; N35/E104/S128/A168; N35/N66/N95/E104/S164/A168; /G267; N35/T54/E104/A168; N35/P45/E104/K141/A168; N35/E104/A168/S332; N35/E104/A168/A297; N35/E104/K141/R145/A168; N35/Q44/E104/A168/S231; N35/T40/T49/S78/E104/A142; /A168; N35/E104/S164/A168/S295; N35/E104/A168/N317; N35/P45/E104/A168; N35/G82/E104/A168; N35/N46/E104/A168/G203/A263; N35/Q58/E104/A168; N35/G69/E104/A168; N35/S67/E104/A168; N35/E104/A168/R199; N35/E104/A168/G203/G268/G269/G270; N35/E104/A168/V324; N35/E104/A168/P266; N35/E104/A168/G245; N35/N66/E104/A168; S24/N35/Q44/T80/E104/A168; N35/E104/A168/T236; N35/E104/A168/K310; N35/E104/R130/A168; N35/N66/S78/E104/A168/S253; N35/N66/E104/S164/A168/S282; N35/E104/A142/A168; N35/E104/A145/A168; N35/E104/A168/S231; N35/E104/A168/Q184; N35/E104/A168/K218; N35/E104/A168/P233; N35/T49/E104/A168/Q184; N35/T40/E104/A168/P327; N35/T54/E104/A168; N35/N66/E104/S164/A168/S231/S253; N35/E104/A168/G203; N35/T49/E104/A168; N35/E104/A168/P266/G267; N35/T49/Q44/N66/E104/A168; N35/S67/E104/A168; N35/E104/A137/A168; N35/T49/E104/S128/A168; N35/T49/E104/A168/K218/N317; N35/I51/E104/A168; N35/E104/A168/A326; N35/P45/E104/A168/T320; N35/N66/E104/A168; N35/E104/A168/V237/P303; N35/P45/E104/A168/K218/N317; N35/T80/E104/A168; N35/A55/E104/A168; N35/E104/K141/A168/P266; N35/E104/A168/S330; N35/N66/E104/A168/R290; N35/E104/N118/A168; N35/E104/A168/A212; N35/K93/E104/R130/A168; N35/E104/A168/G267; N35/P45/T49/E104/A168/N317; N35/E104/A168/V230; N35/E104/A168/S329; N35/P45/E104/A168/A219; N35/S78/E104/S164/A168; N35/E104/A168/S205; N35/E104/A168/Q184; V28/N35/N46/Q58/E104/A168; N35/E104/A142/A168; N35/E104/A168/E336; N35/E104/A168/A280; N35/E104/A168/A219; N35/E104/A168/P303/G305; R34/N35/E104/A168/A280; N35/E104/A168/N187; N35/E104/G136/A168; N35/E104/A168/Q184; N35/T49/E104/A168/N317; N35/T40/T49/S78/E104/A168; R34/N35/K93/E104/R130/R145/A168/R199/K218/A280; N35/T40/E104/A142/A168; and N35/N66/E104/A168, wherein the amino acid positions are numbered with reference to SEQ ID NO:2. In some further embodiments, the GH61 variant proteins comprise at least one amino acid substitution comprising one or more of the following substitutions numbered with reference to SEQ ID NO:2: S24Q; V28H; Y32S; R34E; N35G; T40A/G/L/S; Q44K; P45D/E/K/R/S; N46E/R; T49A/Q/R/Y; I51A; T54G/M/S/W; A55G; A56S; Q58H/P; E64L/S; N66A/D/G/L/M/Q/R/V; S67G/H/T; G69T; T70A; P71A; S78C/D; T80H/L/V; G82A/S; G83R; V88I; K93N/T; N95E; E101T; E104H; A116Q/S; N118E/S; S128K/L/N; R130E/G/H/K/Y; G136H; A137M/S; K141A/N/P/R; A142D/G/L; G144S; R145H/L/N/Q/T; A150Y; G155N; Q161E/R; S164E; A168P; Q184E/H/L/N/R; N187D; R199E; G203E/V/Y; S205T; A212M; K218L/T; A219R/T; V230I/Q; S231A/H/K/I; S232E; P233F/T; D234E/M/N; T236E; V237I; G245A; S253D/T; A263V; P266S; G267D/V; G268A; G269A; G270A; A271T; A280D/T; T281A; S282D; R290K; S295D/L/T; A297T; P303T; G305D; K310I; N317D/H/I/M/Q/R; T320A; V324M; A326C/Q/V; P327F/K/L/M; S329H/I/Q/T/Y; S330A/H/I/T/V; S332C/F/R; V333Q; E336L/R/S; W337R; and/or S339W, wherein the amino acid positions are numbered with reference to SEQ ID NO:2. In some embodiments, the GH61 variant proteins comprise a plurality of substitutions and/or substitution sets as provided therein. In some additional embodiments, the GH61 variant proteins comprise one or more of the following substitution sets: N35G/T40A/E104H/A168P/P327M; N35G/P45D/E104H/A168P/N317R; N35G/E104H/A168P/N317R; N35G/E104H/A168P/N317D/S329Y; N35G/E104H/A137S/A168P/S232E; N35G/E104H/A168P/N317R/T320A; N35G/E104H/A168P/D234E; N35G/T40S/E104H/A142G/A168P; N35G/E104H/R145L/A168P; N35G/T40S/S78C/V88I/E104H/S128K/A168P/D234M; N35G/E104H/A168P/S330V; N35G/E104H/A168P/G203E/P266S; N35G/E104H/A168P/D234N; N35G/E104H/A168P/S330H; N35G/E104H/A168P/W337R; R34E/N35G/E104H/R145T/A168P; Y32S/N35G/E64S/E104H/A168P; V28H/N35G/P45K/E104H/A168P; N35G/E104H/G144S/A168P/V333Q; N35G/N66Q/E104H/A168P; N35G/E104H/A168P/P327K; N35G/E104H/A168P/G203E; N35G/E104H/A168P/

S339W; N35G/P45K/N46E/E104H/A150Y/A168P; N35G/ E104H/A168P/S231K; N35G/T40A/E104H/A168P/D234E/ P327M; N35G/E104H/A168P/S231H; N35G/E104H/ A168P/N317M; N35G/E104H/A168P/S330Y; N35G/ E104H/A168P/S329I; N35G/E104H/A168P/P327F; N35G/ P45D/E104H/A168P; N35G/E104H/A116S/A168P; N35G/ T40A/E104H/A168P/V230I/P327M; N35G/E104H/A168P/ S332R; N35G/E104H/A168P/G203V; N35G/E104H/ R145N/A168P/S329H; N35G/T40S/T49R/E104H/A168P/ D234E; /P327M; N35G/A56S/E104H/A168P; N35G/ E104H/Q161R/A168P; N35G/E104H/A168P/S332F; N35G/P45R/T49A/E104H/A168P/N317R/T320A; N35G/ E104H/A168P/V237I; N35G/E104H/A168P/E336S; N35G/ E104H/A168P/P233T; N35G/E104H/R130H/A168P; N35G/E104H/A168P/P327L; N35G/E104H/A168P/N317I; N35G/Q44K/E104H/A168P; N35G/E104H/A168P/A326V; N35G/E104H/A168P/N317H; N35G/T40L/E104H/S128K/ A168P; N35G/T80V/E104H/A168P/P303T; N35G/E104H/ A116Q/A168P; N35G/E104H/A168P/S231A/S295L; N35G/T40S/E101T/E104H/A168P/P327M; N35G/P45K/ E104H/A168P/A219R/S232E; N35G/N46R/E104H/A168P; N35G/E104H/A168P/A326Q; N35G/E104H/A168P/ G203E/T281A; N35G/E104H/A168P/E336R; N35G/T40S/ E104H/S128K/A142G/A168P; N35G/E104H/N118S/ A168P; N35G/E104H/G155N/A168P; S24Q/N35G/E104H/ A168P/V237I/P303T; N35G/E104H/Q161E/A168P; N35G/ Q44K/S67T/E104H/A168P; V28H/N35G/E104H/A168P; N35G/E104H/A168P/Q184L; N35G/T54G/E104H/A168P; N35G/N66M/E104H/A168P; N35G/E64L/E104H/A168P; N35G/E104H/S164E/A168P/A271T; N35G/N66A/E104H/ A168P; N35G/G83R/E104H/A168P; N35G/E104H/K141A/A168P; N35G/E104H/A168P/N317Q/T320A; N35G/E104H/R130G/A168P; N35G/E104H/R145Q/A168P; N35G/T70A/E104H/A168P; N35G/E104H/R130K/A168P; N35G/E104H/A168P/Q184E; N35G/E104H/A168P/S329T; N35G/T49A/E104H/A168P; Y32S/N35G/E104H/A168P; N35G/E104H/A168P/S3301; N35G/Q58H/E104H/A168P; Y32S/N35G/P71A/E104H/A168P; N35G/E104H/A168P/S330T; N35G/T80V/E104H/A168P; N35G/G82A/E104H/A168P; N35G/E104H/A168P/S295T; N35G/N66G/E104H/A168P; N35G/T54S/E104H/A168P; N35G/P45S/E104H/A168P; N35G/E104H/S128L/A168P; N35G/N66D/N95E/E104H/S164E/A168P; /G267D; N35G/T54W/E104H/A168P; N35G/P45E/E104H/K141R/A168P; N35G/E104H/A168P/S332C; N35G/E104H/A168P/A297T; N35G/E104H/K141P/R145Q/A168P; N35G/Q44K/E104H/A168P/S231T; N35G/T40G/T49R/S78C/E104H/A142G;/A168P; N35G/E104H/S164E/A168P/S295D; N35G/E104H/A168P/N317Q; N35G/P45R/E104H/A168P; N35G/G82S/E104H/A168P; N35G/N46R/E104H/A168P/G203E/A263V; N35G/Q58P/E104H/A168P; N35G/G69T/E104H/A168P; N35G/S67G/E104H/A168P; N35G/E104H/A168P/R199E; N35G/E104H/A168P/G203E/G268A/G269A/G270A; N35G/E104H/A168P/V324M; N35G/E104H/A168P/P266S; N35G/E104H/A168P/G245A; N35G/N66R/E104H/A168P; S24Q/N35G/Q44K/T80H/E104H/A168P; N35G/E104H/A168P/T236E; N35G/E104H/A168P/K310I; N35G/E104H/R130Y/A168P; N35G/N66D/S78D/E104H/A168P/S253D; N35G/N66D/E104H/S164E/A168P/S282D; N35G/E104H/A142L/A168P; N35G/E104H/R145H/A168P; N35G/E104H/A168P/S231T; N35G/E104H/A168P/Q184R; N35G/E104H/A168P/K218L; N35G/E104H/A168P/P233F; N35G/T49A/E104H/A168P/Q184H; N35G/T40S/E104H/A168P/P327M; N35G/T54M/E104H/A168P; N35G/N66D/E104H/S164E/A168P/S231T/S253T; N35G/E104H/A168P/G203Y; N35G/T49Q/E104H/A168P; N35G/E104H/A168P/P266S/G267V; N35G/Q44K/N66V/E104H/A168P; N35G/S67H/E104H/A168P; N35G/E104H/A137M/A168P; N35G/T49A/E104H/S128N/A168P; N35G/T49R/E104H/A168P/K218L/N317Q; N35G/I51A/E104H/A168P; N35G/E104H/A168P/A326C; N35G/P45R/E104H/A168P/T320A; N35G/N66L/E104H/A168P; N35G/E104H/A168P/V237I/P303T; N35G/P45R/E104H/A168P/K218L/N317Q; N35G/T80L/E104H/A168P; N35G/A55G/E104H/A168P; N35G/E104H/K141N/A168P/P266S; N35G/E104H/A168P/S330A; N35G/N66D/E104H/A168P/R290K; N35G/E104H/N118E/A168P; N35G/E104H/A168P/A212M; N35G/K93N/E104H/R130Y/A168P; N35G/E104H/A168P/G267D; N35G/P45R/T49Y/E104H/A168P/N317D; N35G/E104H/A168P/V230Q; N35G/E104H/A168P/S329Q; N35G/P45K/E104H/A168P/A219R; N35G/S78D/E104H/S164E/A168P; N35G/E104H/A168P/S205T; N35G/E104H/A168P/Q184H; V28H/N35G/N46E/Q58H/E104H/A168P; N35G/E104H/A142D/A168P; N35G/E104H/A168P/E336L; N35G/E104H/A168P/A280T; N35G/E104H/A168P/A219T; N35G/E104H/A168P/P303T/G305D; R34E/N35G/E104H/A168P/A280T; N35G/E104H/A168P/N187D; N35G/E104H/G136H/A168P; N35G/E104H/A168P/Q184N; N35G/T49Y/E104H/A168P/N317R; N35G/T40A/T49Q/S78C/E104H/A168P; R34E/N35G/K93T/E104H/R130E/R145T/A168P/R199E/K218T/A280D; N35G/T40L/E104H/A142G/A168P; and/or N35G/N66G/E104H/A168P, wherein the amino acid positions are numbered with reference to SEQ ID NO:2. In some further embodiments, the GH61 variant proteins comprise a plurality of substitutions as provided herein. In some additional embodiments, the GH61 variant proteins comprise polypeptide sequences that are at least about 90%, at least about 91%, at least about 92%, at least about 93%, at least about 94%, at least about 95%, at least about 96%, at least about 97%, at least about 98%, at least about 99%, or 100% identical to any of SEQ ID NOS:2, 3, 5, 6, 8, and/or 9, and/or a biologically active fragment of any of SEQ ID NOS: 2, 3, 5, 6, 8, and/or 9, wherein the fragment has GH61 activity. In still some additional embodiments, the GH61 variant proteins comprise polypeptide sequences that are at least 90%, at least 91%, at least 92%, at least 93%, at least 94%, at least 95%, at least 96%, at least 97%, at least 98%, at least 99%, or 100% identical to any of SEQ ID NOS:2, 3, 5, 6, 8, and/or 9, and/or a biologically active fragment of any of SEQ ID NOS: 2, 3, 5, 6, 8, and/or 9, wherein the fragment has GH61 activity.

The present invention also provides GH61 variant proteins comprising amino acid sequences that are at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any of SEQ ID NOS:2, 3, 5, 6, 8, and/or 9, or a fragment of SEQ ID NOS:2, 3, 5, 6, 8, and/or 9 having GH61 activity, wherein the amino acid sequence of the variant protein has one or more amino acid substitutions with respect to SEQ ID NOS:2, 3, 5, 6, 8, and/or 9 or the fragment, and wherein the substitution(s) in the amino acid sequences result in the variant proteins having increased GH61 activity in a reaction where crystalline cellulose undergoes saccharification by cellulase enzymes that are contained in culture broth from *M. thermophila* cells, compared with a reference protein comprising SEQ ID NO:2, 3, 5, 6, 8, and/or 9 or the fragment, without any substitutions. In some embodiments, the GH61 variant proteins comprise amino acid sequences that are at least 75%, at least 80%, at least 85%, at least 90%, at least 91%, at least 92%, at least 93%, at least 94%, at least 95%, at least 96%, at least 97%, at least 98%, or at least 99% identical to any of SEQ ID NOS:2, 3, 5, 6, 8, and/or 9, or a fragment of SEQ ID NOS:2, 3, 5, 6, 8, and/or 9 having GH61 activity, wherein the amino acid sequence of the variant protein has one or more amino acid substitutions with respect to SEQ ID NOS:2, 3, 5, 6, 8, and/or 9 or the fragment, and wherein the substitution(s) in the amino acid sequences result in the variant proteins having increased GH61 activity in a reaction where crystalline cellulose undergoes saccharification by cellulase enzymes that are contained in culture broth from *M. thermophila* cells, compared with a reference protein comprising SEQ ID NO:2, 3, 5, 6, 8, and/or 9 or the fragment, without any substitutions. In some further embodiments, the present invention provides GH61 variant proteins encoded by polynucleotides, wherein the proteins comprise amino acid sequences that are at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any of SEQ ID NOS:2, 3, 5, 6, 8, and/or 9 or a fragment of SEQ ID NO:2, 3, 5, 6, 8, and/or 9 having GH61 activity, wherein the amino acid sequence of the variant protein has one or more amino acid substitutions with respect to SEQ ID NO:2, 3, 5, 6, 8, and/or 9 or the fragment, and wherein the polynucleotide encoding the GH61 variant protein comprises at least one mutation and/or mutation set selected from t60c/c573g, t60c/c573g/g1026a, c573g, t60c/c291a/c573g, t60c/c291a, t60c/c876t, a312g, t60c, t379a/c380g/g381c, c300t, t204c/t379a/c380g/g381c/c385t, g1026a, c246t, c597g, c72t, c732g/c843t/c882t, c909t, c912g, g921a, c792t, g972t, g921a, t379a/c380g/g381c/c454a/c456a/c732t/c843t/c849t, c520a/c522g, t60c/c573g; t60c/c288t/c573g; t60c/c198t/c573g; and/or t60c/g399a/c573g; wherein the nucleotide positions are numbered with reference to SEQ ID NO:1. In still some further embodiments, the present invention provides GH61 variant proteins encoded by polynucleotides, wherein the proteins comprise amino acid sequences that are at least 75%, at least 80%, at least 85%, at least 90%, at least 91%, at least 92%, at least 93%, at least 94%, at least 95%, at least 96%, at least 97%, at least 98%, or at least 99% identical to any of SEQ ID NOS:2, 3, 5, 6, 8, and/or 9 or a fragment of SEQ ID NO:2, 3, 5, 6, 8, and/or 9 having GH61 activity, wherein the amino acid sequence of the variant protein has one or more amino acid substitutions with respect to SEQ ID NO:2, 3, 5, 6, 8, and/or 9 or the fragment, and wherein the polynucleotide encoding the GH61 variant protein comprises at least one mutation and/or mutation set selected from t60c/c573g, t60c/c573g/g1026a, c573g, t60c/c291a/c573g, t60c/c291a, t60c/c876t, a312g, t60c, t379a/c380g/g381c, c300t, t204c/t379a/c380g/g381c/c385t, g1026a, c246t, c597g, c72t, c732g/c843t/c882t, c909t, c912g, g921a, c792t, g972t, g921a, t379a/c380g/g381c/c454a/c456a/c732t/c843t/c849t, c520a/c522g, t60c/c573g; t60c/c288t/c573g; t60c/c198t/c573g; and/or t60c/g399a/c573g; wherein the nucleotide positions are numbered with reference to SEQ ID NO:1.

The present invention also provides polynucleotides comprising a nucleic acid sequences encoding the GH61 variant proteins provided herein, as well as polynucleotides that hybridize under stringent hybridization conditions to at least one polynucleotide and/or a complement of at least one polynucleotide encoding GH61 variant proteins provided herein. In some embodiments, the present invention provides polynucleotide sequences encoding GH61 variant proteins, wherein the polynucleotide sequences are at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any of SEQ ID NOS:1, 4, 7, and/or 10, or at least one polynucleotide that hybridizes under stringent hybridization conditions to at least one polynucleotide and/or complement of any of SEQ ID NOS:1, 4, 7, and/or 10. In some additional embodiments, the present invention provides polynucleotide sequences encoding GH61 variant proteins, wherein the polynucleotide sequences are at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NOS:1, 4, 7, and/or 10, or at least one polynucleotides that hybridizes under stringent hybridization conditions to at least one polynucleotide and/or complement of any of SEQ ID NOS:1, 4, 7, and/or 10.

The present invention also provides recombinant nucleic acid constructs comprising at least one polynucleotide sequence encoding at least one GH61 protein, wherein the polynucleotide is selected from: (a) a polynucleotide that encodes a polypeptide comprising an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identity to SEQ ID NO:2, 3, 5, 6, 8, and/or 9, wherein the amino acid sequence comprises at least one substitution and/or substitution set provided herein; (b) a polynucleotide that hybridizes under stringent hybridization conditions to at least a fragment of a polynucleotide that encodes a polypeptide having the amino acid sequence of SEQ ID NO:2, 3, 5, 6, 8, and/or 9, and wherein the amino acid sequence comprises at least one substitution and/or at least one substitution set provided herein; and/or (c) a polynucleotide that hybridizes under stringent hybridization conditions to the complement of at least a fragment of a polynucleotide that encodes a polypeptide having the amino acid sequence of SEQ ID NO:2, 3, 5, 6, 8, and/or 9, and wherein the amino acid sequence comprises at least one substitution and/or at least one substitution set provided herein. In some embodiments, the recombinant nucleic acid constructs comprise at least one polynucleotide sequence encoding at least one GH61 protein, wherein the polynucleotide is selected from: (a) a polynucleotide that encodes a polypeptide comprising an amino acid sequence having at least 70%, at least 75%, at least 80%, at least 85%, at least 90%, at least 91%, at least 92%, at least 93%, at least 94%, at least 95%, at least 96%, at least 97%, at least 98%, or at least 99% identity to SEQ ID NO:2, wherein the amino acid sequence comprises at least one substitution and/or substitution set provided herein; (b) a polynucleotide that hybridizes under stringent hybridization conditions to a polynucleotide that encodes a polypeptide having the amino acid sequence of SEQ ID NO:2, and wherein the amino acid sequence comprises at least one substitution and/or at least one substitution set provided herein; and/or (c) a polynucleotide that hybridizes under stringent hybridization conditions to the complement of a polynucleotide that encodes a polypeptide having the amino acid sequence of SEQ ID NO:2, and wherein the amino acid sequence comprises at least one substitution and/or or at least one substitution set provided herein. In some additional embodiments, the recombinant nucleic acid constructs comprise at least one polynucleotide sequence at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to any of SEQ ID NOS:1, 4, 7, and/or 10, and wherein the polynucleotide sequence comprises at least one mutation and/or at least one mutation set provided herein. In some further additional embodiments, the recombinant nucleic acid constructs comprise polynucleotide sequences that are at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to any of SEQ ID NOS:1, 4, 7, and/or 10, and wherein the polynucleotide sequence comprises at least one mutation and/or at least one mutation set provided herein. In some embodiments, the polynucleotides and/or nucleic acid constructs provided herein comprise at least one polynucleotide sequence comprising at least one mutation or mutation set selected from t60c/c573g, t60c/c573g/g1026a, c573g, t60c/c291a/c573g, t60c/c291a, t60c/c876t, a312g, t60c, t379a/c380g/g381c, c300t, t204c/t379a/c380g/g381c/c385t, g1026a, c246t, c597g, c72t, c732g/c843t/c882t, c909t, c912g, g921a, c792t, g972t, g921a, t379a/c380g/g381c/c454a/c456a/c732t/c843t/c849t, c520a/c522g; t60c/c573g; t60c/c288t/c573g; t60c/c198t/c573g; and/or t60c/g399a/c573g. In some additional embodiments, the polynucleotide and/or nucleic acid construct comprise at least one nucleic acid sequence operably linked to a promoter. In some additional embodiments, the promoter is a heterologous promoter. In some further embodiments, the nucleic acid constructs further encode at least one enzyme in addition to the GH61 variant protein. In some embodiments, the nucleic acid constructs comprise at least one additional enzyme is selected from wild-type GH61 enzymes, endoglucanases (EG), beta-glucosidases (BGL), Type 1 cellobiohydrolases (CBH1), Type 2 cellobiohydrolases (CBH2), cellulases, hemicellulases, xylanases, xylosidases, amylases, glucoamylases, proteases, esterases, and lipases. In some further embodiments, at least one additional enzyme is selected from wild-type GH61 enzymes, endoglucanases (EG), beta-glucosidases (BGL), Type 1 cellobiohydrolases (CBH1), Type 2 cellobiohydrolases (CBH2), xylanases, and xylosidases.

The present invention also provides expression constructs comprising at least one polynucleotide or nucleic acid construct as provided herein. In some expression construct embodiments, the nucleic acid construct and/or the polynucleotide is operably linked to a promoter. In some embodiments, the promoter is heterologous. In some further embodiments of the expression constructs provided herein, the nucleic acid sequence is operably linked to at least one additional regulatory sequence.

The present invention also provides host cells that express at least one polynucleotide sequence encoding at least one GH61 variant protein provided herein. In some embodiments, the host cells produce at least one GH61 variant protein provided herein. In some additional embodiments, at least one GH61 variant protein is secreted from the host cells. In some further embodiments, the host cells further produce at least one enzyme selected from wild-type GH61 enzymes, endoglucanases (EG), beta-glucosidases (BGL), Type 1 cellobiohydrolases (CBH1), Type 2 cellobiohydrolases (CBH2), cellulases, hemicellulases, xylanases, xylosidases, amylases, glucoamylases, proteases, esterases, and lipases. In some additional embodiments, the host cell further produces at least one enzyme selected from wild-type GH61 enzymes, endoglucanases (EG), beta-glucosidases (BGL), Type 1 cellobiohydrolases (CBH1), and Type 2 cellobiohydrolases (CBH2). In some embodiments, the host cell is a yeast or filamentous fungal cell. In some embodiments, the filamentous fungal cell is a *Myceliophthora*, a *Chrysosporium* a *Thielavia*, a *Trichoderma*, or an *Aspergillus* cell. In some further embodiments, the filamentous fungal cell is *Myce-* *liophthora thermophila*. In some additional embodiments, the host cell is a yeast cell. In some further additional embodiments, the host cell is *Saccharomyces*. In some further embodiments, the host cells further comprise at least one polynucleotide, polynucleotide construct, and/or expression construct as provided herein.

The present invention also provides methods of producing at least one GH61 variant protein comprising culturing the host cell set forth herein under conditions such that the host cell produces at least one GH61 variant proteins as provided herein. In some embodiments of the methods, the host cell further produces at least one additional enzyme selected from wild-type GH61 enzymes, endoglucanases (EG), beta-glucosidases (BGL), Type 1 cellobiohydrolases (CBH1), Type 2 cellobiohydrolases (CBH2), cellulases, hemicellulases, xylanases, xylosidases, amylases, glucoamylases, proteases, esterases, and lipases. In some embodiments of the methods, the host cell further produces at least one EG, at least one BGL, at least one CBH1, at least one CBH2, and/or at least one wild-type GH61 enzyme. In some further embodiments of the methods, the conditions comprise culturing at about pH 5, while in some alternative embodiments of the methods, the conditions comprise culturing at about pH 6.7. In some embodiments of the methods, the filamentous fungal cell is a *Myceliophthora*, a *Chrysosporium*, a *Thielavia*, a *Trichoderma*, or an *Aspergillus* cell. In some further embodiments of the methods, the filamentous fungal cell is a *Myceliophthora thermophila*. In some additional embodiments of the methods, the host cell is a yeast cell. In some further additional embodiments of the methods, the host cell is *Saccharomyces*.

The present invention also provides enzyme compositions comprising at least one GH61 variant protein as provided herein. In some embodiments, the enzyme compositions further comprise one or more enzymes selected from wild-type GH61 enzymes, endoglucanases (EG), beta-glucosidases (BGL), Type 1 cellobiohydrolases (CBH1), and/or Type 2 cellobiohydrolases (CBH2), cellulases, hemicellulases, xylanases, xylosidases, amylases, glucoamylases, proteases, esterases, and lipases. In some additional embodiments, the enzyme compositions further comprise at least two additional enzymes selected from wild-type GH61 enzymes, endoglucanases (EG), beta-glucosidases (BGL), Type 1 cellobiohydrolases (CBH1), and/or Type 2 cellobiohydrolases (CBH2), cellulases, hemicellulases, xylanases, xylosidases, amylases, glucoamylases, proteases, esterases, and lipases. In some embodiments, the enzyme compositions are produced by the host cells provided herein. In some additional embodiments, the enzyme compositions further comprise a microorganism. In some further embodiments, the microorganism comprises *M. thermophila*. In some embodiments, the enzyme compositions further comprise at least one adjunct composition. In some additional embodiments, the enzyme compositions comprise at least one adjunct composition selected from divalent metal cations, reductants, surfactants, buffers, culture media, and enzyme stabilizing systems. In some further embodiments, the enzyme compositions comprise adjunct composition comprising copper and/or gallic acid. In some additional embodiments, the enzyme compositions find use in saccharification reactions.

The present invention also provides compositions comprising at least one GH61 protein, one or more cellulase enzymes, a cellulosic substrate, and $Cu^{++}$, wherein the GH61 protein is at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% identical to any of SEQ ID NOS:2, 5, 6, 8, 9, 11, and/or 12, and/or a biologically fragment thereof with GH61 activity. In some embodiments, the present invention provides compositions comprising at least one GH61 protein, one or more cellulase enzymes, a cellulosic substrate, and $Cu^{++}$, wherein the GH61 protein is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO:2, 5, 6, 8, 9, 11, and/or 12, and/or a biologically fragment thereof with GH61 activity. In some embodiments, the concentration of $Cu^{++}$ is at least about 4 μM. In some embodiments, the concentration of $Cu^{++}$ is between about 1 μM and about 100 μM, between about 4 μM and about 100 μM, or between about 5 μM and about 100 μM.

The present invention also provides compositions comprising at least one GH61 protein, one or more cellulase enzymes, a cellulosic substrate, and gallic acid, wherein the GH61 protein is at least about 70%, about 80%, about 85%, about 86%, about 87%, about 88%, about 89%, about 90%, about 91%, about 92%, about 93%, about 94%, about 95%, about 96%, about 97%, about 98%, about 99%, or about 100% identical to any of SEQ ID NO:2, 5, 6, 8, 9, 11, and/or 12, and/or a biologically fragment thereof with GH61 activity. The present invention also provides compositions comprising at least one GH61 protein, one or more cellulase enzymes, a cellulosic substrate, and gallic acid, wherein the GH61 protein is at least 70%, 80%, 85%, 86%, 87%, 88%, 89%, 90%, 91%, 92%, 93%, 94%, 95%, 96%, 97%, 98%, 99%, or 100% identical to any of SEQ ID NO:2, 5, 6, 8, 9, 11, and/or 12, and/or a biologically fragment thereof with GH61 activity. In some embodiments, the concentration of gallic acid in the compositions is at least about 0.1 mM. In some embodiments, the compositions comprise gallic acid at a concentration between about 1 mM and about 5 mM. In some embodiments, the concentration of gallic acid in the composition is at least 0.1 mM. In some embodiments, the compositions comprise gallic acid at a concentration between 1 mM and 5 mM. In some embodiments, the compositions comprise at least one GH61 protein comprising SEQ ID NO:2, 5, 6, 8, 9, 11, and/or 12, and/or a biologically active fragment thereof with GH61 activity. In some embodiments, the compositions comprise at least one GH61 variant protein as provided herein. In some embodiments, the compositions comprise at least one cellulase enzyme selected from endoglucanases (EG), beta-glucosidases (BGL), Type 1 cellobiohydrolases (CBH1), and/or Type 2 cellobiohydrolases (CBH2). In some embodiments, the compositions comprise at least one BGL, CBH1, and CBH2. In some additional embodiments, the compositions further comprise at least one additional enzyme. In some further embodiments, at least one additional enzyme is selected from hemicellulases, xylanases, xylosidases, amylases, glucoamylases, proteases, esterases, and lipases. In still some further embodiments of the compositions, the cellulosic substrate is selected from wheat grass, wheat straw, barley straw, sorghum, rice grass, sugarcane straw, bagasse, switchgrass, corn stover, corn fiber, grains, or any combination thereof.

The present invention also provides methods for producing fermentable sugars from a cellulosic substrate, comprising contacting the cellulosic substrate with at least one enzyme composition as provided herein under conditions whereby fermentable sugars are produced. In some embodiments, the methods further comprise pretreating the cellulosic substrate prior to the contacting. In some additional embodiments of the methods, the enzyme composition is added concurrently with pretreating. In some further embodiments of the methods, the cellulosic substrate comprises wheat grass, wheat straw, barley straw, sorghum, rice grass, sugarcane, sugarcane straw, bagasse, switchgrass, corn stover, corn fiber, grains, or any combination thereof. In some additional embodiments of the methods, the fermentable sugars comprise glucose and/or xylose. In some embodiments, the methods further comprise recovering the fermentable sugars. In some embodiments of the methods, the conditions comprise using continuous, batch, and/or fed-batch culturing conditions. In some further embodiments, the method is a batch process, while in some alternative embodiments, the method is a continuous process, and in some still further embodiments, the method is a fed-batch process. In some embodiments, the methods comprise any combination of batch, continuous, and/or fed-batch processes conducted in any order. In still some further embodiments, the methods are conducted in a reaction volume of at least 10,000 liters, while in some other embodiments, the methods are conducted in a reaction volume of at least 100,000 liters. In some embodiments, the methods further comprise use of at least one adjunct composition. In some embodiments, the adjunct composition is selected from at least one divalent metal cation, gallic acid, and/or at least one surfactant. In some embodiments, the divalent metal cation comprises copper and/or gallic acid. In some additional embodiments, the surfactant is selected from TWEEN®-20 non-ionic detergent and polyethylene glycol. In some further embodiments, the methods are conducted at about pH 5.0, while in some alternative embodiments, the methods are conducted at about pH 6.0. In some additional embodiments, the pH is in the range of about 4.5 to about 7. In some embodiments, the methods further comprise contacting the fermentable sugars with a microorganism under conditions such that the microorganism produces at least one fermentation end product. In some embodiments, the fermentation end product is selected from alcohols, fatty acids, lactic acid, acetic acid, 3-hydroxypropionic acid, acrylic acid, succinic acid, citric acid, malic acid, fumaric acid, amino acids, 1,3-propanediol, ethylene, glycerol, fatty alcohols, butadiene, and beta-lactams. In some further embodiments, the fermentation product is an alcohol selected from ethanol and butanol. In some still further embodiments, the alcohol is ethanol.

The present invention also provides methods for increasing production of fermentable sugars from a saccharification reaction comprising combining at least one cellulase substrate, one or more cellulase enzymes, and at least one GH61 protein wherein the protein is at least about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% identical to SEQ ID NO:2, and an adjunct composition in a saccharification reaction, wherein the adjunct composition comprises $Cu^{++}$ at a concentration of at least about 4 μM and/or gallic acid at a concentration of at least about 0.5 mM. The present invention also provides methods for increasing production of fermentable sugars from a saccharification reaction comprising combining at least one cellulase substrate, one or more cellulase enzymes, and at least one GH61 protein wherein the protein is at least 70%, 75%, 80%, 85%, 86%, 87%, 88%, 89%, 90%, 91%, 92%, 93%, 94%, 95%, 96%, 97%, 98%, 99%, or 100% identical to SEQ ID NO:2, and an adjunct composition in a saccharification reaction, wherein the adjunct composition comprises $Cu^{++}$ at a concentration of at least about 4 μM and/or gallic acid at a concentration of at least about 0.5 mM. In some embodiments, at least one GH61 protein comprises SEQ ID NO:2, 5, 6, 8, 9, 11, and/or a biologically active fragment thereof. In some embodiments of the methods, the GH61 protein is at least one GH61 protein variant as provided herein. In some embodiments, the methods further comprise use of at least one surfactant selected from TWEEN®-20 non-ionic detergent and polyethylene glycol. In some additional embodiments, the methods are conducted at about pH 5.0, while in some other embodiments, the methods are conducted at about pH 6.0.

The present invention also provides methods of producing at least one end product from at least one cellulosic substrate, comprising: a) providing at least one cellulosic substrate and at least one enzyme composition as provided herein; b) contacting the cellulosic substrate with the enzyme composition under conditions whereby fermentable sugars are produced from the cellulosic substrate in a saccharification reaction; and c) contacting the fermentable sugars with a microorganism under fermentation conditions such that at least one end product is produced. In some embodiments, the method comprises simultaneous saccharification and fermentation reactions (SSF), while in some alternative embodiments of the methods, saccharification of the cellulosic substrate and fermentation are conducted in separate reactions (SHF). In some additional embodiments, the methods comprise production of at least one enzyme simultaneously with hydrolysis and/or fermentation (e.g., "consolidated bioprocessing"; CBP). In some embodiments, the enzyme composition is produced simultaneously with the saccharification and fermentation reactions. In some additional embodiments at least one enzyme of said composition is produced simultaneously with the saccharification and fermentation reactions. In some embodiments, in which at least one enzyme and/or the enzyme composition is produced simultaneously with the saccharification and fermentation reactions, the methods are conducted in a single reaction vessel. In some embodiments, the methods further comprise use of at least one adjunct composition in the saccharification reaction. In some embodiments of the methods, at least one adjunct composition is selected from at least one divalent metal cation, gallic acid, and/or at least one surfactant. In some further embodiments of the methods, the divalent metal cation comprises copper. In some further embodiments of the methods, the adjunct composition comprises gallic acid. In some additional embodiments of the methods, the surfactant is selected from TWEEN®-20 non-ionic detergent and polyethylene glycol. In some embodiments, the method is conducted at about pH 5.0. In some embodiments, the method is conducted at about pH 6.0. In some further embodiments, the method is conducted at a pH in the range of about 4.5 to about 7.0. In some embodiments, the methods further comprise recovering at least one end product. In some embodiments of the methods the end product comprises at least one fermentation end product. In some further embodiments of the methods, the fermentation end product is selected from alcohols, fatty acids, lactic acid, acetic acid, 3-hydroxypropionic acid, acrylic acid, succinic acid, citric acid, malic acid, fumaric acid, an amino acid, 1,3-propanediol, ethylene, glycerol, fatty alcohols, butadiene, and beta-lactams. In some embodiments of the methods, the fermentation end product is at least one alcohol selected from ethanol and butanol. In some embodiments, the alcohol is ethanol. In some additional embodiments of the methods, the microorganism is a yeast. In some further embodiments, the yeast is Saccharomyces. In some further additional embodiments, the methods further comprise recovering at least one fermentation end product.

The present invention also provides for use of at least one GH61 variant protein provided herein to produce at least one fermentation end product. In some embodiments, at least one GH61 variant protein provided herein is used to produce at least one fermentation end product selected from alcohols, fatty acids, lactic acid, acetic acid, 3-hydroxypropionic acid, acrylic acid, citric acid, malic acid, fumaric acid, succinic acid, amino acids, 1,3-propanediol, ethylene, glycerol, butadiene, fatty alcohols, and beta-lactams. In some embodiments, the fermentation end product is at least one alcohol selected from ethanol and butanol. In some further embodiments, the alcohol is ethanol.

Additional embodiments of the invention are apparent from the present description.

DETAILED DESCRIPTION OF THE INVENTION

Figure 1:
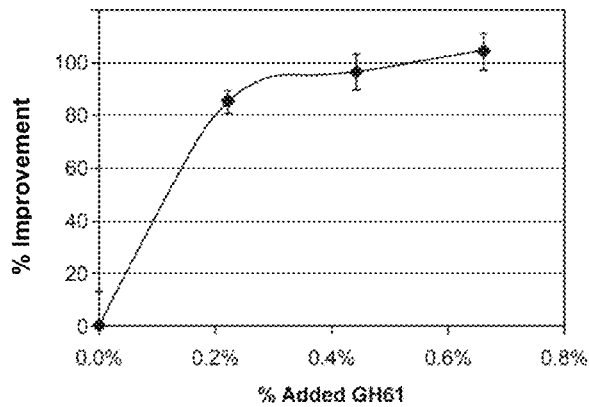
FIG. 1 provides results of an experiment using recombinantly produced GH61a protein having the sequence shown in SEQ ID NO:2. The protein was tested for its ability to promote the activity of cellulases present in culture broth of M. thermophila. The graph shows the improvement in the yield of the fermentable sugar glucose that is attained by adding GH61 to the reaction.

As described herein, the present invention provides GH61 proteins of the filamentous fungus Myceliophthora thermophila that have been genetically modified. These GH61 protein variants exhibit improved activity and other benefits, as compared to wild-type GH61 proteins.

Before modification, the GH61 protein having the sequence shown in SEQ ID NO:2 improves the yield of fermentable sugars produced from a cellulosic substrate through the activity of cellulase enzymes (e.g., endoglucanase, beta-glucosidase (BGL), cellobiohydrolase, and combinations of such enzymes; See, FIG. 1). The GH61 variant proteins of this invention have certain amino acid substitutions in relation to SEQ ID NO:2, either alone or in various combinations. GH61 variant proteins that have gone through one round of optimization, when included in a saccharification assay, improve the yield of fermentable sugars in such reactions by at least about 2-fold, about 3-fold, or more, in relation to the improvement in yield when wild-type GH61a (SEQ ID NO:2) is used instead. (See, FIG. 2). After multiple rounds of optimization, the GH61 activity can be improved by a further 1.5-fold, 2-fold, 3-fold or more.

The GH61 variant proteins of the present invention have important industrial applicability in the processing of cellulosic biomass to produce fermentable sugars, which in turn can be fermented or processed to produce commercially important fermentation products (e.g., "fermentation end-products" or "end-products"), including but not limited to, at least one alcohol, fatty acid, lactic acid, acetic acid, 3-hydroxypropionic acid, acrylic acid, succinic acid, citric acid, malic acid, fumaric acid, amino acid, 1,3-propanediol, ethylene, glycerol, fatty alcohol, butadiene, and/or beta-lactam. In further embodiments, the alcohol is ethanol, butanol, and/or a fatty alcohol. In some embodiments, the fermentation product is ethanol. In some still further embodiments, the fermentation product is a fatty alcohol that is a C8-C20 fatty alcohol. In some embodiments, the fermentation medium comprises at least one product from a saccharification process.

GH61 proteins, their production and use are generally described in PCT/US11/488,700. This application claims priority to U.S. Ser. No. 61/375,788, both of which are incorporated herein by reference in their entirety. Proteins, procedures, and uses described in these applications find use with the GH61 variant proteins of the present invention.

Definitions

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the term "produces" refers to the production of proteins (polypeptides) and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used in this disclosure, the term "GH61 protein" means a protein that has GH61 activity, including GH61 variants and wild-type GH61 enzymes. In some embodiments, the GH61 proteins have been purified from *M. thermophila* cells, while in other embodiments, they are structurally related to the amino acid sequences shown in Tables 1 and 2. The terms also encompasses species and strain homologs and orthologs comprising protein sequences listed in Tables 1 and 2, as well as variants, and fragments of such sequences (produced using any suitable means known in the art), having GH61 activity.

As used herein, the terms "variant," "GH61 variant," refer to a GH61 polypeptide or polynucleotide encoding a GH61 polypeptide comprising one or more modifications relative to wild-type GH61 or the wild-type polynucleotide encoding GH61 (such as substitutions, insertions, deletions, and/or truncations of one or more amino acid residues or of one or more specific nucleotides or codons in the polypeptide or polynucleotide, respectively), and biologically active fragments thereof. In some embodiments, the variant is derived from a *M. thermophila* polypeptide and comprises one or more modifications relative to wild-type *M. thermophila* GH61 or the wild-type polynucleotide encoding wild-type *M. thermophila* GH61, or a biologically active fragment thereof. In some embodiments, a "GH61 variant protein" ("GH61 variant polypeptide") of the present invention is a protein that is structurally related to a reference protein comprising SEQ ID NO:2 or a fragment of SEQ ID NO:2 that has GH61 activity, but has one or more amino acid substitutions in relation to the reference protein. In some embodiments, the GH61 variant is a GH61a variant (i.e., a variant of GH61a enzyme). In some embodiments, the GH61 variant polypeptide is a "polypeptide of interest." In some additional embodiments, the GH61 variant polypeptide is encoded by a "polynucleotide of interest."

The terms "improved" or "improved properties," as used in the context of describing the properties of a GH61 variant, refers to a GH61 variant polypeptide that exhibits an improvement in a property or properties as compared to the wild-type GH61 (e.g., SEQ ID NO:2) or a specified reference polypeptide. Improved properties may include, but are not limited to increased protein expression, increased thermoactivity, increased thermostability, increased pH activity, increased stability (e.g., increased pH stability or pH tolerance at various pH levels), increased product specificity, increased specific activity, increased substrate specificity, increased resistance to substrate or end-product inhibition, increased chemical stability, reduced inhibition by glucose, increased resistance to inhibitors (e.g., acetic acid, lectins, tannic acids, and phenolic compounds), and altered pH/temperature profile.

The term "biologically active fragment," as used herein, refers to a polypeptide that has an amino-terminal and/or carboxy-terminal deletion and/or internal deletion, but where the remaining amino acid sequence is identical to the corresponding positions in the sequence to which it is being compared (e.g., a full-length GH61 variant of the invention) and that retains substantially all of the activity of the full-length polypeptide. A biologically active fragment can comprise about 60%, about 65%, about 70%, about 75%, about 80%, about 85%, at about 90%, about 91%, about 92%, about 93%, about 94%, about 95%, about 96%, about 97%, about 98%, or about 99% of a full-length GH61 polypeptide.

A GH61 variant protein of this invention having "increased GH61 activity" has more GH61 activity when that protein is present in a saccharification reaction with a specified substrate and specified cellulase enzyme(s), compared with a saccharification reaction conducted with the same substrate and enzyme(s) under the same conditions in the presence of a reference protein (e.g., including but not limited to wild-type GH61). The increase is determined by measuring the amount of fermentable sugar produced in the reaction in the presence of the GH61 variant protein, in the presence of the reference protein (Positive Control), and in the absence of either protein (Negative Control). The Improvement Over Positive Control (FIOPC) is calculated as ([Glucose production of the GH61 Variant Protein]−[Glucose production of the Negative Control])/([Glucose production of the Positive Control]−[Glucose production of the Negative Control]).

As used herein, "GH61 activity" is the functional activity of a GH61 protein that results in production of more fermentable sugar from a polysaccharide substrate when the GH61 protein is present in a saccharification reaction, compared with a saccharification reaction conducted under the same conditions in the absence of the GH61 protein.

A GH61 variant protein of this invention having "increased GH61 thermoactivity" has more GH61 activity in a saccharification reaction conducted at an elevated temperature (about 50° C., about 55° C., about 60° C., or higher) with a specified substrate and specified cellulase enzyme(s), compared with a saccharification reaction conducted under the same conditions in the presence of the reference protein (e.g., including but not limited to wild-type GH61).

GH61 proteins of this invention may be said to "enhance", "promote", or "facilitate" activity of one or more cellulase enzymes during hydrolysis of sugar polymers (e.g., cellulosic and/or lignocellulosic biomass) such that the enzyme(s) produce(s) more product over a particular time period, hydrolysis proceeds more rapidly, or goes further to completion when the GH61 protein is present, compared with a similar reaction mixture in which the GH61 protein is absent. This invention may be practiced by following GH61 activity in an empirical fashion using assay methods provided in this disclosure, without knowing the mechanism of operation of the GH61 variant protein being used. However, it is not intended that the present invention be limited to any particular assay system and/or method, as any suitable method known in the art finds use.

The terms "transform" or "transformation," as used in reference to a cell, mean a cell has a non-native nucleic acid sequence integrated into its genome and/or as an episome (e.g., plasmid) that is maintained through multiple generations.

The term "introduced," as used in the context of inserting a nucleic acid sequence into a cell, means that the nucleic acid has been conjugated, transfected, transduced or transformed (collectively "transformed") or otherwise incorporated into the genome of and/or maintained as an episome in the cell. Thus, the term encompasses transformation, transduction, conjugation, transfection, and/or any other suitable method(s) known in the art for inserting nucleic acid sequences into host cells. Any suitable means for the introduction of nucleic acid into host cells find use in the present invention.

The terms "percent identity," "% identity", "percent identical", and "% identical" are used interchangeably to refer to a comparison of two optimally aligned sequences over a comparison window. The comparison window may include additions or deletions in either sequence to optimize alignment. The percentage of identity is the number of positions that are identical between the sequences, divided by the total number of positions in the comparison window (including positions where one of the sequences has a gap). For example, a protein with an amino acid sequence that matches at 310 positions a sequence of GH61a (which has 323 amino acids in the secreted form), would have 310/323=95.9% identity to the reference. Similarly, a protein variant that has 300 residues (i.e., less than full-length) and matches the reference sequence at 280 positions would have 280/300=93.3% identity. Computer-implemented alignment algorithms useful in determining the degree of identity are known in the art, including the BLAST and BLAST 2.0 algorithms (See e.g., Altschul at al., J. Mol. Biol., 215: 403-410 [1990]; and Altschul et al., Nucl. Acids Res., 3389-3402 [1977]).

As used herein, "polynucleotide" refers to a polymer of deoxyribonucleotides or ribonucleotides in either single- or double-stranded form, and complements thereof.

As used herein, the term "allelic variant" refers to any of two or more (e.g., several) alternative forms of a gene occupying the same chromosomal locus. In some embodiments, allelic variation arises naturally through mutation and results in genetic polymorphism within populations. In some embodiments, gene mutations are silent (i.e., there is no change in the encoded polypeptide), while in some other embodiments the genes encode polypeptides that have altered amino acid sequences. An "allelic variant of a polypeptide" is a polypeptide encoded by an allelic variant of a gene.

As used herein, "cDNA" refers to a DNA molecule that can be prepared by reverse transcription from a mature, spliced, mRNA molecule obtained from a eukaryotic or prokaryotic cell. cDNA sequences lack intron sequences that may be present in the corresponding genomic DNA. The initial, primary RNA transcript is a precursor to mRNA that is processed through a series of steps, including splicing, before appearing as mature spliced mRNA.

As used herein, the term "coding sequence" refers to a polynucleotide that directly specifies the amino acid sequence of a polypeptide. The boundaries of the coding sequence are generally determined by an open reading frame, which begins with a start codon (e.g., ATG, GTG, or TTG) and ends with a stop codon (e.g., TAA, TAG, or TGA). In some embodiments, a coding sequence comprises genomic DNA, while in some alternative embodiments, the coding sequence comprises cDNA, synthetic DNA, and/or a combination thereof.

As used herein, the terms "control sequences" and "regulatory sequences" refer to nucleic acid sequences necessary and/or useful for expression of a polynucleotide encoding a polypeptide. In some embodiments, control sequences are native (i.e., from the same gene) or foreign (i.e., from a different gene) to the polynucleotide encoding the polypeptide. Control sequences include, but are not limited to leaders, polyadenylation sequences, propeptide sequences, promoters, signal peptide sequences, and transcription terminators. In some embodiments, at a minimum, control sequences include a promoter, and transcriptional and translational stop signals. In some embodiments, control sequences are provided with linkers for the purpose of introducing specific restriction sites facilitating ligation of the control sequences with the coding region of the polynucleotide encoding the polypeptide.

A nucleic acid construct, nucleic acid (e.g., a polynucleotide), polypeptide, or host cell is referred to herein as "recombinant" when it is non-naturally occurring, artificial or engineered. The present invention also provides recombinant nucleic acid constructs comprising at least one GH61 variant polynucleotide sequence that hybridizes under stringent hybridization conditions to the complement of a polynucleotide which encodes a polypeptide comprising the amino acid sequence of any of SEQ ID NOS:2, 3, 5, 6, 8, 9, 11, and/or 12.

The term "recombinant nucleic acid" has its conventional meaning. A recombinant nucleic acid, or equivalently, "polynucleotide," is one that is inserted into a heterologous location such that it is not associated with nucleotide sequences that normally flank the nucleic acid as it is found in nature (for example, a nucleic acid inserted into a vector or a genome of a heterologous organism). Likewise, a nucleic acid sequence that does not appear in nature, for example a variant of a naturally occurring gene, is recombinant. A cell containing a recombinant nucleic acid, or protein expressed in vitro or in vivo from a recombinant nucleic acid are also "recombinant." Examples of recombinant nucleic acids include a protein-encoding DNA sequence that is (i) operably linked to a heterologous promoter and/or (ii) encodes a fusion polypeptide with a protein sequence and a heterologous signal peptide sequence.

For purposes of this disclosure, a promoter is "heterologous" to a gene sequence if the promoter is not associated in nature with the gene. A signal peptide is "heterologous" to a protein sequence when the signal peptide sequence is not associated with the protein in nature. In some embodiments, "hybrid promoters" find use. Hybrid promoters are promoters comprising portions of two or more (e.g., several) promoters that are linked together to generate a sequence that is a fusion of the portions of the two or more promoters, which when operably linked to a coding sequence, mediates the transcription of the coding sequence into mRNA.

In relation to regulatory sequences (e.g., promoters), the term "operably linked" refers to a configuration in which a regulatory sequence is located at a position relative to a polypeptide encoding sequence such that the regulatory sequence influences the expression of the polypeptide. In relation to a signal sequence, the term "operably linked" refers to a configuration in which the signal sequence encodes an amino-terminal signal peptide fused to the polypeptide, such that expression of the gene produces a pre-protein.

Nucleic acids "hybridize" when they associate, typically in solution. Nucleic acids hybridize due to a variety of well-characterized physico-chemical forces, such as hydrogen bonding, solvent exclusion, base stacking and the like. As used herein, the term "stringent hybridization wash conditions" in the context of nucleic acid hybridization experiments, such as Southern and Northern hybridizations, are sequence dependent, and are different under different environmental parameters. An extensive guide to the hybridization of nucleic acids is found in Tijssen, 1993, "Laboratory Techniques in Biochemistry and Molecular Biology-Hybridization with Nucleic Acid Probes," Part I, Chapter 2 (Elsevier, New York), which is incorporated herein by reference. For polynucleotides of at least 100 nucleotides in length, low to very high stringency conditions are defined as follows: pre-hybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 100 nucleotides in length, the carrier material is finally washed three times each for 15 minutes using 2×SSC, 0.2% SDS 50° C. (low stringency), at 55° C. (medium stringency), at 60° C. (medium-high stringency), at 65° C. (high stringency), or at 70° C. (very high stringency).

As used herein, a "vector" and "nucleic acid construct" comprise nucleic acid (e.g., DNA) constructs for introducing a DNA sequence into a cell. In some embodiments, the vector is an expression vector that is operably linked to a suitable control sequence capable of effecting the expression in a suitable host of the polypeptide encoded in the DNA sequence. The term "expression vector" refers to a DNA molecule, linear or circular, that comprises a segment encoding a polypeptide of the invention, and which is operably linked to additional segments that provide for its transcription (e.g., a promoter, a transcription terminator sequence, enhancers, etc.) and optionally a selectable marker.

As used herein, the term "isolated" refers to a nucleic acid, polypeptide, or other component that is partially or completely separated from components with which it is normally associated in nature. Thus, the term encompasses a substance in a form or environment that does not occur in nature. Non-limiting examples of isolated substances include, but are not limited to: any non-naturally occurring substance; any substance including, but not limited to, any enzyme, variant, polynucleotide, protein, peptide or cofactor, that is at least partially removed from one or more or all of the naturally occurring constituents with which it is associated in nature; any substance modified by the hand of man relative to that substance found in nature; and/or any substance modified by increasing the amount of the substance relative to other components with which it is naturally associated (e.g., multiple copies of a gene encoding the substance; and/or use of a stronger promoter than the promoter naturally associated with the gene encoding the substance). In some embodiments, a polypeptide of interest is used in industrial applications in the form of a fermentation broth product (i.e., the polypeptide is a component of a fermentation broth) used as a product in industrial applications such as ethanol production. In some embodiments, in addition to the polypeptide of interest (e.g., a GH61 variant polypeptide), the fermentation broth product further comprises ingredients used in the fermentation process (e.g., cells, including the host cells containing the gene encoding the polypeptide of interest and/or the polypeptide of interest), cell debris, biomass, fermentation media, and/or fermentation products. In some embodiments, the fermentation broth is optionally subjected to one or more purification steps (e.g., filtration) to remove or reduce at least one components of a fermentation process. Accordingly, in some embodiments, an isolated substance is present in such a fermentation broth product.

As used herein, the terms "peptide," "polypeptide," and "protein" are used interchangeably herein to refer to a polymer of amino acid residues.

As used herein, the term "amino acid" refers to naturally occurring and synthetic amino acids, as well as amino acid analogs. Naturally occurring amino acids are those encoded by the genetic code, as well as those amino acids that are later modified (e.g., hydroxyproline, γ-carboxyglutamate, and O-phosphoserine). Amino acid analogs refers to compounds that have the same basic chemical structure as a naturally occurring amino acid, (i.e., an α-carbon that is bound to a hydrogen, a carboxyl group, an amino group, and an R group, such as homoserine, norleucine, methionine sulfoxide, and methionine methyl sulfonium). Such analogs have modified R groups (e.g., norleucine) or modified peptide backbones, but retain the same basic chemical structure as a naturally occurring amino acid.

An "amino acid substitution" in a protein sequence is replacement of a single amino acid within that sequence with another amino acid. Unless indicated otherwise, variant GH61 proteins of this invention have substitutions as specifically indicated. In some embodiments, the variant GH61 proteins of the present invention also have other substitutions and/or alterations at any position in any combination with the substitutions specifically indicated.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, the amino acid residue number in a test sequence determined by simply counting from the N-terminus will not necessarily be the same as the number of its corresponding position in the reference sequence. For example, in a case where a test sequence has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

As used herein, the term "reference enzyme" refers to an enzyme to which another enzyme of the present invention (e.g., a "test" enzyme) is compared in order to determine the presence of an improved property in the other enzyme being evaluated. In some embodiments, a reference enzyme is a wild-type enzyme (e.g., wild-type GH61). In some embodiments, the reference enzyme is an enzyme with which a test enzyme of the present invention is compared in order to determine the presence of an improved property in the test enzyme being evaluated, including but not limited to improved thermoactivity, improved thermostability, improved activity, and/or improved stability. In some embodiments, a reference enzyme is a wild-type enzyme (e.g., wild-type GH61).

Amino acid substitutions in a GH61 protein are referred to in this disclosure using the following notation: The single-letter abbreviation for the amino acid being substituted; its position in the reference sequence (e.g., the wild-type "parental sequence" set forth in SEQ ID NO:2); and the single-letter abbreviation for the amino acid that replaces it. Thus, the following nomenclature is used herein to describe substitutions in a reference sequence relative to a reference sequence or a variant polypeptide or nucleic acid sequence: "R-#-V," where # refers to the position in the reference sequence, R refers to the amino acid (or base) at that position in the reference sequence, and V refers to the amino acid (or base) at that position in the variant sequence. In some embodiments, an amino acid (or base) may be called "X," by which is meant any amino acid (or base). As a non-limiting example, for a variant polypeptide described with reference to a wild-type GH61 polypeptide (e.g., SEQ ID NO:2), "N35G" indicates that in the variant polypeptide, the asparagine at position 35 of the reference sequence is replaced by glycine, with amino acid position being determined by optimal alignment of the variant sequence with SEQ ID NO:2. Similarly, "H20C/D" describes two variants: a variant in which the histidine at position 20 of the reference sequence is replaced by cysteine and a variant in which the serine at position 20 of the reference sequence is replaced by aspartic acid. In the example "W141X" indicates that the tryptophan at position 131 has been replaced with any amino acid.

As used herein in reference to nucleotide and amino acid sequences, the term "mutation" refers to any change in the sequence, as compared to a reference nucleotide or amino acid sequence, including but not limited to substitutions, deletions, additions, truncations, modifications, etc. Indeed, it is intended that any change in a reference (or "parent" or "starting") nucleotide or amino acid sequence comprises a mutation in the sequence.

As used herein, the terms "amino acid mutation set", "mutation set" when used in the context of amino acid sequences (e.g., polypeptides) refer to a group of amino acid substitutions, insertions, deletions and/or other modifications to the sequence. In some embodiments, "mutation set" refers to the nucleic acid mutation sets present in some of the GH61 variants provided in Table 1 and Table 2.

The term "amino acid substitution set," "substitution set," and "combination of amino acid substitutions" refer to a group (i.e., set of combinations) of amino acid substitutions. A substitution set can have about 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant GH61 enzymes provided herein.

As used herein, the terms "nucleic acid substitution set" and "substitution set" when used in the context of nucleotide sequences (e.g., polynucleotides) refer to a group of nucleic acid substitutions. In some embodiments, mutation set refers to the nucleic acid substitution sets present in some of the variant GH61 proteins provided in Table 1 and Table 2.

As used herein, the terms "nucleic acid mutation set" and "mutation set" when used in the context of nucleotide sequences (e.g., polynucleotides) refer to a group of nucleic acid substitutions, insertions, deletions, and/or other modifications to the sequence. In some embodiments, "mutation set" refers to the amino acid mutation sets present in some of the GH61 variants provided in Table 1 and Table 2.

A "cellulase-engineered" cell is a cell comprising at least one, at least two, at least three, or at least four recombinant sequences encoding a cellulase or cellulase variant, and in which expression of the cellulase(s) or cellulase variant(s) has been modified relative to the wild-type form. Expression of a cellulase is "modified" when a non-naturally occurring cellulase variant is expressed or when a naturally occurring cellulase is over-expressed. One exemplary means to over-express a cellulase is to operably link a strong (optionally constitutive) promoter to the cellulase encoding sequence. Another exemplary way to over-express a cellulase is to increase the copy number of a heterologous, variant, or endogenous cellulase gene. The cellulase-engineered cell may be any suitable fungal cell, including, but not limited to *Myceliophthora*, *Trichoderma*, *Aspergillus*, cells, etc.

As used herein, the terms "host cell" and "host strain" refer to suitable hosts for expression vectors comprising DNA provided herein. In some embodiments, the host cells are prokaryotic or eukaryotic cells that have been transformed or transfected with vectors constructed using recombinant DNA techniques as known in the art. Transformed hosts are capable of either replicating vectors encoding at least one protein of interest and/or expressing the desired protein of interest. In addition, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, etc. In some embodiments, host cells are genetically modified to have characteristics that improve protein secretion, protein stability or other properties desirable for expression and/or secretion of a protein. For example, knockout of Alp1 function results in a cell that is protease deficient. Knockout of pyr5 function results in a cell with a pyrimidine deficient phenotype. In some embodiments, host cells are modified to delete endogenous cellulase protein-encoding sequences or otherwise eliminate expression of one or more endogenous cellulases. In some embodiments, expression of one or more endogenous cellulases is inhibited to increase production of cellulases of interest. Genetic modification can be achieved by any suitable genetic engineering techniques and/or classical microbiological techniques (e.g., chemical or UV mutagenesis and subsequent selection). Using recombinant technology, nucleic acid molecules can be introduced, deleted, inhibited or modified, in a manner that results in increased yields of GH61 variant(s) within the organism or in the culture. For example, knockout of Alp1 function results in a cell that is protease deficient. Knockout of pyr5 function results in a cell with a pyrimidine deficient phenotype. In some genetic engineering approaches, homologous recombination is used to induce targeted gene modifications by specifically targeting a gene in vivo to suppress expression of the encoded protein. In an alternative approach, siRNA, antisense, and/or ribozyme technology finds use in inhibiting gene expression.

As used herein, the term "C1" refers to strains of *Myceliophthora thermophila*, including the fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573, 086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV 13-6 (Accession No. VKM F-3632 D), C1 strain NG7C-19 (Accession No. VKM F-3633 D), and C1 strain UV18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272.77, CBS122190, CBS122189, and VKM F-3500D. Exemplary C1 derivatives include but are not limited to modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#100.f Δalp1 Δpep4 Δalp2, UV18#100.f Δpyr5 Δalp1 Δpep4 Δalp2 and UV18#1001Δpyr4 Δpyr5 ΔaIp1 Δpep4 Δalp2, as described in WO2008073914 and WO2010107303, each of which is incorporated herein by reference.

As used herein, the term "culturing" refers to growing a population of microbial cells under suitable conditions in a liquid, semi-solid, or solid medium.

In general, "saccharification" refers to the process in which substrates (e.g., cellulosic biomass and/or lignocellulosic biomass) are broken down via the action of cellulases to produce fermentable sugars (e.g. monosaccharides, including but not limited to glucose and/or xylose). In particular, "saccharification" is an enzyme-catalyzed reaction that results in hydrolysis of a complex carbohydrate to produce shorter-chain carbohydrate polymers and/or fermentable sugar(s) that are more suitable for fermentation or further hydrolysis. In some embodiments, the enzymes comprise cellulase enzyme(s) such as endoglucanases, beta-glucosidases, cellobiohydrolases (e.g., CBH1 and/or CBH1), a synthetic mixture of any of such enzymes, and/or cellulase enzymes contained in culture broth from an organism that produces cellulase enzymes, such as *M. thermophila* or recombinant yeast cells. Products of saccharification may include disaccharides, and/or monosaccharides such as glucose or xylose.

In some embodiments, the fermentable sugars produced by the methods of the present invention are used to produce an alcohol (e.g., including but not limited to ethanol, butanol, etc.). The variant GH61 proteins of the present invention find use in any suitable method to generate alcohols and/or other biofuels from cellulose and/or lignocellulose, and are not limited necessarily to those described herein. Two methods commonly employed are the separate saccharification and fermentation (SHF) method (See, Wilke et al., Biotechnol. Bioengin. 6:155-75 [1976]) or the simultaneous saccharification and fermentation (SSF) method (See e.g., U.S. Pat. Nos. 3,990,944 and 3,990,945). An additional method that finds use with the present invention is consolidated bioprocessing (CBP), which encompasses the combination of the biological steps used in the conversion of lignocellulosic biomass to bioethanol (e.g., production of cellulase(s), hydrolysis of the polysaccharides in the biomass, and fermentation of hexose and pentose sugars) in one reactor (See e.g., Vertes et al., Biomass to Biofuels: Strategies for Global Industries, John Wiley & Sons, Ltd., [2010], Hoboken, N.J., pp. 324-325).

The SHF method of saccharification comprises the steps of contacting cellulase with a cellulose-containing substrate to enzymatically break down cellulose into fermentable sugars (e.g., monosaccharides such as glucose), contacting the fermentable sugars with an alcohol-producing microorganism to produce alcohol (e.g., ethanol or butanol) and recovering the alcohol. In some embodiments, the method of consolidated bioprocessing (CBP) can be used, in which the cellulase production from the host is simultaneous with saccharification and fermentation either from one host or from a mixed cultivation.

In addition to SHF methods, a SSF method may be used. In some cases, SSF methods result in a higher efficiency of alcohol production than is afforded by the SHF method (See e.g., Drissen et al., Biocat. Biotransform., 27:27-35 [2009]). One disadvantage of SSF over SHF is that higher temperatures are required for SSF than for SHF. In some embodiments, the present invention provides GH61 polypeptides that have higher thermostability than a wild-type GH61s.

Thus, it is contemplated that the present invention will find use in increasing ethanol production in SSF, as well as SHF methods.

As used herein "fermentable sugars" refers to fermentable sugars (e.g., monosaccharides, disaccharides and short oligosaccharides), including but not limited to glucose, xylose, galactose, arabinose, mannose and sucrose. In general, the term "fermentable sugar" refers to any sugar that a microorganism can utilize or ferment.

As used herein, the terms "adjunct material," "adjunct composition," and "adjunct compound" refer to any composition suitable for use in the compositions and/or saccharification reactions provided herein, including but not limited to cofactors, surfactants, builders, buffers, enzyme stabilizing systems, chelants, dispersants, colorants, preservatives, antioxidants, solubilizing agents, carriers, processing aids, pH control agents, etc. In some embodiments, divalent metal cations are used to supplement saccharification reactions and/or the growth of host cells producing GH61 variant proteins. Any suitable divalent metal cation finds use in the present invention, including but not limited to $Cu^{++}$, $Mn^{++}$, $Co^{++}$, $Mg^{++}$, $Ni^{++}$, $Zn^{++}$, and $Ca^{++}$. In addition, any suitable combination of divalent metal cations finds use in the present invention. Furthermore, divalent metal cations find use from any suitable source.

In some embodiments, the host cells producing GH61 variant proteins of the present invention are grown under culture conditions comprising about pH 5, while in some other embodiments, the host cells are grown at about pH 6.7. In some embodiments, the host cells cultured at pH 5 provide improved saccharification in the presence of supplemented copper, when saccharification is conducted at about pH 5 or about pH 6.7. In some alternative embodiments, the host cells cultured at about pH 6.7 provide improved saccharification in the absence of supplemented copper when saccharification is conducted at about pH 5 or about pH 6.

As used herein, the terms "biomass," "biomass substrate," "cellulosic biomass," "cellulosic feedstock," and "cellulosic substrate" refer to any materials that contain cellulose. Biomass can be derived from plants, animals, or microorganisms, and may include, but is not limited to agricultural, industrial, and forestry residues, industrial and municipal wastes, and terrestrial and aquatic crops grown for energy purposes. Examples of cellulosic substrates include, but are not limited to, wood, wood pulp, paper pulp, corn fiber, corn grain, corn cobs, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, corn cobs, distillers grain, grasses, rice hulls, cotton, hemp, flax, sisal, sugar cane bagasse, sorghum, soy, switchgrass, components obtained from milling of grains, trees, branches, roots, leaves, wood chips, sawdust, shrubs and bushes, vegetables, fruits, and flowers and any suitable mixtures thereof. In some embodiments, the cellulosic biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to bagasse (e.g., sugar cane bagasse, beet pulp [e.g., sugar beet], or a combination thereof), agricultural residues (e.g. soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the cellulosic biomass comprises cellulosic waste material and/or forestry waste materials, including but not limited to, paper and pulp processing waste, newsprint, cardboard and the like. In some embodiments, the cellulosic biomass comprises one species of fiber, while in some alternative embodiments, the cellulosic biomass comprises a mixture of fibers that originate from different cellulosic biomasses. In some embodiments, the biomass may also comprise transgenic plants that express ligninase and/or cellulase enzymes (US 2008/0104724 A1).

The terms "lignocellulosic biomass" and "lignocellulosic feedstock" refer to plant biomass that is composed of cellulose and hemicellulose, bound to lignin. The biomass may optionally be pretreated to increase the susceptibility of cellulose to hydrolysis by chemical, physical and biological pretreatments (such as steam explosion, pulping, grinding, acid hydrolysis, solvent exposure, and the like, as well as combinations thereof). Various lignocellulosic feedstocks find use, including those that comprise fresh lignocellulosic feedstock, partially dried lignocellulosic feedstock, fully dried lignocellulosic feedstock, and/or any combination thereof. In some embodiments, lignocellulosic feedstocks comprise cellulose in an amount greater than about 20%, more preferably greater than about 30%, more preferably greater than about 40% (w/w). For example, in some embodiments, the lignocellulosic material comprises from about 20% to about 90% (w/w) cellulose, or any amount therebetween, although in some embodiments, the lignocellulosic material comprises less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, or less than about 5% cellulose (w/w).

Furthermore, in some embodiments, the lignocellulosic feedstock comprises lignin in an amount greater than about 10%, more typically in an amount greater than about 15% (w/w). In some embodiments, the lignocellulosic feedstock comprises small amounts of sucrose, fructose and/or starch. The lignocellulosic feedstock is generally first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In some embodiments, at least 90% by weight of the particles produced from the size reduction have lengths less than between about 1/16 and about 4 in (the measurement may be a volume or a weight average length). In some embodiments, the equipment used to reduce the particle size reduction is a hammer mill or shredder. Subsequent to size reduction, the feedstock is typically slurried in water, as this facilitates pumping of the feedstock. In some embodiments, lignocellulosic feedstocks of particle size less than about 6 inches do not require size reduction.

As used herein, the term "pretreated lignocellulosic feedstock," refers to lignocellulosic feedstocks that have been subjected to physical and/or chemical processes to make the fiber more accessible and/or receptive to the actions of cellulolytic enzymes, as described above.

A cellulosic substrate or lignocellulosic substrate is said to be "pretreated" when it has been processed by some physical and/or chemical means to facilitate saccharification. As described further herein, in some embodiments, the biomass substrate is "pretreated," or treated using methods known in the art, such as chemical pretreatment (e.g., ammonia pretreatment, dilute acid pretreatment, dilute alkali pretreatment, or solvent exposure), physical pretreatment (e.g., steam explosion or irradiation), mechanical pretreatment (e.g., grinding or milling) and biological pretreatment (e.g., application of lignin-solubilizing microorganisms) and combinations thereof, to increase the susceptibility of cellulose to hydrolysis. Thus, the term "cellulosic biomass" encompasses any living or dead biological material that contains a polysaccharide substrate, including but not limited to cellulose, starch, other forms of long-chain carbohydrate polymers, and mixtures of such sources. It may or may not be assembled entirely or primarily from glucose or xylose, and may optionally also contain various other pentose or hexose monomers. Xylose is an aldopentose containing five carbon atoms and an aldehyde group. It is the precursor to hemicellulose, and is often a main constituent of biomass. In some embodiments, the substrate is slurried prior to pretreatment. In some embodiments, the consistency of the slurry is between about 2% and about 30% and more typically between about 4% and about 15%. In some embodiments, the slurry is subjected to a water and/or acid soaking operation prior to pretreatment. In some embodiments, the slurry is dewatered using any suitable method to reduce steam and chemical usage prior to pretreatment. Examples of dewatering devices include, but are not limited to pressurized screw presses (See e.g., WO 2010/022511, incorporated herein by reference) pressurized filters and extruders.

In some embodiments, the pretreatment is carried out to hydrolyze hemicellulose, and/or a portion thereof present in the cellulosic substrate to monomeric pentose and hexose sugars (e.g., xylose, arabinose, mannose, galactose, and/or any combination thereof). In some embodiments, the pretreatment is carried out so that nearly complete hydrolysis of the hemicellulose and a small amount of conversion of cellulose to glucose occurs. In some embodiments, an acid concentration in the aqueous slurry from about 0.02% (w/w) to about 2% (w/w), or any amount therebetween, is typically used for the treatment of the cellulosic substrate. Any suitable acid finds use in these methods, including but not limited to, hydrochloric acid, nitric acid, and/or sulfuric acid. In some embodiments, the acid used during pretreatment is sulfuric acid. Steam explosion is one method of performing acid pretreatment of biomass substrates (See e.g., U.S. Pat. No. 4,461,648). Another method of pretreating the slurry involves continuous pretreatment (i.e., the cellulosic biomass is pumped though a reactor continuously). This methods are well-known to those skilled in the art (See e.g., U.S. Pat. No. 7,754,457).

In some embodiments, alkali is used in the pretreatment. In contrast to acid pretreatment, pretreatment with alkali may not hydrolyze the hemicellulose component of the biomass. Rather, the alkali reacts with acidic groups present on the hemicellulose to open up the surface of the substrate. In some embodiments, the addition of alkali alters the crystal structure of the cellulose so that it is more amenable to hydrolysis. Examples of alkali that find use in the pretreatment include, but are not limited to ammonia, ammonium hydroxide, potassium hydroxide, and sodium hydroxide. One method of alkali pretreatment is Ammonia Freeze Explosion, Ammonia Fiber Explosion or Ammonia Fiber Expansion ("AFEX" process; See e.g., U.S. Pat. Nos. 5,171,592; 5,037,663; 4,600,590; 6,106,888; 4,356,196; 5,939,544; 6,176,176; 5,037,663 and 5,171,592). During this process, the cellulosic substrate is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. In some embodiments, the flashed ammonia is then recovered using methods known in the art. In some alternative methods, dilute ammonia pretreatment is utilized. The dilute ammonia pretreatment method utilizes more dilute solutions of ammonia or ammonium hydroxide than AFEX (See e.g., WO2009/045651 and US 2007/0031953). This pretreatment process may or may not produce any monosaccharides.

Additional pretreatment processes for use in the present invention include chemical treatment of the cellulosic substrate with organic solvents, in methods such as those utilizing organic liquids in pretreatment systems (See e.g., U.S. Pat. No. 4,556,430; incorporated herein by reference). These methods have the advantage that the low boiling point liquids easily can be recovered and reused. Other pretreatments, such as the Organosolv™ process, also use organic liquids (See e.g., U.S. Pat. No. 7,465,791, which is also incorporated herein by reference). Subjecting the substrate to pressurized water may also be a suitable pretreatment method (See e.g., Weil et al., Appl. Biochem. Biotechnol., 68(1-2): 21-40 [1997], which is incorporated herein by reference). In some embodiments, the pretreated cellulosic biomass is processed after pretreatment by any of several steps, such as dilution with water, washing with water, buffering, filtration, or centrifugation, or any combination of these processes, prior to enzymatic hydrolysis, as is familiar to those skilled in the art. The pretreatment produces a pretreated feedstock composition (e.g., a "pretreated feedstock slurry") that contains a soluble component including the sugars resulting from hydrolysis of the hemicellulose, optionally acetic acid and other inhibitors, and solids including unhydrolyzed feedstock and lignin. In some embodiments, the soluble components of the pretreated feedstock composition are separated from the solids to produce a soluble fraction.

In some embodiments, the soluble fraction, including the sugars released during pretreatment and other soluble components (e.g., inhibitors), is then sent to fermentation. However, in some embodiments in which the hemicellulose is not effectively hydrolyzed during the pretreatment one or more additional steps are included (e.g., a further hydrolysis step(s) and/or enzymatic treatment step(s) and/or further alkali and/or acid treatment) to produce fermentable sugars. In some embodiments, the separation is carried out by washing the pretreated feedstock composition with an aqueous solution to produce a wash stream and a solids stream comprising the unhydrolyzed, pretreated feedstock. Alternatively, the soluble component is separated from the solids by subjecting the pretreated feedstock composition to a solids-liquid separation, using any suitable method (e.g., centrifugation, microfiltration, plate and frame filtration, cross-flow filtration, pressure filtration, vacuum filtration, etc.). Optionally, in some embodiments, a washing step is incorporated into the solids-liquids separation. In some embodiments, the separated solids containing cellulose, then undergo enzymatic hydrolysis with cellulase enzymes in order to convert the cellulose to glucose. In some embodiments, the pretreated feedstock composition is fed into the fermentation process without separation of the solids contained therein. In some embodiments, the unhydrolyzed solids are subjected to enzymatic hydrolysis with cellulase enzymes to convert the cellulose to glucose after the fermentation process. In some embodiments, the pretreated cellulosic feedstock is subjected to enzymatic hydrolysis with cellulase enzymes.

As used herein, the term "recovered" refers to the harvesting, isolating, collecting, or recovering of protein from a cell and/or culture medium. In the context of saccharification, it is used in reference to the harvesting the fermentable sugars produced during the saccharification reaction from the culture medium and/or cells. In the context of fermentation, it is used in reference to harvesting the fermentation product from the culture medium and/or cells. Thus, a process can be said to comprise "recovering" a product of a reaction (such as a soluble sugar recovered from saccharification) if the process includes separating the product from other components of a reaction mixture subsequent to at least some of the product being generated in the reaction.

As used herein, the term "slurry" refers to an aqueous solution in which are dispersed one or more solid components, such as a cellulosic substrate.

"Increasing" yield of a product (such as a fermentable sugar) from a reaction occurs when a particular component present during the reaction (such as a GH61 protein) causes more product to be produced, compared with a reaction conducted under the same conditions with the same substrate and other substituents, but in the absence of the component of interest.

"Hydrolyzing" cellulose or other polysaccharide occurs when at least some of the glycosidic bonds between two monosaccharides present in the substrate are hydrolyzed, thereby detaching from each other the two monomers that were previously bonded.

A reaction is said to be "substantially free" of a particular enzyme if the amount of that enzyme compared with other enzymes that participate in catalyzing the reaction is less than about 2%, about 1%, or about 0.1% (wt/wt).

"Fractionating" a liquid (e.g., a culture broth) means applying a separation process (e.g., salt precipitation, column chromatography, size exclusion, and filtration) or a combination of such processes to provide a solution in which a desired protein (e.g., GH61 protein, cellulase enzyme, or combination thereof) comprises a greater percentage of total protein in the solution than in the initial liquid product.

GH61 Variant Proteins with Improved Activity

GH61 variant proteins of the present invention have certain amino acid substitutions in relation to wild-type GH61a protein. In saccharification reactions, wild-type GH61a protein increases the yield of fermentable sugars. An equivalent amount of GH61 variant proteins instead of the wild type increases the yield of fermentable sugars still further. The present invention provides numerous GH61 variants, as indicated herein. Substitutions that have been shown to improve GH61 activity are included in Table 1, below.

TABLE 1

GH61 Variants with Improved Activity

| Var. No. | Amino Acid Changes | Silent Nucleotide Changes |
|---|---|---|
| 1 | N35G/E104H/A168P (SEQ ID NO: 5) | t60c/c573g |
| 2 | W42P/E104H/K167A | t60c/c573g/ g1026a |
| 3 | N35G/W42P/V97Q/ A191N | |
| 4 | W42P/E104H | c573g |
| 5 | E104H/K167A | t60c/c291a/ c573g |
| 6 | W42P/A191N | t60c/c291a |
| 7 | N35G/W42P/A191N | t60c/c291a |
| 8 | H20D | |
| 9 | V97Q/A191N | |
| 10 | N35G/E104H/A191N | t60c/c876t |
| 11 | E104H | |

TABLE 1-continued

GH61 Variants with Improved Activity

| Var. No. | Amino Acid Changes | Silent Nucleotide Changes |
|---|---|---|
| 12 | E104Q | |
| 13 | H20D/E104D/Q190H/ Y192H | |
| 14 | H20D/Q190E/Y192Q | a312g |
| 15 | H20D/E104C | |
| 16 | H20D/P103H/E104C | |
| 17 | H20D/P103H | a312g |
| 18 | N35G/E104H | t60c/c573g |
| 19 | H20D/P103H/E104Q/ Q190E | |
| 20 | H20D/P103H/E104C/ Y192Q | |
| 21 | E104D | t60c |
| 22 | N35G/W42P | t60c/c573g |
| 23 | A137P | |
| 24 | H20D/P103H/E104Q | |
| 25 | P103E/E104D | t60c |
| 26 | N35G/F68Y/A191N | t379a/c380g/ g381c |
| 27 | W42P/A168P | |
| 28 | H20D/E104C/Q190E/ Y192Q | |
| 29 | A142W | |
| 30 | N35G | |
| 31 | H20C/Q190E | |
| 32 | W42P/A212P/T236P | |
| 33 | N35G/W42P/V97Q/ K167A/ A168P | t60c/c573g |
| 34 | V97Q/A168P | c573g |
| 35 | S232A | |
| 36 | W42P/E104H/K167A/ A168P/Q190E | c573g |
| 37 | W42P/A168P/A212P/ T236P | |
| 38 | N35G/V97Q/K167A | |
| 39 | N35G/V97Q | |
| 40 | N35G/A191N | |
| 41 | S127T/K167A/ A191N | |
| 42 | W42P | |
| 43 | W42P/E104C/K167A/ A168P | t60c/c291a/ c573g |
| 44 | K167Q | |
| 45 | W131V | |
| 46 | E176C | |
| 47 | K167I/P273S | c300t |
| 48 | W42P/T87P | |
| 49 | W42P/A212P | |
| 50 | K133H | |
| 51 | D165N | |
| 52 | D165A | |
| 53 | A168D | |
| 54 | K218T | |
| 55 | P45T | |
| 56 | Q44V | |
| 57 | S164W | |
| 58 | I177F | |
| 59 | A191N | |
| 60 | I134P | |
| 61 | K133F | |
| 62 | I134D | |
| 63 | N35G/K167A | t60c/c291a/ c573g |
| 64 | I162R | |
| 65 | N35G/K167A | t204c/t379a c380g/ g381c/c385t |
| 66 | D165W/A246T | |
| 67 | I162L | |
| 68 | S164M | |
| 69 | F132D/A244D | |
| 70 | H181Q | |
| 71 | I177G | g1026a |

TABLE 1-continued

GH61 Variants with Improved Activity

| Var. No. | Amino Acid Changes | Silent Nucleotide Changes |
|---|---|---|
| 72 | L166W | |
| 73 | I162F | |
| 74 | I134V | |
| 75 | E176Q | |
| 76 | H181S | |
| 77 | I178A | |
| 78 | K167A | |
| 79 | V172K | |
| 80 | I177H | |
| 81 | I134N | |
| 82 | K133Y | |
| 83 | N35G/Y139L | |
| 84 | A168G | |
| 85 | T12A/I162G | c246t |
| 86 | D165E | |
| 87 | D165M | |
| 88 | I134M | |
| 89 | A168P | |
| 90 | I177D | |
| 91 | S164P | |
| 92 | H175T | |
| 93 | N187K/S330R | c597g |
| 94 | H175R | |
| 95 | L166H | |
| 96 | I178L | |
| 97 | L173H | |
| 98 | I177T | |
| 99 | N170Y | |
| 100 | H175S | |
| 101 | K167T | |
| 102 | L166R | |
| 103 | V172Y | |
| '104 | P163S/E176D | |
| 105 | S164I | |
| 106 | H175M | |
| 107 | A168N | |
| 108 | A179W | |
| 109 | W131K/H175Q | g1026a |
| 110 | Y171A | |
| 111 | N170H | |
| 112 | P163R | |
| 113 | A168C | |
| 114 | G169T | |
| 115 | R174F | |
| 116 | W131Y | |
| 117 | I134L | |
| 118 | I177V | |
| 119 | K167E | |
| 120 | H175C | |
| 121 | W131I | |
| 122 | W42P/A143P | |
| 123 | I178G | c72t |
| 124 | N170P | |
| 125 | A179D/N317K | c732g/c843t/ c882t/c909t/ c912g |
| 126 | I162V | |
| 127 | I178M | |
| 128 | V172A | |
| 129 | K167A/A191N | t60c/c291a |
| 130 | F132A | |
| 131 | P163E | |
| 132 | F132M | |
| 133 | A179G | |
| 134 | I177S | |
| 135 | K167A | g921a |
| 136 | K167F | |
| 137 | A168I | |
| 138 | A179N | |
| 139 | I134A | c792t |
| 140 | K167E | g972t |
| 141 | R174K | |
| 142 | S164F | |
| 143 | V172L | |
| 144 | A168H | |
| 145 | I134T | |
| 146 | K167H | |
| 147 | L166A | |
| 148 | S164R | |
| 149 | R174C | |
| 150 | A179P | |
| 151 | G169R | g1026a |
| 152 | L173M | |
| 153 | D165K | |
| 154 | E176S | |
| 155 | F132L | |
| 156 | F132I/A179I | |
| 157 | F132P | |
| 158 | S164Q | |
| 159 | V172Q | |
| 160 | W131D | |
| 161 | W131Q | |
| 162 | A179H | |
| 163 | I134H/G270S | |
| 164 | N170G | |
| 165 | A168T | |
| 166 | A179C | |
| 167 | K133N | |
| 168 | K167L | |
| 169 | L180M | |
| 170 | W131F | |
| 171 | I134W | g1026a |
| 172 | I178H | |
| 173 | N170A | |
| 174 | V172H | |
| 175 | A168H/S205N | |
| 176 | I134H | g921a |
| 177 | S164C | |
| 178 | S164K | |
| 179 | I177C | |
| 180 | I178Q | |
| 181 | L180W | |
| 182 | I177M | |
| 183 | R174D | |
| 184 | V172M | |
| 185 | A179M | |
| 186 | H175Y | |
| 187 | I178P | |
| 188 | L173A | |
| 189 | N170E | |
| 190 | N170F | |
| 191 | N35G/A191N/T258I/ T323P/ G328A/C341R | t379a/c380g/ g381c/ c454a/c456a/ c732t/c843t/ c849t |
| 192 | A168R | |
| 193 | D165I | |
| 194 | I162M | |
| 195 | K167V | |
| 196 | A179S | |
| 197 | E176N | |
| 198 | I134L/P322L | |
| 199 | P163L | |
| 200 | H181D | |
| 201 | N170S | |
| 202 | R174G | |
| 203 | I177R | |
| 204 | K167C | |
| 205 | L166Q | |
| 206 | P163I | |
| 207 | S164L/L166I | |
| 208 | Y171R | |
| 209 | F132P/Q190E/A191T | |
| 210 | F132Q | |
| 211 | I134C | |
| 212 | I177A | |
| 213 | E176R | |

TABLE 1-continued

GH61 Variants with Improved Activity

| Var. No. | Amino Acid Changes | Silent Nucleotide Changes |
|---|---|---|
| 214 | G169A | |
| 215 | G169K | |
| 216 | H181A | |
| 217 | I177L | |
| 218 | A168G | |
| 219 | A179R | |
| 220 | D165T | |
| 221 | K167R | |
| 222 | L166V | |
| 223 | N170C | |
| 224 | I178R | |
| 225 | R174H | |
| 226 | S164H | |
| 227 | W131R/L166I | |
| 228 | I162A/A191T | |
| 229 | L173F | |
| 230 | N170Q | |
| 231 | I177P | |
| 232 | R174N | |
| 233 | V172K/S215W | |
| 234 | D165R | |
| 235 | G239D | c520a/c522g |
| 236 | H175V | |
| 237 | H181R | |
| 238 | I134Y | |
| 239 | V172F | |
| 240 | V172G | |

Positions that were changed in variants with improved GH61 activity listed in Table 1 include 20, 34, 35, 42, 44, 45, 68, 87, 97, 103, 104, 127, 131, 132, 133, 137, 139, 142, 143, 162, 163, 164, 165, 166, 167, 168, 169, 170, 171, 172, 173, 174, 175, 176, 177, 178, 179, 180, 181, 190, 191, 192, 192, 205, 212, 215, 218, 232, 236, 239, 244, 246, 258, 270, 273, 317, 322, 323, 328, 330, and 341, wherein the amino acid positions are numbered with reference to SEQ ID NO:2.

Residues that were changed in variants with improved GH61 activity listed in Table 1 include H20, I134, N35, W42, Q44, P45, F68, T87, V97, P103, E104, S127, W131, F132, K133, A137, Y139, A142, A143, I162, P163, S164, D165, L166, K167, A168, G169, N170, Y171, V172, L173, R174, H175, E176, I177, I178, A179, L180, H181, Q190, A191, Y192, Y192, S205, A212, S215, K218, S232, T236, G239, A244, A246, T258, G270, P273, N317, P322, T323, G328, S330, and C341, wherein the amino acid positions are numbered with reference to SEQ ID NO:2.

Substitutions occurring in variants with improved GH61 activity listed in Table 1 include H20C/D, I134X, N35G, W42P, Q44V, P45T, F68Y, T87P, V97Q, P103E/H, E104C/D/H/Q, S127T, W131X, F132X, K133X, A137P, Y139L, A142W, A143P, I162X, P163X, S164X, D165X, L166X, K167A/X, A168P/X, G169X, N170X, Y171A/R, V172X, L173X, R174X, H175X, E176X, I177X, I178X, A179X, L180M/W, H181X, Q190E/H, A191N/T, Y192H, Y192Q, S205N, A212P, S215W, K218T, S232A, T236P, G239D, A244D, A246T, T258I, G270S, P273S, N317K, P322L, T323P, G328A, S330R, and C341R, wherein the amino acid positions are numbered with reference to SEQ ID NO:2.

As shown herein, the changed residues and substitutions of the GH61 variants of this invention may be combined in a manner that produces an effect that is cumulative or synergistic. Cumulative effects occur when adding an additional mutation increases the effect beyond those of the mutations already present. Synergistic effects occur when having two more mutations in a variant produces an effect than is more than the product of the mutations when incorporated by themselves. This invention includes without limitation any and all combinations of any two, three, four, five, six, seven, eight, nine, ten, or more than ten of the mutations listed in this disclosure.

Useful combinations include but are not limited to the mutations and mutation sets: N35G/E104H/A168P (SEQ ID NO:5); W42P/E104H/K167A; N35G/W42P/V97Q/A191N; W42P/E104H; E104H/K167A; W42P/A191N; N35G/W42P/A191N; V97Q/A191N; N35G/E104H/A191N; H20D/E104D/Q190H/Y192H; H20D/Q190E/Y192Q; H20D/E104C; H20D/P103H/E104C; H20D/P103H; N35G/E104H; H20D/P103H/E104Q/Q190E; H20D/P103H/E104C/Y192Q; N35G/W42P; H20D/P103H/E104Q; P103E/E104D; N35G/F68Y/A191N; W42P/A168P; H20D/E104C/Q190E/Y192Q; H20C/Q190E; W42P/A212P/T236P; N35G/W42P/V97Q/K167A/V97Q/A168P; W42P/E104H/K167A/A168P/Q190E; W42P/A168P/A212P/T236P; N35G/V97Q/K167A; N35G/V97Q; N35G/A191N; S127T/K167A/A191N; W42P/E104C/K167A/A168P; K167I/P273S; W42P/T87P; W42P/A212P; N35G/K167A; N35G/K167A; D165W/A246T; F132D/A244D; N35G/Y139L; T12A/I162G; N187K/S330R; P163S/E176D; W131K/H175Q; W42P/A143P; A179D/N317K; K167A/A191N; F132I/A179I; I134H/G270S; A168H/S205N; N35G/A191N/T258I/T323P/G328A/C341R; I134L/P322E; S164E/L166I; F132P/Q190E/A191T; W131R/L166I; I162A/A191T; and V172K/S215W, wherein the amino acid positions are numbered with reference to SEQ ID NO:2.

GH61 Variant Proteins Made with Multiple Rounds of Activity Enhancement

GH61 variant proteins can be generated that have been further optimized by subjecting to multiple rounds of variation and selection. In some embodiments, additional rounds of optimization increase saccharification reaction yields beyond what is achieved with one round of variation and selection. Substitutions improving GH61 activity are compiled in Table 2 below.

Table 2 shows GH61a variants derived from the GH61a protein designated "Variant 1" (SEQ ID NO:5) in Table 1 with improved thermoactivity. The second-round variants usually retained the alterations of Variant 1 compared with wild-type GH61a (N35G/E104H/A168P), along with additional modifications.

TABLE 2

GH61 Variants with Improved Activity Compared to Variant 1

| Var. No. | Amino Acid Changes | Silent Nucleotide Changes |
|---|---|---|
| 241 | N35G/T40A/E104H/A168P/P327M | t60c/c573g |
| 242 | N35G/P45D/E104H/A168P/N317R | t60c/c573g |
| 243 | N35G/E104H/A168P/N317R | t60c/c573g |
| 244 | N35G/E104H/A168P/N317L | t60c/c573g |
| 245 | N35G/T54H/E104H/A168P | t60c/c573g |
| 246 | N35G/E104H/A168P/N317D/S329Y | t60c/c573g |
| 247 | N35G/E104H/A137S/A168P/S232E | t60c/c573g |
| 248 | N35G/E104H/A168P/N317R/T320A | t60c/c573g |
| 249 | N35G/E104H/A168P/D234E | t60c/c573g |

TABLE 2-continued

GH61 Variants with Improved Activity Compared to Variant 1

| Var. No. | Amino Acid Changes | Silent Nucleotide Changes |
|---|---|---|
| 250 | N35G/T40S/E104H/A142G/A168P | t60c/c573g |
| 251 | N35G/T40S/S78C/V88I/E104H/S128K/A168P/D234M | t60c/c573g |
| 252 | N35G/E104H/A168P/S330V | t60c/c573g |
| 253 | N35G/E104H/A168P/G203E/P266S | t60c/c573g |
| 254 | N35G/E104H/A168P/D234N | t60c/c573g |
| 255 | N35G/E104H/A168P/S286N/S329H | t60c/c573g |
| 256 | N35G/E104H/A168P/S330H | t60c/c573g |
| 257 | N35G/E104H/A168P/W337R | t60c/c573g |
| 258 | N35G/N66D/E104H/S164E/A168P/G267T | t60c/c573g |
| 259 | N35G/E104H/A168P/P233V | t60c/c573g |
| 260 | R34E/N35G/E104H/R145T/A168P | t60c/c573g |
| 261 | S24Q/N35G/E104H/A168P/V237I | t60c/c573g |
| 262 | Y32S/N35G/E64S/E104H/A168P | t60c/c573g |
| 263 | N35G/E104H/A168P/V333R | t60c/c573g |
| 264 | N35G/E104H/G144S/A168P/V333Q | t60c/c573g |
| 265 | V28H/N35G/P45K/E104H/A168P | t60c/c573g |
| 266 | N35G/E104H/A168P/P327K | t60c/c573g |
| 267 | N35G/N66Q/E104H/A168P | t60c/c573g |
| 268 | N35G/E104H/A168P/G203E | t60c/c573g |
| 269 | N35G/E104H/A168P/S339W | t60c/c573g |
| 270 | N35G/P45K/N46E/E104H/A150Y/A168P | t60c/c573g |
| 271 | N35G/E104H/R130S/A168P | t60c/c573g |
| 272 | N35G/E104H/R145T/A168P | t60c/c573g/g891a |
| 273 | N35G/E104H/A168P/S231K | t60c/c573g |
| 274 | N35G/T40A/E104H/A168P/D234E/P327M | t60c/c573g |
| 275 | N35G/E104H/A168P/S231H | t60c/c573g |
| 276 | N35G/E104H/A168P/N317M | t60c/c573g |
| 277 | N35G/E104H/A168P/S330Y | t60c/c573g |
| 278 | N35G/E104H/A168P/S329I | t60c/c573g |
| 279 | N35G/E104H/A168P/S329R | t60c/c573g |
| 280 | N35G/N66D/E104H/A168P/P322R/S329L | t60c/c573g |
| 281 | N35G/E104H/A168P/P327F | t60c/c288t/c573g |
| 282 | N35G/P45D/E104H/A168P | t60c/c573g |
| 283 | N35G/E104H/A168P/S332R | t60c/c573g |
| 284 | N35G/E104H/A116S/A168P | t60c/c573g |
| 285 | N35G/T40A/E104H/A168P/V230I/P327M | t60c/c573g |
| 286 | N35G/T49A/E104H/A168P | t60c/c573g |
| 287 | N35G/E104H/A168P/N317T | t60c/c573g |
| 288 | N35G/N46Y/E104H/A168P | t60c/c573g |
| 289 | N35G/E104H/A168P/G203V | t60c/c573g |
| 290 | N35G/E104H/A168P/S329L | t60c/c573g |
| 291 | N35G/E104H/R145N/A168P/S329H | t60c/c573g |
| 292 | N35G/A56S/E104H/A168P | t60c/c573g |
| 293 | N35G/T40S/T49R/E104H/A168P/D234E/P327M | t60c/c573g |
| 294 | N35G/E104H/Q161R/A168P | t60c/c573g |
| 295 | N35G/E104H/A168P/S332F | t60c/c573g |
| 296 | N35G/P45R/T49A/E104H/A168P/N317R/T320A | t60c/c573g |
| 297 | N35G/E104H/A168P/V237I | t60c/c573g |
| 298 | N35G/Q44K/T80V/E104H/A168P | t60c/c573g |
| 299 | N35G/E104H/A168P/E336S | t60c/c573g |
| 300 | N35G/E104H/A168P/P233T | t60c/c573g |
| 301 | N35G/E104H/A168P/S329Y | t60c/c573g |
| 302 | N35G/E104H/A168P/P327L | t60c/c573g |
| 303 | N35G/E104H/A168P/N317I | t60c/c573g |
| 304 | N35G/E104H/R130H/A168P | t60c/c573g |
| 305 | N35G/Q44K/E104H/A168P | t60c/c573g |
| 306 | N35G/N66D/E104H/A168P | t60c/c573g |
| 307 | N35G/E104H/A168P/S329V | t60c/c573g |
| 308 | N35G/E104H/A168P/W337F | t60c/c573g |
| 309 | N35G/E104H/A168P/N317H | t60c/c573g |
| 310 | N35G/T40L/E104H/S128K/A168P | t60c/c573g |
| 311 | N35G/E104H/A168P/A326V | t60c/c573g |
| 312 | N35G/T80V/E104H/A168P/P303T | t60c/c573g |
| 313 | N35G/E104H/A168P/S231A/S295L | t60c/c573g |
| 314 | N35G/E104H/A116Q/A168P | t60c/c573g |
| 315 | N35G/E104H/A168P/S330C | t60c/c573g |
| 316 | N35G/T40S/E101T/E104H/A168P/P327M | t60c/c573g |
| 317 | N35G/E104H/A168P//A326Q | t60c/c573g |
| 318 | N35GN46R/E104H/A168P | t60c/c573g |
| 319 | N35G/P45K/E104H/A168P/A219R/S232E | t60c/c573g |

TABLE 2-continued

GH61 Variants with Improved Activity Compared to Variant 1

| Var. No. | Amino Acid Changes | Silent Nucleotide Changes |
|---|---|---|
| 320 | S24Q/N35G/E104H/A168P/V237I/P303T | t60c/c573g |
| 321 | N35G/E104H/A168P/G203E/T281A | t60c/c573g |
| 322 | N35G/A56N/E104H/A168P | t60c/c573g |
| 323 | N35G/E104H/A168P/E336G | t60c/c573g |
| 324 | N35G/E104H/A168P/E336R | t60c/c573g |
| 325 | N35G/T40S/E104H/S128K/A142G/A168P | t60c/c573g |
| 326 | N35G/Q44K/S67T/E104H/A168P | t60c/c198t/c573g |
| 327 | N35G/E104H/A168P/N317A | t60c/c573g |
| 328 | N35G/E104H/G155N/A168P | t60c/c573g |
| 329 | N35G/E104H/Q161E/A168P | t60c/c573g |
| 330 | N35G/E104H/N118S/A168P | t60c/c573g |
| 331 | N35G/P45T/V97Q/E104H/A168P/G267S | t60c/c573g |
| 332 | V28H/N35G/E104H/A168P | t60c/c573g |
| 333 | N35G/E104H/A168P/Q184L | t60c/c573g |
| 334 | N35G/E104H/A168P/N317V | t60c/c573g |
| 335 | N35G/Q44L/E104H/A168P | t60c/c573g |
| 336 | N35G/E104H/A168P/S330G | t60c/c573g |
| 337 | N35G/E104H/A168P/T320A/V333W | t60c/c573g |
| 338 | N35G/E104H/A168P/E336A | t60c/c573g |
| 339 | N35G/E104H/A168P/N335S | t60c/c573g |
| 340 | N35G/N66M/E104H/A168P | t60c/c573g |
| 341 | N35G/T54G/E104H/A168P | t60c/c573g |
| 342 | N35G/E104H/A168P/N317S | t60c/c573g |
| 343 | N35G/E64L/E104H/A168P | t60c/c573g |
| 344 | N35G/E104H/S164E/A168P/A271T | t60c/c573g |
| 345 | N35G/N66A/E104H/A168P | t60c/c573g |
| 346 | N35G/G83R/E104H/A168P | t60c/c573g |
| 347 | N35G/E104H/A168P/N317Q/T320A | t60c/c573g |
| 348 | N35G/E104H/K141A/A168P | t60c/c573g |
| 349 | N35G/P71T/E104H/A168P | t60c/c573g |
| 350 | N35G/P71S/E104H/A168P | t60c/c573g |
| 351 | N35G/E104H/R130G/A168P | t60c/c573g |
| 352 | N35G/E104H/R145Q/A168P | t60c/c573g |
| 353 | N35G/T70A/E104H/A168P | t60c/c573g |
| 354 | N35G/E104H/A168P/K218R | t60c/c573g |
| 355 | N35G/E104H/A168P/Q184E | t60c/c573g |
| 356 | N35G/E104H/R130K/A168P | t60c/c573g |
| 357 | N35G/Q58H/E104H/A168P | t60c/c573g |
| 358 | Y32S/N35G/E104H/A168P | t60c/c573g |
| 359 | N35G/E104H/A168P/S329T | t60c/c573g |
| 360 | N35G/E104H/A168P/S330I | t60c/c573g |
| 361 | Y32S/N35G/P71A/E104H/A168P | t60c/c573g |
| 362 | N35G/E104H/A168P/S330T | t60c/c573g |
| 363 | N35G/G82A/E104H/A168P | t60c/c573g |
| 364 | N35G/T80V/E104H/A168P | t60c/c573g |
| 365 | N35G/E104H/A168P/S295T | t60c/c573g |
| 366 | N35G/N66G/E104H/A168P | t60c/c573g |
| 367 | N35G/E104H/R145L/A168P | t60c/c573g |
| 368 | N35G/S67H/E104H/A168P/V230M | t60c/c573g |
| 369 | N35G/E104H/G136E/A168P | t60c/c573g |
| 370 | N35G/T54S/E104H/A168P | t60c/c573g |
| 371 | N35G/P45S/E104H/A168P | t60c/c573g |
| 372 | N35G/E104H/A168P/A326M | t60c/c573g/c882t |
| 373 | N35G/N66D/N95E/E104H/S164E/A168P/G267D | t60c/c573g |
| 374 | N35G/E104H/A168P/S332C | t60c/c573g |
| 375 | N35G/E104H/S128L/A168P | t60c/c573g |
| 376 | N35G/T54W/E104H/A168P | t60c/c573g |
| 377 | N35G/E104H/A168P/G268A/G269A/G270A | t60c/c573g |
| 378 | N35G/Q44K/E104H/A168P/S231T | t60c/c573g |
| 379 | R34E/N35G/E104H/A168P/A280D | t60c/c573g |
| 380 | N35G/E104H/A168P/A297T | t60c/g399a/c573g |
| 381 | N35G/E104H/K141P/R145Q/A168P | t60c/c573g |
| 382 | N35G/P45E/E104H/K141R/A168P | t60c/c573g |
| 383 | N35G/N66T/E104H/A168P | t60c/c573g |
| 384 | N35G/E104H/S164E/A168P/S295D | t60c/c573g |
| 385 | N35G/E104H/A168P/N317F | t60c/c573g |
| 386 | N35G/E104H/A168P/N317Q | t60c/c573g |
| 387 | N35G/T40G/T49R/S78C/E104H/A142G/A168P | t60c/c573g |
| 388 | N35G/G82S/E104H/A168P | t60c/c573g |
| 389 | N35G/Q58P/E104H/A168P | t60c/c573g |
| 390 | N35G/N46R/E104H/A168P/G203E/A263V | t60c/c573g |

TABLE 2-continued

GH61 Variants with Improved Activity Compared to Variant 1

| Var. No. | Amino Acid Changes | Silent Nucleotide Changes |
|---|---|---|
| 391 | N35G/P45R/E104H/A168P | t60c/c573g |
| 392 | N35G/S67G/E104H/A168P | t60c/c573g |
| 393 | N35G/E104H/A168P/R199E | t60c/c573g |
| 394 | N35G/G69T/E104H/A168P | t60c/c573g |
| 395 | N35G/E104H/A168P/G203E/G268A/G269A/G270A | t60c/c573g |
| 396 | N35G/E104H/A168P/P266S | t60c/c573g |
| 397 | N35G/E104H/A168P/V324M | t60c/c573g |
| 398 | N35G/E104H/A168P/G245A | t60c/c573g |
| 399 | N35G/N66R/E104H/A168P | t60c/c573g |
| 400 | N35G/E104H/A168P/T236E | t60c/c573g |
| 401 | S24Q/N35G/Q44K/T80H/E104H/A168P | t60c/c573g |
| 402 | N35G/E104H/S128D/A168P | t60c/c573g |
| 403 | N35G/N66D/S78D/E104H/A168P/S253D | t60c/c573g |
| 404 | N35G/E104H/R130Y/A168P | t60c/c573g |
| 405 | N35G/E104H/A168P/K310I | t60c/c573g |
| 406 | N35G/E104H/R145E/A168P | t60c/c573g |
| 407 | N35G/N66D/E104H/S164E/A168P/S282D | t60c/c573g |
| 408 | N35G/E104H/K141P/A168P | t60c/c573g |
| 409 | N35G/E104H/A168P/Q184R | t60c/c573g |
| 410 | N35G/E104H/A168P/S231T | t60c/c573g |
| 411 | N35G/N66V/E104H/A168P | t60c/c573g |
| 412 | N35G/E104H/A142L/A168P | t60c/c573g |
| 413 | N35G/E104H/R145H/A168P | t60c/c573g |
| 414 | N35G/E104H/A168P/K218L | t60c/c573g |
| 415 | N35G/E104H/K141T/A168P | t60c/c573g |
| 416 | N35G/E104H/A168P/P233F | t60c/c573g |
| 417 | N35G/T40S/E104H/A168P/P327M | t60c/c573g |
| 418 | N35G/T54M/E104H/A168P | t60c/c573g |
| 419 | S24T/N35G/E104H/S164E/A168P | t60c/c573g |
| 420 | N35G/P45T/E104H/A168P | t60c/c573g |
| 421 | N35G/N66D/E104H/S164E/A168P/S231T/S253T | t60c/c573g |
| 422 | N35G/G69H/E104H/A168P | t60c/c573g |
| 423 | N35G/E104H/S128Y/A168P | t60c/c573g |
| 424 | N35G/T49Q/E104H/A168P | t60c/c573g |
| 425 | N35G/T49A/E104H/A168P/Q184H | t60c/c573g |
| 426 | N35G/E104H/A168P/G203Y | t60c/c573g |
| 427 | N35G/Q44K/N66V/E104H/A168P | t60c/c573g |
| 428 | N35G/E104H/A137M/A168P | t60c/c573g |
| 429 | N35G/E104H/A168P/P327C | t60c/c573g |
| 430 | N35G/E104H/A168P/T236R | t60c/c573g |
| 431 | N35G/I51A/E104H/A168P | t60c/c573g |
| 432 | N35G/S67H/E104H/A168P | t60c/c573g |
| 433 | N35G/E104H/A168P/A326C | t60c/c573g |
| 434 | N35G/T49A/E104H/S128N/A168P | t60c/c573g |
| 435 | N35G/T49R/E104H/A168P/K218L/N317Q | t60c/c573g |
| 436 | N35G/E104H/A168P/P266S/G267V | t60c/c573g |
| 437 | N35G/E104H/A168P/V237I/P303T | t60c/c573g |
| 438 | N35G/T49E/E104H/A168P | t60c/c573g |
| 439 | N35G/P45R/E104H/A168P/T320A | t60c/c573g |
| 440 | N35G/N66L/E104H/A168P | t60c/c573g |
| 441 | N35G/P45R/E104H/A168P/K218L/N317Q | t60c/c573g |
| 442 | N35G/E104H/R145V/A168P | t60c/c573g |
| 443 | N35G/N66D/E104H/A168P/R290K | t60c/c573g |
| 444 | N35G/T80L/E104H/A168P | t60c/c573g |
| 445 | N35G/A55G/E104H/A168P | t60c/c573g |
| 446 | N35G/E104H/A168P/S330A | t60c/c573g |
| 447 | N35G/E104H/K141N/A168P/P266S | t60c/c573g |
| 448 | N35G/E104H/A142S/A168P | t60c/c573g |
| 449 | N35G/E104H/A168P/Q184G | t60c/c573g |
| 450 | N35G/E104H/N118E/A168P | t60c/c573g |
| 451 | N35G/E104H/A168P/A212M | t60c/c573g |
| 452 | N35G/E104H/A168P/G267D | t60c/c573g |
| 453 | N35G/K93N/E104H/R130Y/A168P | t60c/c573g |
| 454 | N35G/P45R/T49Y/E104H/A168P/N317D | t60c/c573g |
| 455 | N35G/E104H/A168P/S329Q | t60c/c573g |
| 456 | N35G/E104H/A168P/V230Q | t60c/c573g |
| 457 | N35G/P45K/E104H/A168P/A219R | t60c/c573g |
| 458 | N35G/E104H/A142G/A168P | t60c/c573g |
| 459 | N35G/E104H/A168P/S205T | t60c/c573g |
| 460 | N35G/S78D/E104H/S164E/A168P | t60c/c573g |

TABLE 2-continued

GH61 Variants with Improved Activity Compared to Variant 1

| Var. No. | Amino Acid Changes | Silent Nucleotide Changes |
|---|---|---|
| 461 | N35G/E104H/R130E/A168P | t60c/c573g |
| 462 | N35G/E104H/A168P/Q184H | t60c/c573g |
| 463 | N35G/E104H/A116P/A168P | t60c/c573g |
| 464 | N35G/E104H/A142D/A168P | t60c/c573g |
| 465 | V28H/N35G/N46E/Q58H/E104H/A168P | t60c/c573g |
| 466 | N35G/E104H/A168P/A280T | t60c/c573g |
| 467 | R34E/N35G/E104H/A168P/A280T | t60c/c573g |
| 468 | N35G/E104H/A168P/E336L | t60c/c573g |
| 469 | N35G/T49D/E104H/A168P | t60c/c573g |
| 470 | N35G/E104H/A168P/A219T | t60c/c573g |
| 471 | N35G/E104H/A142W/A168P | t60c/c573g |
| 472 | N35G/E104H/A168P/P303T/G305D | t60c/c573g |
| 473 | N35G/Q44V/E104H/A168P | t60c/c573g |
| 474 | N35G/E104H/A168P/N187D | t60c/c573g |
| 475 | N35G/E104H/G136H/A168P | t60c/c573g |
| 476 | S24Q/N35G/Q44K/E104H/A168P/P303T/S332D | t60c/c573g |
| 477 | N35G/E104H/A168P/Q184N | t60c/c573g |
| 478 | N35G/E104H/A168P/S332L | t60c/c573g |
| 479 | S24T/N35G/N66D/S78D/E104H/A168P/S205T/S253T | t60c/c573g |
| 480 | N35G/E104H/A168P/P327A | t60c/c573g |
| 481 | N35G/T40A/T49Q/S78C/E104H/A168P | t60c/c573g |
| 482 | N35G/T40L/E104H/A142G/A168P | t60c/c573g |
| 483 | N35G/T49Y/E104H/A168P/N317R | t60c/c573g |
| 484 | R34E/N35G/K93T/E104H/R130E/R145T/A168P/R199E/K218T/A280D | t60c/c573g |

Positions that were changed in variants with improved GH61 activity listed in Table 2 include 24, 28, 32, 34, 35, 40, 44, 45, 46, 49, 51, 54, 55, 56, 58, 64, 66, 67, 69, 70, 71, 78, 80, 82, 83, 88, 93, 95, 101, 104, 116, 118, 128, 130, 136, 137, 141, 142, 144, 145, 150, 155, 161, 164, 168, 184, 187, 199, 203, 205, 212, 218, 219, 230, 231, 232, 233, 234, 236, 237, 245, 253, 263, 266, 267, 268, 269, 270, 271, 280, 281, 282, 290, 295, 297, 303, 305, 310, 317, 320, 324, 326, 327, 329, 330, 332, 333, 336, 337, and 339, wherein the amino acid positions are numbered with reference to SEQ ID NO:2.

Residues that were changed in variants with improved GH61 activity listed in Table 2 include S24, V28, Y32, R34, N35, T40, Q44, P45, N46, T49, I51, T54, A55, A56, Q58, E64, N66, S67, G69, T70, P71, S78, T80, G82, G83, V88, K93, N95, E101, E104, A116, N118, S128, R130, G136, A137, K141, A142, G144, R145, A150, G155, Q161, S164, A168, Q184, N187, R199, G203, S205, A212, K218, A219, V230, S231, S232, P233, D234, T236, V237, G245, S253, A263, P266, G267, G268, G269, G270, A271, A280, T281, S282, R290, S295, A297, P303, G305, K310, N317, T320, V324, A326, P327, S329, S330, S332, V333, E336, W337, and S339, wherein the amino acid positions are numbered with reference to SEQ ID NO:2.

Substitutions occurring in variants with improved GH61 activity listed in Table 2 include S24Q, V28H, Y32S, R34E, N35G, T40A/G/L/S, Q44K, P45D/E/K/R/S, N46E/R, T49A/Q/R/Y, I51A, T54G/M/S/W, A55G, A56S, Q58H/P, E64L/S, N66A/D/G/L/M/Q/R/V, S67G/H/T, G69T, T70A, P71A, S78C/D, T80H/L/V, G82A/S, G83R, V88I, K93N/T, N95E, E101T, E104H, A116Q/S, N118E/S, S128K/L/N, R130E/G/H/K/Y, G136H, A137M/S, K141A/N/P/R, A142D/G/L, G144S, R145H/L/N/Q/T, A150Y, G155N, Q161E/R, S164E, A168P, Q184E/H/L/N/R, N187D, R199E, G203E/V/Y, S205T, A212M, K218L/T, A219R/T, V230I/Q, S231A/H/K/I, S232E, P233F/T, D234E/M/N, T236E, V237I, G245A, S253D/T, A263V, P266S, G267D/V, G268A, G269A, G270A, A271T, A280D/T, T281A, S282D, R290K, S295D/L/T, A297T, P303T, G305D, K310I, N317D/H/I/M/Q/R, T320A, V324M, A326C/Q/V, P327F/K/L/M, S329H/I/Q/T/Y, S330A/H/I/T/V, S332C/F/R, V333Q, E336L/R/S, W337R, and S339W.

In some embodiments, the changed residues and substitutions of the GH61 variants of this invention may be combined in a manner that produces an effect that is cumulative or synergistic. Cumulative effects occur when adding an additional mutation increases the effect beyond those of the mutations already present. Synergistic effects occur when having two more mutations in a variant produces an effect than is greater than the product of the mutations when incorporated by themselves. This invention includes without limitation any and all combinations of any two, three, four, five, six, seven, eight, nine, ten, or more than ten of the mutations listed in Table 1, Table 2, or both Tables.

Useful combinations of mutated positions include but are not limited to N35/T40/E104/A168/P327; N35/P45/E104/A168/N317; N35/E104/A168/N317; N35/E104/A168/N317/S329; N35/E104/A137/A168/S232; N35/E104/A168/N317/T320; N35/E104/A168/D234; N35/T40/E104/A142/A168; N35/E104/R145/A168; N35/T40/S78/V88/E104/S128K/A168/D234; N35/E104/A168/S330; N35/E104/A168/G203/P266; N35/E104/A168/D234; N35/E104/A168/S330; N35/E104/A168/W337; R34/N35/E104/R145/A168; Y32/N35/E64/E104/A168; V28/N35/P45/E104/A168; N35/E104/G144/A168/V333; N35/N66/E104/A168; N35/E104/A168/P327; N35/E104/A168/G203; N35/E104/A168/S339; N35/P45/N46/E104/A150/A168; N35/E104/A168/S231; N35/T40/E104/A168/D234/P327; N35/E104/A168/S231; N35/E104/A168/N317; N35/E104/A168/S330; N35/E104/A168/S329; N35/E104/A168/P327; N35/P45/E104/A168; N35/E104/A116/A168; N35/T40/E104/A168/V230/P327; and N35/E104/A168/S332.

Useful combinations of mutated residues further include but are not limited to N35/E104/A168/G203; N35/E104/R145/A168/S329; N35/T40/T49/E104/A168/D234/P327; N35/A56/E104/A168; N35/E104/Q161/A168; N35/E104/A168/S332; N35/P45/T49/E104/A168/N317/T320; N35/E104/A168/V237; N35/E104/A168/E336; N35/E104/A168/P233; N35/E104/R130/A168; N35/E104/A168/P327; N35/E104/A168/N317; N35/Q44/E104/A168; N35/E104/A168/A326; N35/E104/A168/N317; N35/T40/E104/S128/A168; N35/T80/E104/A168/P303; N35/E104/A116/A168; N35/E104/A168/S231/S295; N35/T40/E101/E104/A168/P327; N35/P45/E104/A168/A219/S232; N35/N46/E104/A168; N35/E104/A168/A326; N35/E104/A168/G203/T281; N35/

E104/A168/E336; N35/T40/E104/S128/A142/A168; N35/E104/N118/A168; N35/E104/G155/A168; S24/N35/E104/A168/V237/P303; N35/E104/Q161/A168; N35/Q44/S67/E104/A168; V28/N35/E104/A168; N35/E104/A168/Q184; N35/T54/E104/A168; N35/N66/E104/A168; N35/E64/E104/A168; N35/E104/S164/A168/A271; N35/N66/E104/A168; N35/G83/E104/A168; N35/E104/K141/A168; and N35/E104/A168/N317/T320.

Useful combinations of mutated residues include but are not limited to N35/E104/R130/A168; N35/E104/R145/A168; N35/T70/E104/A168; N35/E104/R130/A168; N35/E104/A168/Q184; N35/E104/A168/S329; N35/T49/E104/A168; Y32/N35/E104/A168; N35/E104/A168/S330; N35/Q58/E104/A168; Y32/N35/P71/E104/A168; N35/E104/A168/S330; N35/T80/E104/A168; N35/G82/E104/A168; N35/E104/A168/S295; N35/N66/E104/A168; N35/T54/E104/A168; N35/P45/E104/A168; N35/E104/S128/A168; N35/N66/N95/E104/S164/A168; /G267; N35/T54/E104/A168; N35/P45/E104/K141/A168; N35/E104/A168/S332; N35/E104/A168/A297; N35/E104/K141/R145/A168; N35/Q44/E104/A168/S231; N35/T40/T49/S78/E104/A142; /A168; N35/E104/S164/A168/S295; N35/E104/A168/N317; N35/P45/E104/A168; N35/G82/E104/A168; N35/N46/E104/A168/G203/A263; N35/Q58/E104/A168; N35/G69/E104/A168; N35/S67/E104/A168; N35/E104/A168/R199; N35/E104/A168/G203/G268/G269/G270; N35/E104/A168/V324; N35/E104/A168/P266; N35/E104/A168/G245; N35/N66/E104/A168; and S24/N35/Q44/T80/E104/A168.

Useful combinations of mutated residues further include but are not limited to N35/E104/A168/T236; N35/E104/A168/K310; N35/E104/R130/A168; N35/N66/S78/E104/A168/S253; N35/N66/E104/S164/A168/S282; N35/E104/A142/A168; N35/E104/R145/A168; N35/E104/A168/S231; N35/E104/A168/Q184; N35/E104/A168/K218; N35/E104/A168/P233; N35/T49/E104/A168/Q184; N35/T40/E104/A168/P327; N35/T54/E104/A168; N35/N66/E104/S164/A168/S231/S253; N35/E104/A168/G203; N35/T49/E104/A168; N35/E104/A168/P266/G267; N35/Q44/N66/E104/A168; N35/S67/E104/A168; N35/E104/A137/A168; N35/T49/E104/S128/A168; N35/T49/E104/A168/K218/N317; N35/I51/E104/A168; N35/E104/A168/A326; N35/P45/E104/A168/T320; N35/N66/E104/A168; N35/E104/A168/V237/P303; N35/P45/E104/A168/K218/N317; N35/T80/E104/A168; N35/A55/E104/A168; N35/E104/K141/A168/P266; N35/E104/A168/S330; N35/N66/E104/A168/R290; N35/E104/N118/A168; N35/E104/A168/A212; N35/K93/E104/R130/A168; N35/E104/A168/G267; N35/P45/T49/E104/A168/N317; N35/E104/A168/V230; N35/E104/A168/S329; N35/P45/E104/A168/A219; N35/S78/E104/S164/A168; N35/E104/A168/S205; N35/E104/A168/Q184; V28/N35/N46/Q58/E104/A168; N35/E104/A142/A168; N35/E104/A168/E336; N35/E104/A168/A280; N35/E104/A168/A219; N35/E104/A168/P303/G305; R34/N35/E104/A168/A280; N35/E104/A168/N187; N35/E104/G136/A168; N35/E104/A168/Q184; N35/T49/E104/A168/N317; N35/T40/T49/S78/E104/A168; R34/N35/K93/E104/R130/R145/A168/R199/K218/A280; N35/T40/E104/A142/A168; and N35/N66/E104/A168.

Useful combinations of mutations further include but are not limited to N35G/T40A/E104H/A168P/P327M; N35G/P45D/E104H/A168P/N317R; N35G/E104H/A168P/N317R; N35G/E104H/A168P/N317D/S329Y; N35G/E104H/A137S/A168P/S232E; N35G/E104H/A168P/N317R/T320A; N35G/E104H/A168P/D234E; N35G/T40S/E104H/A142G/A168P; N35G/E104H/R145L/A168P; N35G/T40S/S78C/V88I/E104H/S128K/A168P/D234M; N35G/E104H/A168P/S330V; N35G/E104H/A168P/G203E/P266S; N35G/E104H/A168P/D234N; N35G/E104H/A168P/S330H; N35G/E104H/A168P/W337R; R34E/N35G/E104H/R145T/A168P; Y32S/N35G/E64S/E104H/A168P; V28H/N35G/P45K/E104H/A168P; N35G/E104H/G144S/A168P/V333Q; N35G/N66Q/E104H/A168P; N35G/E104H/A168P/P327K; N35G/E104H/A168P/G203E; N35G/E104H/A168P/S339W; N35G/P45K/N46E/E104H/A150Y/A168P; N35G/E104H/A168P/S231K; N35G/T40A/E104H/A168P/D234E/P327M; N35G/E104H/A168P/S231H; N35G/E104H/A168P/N317M; N35G/E104H/A168P/S330Y; N35G/E104H/A168P/S329I; N35G/E104H/A168P/P327F; N35G/P45D/E104H/A168P; N35G/E104H/A116S/A168P; N35G/T40A/E104H/A168P/V230I/P327M; and N35G/E104H/A168P/S332R.

Useful combinations of mutations further include but are not limited to N35G/E104H/A168P/G203V; N35G/E104H/R145N/A168P/S329H; N35G/T40S/T49R/E104H/A168P/D234E; /P327M; N35G/A56S/E104H/A168P; N35G/E104H/Q161R/A168P; N35G/E104H/A168P/S332F; N35G/P45R/T49A/E104H/A168P/N317R/T320A; N35G/E104H/A168P/V237I; N35G/E104H/A168P/E336S; N35G/E104H/A168P/P233T; N35G/E104H/R130H/A168P; N35G/E104H/A168P/P327L; N35G/E104H/A168P/N317I; N35G/Q44K/E104H/A168P; N35G/E104H/A168P/A326V; N35G/E104H/A168P/N317H; N35G/T40L/E104H/S128K/A168P; N35G/T80V/E104H/A168P/P303T; N35G/E104H/A116Q/A168P; N35G/E104H/A168P/S231A/S295L; N35G/T40S/E101T/E104H/A168P/P327M; N35G/P45K/E104H/A168P/A219R/S232E; N35G/N46R/E104H/A168P; N35G/E104H/A168P/A326Q; N35G/E104H/A168P/G203E/T281A; N35G/E104H/A168P/E336R; N35G/T40S/E104H/S128K/A142G/A168P; N35G/E104H/N118S/A168P; N35G/E104H/G155N/A168P; S24Q/N35G/E104H/A168P/V237I/P303T; N35G/E104H/Q161E/A168P; N35G/Q44K/S67T/E104H/A168P; V28H/N35G/E104H/A168P; N35G/E104H/A168P/Q184L; N35G/T54G/E104H/A168P; N35G/N66M/E104H/A168P; N35G/E64L/E104H/A168P; N35G/E104H/S164E/A168P/A271T; N35G/N66A/E104H/A168P; N35G/G83R/E104H/A168P; N35G/E104H/K141A/A168P; and N35G/E104H/A168P/N317Q/T320A.

Useful combinations of mutations further include but are not limited to N35G/E104H/R130G/A168P; N35G/E104H/R145Q/A168P; N35G/T70A/E104H/A168P; N35G/E104H/R130G/A168P; N35G/E104H/A168P/Q184E; N35G/E104H/A168P/S329T; N35G/T49A/E104H/A168P; Y32S/N35G/E104H/A168P; N35G/E104H/A168P/S330I; N35G/Q58H/E104H/A168P; Y32S/N35G/P71A/E104H/A168P; N35G/E104H/A168P/S330T; N35G/T80V/E104H/A168P; N35G/G82A/E104H/A168P; N35G/E104H/A168P/S295T; N35G/N66G/E104H/A168P; N35G/T54S/E104H/A168P; N35G/P45S/E104H/A168P; N35G/E104H/S128L/A168P; N35G/N66D/N95E/E104H/S164E/A168P/G267D; N35G/T54W/E104H/A168P; N35G/P45E/E104H/K141R/A168P; N35G/E104H/A168P/S332C; N35G/E104H/A168P/A297T; N35G/E104H/K141P/R145Q/A168P; N35G/Q44K/E104H/A168P/S231T; N35G/T40G/T49R/S78C/E104H/A142G; /A168P; N35G/E104H/S164E/A168P/S295D; N35G/E104H/A168P/N317Q; N35G/P45R/E104H/A168P; N35G/G82S/E104H/A168P; N35G/N46R/E104H/A168P/G203E/A263V; N35G/Q58P/E104H/A168P; N35G/G69T/E104H/A168P; N35G/S67G/E104H/A168P; N35G/E104H/A168P/R199E; N35G/E104H/A168P/G203E/G268A/G269A/G270M; N35G/E104H/A168P/V324M; N35G/E104H/A168P/P266S; N35G/E104H/A168P/G245A; N35G/N66R/E104H/A168P; and S24Q/N35G/Q44K/T80H/E104H/A168P.

Useful combinations of mutations further include but are not limited to N35G/E104H/A168P/T236E; N35G/E104H/A168P/K310I; N35G/E104H/R130Y/A168P; N35G/N66D/S78D/E104H/A168P/S253D; N35G/N66D/E104H/S164E/A168P/S282D; N35G/E104H/A142L/A168P; N35G/E104H/R145H/A168P; N35G/E104H/A168P/S231T; N35G/E104H/A168P/Q184R; N35G/E104H/A168P/K218L; N35G/E104H/A168P/P233F; N35G/T49A/E104H/A168P/Q184H; N35G/T40S/E104H/A168P/P327M; N35G/T54M/E104H/A168P; N35G/N66D/E104H/S164E/A168P/S231T/S253T; N35G/E104H/A168P/G203Y; N35G/T49Q/E104H/A168P; N35G/E104H/A168P/P266S/G267V; N35G/Q44K/N66V/E104H/A168P; N35G/S67H/E104H/A168P; N35G/E104H/A137M/A168P; N35G/T49A/E104H/S128N/A168P; N35G/T49R/E104H/A168P/K218L/N317Q; N35G/I51A/E104H/A168P; N35G/E104H/A168P/A326C; N35G/P45R/E104H/A168P/T320A; N35G/N66L/E104H/A168P; N35G/E104H/A168P/V237I/P303T; N35G/P45R/E104H/A168P/K218L/N317Q; N35G/T80L/E104H/A168P; N35G/A55G/E104H/A168P; N35G/E104H/K141N/A168P/P266S; N35G/E104H/A168P/S330A; N35G/N66D/E104H/A168P/R290K; N35G/E104H/N118E/A168P; N35G/E104H/A168P/A212M; N35G/K93N/E104H/R130Y/A168P; N35G/E104H/A168P/G267D; N35G/P45R/T49Y/E104H/A168P/N317D; N35G/E104H/A168P/V230Q; N35G/E104H/A168P/S329Q; N35G/P45K/E104H/A168P/A219R; N35G/S78D/E104H/S164E/A168P; N35G/E104H/A168P/S205T; N35G/E104H/A168P/Q184H; V28H/N35G/N46E/Q58H/E104H/A168P; N35G/E104H/A142D/A168P; N35G/E104H/A168P/E336L; N35G/E104H/A168P/A280T; N35G/E104H/A168P/A219T; N35G/E104H/A168P/P303T/G305D; R34E/N35G/E104H/A168P/A280T; N35G/E104H/A168P/N187D; N35G/E104H/G136H/A168P; N35G/E104H/A168P/Q184N; N35G/T49Y/E104H/A168P/N317R; N35G/T40A/T49Q/S78C/E104H/A168P; R34E/N35G/K93T/E104H/R130E/R145T/A168P/R199E/K218T/A280D; N35G/T40L/E104H/A142G/A168P; and N35G/N66G/E104H/A168P.

Production of GH61 Variant Proteins

In some embodiments, the GH61 variant proteins of this invention are produced by recombinant expression in a host cell. Any suitable method for recombinant expression in any suitable host cell finds use in the present invention. In some embodiments, a nucleotide sequence encoding the protein is obtained, and introduced into a suitable host cell by way of a suitable transfer vector or expression vector. In some embodiments, the nucleotide sequence is operably linked to a promoter that promotes expression in the host cell. The promoter sequence is often selected to optimize in a cell that is not *M. thermophila*, in which case the promoter is typically heterologous to the GH61 variant protein encoding sequence. In some embodiments, the host cell is a eukaryotic cell and the GH61 variant protein comprises a heterologous signal peptide at the N-terminus.

Optionally, in some embodiments, the encoding sequence is codon-optimized for the host cell (e.g., a particular species of yeast cell). Any suitable method for obtaining codon-optimized sequences find use in the present invention (e.g., GCG CodonPreference, Genetics Computer Group Wisconsin Package; Codon W, John Peden, University of Nottingham; and McInerney, Bioinform., 14:372-73 [1998]).

General reference texts relating to gene expression include but are not limited to the most recent editions of *Protocols in Molecular Biology* (Ausubel et al. eds.); *Molecular Cloning: A Laboratory Manual* (Sambrook et al. eds.); *Advances In Fungal Biotechnology For Industry, Agriculture, And Medicine* (Tkacz and Lange, 2004); and *Fungi: Biology and Applications* (K. Kavanagh ed., 2005).

In some embodiments, culture broth from GH61 protein-producing cells is collected and combined directly with cellulase enzymes in a saccharification reaction. In some alternative embodiments, the broth is fractionated to any extent desired to provide partially or substantially purified GH61 protein, following the activity during the separation process using a GH61 activity assay, using standard protein separation techniques, and following GH61 activity during fractionation with a suitable GH61 activity assay. Such protocols may combine one or more of the following methods (but are not limited to these particular methods): salt precipitation, solid phase binding, affinity chromatography, ion exchange chromatography, molecular size separation, and/or filtration. Protein separation techniques are generally described in *Protein Purification: Principles, High Resolution Methods, and Applications*, (J. C. Janson, ed., 2011); *High Throughput Protein Expression and Purification: Methods and Protocols* (S. A. Doyle ed., 2009).

The present invention provides GH61 variant protein having an amino acid sequence that is at least about 60%, at least about 65%, at least about 70%, about 75%, about 80%, about 85%, about 90%, about 91%, about 92%, about 93%, about 94%, about 95%, about 96%, about 97%, about 98%, or about 99% identical to SEQ ID NO:2 or a fragment of SEQ ID NO:2 having GH61 activity. In some embodiments, the amino acid sequence of the variant proteins have one or more amino acid substitutions with respect to SEQ ID NO:2 or said fragment. In some embodiments, the substitution(s) that are present in the amino acid sequence result in the variant protein having increased GH61 activity in a saccharification reaction by certain cellulase enzymes under specified conditions, compared with a reference protein comprising SEQ ID NO:2 or said fragment, without any of the substitutions.

In some embodiments, GH61 variant proteins of this invention comprise one or more of SEQ ID NOS:5, 6, 8, 9, 11, and/or 12, or biologically-active fragments of these sequences having GH61 activity. These correspond to Variants 1 (SEQ ID NOS:5 and 6), Variant 5 (SEQ ID NOS: 8 and 9), and Variant 9 (SEQ ID NOS: 11 and 12). In some embodiments, the variants have more than about 2-fold, 3-fold, or more than 3-fold GH61 activity compared with wild-type GH61a (i.e., SEQ ID NO:2). The combined effect of multiple rounds of optimization yield GH61 variant proteins that have about 3-fold, about 5-fold, about 8-fold, or about 10-fold activity compared with the original parental sequence (SEQ ID NO:2).

Also provided are polynucleotides encoding such GH61 variant proteins, expression vectors comprising such polynucleotides, and host cells that have been transfected with such vectors so as to express the GH61 variant proteins that are encoded.

Fragments and Variants

GH61 variant proteins of this invention may comprise one or more substitutions, deletions, or additions in the sequence in addition to the substitutions highlighted above. By way of illustration, the GH61 protein may be longer or shorter by at least about 5, 10, 20, 40, 75, 100, 125, 150, or 200 amino acids; or by about 1%, 2%, 3%, 4%, 5%, 6%, 7%, 8%, 9%, 10%, 15%, 20%, 15%, 30%, 35%, 40%, 45%, 50%, 60%, 70%, or 80% of the total number of amino acids in the polypeptide, compared with SEQ ID NO:2. The variant or any of these fragments may also be part of a fusion protein in which a portion having GH61 activity is joined to one or more other sequences. Providing the protein retains a degree of GH61 activity or other commercial applicability, the variations may comprise any combination of amino acid substitutions at any position that is not specifically indicated otherwise. Depending on the circumstances, a conservative amino acid substitution may be preferred over other types of substitutions.

Where an amino acid substitution is a "conservative" substitution, the substituted amino acid that shares one or more chemical property with the amino acid it is replacing. Shared properties include the following: Basic amino acids: arginine (R), lysine (K), histidine (H); acidic amino acids: glutamic acid (E) and aspartic acid (D); uncharged polar amino acids: glutamine (Q) and asparagine (N); hydrophobic amino acids: leucine (L), isoleucine (I), valine (V); aromatic amino acids: phenylalanine (F), tryptophan (W), and tyrosine (Y); sulphur-containing amino acids: cysteine (C), methionine (M); small amino acids: glycine (G), alanine (A), serine (S), threonine (T), proline (P), cysteine (C), and methionine (M).

Obtaining Functional Fragments and Variants

Functional fragments of GH61 protein variants of this invention can be identified by standard methodology for mapping function within a polypeptide. In some embodiments, recombinant protein is expressed that has effectively been trimmed at the N- or C-terminus, and then tested in a GH61 activity assay. Trimming can continue until activity is lost, at which point the minimum functional unit of the protein would be identified. Fragments containing any portion of the protein down to the identified size would typically be functional, as would be fusion constructs containing at least the functional core of the protein.

To generate further variants that incorporate one or more amino acid changes in a GH61 encoding sequence, the skilled artisan can change particular nucleotides, and then retest the expressed protein for GH61 activity.

An effective way to generate a large collection of functional variants is to use a random mutation strategy. The standard texts *Protocols in Molecular Biology* (Ausubel et al. eds.) and *Molecular Cloning: A Laboratory Manual* (Sambrook et al. eds.) describe techniques employing chemical mutagenesis, cassette mutagenesis, degenerate oligonucleotides, mutually priming oligonucleotides, linker-scanning mutagenesis, alanine-scanning mutagenesis, and error-prone PCR. Other efficient methods include the *E. coli* mutator strains of Stratagene (See e.g., Greener et al., Methods Mol. Biol. 57:375 [1996]) and the DNA shuffling technique of Maxygen (See e.g., Patten et al., Curr. Opin. Biotechnol., 8:724 [1997]; Harayama, Tr. Biotechnol., 16:76 [1998]; U.S. Pat. Nos. 5,605,793 and 6,132,970). To increase variation, a technology can be used that generates more abrupt changes, such as DNA shuffling techniques.

Mutagenesis may be performed in accordance with any of the techniques known in the art, including random and site-specific mutagenesis. Directed evolution can be performed with any of the techniques known in the art to screen for production of variants including shuffling. Mutagenesis and directed evolution methods are well known in the art (See e.g., U.S. Pat. Nos. 5,605,793, 5,830,721, 6,132,970, 6,420, 175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 603, 344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related US and non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

There are commercially available services and kits available to the skilled reader to use in obtaining variants of the claimed proteins. By way of illustration, systems specifically designed for mutagenesis projects include the following: the GeneTailor™ Site-Directed Mutagenesis System sold by InVitrogen™ Life Technologies; the BD Diversify™ PCR Random Mutagenesis Kit™, sold by BD Biosciences/Clontech; the Template Generation System™, sold by MJ Research Inc., the XL1-Red™ mutator strain of *E. coli*, sold by Stratagene; and the GeneMorph® Random Mutagenesis Kit™, also sold by Stratagene. By employing any of these systems in conjunction with a suitable GH61 activity assay, variants can be generated and tested in a high throughput manner.

Alternatively or in addition, the user may conduct further evolution of the encoded protein (See e.g., U.S. Pat. No. 7,981,614; US Pat. Appln. Publ. No. 2011/0034342; U.S. Pat. Nos. 7,795,030; 7,647,184; 6,939,689; and 6,773,900).

After each iteration of mutagenesis, the user can test and select the desired clones retaining GH61 activity. Optionally, the selected clones can be subject to further rounds of mutagenesis, until the desired degree of variation from the original sequence has been achieved.

Cellulase Enzymes and Compositions

The GH61 proteins of this invention are useful for increasing the yield of fermentable sugars in a saccharification reaction with one or more cellulase enzymes. The cellulase enzymes can be produced in the same cell as the GH61 protein or in a different cell. In either case, the cellulase enzymes can be expressed from a recombinant encoding region or from a constitutive gene. The cellulase enzymes can be provided in the form of a culture broth (with or without the microorganism producing the enzyme(s)) or supernatant, or purified to any extent desired.

The terms "cellulase" and "cellulase enzyme" broadly refer to enzymes that catalyze the hydrolysis of the beta-1,4-glycosidic bonds joining individual glucose units in a cellulose containing substrate. Examples of cellulase enzymes suitable for use with the GH61 proteins of this invention are described in more detail later in this section.

Endoglucanases (EGs), comprise a group of cellulase enzymes classified as E.C. 3.2.1.4. These enzymes catalyze the hydrolysis of internal beta-1,4 glycosidic bonds of cellulose. In some embodiments, the present invention comprises an endogenous *M. thermophila* endoglucanase such as *M. thermophila* EG2 (See, WO 2007/109441) or a variant thereof. In some additional embodiments, the EG is from *S. avermitilis*, having a sequence set forth in GenBank accession NP_821730, or a variant thereof (See e.g., US Pat. Appln. Publ. No. 2010/0267089 A1). In some additional embodiments, the EG is a *Thermoascus aurantiacus* EG or variant thereof. In some further embodiments, the EG is an endogenous EG from a bacteria, a yeast, or a filamentous fungus other than *M. thermophila*. Indeed, it is contemplated that any suitable EG will find use in combination with the GH61 proteins provided herein. It is not intended that the present invention be limited to any specific EG.

Beta-glucosidases (BGL), comprise a group of cellulase enzymes classified as E.C. 3.2.1.21. These enzymes hydrolyze cellobiose to glucose. In some embodiments, the BGL is an endogenous *M. thermophila* enzyme, or a variant thereof (See e.g., US Pat. Appln. Publ. No. 2011/0129881 A1; and US Pat. Appln. Publ. No. 2011/0124058 A1). In some alternative embodiments, the BGL is from *Azospirillum irakense* (CelA), or a variant thereof (See e.g., US Pat. Appln. Publ. No. 2011/0114744 A1; and PCT/US2010/038902). Indeed, it is contemplated that any suitable BGL will find use in combination with the GH61 proteins provided herein. It is not intended that the present invention be limited to any specific BGL.

Cellobiohydrolases comprise a group of cellulase enzymes classified as E.C. 3.2.1.91. Type 1 cellobiohydrolase (CBH1) hydrolyzes cellobiose processively from the reducing end of cellulose chains. Type 2 cellobiohydrolase (CBH2) hydrolyzes cellobiose processively from the nonreducing end of cellulose chains. In some embodiments, the CBH1 and/or CBH2 enzymes used in the present invention are endogenous to *M. thermophila*, while in some other embodiments, the CBH1 and/or CBH2 enzymes used in the present invention are obtained from bacteria, yeast, and/or a filamentous fungus other than *M. thermophila*. Indeed, it is contemplated that any suitable CBHs will find use in combination with the GH61 proteins provided herein. It is not intended that the present invention be limited to any specific CBHs. The invention provides compositions comprising a GH61 variant protein in combination with at least one, at least two, at least three, or more than three cellulases selected from EG, BGL, CBH1, CBH2, xylosidase, and/or xylanase. In some embodiments, enzymes are purified or partly purified before combining them, so that the combined mass of the GH61, EG, BGL, CBH1 and CBH2 is at least about 50% or at least about 70% of the total cell-free protein in compositions.

In addition to one or more cellulase enzymes such as those listed above, in some embodiments, GH61 variant enzymes are combined with other enzymes to produce mixtures with industrial applicability. Such combinations are useful, for example, in rendering a cellulose-containing source into an intermediate that is more amenable to hydrolysis by the cellulase enzymes in the mixture. For example, in some embodiments, enzymes are selected to digest or hydrolyze other components of a particular cellulosic biomass, such as hemicellulose, arabinogalactan, pectin, rhamnogalacturonan and/or lignin.

In some embodiments, the compositions comprise enzymes selected from endoxylanases (EC 3.2.1.8); β-xylosidases (EC 3.2.1.37); alpha-L-arabinofuranosidases (EC 3.2.1.55); alpha-glucuronidases (EC 3.2.1.139); acetylxylanesterases (EC 3.1.1.72); feruloyl esterases (EC 3.1.1.73); coumaroyl esterases (EC 3.1.1.73); alpha-galactosidases (EC 3.2.1.22); beta-galactosidases (EC 3.2.1.23); beta-mannanases (EC 3.2.1.78); beta-mannosidases (EC 3.2.1.25); endo-polygalacturonases (EC 3.2.1.15); pectin methyl esterases (EC 3.1.1.11); endo-galactanases (EC 3.2.1.89); pectin acetyl esterases (EC 3.1.1.6); endo-pectin lyases (EC 4.2.2.10); pectate lyases (EC 4.2.2.2); alpha rhamnosidases (EC 3.2.1.40); exo-poly-alpha-galacturonosidase (EC 3.2.1.82); 1,4-alpha-galacturonidase (EC 3.2.1.67); exopolygalacturonate lyases (EC 4.2.2.9); rhamnogalacturonan endolyases EC (4.2.2.B3); rhamnogalacturonan acetylesterases (EC 3.2.1.B11); rhamnogalacturonan galacturonohydrolases (EC 3.2.1.B11); endo-arabinanases (EC 3.2.1.99); laccases (EC 1.10.3.2); manganese-dependent peroxidases (EC 1.10.3.2); amylases (EC 3.2.1.1), glucoamylases (EC 3.2.1.3), proteases, lipases, and lignin peroxidases (EC 1.11.1.14). Any combination of one, two, three, four, five, or more than five enzymes find use in the compositions of the present invention.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, the GH61 variant polypeptides of the present invention are present in mixtures comprising enzymes other than cellulases that degrade cellulose, hemicellulose, pectin, and/or lignocellulose.

In some embodiments, the present invention provides at least one GH61 variant and at least one endoxylanase. Endoxylanases (EC 3.2.1.8) catalyze the endo hydrolysis of 1,4-beta-D-xylosidic linkages in xylans. This enzyme may also be referred to as endo-1,4-beta-xylanase or 1,4-beta-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some embodiments, the present invention provides at least one GH61 variant and at least one beta-xylosidase. Beta-xylosidases (EC 3.2.1.37) catalyze the hydrolysis of 1,4-beta-D-xylans, to remove successive D-xylose residues from the non-reducing termini. This enzyme may also be referred to as xylan 1,4-beta-xylosidase, 1,4-beta-D-xylan xylohydrolase, exo-1,4-beta-xylosidase or xylobiase.

In some embodiments, the present invention provides at least one GH61 variant and at least one α-L-arabinofuranosidase. Alpha-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some embodiments, the present invention provides at least one GH61 variant and at least one alpha-glucuronidase. Alpha-glucuronidases (EC 3.2.1.139) catalyze the hydrolysis of an alpha-D-glucuronoside to D-glucuronate and an alcohol.

In some embodiments, the present invention provides at least one GH61 variant and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some embodiments, the present invention provides at least one GH61 variant and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some embodiments, the present invention provides at least one GH61 variant and at least one coumaroyl esterase. Coumaroyl esterases (EC 3.1.1.73) catalyze a reaction of the form: coumaroyl-saccharide+$H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73; it may also be referred to as a "feruloyl esterase."

In some embodiments, the present invention provides at least one GH61 variant and at least one alpha-galactosidase. Alpha-galactosidases (EC 3.2.1.22) catalyze the hydrolysis of terminal, non-reducing alpha-D-galactose residues in alpha-D-galactosides, including galactose oligosaccharides, galactomannans, galactans and arabinogalactans. This enzyme may also be referred to as "melibiase."

In some embodiments, the present invention provides at least one GH61 variant and at least one beta-galactosidase. Beta-galactosidases (EC 3.2.1.23) catalyze the hydrolysis of terminal non-reducing beta-D-galactose residues in beta-D-galactosides. In some embodiments, the polypeptide is also capable of hydrolyzing alpha-L-arabinosides. This enzyme may also be referred to as exo-(1->4)-beta-D-galactanase or lactase.

In some embodiments, the present invention provides at least one GH61 variant and at least one beta-mannanase. Beta-mannanases (EC 3.2.1.78) catalyze the random hydrolysis of 1,4-beta-D-mannosidic linkages in mannans, galactomannans and glucomannans. This enzyme may also be referred to as "mannan endo-1,4-beta-mannosidase" or "endo-1,4-mannanase."

In some embodiments, the present invention provides at least one GH61 variant and at least one beta-mannosidase. Beta-mannosidases (EC 3.2.1.25) catalyze the hydrolysis of terminal, non-reducing beta-D-mannose residues in beta-D-mannosides. This enzyme may also be referred to as mannanase or mannase.

In some embodiments, the present invention provides at least one GH61 variant and at least one glucoamylase. Glucoamylases (EC 3.2.1.3) catalyzes the release of D-glucose from non-reducing ends of oligo- and poly-saccharide molecules. Glucoamylase is also generally considered a type of amylase known as amylo-glucosidase.

In some embodiments, the present invention provides at least one GH61 variant and at least one amylase. Amylases (EC 3.2.1.1) are starch cleaving enzymes that degrade starch and related compounds by hydrolyzing the alpha-1,4 and/or alpha-1,6 glucosidic linkages in an endo- or an exo-acting fashion. Amylases include alpha-amylases (EC 3.2.1.1); beta-amylases (3.2.1.2), amylo-amylases (EC 3.2.1.3), alpha-glucosidases (EC 3.2.1.20), pullulanases (EC 3.2.1.41), and isoamylases (EC 3.2.1.68). In some embodiments, the amylase is an alpha-amylase.

In some embodiments one or more enzymes that degrade pectin are included in enzyme mixtures that comprise at least one GH61 variant of the present invention. Pectinases catalyze the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some embodiments, the present invention provides at least one GH61 variant and at least one endo-polygalacturonase, Endo-polygalacturonases (EC 3.2.1.15) catalyze the random hydrolysis of 1,4-alpha-D-galactosiduronic linkages in pectate and other galacturonans. This enzyme may also be referred to as "polygalacturonase pectin depolymerase," "pectinase," "endopolygalacturonase," "pectolase," "pectin hydrolase," "pectin polygalacturonase," "poly-alpha-1,4-galacturonide glycanohydrolase," "endogalacturonase," "endo-D-galacturonase" or "poly(1,4-alpha-D-galacturonide) glycanohydrolase."

In some embodiments, the present invention provides at least one GH61 variant and at least one pectin methyl esterase. Pectin methyl esterases (EC 3.1.1.11) catalyze the reaction: pectin+n $H_2O$=n methanol+pectate. The enzyme may also been known as "pectin esterase," "pectin demethoxylase," "pectin methoxylase," "pectin methylesterase," "pectase," "pectinoesterase," or "pectin pectylhydrolase."

In some embodiments, the present invention provides at least one GH61 variant and at least one endo-galactanase. Endo-galactanases (EC 3.2.1.89) catalyze the endohydrolysis of 1,4-beta-D-galactosidic linkages in arabinogalactans. The enzyme may also be known as "arabinogalactan endo-1,4-beta-galactosidase," "endo-1,4-beta-galactanase," "galactanase," "arabinogalactanase," or "arabinogalactan 4-beta-D-galactanohydrolase."

In some embodiments, the present invention provides at least one GH61 variant and at least one pectin acetyl esterase. Pectin acetyl esterases catalyze the deacetylation of the acetyl groups at the hydroxyl groups of GalUA residues of pectin.

In some embodiments, the present invention provides at least one GH61 variant and at least one endo-pectin lyase. Endo-pectin lyases (EC 4.2.2.10) catalyze the eliminative cleavage of (1→4)-alpha-D-galacturonan methyl ester to give oligosaccharides with 4-deoxy-6-O-methyl-α-D-galact-4-enuronosyl groups at their non-reducing ends. The enzyme may also be known as "pectin lyase," "pectin trans-eliminase," "endo-pectin lyase," "polymethylgalacturonic transeliminase," "pectin methyltranseliminase," "pectolyase," "PL," "PNL," "PMGL," or "(1→4)-6-O-methyl-alpha-D-galacturonan lyase."

In some embodiments, the present invention provides at least one GH61 variant and at least one pectate lyase. Pectate lyases (EC 4.2.2.2) catalyze the eliminative cleavage of (1→4)-alpha-D-galacturonan to give oligosaccharides with 4-deoxy-alpha-D-galact-4-enuronosyl groups at their non-reducing ends. The enzyme may also be known "polygalacturonic transeliminase," "pectic acid transeliminase," "polygalacturonate lyase," "endopectin methyltranseliminase," "pectate transeliminase," "endogalacturonate transeliminase," "pectic acid lyase," "pectic lyase," alpha-1,4-D-endopolygalacturonic acid lyase," "PGA lyase," "PPase-N," "endo-alpha-1,4-polygalacturonic acid lyase," "polygalacturonic acid lyase," "pectin trans-eliminase," "polygalacturonic acid trans-eliminase," or "(1→4)-alpha-D-galacturonan lyase,"

In some embodiments, the present invention provides at least one GH61 variant and at least one alpha-rhamnosidase. Alpha-rhamnosidases (EC 3.2.1.40) catalyze the hydrolysis of terminal non-reducing alpha-L-rhamnose residues in alpha-L-rhamnosides or alternatively in rhamnogalacturonan. This enzyme may also be known as "alpha-L-rhamnosidase T," "alpha-L-rhamnosidase N," or "alpha-L-rhamnoside rhamnohydrolase."

In some embodiments, the present invention provides at least one GH61 variant and at least one exo-galacturonase. Exo-galacturonases (EC 3.2.1.82) hydrolyze pectic acid from the non-reducing end, releasing digalacturonate. The enzyme may also be known as "exo-poly-alpha-galacturonosidase," "exopolygalacturonosidase," or "exopolygalacturanosidase."

In some embodiments, the present invention provides at least one GH61 variant and at least one-galacturan 1,4-alpha galacturonidase. Exo-galacturonases (EC 3.2.1.67) catalyze a reaction of the following type: $(1,4-\alpha-D-galacturonide)n + H_2O = (1,4-\alpha-D-galacturonide)n-i + D-galacturonate$. The enzyme may also be known as "poly [1->4) alpha-D-galacturonide] galacturonohydrolase," "exopolygalacturonase," "poly(galacturonate) hydrolase," "exo-D-galacturonase," "exo-D-galacturonanase," "exopoly-D-galacturonase," or "poly(1,4-alpha-D-galacturonide) galacturonohydrolase."

In some embodiments, the present invention provides at least one GH61 variant and at least one exopolygalacturonate lyase. Exopolygalacturonate lyases (EC 4.2.2.9) catalyze eliminative cleavage of 4-(4-deoxy-alpha-D-galact-4-enuronosyl)-D-galacturonate from the reducing end of pectate (i.e., de-esterified pectin). This enzyme may be known as "pectate disaccharide-lyase," "pectate exo-lyase," "exopectic acid transeliminase," "exopectate lyase," "exopolygalacturonic acid-trans-eliminase," "PATE," "exo-PATE," "exo-PGL," or "(1→4)-alpha-D-galacturonan reducing-end-disaccharide-lyase."

In some embodiments, the present invention provides at least one GH61 variant and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some embodiments, the present invention provides at least one GH61 variant and at least one rhamnogalacturonan lyase. Rhamnogalacturonan lyases cleave alpha-L-Rhap-(1→4)-alpha-D-GalpA linkages in an endo-fashion in rhamnogalacturonan by beta-elimination.

In some embodiments, the present invention provides at least one GH61 variant and at least one rhamnogalacturonan acetyl esterase. Rhamnogalacturonan acetyl esterases catalyze the deacetylation of the backbone of alternating rhamnose and galacturonic acid residues in rhamnogalacturonan.

In some embodiments, the present invention provides at least one GH61 variant and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as "xylogalacturonan hydrolase."

In some embodiments, the present invention provides at least one GH61 variant and at least one endo-arabinanase. Endo-arabinanases (EC 12.1.99) catalyze endohydrolysis of 1,5-alpha-arabinofuranosidic linkages in 1,5-arabinans. The enzyme may also be known as "endo-arabinase," "arabinan endo-1,5-alpha-L-arabinosidase," "endo-1,5-alpha-L-arabinanase," "endo-alpha-1,5-arabanase," "endo-arabanase," or "1,5-alpha-L-arabinan 1,5-alpha-L-arabinanohydrolase.".

In some embodiments, the present invention provides at least one GH61 variant and at least one enzyme that participates in lignin degradation in an enzyme mixture. Enzymatic lignin depolymerization can be accomplished by lignin peroxidases, manganese peroxidases, laccases, and/or cellobiose dehydrogenases (CDH), often working in synergy. These extracellular enzymes are often referred to as "lignin-modifying enzymes" or "LMEs." Three of these enzymes comprise two glycosylated heme-containing peroxidases, namely lignin peroxidase (LIP), Mn-dependent peroxidase (MNP), and copper-containing phenoloxidase laccase (LCC).

In some embodiments, the present invention provides at least one GH61 variant and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some embodiments, the present invention provides at least one GH61 variant and at least one Mn-dependent peroxidase. The enzymatic activity of Mn-dependent peroxidase (MnP) in is dependent on $Mn^{2+}$. Without being bound by theory, it has been suggested that the main role of this enzyme is to oxidize $Mn^{2+}$ to $Mn^{3+}$ (See e.g, Glenn et al., Arch. Biochem. Biophys., 251:688-696 [1986]). Subsequently, phenolic substrates are oxidized by the $Mn^{3+}$ generated.

In some embodiments, the present invention provides at least one GH61 variant and at least one lignin peroxidase. Lignin peroxidase is an extracellular heme peroxidase that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., FEBS Lett., 195:242-246 [1986]).

In some embodiments, the present invention provides at least one GH61 variant and at least one protease, amylase, glucoamylase, and/or a lipase that participates in cellulose degradation.

As used herein, the term "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention. Some specific types of proteases include, cysteine proteases including pepsin, papain and serine proteases including chymotrypsins, carboxypeptidases and metalloendopeptidases.

As used herein, the term "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one GH61 variant and at least one expansin or expansin-like protein, such as a swollenin (See e.g., Salheimo et al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some embodiments, the present invention provides at least one GH61 variant and at least one polypeptide product of a cellulose integrating protein, scaffoldin or a scaffoldin-like protein, for example CipA or CipC from *Clostridium thermocellum* or *Clostridium cellulolyticum*, respectively. Scaffoldins and cellulose integrating proteins are multi-functional integrating subunits which may organize cellulolytic subunits into a multi-enzyme complex. This is accomplished by the interaction of two complementary classes of domains (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both such domains.

In some embodiments, the present invention provides at least one GH61 variant and at least one cellulose induced protein or modulating protein, for example as encoded by a cip1 or cip2 gene or similar genes from *Trichoderma reesei* (See e.g., Foreman et al., J. Biol. Chem., 278:31988-31997 [2003]).

In some embodiments, the present invention provides at least one GH61 variant and at least one member of each of the classes of the polypeptides described above, several members of one polypeptide class, or any combination of these polypeptide classes to provide enzyme mixtures suitable for various uses.

In some embodiments, the enzyme mixture comprises other types of cellulases, selected from but not limited to cellobiohydrolase, endoglucanase, beta-glucosidase, and glycoside hydrolase 61 protein (GH61) cellulases. These enzymes may be wild-type or recombinant enzymes. In some embodiments, the cellobiohydrolase is a type 1 cellobiohydrolase (e.g., a *T. reesei* cellobiohydrolase I). In some embodiments, the endoglucanase comprises a catalytic domain derived from the catalytic domain of a *Streptomyces avermitilis* endoglucanase (See e.g., US Pat. Appln. Pub. No. 2010/0267089; U.S. Pat. No. 8,206,960; and U.S. Pat. No. 8,088,608, each of which is incorporated herein by reference). In some embodiments, at least one cellulase in the mixtures of the present invention is derived from *Acidothermus cellulolyticus, Thermobifida fusca, Humicola grisea, Myceliophthora thermophila, Chaetomium thermophilum, Acremonium* sp., *Thielavia sp, Trichoderma reesei, Aspergillus* sp., or a *Chrysosporium* sp. In some embodiments, cellulase enzymes of the cellulase mixture work together resulting in decrystallization and hydrolysis of the cellulose from a biomass substrate to yield fermentable sugars, such as but not limited to glucose.

Some cellulase mixtures for efficient enzymatic hydrolysis of cellulose are known (See e.g., Viikari et al., Adv. Biochem. Eng. Biotechnol., 108:121-45 [2007]; and US Pat. Appln. Pubin. Nos. US 2009/0061484, US 2008/0057541, and US 2009/0209009, each of which is incorporated herein by reference in their entireties). In some embodiments, mixtures of purified naturally occurring or recombinant enzymes are combined with cellulosic feedstock or a product of cellulose hydrolysis. Alternatively or in addition, one or more cell populations, each producing one or more naturally occurring or recombinant cellulase, are combined with cellulosic feedstock or a product of cellulose hydrolysis.

In some embodiments, the enzyme mixture comprises commercially available purified cellulases. Commercial cellulases are known and available (e.g., C2730 cellulase from *Trichoderma reesei* ATCC No. 25921 available from Sigma-Aldrich, Inc.) Any suitable commercially available enzyme finds use in the present invention.

In some embodiments, the enzyme mixture comprises at least one isolated GH61 variant as provided herein and at least one or more isolated enzymes, including but not limited to at least one isolated CBH1a, isolated CBH2b, isolated endoglucanase (EG) (e.g., EG2 and/or EG1), and/or isolated beta-glucosidase (BGL). In some embodiments, at least 5%, at least 10%, at last 15%, at least 20%, at least 25%, at least 30%, at least 35%, at least 40%, at least 45%, or at least 50% of the enzyme mixture is GH61. In some embodiments, the enzyme mixture further comprises a cellobiohydrolase type 1a (e.g., CBH1a), and GH61, wherein the enzymes together comprise at least 25%, at least 30%, at least 35%, at least 40%, at least 45%, at least 50%, at least 55%, at least 60%, at least 65%, at least 70%, at least 75%, or at least 80% of the enzyme mixture. In some embodiments, the enzyme mixture further comprises a beta-glucosidase (BGL), GH61, and CBH, wherein the three enzymes together comprise at least 30%, at least 35%, at least 40%, at least 45%, at least 50%, at least 55%, at least 60%, at least 65%, at least 70%, at least 75%, at least 80%, or at least 85% of the enzyme mixture. In some embodiments, the enzyme mixture further comprises an endoglucanase (EG), GH61, CBH2b, CBH1a, BGL, wherein the five enzymes together comprise at least 35%, at least 40%, at least 45%, at least 50%, at least 55%, at least 60%, at least 65%, at least 70%, at least 75%, at least 80%, at least 85%, or at least 90% of the enzyme mixture. In some embodiments, the enzyme mixture comprises GH61, CBH2b, CBH1, BGL, and at least one EG, in any suitable proportion for the desired reaction.

In some embodiments, the enzyme mixture composition comprises isolated cellulases in the following proportions by weight (wherein the total weight of the cellulases is 100%): about 20%-10% of GH61, about 20%-10% of BGL, about 30%-25% of CBH1a, about 10%-30% of GH61, about 20%-10% of EG, and about 20%-25% of CBH2b. In some embodiments, the enzyme mixture composition comprises isolated cellulases in the following proportions by weight: about 20%-10% of GH61, about 25%-15% of BGL, about 20%-30% of CBH1a, about 10%-15% of EG, and about 25%-30% of CBH2b. In some embodiments, the enzyme mixture composition comprises isolated cellulases in the following proportions by weight: about 30%-20% of GH61, about 15%-10% of BGL, about 25%-10% of CBH1a, about 25%-10% of CBH2b, about 15%-10% of EG. In some embodiments, the enzyme mixture composition comprises isolated cellulases in the following proportions by weight: about 40-30% of GH61, about 15%-10% of BGL, about 20%-10% of CBH1a, about 20%-10% of CBH2b, and about 15%-10% of EG.

In some embodiments, the enzyme mixture composition comprises isolated cellulases in the following proportions by weight: about 50-40% of GH61, about 15%-10% of BGL, about 20%-5% of CBH1a, about 15%-10% of CBH2b, and about 10%-5% of EG. However, in some embodiments, the enzyme mixture composition comprises no EG (e.g., EG2). In some embodiments, the enzyme mixture composition comprises isolated cellulases in the following proportions by weight: about 10%-15% of GH61, about 20%-25% of BGL, about 30%-20% of CBH1a, about 15%-5% of EG, and about 25%-35% of CBH2b. In some embodiments, the enzyme mixture composition comprises isolated cellulases in the following proportions by weight: about 15%-5% of GH61, about 15%-10% of BGL, about 45%-30% of CBH1a, about 25%-5% of EG, and about 40%-10% of CBH2b. In some embodiments, the enzyme mixture composition comprises isolated cellulases in the following proportions by weight: about 10% of GH61, about 15% of BGL, about 40% of CBH1a, about 25% of EG, and about 10% of CBH2b.

In some embodiments, the enzyme mixtures provided herein further comprise at least one xylan-active enzyme and/or at least one ester-active enzyme. In some embodiments, the enzyme mixture compositions comprise about 0-25% xylanase (e.g., about 2%-5%, about 1%-10%, about 10%-15%, about 15%-25%, about 1%, about 2%, about 3%, about 4%, about 5%, about 6%, about 7%, about 8%, about 9%, about 10%, about 11%, about 12%, about 13%, about 14%, or about 15% xylanase) by weight. In some embodiments, the enzyme mixture compositions comprise about 0-15% xylosidase (e.g., about 2%-5%, about 1%-10%, about 10%-15%, about 1%, about 2%, about 3%, about 4%, about 5%, about 6%, about 7%, about 8%, about 9%, about 10%, about 11%, about 12%, about 13%, about 14%, or about 15% xylosidase) by weight. In some embodiments, the enzyme mixture compositions comprise about 0-15% esterase (e.g., about 2%-5%, about 1%-10%, about 10%-15%, about 1%, about 2%, about 3%, about 4%, about 5%, about 6%, about 7%, about 8%, about 9%, about 10%, about 11%, about 12%, about 13%, about 14%, or about 15% esterase) by weight. It is contemplated that any suitable combination of enzymes and suitable enzyme concentrations will find use in the present invention, as applied using various saccharification reactions and conditions.

In some embodiments, the enzyme component comprises more than one CBH1a, CBH2b, EG, BGL, and/or GH61 variant enzyme (e.g., 2, 3 or 4 different enzymes), in any suitable combination. In some embodiments, an enzyme mixture composition of the invention further comprises at least one additional protein and/or enzyme. In some embodiments, enzyme mixture compositions of the present invention further comprise at least one additional enzyme other than at least one GH61 variant, BGL, CBH1a, wild-type GH61, and/or CBH2b. In some embodiments, the enzyme mixture compositions of the invention further comprise at least one additional cellulase, other than at least one GH61 variant, BGL, CBH1a, GH61, and/or CBH2b as described herein. In some embodiments, the GH61 polypeptide variant of the invention is also present in mixtures with non-cellulase enzymes that degrade cellulose, hemicellulose, pectin, and/or lignocellulose.

In some embodiments, GH61 polypeptide variant of the present invention is used in combination with other optional ingredients such as at least one buffer, surfactant, and/or scouring agent. In some embodiments, at least one buffer is used with the GH61 polypeptide variant of the present invention (optionally combined with other enzymes) to maintain a desired pH within the solution in which the GH61 variant is employed. The exact concentration of buffer employed depends on several factors which the skilled artisan can determine. Suitable buffers are well known in the art. In some embodiments, at least one surfactant is used in with the GH61 variant of the present invention. Suitable surfactants include any surfactant compatible with the GH61 variant and, optionally, with any other enzymes being used in the mixture. Exemplary surfactants include, but are not limited to anionic, non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter ions for anionic surfactants include, for example, alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, for example, quaternary ammonium salt sulfonates, betaine-type ampholytic surfactants, and the like. Suitable nonionic surfactants generally include polyoxalkylene ethers, as well as higher fatty acid alkanolamides or alkylene oxide adduct thereof, fatty acid glycerine monoesters, and the like. Mixtures of surfactants also find use in the present invention, as is known in the art.

Exemplary Mixtures of Cellulolytic Enzymes and Cofactors

As a further guide to the reader, yet without implying any limitation in the practice of the present invention, exemplary mixtures of components that may be used as catalysts in a saccharification reaction to generate fermentable sugars from a cellulosic substrate are provided herein. Concentrations are given in wt/vol of each component in the final reaction volume with the cellulose substrate. Also provided are percentages of each component (wt/wt) in relation to the total mass of the components that are listed for addition into each mixture (the "total protein"). This may be a mixture of purified enzymes and/or enzymes in a culture supernatant.

By way of example, the invention embodies mixtures that comprise at least four, at least five, or all six of the following components. In some embodiments, cellobiohydrolase 1 (CBH1) finds use; in some embodiments CBH1 is present at a concentration of about 0.14 to about 0.23 g/L (about 15% to about 25% of total protein). Exemplary CBH1 enzymes include, but are not limited to *T. emersonii* CBH1 (wild-type) (e.g., SEQ ID NO:125), *M. thermophila* CBH1a (wild-type) (e.g., SEQ ID NO:128), and the variants CBH1a-983 (SEQ ID NO:134) and CBH1a-145 (SEQ ID NO:131). In some embodiments, cellobiohydrolase 2 (CBH2) finds use; in some embodiments, CBH2 is present at a concentration of about 0.14 to about 0.23 g/L (about 15% to about 25% of total protein). Exemplary CBH2 enzymes include but are not limited to CBH2b from *M. thermophila* (wild-type) (e.g., SEQ ID NO:137). In some embodiments, endoglucanase 2 (EG2) finds use; in some embodiments, EG2 is present at a concentration of 0 to about 0.05 g/L (0 to about 5% of total protein). Exemplary EGs include, but are not limited to *M. thermophila* EG2 (wild-type) (e.g., SEQ ID NO:113). In some further embodiments, endoglucanase 1 (EG1) finds use; in some embodiments, EG1 is present at a concentration of about 0.05 to about 0.14 g/L (about 5% to about 15% of total protein). Exemplary EG1s include, but are not limited to *M. thermophila* EG1b (wild-type) (e.g., SEQ ID NO:110). In some embodiments, beta-glucosidase (BGL) finds use in the present invention; in some embodiments, BGL is present at a concentration of about 0.05 to about 0.09 g/L (about 5% to about 10% of total protein). Exemplary beta-glucosidases include, but are not limited to *M. thermophila* BGL1 (wild-type) (e.g., SEQ ID NO:116), variant BGL-900 (SEQ ID NO:122), and variant BGL-883 (SEQ ID NO:119). In some further embodiments, GH61 protein and/or protein variants find use; in some embodiments, GH61 enzymes are present at a concentration of about 0.23 to about 0.33 g/L (about 25% to about 35% of total protein). Exemplary GH61s include, but are not limited to *M. thermophila* GH61a wild-type (SEQ ID NO:2), Variant 1 (SEQ ID NO:5), Variant 5 (SEQ ID NO:8)

and/or Variant 9 (SEQ ID NO:11), and/or any other GH61a variant proteins, as well as any of the other GH61 enzymes (e.g., GH61b, GH61c, GH61d, GH61e, GH61f, GH61g, GH61h, GH161i, GH61j, GH61k, GH61l, GH61m, GH61n, GH61o, GH61p, GH61q, GH61r, GH61s, GH61t, GH61u, GH61v, GH61w, GH61x, and/or GH61y) as provided herein.

In some embodiments, one, two or more than two enzymes are present in the mixtures of the present invention. In some embodiments, GH61p is present at a concentration of about 0.05 to about 0.14 g/L (e.g, about 1% to about 15% of total protein). Exemplary *M. thermophila* GH61p enzymes include those set forth in SEQ ID NOS:70 and 73. In some embodiments, GH61f is present at a concentration of about 0.05 to about 0.14 g/L (about 1% to about 15% of total protein). An exemplary *M. thermophila* GH61f is set forth in SEQ ID NO:29. In some additional embodiments, at least one additional GH61 enzyme provided herein (e.g., GH61b, GH61c, GH61d, GH61e, GH61g, GH61h, GH61i, GH61j, GH61k, GH61l, GH61m, GH61n, GH61n, GH61o, GH61q, GH61r, GH61s, GH61t, GH61u, GH61v, GH61w, GH61x, and/or GH61y, finds use at an appropriate concentration (e.g., about 0.05 to about 0.14 g/L [about 1% to about 15% of total protein]).

In some embodiments, at least one xylanase at a concentration of about 0.05 to about 0.14 g/L (about 1% to about 15% of total protein) finds use in the present invention. Exemplary xylanases include but are not limited to the *M. thermophila* xylanase-3 (SEQ ID NO:149), xylanase-2 (SEQ ID NO:152), xylanase-1 (SEQ ID NO:155), xylanase-6 (SEQ ID NO:158), and xylanase-5 (SEQ ID NO:161).

In some additional embodiments, at least one beta-xylosidase at a concentration of about 0.05 to about 0.14 g/L (e.g., about 1% to about 15% of total protein) finds use in the present invention. Exemplary beta-xylosidases include but are not limited to the *M. thermophila* beta-xylosidase (SEQ ID NO:164).

In still some additional embodiments, at least one acetyl xylan esterase at a concentration of about 0.05 to about 0.14 g/L (e.g., about 1% to about 15% of total protein) finds use in the present invention. Exemplary acetylxylan esterases include but are not limited to the *M. thermophila* acetylxylan esterase (SEQ ID NO:167).

In some further additional embodiments, at least one ferulic acid esterase at a concentration of about 0.05 to about 0.14 g/L (e.g., about 1% to about 15% of total protein) finds use in the present invention. Exemplary ferulic esterases include but are not limited to the *M. thermophila* ferulic acid esterase (SEQ ID NO:170).

In some embodiments, the enzyme mixtures comprise at least one GH61 variant protein as provided herein and at least one cellulase, including but not limited to any of the enzymes described herein. In some embodiments, the enzyme mixtures comprise at least one GH61 variant protein and at least one wild-type GH61 protein. In some embodiments, the enzyme mixtures comprise at least one GH61 variant protein and at least one non-cellulase enzyme. Indeed, it is intended that any combination of enzymes will find use in the enzyme compositions comprising at least one GH61 variant of the present invention.

The concentrations listed above are appropriate for a final reaction volume with the biomass substrate in which all of the components listed (the "total protein") is about 0.75 g/L, and the amount of glucan is about 93 g/L, subject to routine optimization. The user may empirically adjust the amount of each component and total protein for cellulosic substrates that have different characteristics and/or are processed at a different concentration. Any one or more of the components may be supplemented or substituted with variants with common structural and functional characteristics, as described below.

Without implying any limitation, the following mixtures further describe some embodiments of the present invention.

Some mixtures comprise CBH1a within a range of about 15% to about 30% total protein, typically about 20% to about 25%; CBH2 within a range of about 15% to about 30%, typically about 17% to about 22%; EG2 within a range of about 1% to about 10%, typically about 2% to about 5%; BGL1 within a range of about 5% to about 15%, typically about 8% to about 12%; GH61a within a range of about 10% to about 40%, typically about 20% to about 30%; EG1b within a range of about 5% to about 25%, typically about 10% to about 18%; and GH61f within a range of 0% to about 30%; typically about 5% to about 20%.

In some mixtures, exemplary BGL1s include the BGL1 variant 900 (SEQ ID NO:122) and/or variant 883 (SEQ ID NO:119). In some embodiments, other enzymes are *M. thermophila* wild-type: CBH1a (SEQ ID NO:128), CBH2b (SEQ ID NO:137), EG2 (SEQ ID NO:113), GH61a (SEQ ID NO:2), EG1b (SEQ ID NO:110) and GH61f (SEQ ID NO:29). Any one or more of the components may be supplemented or substituted with variants having common structural and functional characteristics with the component being substituted or supplemented, as described below. In a saccharification reaction, the amount of glucan is generally about 50 to about 300 g/L, typically about 75 to about 150 g/L. The total protein is about 0.1 to about 10 g/L, typically about 0.5 to about 2 g/L, or about 0.75 g/L.

Some mixtures comprise CBH1 within a range of about 10% to about 30%, typically about 15% to about 25%; CBH2b within a range of about 10% to about 25%, typically about 15% to about 20%; EG2 within a range of about 1% to about 10%, typically about 2% to about 5%; EG1b within a range of about 2% to about 25%, typically about 6% to about 14%; GH61a within a range of about 5% to about 50%, typically about 10% to about 35%; and BGL1 within a range of about 2% to about 15%, typically about 5% to about 12%. Also included is copper sulfate to generate a final concentration of $Cu^{++}$ of about 4 µM to about 200 µM, typically about 25 µM to about 60 µM. However, it is not intended that the added copper be limited to any particular concentration, as any suitable concentration finds use in the present invention and will be determined based on the reaction conditions.

In an additional mixture, an exemplary CBH1 is wild-type CBH1 from *T. emersonii* (SEQ ID NO:125), as well as wild-type *M. thermophila* CBH1a (SEQ ID NO:128), Variant 983 (SEQ ID NO:134), and Variant 145 (SEQ ID NO:131); exemplary CBH2 enzymes include the wild-type (SEQ ID NO:137), Variant 962 (SEQ ID NO:146), Variant 196 (SEQ ID NO:140), and Variant 287 (SEQ ID NO:143); an exemplary EG2 is the wild-type *M. thermophila* (SEQ ID NO:113); an exemplary EG1b is the wild-type (SEQ ID NO:110); exemplary GH61a enzymes include wild-type *M. thermophila* (SEQ ID NO:2), Variant 1 (SEQ ID NO:5), Variant 5 (SEQ ID NO:11), and Variant 9 (SEQ ID NO:11); and exemplary BGLs include wild-type *M. thermophila* BGL (SEQ ID NO:116), Variant 883 (SEQ ID NO:119), and Variant 900 (SEQ ID NO:122). Any one or more of the components may be supplemented or substituted with other variants having common structural and functional characteristics with the component being substituted or supplemented, as described below. In a saccharification reaction, the amount of glucan is generally about 50 to about 300 g/L, typically about 75 to about 150 g/L. The total protein is about 0.1 to about 10 g/L, typically about 0.5 to about 2 g/L, or about 0.75 g/L.

Any or all of the components listed in the mixtures referred to above may be supplemented or substituted with variant proteins that are structurally and functionally related, as described herein.

In some embodiments, the CBH1 cellobiohydrolase used in mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to either SEQ ID NO:128 (*M. thermophila*), SEQ ID NO:125 (*T. emersonii*), or a fragment of either SEQ ID NO:128 or SEQ ID NO:125 having cellobiohydrolase activity, as well as variants of *M. thermophila* CBH1a (e.g., SEQ ID NO:131 and/or SEQ ID NO:133), and variant fragment(s) having cellobiohydrolase activity. Exemplary CBH1 enzymes include, but are not limited to those described in US Pat. Appln. Publn. No. 2012/0003703 A1, which is hereby incorporated herein by reference in its entirety for all purposes.

In some embodiments, the CBH2b cellobiohydrolase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:127 or a fragment of SEQ ID NO:127, as well as at least one variant *M. thermophila* CBH2b enzyme (e.g., SEQ ID NO:140, 143, and/or 146) and/or variant fragment(s) having cellobiohydrolase activity. Exemplary CBH2b enzymes are described in U.S. Patent Appln. Ser. Nos. 61/479,800, 13/459,038, both of which are hereby incorporated herein by reference in their entirety for all purposes.

In some embodiments, the EG2 endoglucanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:113 or a fragment of SEQ ID NO:113 having endoglucanase activity. Exemplary EG2 enzymes are described in U.S. patent application Ser. No. 13/332,114, and WO 2012/088159, both of which are hereby incorporated herein by reference in their entirety for all purposes.

In some embodiments, the EG1b endoglucanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:110 or a fragment of SEQ ID NO:110 having endoglucanase activity.

In some embodiments, the BGL1 beta-glucosidase used the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NOS:116, 119, and/or 122, or a fragment of SEQ ID NOS:116, 119, and/or 122 having beta-glucosidase activity. Exemplary BGL1 enzymes include, but are not limited to those described in US Pat. Appln. Publ. No. 2011/0129881, WO 2011/041594, and US Pat. Appln. Publ. No. 2011/0124058 A1, all of which are hereby incorporated herein by reference in their entireties for all purposes.

In some embodiments, the GH61f protein used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:29, or a fragment of SEQ ID NO:29 having GH61 activity, assayed as described elsewhere in this disclosure.

In some embodiments, the GH61p protein used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:70, SEQ ID NO:73, or a fragment of such sequence having GH61p activity.

In some embodiments, the xylanase used in the mixtures of the present invention comprises at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:149, SEQ ID NO:151, or a fragment of such sequence having xylanase activity.

GH61 Activity Assays

The cellulase enhancing activity of GH61 proteins of the invention can be determined using any suitable GH61 activity assay. For example, in some embodiments, a purified and/or recombinant GH61 protein of this invention is obtained, and then assayed for GH61 activity by combining it with cellulase enzymes in a saccharification reaction, and determining if there is an increase in glucose yield, as compared to the same saccharification reaction conducted without the GH61.

In one approach, GH61 activity can be assayed by combining a cellulosic substrate with cellulase enzymes (e.g., 5-10 mg total weight of cellulase enzymes per gram of substrate) in the presence and absence of GH61 protein. In some embodiments, the cellulase enzymes comprise a defined set of recombinant cellulase enzymes from *M. thermophila*.

In another approach, broth from a culture of wild-type *M. thermophila* is used (with and without supplementation with GH61 protein and/or GH61 variants). GH61 activity is evidenced by enhanced glucose yield in the presence of exogenous GH61 (i.e., beyond any enhancement resulting from endogenous GH61 in the broth). It is also possible to use a broth supplemented with one or more purified enzymes.

Suitable enzymes include isolated recombinant enzymes cloned from *M. thermophila*, including but not limited to EG, BGL, CBH1, and/or CBH2, in any combination suitable for the chosen substrate to yield a measurable product.

In one exemplary assay for measuring GH61 activity from *M. thermophila* derived GH61 proteins and variant proteins, the cellulase enzymes used are *M. thermophila* BGL1 (e.g., SEQ ID NOS:116, 119, and/or 122); See e.g., Badhan et al., Biores. Technol., 98:504-10 [2007]); *M. thermophila* CBH1 (SEQ ID NOS:128, 131, and/or 134); and *M. thermophila* CBH2 (SEQ ID NOS:137, 140, 143 and/or 146). In some embodiments, endoglucanase is also used, such as *M. thermophila* EG2 (SEQ ID NO:113; See e.g., Rosgaard et al., Prog., 22:493-8 [2006]; and Badhan et al., supra).

Alternatively, commercially available preparations comprising a mixture of cellulase enzymes may be used, such as Laminex™ and Spezyme™ (Genencor), Rohament™ (Rohm GmbH), and Celluzyme™, Cereflo™ and Ultraflo™ (Novozymes).

Assays with cellulose enzymes are typically done at 50° C., but in some embodiments, other temperatures find use (e.g., 35, 45, 55, 60, or 65° C.). In some embodiments, the GH61 enzymes and any other desired enzymes are combined with the substrate and incubated so as to produce fermentable sugars. The sugars are then recovered and quantitated for yield of glucose. One suitable substrate is wheat straw (e.g., pre-treated wheat straw). Other cellulosic substrates listed in this disclosure may be used as an alternative, including corn stover pretreated with sulfuric acid (See e.g., U.S. Pat. No. 7,868,227). Assay methods are known in the art. For example, the method of Harris et al., (Harris et al., Biochem., 49:3305-3316 [2010], incorporated herein by reference) finds use. In this method, corn stover is pretreated with sulfuric acid, washed, incubated with cellulase enzymes and GH61 for several days, and then the yield of sugars quantitated by refraction. Another method is described in U.S. Pat. No. 7,868,227 (incorporated herein by reference). In this method, the cellulosic substrate is PCS (corn stover pretreated with heat and dilute sulfuric acid, as described in WO 2005/074647; and a cellulose enzyme mixture is Cellucast®, a blend of cellulase enzymes from the fungus *Trichoderma reesei* (Sigma-Aldrich). Hydrolysis of PCS is conducted in a total reaction volume of 1.0 mL and a PCS concentration of 50 mg/mL in 1 mM manganese sulfate, 50 mM sodium acetate buffer pH 5.0. The test protein is combined with the base cellulase mixture at relative concentrations between 0 and 100% total protein. The protein composition is incubated with the PCS at 65° C. for 7 days. The combined yield of glucose and cellobiose is measured by refractive index detection.

GH61 activity is calculated as an increase in glucose production from the substrate by the cellulase(s) in the presence of GH61 protein, in comparison with the same reaction mixture in the absence of GH61 protein. Typically, the increase is dose-dependent within at least a 3-fold range of concentrations. GH61 activity can be expressed as a degree of "synergy".

Use of GH61 Variant Protein to Promote Saccharification

The GH61 variant proteins of the present invention can be used industrially to promote or otherwise modulate the activity of cellulase enzymes.

In some embodiments, suitably prepared lignocellulose is subjected to enzymatic hydrolysis using one or more cellulase enzymes in the presence of one or more GH61 variant proteins or preparations according to this invention. Thus, in some embodiments, saccharification reactions are carried out by exposing biomass to GH61 variant protein and cellulases, which work in concert to break down the biomass. Typically, the cellulases include at least one endoglucanase (EG), at least one beta-glucosidase (BGL), at least one Type 1 cellobiohydrolase (CBH1), and/or at least one Type 2 cellobiohydrolase (CBH2). In some alternative embodiments, a minimum enzyme mixture is used, for example, comprising GH61 protein in combination with BGL and either CBH1 or CBH2, or both, but with substantially no EG.

Hydrolysis of the hemicellulose and cellulose components of a lignocellulosic feedstock yields a lignocellulosic hydrolysate comprising xylose and glucose. Other sugars typically present include galactose, mannose, arabinose, fucose, rhamnose, or a combination thereof. Regardless of the means of hydrolyzing the lignocellulosic feedstock (e.g., full acid hydrolysis or chemical pretreatment with or without subsequent enzymatic hydrolysis), the xylose and glucose generally make up a large proportion of the sugars present. In some embodiments, if the lignocellulosic hydrolysate is a hemicellulose hydrolysate resulting from acid pretreatment, xylose will likely be the predominant sugar and lesser amounts of glucose will be present. The relative amount of xylose present in the lignocellulosic hydrolysate will depend on the feedstock and the pretreatment that is employed.

The cells and compositions of the present invention (including culture broth and/or cell lysates) find use in the production of fermentable sugars from cellulosic biomass. The biomass substrate may be converted to a fermentable sugar by (a) optionally pretreating a cellulosic substrate to increase its susceptibility to hydrolysis; (b) contacting the optionally pretreated cellulosic substrate of step (a) with a composition, culture medium or cell lysate containing at least one GH61 variant and any additional cellulases under conditions suitable for the production of cellobiose and fermentable sugars such as glucose.

In some embodiments, each of the at least one GH61 variant and additional cellulase enzymes described herein are partially or substantially purified, and the purified proteins are added to the biomass. Alternatively or in addition, the various individual enzymes are recombinantly expressed in different cells, and the media containing the secreted proteins are added to the biomass. The GH61 variant protein(s) and cellulase enzymes are then reacted with the biomass at a suitable temperature for a suitable period.

In some embodiments, sugars produced by methods of this invention are used to produce an end product such as an alcohol, such as ethanol. Other end-products may be produced, such as acetone, amino acid(s) (e.g., glycine, or lysine), organic acids (e.g., lactic acid, acetic acid, formic acid, citric acid, oxalic acid, or uric acid), glycerol, diols (e.g., 1,3 propanediol or butanediol), or at least one hydrocarbon with 1 to 20 carbon atoms. In some embodiments, cellulosic biomass is treated with at least one composition of the present invention to prepare an animal feed.

In some embodiments, when GH61 protein (e.g., at least one GH61 variant) is used to increase the yield of fermentable sugars in a saccharification reaction, at least one divalent metal cation or additional cofactor or adjunct compound is added to the reaction at a concentration of about 1 to 100 uM. In some embodiments, the divalent metal cation (e.g., copper) is included at a concentration of about 1 to 90 uM, about 10 to 80 uM, about 15 to 75 uM, about 20 to 70 uM, about 30 to 60 uM, about 40 to 50 uM, about 5 to 10 uM, about 10 to 20 μM, about 15 to 25 uM, about 20 to 30 uM, about 25 to 35 uM, about 30 to 40 uM, about 35 to 45 uM, about 40 to 50 uM, about 45 to 55 uM, about 50 to 60 uM, about 55 to 65 uM, about 60 to 70 uM, about 65 to 75 uM, about 70 to 80 uM, about 75 to 85 uM, about 80 to 90 uM, about 85 to 95 uM, about 90 to 100 uM, about 95 to 100 uM, or about 1 uM, about 2 uM, about 3 uM, about 4 uM, about 5 uM, about 6 uM, about 7 uM, about 8 uM, about 9 uM, about 10 uM, about 11 uM, about 12 uM, about 13 uM, about 14 uM, about 15 uM, about 16 uM, about 17 uM, about 18 uM, about 19 uM, about 20 uM, about 25 uM, about 30 uM, about 35 uM, about 40 uM, about 45 uM, about 50 uM, about 55 uM, about 60 uM, about 65 uM, about 70 uM, about 75 uM, about 80 uM, about 85 uM, about 90 uM, about 95 uM, or about 100 uM. Divalent cations present in the reaction include, but are not limited to $Cu^{++}$, $Mn^{++}$, $Co^{++}$, $Mg^{++}$, $Ni^{++}$, $Zn^{++}$, and $Ca^{++}$ at concentrations of 0.001 to 50 mM, 1 μM to 1 mM, or 10-50 μM. Indeed, it is not intended that the concentration of divalent metal cation(s) be limited to any particular value, as any suitable concentration finds use in the present invention and will depend upon the reaction conditions, as known in the art.

Fermentation of Sugars

In some embodiments, once a suitable cellulosic biomass substrate has been treated with cellulase(s) and at least one GH61 variant protein(s) according to this invention, sugars and other components in the product are fermented to produce various fermentation end products, including but not limited to biofuels, such as ethanol or alcohol mixtures. Depending on the substrate used, other components (e.g., long-chain esters) may also be present.

Fermentation is the process of extracting energy from the oxidation of organic compounds, such as carbohydrates, using an endogenous electron acceptor. Alcoholic fermentation is a process in which sugars such as xylulose, glucose, fructose, and sucrose are converted into a fermentation end product, including but not limited to biofuel. For example, the fermentation product may comprise alcohol (such as ethanol or butanol) and/or a sugar alcohol, such as xylitol.

In some embodiments, enzyme compositions comprising at least one GH61 variant of the present invention is reacted with a biomass substrate in the range of about 25° C. to 100° C., about 30° C. to 90° C., about 30° C. to 80° C., and about 30° C. to 70° C. In some embodiments, the biomass is reacted with the enzyme compositions at about 25° C., at about 30° C., at about 35° C., at about 40° C., at about 45° C., at about 50° C., at about 55° C., at about 60° C., at about 65° C., at about 70° C., at about 75° C., at about 80° C., at about 85° C., at about 90° C., at about 95° C. and at about 100° C. In general, the pH range is from about pH 3.0 to 8.5, pH 3.5 to 8.5, pH 4.0 to 7.5, pH 4.0 to 7.0 and pH 4.0 to 6.5. The incubation time may vary for example from 1.0 to 240 hours, from 5.0 to 180 hrs and from 10.0 to 150 hrs. For example, the incubation time is generally at least 1 h, at least 5 hrs, at least 10 hrs, at least 15 hrs, at least 25 hrs, at least 50 h, at least 100 hrs, at least 180, or longer. Incubation of the cellulase under these conditions and subsequent contact with the substrate may result in the release of substantial amounts of fermentable sugars from the substrate (e.g., glucose when the cellulase is combined with beta-glucosidase). For example at least 20%, at least 30%, at least 40%, at least 50%, at least 60%, at least 70%, at least 80%, at least 90% or more fermentable sugar may be available as compared to the release of sugar by a wild-type polypeptide.

Any suitable micro-organism finds use in converting sugar in the sugar hydrolysate to ethanol or other fermentation products. These include yeast from the genera *Saccharomyces, Hansenula, Pichia, Khtyveromyces*, and *Candida*. Commercially available yeasts also find use, including but not limited to ETHANOLRED® SAFDISTIL®, THERMOSACC®, FERMIOL®, FERMIVIN®, or Superstart™.

In some embodiments, the yeast is genetically engineered to ferment both hexose and pentose sugars to at least one end-product, including but not limited to ethanol. Alternatively, in some embodiments, the yeast is a strain that has been made capable of xylose and glucose fermentation by one or more non-recombinant methods, such as adaptive evolution or random mutagenesis and selection. For example, in some embodiments, the fermentation is performed with recombinant *Saccharomyces*. In some embodiments, the recombinant yeast is a strain that has been made capable of xylose fermentation by recombinant incorporation of genes encoding xylose reductase (XEL) and xylitol dehydrogenase (XDH) (See e.g., U.S. Pat. Nos. 5,789,210, 5,866,382, 6,582,944 and 7,527,927; and EP 450 530) and/or gene(s) encoding one or more xylose isomerase (XI) (See e.g., U.S. Pat. Nos. 6,475, 768 and 7,622,284). In some additional embodiments, the modified yeast strain overexpresses an endogenous and/or heterologous gene encoding xylulokinase (XK). Other yeast can ferment hexose and pentose sugars to at least one end-product, including but not limited to ethanol, such as yeast of the genera *Hansenula, Pichia, Kluyveromyces* and *Candida* (See e.g., WO 2008/130603).

A typical temperature range for the fermentation of xylose to ethanol using *Saccharomyces* spp. is between about 25° C. to about 37° C., although the temperature may be higher (up to 55° C.) if the yeast is naturally or genetically modified to be thermostable. The pH of a typical fermentation employing *Saccharomyces* spp. is between about 3 and about 6, depending on the pH optimum of the fermentation microorganism. The sugar hydrolysate may also be supplemented with additional nutrients required for growth and fermentation performance of the fermentation microorganism. For example, yeast extract, specific amino acids, phosphate, nitrogen sources, salts, trace elements and vitamins (See e.g., Verduyn et al., Yeast 8:501-170 [1992]; Jorgensen, Appl. Biochem. Biotechnol., 153:44-57 [2009]; and Zhao et al., J. Biotechnol., 139:55-60 [2009]). In some embodiments, the fermentation is conducted under anaerobic conditions, although aerobic or microaerobic conditions also find use.

Use of Copper, Gallic Acid, and Biomass Pretreatment Filtrate to Enhance GH61 Activity In some embodiments, GH61 proteins and variants exhibit increased activity in a saccharification reaction when $Cu^{++}$, gallic acid, and/or pretreatment filtrate are added. In some embodiments, wild-type GH61a (SEQ ID NO:2) and/or Variant 1 (SEQ ID NO:5) are used. Similarly, in some embodiments, the present invention encompasses the supplemental addition of $Cu^{++}$, gallic acid, and/or pretreatment filtrate as an enhancing agent in saccharification reactions conducted using any of the GH61a variants shown in Tables 1 and 2, any of the other GH61 proteins described herein, and any active variant or fragment thereof such as may be obtained using any suitable method, including but not limited to the methods provided herein. In some embodiments, enhancing GH61 activity allows saccharification reactions to proceed more quickly and/or with less GH61 or cellulase enzyme.

In some embodiments, $Cu^{++}$, gallic acid, and other potential cofactors are tested by titrating into a saccharification reaction comprising a GH61 protein, one or more cellulase enzymes (e.g., CBH1, CBH2, and/or BGL), and a cellulosic substrate, and measuring the relative rate of glucose production. Controls may include the combination of GH61 protein, cellulase enzymes, and substrate in the absence of the putative cofactor (to test the relative enhancement), and combinations of cellulase enzymes and substrate with or without cofactor in the absence of GH61 protein (to determine the effect of the putative cofactor on other enzymes in the reaction).

As shown herein, in some embodiments, $Cu^{++}$ can enhance the activity of GH61a Variant 1 (SEQ ID NO:5). The source of $Cu^{++}$ used in the example was $CuSO_4$, although any effective copper source can be used as an alternative. Effective supplemental copper sources include copper salts and metallic copper, or mixtures thereof. Copper salts include copper(II) ($Cu^{++}$) salts and copper(I) ($Cu^{+}$) salts. Copper in metallic copper(0) and copper(I) salts can be oxidized to $Cu^{++}$ in water by oxygen (e.g., by oxygen present in air). Suitable copper(II) and copper(I) salts include sulfates, chlorides, oxides, hydroxides, nitrates, carbonates, hydroxycarbonates (basic carbonates), oxychlorides, and acetates. Suitable sources of metallic copper include metallic copper refined from copper ores, including copper vessels and piping in contact with water and oxygen (e.g., in air).

In some embodiments, as shown herein, gallic acid and/or pretreated biomass filtrate can also be used to enhance the activity of GH61 protein. In some embodiments, the gallic acid and/or pretreated biomass filtrate are titrated to the optimal dose for the reaction conditions used. Thus, an effective concentration of gallic acid can be determined empirically by titrating it into the reaction mixture, depending on the enzymes being used and the total biomass. In some embodiments, in which gallic acid is utilized, an effective concentration of gallic acid is within the range of about 0.1 to 20 mM, about 0.5 to 5 mM, or about 1 to 2 mM. However, it is not intended that the present invention be limited to any particular concentration of gallic acid, as any suitable concentration finds use in the present invention, depending upon the reaction conditions.

A cofactor of GH61 in a reaction volume such as $Cu^{++}$ is said to be "supplemented" if it has been added into the reaction volume as a separate reagent, which is in addition to any metal ions that may be bound to GH61 or other reactants beforehand. Depending on the amount or molar ratio of cofactors such as $Cu^{++}$ already present in a GH61 preparation, addition of such cofactors into the reaction may increase the amount of glucose produced per weight of GH61 by 25%, 50%, 2-fold, or more.

Effective concentrations of supplemented $Cu^{++}$ in the reaction volume may be readily determined empirically as described herein. Depending on reaction conditions, effective supplemented concentrations include but are not limited to 1 µM to 200 µM, 4 µM to 100 µM, 10 µM to 100 µM, or at least 1 µM, 4 µM, 10 µM, 20 µM, 30 µM, 40 µM, or 50 µM in the reaction volume (i.e., the concentration of supplemented copper in the reaction volume). However, it is not intended that the present invention be limited to any particular copper concentration or range of concentrations, as any suitable concentration finds use and will depend upon the reaction conditions used. In some embodiments, prior to or without copper supplementation, copper is present in the GH61 protein preparation, the other enzymes, the cellulase fermentation production media, the pretreated biomass, and/or any other component of the reaction volume (i.e., in some embodiments, there are other sources of copper present in the reaction than any copper added to the reaction as a supplement). Thus, in some embodiments, the reaction is conducted without the supplemental addition of copper as described herein.

In some embodiments, inclusion of copper and/or gallic acid in the reaction mixture at an effective concentration or ratio, less GH61 protein is needed to produce the same amount of fermentable sugars from the same cellulase enzymes. In some embodiments, this provides a cost reduction associated with saccharification reactions.

Vectors, Promoters, Other Expression Elements, Host Cells, and Signal Peptides.

There are numerous general texts that describe molecular biological techniques including the use of vectors, promoters, in vitro amplification methods including the polymerase chain reaction (PCR) and the ligase chain reaction (LCR) (See e.g., Berger and Kimmel, *Guide to Molecular Cloning Techniques, Methods in Enzymology*, Volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989; and *Current Protocols in Molecular Biology*, F. M. Ausubel et al., eds., Current Protocols [as supplemented through 2009]). Introduction of a vector or a DNA construct into a host cell can be effected by any suitable method, including but not limited to calcium phosphate transfection, DEAE-Dextran mediated transfection, electroporation, or other common techniques (See Davis et al., 1986, *Basic Methods in Molecular Biology*). General references on cell culture techniques and nutrient media for fungal host cells include *Gene Manipulations in Fungi*, Bennett, J. W. et al., Ed., Academic Press, 1985; *More Gene Manipulations in Fungi*, Bennett, J. W. et al., Ed., Academic Press, 1991; and *The Handbook of Microbiological Media*, CRC Press, Boca Raton, Fla., 1993.

Vectors

The present invention makes use of recombinant constructs comprising at least one sequence encoding at least one GH61 variant as described above. In some embodiments, the present invention provides expression vectors comprising at least one GH61 variant polynucleotide operably linked to a heterologous promoter. Expression vectors of the present invention may be used to transform an appropriate host cell to permit the host to express the GH61 variant protein. Methods for recombinant expression of proteins in fungi and other organisms are well known in the art, and a number expression vectors are available or can be constructed using routine methods (See, e.g., Tkacz and Lange, 2004, *Advances in fungal biotechnology for industry, agriculture, and medicine*, Kluwer Academic/Plenum Publishers, New York; Zhu et al., Plasmid 6:128-33 [2009]; and Kavanagh, K. 2005, *Fungi: biology and applications*, Wiley, all of which are incorporated herein by reference).

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted. Polynucleotides of the present invention can be incorporated into any one of a variety of expression vectors suitable for expressing a polypeptide. Suitable vectors include, but are not limited to chromosomal, nonchromosomal and synthetic DNA sequences (e.g., derivatives of SV40); bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

In some embodiments, the construct further comprises regulatory sequences, including, for example, a promoter, operably linked to the protein encoding sequence. Large numbers of suitable vectors and promoters are known to those of skill in the art.

Promoters

In order to obtain high levels of expression in a particular host it is often useful to express the GH61 variant of the present invention under the control of a heterologous promoter. A promoter sequence may be operably linked to the 5' region of the GH61 variant coding sequence using routine methods.

Examples of useful promoters for expression of GH61 enzymes include promoters from fungi. In some embodiments, a promoter sequence that drives expression of a gene other than a GH61 gene in a fungal strain may be used. As a non-limiting example, a fungal promoter from a gene encoding an endoglucanase may be used. In some embodiments, a promoter sequence that drives the expression of a GH61 gene in a fungal strain other than the fungal strain from which the GH61 variant was derived may be used. As a non-limiting example, if the GH61 variant is derived from C1, a promoter from a *T. reesei* GH61 gene may be used or a promoter as described in WO 2010/107303, such as but not limited to the sequences identified as SEQ ID NO:25, SEQ ID NO:26, SEQ ID NO:27, SEQ ID NO:28, or SEQ ID NO:29 in WO 2010/107303.

Examples of other suitable promoters useful for directing the transcription of the nucleotide constructs of the present invention in a filamentous fungal host cell are promoters obtained from the genes for *Aspergillus oryzae* TAKA amylase, *Rhizomucor miehei* aspartic proteinase, *Aspergillus* niger neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (Nunberg et al., Mol. Cell Biol., 4:2306-2315 [1984]; Boel et al., EMBO J, 3:1581-85 [1984]; and European Pat. Publ. 137280, all of which are incorporated herein by reference), and mutant, truncated, and hybrid promoters thereof. In a yeast host, useful promoters can be from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH2/GAP), and *S. cerevisiae* 3-phosphoglycerate kinase. Other useful promoters for yeast host cells are known (See e.g., Romanos et al., Yeast 8:423-488 [1992], incorporated herein by reference. Promoters associated with chitinase production in fungi may be used (See, e.g., Blaiseau and Lafay, Gene 120243-248 [1992] (filamentous fungus *Aphanocladium album*); Limon et al., Curr. Genet, 28:478-83 [1995] (*Trichoderma harzianum*), both of which are incorporated herein by reference).

Promoters known to control expression of genes in prokaryotic or eukaryotic cells or their viruses and which can be used in some embodiments of the invention include SV40 promoter, *E. coli* lac or trp promoter, phage lambda $P_L$ promoter, tac promoter, T7 promoter, and the like. In bacterial host cells, suitable promoters include the promoters obtained from the *E. coli* lac operon, *Streptomyces coelicolor* agarase gene (dagA), *Bacillus subtilis* levansucranse gene (sacB), *Bacillus licheniformis* α-amylase gene (amyL), *Bacillus stearothermophilus* maltogenic amylase gene (amyM), *Bacillus amyloliquefaciens* α-amylase gene (amyQ), *Bacillus subtilis* xylA and xylB genes and prokaryotic beta-lactamase gene.

Any other promoter sequence that drives expression in a suitable host cell may be used. Suitable promoter sequences can be identified using well known methods. In one approach, a putative promoter sequence is linked 5' to a sequence encoding a reporter protein, the construct is transfected into the host cell (e.g., *M. thermophila*) and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See e.g., Henriksen et al, Microbiol., 145:729-34 [1999], incorporated herein by reference) or a lacZ reporter gene (Punt et al., Gene, 197:189-93 [1997], incorporated herein by reference). Functional promoters may be derived from naturally occurring promoter sequences by directed evolution methods (See, e.g, Wright et al., Human Gene Therapy, 16:881-892 [2005], incorporated herein by reference.

Additional promoters include those from *M. thermophila*, provided in U.S. Prov. Patent Appln. Ser. Nos. 61/375,702, 61/375,745, 61/375,753, 61/375,755, and 61/375,760, all of which were filed on Aug. 20, 2010, and are hereby incorporated by reference in their entireties, as well as WO 2010/107303.

Other Expression Elements

Cloned GH61 variants may also have a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Suitable transcription terminators are known in the art (See e.g., U.S. Pat. No. 7,399,627, incorporated herein by reference).

Exemplary terminators for yeast host cells include those obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., Yeast 8:423-88 [1992]).

A suitable leader sequence may be part of a cloned GH61 variant sequence, which is a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, sequences also contain a polyadenylation sequence, which is a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known in the art (See e.g., Guo and Sherman, Mol. Cell. Biol., 15:5983-5990 [1995]).

The expression vector of the present invention optionally contains one or more selectable markers, which facilitate easy selection of transformed cells. A selectable marker is a typically gene, the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

Suitable markers for yeast host cells include but are not limited to ADE2, HIS3, LEU2, LYS2, MET3, TRP1, and URA3.

Host Cells

In some embodiments, at least one GH61 variant protein of the present invention is expressed from a nucleic acid that has been recombinantly introduced into a suitable host cell line. In some embodiments, the host cell also expresses other proteins of interest, particularly one or more cellulase enzymes that work in concert with at least one GH61 variant protein in the process of saccharification. The cellulase enzymes may be constitutively expressed by the parent strain of the host cell, or they may be expressed from other recombinant nucleic acids that were introduced serially or simultaneously with the GH61 variant encoding sequence.

Rather than expressing at least one GH61 variant protein and at least one additional cellulase enzyme in the same cell, in some embodiments, the invention is practiced by producing at least one GH61 variant protein in one host cell, and producing one or more cellulases together in another host cell, or in a plurality of host cells. Once such cells have been engineered, cells expressing GH61 protein and cells expressing cellulase enzymes can be combined and cultured together to produce compositions of this invention containing both GH61 variant proteins and other cellulase enzymes. Alternatively, the culture supernatant or broth from each cell line can be collected separately, optionally fractionated to enrich for the respective activities, and then mixed together to produce the desired combination.

Suitable fungal host cells include, but are not limited to *Ascomycota, Basidiomycota, Deuteromycota, Zygomycota*, and *Fungi imperfecti*. In some embodiments, preferred fungal host cells are yeast cells, and filamentous fungal cells, including all filamentous forms of the subdivision *Eumycotina* and *Oomycota*. Filamentous fungi are characterized by a vegetative mycelium with a cell wall composed of chitin, cellulose and other complex polysaccharides, and are morphologically distinct from yeast. In some embodiments, *Trichoderma* is a source of one or more cellulases for use in combination with GH61 variant proteins.

Any suitable host cell finds use in the present invention, including but not limited to host cells that are species of *Achlya, Acremonium, Aspergillus, Aureobasidium, Azospirillum, Bjerkandera, Cellulomonas, Cephalosporium, Ceriporiopsis, Chrysosporium, Clostridium, Coccidioides, Cochliobolus, Coprinus, Coriolus, Corynascus, Cryphonectria, Cryptococcus, Dictyostelium, Diplodia, Elizabethkingia, Endothia, Erwinia, Escherichia, Fusarium, Gibberella, Gliocladium, Gluconacetobacter, Humicola, Hypocrea, Kuraishia, Mucor, Myceliophthora, Neurospora, Nicotiana, Paenibacillus, Penicillium, Periconia, Phaeosphaeria, Phlebia, Piromyces, Podospora, Prevotella, Pyricularia, Rhizobium, Rhizomucor, Rhizopus, Ruminococcus, Saccharomycopsis, Salmonella, Schizophyllum, Scytalidium, Septoria, Sporotrichum, Streptomyces, Talaromyces, Thermoanaerobacter, Thermoascus, Thermotoga, Thielavia, Tolypocladium, Trametes, Trichoderma, Tropaeolum, Uromyces, Verticillium, Volvariella, Wickerhamomyces*, or corresponding teleomorphs, or anamorphs, and synonyms or taxonomic equivalents thereof.

An exemplary host cell is yeast, including but not limited to *Candida, Hansenula, Saccharomyces, Schizosaccharomyces, Pichia, Kluyveromyces*, or *Yarrowia*. In some embodiments, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

Another exemplary host cell is a *Myceliophthora* species, such as *M. thermophila*. As used herein, the term "C1" refers to *Myceliophthora thermophila*, including a fungal strain described by Garg (See, Garg, Mycopathol., 30: 3-4 [1966]). As used herein, "*Chrysosporium lucknowense*" includes the strains described in U.S. Pat. Nos. 6,015,707, 5,811,381 and 6,573,086; US Pat. Pub. Nos. 2007/0238155, US 2008/0194005, US 2009/0099079; International Pat. Pub. Nos., WO 2008/073914 and WO 98/15633, all of which are incorporated herein by reference, and include, without limitation, *Chrysosporium lucknowense* Garg 27K, VKM-F 3500 D (Accession No. VKM F-3500-D), C1 strain UV13-6 (Accession No. VKM F-3632 D), C1 strain NG7C-19 (Accession No. VKM F-3633 D), and C1 strain UV 18-25 (VKM F-3631 D), all of which have been deposited at the All-Russian Collection of Microorganisms of Russian Academy of Sciences (VKM), Bakhurhina St. 8, Moscow, Russia, 113184, and any derivatives thereof. Although initially described as *Chrysosporium lucknowense*, C1 may currently be considered a strain of *Myceliophthora thermophila*. Other C1 strains include cells deposited under accession numbers ATCC 44006, CBS (Centraalbureau voor Schimmelcultures) 122188, CBS 251.72, CBS 143.77, CBS 272,77, CBS122190, CBS122189, and VKM F-3500D. Exemplary C1 derivatives include modified organisms in which one or more endogenous genes or sequences have been deleted or modified and/or one or more heterologous genes or sequences have been introduced. Derivatives include, but are not limited to UV18#100f Δalp1, UV18#100f Δpyr5 Δalp1, UV18#1001Δalp1 Δpep4 Δalp2, UV18#1001 Δpyr5 Δalp1 Δpep4 Δalp2 and UV18#1001Δpyr4 Δpyr5 Δalp1 Δpep4 Δalp2, as described in WO2008073914 and WO2010107303, each of which is incorporated herein by reference.

In some embodiments, the host cell is a *Trichoderma* species, such as *T. longibrachiatum, T. viride, Hypocrea jecorina* or *T. reesei, T. koningii*, and *T. harzianum*.

In some embodiments, the host cell is a *Aspergillus* species, such as *A. awamori, A. funigatus, A. japonicus, A. nidulans, A. niger, A. aculeatus, A. foetidus, A. oryzae, A. sojae*, and *A. kawachi*.

In some additional embodiments, the host cell is a *Fusarium* species, such as *F. bactridioides, F. cerealis, F. crookwellense, F. culmorum, F. graminearum, F. graminum. F. oxysporum, F. roseum*, and *F. venenatum*.

The host cell may also be a *Neurospora* species, such as *N. crassa*. Alternatively, the host cell is a *Humicola* species, such as *H. insolens, H. grisea*, and *H. lanuginosa*. Alternatively, the host cell is a *Mucor* species, such as *M. miehei* and *M. circinelloides*. Alternatively, the host cell is a *Rhizopus* species, such as *R. oryzae* and *R. niveus*. Alternatively, the host cell is a *Penicillum* species, such as *P. purpurogenum, P. chrysogenum*, and *P. verruculosum*.

In some embodiments, the host cell is a *Thielavia* species, such as *T. terrestris*. Alternatively, the host cell is a *Tolypocladium* species, such as *T. inflatum* and *T. geodes*. Alternatively, the host cell is a the *Trametes* species, such as *T. villosa* and *T. versicolor*.

In some embodiments, the host cell is of a *Chrysosporium* species, such as *C. lucknowense, C. keratinophilum, C. tropicum, C. merdarium, C. mops, C. pannicola*, and *C. zonatum*. In a particular embodiment the host is *C. lucknowense*. Alternatively, the host cell is an algae such as *Chlamydotnonas* (e.g., *C. reinhardtii*) or *Phormidium* (P. sp. ATCC29409).

In some alternative embodiments, the host cell is a prokaryotic cell. Suitable prokaryotic cells include Gram-positive, Gram-negative and Gram-variable bacterial cells. Examples of bacterial host cells include, but are not limited to *Bacillus* (e.g., *B. subtilis, B. licheniformis, B. megaterium, B. stearothermophilus* and *B. amyloliquefaciens*), *Streptomyces* (e.g., *S. ambofaciens, S. achromogenes, S. avermitilis, S. coelicolor, S. aureofaciens, S. aureus, S. fungicidicus, S. griseus,* and *S. lividans*), and *Streptococcus* (e.g., *S. equisimiles, S. pyogenes,* and *S. uberis*) species.

Any suitable eukaryotic or prokaryotic species finds use as host cells, including but not limited to *Aspergillus aculeatus, Azospirillum irakense* KBC 1, *Bacillus* sp. GL1, *Cellulomonas biazotea, Clostridium thermocellum, Thermoanaerobacter brockii, Coccidioides posadasii, Dictyostelium discoideum, Elizabethkingia meningoseptica, Erwinia chrysanthemi, Escherichia coli, Gluconacetobacter xylinus, Hypocrea jecorina, Kuraishia capsulata, Nicotiana tabacum, Paenibacillus* sp. C7, *Penicillium brasilianum, Periconia* sp. BCC 2871, *Phaeosphaeria avenaria, Prevotella albensis, Rhizobium leguminosarum, Rhizomucor miehei, Ruminococcus albus, Saccharomycopsis fibuligera, Salmonella typhimurium, Septoria lycopersici, Streptomyces coelicolor, Talaromyces emersonii, Thermotoga maritima, Tropaeolum mains, Uromyces viciae-fabae,* and *Wickerhamomyces anomalus.*

Strains that may be used in the practice of the invention (both prokaryotic and eukaryotic strains) may be obtained from any suitable source, including but not limited to the American Type Culture Collection (ATCC), or other biological depositories such as Deutsche Sammlung von Mikroorganismen und Zellkulturen GmbH (DSM), Centraalbureau Voor Schimmelcultures (CBS), and the Agricultural Research Service Patent Culture Collection, Northern Regional Research Center (NRRL).

In some embodiments, host cells are genetically modified to have characteristics that improve genetic manipulation, protein secretion, protein stability or other properties desirable for expression or secretion of a protein. For example, knock-out of Alp1 function results in a cell that is protease deficient. Knock-out of pyr5 function results in a cell with a pyrimidine deficient phenotype. Host cells may be modified to delete endogenous cellulase protein-encoding sequences or otherwise eliminate expression of one or more endogenous cellulases. Expression of one or more unwanted endogenous cellulases may be inhibited to increase the proportion of cellulases of interest, for example, by chemical or UV mutagenesis and subsequent selection. Homologous recombination can be used to induce targeted gene modifications by specifically targeting a gene in vivo to suppress expression of the encoded protein.

Signal Peptides

In general, polypeptides are secreted from the host cell after being expressed as a pre-protein including a signal peptide (i.e., an amino acid sequence linked to the amino terminus of a polypeptide which directs the encoded polypeptide into the cell's secretory pathway).

In some embodiments, the secreted part of a GH61 variant is linked at the N-terminal to a heterologous signal peptide, depending on the host cell and other factors. Effective signal peptide coding regions for filamentous fungal host cells include but are not limited to signal peptide coding regions obtained from *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola lanuginosa* lipase, and *T. reesei* cellobiohydrolase II (TrCBH2).

Effective signal peptide coding regions for bacterial host cells include but are not limited to signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., described by Simonen and Palva, Microbiol. Rev., 57:109-137 [1993]).

Useful signal peptides for yeast host cells also include those from the genes for *Saccharomyces cerevisiae* alpha-factor, *Saccharomyces cerevisiae* SUC2 invertase (see Taussig and Carlson, Nucl. Acids Res., 11:1943-54 [1983]; SwissProt Accession No. P00724; and Romanos et al., Yeast 8:423-488 [1992]). Variants of these signal peptides and other signal peptides are suitable. In addition, the signal peptides provided herein find use in the present invention.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and μm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); HPLC (high pressure liquid chromatography); MES (2-N-morpholino ethanesulfonic acid); FIOPC (fold improvements over positive control); YPD (10 g/L yeast extract, 20 g/L peptone, and 20 g/L dextrose); SOE-PCR (splicing by overlapping extension PCR); PEG (polyethylene glycol); TWEEN®-20 (TWEEN® non-ionic surfactant; Sigma-Aldrich); ARS (ARS Culture Collection or NRRL Culture Collection, Peoria, Ill.); Axygen (Axygen, Inc., Union City, Calif.); Lallemand (Lallemand Ethanol Technology, Milwaukee, Wis.); Dual Biosystems (Dual Biosystems AG, Schlieven, Switzerland); US Biological (United States Biological, Swampscott, Mass.); Megazyme (Megazyme International Ireland, Ltd., Wicklow, Ireland); Genetix (Genetix USA, Inc., Beaverton, Oreg.); Sigma-Aldrich (Sigma-Aldrich, St. Louis, Mo.); Dasgip (Dasgip Biotools, LLC, Shrewsbury, Mass.); Difco (Difco Laboratories, BD Diagnostic Systems, Detroit, Mich.); PCRdiagnostics (PCR-diagnostics, by *E. coli* SRO, Slovak Republic); Agilent (Agilent Technologies, Inc., Santa Clara, Calif.); Molecular Devices (Molecular Devices, Sunnyvale, Calif.); Symbio (Symbio, Inc., Menlo Park, Calif.); Newport (Newport Scientific, Australia); and Bio-Rad (Bio-Rad Laboratories, Hercules, Calif.).

The *M. thermophila* strains included in the development of the present invention included a "Strain CF-400" (Δcdh1), which is a derivative of C1 strain ("UV18#100fΔalp1Δpyr5"), modified by deletion of cdh1, wherein cdh1 comprises the polynucleotide sequence of SEQ ID NO:5 of U.S. Pat. No. 8,236,551. "Strain CF-401" (Δcdh1 Δcdh2) (ATCC No. PTA-12255), is a derivative of the C1 strain modified by deletion of both a cdh1 and a cdh2, wherein cdh2 comprises the polynucleotide sequence of SEQ ID NO:7 of U.S. Pat. No. 8,236,551. "Strain CF-402" (+Bgl1) is a derivative of the C1 strain further modified for overexpression of an endogenous beta-glucosidase 1 enzyme (Bgl1). "Strain CF-403" is a derivative of the C1 strain modified with a deletion of cdh1 and further modified to overexpress bgl1

"Strain CF-404" is a derivative of the C1 strain further modified to overexpress bgl1 with a deletion of both cdh1 and cdh2. "Strain CF-416" is a derivative of the CF-404 strain, further modified to overexpress wild-type GH61a enzyme.

The following sequences are referred to herein and find use in the present invention

```
Wild-type M. thermophila C1 GH61a cDNA sequence:
                                                        (SEQ ID NO: 1)
ATGTCCAAGGCCTCTGCTCTCCTCGCTGGCCTGACGGGCGCGGCCCTCGTCGCTGCACATGG

CCACGTCAGCCACATCGTCGTCAACGGCGTCTACTACAGGAACTACGACCCCACGACAGACT

GGTACCAGCCCAACCCGCCAACAGTCATCGGCTGGACGGCAGCCGATCAGGATAATGGCTT

CGTTGAACCCAACAGCTTTGGCACGCCAGATATCATCTGCCACAAGAGCGCCACCCCCGGCG

GCGGCCACGCTACCGTTGCTGCCGGAGACAAGATCAACATCGTCTGGACCCCCGAGTGGCCC

GAATCCCACATCGGCCCCGTCATTGACTACCTAGCCGCCTGCAACGGTGACTGCGAGACCGT

CGACAAGTCGTCGCTGCGCTGGTTCAAGATTGACGGCGCCGGCTACGACAAGGCCGCCGGC

CGCTGGGCCGCCGACGCTCTGCGCGCCAACGGCAACAGCTGGCTCGTCCAGATCCCGTCGGA

TCTCAAGGCCGGCAACTACGTCCTCCGCCACGAGATCATCGCCCTCCACGGTGCTCAGAGCC

CCAACGGCGCCCAGGCCTACCCGCAGTGCATCAACCTCCGCGTCACCGGCGGCGGCAGCAA

CCTGCCCAGCGGCGTCGCCGGCACCTCGCTGTACAAGGCGACCGACCCGGGCATCCTCTTCA

ACCCCTACGTCTCCTCCCCGGATTACACCGTCCCCGGCCCGGCCCTCATTGCCGGCGCCGCC

AGCTCGATCGCCCAGAGCACGTCGGTCGCCACTGCCACCGGCACGGCCACCGTTCCCGGCGG

CGGCGGCGCCAACCCTACCGCCACCACCACCGCCGCCACCTCCGCCGCCCCGAGCACCACCC

TGAGGACGACCACTACCTCGGCCGCGCAGACTACCGCCCCGCCCTCCGGCGATGTGCAGACC

AAGTACGGCCAGTGTGGTGGCAACGGATGGACGGGCCCGACGGTGTGCGCCCCCGGCTCGA

GCTGCTCCGTCCTCAACGAGTGGTACTCCCAGTGTTTGTAA

Wild-type M. thermophila C1 GH61a polypeptide sequence:
                                                        (SEQ ID NO: 2)
MSKASALLAGLTGAALVAAHGHVSHIVVNGVYYRNYDPTTDWYQPNPPTVIGWTAADQDNGF

VEPNSEGTPDIICHKSATPGGGHATVAAGDKINIVWTPEWPESHIGPVIDYLAACNGDCETVDKSS

LRWFKIDGAGYDKAAGRWAADALRANGNSWLVQIPSDLKAGNYVLRHEIIALHGAQSPNGAQ

AYPQCINLRVTGGGSNLPSGVAGTSLYKATDPGILFNPYVSSPDYTVPGPALIAGAASSIAQSTSV

ATATGTATVPGGGGANPTATTTAATSAAPSTTLRTTTTSAAQTTAPPSGDVQTKYGQCGGNGW

TGPTVCAPGSSCSVLNEWYSQCL

Wild-type M. thermophila C1 GH61a polypeptide sequence
without the signal sequence:
                                                        (SEQ ID NO: 3)
HGHVSHIVVNGVYYRNYDPTTDWYQPNPPTVIGWTAADQDNGFVEPNSFGTPDIICHKSATPGG

GHATVAAGDKINIVWTPEWPESHIGPVIDYLAACNGDCETVDKSSERWFKIDGAGYDKAAGRW

AADALRANGNSWLVQIPSDLKAGNYVLRHEIIALHGAQSPNGAQAYPQCINLRVTGGGSNLPSG

VAGTSLYKATDPGILFNPYVSSPDYTVPGPALIAGAASSIAQSTSVATATGTATVPGGGGANPTA

TTTAATSAAPSTTLRTTTTSAAQTTAPPSGDVQTKYGQCGGNGWTGPTVCAPGSSCSVLNEWYS

QCL

GH61a Variant 1 cDNA sequence:
                                                        (SEQ ID NO: 4)
ATGTCCAAGGCCTCTGCTCTCCTCGCTGGCCTGACGGGCGCGGCCCTCGTCGCTGCACACGG

CCACGTCAGCCACATCGTCGTCAACGGCGTCTACTACAGGGGCTACGACCCCACGACAGACT

GGTACCAGCCCAACCCGCCAACAGTCATCGGCTGGACGGCAGCCGATCAGGATAATGGCTT
```

-continued

```
CGTTGAACCCAACAGCTTTGGCACGCCAGATATCATCTGCCACAAGAGCGCCACCCCCGGCG

GCGGCCACGCTACCGTTGCTGCCGGAGACAAGATCAACATCGTCTGGACCCCCGAGTGGCCC

CACTCCCACATCGGCCCCGTCATTGACTACCTAGCCGCCTGCAACGGTGACTGCGAGACCGT

CGACAAGTCGTCGCTGCGCTGGTTCAAGATTGACGGCGCCGGCTACGACAAGGCCGCCGGC

CGCTGGGCCGCCGACGCTCTGCGCGCCAACGGCAACAGCTGGCTCGTCCAGATCCCGTCGGA

TCTCAAGCCCGGCAACTACGTCCTCCGCCACGAGATCATCGCCCTCCACGGTGCTCAGAGCC

CCAACGGCGCCCAGGCGTACCCGCAGTGCATCAACCTCCGCGTCACCGGCGGCGGCAGCAA

CCTGCCCAGCGGCGTCGCCGGCACCTCGCTGTACAAGGCGACCGACCCGGGCATCCTCTTCA

ACCCCTACGTCTCCTCCCCGGATTACACCGTCCCCGGCCCGGCCCTCATTGCCGGCGCCGCC

AGCTCGATCGCCCAGAGCACGTCGGTCGCCACTGCCACCGGCACGGCCACCGTTCCCGGCGG

CGGCGGCGCCAACCCTACCGCCACCACCACCGCCGCCACCTCCGCCGCCCCGAGCACCACCC

TGAGGACGACCACTACCTCGGCCGCGCAGACTACCGCCCCGCCCTCCGGCGATGTGCAGACC

AAGTACGGCCAGTGTGGTGGCAACGGATGGACGGGCCCGACGGTGTGCGCCCCCGGCTCGA

GCTGCTCCGTCCTCAACGAGTGGTACTCCCAGTGTTTGTAA

GH61a Variant 1 polypeptide sequence:
                                                   (SEQ ID NO: 5)
MSKASALLAGLTGAALVAAHGHVSHIVVNGVYYRGYDPTTDWYQPNPPTVIGWTAADQDNGF

VEPNSFGTPDIICHKSATPGGGHATVAAGDKINIVWTPEWPHSHIGPVIDYLAACNGDCETVDKS

SLRWFKIDGAGYDKAAGRWAADALRANGNSWLVQIPSDLKPGNYVLRHEIIALHGAQSPNGAQ

AYPQCINLRVTGGGSNLPSGVAGTSLYKATDPGILFNPYVSSPDYTVPGPALIAGAASSIAQSTSV

ATATGTATVPGGGGANPTATTTAATSAAPSTTLRTTTTSAAQTTAPPSGDVQTKYGQCGGNGW

TGPTVCAPGSSCSVLNEWYSQCL

GH61a Variant 1 polypeptide sequence without the
signal sequence:
                                                   (SEQ ID NO: 6)
HGHVSHIVVNGVYYRGYDPTTDWYQPNPPTVIGWTAADQDNGFVEPNSFGTPDIICHKSATPGG

GHATVAAGDKINIVWTPEWPHSHIGPVIDYLAACNGDCETVDKSSLAWFKIDGAGYDKAAGRW

AADALRANGNSWINQIPSDLKPGNYVLRHEIIALHGAQSPNGAQAYPQCINLRVTGGGSNLPSG

VAGTSLYKATDPGILFNPYYSSPDYTVPGPALIAGAASSIAQSTSVATATGTATVPGGGGANPTA

TTTAATSAAPSTTLRTTTTSAAQTTAPPSGDVQTKYGQCGGNGWTGPTVCAPGSSCSVLNEWYS

QCL

GH61a Variant 5 cDNA sequence
                                                   (SEQ ID NO: 7)
ACACAAATGTCCAAGGCCTCTGCTCTCCTCGCTGGCCTGACGGGCGCGGCCCTCGTCGCTGC

ACACGGCCACGTCAGCCACATCGTCGTCAACGGCGTCTACTACAGGAACTACGACCCCACG

ACAGACTGGTACCAGCCCAACCCGCCAACAGTCATCGGCTGGACGGCAGCCGATCAGGATA

ATGGCTTCGTTGAACCCAACAGCTTTGGCACGCCAGATATCATCTGCCACAAGAGCGCCACC

CCCGGCGGCGGCCACGCTACCGTTGCTGCCGGAGACAAGATCAACATCGTATGGACCCCCG

AGTGGCCCCACTCCCACATCGGCCCCGTCATTGACTACCTAGCCGCCTGCAACGGTGACTGC

GAGACCGTCGACAAGTCGTCGCTGCGCTGGTTCAAGATTGACGGCGCCGGCTACGACAAGG

CCGCCGCCGCTGGGCCGCCGACGCTCTGCGCGCCAACGGCAACAGCTGGCTCGTCCAGATC

CCGTCGGATCTCGCGGCCGGCAACTACGTCCTCCGCCACGAGATCATCGCCCTCCACGGTGC

TCAGAGCCCAACGGCGCCCAGGCGTACCCGCAGTGCATCAACCTCCGCGTCACCGGCGGC

GGCAGCAACCTGCCCAGCGGCGTCGCCGGCACCTCGCTGTACAAGGCGACCGACCCGGGCA
```

-continued

```
TCCTCTTCAACCCCTACGTCTCCTCCCCGGATTACACCGTCCCCGGCCCGGCCCTCATTGCCG

GCGCCGCCAGCTCGATCGCCCAGAGCACGTCGGTCGCCACTGCCACCGGCACGGCCACCGTT

CCCGGCGGCGGCGGCGCCAACCCTACCGCCACCACCACCGCCGCCACCTCCGCCGCCCCGA

GCACCACCCTGAGGACGACCACTACCTCGGCCGCGCAGACTACCGCCCCGCCCTCCGGCGAT

GTGCAGACCAAGTACGGCCAGTGTGGTGGCAACGGATGGACGGGCCCGACGGTGTGCGCCC

CCGGCTCGAGCTGCTCCGTCCTCAACGAGTGGTACTCCCAGTGTTTGTAA
```

GH61a Variant 5 polypeptide sequence:
(SEQ ID NO: 8)

```
MSKASALLAGLTGAALVAAHGHVSHIVVNGVYYRNYDPTTDWYQPNPPTVIGWTAADQDNGF

VEPNSEGTPDIICHKSATPGGGHATVAAGDKINIVWTPEWPHSHIGPVIDYLAACNGDCETVDKS

SLRWFKIDGAGYDKAAGRWAADALRANGNSWINQIPSDLAAGNYVLRHEIIALHGAQSPNGAQ

AYPQCINLRVTGGGSNLPSGVAGTSLYKATDPGILFNPYVSSPDYTVPGPALIAGAASSIAQSTSV

ATATGTATVPGGGGANPTATTTAATSAAPSTTLRITTTSAAQTTAPPSGDVQTKYGQCGGNGW

TGPTVCAPGSSCSVLNEWYSQCL
```

GH61a Variant 5 polypeptide sequence without the signal sequence:
(SEQ ID NO: 9)

```
HGHVSHIVVNGVYYRNYDPTTDWYQPNPPTVIGWTAADQDNGFVEPNSEGTPDIICHKSATPGG

GHATVAAGDKINIVWTPEWPHSHIGPVIDYLAACNGDCETVDKSSIRWFKIDGAGYDKAAGRW

AADALRANGNSWLVQIPSDLAAGNYVLRHEIIALHGAQSPNGAQAYPQCINLRVTGGGSNLPSG

VAGTSLYKATDPGILFNPYVSSPDYTVPGPALIAGAASSIAQSTSVATATGTATVPGGGGANPTA

TTTAATSAAPSTTLRTTTTSAAQTTAPPSGDVQTKYGQCGGNGWTGPTVCAPGSSCSVLNEWYS

QCL
```

GH61a Variant 9 cDNA sequence:
(SEQ ID NO: 10)

```
ACAAACATGTCCAAGGCCTCTGCTCTCCTCGCTGGCCTGACGGGCGCGGCCCTCGTCGCTGC

ACATGGCCACGTCAGCCACATCGTCGTCAACGGCGTCTACTACAGGAACTACGACCCCACGA

CAGACTGGTACCAGCCCAACCCGCCAACAGTCATCGGCTGGACGGCAGCCGATCAGGATAA

TGGCTTCGTTGAACCCAACAGCTTTGGCACGCCAGATATCATCTGCCACAAGAGCGCCACCC

CCGGCGGCGGCCACGCTACCGTTGCTGCCGGAGACAAGATCAACATCCAGTGGACCCCCGA

GTGGCCCGAATCCCACATCGGCCCCGTCATTGACTACCTAGCCGCCTGCAACGGTGACTGCG

AGACCGTCGACAAGTCGTCGCTGCGCTGGTTCAAGATTGACGGCGCCGGCTACGACAAGGC

CGCCGGCCGCTGGGCCGCCGACGCTCTGCGCGCCAACGGCAACAGCTGGCTCGTCCAGATCC

CGTCGGATCTCAAGGCCGGCAACTACGTCCTCCGCCACGAGATCATCGCCCTCCACGGTGCT

CAGAGCCCCAACGGCGCCCAGAACTACCCGCAGTGCATCAACCTCCGCGTCACCGGCGGCG

GCAGCAACCTGCCCAGCGGCGTCGCCGGCACCTCGCTGTACAAGGCGACCGACCCGGGCAT

CCTCTTCAACCCCTACGTCTCCTCCCCGGATTACACCGTCCCCGGCCCGGCCCTCATTGCCGG

CGCCGCCAGCTCGATCGCCCAGAGCACGTCGGTCGCCACTGCCACCGGCACGGCCACCGTTC

CCGGCGGCGGCGGCGCCAACCCTACCGCCACCACCACCGCCGCCACCTCCGCCGCCCCGAG

CACCACCCTGAGGACGACCACTACCTCGGCCGCGCAGACTACCGCCCCGCCCTCCGGCGATG

TGCAGACCAAGTACGGCCAGTGTGGTGGCAACGGATGGACGGGCCCGACGGTGTGCGCCCC

CGGCTCGAGCTGCTCCGTCCTCAACGAGTGGTACTCCCAGTGTTTGTAA
```

-continued

GH61a Variant 9 polypeptide sequence:
(SEQ ID NO: 11)
<u>MSKASALLAGLTGAALVAA</u>HGHVSHIVVNGVYYRNYDPTTDWYQPNPPTVIGWTAADQDNGF

VEPNSEGTPDIICHKSATPGGGHATVAAGDKINIQWTPEWPESHIGPVIDYLAACNGDCETVDKSS

LRWFKIDGAGYDKAAGRWAADALRANGNSWLVQIPSDLKAGNYVLRHEIIALHGAQSPNGAQ

NYPQCINLRVTGGGSNLPSGVAGTSLYKATDPGILFNPYVSSPDYTVPGPALIAGAASSIAQSTSV

ATATGTATVPGGGGANPTATTTAATSAAPSTTLRTTTTSAAQTTAPPSGDVQTKYGQCGGNGW

TGPTVCAPGSSCSVLNEWYSQCL

GH61a Variant 9 polypeptide sequence without the signal sequence:
(SEQ ID NO: 12)
<u>MSKASALLAGLTGAALVAA</u>HGHVSHIVVNGVYYRNYDPTTDWYQPNPPTVIGWTAADQDNGF

VEPNSFGTPDIICHKSATPGGGHATVAAGDKINIQWTPEWPESHIGPVIDYLAACNGDCETVDKSS

LRWFKIDGAGYDKAAGRWAADALRANGNSWLVQIPSDLKAGNYVLRHEIIALHGAQSPNGAQ

NYPQCINLRVTGGGSNLPSGVAGTSLYKATDPGILFNPYVSSPDYTVPGPALIAGAASSIAQSTSV

ATATGTATVPGGGGANPTATTTAATSAAPSTTLRTTTTSAAQTTAPPSGDVQTKYGQCGGNGW

TGPTVCAPGSSCSVLNEWYSQCL

The polynucleotide (SEQ ID NO:13) and amino acid (SEQ ID NO:14) sequences of an *M. thermophila* GH61b are provided below. The signal sequence is shown underlined in SEQ ID NO:14. SEQ ID NO:15 provides the sequence of this GH61b without the signal sequence.

The polynucleotide (SEQ ID NO:16) and amino acid (SEQ ID NO:17) sequences of an *M. thermophila* GH61c are provided below. The signal sequence is shown underlined in SEQ ID NO:17. SEQ ID NO:18 provides the sequence of this GH61c without the signal sequence.

(SEQ ID NO: 13)
ATGAAGCTCTCCCTCTTTTCCGTCCTGGCCACTGCCCTCACCGTCGAGGGGCATGCCATCTTC

CAGAAGGTCTCCGTCAACGGAGCGGACCAGGGCTCCCTCACCGGCCTCCGCGCTCCCAACA

ACAACAACCCCGTGCAGAATGTCAACAGCCAGGACATGATCTGCGGCCAGTCGGGATCGAC

GTCGAACACTATCATCGAGGTCAAGGCCGGCGATAGGATCGGTGCCTGGTATCAGCATGTCA

TCGGCGGTGCCCAGTTCCCCAACGACCCAGACAACCCGATTGCCAAGTCGCACAAGGGCCC

CGTCATGGCCTACCTCGCCAAGGTTGACAATGCCGCAACCGCCAGCAAGACGGGCCTGAAG

TGGTTCAAGATTTGGGAGGATACCTTTAATCCCAGCACCAAGACCTGGGGTGTCGACAACCT

CATCAACAACAACGGCTGGGTGTACTTCAACCTCCCGCAGTGCATCGCCGACGGCAACTACC

TCCTCCGCGTCGAGGTCCTCGCTCTGCACTCGGCCTACTCCCAGGGCCAGGCTCAGTTCTACC

AGTCCTGCGCCCAGATCAACGTATCCGGCGGCGGCTCCTTCACGCCGGCGTCGACTGTCAGC

TTCCCGGGTGCCTACAGCGCCAGCGACCCCGGTATCCTGATCAACATCTACGGCGCCACCGG

CCAGCCCGACAACAACGGCCAGCCGTACACTGCCCCTGGGCCCGCGCCCATCTCCTGC (SEQ ID NO: 14)
<u>MKLSLFSVLATALTVEGHA</u>IFQKVSVNGADQGSLTGLRAPNNNNPVQNVNSQDMICGQSGSTSN

TIIEVKAGDRIGAWYQHVIGGAQFPNDPDNPIAKSHKGPVMAYLAKVDNAATASKTGLKWFKI

WEDTFNPSTKTWGVDNLINNNGWVYFNLPQCIADGNYLLRVEVLALHSAYSQGQAQFYQSCAQ

INVSGGGSFTPASTVSFPGAYSASDPGILINIYGATGQPDNNGQPYTAPGPAPISC (SEQ ID NO: 15)
IFQKVSVNGADQGSLTGLRAPNNNNPVQNVNSQDMICGQSGSTSNTIIEVKAGDRIGAWYQHVI

GGAQFPNDPDNPIAKSHKGPVMAYLAKVDNAATASKTGLKWFKIWEDTFNPSTKTWGVDNLIN

NNGWVYFNLPQCIADGNYLLRVEVLALHSAYSQGQAQFYQSCAQINVSGGGSFTPASTVSFPGA

YSASDPGILINIYGATGQPDNNGQPYTAPGPAPISC (SEQ ID NO: 16)
ATGGCCCTCCAGCTCTTGGCGAGCTTGGCCCTCCTCTCAGTGCCGGCCCTTGCCCACGGTGGC

TTGGCCAACTACACCGTCGGTGATACTTGGTACAGAGGCTACGACCCAAACCTGCCGCCGGA

GACGCAGCTCAACCAGACCTGGATGATCCAGCGGCAATGGGCCACCATCGACCCCGTCTTCA

CCGTGTCGGAGCCGTACCTGGCCTGCAACAACCCGGGCGCGCCGCCGCCCTCGTACATCCCC

ATCCGCGCCGGTGACAAGATCACGGCCGTGTACTGGTACTGGCTGCACGCCATCGGGCCCAT

GAGCGTCTGGCTCGCGCGGTGCGGCGACACGCCCGCGGCCGACTGCCGCGACGTCGACGTC

AACCGGGTCGGCTGGTTCAAGATCTGGGAGGGCGGCCTGCTGGAGGGTCCCAACCTGGCCG

AGGGGCTCTGGTACCAAAAGGACTTCCAGCGCTGGGACGGCTCCCCGTCCCTCTGGCCCGTC

ACGATCCCCAAGGGGCTCAAGAGCGGGACCTACATCATCCGGCACGAGATCCTGTCGCTTCA

CGTCGCCCTCAAGCCCCAGTTTTACCCGGAGTGTGCGCATCTGAATATTACTGGGGGCGGAG

ACTTGCTGCCACCCGAAGAGACTCTGGTGCGGTTTCCGGGGGTTTACAAAGAGGACGATCCC

TCTATCTTCATCGATGTCTACTCGGAGGAGAACGCGAACCGGACAGATTATACGGTTCCGGG

AGGGCCAATCTGGGAAGGG (SEQ ID NO: 17)
<u>MALQLLASLALLSVPALAHGG</u>LANYTVGDTWYRGYDPNLPPETQLNQTWMIQRQWATIDPVFT

VSEPYLACNNPGAPPPSYIPLRAGDKITAVYWYWLHAIGPMSVWLARCGDTPAADCRDVDVNR

VGWFKIWEGGLLEGPNLAEGLWYQKDFQRWDGSPSLWPVTIPKGLKSGTYIIRHEILSLHVALKP

QFYPECAHLNITGGGDLLPPEETLVRFPGVYKEDDPSIFIDVYSEENANRTDYTVPGGPIWEG (SEQ ID NO: 18)
NYTVGDTWYRGYDPNLPPETQLNQTWMIQRQWATIDPVFTVSEPYLACNNPGAPPPSYIPIRAG

DKITAVYWYWLHAIGPMSVWLARCGDTPAADCRDVDVNRVGWFKIWEGGLLEGPNLAEGLW

YQKDFQRWDGSPSLWPVTIPKGLKSGTYIIRHEILSLHVALKPQFYPECAHLNITGGGDLLPPEET

LVRFPGVYKEDDPSIFIDVYSEENANRTDYTVPGGPIWEG

The polynucleotide (SEQ ID NO:19) and amino acid (SEQ ID NO:20) sequences of an *M. thermophila* GH61d are provided below. The signal sequence is shown underlined in SEQ ID NO:20. SEQ ID NO:21 provides the sequence of this GH61d without the signal sequence.

(SEQ ID NO: 19)
ATGAAGGCCCTCTCTCTCCTTGCGGCTGCCGGGGCAGTCTCTGCGCATACCATCTTCGTCCAG

CTCGAAGCAGACGGCACGAGGTACCCGGTTTCGTACGGGATCCGGGACCCAACCTACGACG

GCCCCATCACCGACGTCACATCCAACGACGTTGCTTGCAACGGCGGTCCGAACCCGACGACC

CCCTCCAGCGACGTCATCACCGTCACCGCGGGCACCACCGTCAAGGCCATCTGGAGGCACAC

CCTCCAATCCGGCCCGGACGATGTCATGGACGCCAGCCACAAGGGCCCGACCCTGGCCTAC

ATCAAGAAGGTCGGCGATGCCACCAAGGACTCGGGCGTCGGCGGTGGCTGGTTCAAGATCC

AGGAGGACGGTTACAACAACGGCCAGTGGGGCACCAGCACCGTTATCTCCAACGGCGGCGA

GCACTACATTGACATCCCGGCCTGCATCCCCGAGGGTCAGTACCTCCTCCGCGCCGAGATGA

TCGCCCTCCACGCGGCCGGGTCCCCGGCGGCGCTCAGCTCTACATGGAATGTGCCCAGATC

AACATCGTCGGCGGCTCCGGCTCGGTGCCCAGCTCGACGGTCAGCTTCCCCGGCGCGTATAG

CCCCAACGACCCGGGTCTCCTCATCAACATCTATTCCATGTCGCCCTCGAGCTCGTACACCAT

CCCGGGCCCGCCCGTTTTCAAGTGC

-continued (SEQ ID NO: 20)
<u>MKALSLLAAAGAVSA</u>HTIFVQLEADGTRYPVSYGIRDPTYDGPITDVTSNDVACNGGPNPTTPSS

DVITVTAGTTVKAIWRHTLQSGPDDVMDASHKGPTLAYIKKVGDATKDSGVGGGWFKIQEDGY

NNGQWGTSTVISNGGEHYIDIPACIPEGQYLLRAEMIALHAAGSPGGAQLYMECAQINIVOGSGS

VPSSTVSFPGAYSPNDPGLLINIYSMSPSSSYTIPGPPVFKC (SEQ ID NO: 21)
HTIFVQLEADGTRYPVSYGIRDPTYDGPITDVTSNDVACNGGPNPTTPSSDVITVTAGTTVKAIWR

HTLQSGPDDVMDASHKGPTLAYIKKVGDATKDSGVGGGWFKIQEDGYNNGQWGTSTVISNGG

EHYIDIPACIPEGQYLLRAEMIALHAAGSPGGAQLYMECAQINIVGGSGSVPSSTVSFPGAYSPND

PGLLINIYSMSPSSSYTIPGPPVFKC

The polynucleotide (SEQ ID NO:22) and amino acid (SEQ ID NO:23) sequences of an *M. thermophila* GH61e are provided below. The signal sequence is shown underlined in SEQ ID NO:23. SEQ ID NO:24 provides the sequence of this GH61d without the signal sequence, The polynucleotide (SEQ ID NO:25) and amino acid (SEQ ID NO:26) sequences of an alternative *M. thermophila* GH61e are provided below. The signal sequence is shown underlined in SEQ ID NO:26. SEQ ID NO:27 provides the sequence of this GH61e without the signal sequence.

(SEQ ID NO: 22)
ATGAAGTCGTCTACCCCGGCCTTGTTCGCCGCTGGGCTCCTTGCTCAGCATGCTGCGGCCCAC

TCCATCTTCCAGCAGGCGAGCAGCGGCTCGACCGACTTTGATACGCTGTGCACCCGGATGCC

GCCCAACAATAGCCCCGTCACTAGTGTGACCAGCGGCGACATGACCTGCAAAGTCGGCGGC

ACCAAGGGGGTGTCCGGCTTCTGCGAGGTGAACGCCGGCGACGAGTTCACGGTTGAGATGC

ACGCGCAGCCCGGCGACCGCTCGTGCGCCAACGAGGCCATCGGCGGGAACCACTTCGGCCC

GGTCCTCATCTACATGAGCAAGGTCGACGACGCCTCCACCGCCGACGGGTCCGGCGACTGGT

TCAAGGTGGACGAGTTCGGCTACGACGCAAGCACCAAGACCTGGGGCACCGACAAGCTCAA

CGAGAACTGCGGCAAGCGCACCTTCAACATCCCCAGCCACATCCCCGCGGGCGACTATCTCG

TCCGGGCCGAGGCTATCGCGCTACACACTGCCAACCAGCCAGGCGGCGCGCAGTTCTACATG

AGCTGCTATCAAGTCAGGATTTCCGGCGGCGAAGGGGCCAGCTGCCTGCCGGAGTCAAGA

TCCCGGGCGCGTACAGTGCCAACGACCCCGGCATCCTTGTCGACATCTGGGGTAACGATTTC

AACGACCCTCCAGGACACTCGGCCCGTCACGCCATCATCATCATCAGCAGCAGCAGCAACA

ACAGCGGCGCCAAGATGACCAAGAAGATCCAGGAGCCCACCATCACATCGGTCACGGACCT

CCCCACCGACGAGGCCAAGTGGATCGCGCTCCAAAAGATCTCGTACGTGGACCAGACGGGC

ACGGCGCGGACATACGAGCCGGCGTCGCGCAAGACGCGGTCGCCAAGAGTCTAG (SEQ ID NO: 23)
<u>MKSSTPALFAAGLLAQHAAA</u>HSIFQQASSGSTDFDTLCTRMPPNNSPVTSVTSGDMTCKVGGTK

GVSGFCEVNAGDEETVEMHAQPGDRSCANEAIGGNHFGPVLIYMSKVDDASTADGSGDWFKVD

EFGYDASTKTWGTDKLNENCGKRTFNIPSHIPAGDYLVRAEAIALHTANQPGGAQFYMSCYQVR

ISGGEGGQLPAGVKIPGAYSANDPGILVDIWGNDFNDPPGHSARHAIIISSSSNNSGAKMTKKIQE

PTITSVTDLPTDEAKWIALQKISYVDQTGTARTYEPASRKTRSPRV (SEQ ID NO: 24)
HSIFQQASSGSTDFDTLETRMPPNNSPVTSVTSGDMTCKVGGTKGVSGFCEVNAGDEFTVEMHA

QPGDRSCANEAIGGNHFGPVLIYMSKVDDASTADGSGDWFKVDEFGYDASTKTWGTDKLNENC

GKRTFNIPSHIPAGDYLVRAEAIALHTANQPGGAQFYMSCYQVRISGGEGGQLPAGVKIPGAYSA

NDPGILVDIWGNDFNDPPGHSARHAIIISSSSNNSGAKMTKKIQEPTITSVTDEPTDEAKWIALQKI

SYVDQTGTARTYEPASRKTRSPRV (SEQ ID NO: 25)
ATGAAGTCGTCTACCCCGGCCTTGTTCGCCGCTGGGCTCCTTGCTCAGCATGCTGCGGCCCAC

TCCATCTTCCAGCAGGCGAGCAGCGGCTCGACCGACTTTGATACGCTGTGCACCCGGATGCC

GCCCAACAATAGCCCCGTCACTAGTGTGACCAGCGGCGACATGACCTGCAACGTCGGCGGC

ACCAAGGGGGTGTCGGGCTTCTGCGAGGTGAACGCCGGCGACGAGTTCACGGTTGAGATGC

ACGCGCAGCCCGGCGACCGCTCGTGCGCCAACGAGGCCATCGGCGGGAACCACTTCGGCCC

GGTCCTCATCTACATGAGCAAGGTCGACGACGCCTCCACTGCCGACGGGTCCGGCGACTGGT

TCAAGGTGGACGAGTTCGGCTACGACGCAAGCACCAAGACCTGGGGCACCGACAAGCTCAA

CGAGAACTGCGGCAAGCGCACCTTCAACATCCCCAGCCACATCCCCGCGGGCGACTATCTCG

TCCGGGCCGAGGCTATCGCGCTACACACTGCCAACCAGCCAGGCGGCGCGCAGTTCTACATG

AGCTGCTATCAAGTCAGGATTTCCGGCGGCGAAGGGGCCAGCTGCCTGCCGGAGTCAAGA

TCCCGGGCGCGTACAGTGCCAACGACCCCGGCATCCTTGTCGACATCTGGGGTAACGATTTC

AACGAGTACGTTATTCCGGGCCCCCCGGTCATCGACAGCAGCTACTTC (SEQ ID NO: 26)
MKSSTPALFAAGLLAQHAAAHSIFQQASSGSTDFDTLCTRMPPNNSPVTSVTSGDMTCNVGGTK

GVSGFCEVNAGDEFTVEMHAQPGDRSCANEAIGGNHFGPVLIYMSKVDDASTADGSGDWFKVD

EFGYDASTKTWGTDKLNENCGKRTFNIPSHIPAGDYLVRAEAIALHTANQPGGAQFYMSCYQVR

ISGGEGGQLPAGVKIPGAYSANDPGILVDIWGNDFNEYVIPGPPVIDSSYF (SEQ ID NO: 27)
HSIFQQASSGSTDFDTLCTRMPPNNSPVTSVTSGDMTCNVGGTKGVSGFCEVNAGDEFTVEMHA

QPGDRSCANEAIGGNHFGPVLIYMSKVDDASTADGSGDWFKVDEFGYDASTKTWGTDKLNENC

GKRTFNIPSHIPAGDYLVRAEAIALHTANQPGGAQFYMSCYQVRISGGEGGQLPAGVKIPGAYSA

NDPGILVDIWGNDFNEYVIPGPPVIDSSYF

The polynucleotide (SEQ ID NO:28) and amino acid (SEQ ID NO:29) sequences of a *M. thermophila* GH61f are provided below. The signal sequence is shown underlined in SEQ ID NO:29. SEQ ID NO:30 provides the sequence of this GH61f without the signal sequence.

(SEQ ID NO: 28)
ATGAAGTCCTTCACCCTCACCACTCTGGCCGCCCTGGCTGGCAACGCCGCCGCTCACGCGAC

CTTCCAGGCCCTCTGGGTCGACGGCGTCGACTACGGCGCGCAGTGTGCCCGTCTGCCCGCGT

CCAACTCGCCGGTCACCGACGTGACCTCCAACGCGATCCGCTGCAACGCCAACCCCTCGCCC

GCTCGGGGCAAGTGCCCGGTCAAGGCCGGCTCGACCGTTACGGTCGAGATGCATCAGCAAC

CCGGTGACCGCTCGTGCAGCAGCGAGGCGATCGGCGGGCGCACTACGGCCCCGTGATGGT

GTACATGTCCAAGGTGTCGGACGCGGCGTCGGCGGACGGGTCGTCGGGCTGGTTCAAGGTG

TTCGAGGACGGCTGGGCCAAGAACCCGTCCGGCGGGTCGGGCGACGACGACTACGGGGCA

CCAAGGACCTGAACTCGTGCTGCGGGAAGATGAACGTCAAGATCCCCGCCGACCTGCCCTC

GGGCGACTACCTGCTCCGGGCCGAGGCCTCGCGCTGCACACGGCCGGCAGCGCGGGCGGC

GCCCAGTTCTACATGACCTGCTACCAGCTCACCGTGACCGGCTCCGGCAGCGCCAGCCCGCC

CACCGTCTCCTTCCCGGGCGCCTACAAGGCCACCGACCCGGGCATCCTCGTCAACATCCACG

CCCCGCTGTCCGGCTACACCGTGCCCGGCCCGGCCGTCTACTCGGGCGGCTCCACCAAGAAG

GCCGGCAGCGCCTGCACCGGCTGCGAGTCCACTTGCGCCGTCGGCTCCGGCCCCACCGCCAC

CGTCTCCCAGTCGCCCGGTTCCACCGCCACCTCGGCCCCCGGCGGCGGCGGCGGCTGCACCG

```
TCCAGAAGTACCAGCAGTGCGGCGGCCAGGGCTACACCGGCTGCACCAACTGCGCGTCCGG

CTCCACCTGCAGCGCGGTCTCGCCGCCCTACTACTCGCAGTGCGTC
```

```
                                                        (SEQ ID NO: 29)
MKSFTLTTLAALAGNAAAHATFQALWVDGVDYGAQCARLPASNSPVTDVTSNAIRCNANPSPA

RGKCPVKAGSTVTVEMHQQPGDRSCSSEAIGGAHYGPVMVYMSKVSDAASADGSSGWFKVFE

DGWAKNPSGGSGDDDYWGTKDLNSCCGKMNVKIPADLPSGDYLLRAEALALHTAGSAGGAQF

YMTCYQLTVTGSGSASPPTVSFPGAYKATDPGILVNIHAPLSGYTVPGPAVYSGGSTKKAGSACT

GCESTCAVGSGPTATVSQSPGSTATSAPGGGGGCTVQKYQQCGGQGYTGCTNCASGSTCSAVSP

PYYSQCV
```

```
                                                        (SEQ ID NO: 30)
HATFQALWVDGVDYGAQCARLPASNSPVTDVTSNAIRCNANPSPARGKCPVKAGSTVTVEMHQ

QPGDRSCSSEAIGGAHYGPVMVYMSKVSDAASADGSSGWFKVFEDGWAKNPSGGSGDDDYW

GTKDINSCCGKMNVKIPADLPSGDYLLRAEALALHTAGSAGGAQFYMTCYQLTVTGSGSASPP

TVSFPGAYKATDPGILVNIHAPLSGYTVPGPAVYSGGSTKKAGSACTGCESTCAVGSGPTATVSQ

SPGSTATSAPGGGGGCTVQKYQQCGGQGYTGCTNCASGSTCSAVSPPYYSQCV
```

The polynucleotide (SEQ ID NO:31) and amino acid (SEQ ID NO:32) sequences of an *M. thermophila* GH61g are provided below. The signal sequence is shown underlined in SEQ ID NO:32. SEQ ID NO:33 provides the sequence of this GH61g without the signal sequence.

```
                                                        (SEQ ID NO: 31)
ATGAAGGGACTCCTCGGCGCCGCCGCCCTCTCGCTGGCCGTCAGCGATGTCTCGGCCCACTA

CATCTTTCAGCAGCTGACGACGGGCGGCGTCAAGCACGCTGTGTACCAGTACATCCGCAAGA

ACACCAACTATAACTCGCCCGTGACCGATCTGACGTCCAACGACCTCCGCTGCAATGTGGGT

GCTACCGGTGCGGGCACCGATACCGTCACGGTGCGCGCCGGCGATTCGTTCACCTTCACGAC

CGATACGCCCGTTTACCACCAGGGCCCGACCTCGATCTACATGTCCAAGGCCCCCGGCAGCG

CGTCCGACTACGACGGCAGCGGCGGCTGGTTCAAGATCAAGGACTGGGCTGACTACACCGC

CACGATTCCGGAATGTATTCCCCCCGGCGACTACCTGCTTCGCATCCAGCAACTCGGCATCC

ACAACCCTTGGCCCGCGGGCATCCCCCAGTTCTACATCTCTTGTGCCCAGATCACCGTGACT

GGTGGCGGCAGTGCCAACCCCGGCCCGACCGTCTCCATCCCAGGCGCCTTCAAGGAGACCG

ACCCGGGCTACACTGTCAACATCTACAACAACTTCCACAACTACACCGTCCCTGGCCCAGCC

GTCTTCACCTGCAACGGTAGCGGCGGCAACAACGGCGGCGGCTCCAACCCAGTCACCACCA

CCACCACCACCACCAGGCCGTCCACCAGCACCGCCCAGTCCCAGCCGTCGTCGAGCCCG

ACCAGCCCCTCCAGCTGCACCGTCGCGAAGTGGGGCCAGTGCGGAGGACAGGGTTACAGCG

GCTGCACCGTGTGCGCGGCCGGGTCGACCTGCCAGAAGACCAACGACTACTACAGCCAGTG

CTTGTAG
```

```
                                                        (SEQ ID NO: 32)
MKGLLGAAALSLAVSDVSAHYIFQQLTTGGVKHAVYQYIRKNTNYNSPVTDLTSNDLRCNVGA

TGAGTDTVTVRAGDSFTFTTDTPVYHQGPTSIYMSKAPGSASDYDGSGGWFKIKDWADYTATIP

ECIPPGDYLLRIQQLGIHNPWPAGIPQFYISCAQITVTGGGSANPGPTVSIPGAFKETDPGYTVNIY

NNFHNYTVPGPAVFTCNGSGGNNGGGSNPVTTTTTTTRPSTSTAQSQPSSSPTSPSSCTVAKWG

QCGGQGYSGCTVCAAGSTCQKTNDYYSQCL
```

-continued (SEQ ID NO: 33)
HYIFQQLTTGGVKHAVYQYIRKNTNYNSPVTDLTSNDLRCNVGATGAGTDTVTVRAGDSFTFTT

DTPVYHQGPTSIYMSKAPGSASDYDGSGGWFKIKDWADYTATIPECIPPGDYLLRIQQLGIHNPW

PAGIPQFYISCAQITVTGGGSANPGPTVSIPGAFKETDPGYTVNIYNNFHNYTVPGPAVFTCNGSG

GNNGGGSNPVTTTTTTTTRPSTSTAQSQPSSSPTSPSSCTVAKWGQCGGQGYSGCTVCAAGSTCQ

KTNDYYSQCL

The polynucleotide (SEQ ID NO:34) and amino acid (SEQ ID NO:35) sequences of an alternative *M. thermophila* GH61g are provided below. The signal sequence is shown underlined in SEQ ID NO:35. SEQ ID NO:36 provides the sequence of this GH61g without the signal sequence.

The polynucleotide (SEQ ID NO:37) and amino acid (SEQ ID NO:38) sequences of an *M. thermophila* GH61h are provided below. The signal sequence is shown underlined in SEQ ID NO:38. SEQ ID NO:39 provides the sequence of this GH61h without the signal sequence.

(SEQ ID NO: 34)
CTGACGACGGGCGGCGTCAAGCACGCTGTGTACCAGTACATCCGCAAGAACACCAACTATA

ACTCGCCCGTGACCGATCTGACGTCCAACGACCTCCGCTGCAATGTGGGTGCTACCGGTGCG

GGCACCGATACCGTCACGGTGCGCGCCGGCGATTCGTTCACCTTCACGACCGATACGCCCGT

TTACCACCAGGGCCCGACCTCGATCTACATGTCCAAGGCCCCCGGCAGCGCGTCCGACTACG

ACGGCAGCGGCGGCTGGTTCAAGATCAAGGACTGGGGTGCCGACTTTAGCAGCGGCCAGGC

CACCTGGACCTTGGCGTCTGACTACACCGCCACGATTCCGGAATGTATTCCCCCCGGCGACT

ACCTGCTTCGCATCCAGCAACTCGGCATCCACAACCCTTGGCCCGCGGGCATCCCCCAGTTC

TACATCTCTTGTGCCCAGATCACCGTGACTGGTGGCGGCAGTGCCAACCCCGGCCCGACCGT

CTCCATCCCAGGCGCCTTCAAGGAGACCGACCCGGGCTACACTGTCAACATCTACAACAACT

TCCACAACTACACCGTCCCTGGCCCAGCCGTCTTCACCTGCAACGGTAGCGGCGGCAACAAC

GGCGGCGGCTCCAACCCAGTCACCACCACCACCACCACCACCACCAGGCCGTCCACCAGCA

CCGCCCAGTCCCAGCCGTCGTCGAGCCCGACCAGCCCCTCCAGCTGCACCGTCGCGAAGTGG

GGCCAGTGCGGAGGACAGGGTTACAGCGGCTGCACCGTGTGCGCGGCCGGGTCGACCTGCC

AGAAGACCAACGACTACTACAGCCAGTGCTTG (SEQ ID NO: 35)
<u>MKGLLGAAALSLAVSDVSA</u>HYTFQQLTTGGVKHAVYQYIRKNTNYNSPVTDLTSNDLRCNVGA

TGAGTDTVTVRAGDSFTFTTDTPVYHQGPTSIYMSKAPGSASDYDGSGGWFKIKDWGADFSSGQ

ATWTLASDYTATIPECIPPGDYLLRIQQLGIHNPWPAGIPQFYISCAQITVTGGGSANPGPTVSIPG

AFKETDPGYTVNIYNNFHNYTVPGPAVFTCNGSGGNNGGGSNPVTTTTTTTRPSTSTAQSQPSS

SPTSPSSCTVAKWGQCGGQGYSGCTVCAAGSTCQKTNDYYSQCL (SEQ ID NO: 36)
HYIFQQLTTGGVKHAVYQYIRKNTNYNSPVTDLTSNDLRCNVGATGAGTDTVTVRAGDSFTFTT

DTPVYHQGPTSIYMSKAPGSASDYDGSGGWFKIKDWGADFSSGQATWTLASDYTATIPECIPPG

DYLLRIQQLGIHNPWPAGIPQFYISCAQITVTGGGSANPGPTVSIPGAFKETDPGYTVNIYNNFHN

YTVPGPAVFTCNGSGGNNGGGSNPVTTTTTTTTRPSTSTAQSQPSSSPTSPSSCTVAKWGQCGGQ

GYSGCTVCAAGSTCQKTNDYYSQCL (SEQ ID NO: 37)
ATGTCTTCCTTCACCTCCAAGGGTCTCCTTTCCGCCCTCATGGGCGCGGCAACGGTTGCCGCC

CACGGTCACGTCACCAACATCGTCATCAACGGCGTCTCATACCAGAACTTCGACCCATTCAC

GCACCCTTATATGCAGAACCCTCCGACGGTTGTCGGCTGGACCGCGAGCAACACGGACAAC

GGCTTCGTCGGCCCCGAGTCCTTCTCTAGCCCGGACATCATCTGCCACAAGTCCGCCACCAA

CGCTGGCGGCCATGCCGTCGTCGCGGCCGGCGATAAGGTCTTCATCCAGTGGGACACCTGGC

CCGAGTCGCACCACGGTCCGGTCATCGACTATCTCGCCGACTGCGGCGACGCGGGCTGCGAG

AAGGTCGACAAGACCACGCTCAAGTTCTTCAAGATCAGCGAGTCCGGCCTGCTCGACGGCA

CTAACGCCCCCGGCAAGTGGGCGTCCGACACGCTGATCGCCAACAACAACTCGTGGCTGGTC

CAGATCCCGCCCAACATCGCCCCGGGCAACTACGTCCTGCGCCACGAGATCATCGCCCTGCA

CAGCGCCGGCCAGCAGAACGGCGCCCAGAACTACCCTCAGTGCTTCAACCTGCAGGTCACC

GGCTCCGGCACTCAGAAGCCCTCCGGCGTCCTCGGCACCGAGCTCTACAAGGCCACCGACGC

CGGCATCCTGGCCAACATCTACACCTCGCCCGTCACCTACCAGATCCCCGGCCCGGCCATCA

TCTCGGGCGCCTCCGCCGTCCAGCAGACCACCTCGGCCATCACCGCCTCTGCTAGCGCCATC

ACCGGCTCCGCTACCGCCGCGCCCACGGCTGCCACCACCACCGCCGCCGCCGCCGCCACCAC

TACCACCACCGCTGGCTCCGGTGCTACCGCCACGCCCTCGACCGGCGGCTCTCCTTCTTCCGC

CCAGCCTGCTCCTACCACCGCTGCCGCTACCTCCAGCCCTGCTCGCCCGACCCGCTGCGCTG

GTCTGAAGAAGCGCCGTCGCCACGCCCGTGACGTCAAGGTTGCCCTC (SEQ ID NO: 38)
<u>MSSFTSKGLLSALMGAATVA</u>AHGHVTNIVINGVSYQNFDPFTHPYMQNPPTVVGWTASNTDNG

FVGPESFSSPDIICHKSATNAGGHAVVAAGDKVFIQWDTWPESHHGPVIDYLADCGDAGCEKVD

KTTLKFFKISESGLLDGTNAPGKWASDTLIANNNSWVQIPPNIAPGNYVLRHEIIALHSAGQQNG

AQNYPQCFNLQVTGSGTQKPSGVLGTELYKATDAGILANIYTSPVTYQIPGPAIISGASAVQQTTS

AITASASAITGSATAAPTAATTTAAAAATTTTTAGSGATATPSTGGSPSSAQPAPTTAAATSSPAR

PTRCAGLKKRRRHARDVKVAL (SEQ ID NO: 39)
AHGHVTNIVINGVSYQNFDPFTHPYMQNPPTVVGWTASNTDNGFVGPESFSSPDIICHKSATNAG

GHAVVAAGDKVFIQWDTWPESHHGPVIDYLADCGDAGCEKVDKTTLKFFKISESGLLDGTNAP

GKWASDTLIANNNSWLVQIPPNIAPGNYVLRHEIIALHSAGQQNGAQNYPQCFNLQVTGSGTQK

PSGVLGTELYKATDAGILANIYTSPVTYQIPGPAIISGASAVQQTTSAITASASAITGSATAAPTAA

TTTAAAAATTTTTAGSGATATPSTGGSPSSAQPAPTTAAATSSPARPTRCAGLKKRRRHARDVK

VAL

The polynucleotide (SEQ ID NO:40) and amino acid (SEQ ID NO:41) sequences of an *M. thermophila* GH61i are provided below. The signal sequence is shown underlined in SEQ ID NO:41. SEQ ID NO:42 provides the sequence of this GH61i without the signal sequence.

(SEQ ID NO: 40)
ATGAAGACGCTCGCCGCCCTCGTGGTCTCGGCCGCCCTCGTGGCCGCGCACGGCTATGTTGA

CCACGCCACGATCGGTGGCAAGGATTATCAGTTCTACCAGCCGTACCAGGACCCTTACATGG

GCGACAACAAGCCCGATAGGGTTTCCCGCTCCATCCCGGGCAACGGCCCCGTGGAGGACGT

CAACTCCATCGACCTCCAGTGCCACGCCGGTGCCGAACCGGCCAAGCTCCACGCCCCCGCCG

CCGCCGGCTCGACCGTGACGCTCTACTGGACCCTCTGGCCCGACTCCCACGTCGGCCCCGTC

```
ATCACCTACATGGCTCGCTGCCCCGACACCGGCTGCCAGGACTGGTCCCCGGGAACTAAGCC

CGTTTGGTTCAAGATCAAGGAAGGCGGCCGTGAGGGCACCTCCAATACCCCGCTCATGACG

GCCCCCTCCGCCTACACCTACACGATCCCGTCCTGCCTCAAGAGCGGCTACTACCTCGTCCG

CCACGAGATCATCGCCCTGCACTCGGCCTGGCAGTACCCCGGCGCCCAGTTCTACCCGGGCT

GCCACCAGCTCCAGGTCACCGGCGGCGGCTCCACCGTGCCCTCTACCAACCTGGTCTCCTTC

CCCGGCGCCTACAAGGGGAGCGACCCCGGCATCACCTACGACGCTTACAAGGCGCAACCTT

ACACCATCCCTGGCCCGGCCGTGTTTACCTGCTGA (SEQ ID NO: 41)
MKTLAALVVSAALVAAHGYVDHATIGGKDYQFYQPYQDPYMGDNKEDRVSRSIPGNGPVEDV

NSIDLQCHAGAEPAKLHAPAAAGSTVTLYWTLWPDSHVGPVITYMARCPDTGCQDWSPGTKPV

WFKIKEGGREGTSNTPLMTAPSAYTYTIPSCLKSGYYLVRHEIIALHSAWQYPGAQFYPGCHQLQ

VTGGGSTVPSTNLVSFPGAYKGSDPGITYDAYKAQPYTIPGPAVFTC (SEQ ID NO: 42)
YVDHATIGGKDYQFYQPYQDPYMGDNKPDRVSRSIPGNGPVEDVNSIDLQCHAGAEPAKLHAP

AAAGSTVTLYWTLWPDSHVGPVITYMARCPDTGCQDWSPGTKPVWFKIKEGGREGTSNTPLMT

APSAYTYTIPSCLKSGYYLVRHEIIALHSAWQYPGAQFYPGCHQLQVTGGGSTVPSTNLVSFPGA

YKGSDPGITYDAYKAQPYTIPGPAVFTC
```

The polynucleotide (SEQ ID NO:43) and amino acid (SEQ ID NO:44) sequences of an alternative *M. thermophila* GH61i are provided below. The signal sequence is shown underlined in SEQ ID NO:44. SEQ ID NO:45 provides the sequence of this GH61i without the signal sequence.

```
                                                 (SEQ ID NO: 43)
ATGAAGACGCTCGCCGCCCTCGTGGTCTCGGCCGCCCTCGTGGCCGCGCACGGCTATGTTGA

CCACGCCACGATCGGTGGCAAGGATTATCAGTTCTACCAGCCGTACCAGGACCCTTACATGG

GCGACAACAAGCCCGATAGGGTTTCCCGCTCCATCCCGGGCAACGGCCCCGTGGAGGACGT

CAACTCCATCGACCTCCAGTGCCACGCCGGTGCCGAACCGGCCAAGCTCCACGCCCCCGCCG

CCGCCGGCTCGACCGTGACGCTCTACTGGACCCTCTGGCCCGACTCCCACGTCGGCCCCGTC

ATCACCTACATGGCTCGCTGCCCCGACACCGGCTGCCAGGACTGGTCCCCGGGAACTAAGCC

CGTTTGGTTCAAGATCAAGGAAGGCGGCCGTGAGGGCACCTCCAATGTCTGGGCTGCTACCC

CGCTCATGACGGCCCCCTCCGCCTACACCTACACGATCCCGTCCTGCCTCAAGAGCGGCTAC

TACCTCGTCCGCCACGAGATCATCGCCCTGCACTCGGCCTGGCAGTACCCCGGCGCCCAGTT

CTACCCGGGCTGCCACCAGCTCCAGGTCACCGGCGGCGGCTCCACCGTGCCCTCTACCAACC

TGGTCTCCTTCCCCGGCGCCTACAAGGGGAGCGACCCCGGCATCACCTACGACGCTTACAAG

GCGCAACCTTACACCATCCCTGGCCCGGCCGTGTTTACCTGC (SEQ ID NO: 44)
MKTLAALVVSAALVAAHGYVDHATIGGKDYQFYQPYQDPYMGDNKPDRVSRSIPGNGPVEDV

NSIDLQCHAGAEPAKLHAPAAAGSTVTLYWTLWPDSHVGPVITYMARCPDTGCQDWSPGTKPV

WFKIKEGGREGTSNVWAATPLMTAPSAYTYTIPSCLKSGYYLVRHEIIALHSAWQYPGAQFYPG

CHQLQVTGGGSTVPSTNLVSFPGAYKGSDPGITYDAYKAQPYTIPGPAVFTC
```

-continued (SEQ ID NO: 45)
YVDHATIGGKDYQFYQPYQDPYMGDNKPDRVSRSIPGNGPVEDVNSIDLQCHAGAEPAKLHAP

AAAGSTVTLYWTLWPDSHVGPVITYMARCPDTGCQDWSPGTKPVWFKIKEGGREGTSNVWAA

TPLMTAPSAYTYTIPSCLKSGYYLVRHEIIALHSAWQYPGAQFYPGCHQLQVTGGGSTVPSTNLV

SFPGAYKGSDPGITYDAYKAQPYTIPGPAVFTC

The polynucleotide (SEQ ID NO:46) and amino acid (SEQ ID NO:47) sequences of an *M. thermophila* GH61j are provided below. The signal sequence is shown underlined in SEQ ID NO:47. SEQ ID NO:48 provides the sequence of this GH61j without the signal sequence.

(SEQ ID NO: 46)
ATGAGATACTTCCTCCAGCTCGCTGCGGCCGCGGCCTTTGCCGTGAACAGCGCGGCGGGTCA

CTACATCTTCCAGCAGTTCGCGACGGGCGGGTCCAAGTACCCGCCCTGGAAGTACATCCGGC

GCAACACCAACCCGGACTGGCTGCAGAACGGGCCGGTGACGGACCTGTCGTCGACCGACCT

GCGCTGCAACGTGGGCGGGCAGGTCAGCAACGGGACCGAGACCATCACCTTGAACGCCGGC

GACGAGTTCAGCTTCATCCTCGACACGCCCGTCTACCATGCCGGCCCCACCTCGCTCTACAT

GTCCAAGGCGCCCGGAGCTGTGGCCGACTACGACGGCGGCGGGGCCTGGTTCAAGATCTAC

GACTGGGGTCCGTCGGGGACGAGCTGGACGTTGAGTGGCACGTACACTCAGAGAATTCCCA

AGTGCATCCCTGACGGCGAGTACCTCCTCCGCATCCAGCAGATCGGGCTCCACAACCCCGGC

GCCGCGCCACAGTTCTACATCAGCTGCGCTCAAGTCAAGGTCGTCGATGGCGGCAGCACCAA

TCCGACCCCGACCGCCCAGATTCCGGGAGCCTTCCACAGCAACGACCCTGGCTTGACTGTCA

ATATCTACAACGACCCTCTCACCAACTACGTCGTCCCGGGACCTAGAGTTTCGCACTGG (SEQ ID NO: 47)
<u>MRYFLQLAAAAAFAVNSAAG</u>HYIFQQFATGGSKYPPWKYIRRNTNPDWLQNGPVTDLSSTDLR

CNVGGQVSNGTETITLNAGDEFSFILDTPVYHAGPTSLYMSKAPGAVADYDGGGAWFKIYDWG

PSGTSWTLSGTYTQRIPKCIPDGEYLLRIQQIGLHNPGAAPQFYISCAQVKVVDGGSTNPTPTAQIP

GAFHSNDPGLTVNIYNDPLTNYVVPGPRVSHW (SEQ ID NO: 48)
HYIFQQFATGGSKYPPWKYIRRNTNPDWLQNGPVTDLSSTDLRCNVGGQVSNGTETITLNAGDE

FSFILDTPVYHAGPTSLYMSKAPGAVADYDGGGAWFKIYDWGPSGTSWTLSGTYTQRIPKCIPD

GEYLLRIQQIGLHNPGAAPQFYISCAQVKVVDGGSTNPTPTAQIPGAFHSNDPGLTVNIYNDPLTN

YVVPGPRVSHW

The polynucleotide (SEQ ID NO:49) and amino acid (SEQ ID NO:50) sequences of an *M. thermophila* GH61k are provided below. The signal sequence is shown underlined in SEQ ID NO:50. SEQ ID NO:51 provides the sequence of this GH61k without the signal sequence.

(SEQ ID NO: 49)
ATGCACCCCTCCCTTCTTTTCACGCTTGGGCTGGCGAGCGTGCTTGTCCCCCTCTCGTCTGCA

CACACTACCTTCACGACCCTCTTCGTCAACGATGTCAACCAAGGTGATGGTACCTGCATTCG

CATGGCGAAGAAGGGCAATGTCGCCACCCATCCTCTCGCAGGCGGTCTCGACTCCGAAGAC

ATGGCCTGTGGTCGGGATGGTCAAGAACCCGTGGCATTTACGTGTCCGGCCCCAGCTGGTGC

CAAGTTGACTCTCGAGTTTCGCATGTGGGCCGATGCTTCGCAGTCCGGATCGATCGATCCAT

CCCACCTTGGCGTCATGGCCATCTACCTCAAGAAGGTTTCCGACATGAAATCTGACGCGGCC

-continued

```
GCTGGCCCGGGCTGGTTCAAGATTTGGGACCAAGGCTACGACTTGGCGGCCAAGAAGTGGG

CCACCGAGAAGCTCATCGACAACAACGGCCTCCTGAGCGTCAACCTTCCAACCGGCTTACCA

ACCGGCTACTACCTCGCCCGCCAGGAGATCATCACGCTCCAAAACGTTACCAATGACAGGCC

AGAGCCCCAGTTCTACGTCGGCTGCGCACAGCTCTACGTCGAGGGCACCTCGGACTCACCCA

TCCCCTCGGACAAGACGGTCTCCATTCCCGGCCACATCAGCGACCCGGCCGACCCGGGCCTG

ACCTTCAACGTCTACACGGGCGACGCATCCACCTACAAGCCGCCCGGCCCCGAGGTTTACTT

CCCCACCACCACCACCACCACCTCCTCCTCCTCCGGAAGCAGCGACAACAAGGGAGCCA

GGCGCCAGCAAACCCCCGACGACAAGCAGGCCGACGGCCTCGTTCCAGCCGACTGCCTCGT

CAAGAACGCGAACTGGTGCGCCGCTGCCCTGCCGCCGTACACCGACGAGGCCGGCTGCTGG

GCCGCCGCCGAGGACTGCAACAAGCAGCTGGACGCGTGCTACACCAGCGCACCCCCCTCGG

GCAGCAAGGGGTGCAAGGTCTGGGAGGAGCAGGTGTGCACCGTCGTCTCGCAGAAGTGCGA

GGCCGGGGATTTCAAGGGGCCCCCGCAGCTCGGGAAGGAGCTCGGCGAGGGGATCGATGAG

CCTATTCCGGGGGGAAAGCTGCCCCCGGCGGTCAACGCGGGAGAGAACGGGAATCATGGCG

GAGGTGGTGGTGATGATGGTGATGATGATAATGATGAGGCCGGGGCTGGGGCAGCGTCGAC

TCCGACTTTTGCTGCTCCTGGTGCGGCCAAGACTCCCCAACCAAACTCCGAGAGGGCCCGGC

GCCGTGAGGCGCATTGGCGGCGACTGGAATCTGCTGAG
```

```
                                                    (SEQ ID NO: 50)
MHPSLLFTLGLASVLVPLSSAHTTFTTLFVNDVNQGDGTCIRMAKKGNVATHPLAGGLDSEDMA

CGRDGQEPVAFTCPAPAGAKLTLEFRMWADASQSGSIDPSHLGVMAIYLKKVSDMKSDAAAGP

GWFKIWDQGYDLAAKKWATEKLIDNNGLLSVNLPTGLPTGYYLARQEIITLQNVTNDRPEPQFY

VGCAQLYVEGTSDSPIPSDKTVSIPGHISDPADPGLTFNVYTGDASTYKPPGPEVYFPTTTTTSSS

SSGSSDNKGARRQQTPDDKQADGLVPADCLVKNANWCAAALPPYTDEAGCWAAAEDCNKQL

DACYTSAPPSGSKGCKVWEEQVCTVVSQKCEAGDFKGPPQLGKELGEGIDEPIPGGKLPPAVNA

GENGNHGGGGGDDGDDDNDEAGAGAASTPTFAAPGAAKTPQPNSERARRREAHWRRLESAE
```

```
                                                    (SEQ ID NO: 51)
HTTFTTLFVNDVNQGDGTCIRMAKKGNVATHPLAGGLDSEDMACGRDGQEPVAFTCPAPAGAK

LTLEFRMWADASQSGSIDPSHLGVMAIYLKKVSDMKSDAAAGPGWFKIWDQGYDLAAICKWAT

EKLIDNNGLLSVNLPTGLPTGYYLARQEIITLQNVTNDRPEPQFYVGCAQLYVEGTSDSPSDKT

VSIPGHISDPADPGLTFNVYTGDASTYKPPGPEVYFPTTTTTTSSSSSGSSDNKGARRQQTPDDKQ

ADGLVPADCLVKNANWCAAALPPYTDEAGCWAAAEDCNKQLDACYTSAPPSGSKGCKVWEE

QVCTVVSQKCEAGDFKGPPQLGKELGEGIDEPIPGGKLPPAVNAGENGNHGGGGGDDGDDDND

EAGAGAASTPTFAAPGAAKTPQPNSERARRREAHWRRLESAE
```

The polynucleotide (SEQ ID NO:52) and amino acid (SEQ ID NO:53) sequences of a *M. thermophila* GH61l are provided below. The signal sequence is shown underlined in SEQ ID NO:53. SEQ ID NO:54 provides the sequence of this GH61l without the signal sequence.

```
                                                    (SEQ ID NO: 52)
ATGTTTTCTCTCAAGTTCTTTATCTTGGCCGGTGGGCTTGCTGTCCTCACCGAGGCTCACATA

AGACTAGTGTCGCCCGCCCCTTTTACCAACCCTGACCAGGGCCCCAGCCCACTCCTAGAGGC

TGGCAGCGACTATCCCTGCCACAACGGCAATGGGGGCGGTTATCAGGGAACGCCAACCCAG

ATGGCAAAGGGTTCTAAGCAGCAGCTAGCCTTCCAGGGGTCTGCCGTTCATGGGGGTGGCTC

CTGCCAAGTGTCCATCACCTACGACGAAAACCCGACCGCTCAGAGCTCCTTCAAGGTCATTC
```

-continued

```
ACTCGATTCAAGGTGGCTGCCCCGCCAGGGCCGAGACGATCCCGGATTGCAGCGCACAAA

TATCAACGCCTGCAATATAAAGCCCGATAATGCCCAGATGGACACCCCGGATAAGTATGAG

TTCACGATCCCGGAGGATCTCCCCAGTGGCAAGGCCACCCTCGCCTGGACATGGATCAACAC

TATCGGCAACCGCGAGTTTTATATGGCATGCGCCCCGGTTGAGATCACCGGCGACGGCGGTA

GCGAGTCGGCTCTGGCTGCGCTGCCCGACATGGTCATTGCCAACATCCCGTCCATCGGAGGA

ACCTGCGCGACCGAGGAGGGGAAGTACTACGAATATCCCAACCCCGGTAAGTCGGTCGAAA

CCATCCCGGGCTGGACCGATTTGGTTCCCCTGCAAGGCGAATGCGGTGCTGCCTCCGGTGTC

TCGGGCTCCGGCGGAAACGCCAGCAGTGCTACCCCTGCCGCAGGGGCCGCCCCGACTCCTGC

TGTCCGCGGCCGCCGTCCCACCTGGAACGCC
```

(SEQ ID NO: 53)
```
MFSLKFFILAGGLAVLTEAHIRLVSPAPFTNPDQGPSPLLEAGSDYPCHNGNGGGYQGTPTQMAK

GSKQQLAFQGSAVHGGGSCQVSITYDENPTAQSSFKVIHSIQGGCPARAETIPDCSAQNINACNIK

PDNAQMDTPDKYEFTIPEDLPSGKATLAWTWINTIGNREFYMACAPVEITGDGGSESALAALPD

MVIANIPSIGGTCATEEGKYVEYPNEGKSVETIPGWTDLVELQGECGAASGVSGSGGNASSATEA

AGAAPTPAVRGRRPTWNA
```

(SEQ ID NO: 54)
```
HIRLVSPAPFTNPDQGPSPLLEAGSDYPCHNGNGGGYQGTPTQMAKGSKQQLAFQGSAVHGGGS

CQVSITYDENPTAQSSEKVIESIQGGCPARAETIPDCSAQNINACNIKPDNAQMDTPDKYEFTIPED

LPSGKATLAWTWINTIGNREFYMACAPVEITGDGGSESALAALPDMVIANIESIGGTCATEEGKY

YEYPNPGKSVETIPGWTDLVPLQGECGAASGVSGSGGNASSATPAAGAAPTPAVRGRRPTWNA
```

The polynucleotide (SEQ ID NO:55) and amino acid (SEQ ID NO:56) sequences of a *M. thermophila* GH61m are provided below. The signal sequence is shown underlined in SEQ ID NO:56. SEQ ID NO:57 provides the sequence of this GH61m without the signal sequence.

(SEQ ID NO: 55)
```
ATGAAGCTCGCCACGCTCCTCGCCGCCCTCACCCTCGGGGTGGCCGACCAGCTCAGCGTCGG

GTCCAGAAAGTTTGGCGTGTACGAGCACATTCGCAAGAACACGAACTACAACTCGCCCGTTA

CCGACCTGTCGGACACCAACCTGCGCTGCAACGTCGGCGGGGGCTCGGGCACCAGCACCAC

CGTGCTCGACGTCAAGGCCGGAGACTCGTTCACCTTCTTCAGCGACGTTGCCGTCTACCACC

AGGGGCCCATCTCGCTGTGCGTGGACCGGACCAGTGCAGAGAGCATGGATGGACGGGAACC

GGACATGCGCTGCCGAACTGGCTCACAAGCTGGCTACCTGGCGGTGACTGACTACGACGGG

TCCGGTGACTGTTTCAAGATCTATGACTGGGGACCGACGTTCAACGGGGGCCAGGCGTCGTG

GCCGACGAGGAATTCGTACGAGTACAGCATCCTCAAGTGCATCAGGGACGGCGAATACCTA

CTGCGGATTCAGTCCCTGGCCATCCATAACCCAGGTGCCCTTCCGCAGTTCTACATCAGCTGC

GCCCAGGTGAATGTGACGGGCGGAGGCACCGTCACCCCGAGATCAAGGCGACCGATCCTGA

TCTATTTCAACTTCCACTCGTATATCGTCCCTGGGCCGGCAGTGTTCAAGTGCTAG
```

(SEQ ID NO: 56)
```
MKLATLLAALTLGVADQLSVGSRKFGVYEHIRKNTNYNSPVTDLSDTNLRCNVGGGSGTSTTVL

DVKAGDSFTFFSDVAVYHQGPISLCVDRTSAESMDGREPDMRCRTGSQAGYLAVTDYDGSGDC

FKIYDWGPTFNGGQASWPTRNSYEYSILKCIRDGEYLLRIQSLAIHNPGALPQFYISCAQVNVTGG

GTVTPRSRRPILIYFNFHSYIVPGPAVFKC
```

-continued (SEQ ID NO: 57)
DQLSVGSRKFGVYEHIRKNTNYNSPVTDLSDTNLRCNVGGGSGTSTTVLDVKAGDSFTFFSDVA

VYHQGPISLCVDRTSAESMDGREPDMRCRTGSQAGYLAVTDYDGSGDCFKIYDWGPTFNGGQA

SWPTRNSYEYSILKCIRDGEYLLRIQSLAIHNPGALPQFYISCAQVNVTGGGTVTPRSRRPILIYFNF

HSYIVPGPAVFKC

The polynucleotide (SEQ ID NO:58) and amino acid (SEQ ID NO:59) sequences of an alternative *M. thermophila* GH61m are provided below. The signal sequence is shown underlined in SEQ ID NO:59. SEQ ID NO:60 provides the sequence of this GH61m without the signal sequence.

(SEQ ID NO: 58)
ATGAAGCTCGCCACGCTCCTCGCCGCCCTCACCCTCGGGCTCAGCGTCGGGTCCAGAAAGTT

TGGCGTGTACGAGCACATTCGCAAGAACACGAACTACAACTCGCCCGTTACCGACCTGTCGG

ACACCAACCTGCGCTGCAACGTCGGCGGGGGCTCGGGCACCAGCACCACCGTGCTCGACGT

CAAGGCCGGAGACTCGTTCACCTTCTTCAGCGACGTTGCCGTCTACCACCAGGGGCCCATCT

CGCTGTGCGTGGACCGGACCAGTGCAGAGAGCATGGATGGACGGGAACCGGACATGCGCTG

CCGAACTGGCTCACAAGCTGGCTACCTGGCGGTGACTGTGATGACTGTGACTGACTACGACG

GGTCCGGTGACTGTTTCAAGATCTATGACTGGGGACCGACGTTCAACGGGGGCCAGGCGTCG

TGGCCGACGAGGAATTCGTACGAGTACAGCATCCTCAAGTGCATCAGGGACGGCGAATACC

TACTGCGGATTCAGTCCCTGGCCATCCATAACCCAGGTGCCCTTCCGCAGTTCTACATCAGCT

GCGCCCAGGTGAATGTGACGGGCGGAGGCACCATCTATTTCAACTTCCACTCGTATATCGTC

CCTGGGCCGGCAGTGTTCAAGTGC (SEQ ID NO: 59)
<u>MKLATLLAALTLGLSVGS</u>RKFGVYEHIRKNTNYINTSPVTDESDTNERCNVGGGSGTSTTVLDVKA

GDSFTFFSDVAVYHQGPISLCVDRTSAESMDGREPDMRCRTGSQAGYLAVTVMTVTDYDGSGD

CFKIYDWGPTFNGGQASWPTRNSYEYSILKCIRDGEYLLRIQSLAIHNPGALPQFYISCAQVNVTG

GGTIYFNFHSYIVPGPAVFKC (SEQ ID NO: 60)
RKFGVYEHIRKNTNYNSPVTDLSDTNLRCNVGGGSGTSTTVLDVKAGDSFTFFSDVAVYHQGPI

SLCVDRTSAESMDGREPDMRCRTGSQAGYLAVTVMTVTDYDGSGDCFKIYDWGPTENGGQAS

WPTRNSYEYSILKCIRDGEYLLRIQSLAIHNPGALPQFYISCAQVNVTGGGTIYENFHSYIVPGPAV

FKC

The polynucleotide (SEQ ID NO:61) and amino acid (SEQ ID NO:62) sequences of a *M. thermophila* GH61n are provided below.

(SEQ ID NO: 61)
ATGACCAAGAATGCGCAGAGCAAGCAGGGCGTTGAGAACCCAACAAGCGGCGACATCCGCT

GCTACACCTCGCAGACGGCGGCCAACGTCGTGACCGTGCCGGCCGGCTCGACCATTCACTAC

ATCTCGACCCAGCAGATCAACCACCCCGGCCCGACTCAGTACTACCTGGCCAAGGTACCCCC

CGGCTCGTCGGCCAAGACCTTTGACGGGTCCGGCGCCGTCTGGTTCAAGATCTCGACCACGA

TGCCTACCGTGGACAGCAACAAGCAGATGTTCTGGCCAGGGCAGAACACTTATGAGACCTC

AAACACCACCATTCCCGCCAACACCCCGGACGGCGAGTACCTCCTTCGCGTCAAGCAGATCG

CCCTCCACATGGCGTCTCAGCCCAACAAGGTCCAGTTCTACCTCGCCTGCACCCAGATCAAG

```
ATCACCGGTGGTCGCAACGGCACCCCCAGCCCGCTGGTCGCGCTGCCCGGAGCCTACAAGA

GCACCGACCCCGGCATCCTGGTCGACATCTACTCCATGAAGCCCGAATCGTACCAGCCTCCC

GGGCCGCCCGTCTGGCGCGGCTAA
```

```
                                                    (SEQ ID NO: 62)
MTKNAQSKQGVENPTSGDIRCYTSQTAANVVTVPAGSTIHYISTQQINHPGPTQYYLAKVPPGSS

AKTEDGSGAVWFKISTTMPTVDSNKQMFWPGQNTYETSNTTIPANTPDGEYLLRVKQIALHMAS

QPNKVQFYLACTQIKITGGRNGTPSPLVALPGAYKSTDPGILVDIYSMKPESYQPPGPPVWRG
```

The polynucleotide (SEQ ID NO:63) and amino acid (SEQ ID NO:64) sequences of an alternative *M. thermophila* GH61n are provided below. The signal sequence is shown underlined in SEQ ID NO:64. SEQ ID NO:65 provides the sequence of this GH61n without the signal sequence.

```
                                                    (SEQ ID NO: 63)
ATGAGGCTTCTCGCAAGCTTGTTGCTCGCAGCTACGGCTGTTCAAGCTCACTTTGTTAACGGA

CAGCCCGAAGAGAGTGACTGGTCAGCCACGCGCATGACCAAGAATGCGCAGAGCAAGCAG

GGCGTTGAGAACCCAACAAGCGGCGACATCCGCTGCTACACCTCGCAGACGGCGGCCAACG

TCGTGACCGTGCCGGCCGGCTCGACCATTCACTACATCTCGACCCAGCAGATCAACCACCCC

GGCCCGACTCAGTACTACCTGGCCAAGGTACCCCCCGGCTCGTCGGCCAAGACCTTTGACGG

GTCCGGCGCCGTCTGGTTCAAGATCTCGACCACGATGCCTACCGTGGACAGCAACAAGCAG

ATGTTCTGGCCAGGGCAGAACACTTATGAGACCTCAAACACCACCATTCCCGCCAACACCCC

GGACGGCGAGTACCTCCTTCGCGTCAAGCAGATCGCCCTCCACATGGCGTCTCAGCCCAACA

AGGTCCAGTTCTACCTCGCCTGCACCCAGATCAAGATCACCGGTGGTCGCAACGGCACCCCC

AGCCCGCTGGTCGCGCTGCCCGGAGCCTACAAGAGCACCGACCCCGGCATCCTGGTCGACAT

CTACTCCATGAAGCCCGAATCGTACCAGCCTCCCGGGCCGCCCGTCTGGCGCGGC
```

```
                                                    (SEQ ID NO: 64)
MRLLASLLLAATAVQAHFVNGQPEESDWSATRMTKNAQSKQGVENPTSGDIRCYTSQTAANVV

TVPAGSTIHYISTQQINHPGPTQYYLAKVPPGSSAKTFDGSGAVWFKISTTMPTVDSNKQMFWPG

QNTYETSNTTIPANTPDGEYLLRVKQIALHMASQPNKVQFYLACTQIKITGGRNGTPSPLVALPG

AYKSTDPGILVDIYSMKPESYQPPGPPVWRG
```

```
                                                    (SEQ ID NO: 65)
HFVNGQPEESDWSATRMTKNAQSKQGVENPTSGDIRCYTSQTAANVVTVPAGSTIHYISTQQIN

HPGPTQYYLAKVPPGSSAKTFDGSGAVWFKISTTMPTVDSNKQMFWPGQNTYETSNTTIPANTP

DGEYLLRVKQIALHMASQPNKVQFYLACTQIKITGGRNGTPSPLVALPGAYKSTDPGILVDIYSM

KPESYQPPGPPVWRG
```

The polynucleotide (SEQ ID NO:66) and amino acid (SEQ ID NO:67) sequences of an alternative *M. thermophila* GH61o are provided below. The signal sequence is shown underlined in SEQ ID NO:67. SEQ ID NO:68 provides the sequence of this GH61o without the signal sequence.

```
                                                    (SEQ ID NO: 66)
ATGAAGCCCTTTAGCCTCGTCGCCCTGGCGACTGCCGTGAGCGGCCATGCCATCTTCCAGCG

GGTGTCGGTCAACGGGCAGGACCAGGGCCAGCTCAAGGGGGTGCGGGCGCCGTCGAGCAAC

TCCCCGATCCAGAACGTCAACGATGCCAACATGGCCTGCAACGCCAACATTGTGTACCACGA

CAACACCATCATCAAGGTGCCCGCGGGAGCCCGCGTCGGCGCGTGGTGGCAGCACGTCATC
```

-continued

```
GGCGGGCCGCAGGGCGCCAACGACCCGGACAACCCGATCGCCGCCTCCCACAAGGGCCCCA

TCCAGGTCTACCTGGCCAAGGTGGACAACGCGGCGACGGCGTCGCCGTCGGGCCTCAAGTG

GTTCAAGGTGGCCGAGCGCGGCCTGAACAACGGCGTGTGGGCCTACCTGATGCGCGTCGAG

CTGCTCGCCCTGCACAGCGCCTCGAGCCCCGGCGGCGCCCAGTTCTACATGGGCTGTGCACA

GATCGAAGTCACTGGCTCCGGCACCAACTCGGGCTCCGACTTTGTCTCGTTCCCCGGCGCCT

ACTCGGCCAACGACCCGGGCATCTTGCTGAGCATCTACGACAGCTCGGGCAAGCCCAACAA

TGGCGGGCGCTCGTACCCGATCCCCGGCCCGCGCCCCATCTCCTGCTCCGGCAGCGGCGGCG

GCGGCAACAACGGCGGCGACGGCGGCGACGACAACAACGGTGGTGGCAACAACAACGGCG

GCGGCAGCGTCCCCCTGTACGGGCAGTGCGGCGGCATCGGCTACACGGGCCCGACCACCTG

TGCCCAGGGAACTTGCAAGGTGTCGAACGAATACTACAGCCAGTGCCTCCCC
```

(SEQ ID NO: 67)
```
MKPFSLVALATAVSGHAIFQRVSVNGQDQGQLKGVRAPSSNSPIQNVNDANMACNANIVYHDN

TIIKVPAGARVGAWWQHVIGGPQGANDPDNPIAASHKGPIQVYLAKVDNAATASPSGLKWEKV

AERGLNNGVWAYLMRVELLALHSASSPGGAQFYMGCAQIEVTGSGTNSGSDFVSFPGAYSAND

PGILLSIYDSSGKPNNGGRSYPIPGPRPISCSGSGGGGNNGGDGGDDNNGGGNNNGGGSVPLYGQ

CGGIGYTGPTTCAQGTCKVSNEYYSQCLP
```

(SEQ ID NO: 68)
```
HAIFQRVSVNGQDQGQLKGVRAPSSNSPIQNVNDANMACNANIVYHDNTIIKVPAGARVGAWW

QHVIGGPQGANDPDNPIAASHKGPIQVYLAKVDNAATASPSGLKWFKVAERGLNNGVWAYLM

RVELLALHSASSPGGAQFYMGCAQIEVTGSGTNSGSDFVSFPGAYSANDPGILLSIYDSSGKPNN

GGRSYPIPGPRPISCSGSGGGGNNGGDGGDDNNGGGNNNGGGSVPLYGQCGGIGYTGPTTCAQG

TCKVSNEYYSQCLP
```

The polynucleotide (SEQ ID NO:69) and amino acid (SEQ ID NO:70) sequences of a *M. thermophila* GH61p are provided below. The signal sequence is shown underlined in SEQ ID NO:70, SEQ ID NO:71 provides the sequence of this GH61p without the signal sequence.

(SEQ ID NO: 69)
```
ATGAAGCTCACCTCGTCCCTCGCTGTCCTGGCCGCTGCCGGCGCCCAGGCTCACTATACCTTC

CCTAGGGCCGGCACTGGTGGITCGCTCTCTGGCGAGTGGGAGGTGGTCCGCATGACCGAGA

ACCATTACTCGCACGGCCCGGTCACCGATGTCACCAGCCCCGAGATGACCTGCTATCAGTCC

GGCGTGCAGGGTGCGCCCCAGACCGTCCAGGTCAAGGCGGGCTCCCAATTCACCTTCAGCGT

GGATCCCTCCATCGGCCACCCCGGCCCTCTCCAGTTCTACATGGCTAAGGTGCCGTCGGGCC

AGACGGCCGCCACCTTTGACGGCACGGGAGCCGTGTGGTTCAAGATCTACCAAGACGGCCC

GAACGGCCTCGGCACCGACAGCATTACCTGGCCCAGCGCCGGCAAAACCGAGGTCTCGGTC

ACCATCCCCAGCTGCATCGAGGATGGCGAGTACCTGCTCCGGGTCGAGCACACCCCCCTCCC

TACAGCGCCAGCAGCGCAAAACCGAGCTCGCTCGTCACCATCCCCAGCTGCATACAAGGCC

ACCGACCCGGGCATCCTCTTCCAGCTCTACTGGCCCATCCCGACCGAGTACATCAACCCCGG

CCCGGCCCCCGTCTCTTGCTAA
```

(SEQ ID NO: 70)
MKLTSSLAVLAAAGAQAHYTFPRAGTGGSLSGEWEVVRMTENHYSHGPVTDVTSPEMTCYQS

GVQGAPQTVQVKAGSQFTFSVDPSIGHPGPLQFYMAKVPSGQTAATFDGTGAVWFKIYQDGPN

GLGTDSITWPSAGKTEVSVTIPSCIEDGEYLLRVEHTPLPTAPAAQNRARSSPSPAAYKATDPGILF

QLYWPIPTEYINPGPAPVSC (SEQ ID NO: 71)
HYTFPRAGTGGSLSGEWEVVRMTENHYSHGPVTDVTSPEMTCYQSGVQGAPQTVQVKAGSQFT

FSVDPSIGHPGPLQFYMAKVPSGQTAATFDGTGAVWFKIYQDGPNGLGTDSITWPSAGKTEVSV

TIPSCIEDGEYLLRVEHTPLPTAPAAQNRARSSPSPAAYKATDPGILFQLYWPIPTEYINPGPAPVS

C

The polynucleotide (SEQ ID NO:72) and amino acid (SEQ ID NO:73) sequences of an alternative *M. thermophila* GH61p are provided below. The signal sequence is shown underlined in SEQ ID NO:73. SEQ ID NO:74 provides the sequence of this GH61p without the signal sequence.

(SEQ ID NO: 72)
ATGAAGCTCACCTCGTCCCTCGCTGTCCTGGCCGCTGCCGGCGCCCAGGCTCACTATACCTTC

CCTAGGGCCGGCACTGGTGGTTCGCTCTCTGGCGAGTGGGAGGTGGTCCGCATGACCGAGAC

CATTACTCGCACGGCCCGGTCACCGATGTCACCAGCCCCGAGATGACCTGCTATCAGTCCGG

CGTGCAGGGTGCGCCCCAGACCGTCCAGGTCAAGGCGGGCTCCCAATTCACCTTCAGCGTGG

ATCCCTCCATCGGCCACCCCGGCCCTCTCCAGTTCTACATGGCTAAGGTGCCGTCGGGCCAG

ACGGCCGCCACCTTTGACGGCACGGGAGCCGTGTGGTTCAAGATCTACCAAGACGGCCCGA

ACGGCCTCGGCACCGACAGCATTACCTGGCCCAGCGCCGGCAAAACCGAGGTCTCGGTCAC

CATCCCCAGCTGCATCGAGGATGGCGAGTACCTGCTCCGGGTCGAGCACATCGCGCTCCACA

GCGCCAGCAGCGTGGGCGGCGCCCAGTTCTACATCGCCTGCGCCCAGCTCTCCGTCACCGGC

GGCTCCGGCACCCTCAACACGGGCTCGCTCGTCTCCCTGCCCGGCGCCTACAAGGCCACCGA

CCCCGGGCATCCTCTTCCAGCTCTACTGGCCCATCCCGACCGAGTACATCAACCCCGGCCCGG

CCCCCGTCTCTTGC (SEQ ID NO: 73)
MKLTSSLAVLAAAGAQAHYTFPRAGTGGSLSGEWEVVRMTENHYSHGPVTDVTSPEMTCYQS

GVQGAPQTVQVKAGSQFTFSVDPSIGHPGPLQFYMAKVPSGQTAATFDGTGAVWFKIYQDGPN

GLGTDSITWPSAGKTEVSVTIPSCIEDGEYLLRVEHIALHSASSVGGAQFYIACAQLSVTGGSGTL

NTGSLVSLPGAYKATDPGILFQLYWPIPTEYINPGPAPVSC (SEQ ID NO: 74)
HYTFPRAGTGGSLSGEWEVVRMTENHYSHGPVTDVTSPEMTCYQSGVQGAPQTVQVKAGSQFT

FSVDPSIGHPGPLQFYMAKVPSGQTAATFDGTGAVWFKIYQDGPNGLGTDSITWPSAGKTEVSV

TIPSCIEDGEYLLRVEHIALHSASSVGGAQFYIACAQLSVTGGSGTLNTGSLVSLPGAYKATDPGIL

FQLYWPIPTEYINPGPAPVSC

The polynucleotide (SEQ ID NO:75) and amino acid (SEQ ID NO:76) sequences of an alternative *M. thermophila* GH61q are provided below. The signal sequence is shown underlined in SEQ ID NO:76. SEQ ID NO:77 provides the sequence of this GH61q without the signal sequence.

(SEQ ID NO: 75)
ATGCCGCCACCACGACTGAGCACCCTCCTTCCCCTCCTAGCCTTAATAGCCCCCACCGCCCTG

GGGCACTCCCACCTCGGGTACATCATCATCAACGGCGAGGTATACCAAGGATTCGACCCGCG

```
GCCGGAGCAGGCGAACTCGCCGTTGCGCGTGGGCTGGTCGACGGGGCAATCGACGACGGG

TTCGTGGCGCCGGCCAACTACTCGTCGCCCGACATCATCTGCCACATCGAGGGGGCCAGCCC

GCCGGCGCACGCGCCCGTCCGGGCGGGCGACCGGGTGCACGTGCAATGGAACGGCTGGCCG

CTCGGACACGTGGGGCCGGTGCTGTCGTACCTGGCGCCCTGCGGCGGGCTGGAGGGGTCCG

AGAGCGGGTGCGCCGGGGTGGACAAGCGGCAGCTGCGGTGGACCAAGGTGGACGACTCGCT

GCCGGCGATGGAGCTG (SEQ ID NO: 76)
MPPPRLSTLLPLLALIAPTALGHSHLGYIIINGEVYQGFDPRPEQANSPLRVGWSTGAIDDGFVAP

ANYSSPDIICHIEGASPPAHAPVRAGDRVHVQWNGWPLGHVGPVLSYLAPCGGLEGSESGCAGV

DKRQLRWTKVDDSLPAMEL (SEQ ID NO: 77)
HSHLGYIIINGEVYQGFDPRPEQANSPLRVGWSTGAIDDGFVAPANYSSPDIICHIEGASPPAHAPV

RAGDRVHVQWNGWPLGHVGPVLSYLAPCGGLEGSESGCAGVDKRQLRWTKVDDSLPAMEL
```

The polynucleotide (SEQ ID NO:78) and amino acid (SEQ ID NO:79) sequences of an alternative *M. thermophila* GH61q are provided below. The signal sequence is shown underlined in SEQ ID NO:79. SEQ ID NO:80 provides the sequence of this GH61q without the signal sequence.

```
                                                        (SEQ ID NO: 78)
ATGCCGCCACCACGACTGAGCACCCTCCTTCCCCTCCTAGCCTTAATAGCCCCCACCGCCCTG

GGGCACTCCCACCTCGGGTACATCATCATCAACGGCGAGGTATACCAAGGATTCGACCCGCG

GCCGGAGCAGGCGAACTCGCCGTTGCGCGTGGGCTGGTCGACGGGGCAATCGACGACGGG

TTCGTGGCGCCGGCCAACTACTCGTCGCCCGACATCATCTGCCACATCGAGGGGGCCAGCCC

GCCGGCGCACGCGCCCGTCCGGGCGGGCGACCGGGTGCACGTGCAATGGAAACGGCTGGCC

GCTCGGACACGTGGGGCCGGTGCTGTCGTACCTGGCGCCCTGCGGCGGGCTGGAGGGGTCC

GAGAGCGGGTGGACGACTCGCTGCCGGCGATGGAGCTGGTCGGGGCCGCGGGGGCGCGG

GGGGCGAGGACGACGGCAGCGGCAGCGACGGCAGCGGCAGCGGCGGCAGCGGACGCGTCG

GCGTGCCCGGGCAGCGCTGGGCCACCGACGTGTTGATCGCGGCCAACAACAGCTGGCAGGT

CGAGATCCCGCGCGGGCTGCGGGACGGGCCGTACGTGCTGCGCCACGAGATCGTCGCGCTG

CACTACGCGGCCGAGCCCGGCGGCGCGCAGAACTACCCGCTCTGCGTCAACCTGTGGGTCG

AGGGCGGCGACGGCAGCATGGAGCTGGACCACTTCGACGCCACCCAGTTCTACCGGCCCGA

CGACCCGGGCATCCTGCTCAACGTGACGGCCGGCCTGCGCTCATACGCCGTGCCGGGCCCGA

CGCTGGCCGCGGGGGCGACGCCGGTGCCGTACGCGCAGCAGAACATCAGCTCGGCGAGGGC

GGATGGAACCCCCGTGATTGTCACCAGGAGCACGGAGACGGTGCCCTTCACCGCGGCACCC

ACGCCAGCCGAGACGGCAGAAGCCAAAGGGGGAGGTATGATGACCAAACCCGAACTAAA

GACCTAAATGAACGCTTCTTTTATAGTAGCCGGCCAGAACAGAAGAGGCTGACAGCGACCT

CAAGAAGGGAACTAGTTGATCATCGTACCCGGTACCTCTCCGTAGCTGTCTGCGCAGATTTC

GGCGCTCATAAGGCAGCAGAAACCAACCACGAAGCTTTGAGAGGCGGCAATAAGCACCATG

GCGGTGTTTCAGAG (SEQ ID NO: 79)
MPPPRLSTLLPLLALIAPTALGHSHLGYIIINGEVYQGFDPRPEQANSPLRVGWSTGAIDDGEVAP

ANYSSPDHCHIEGASPPAHAPVRAGDRVHVQWKRLAARTRGAGAVVPGALRRAGGVRERVDD

SLPAMELVGAAGGAGGEDDGSGSDGSGSGGSGRVGVPGQRWATDVLIAANNSWQVEIPRGLR
```

-continued

```
DGPYVLRHEIVALHYAAEPGGAQNYPLCVNLWVEGGDGSMELDHFDATQFYRPDDPGILLNVT

AGLRSYAVPGPTLAAGATPVPYAQQNISSARADGTPVIVTRSTETVPFTAAPTPAETAEAKGGRY

DDQTRTKDLNERFFYSSRPEQKRLTATSRRELVDHRTRYLSVAVCADFGAHKAAETNHEALRG

GNKHHGGVSE
```

```
                                                       (SEQ ID NO: 80)
HSHLGYIIINGEVYQGFDPRPEQANSPLRVGWSTGAIDDGFVAPANYSSPDIECHIEGASPPAFIAPV

RAGDRVHVQWKRLAARTRGAGAVVPGALRRAGGVRERVDDSLPAMELVGAAGGAGGEDDGS

GSDGSGGGSRVGVPGQRWATDVLIAANNSWQVEIPRGLRDGPYVLRITEIVALHYAAEPGGA

QNYPLCVNLWVEGGDGSMELDHFDATQFYRPDDPGILLNVTAGLRSYAVPGPTLAAGATPVPY

AQQNISSARADGTPVIVTRSTETVPFTAAPTPAETAEAKGGRYDDQTRTKDLNERFFYSSRPEQK

RLTATSRRELVDHRTRYLSVAVCADFGAHKAAETNHEALRGGNKHHGGVSE
```

The polynucleotide (SEQ ID NO:81) and amino acid (SEQ ID NO:82) sequences of an *M. thermophila* GH61r are provided below. The signal sequence is shown underlined in SEQ ID NO:82. SEQ ID NO:83 provides the sequence of this GH61r without the signal sequence.

```
                                                       (SEQ ID NO: 81)
ATGAGGTCGACATTGGCCGGTGCCCTGGCAGCCATCGCTGCTCAGAAAGTAGCCGGCCACG

CCACGTTTCAGCAGCTCTGGCACGGCTCCTCCTGTGTCCGCCTTCCGGCTAGCAACTCACCCG

TCACCAATGTGGGAAGCAGAGACTTCGTCTGCAACGCTGGCACCCGCCCCGTCAGTGGCAA

GTGCCCCGTGAAGGCTGGCGGCACCGTCACCATCGAGATGCACCAGCAACCCGGCGACCGC

AGCTGCAACAACGAAGCCATCGGAGGGGCGCATTGGGGCCCCGTCCAGGTGTACCTGACCA

AGGTTCAGGACGCCGCGACGGCCGACGGCTCGACGGGCTGGTTCAAGATCTTCTCCGACTCG

TGGTCCAAGAAGCCCGGGGGCAACTTGGGCGACGACGACAACTGGGGCACGCGCGACCTGA

ACGCCTGCTGCGGGAAGATGGAC
```

```
                                                       (SEQ ID NO: 82)
MRSTLAGALAAIAAQKVAGHATFQQLWHGSSCVRLPASNSPVTNVGSRDFVCNAGTRPVSGKC

PVKAGGTVTIEMHQQPGDRSCNNEAIGGAHWGPVQVYLTKVQDAATADGSTGWFKIFSDSWSK

KPGGNLGDDDNWGTRDLNACCGKMD
```

```
                                                       (SEQ ID NO: 83)
HATFQQLWHGSSCVRLPASNSPVTNVGSRDFVCNAGTRPVSGKCPVKAGGTVTIEMIIQQPGDR

SCNNEAIGGAHWGPVQVYLTKVQDAATADGSTGWFKIFSDSWSKKPGGNLGDDDNWGTRDLN

ACCGKMD
```

The polynucleotide (SEQ ID NO:84) and amino acid (SEQ ID NO:85) sequences of an alternative *M. thermophila* GH61r are provided below. The signal sequence is shown underlined in SEQ ID NO:85. SEQ ID NO:86 provides the sequence of this GH61r without the signal sequence.

```
                                                       (SEQ ID NO: 84)
ATGAGGTCGACATTGGCCGGTGCCCTGGCAGCCATCGCTGCTCAGAAAGTAGCCGGCCACG

CCACGTTTCAGCAGCTCTGGCACGGCTCCTCCTGTGTCCGCCTTCCGGCTAGCAACTCACCCG

TCACCAATGTGGGAAGCAGAGACTTCGTCTGCAACGCTGGCACCCGCCCCGTCAGTGGCAA

GTGCCCCGTGAAGGCTGGCGGCACCGTCACCATCGAGATGCACCAGCAACCCGGCGACCGC

AGCTGCAACAACGAAGCCATCGGAGGGGCGCATTGGGGCCCCGTCCAGGTGTACCTGACCA
```

-continued

```
AGGTTCAGGACGCCGCGACGGCCGACGGCTCGACGGGCTGGTTCAAGATCTTCTCCGACTCG

TGGTCCAAGAAGCCCGGGGGCAACTCGGGCGACGACGACAACTGGGGCACGCGCGACCTGA

ACGCCTGCTGCGGGAAGATGGACGTGGCCATCCCGGCCGACATCGCGTCGGGCGACTACCT

GCTGCGGGCCGAGGCGCTGGCCCTGCACACGGCCGGACAGGCCGGCGGCGCCCAGTTCTAC

ATGAGCTGCTACCAGATGACGGTCGAGGGCGGCTCCGGGACCGCCAACCCGCCCACCGTCA

AGTTCCCGGGCGCCTACAGCGCCAACGACCCGGGCATCCTCGTCAACATCCACGCCCCCCTT

TCCAGCTACACCGCGCCCGGCCCGGCCGTCTACGCGGGCGGCACCATCCGCGAGGCCGGCTC

CGCCTGCACCGGCTGCGCGCAGACCTGCAAGGTCGGGTCGTCCCCGAGCGCCGTTGCCCCCG

GCAGCGGCGCGGGCAACGGCGGCGGGTTCCAACCCCGA
```

```
                                                      (SEQ ID NO: 85)
MRSTLAGALAAIAAQKVAGHATFQQLWHGSSCVRLPASNSPVTNVGSRDFVCNAGTRPVSGKC

PVKAGGTVTIEMHQQPGDRSCNNEAIGGAHWGPVQVYLTKVQDAATADGSTGWFKIFSDSWSK

KPGGNSGDDDNWGTRDLNACCGKMDVAIPADIASGDYLLRAEALALHTAGQAGGAQFYMSCY

QMTVEGGSGTANPPTVKFPGAYSANDPGILVNIHAPLSSYTAPGPAVYAGGTIREAGSACTGCAQ

TCKVGSSPSAVAPGSGAGNGGGFQPR
```

```
                                                      (SEQ ID NO: 86)
HATFQQLWHGSSCVRLPASNSPVTNVGSRDFVCNAGTRPVSGKCPVKAGGTVTIEMHQQPGDR

SCNNEAIGGAHWGPVQVYLTKVQDAATADOSTGWFKIFSDSWSKKPGGNSGDDDNWGTRDLN

ACCGKMDVAIPADIASGDYELRAEALALHTAGQAGGAQFYMSCYQMTVEGGSGTANPPTVKFP

GAYSANDPGILVNIHAPLSSYTAPGPAVYAGGTIREAGSACTGCAQTCKVGSSPSAVAPGSGAGN

GGGFQPR
```

The polynucleotide (SEQ ID NO:87) and amino acid (SEQ ID NO:88) sequences of an *M. thermophila* GH61s are provided below. The signal sequence is shown underlined in SEQ ID NO:88. SEQ ID NO:89 provides the sequence of this GH61s without the signal sequence.

```
                                                      (SEQ ID NO: 87)
ATGCTCCTCCTCACCCTAGCCACACTCGTCACCCTCCTGGCGCGCCACGTCTCGGCTCACGCC

CGGCTGTTCCGCGTCTCTGTCGACGGGAAAGACCAGGGCGACGGGCTGAACAAGTACATCC

GCTCGCCGGCGACCAACGACCCCGTGCGCGACCTCTCGAGCGCCGCCATCGTGTGCAACACC

CAGGGGTCCAAGGCCGCCCCGGACTTCGTCAGGGCCGCGCCGGCGACAAGCTGACCTTCC

TCTGGGCGCACGACAACCCGGACGACCCGGTCGACTACGTCCTCGACCCGTCCCACAAGGG

CGCCATCCTGACCTACGTCGCCGCCTACCCCTCCGGGGACCCGACCGGCCCATCTGGAGCA

AGCTTGCCGAGGAAGGATTCACCGGCGGGCAGTGGGCGACCATCAAGATGATCGACAACGG

CGGCAAGGTCGACGTGACGCTGCCCGAGGCCCTTGCGCCGGGAAAGTACCTGATCCGCCAG

GAGCTGCTGGCCCTGCACCGGGCCGACTTTGCCTGCGACGACCCGGCCCACCCCAACCGCGG

CGCCGAGTCGTACCCCAACTGCGTCCAGGTGGAGGTGTCGGGCAGCGGCGACAAGAAGCCG

GACCAGAACTTTGACTTCAACAAGGGCTATACCTGCGATAACAAAGGACTCCACTTTAAGAT

CTACATCGGTCAGGACAGCCAGTATGTGGCCCCGGGGCCGCGGCCTTGGAATGGGAGC
```

```
                                                      (SEQ ID NO: 88)
MLLLTLATLVTLLARHVSAHARLFRVSVDGKDQGDGLNKYIRSPATNDPVRDLSSAAIVCNTQG

SKAAPDEVRAAAGDKLTFLWAHDNPDDPVDYVLDPSHKGAILTYVAAYPSGDPTGPIWSKLAE
```

-continued

EGFTGGQWATIKMLDNGGKVDVTLPEALAPGKYLIRQELLALHRADFACDDPAHPNRGAESYPN

CVQVEVSGSGDKKPDQNFDFNKGYTCDNKGLRFKIYIGQDSQYVAPGPRPWNGS (SEQ ID NO: 89)
HARLFRVSVDGKDQGDGLNKYIRSPATNDPVRDLSSAAIVCNTQGSKAAPDFVRAAAGDKLTFL

WAHDNPDDPVDYVLDPSHKGAILTYVAAYPSGDPTGPIWSKLAEEGFTGGQWATIKMIDNGGK

VDVTLPEALAPGKYLIRQELLALHRADFACDDPAHPNRGAESYPNCVQVEVSGSGDICKPDQNFD

FNKGYTCDNKGLHFKIYIGQDSQYVAPGPRPWNGS

The polynucleotide (SEQ ID NO:90) and amino acid (SEQ ID NO:91) sequences of an *M. thermophila* GH61t are provided below.

(SEQ ID NO: 90)
ATGTTCACTTCGCTTTGCATCACAGATCATTGGAGGACTCTTAGCAGCCACTCTGGGCCAGTC

ATGAACTATCTCGCCCATTGCACCAATGACGACTGCAAGTCTTTCAAGGGCGACAGCGGCAA

CGTCTGGGTCAAGATCGAGCAGCTCGCGTACAACCCGTCAGCCAACCCCCCTGGGCGTCTG

ACCTCCTCCGTGAGCACGGTGCCAAGTGGAAGGTGACGATCCCGCCCAGTCTTGTCCCCGGC

GAATATCTGCTGCGGCACGAGATCCTGGGGTTGCACGTCGCAGGAACCGTGATGGGCGCCC

AGTTCTACCCCGGCTGCACCCAGATCAGGGTCACCGAAGGCGGGAGCACGCAGCTGCCCTC

GGGTATTGCGCTCCCAGGCGCTTACGGCCCACAAGACGAGGGTATCTTGGTCGACTTGTGGA

GGGTTAACCAGGGCCAGGTCAACTACACGGCGCCTGGAGGACCCGTTTGGAGCGAAGCGTG

GGACACCGAGTTTGGCGGGTCCAACACGACCGAGTGCGCCACCATGCTCGACGACCTGCTC

GACTACATGGCGGCCAACGACGAGTGGATCGGCTGGACGGCCTAG (SEQ ID NO: 91)
MFTSLCITDHWRTLSSHSGPVMNYLAHCTNDDCKSFKGDSGNVWVKIEQLAYNPSANPPWASD

LLREHGAKWKVTIPPSLVPGEYLLRHEILGLHVAGTVMGAQFYPGCTQIRVTEGGSTQLPSGIAL

PGAYGPQDEGILVDLWRVNQGQVNYTAPGGPVWSEAWDTEFGGSNTTECATMLDDLLDYMA

ANDEWIGWTA

The polynucleotide (SEQ ID NO:92) and amino acid (SEQ ID NO:93) sequences of an alternative *M. thermophila* GH61t are provided below.

(SEQ ID NO: 92)
ATGAACTATCTCGCCCATTGCACCAATGACGACTGCAAGTCTTTCAAGGGCGACAGCGGCAA

CGTCTGGGTCAAGATCGAGCAGCTCGCGTACAACCCGTCAGCCAACCCCCCTGGGCGTCTG

ACCTCCTCCGTGAGCACGGTGCCAAGTGGAAGGTGACGATCCCGCCCAGTCTTGTCCCCGGC

GAATATCTGCTGCGGCACGAGATCCTGGGGTTGCACGTCGCAGGAACCGTGATGGGCGCCC

AGTTCTACCCCGGCTGCACCCAGATCAGGGTCACCGAAGGCGGGAGCACGCAGCTGCCCTC

GGGTATTGCGCTCCCAGGCGCTTACGGCCCACAAGACGAGGGTATCTTGGTCGACTTGTGGA

GGGTTAACCAGGGCCAGGTCAACTACACGGCGCCTGGAGGACCCGTTTGGAGCGAAGCGTG

GGACACCGAGTTTGGCGGGTCCAACACGACCGAGTGCGCCACCATGCTCGACGACCTGCTC

GACTACATGGCGGCCAACGACGACCCATGCTGCACCGACCAGAACCAGTTCGGGAGTCTCG

AGCCGGGGAGCAAGGCGGCCGGCGGCTCGCCGAGCCTGTACGATACCGTCTTGGTCCCCGTT

CTCCAGAAGAAAGTGCCGACAAAGCTGCAGTGGAGCGGACCGGCGAGCGTCAACGGGGAT

GAGTTGACAGAGAGGCCC

-continued (SEQ ID NO: 93)
MNYLAHCTNDDCKSFKGDSGNVWVKIEQLAYNPSANPPWASDLLREHGAKWKVTIPPSLVPGE

YLLRBEELGLHVAGTVMGAQFYPGCTQIRVTEGGSTQLPSGIALPGAYGPQDEGILVDLWRVNQ

GQVNYTAPGGPVWSEAWDTEFGGSNTTECATMLDDLLDYMAANDDPCCTDQNQFGSLEPGSK

AAGGSPSLYDTVLVPVLQKKVPTKLQWSGPASVNGDELTERP

The polynucleotide (SEQ ID NO:94) and amino acid (SEQ ID NO:95) sequences of an *M. thermophila* GH61u are provided below. The signal sequence is shown underlined in SEQ ID NO:95. SEQ ID NO:96 provides the sequence of this GH61u without the signal sequence.

(SEQ ID NO: 94)
ATGAAGCTGAGCGCTGCCATCGCCGTGCTCGCGGCCGCCCTTGCCGAGGGGCACTATACCTT

CCCCAGCATCGCCAACACGGCCGACTGGCAATATGTGCGCATCACGACCAACTTCCAGAGC

AACGGCCCCGTGACGGACGTCAACTCGGACCAGATCCGGTGCTACGAGCGCAACCCGGGCA

CCGGCGCCCCCGGCATCTACAACGTCACGGCCGGCACAACCATCAACTACAACGCCAAGTC

GTCCATCTCCCACCCGGGACCCATGGCCTTCTACATTGCCAAGGTTCCCGCCGGCCAGTCGG

CCGCCACCTGGGACGGTAAGGGCGCCGTCTGGTCCAAGATCCACCAGGAGATGCCGCACTTT

GGCACCAGCCTCACCTGGGACTCCAACGGCCGCACCTCCATGCCCGTCACCATCCCCCGCTG

TCTGCAGGACGGCGAGTATCTGCTGCGTGCAGAGCACATTGCCCTCCACAGCGCCGGCAGCC

CCGGCGGCGCCCAGTTCTACATTTCTTGTGCCCAGCTCTCAGTCACCGGCGGCAGCGGGACC

TGGAACCCCAGGAACAAGGTGTCGTTCCCCGGCGCCTACAAGGCCACTGACCCGGGCATCCT

GATCAACATCTACTACCCCGTCCCGACTAGCTACACTCCCGCTGGTCCCCCCGTCGACACCT

GC (SEQ ID NO: 95)
<u>MKLSAAIAVLAAALAEG</u>HYTFPSIANTADWQYVRITTNFQSNGPVTDVNSDQIRCYERNPGTGA

PGTYNVTAGTTINYNAKSSISHPGPMAFYIAKVPAGQSAATWDGKGAVWSKIHQEMPHFGTSLT

WDSNGRTSMPVTIPRCLQDGEYLLRAEHIALHSAGSPGGAQFYISCAQLSVTGGSGTWNPRNKV

SFPGAYKATDPGILINIYYPVPTSYTPAGPPVDTC (SEQ ID NO: 96)
HYTEPSIANTADWQYVRITTNFQSNGPVTDVNSDQIRCYERNPGTGAPGIYNVTAGTTINYNAKS

SISHPGPMAFYIAKVPAGQSAATWDGKGAVWSKIHQEMPHFGTSLTWDSNGRTSMPVTIPRCLQ

DGEYLLRAEHIALHSAGSPGGAQFYISCAQLSVTGGSGTWNPRNKVSFPGAYKATDPGILINIYYP

VPTSYTPAGPPVDTC

The polynucleotide (SEQ ID NO:97) and amino acid (SEQ ID NO:98) sequences of an *M. thermophila* GH61v are provided below. The signal sequence is shown underlined in SEQ ID NO:98. SEQ ID NO:99 provides the sequence of this GH61v without the signal sequence.

(SEQ ID NO: 97)
ATGTACCGCACGCTCGGTTCCATTGCCCTGCTCGCGGGGGGCGCTGCCGCCCACGGCGCCGT

GACCAGCTACAACATTGCGGGCAAGGACTACCCTGGATACTCGGGCTTCGCCCCTACCGGCC

AGGATGTCATCCAGTGGCAATGGCCCGACTATAACCCCGTGCTGTCCGCCAGCGACCCCAAG

CTCCGCTGCAACGGCGGCACCGGGGCGGCGCTGTATGCCGAGGCGGCCCCCGGCGACACCA

TCACGGCCACCTGGGCCCAGTGGACGCACTCCCAGGGCCCGATCCTGGTGTGGATGTACAAG

-continued

```
TGCCCCGGCGACTTCAGCTCCTGCGACGGCTCCGGCGCGGGTTGGTTCAAGATCGACGAGGC

CGGCTTCCACGGCGACGGCACGACCGTCTTCCTCGACACCGAGACCCCCTCGGGCTGGGACA

TTGCCAAGCTGGTCGGCGGCAACAAGTCGTGGAGCAGCAAGATCCCTGACGGCCTCGCCCC

GGGCAATTACCTGGTCCGCCACGAGCTCATCGCCCTGCACCAGGCCAACAACCCGCAATTCT

ACCCCGAGTGCGCCCAGATCAAGGTCACCGGCTCTGGCACCGCCGAGCCCGCCGCCTCCTAC

AAGGCCGCCATCCCCGGCTACTGCCAGCAGAGCGACCCCAACATTTCGTTCAACATCAACGA

CCACTCCCTCCCGCAGGAGTACAAGATCCCCGGTCCCCGGTCTTCAAGGGCACCGCCTCCG

CCAAGGCTCGCGCTTTCCAGGCC
```

```
                                                    (SEQ ID NO: 98)
MYRTLGSIALLAGGAAAHGAVTSYNIAGKDYPGYSGFAPTGQDVIQWQWPDYNPVLSASDPKE

RCNGGTGAALYAEAAPGDTITATWAQWTHSQGPILVWMYKCPGDFSSCDGSGAGWFKIDEAGF

HGDGTTVFLDTETPSGWDIAKLVGGNKSWSSKIPDGLAPGNYLVRHELIALHQANNPQFYPECA

QIKVTGSGTAEPAASYKAAIPGYCQQSDPNISFNINDHSLPQEYKIPGPPVFKGTASAKARAFQA
```

```
                                                    (SEQ ID NO: 99)
AVTSYNIAGKDYPGYSGFAPTGQDVIQWQWPDYNPVLSASDPKIRCNGGTGAALYAEAAPGDT

ITATWAQWTHSQGPILVWMYKCPGDFSSCDGSGAGWFKIDEAGFHGDGTTVFLDTETPSGWDI

AKLVGGNKSWSSKIPDGLAPGNYLVRHELIALHQANNPQFYPECAQIKVTGSGTAEPAASYKAA

IPGYCQQSDPNISFNINDHSLPQEYKIPGPPVFKGTASAKARAFQA
```

The polynucleotide (SEQ ID NO:100) and amino acid (SEQ ID NO:101) sequences of an *M. thermophila* GH61w are provided below. The signal sequence is shown underlined in SEQ ID NO:101. SEQ ID NO:102 provides the sequence of this GH61w without the signal sequence.

```
                                                    (SEQ ID NO: 100)
ATGCTGACAACAACCTTCGCCCTCCTGACGGCCGCTCTCGGCGTCAGCGCCCATTATACCCT

CCCCAGGGTCGGGACCGGTTCCGACTGGCAGCACGTGCGGCGGGCTGACAACTGGCAAAAC

AACGGCTTCGTCGGCGACGTCAACTCGGAGCAGATCAGGTGCTTCCAGGCGACCCCTGCCGG

CGCCCAAGACGTCTACACTGTTCAGGCGGGATCGACCGTGACCTACCACGCCAACCCCAGTA

TCTACCACCCCGGCCCCATGCAGTTCTACCTGGCCCGCGTTCCGGACGGACAGGACGTCAAG

TCGTGGACCGGCGAGGGTGCCGTGTGGTTCAAGGTGTACGAGGAGCAGCCTCAATTTGGCG

CCCAGCTGACCTGGCCTAGCAACGGCAAGAGCTCGTTCGAGGTTCCTATCCCCAGCTGCATT

CGGGCGGGCAACTACCTCCTCCGCGCTGAGCACATCGCCCTGCACGTTGCCCAAAGCCAGGG

CGGCGCCCAGTTCTACATCTCGTGCGCCCAGCTCCAGGTCACTGGTGGCGGCAGCACCGAGC

CTTCTCAGAAGGTTTCCTTCCCGGGTGCCTACAAGTCCACCGACCCCGGCATTCTTATCAACA

TCAACTACCCCGTCCCTACCTCGTACCAGAATCCGGGTCCGGCTGTCTTCCGTTGC
```

```
                                                    (SEQ ID NO: 101)
MLTTTFALLTAALGVSAHYTLERVGTGSDWQHVRRADNWQNNGFVGDVNSEQIRCFQATPAG

AQDVYTVQAGSTVTYHANPSIYHPGPMQFYLARVPDGQDVKSWTGEGAVWFKVYEEQPQFGA

QLTWPSNGKSSFEVPIPSCIRAGNYLLRAEHIALHVAQSQGGAQFYISCAQLQVTGGGSTEPSQK

VSFPGAYKSTDPGILININYPVPTSYQNPGPAVFRC
```

```
                                                    (SEQ ID NO: 102)
HYTLPRVGTGSDWQHVRRADNWQNNGFVGDVNSEQIRCFQATPAGAQDVYTVQAGSTVTYHA

NPSIYHPGPMQFYLARVPDGQDVKSWTGEGAVWFKVYEEQPQFGAQLTWPSNGKSSFEVPIPSC

IRAGNYLLRAEHIALHVAQSQGGAQFYISCAQLQVTGGGSTEPSQKVSFPGAYKSTDPGILININY

PVPTSYQNPGPAVFRC
```

The polynucleotide (SEQ ID NO:103) and amino acid (SEQ ID NO:104) sequences of a *M. thermophila* GH61x are provided below. The signal sequence is shown underlined in SEQ ID NO:104. SEQ ID NO:105 provides the sequence of this GH61x without the signal sequence.

```
                                                    (SEQ ID NO: 103)
ATGAAGGTTCTCGCGCCCCTGATTCTGGCCGGTGCCGCCAGCGCCCACACCATCTTCTCATCC

CTCGAGGTGGGCGGCGTCAACCAGGGCATCGGGCAGGGTGTCCGCGTGCCGTCGTACAACG

GTCCGATCGAGGACGTGACGTCCAACTCGATCGCCTGCAACGGGCCCCCCAACCCGACGAC

GCCGACCAACAAGGTCATCACGGTCCGGGCCGGCGAGACGGTGACGGCCGTCTGGCGGTAC

ATGCTGAGCACCACCGGCTCGGCCCCCAACGACATCATGGACAGCAGCCACAAGGGCCCGA

CCATGGCCTACCTCAAGAAGGTCGACAACGCCACCACCGACTCGGGCGTCGGCGGCGGCTG

GTTCAAGATCCAGGAGGACGGCCTTACCAACGGCGTCTGGGGCACCGAGCGCGTCATCAAC

GGCCAGGGCCGCCACAACATCAAGATCCCCGAGTGCATCGCCCCCGGCCAGTACCTCCTCCG

CGCCGAGATGCTTGCCCTGCACGGAGCTTCCAACTACCCCGCGCTCAGTTCTACATGGAGT

GCGCCCAGCTCAATATCGTCGGCGGCACCGGCAGCAAGACGCCGTCCACCGTCAGCTTCCCG

GGCGCTTACAAGGGTACCGACCCCGGAGTCAAGATCAACATCTACTGGCCCCCCGTCACCAG

CTACCAGATTCCCGGCCCCGGCGTGTTCACCTGC
                                                    (SEQ ID NO: 104)
MKVLAPLILAGAASAHTIFSSLEVGGVNQGIGQGVRVPSYNGPIEDVTSNSIACNGPPNPTTPTNK

VITVRAGETVTAVWRYMLSTTGSAPNDIMDSSHKGPTMAYLKKVDNATTDSGVGGGWFKIQED

GLTNGVWGTERVINGQGRHNIKIPECIAPGQYLLRAEMLALHGASNYPGAQFYMECAQLNIVGG

TGSKTPSTVSFPGAYKGTDPGVKINIYWPPVTSYQIPGPGVFTC
                                                    (SEQ ID NO: 105)
HTIFSSLEVGGVNQGIGQGVRVPSYNGPIEDVTSNSIACNGPPNPTTPTNKVITVRAGETVTAVWR

YMLSTTGSAPNDIMDSSHKGPTMAYLKKVDNATTDSGVGGGWFKIQEDGIANGVWGTERVIN

GQGRHNIKIPECIAPGQYLLRAEMLALHGASNYPGAQFYMECAQLNIVGGTGSKTPSTVSFPGAY

KGTDPGVKINIYWPPVTSYQIPGPGVFTC
```

The polynucleotide (SEQ ID NO:106) and amino acid (SEQ ID NO:107) sequences of an *M. thermophila* GH61y are provided below. The signal sequence is underlined in SEQ ID NO:107. SEQ ID NO:108 provides the sequence of GH61y, without the signal sequence.

```
                                                    (SEQ ID NO: 106)
ATGATCGACAACCTCCCTGATGACTCCCTACAACCCGCCTGCCTCCGCCCGGGCCACTACCT

CGTCCGCCACGAGATCATCGCGCTGCACTCGGCCTGGGCCGAGGGCGAGGCCCAGTTCTACC

CCTTCCCCCTTTTTCCTTTTTTTCCCTCCCTTCTTTTGTCCGGTAACTACACGATTCCCGGTCCC

GCGATCTGGAAGTGCCCAGAGGCACAGCAGAACGAG
```

(SEQ ID NO: 107)
MIDNLPDDSLQPACLRPGHYLVRHEIIALHSAWAEGEAQFYPFPLFPFFPSELLSGNYTIPGPAIWK

CPEAQQNE (SEQ ID NO: 108)
HYLVRHEIIALHSAWAEGEAQFYPFPLFPFTPSLLLSGNYTIPGPAIWKCPEAQQNE

Additional enzymes (i.e., non-GH61 enzymes) that find us in the present invention include, but are not limited to the following enzymes.

Wild-type EG1b cDNA (SEQ ID NO:109) and amino acid (SEQ ID NO:110) sequences are provided below. The signal sequence is underlined in SEQ ID NO:110. SEQ ID NO:111 provides the sequence of EG1b, without the signal sequence.

(SEQ ID NO: 109)
ATGGGGCAGAAGACTCTCCAGGGGCTGGTGGCGGCGGCGGCACTGGCAGCCTCGGTGGCGA

ACGCGCAGCAACCGGGCACCTTCACGCCCGAGGTGCATCCGACGCTGCCGACGTGGAAGTG

CACGACGAGCGGCGGGTGCGTCCAGCAGGACACGTCGGTGGTGCTCGACTGGAACTACCGC

TGGTTCCACACCGAGGACGGTAGCAAGTCGTGCATCACCTCTAGCGGCGTCGACCGGACCCT

GTGCCCGGACGAGGCGACGTGCGCCAAGAACTGCTTCGTCGAGGGCGTCAACTACACGAGC

AGCGGGGTCGAGACGTCCGGCAGCTCCCTCACCCTCCGCCAGTTCTTCAAGGGCTCCGACGG

CGCCATCAACAGCGTCTCCCCGCGCGTCTACCTGCTCGGGGGAGACGGCAACTATGTCGTGC

TCAAGCTCCTCGGCCAGGAGCTGAGCTTCGACGTGGACGTATCGTCGCTCCCGTGCGGCGAG

AACGCGGCCCTGTACCTGTCCGAGATGGACGCGACGGGAGGACGGAACGAGTACAACACGG

GCGGGGCCGAGTACGGGTCGGGCTACTGTGACGCCCAGTGCCCCGTGCAGAACTGGAACAA

CGGGACGCTCAACACGGGCCGGGTGGGCTCGTGCTGCAACGAGATGGACATCCTCGAGGCC

AACTCCAAGGCCGAGGCCTTCACGCCGCACCCCTGCATCGGCAACTCGTGCGACAAGAGCG

GGTGCGGCTTCAACGCGTACGCGCGCGGTTACCACAACTACTGGGCCCCCGGCGGCACGCTC

GACACGTCCCGGCCTTTCACCATGATCACCCGCTTCGTCACCGACGACGGCACCACCTCGGG

CAAGCTCGCCCGCATCGAGCGCGTCTACGTCCAGGACGGCAAGAAGGTGCCCAGCGCGGCG

CCCGGGGGGACGTCATCACGGCCGACGGGTGCACCTCCGCGCAGCCCTACGGCGGCCTTTC

CGGCATGGGCGACGCCCTCGGCCGCGGCATGGTCCTGGCCCTGAGCATCTGGAACGACGCG

TCCGGGTACATGAACTGGCTCGACGCCGGCAGCAACGGCCCCTGCAGCGACACCGAGGGTA

ACCCGTCCAACATCCTGGCCAACCACCCGGACGCCCACGTCGTGCTCTCCAACATCCGCTGG

GGCGACATCGGCTCCACCGTCGACACCGGCGATGGCGACAACAACGGCGGCGGCCCCAACC

CGTCATCCACCACCACCGCTACCGCTACCACCACCTCCTCCGGCCCGGCCGAGCCTACCCAG

ACCCACTACGGCCAGTGTGGAGGGAAAGGATGGACGGGCCCTACCCGCTGCGAGACGCCCT

ACACCTGCAAGTACCAGAACGACTGGTACTCGCAGTGCCTGTAG (SEQ ID NO: 110)
<u>MGQKTLQGLVAAAALAASVANA</u>QQPGTFTPEVHPTLPTWKCTTSGGCVQQDTSVVLDWNYR

WFHTEDGSKSCITSSGVDRTLCPDEATCAKNCFVEGVNYTSSGVETSGSSLTLRQFFKGSDGAIN

SVSPRVYLLGGDGNYVVLKLLGQELSFDVDVSSLPCGENAALYLSEMDATGGRNEYNTGGAEY

GSGYCDAQCPVQNWNNGTLNTGRVGSCCNEMDILEANSKAEAFTPITPCIGNSCDKSGCGENAY

-continued

ARGYHNYWAPGGTLDTSRPFTMITRFVTDDGTTSGKLARIERVYVQDGKKVPSAAPGGDVITAD

GCTSAQPYGGLSGMGDALGRGMVLALSIWNDASGYMNWLDAGSNGPCSDTEGNPSNILANHP

DAHVVLSNIRWGDIGSTVDTGDGDNNGGGPNPSSTTTATATTTSSGPAEPTQTHYGQCGGKGW

TGPTRCETPYTCKYQNDWYSQCL (SEQ ID NO: 111)
QQPGTFTPEVHPTLPTWKCTTSGGCVQQDTSVVLDWNYRWFHTEDGSKSCITSSGVDRTLCPDE

ATCAKNCFVEGVNYTSSGVETSGSSLTLRQFFKGSDGAINSVSPRVYLLGGDGNYVVLKLLGQE

LSFDVDVSSLPCGENAALYLSEMDATGGRNEYNTGGAEYGSGYCDAQCPVQNWNNGTLNTGR

VGSCCNEMDILEANSKAEAFTPHPCIGNSCDKSGCGENAYARGYHNYWAPGGTLDTSRPFTMIT

REVTDDGTTSGKLARIERVYVQDGKKVPSAAPGGDVITADGCTSAQPYGGLSGMGDALGRGMV

LALSIWNDASGYMNWLDAGSNGPCSDTEGNPSNILANHPDAHVVLSNIRWGDIGSTVDTGDGD

NNGGGPNPSSTTTATATTTSSGPAEPTQTHYGQCGGKGWTGPTRCETPYTCKYQNDWYSQCL

Wild-type *M. thermophila* EG2 polynucleotide (SEQ ID NO:112) and amino acid (SEQ ID NO:113) sequences are provided below. The signal sequence is underlined in SEQ ID NO:113. SEQ ID NO:114 provides the sequence of EG2, without the signal sequence.

(SEQ ID NO: 112)
ATGAAGTCCTCCATCCTCGCCAGCGTCTTCGCCACGGGCGCCGTGGCTCAAAGTGGTCCGTG

GCAGCAATGTGGTGGCATCGGATGGCAAGGATCGACCGACTGTGTGTCGGGTTACCACTGC

GTCTACCAGAACGATTGGTACAGCCAGTGCGTGCCTGGCGCGGCGTCGACAACGCTCCAGA

CATCTACCACGTCCAGGCCCACCGCCACCAGCACCGCCCCTCCGTCGTCCACCACCTCGCCT

AGCAAGGGCAAGCTCAAGTGGCTCGGCAGCAACGAGTCGGGCGCCGAGTTCGGGGAGGGC

AACTACCCCGGCCTCTGGGGCAAGCACTTCATCTTCCCGTCGACTTCGGCGATTCAGACGCT

CATCAATGATGGATACAACATCTTCCGGATCGACTTCTCGATGGAGCGTCTGGTGCCCAACC

AGTTGACGTCGTCCTTCGACGAGGGCTACCTCCGCAACCTGACCGAGGTGGTCAACTTCGTG

ACGAACGCGGGCAAGTACGCCGTCCTGGACCCGCACAACTACGGCCGGTACTACGGCAACG

TCATCACGGACACGAACGCGTTCCGGACCTTCTGGACCAACCTGGCCAAGCAGTTCGCCTCC

AACTCGCTCGTCATCTTCGACACCAACAACGAGTACAACACGATGGACCAGACCCTGGTGCT

CAACCTCAACCAGGCCGCCATCGACGGCATCCGGGCCGCCGGCGCGACCTCGCAGTACATCT

TCGTCGAGGGCAACGCGTGGAGCGGGGCCTGGAGCTGGAACACGACCAACACCAACATGGC

CGCCCTGACGGACCCGCAGAACAAGATCGTGTACGAGATGCACCAGTACCTCGACTCGGAC

AGCTCGGGCACCCACGCCGAGTGCGTCAGCAGCAACATCGGCGCCCAGCGCGTCGTCGGAG

CCACCCAGTGGCTCCGCGCCAACGGCAAGCTCGGCGTCCTCGGCGAGTTCGCCGGCGGCGCC

AACGCCGTCTGCCAGCAGGCCGTCACCGGCCTCCTCGACCACCTCCAGGACAACAGCGACGT

CTGGCTGGGTGCCCTCTGGTGGGCCGCCGGTCCCTGGTGGGCGACTACATGTACTCGTTCG

AGCCTCCTTCGGGCACCGGCTATGTCAACTACAACTCGATCCTAAAGAAGTACTTGCCGTAA (SEQ ID NO: 113)
<u>MKSSILASVFATGAVA</u>QSGPWQQCGGIGWQGSTDCVSGYHCVYQNDWYSQCVPGAASTTLQT

STTSRPTATSTAPPSSTTSPSKGKLKWLGSNESGAEFGEGNYPGLWGKHFIFPSTSAIQTLINDGYN

IFRIDFSMERLVPNQLTSSFDEGYLRNLTEVVNFVTNAGKYAVLDPHNYGRYYGNVITDINAFRT

FWTNLAKQFASNSLVIFDTNNEYNTMDQTLVLNLNQAAIDGIRAAGATSQYIFVEGNAWSGAW

SWNTTNTNMAALTDPQNKIVYEMHQYLDSDSSGTHAECVSSNIGAQRVVGATQWLRANGKLG

-continued

VLGEFAGGANAVCQQAVTGLLDHLQDNSEVWLGALWWAAGPWWGDYMYSFEPPSGTGYVN

YNSILKKYLP (SEQ ID NO: 114)
QSGPWQQCGGIGWQGSTDCVSGYHCVYQNDWYSQCVPGAASTTLQTSTTSRPTATSTAPPSSTT

SPSKGKLKWLGSNESGAEFGEGNYPGLWGKHFIFPSTSAIQTLINDGYNIFRIDFSMERLVPNQLT

SSFDEGYLRNLTEVVNFVINAGKYAVLDPHNYGRYYGNVITDTNAFRTFWTNLAKQFASNSLVI

FDTNNEYNTMDQTLVLNLNQAAIDGIRAAGATSQYIFVEGNAWSGAWSWNTTNTNMAALTDP

QNKIVYEMHQYLDSDSSGTHAECVSSNIGAQRVVGATQWLRANGKLGVLGEFAGGANAVCQQ

AVTGLLDHLQDNSEVWLGALWWAAGPWWGDYMYSFEPPSGTGYVNYNSILKKYLP

The polynucleotide (SEQ ID NO:115) and amino acid (SEQ ID NO:116) sequences of a wild-type BGL are provided below. The signal sequence is underlined in SEQ ID NO:116. SEQ ID NO:117 provides the polypeptide sequence without the signal sequence.

(SEQ ID NO: 115)
ATGAAGGCTGCTGCGCTTTCCTGCCTCTTCGGCAGTACCCTTGCCGTTGCAGGCGCCATTGAA

TCGAGAAAGGTTCACCAGAAGCCCCTCGCGAGATCTGAACCTTTTTACCCGTCGCCATGGAT

GAATCCCAACGCCGACGGCTGGGCGGAGGCCTATGCCCAGGCCAAGTCCTTTGTCTCCCAAA

TGACTCTGCTAGAGAAGGTCAACTTGACCACGGGAGTCGGCTGGGGGGCTGAGCAGTGCGT

CGGCCAAGTGGGCGCGATCCCTCGCCTTGGACTTCGCAGTCTGTGCATGCATGACTCCCCTC

TCGGCATCCGAGGAGCCGACTACAACTCAGCGTTCCCCTCTGGCCAGACCGTTGCTGCTACC

TGGGATCGCGGTCTGATGTACCGTCGCGGCTACGCAATGGGCCAGGAGGCCAAAGGCAAGG

GCATCAATGTCCTTCTCGGACCAGTCGCCGGCCCCCTTGGCCGCATGCCCGAGGGCGGTCGT

AACTGGGAAGGCTTCGCTCCGGATCCCGTCCTTACCGGCATCGGCATGTCCGAGACGATCAA

GGGCATTCAGGATGCTGGCGTCATCGCTTGTGCGAAGCACTTTATTGGAAACGAGCAGGAGC

ACTTCAGACAGGTGCCAGAAGCCCAGGGATACGGTTACAACATCAGCGAAACCCTCTCCTCC

AACATTGACGACAAGACCATGCACGAGCTCTACCTTTGGCCGTTTGCCGATGCCGTCCGGGC

CGGCGTCGGCTCTGTCATGTGCTCGTACCAGCAGGTCAACAACTCGTACGCCTGCCAGAACT

CGAAGCTGCTGAACGACCTCCTCAAGAACGAGCTTGGGTTTCAGGGCTTCGTCATGAGCGAC

TGGCAGGCACAGCACACTGGCGCAGCAAGCGCCGTGGCTGGTCTCGATATGTCCATGCCGG

GCGACACCCAGTTCAACACTGGCGTCAGTTTCTGGGGCGCCAATCTCACCCTCGCCGTCCTC

AACGGCACAGTCCCTGCCTACCGTCTCGACGACATGGCCATGCGCATCATGGCCGCCCTCTT

CAAGGTCACCAAGACCACCGACCTGGAACCGATCAACTTCTCCTTCTGGACCGACGACACTT

ATGGCCCGATCCACTGGGCCGCCAAGCAGGGCTACCAGGAGATTAATTCCCACGTTGACGTC

CGCGCCGACCACGGCAACCTCATCCGGGAGATTGCCGCCAAGGGTACGGTGCTGCTGAAGA

ATACCGGCTCTCTACCCCTGAACAAGCCAAAGTTCGTGGCCGTCATCGGCGAGGATGCTGGG

TCGAGCCCCAACGGGCCCAACGGCTGCAGCGACCGCGGCTGTAACGAAGGCACGCTCGCCA

TGGGCTGGGGATCCGGCACAGCCAACTATCCGTACCTCGTTTCCCCCGACGCCGCGCTCCAG

GCCCGGGCCATCCAGGACGGCACGAGGTACGAGAGCGTCCTGTCCAACTACGCCGAGGAAA

AGACAAAGGCTCTGGTCTCGCAGGCCAATGCAACCGCCATCGTCTTCGTCAATGCCGACTCA

GGCGAGGGCTACATCAACGTGGACGGTAACGAGGGCGACCGTAAGAACCTGACTCTCTGGA

ACAACGGTGATACTCTGGTCAAGAACGTCTCGAGCTGGTGCAGCAACACCATCGTCGTCATC

-continued

```
CACTCGGTCGGCCCGGTCCTCCTGACCGATTGGTACGACAACCCCAACATCACGGCCATTCT

CTGGGCTGGTCTTCCGGGCCAGGAGTCGGGCAACTCCATCACCGACGTGCTTTACGGCAAGG

TCAACCCCGCCGCCCGCTCGCCCTTCACTTGGGGCAAGACCCGCGAAAGCTATGGCGCGGAC

GTCCTGTACAAGCCGAATAATGGCAATGGTGCGCCCCAACAGGACTTCACCGAGGGCGTCTT

CATCGACTACCGCTACTTCGACAAGGTTGACGATGACTCGGTCATCTACGAGTTCGGCCACG

GCCTGAGCTACACCACCTTCGAGTACAGCAACATCCGCGTCGTCAAGTCCAACGTCAGCGAG

TACCGGCCCACGACGGGCACCACGGCCCAGGCCCCGACGTTTGGCAACTTCTCCACCGACCT

CGAGGACTATCTCTTCCCCAAGGACGAGTTCCCCTACATCTACCAGTACATCTACCCGTACCT

CAACACGACCGACCCCCGGAGGGCCTCGGCCGATCCCCACTACGGCCAGACCGCCGAGGAG

TTCCTCCCGCCCCACGCCACCGATGACGACCCCCAGCCGCTCCTCCGGTCCTCGGGCGGAAA

CTCCCCCGGCGGCAACCGCCAGCTGTACGACATTGTCTACACAATCACGGCCGACATCACGA

ATACGGGCTCCGTTGTAGGCGAGGAGGTACCGCAGCTCTACGTCTCGCTGGGCGGTCCCGAG

GATCCCAAGGTGCAGCTGCGCGACTTTGACAGGATGCGGATCGAACCCGGCGAGACGAGGC

AGTTCACCGGCCGCCTGACGCGCAGAGATCTGAGCAACTGGGACGTCACGGTGCAGGACTG

GGTCATCAGCAGGTATCCCAAGACGGCATATGTTGGGAGGAGCAGCCGGAAGTTGGATCTC

AAGATTGAGCTTCCTTGA
```

(SEQ ID NO: 116)
<u>MKAAALSCLFGSTLAVAGA</u>IESRKVHQKPLARSEPFYPSPWMNPNADGWAEAYAQAKSEVSQM
TELEKVNLTTGVGWGAEQCVGQVGAIPRLGLRSLCMHDSPLGIRGADYNSAFPSGQTVAATWD
RGLMYRRGYAMGQEAKGKGINVLLGPVAGPLGRMPEGGRNWEGFAPDPVLTGIGMSETIKGIQ
DAGVIACAKHEIGNEQEFIMVPEAQGYGYNISETLSSNIDDKTMHELYLWPFADAVRAGVGSV
MCSYQQVNNSYACQNSKLLNDLLKNELGFQGFVMSDWQAQHTGAASAVAGLDMSMPGDTQF
NTGVSFWGANLTLAVINGTVPAYRLDDMAMRIMAALFKVTKTTDLEPINFSFWTDDTYGPIHW
AAKQGYQEINSHVDVRADHGNLIREIAAKGTVLLKNTGSLPLNKPKFVAVIGEDAGSSPNGPNG
CSDRGCNEGTLAMGWGSGTANYPYLVSPDAALQARAIQDGTRYESVLSNYAEEKTKALVSQAN
ATAIVFVNADSGEGYINVDGNEGDRKNETEWNNGDTLVKNVSSWCSNTIVVIHSVGPVELTDW
YDNPNITAILWAGLPGQESGNSITDVLYGKVNPAARSPFTWGKTRESYGADVLYKPNNGNGAPQ
QDFTEGVFIDYRYFDKVDDDSVIYEFGHGLSYTTFEYSNIRVVKSNVSEYRPTTGTTAQAPTEGN
FSTDLEDYLFPKDEFPYIYQYIYPYLNTTDPRRASADPHYGQTAEEFLPPHATDDDPQPLLRSSGG
NSPGGNRQLYDIVYTITADITNTGSVVGEEVPQLYVSLGGPEDPKVQLRDFDRMRIEPGETRQFT
GRLTRRDLSNWDVTVQDWVISRYPKTAYVGRSSRKLDLKIELP (SEQ ID NO: 117)
IESRKVHQKPLARSEPFYPSPWMNPNADGWAEAYAQAKSFVSQMTLLEKVNLTTGVGWGAEQ
CVGQVGAIPRLGLRSLCMHDSPLGIRGADYNSAFPSGQTVAATWDRGLMYRRGYAMGQEAKG
KGINVLLGPVAGPLGRMPEGGRNWEGFAPDPVLTGIGMSETIKGIQDAGVIACAKHFIGNEQEHF
RQVPEAQGYGYNISETLSSNIDDKTMBELYEWPFADAVRAGVGSVMCSYQQVNNSYACQNSKL
LNDLLKNELGFQGFVMSDWQAQHTGAASAVAGLDMSMPGDTQFNTGVSFWGANLTLAVLNG
TVPAYRLDDMAMRIMAALFKVTKTTDLEPINFSFWTDDTYGPIHWAAKQGYQEINSHVDVRAD
HGNLIREIAAKGTVLLKNTGSLPLNKPKFVAVIGEDAGSSPNGPNGCSDRGCNEGTLAMGWGSG
TANYPYLVSPDAALQARAIQDGTRYESVLSNYAEEKTKALVSQANATAIVEVNADSGEGYINVD
GNEGDRKNLTLWNNGDTLVKNVSSWCSNTIVVIHSVGPVLLTDWYDNPNITAILWAGLPGQES

-continued

```
GNSITDVLYGKVNPAARSPFTWGKTRESYGADVLYKPNNGNGAPQQDFTEGVFIDYRYFDKVD

DDSVIYEFGHGLSYTTFEYSNIRVVKSNVSEYRPTTGTTAQAPTFGNFSTDLEDYLFPKDEFPYIY

QYIYPYLNTTDPRRASADPHYGQTAEEFLPPHATDDDPQPLLRSSGGNSPGGNRQLYDIVYTITA

DITNTGSVVGEEVPQLYVSLGGPEDPKVQLRDFDRMRIEPGETRQFTGRLTRRDLSNWDVTVQD

WVISRYPKTAYVGRSSRKLDLKIELP
```

The polynucleotide (SEQ ID NO:118) and amino acid (SEQ ID NO:119) sequences of a BGL variant ("Variant 883") are provided below. The signal sequence is underlined in SEQ ID NO:119. SEQ ID NO:120 provides the sequence of this BGL variant, without the signal sequence.

```
                                                    (SEQ ID NO: 118)
ATGAAGGCTGCTGCGCTTTCCTGCCTCTTCGGCAGTACCCTTGCCGTTGCAGGCGCCATTGAA

TCGAGAAAGGTTCACCAGAAGCCCCTCGCGAGATCTGAACCTTTTTACCCGTCGCCATGGAT

GAATCCCAACGCCGACGGCTGGGCGGAGGCCTATGCCCAGGCCAAGTCCTTTGTCTCCCAAA

TGACTCTGCTAGAGAAGGTCAACTTGACCACGGGAGTCGGCTGGGGGGCTGAGCAGTGCGT

CGGCCAAGTGGGCGCGATCCCTCGCCTTGGACTTCGCAGTCTGTGCATGCATGACTCCCCTC

TCGGCATCCGAGGAGCCGACTACAACTCAGCGTTCCCCTCTGGCCAGACCGTTGCTGCTACC

TGGGATCGCGGTCTGATGTACCGTCGCGGCTACGCAATGGGCCAGGAGGCCAAAGGCAAGG

GCATCAATGTCCTTCTCGGACCAGTCGCCGGCCCCCTTGGCCGCATGCCCGAGGGCGGTCGT

AACTGGGAAGGCTTCGCTCCGGATCCCGTCCTTACCGGCATCGGCATGTCCGAGACGATCAA

GGGCATTCAGGATGCTGGCGTCATCGCTTGTGCGAAGCACTTTATTGGAAACGAGCAGGAGC

ACTTCAGACAGGTGCCAGAAGCCCAGGGATACGGTTACAACATCAGCGAAACCCTCTCCTCC

AACATTGACGACAAGACCATGCACGAGCTCTACCTTTGGCCGTTTGCCGATGCCGTCCGGGC

CGGCGTCGGCTCTGTCATGTGCTCGTACAACCAGGTCAACAACTCGTACGCCTGCCAGAACT

CGAAGCTGCTGAACGACCTCCTCAAGAACGAGCTTGGGTTTCAGGGCTTCGTCATGAGCGAC

TGGTGGGCACAGCACACTGGCGCAGCAAGCGCCGTGGCTGGTCTCGATATGTCCATGCCGG

GCGACACCATGTTCAACACTGGCGTCAGTTTCTGGGGCGCCAATCTCACCCTCGCCGTCCTC

AACGGCACAGTCCCTGCCTACCGTCTCGACGACATGGCCATGCGCATCATGGCCGCCCTCTT

CAAGGTCACCAAGACCACCGACCTGGAACCGATCAACTTCTCCTTCTGGACCCGCGACACTT

ATGGCCCGATCCACTGGGCCGCCAAGCAGGGCTACCAGGAGATTAATT' CCCACGTTGACGTC

CGCGCCGACCACGGCAACCTCATCCGGAACATTGCCGCCAAGGGTACGGTGCTGCTGAAGA

ATACCGGCTCTCTACCCCTGAACAAGCCAAAGTTCGTGGCCGTCATCGGCGAGGATGCTGGG

CCGAGCCCAACGGGCCCAACGGCTGCAGCGACCGCGGCTGTAACGAAGGCACGCTCGCCA

TGGGCTGGGGATCCGGCACAGCCAACTATCCGTACCTCGTTTCCCCCGACGCCGCGCTCCAG

TTGCGGGCCATCCAGGACGGCACGAGGTACGAGAGCGTCCTGTCCAACTACGCCGAGGAAA

ATACAAAGGCTCTGGTCTCGCAGGCCAATGCAACCGCCATCGTCTTCGTCAATGCCGACTCA

GGCGAGGGCTACATCAACGTGGACGGTAACGAGGGCGACCGTAAGAACCTGACTCTCTGGA

ACAACGGTGATACTCTGGTCAAGAACGTCTCGAGCTGGTGCAGCAACACCATCGTCGTCATC

CACTCGGTCGGCCCGGTCCTCCTGACCGATTGGTACGACAACCCCAACATCACGGCCATTCT

CTGGGCTGGTCTTCCGGGCCAGGAGTCGGGCAACTCCATCACCGACGTGCTTTACGGCAAGG

TCAACCCCGCCGCCCGCTCGCCCTTCACTTGGGGCAAGACCCGCGAAAGCTATGGCGCGGAC

GTCCTGTACAAGCCGAATAATGGCAATTGGGCGCCCCAACAGGACTTCACCGAGGGCGTCTT
```

```
CATCGACTACCGCTACTTCGACAAGGTTGACGATGACTCGGTCATCTACGAGTTCGGCCACG

GCCTGAGCTACACCACCTTCGAGTACAGCAACATCCGCGTCGTCAAGTCCAACGTCAGCGAG

TACCGGCCCACGACGGGCACCACGATTCAGGCCCCGACGTTTGGCAACTTCTCCACCGACCT

CGAGGACTATCTCTTCCCCAAGGACGAGTTCCCCTACATCCCGCAGTACATCTACCCGTACC

TCAACACGACCGACCCCCGGAGGGCCTCGGCCGATCCCCACTACGGCCAGACCGCCGAGGA

GTTCCTCCCGCCCCACGCCACCGATGACGACCCCCAGCCGCTCCTCCGGTCCTCGGGCGGAA

ACTCCCCCGGCGGCAACCGCCAGCTGTACGACATTGTCTACACAATCACGGCCGACATCACG

AATACGGGCTCCGTTGTAGGCGAGGAGGTACCGCAGCTCTACGTCTCGCTGGGCGGTCCCGA

GGATCCCAAGGTGCAGCTGCGCGACTTTGACAGGATGCGGATCGAACCCGGCGAGACGAGG

CAGTTCACCGGCCGCCTGACGCGCAGAGATCTGAGCAACTGGGACGTCACGGTGCAGGACT

GGGTCATCAGCAGGTATCCCAAGACGGCATATGTTGGGAGGAGCAGCCGGAAGTTGGATCT

CAAGATTGAGCTTCCTTGA
```

(SEQ ID NO: 119)
<u>MKAAALSCLFGSTLAVAGA</u>IESRKVHQKPLARSEPFYPSPWMNPNADGWAEAYAQAKSFVSQM
TLLEKVNLTTGVGWGAEQCVGQVGAIPRLGLRSLCMHDSPLGIRGADYNSAFPSGQTVAATWD
RGLMYRRGYAMGQEAKGKGINVLLGPVAGPLGRMPEGGRNWEGFAPDPVLTGIGMSETIKGIQ
DAGVIACAKHFIGNEQEHFRQVPEAQGYGYNISETLSSNIDDKTMHELYLWPFADAVRAGVGSV
MCSYNQVNNSYACQNSKLLNDLLKNELGFQGFVMSDWWAQHTGAASAVAGLDMSMPGDTM
FNTGVSFWGANLTLAVLNGTVPAYRLDDMAMRIMAALFKVTKTTDLEPINFSFWTRDTYGPIH
WAAKQGYQEINSHVDVRADHGNLJRNIAAKGTVLLKNTGSLPLNKPKFVAVIGEDAGPSPNGPN
GCSDRGCNEGTLAMGWGSGTANYPYLVSPDAALQLRAIQDGTRYESVLSNYAEENTKALVSQA
NATAIVEVNADSGEGYINVDGNEGDRKNLTLWNNGDTLVKNVSSWCSNTIVVIHSVGPVLLTD
WYDNPNITAILWAGLPGQESGNSITDVLYGKVNPAARSPFTWGKTRESYGADVLYKPNNGNWA
PQQDFTEGVFIDYRYEDKVDDDSVIYEFGHGLSYTTFEYSNIRVVKSNVSEYRPTTGTTIQAPTEG
NFSTDLEDYLFPKDEFPYIPQYIYPYLNTTDPRRASADPHYGQTAEEFLPPHATDDDPQPLLRSSG
GNSPGGNRQLYDIVYTITADITNTGSVVGEEVPQLYVSLGGPEDPKVQLRDFDRMRIEPGETRQF
TGRLTRRDLSNWDVTVQDWVISRYPKTAYVGRSSRKLDLKIELP (SEQ ID NO: 120)
IESRKVHQKPLARSEPFYPSPWMNPNADGWAEAYAQAKSFVSQMTLLEKVNLTTGVGWGAEQ
CVGQVGAIPRLGIRSLCMHDSPLGIRGADYNSAFPSGQTVAATWDRGLMYRRGYAMGQEAKG
KGINVLLGPVAGPLGRMPEGGRNWEGFAPDPVLTGIGMSETIKGIQDAGVIACAKHFIGNEQEHF
RQVPEAQGYGYNISETLSSNIDDKTMHELYLWPFADAVRAGVGSVMCSYNQVNNSYACQNSKL
LNDLLKNELGFQGFVMSDWWAQHTGAASAVAGLDMSMPGDTMFNTGVSFWGANLTLAVLNG
TVPAYRLDDMAMRIMAALFKVTKTTDLEPINFSFWTRDTYGPIHWAAKQGYQEINSHVDVRAD
HGNLIRNIAAKGTVLLKNTGSLPLNKPKFVAVIGEDAGPSPNGPNGCSDRGCNEGTLAMGWGSG
TANYPYLVSPDAALQLRAIQDGTRYESVLSNYAEENTKALVSQANATAIVEVNADSGEGYINVD
GNEGDRKNLTLWNNGDTLVKNVSSWCSNTIVVIHSVGPVLLTDWYDNPNITAILWAGLPGQES
GNSITDVLYGKVNPAARSPFTWGKTRESYGADVLYKPNNGNWAPQQDFTEGVFIDYRYFDKVD

-continued
DDSVIYEFGHGLSYTTFEYSNIRVVKSNVSEYRPTTGTTIQAPTFGNFSTDLEDYLFPKDEFPYIPQ

YIYPYLNTTDPRRASADPHYGQTAEEFLPPHATDDDPQPLLRSSGGNSPGGNRQLYDIVYTITADI

TNTGSVVGEEVPQLYVSLGGPEDPKVQLRDFDRMRIEPGETRQFTGRLTRRDLSNWDVTVQDW

VISRYPKTAYVGRSSRKLDLKIELP

The polynucleotide (SEQ ID NO:121) and amino acid (SEQ ID NO:122) sequences of a BGL variant ("Variant 900") are provided below. The signal sequence is underlined in SEQ ID NO:122. SEQ ID NO:123 provides the sequence of this BGL variant, without the signal sequence.

(SEQ ID NO: 121)
ATGAAGGCTGCTGCGCTTTCCTGCCTCTTCGGCAGTACCCTTGCCGTTGCAGGCGCCATTGAA

TCGAGAAAGGTTCACCAGAAGCCCCTCGCGAGATCTGAACCTTTTTACCCGTCGCCATGGAT

GAATCCCAACGCCATCGGCTGGGCGGAGGCCTATGCCCAGGCCAAGTCCTTTGTCTCCCAAA

TGACTCTGCTAGAGAAGGTCAACTTGACCACGGGAGTCGGCTGGGGGAGGAGCAGTGCGT

CGGCAACGTGGGCGCGATCCCTCGCCTTGGACTTCGCAGTCTGTGCATGCATGACTCCCCTC

TCGGCGTGCGAGGAACCGACTACAACTCAGCGTTCCCCTCTGGCCAGACCGTTGCTGCTACC

TGGGATCGCGGTCTGATGTACCGTCGCGGCTACGCAATGGGCCAGGAGGCCAAAGGCAAGG

GCATCAATGTCCTTCTCGGACCAGTCGCCGGCCCCCTTGGCCGCATGCCCGAGGGCGGTCGT

AACTGGGAAGGCTTCGCTCCGGATCCCGTCCTTACCGGCATCGGCATGTCCGAGACGATCAA

GGGCATTCAGGATGCTGGCGTCATCGCTTGTGCGAAGCACTTTATTGGAAACGAGCAGGAGC

ACTTCAGACAGGTGCCAGAAGCCCAGGGATACGGTTACAACATCAGCGAAACCCTCTCCTCC

AACATTGACGACAAGACCATGCACGAGCTCTACCTTTGGCCGTTTGCCGATGCCGTCCGGGC

CGGCGTCGGCTCTGTCATGTGCTCGTACAACCAGGGCAACAACTCGTACGCCTGCCAGAACT

CGAAGCTGCTGAACGACCTCCTCAAGAACGAGCTTGGGTTTCAGGGCTTCGTCATGAGCGAC

TGGTGGGCACAGCACACTGGCGCAGCAAGCGCCGTGGCTGGTCTCGATATGTCCATGCCGG

GCGACACCATGGTCAACACTGGCGTCAGTTTCTGGGGCGCCAATCTCACCCTCGCCGTCCTC

AACGGCACAGTCCCTGCCTACCGTCTCGACGACATGTGCATGCGCATCATGGCCGCCCTCTT

CAAGGTCACCAAGACCACCGACCTGGAACCGATCAACTTCTCCTTCTGGACCCGCGACACTT

ATGGCCCGATCCACTGGGCCGCCAAGCAGGGCTACCAGGAGATTAATTCCCACGTTGACGTC

CGCGCCGACCACGGCAACCTCATCCGGAACATTGCCGCCAAGGGTACGGTGCTGCTGAAGA

ATACCGGCTCTCTACCCCTGAACAAGCCAAAGTTCGTGGCCGTCATCGGCGAGGATGCTGGG

CCGAGCCCAACGGGCCCAACGGCTGCAGCGACCGCGGCTGTAACGAAGGCACGCTCGCCA

TGGGCTGGGGATCCGGCACAGCCAACTATCCGTACCTCGTTTCCCCCGACGCCGCGCTCCAG

GCGCGGGCCATCCAGGACGGCACGAGGTACGAGAGCGTCCTGTCCAACTACGCCGAGGAAA

ATACAAAGGCTCTGGTCTCGCAGGCCAATGCAACCGCCATCGTCTTCGTCAATGCCGACTCA

GGCGAGGGCTACATCAACGTGGACGGTAACGAGGGCGACCGTAAGAACCTGACTCTCTGGA

ACAACGGTGATACTCTGGTCAAGAACGTCTCGAGCTGGTGCAGCAACACCATCGTCGTCATC

CACTCGGTCGGCCCGGTCCTCCTGACCGATTGGTACGACAACCCCAACATCACGGCCATTCT

CTGGGCTGGTCTTCCGGGCCAGGAGTCGGGCAACTCCATCACCGACGTGCTTTACGGCAAGG

TCAACCCCGCCGCCCGCTCGCCCTTCACTTGGGGCAAGACCCGCGAAAGCTATGGCGCGGAC

GTCCTGTACAAGCCGAATAATGGCAATTGGGCGCCCCAACAGGACTTCACCGAGGGCGTCTT

CATCGACTACCGCTACTTCGACAAGGTTGACGATGACTCGGTCATCTACGAGTTCGGCCACG

-continued

```
GCCTGAGCTACACCACCTTCGAGTACAGCAACATCCGCGTCGTCAAGTCCAACGTCAGCGAG

TACCGGCCCACGACGGGCACCACGATTCAGGCCCCGACGTTTGGCAACTTCTCCACCGACCT

CGAGGACTATCTCTTCCCCAAGGACGAGTTCCCCTACATCCCGCAGTACATCTACCCGTACC

TCAACACGACCGACCCCCGGAGGGCCTCGGGCGATCCCCACTACGGCCAGACCGCCGAGGA

GTTCCTCCCGCCCCACGCCACCGATGACGACCCCCAGCCGCTCCTCCGGTCCTCGGGCGGAA

ACTCCCCCGGCGGCAACCGCCAGCTGTACGACATTGTCTACACAATCACGGCCGACATCACG

AATACGGGCTCCGTTGTAGGCGAGGAGGTACCGCAGCTCTACGTCTCGCTGGGCGGTCCCGA

GGATCCCAAGGTGCAGCTGCGCGACTTTGACAGGATGCGGATCGAACCCGGCGAGACGAGG

CAGTTCACCGGCCGCCTGACGCGCAGAGATCTGAGCAACTGGGACGTCACGGTGCAGGACT

GGGTCATCAGCAGGTATCCCAAGACGGCATATGTTGGGAGGAGCAGCCGGAAGTTGGATCT

CAAGATTGAGCTTCCTTGA
```

(SEQ ID NO: 122)
<u>MKAAALSCLFGSTLAVAGA</u>IESRKVHQKPLARSEPFYPSPWMNPNAIGWAEAYAQAKSFVSQM
TLLEKVNLTTGVGWGEEQCVGNVGAIPRLGLRSLCMHDSPLGVRGTDYNSAFPSGQTVAATWD
RGLMYRRGYAMGQEAKGKGINVLLGPVAGPLGRMPEGGRNWEGFAPDPVLTGIGMSETIKGIQ
DAGVIACAKITFIGNEQEHFRQVPEAQGYGYNISETLSSNIDDKTMHELYLWPFADAVRAGVGSV
MCSYNQGNNSYACQNSKLLNDLLKNELGFQGFVMSDWWAQHTGAASAVAGLDMSMPGDTM
VNTGVSFWGANLTLAVLNGTVPAYRLDDMCRIMAALFKVTKTTDLEPINFSFWTRDTYGPIH
WAAKQGYQEINSHVDVRADHGNLIRNIAAKGTVLLKNTGSLPLNKPKEVAVIGEDAGPSPNGPN
GCSDRGCNEGTLAMGWGSGTANYPYLVSPDAALQARAIQDGTRYESVLSNYAEENTKALVSQA
NATAIVFVNADSGEGYINVDGNEGDRKNLTLWNNGDTLVKNVSSWCSNTIVVIHSVGPVLLTD
WYDNPNITAILWAGLPGQESGNSITDVLYGKVNPAARSPFTWGKTRESYGADVLYKPNNGNWA
PQQDFTEGVFIDYRYFDKVDDDSVIYEFGHGLSYTTFEYSNIRVVKSNVSEYRPTTGTTIQAPTFG
NFSTDLEDYLFPKDEFPYIPQYIYPYLNTTDPRRASGDPHYGQTAEEFLPPHATDDDPQPLLASSG
GNSPGGNRQLYDIVYTITADITNTGSVVGEEVPQLYVSLGGPEDPKVQLRDFDRMRIEPGETRQF
TGRLTRRDLSNWDVTVQDWVISRYPKTAYVGRSSRKLDLKIELP (SEQ ID NO: 123)
IESRKVHQKPLARSEPFYPSPWMNPNAIGWAEAYAQAKSFVSQMTLLEKVNLTTGVGWGEEQC
VGNVGAIPRLGLRSLCMHDSPLGVRGTDYNSAFPSGQTVAATWDRGLMYRRGYAMGQEAKGK
GINVLLGPVAGPLGRMPEGGRNWEGFAPDPVLTGIGMSETIKGIQDAGVIACAKHFIGNEQEHFR
QVPEAQGYGYNISETLSSNIDDKTMHELYLWPFADAVRAGVGSVMCSYNQGNNSYACQNSKLL
NDLLKNELGFQGFVMSDWWAQHTGAASAVAGLDMSMPGDTMVNTGVSFWGANLTLAVLNG
TVPAYRLDDMCRIMAALFKVTKTTDLEPINFSFWTRDTYGPIHWAAKQGYQEINSHVDVRAD
HGNLIRNIAAKGTVLLKNTGSLPLNKPKFVAVIGEDAGPSPNGPNGCSDRGCNEGTLAMGWGSG
TANYPYLVSPDAALQARAIQDGTRYESVLSNYAEENTKALVSQANATAIVFVNADSGEGYINVD
GNEGDRKNLTLWNNGDTLVKNVSSWCSNTIVVIHSVGPVLLTDWYDNPNITAILWAGLPGQES
GNSITDVLYGKVNPAARSPFTWGKTRESYGADVLYICPNNGNWAPQQDFTEGVFIDYRYFDKVD
DDSVIYEFGHGLSYTTFEYSNIRVVKSNVSEYRPTTGTTIQAPTFGNFSTDLEDYLFPKDEFPYIPQ
YIYPYLNTTDPRRASGDPHYGQTAEEFLPPHATDDDPQPLLRSSGGNSPGGNRQTYDIVYTITADI
TNTGSVVGEEVPQLYVSLGGPEDPKVQLRDTDRMRIEPGETRQFTGRLTRRDLSNWDVTVQDW
VISRYPKTAYVGRSSRKLDLKIELP

The polynucleotide (SEQ ID NO:124) and amino acid (SEQ ID NO:125) sequences of wild-type *Talaromyces emersonii* CBH1 are provided below. The signal sequence is shown underlined in SEQ ID NO:125. SEQ ID NO:126 provides the sequence of this CBH1, without the signal sequence.

(SEQ ID NO: 124)
ATGCTTCGACGGGCTCTTCTTCTATCCTCTTCCGCCATCCTTGCTGTCAAGGCACAGCAGGCC

GGCACGGCGACGGCAGAGAACCACCCGCCCCTGACATGGCAGGAATGCACCGCCCCTGGGA

GCTGCACCACCCAGAACGGGGCGGTCGTTCTTGATGCGAACTGGCGTTGGGTGCACGATGTG

AACGGATACACCAACTGCTACACGGGCAATACCTGGGACCCCACGTACTGCCCTGACGACG

AAACCTGCGCCCAGAACTGTGCGCTGGACGGCGCGGATTACGAGGGCACCTACGGCGTGAC

TTCGTCGGGCAGCTCCTTGAAACTCAATTTCGTCACCGGGTCGAACGTCGGATCCCGTCTCTA

CCTGCTGCAGGACGACTCGACCTATCAGATCTTCAAGCTTCTGAACCGCGAGTTCAGCTTTG

ACGTCGATGTCTCCAATCTTCCGTGCGGATTGAACGGCGCTCTGTACTTTGTCGCCATGGACG

CCGACGGCGGCGTGTCCAAGTACCCGAACAACAAGGCTGGTGCCAAGTACGGAACCGGGTA

TTGCGACTCCCAATGCCCACGGGACCTCAAGTTCATCGACGGCGAGGCCAACGTCGAGGGCT

GGCAGCCGTCTTCGAACAACGCCAACACCGGAATTGGCGACCACGGCTCCTGCTGTGCGGA

GATGGATGTCTGGGAAGCAAACAGCATCTCCAATGCGGTCACTCCGCACCCGTGCGACACG

CCAGGCCAGACGATGTGCTCTGGAGATGACTGCGGTGGCACATACTCTAACGATCGCTACGC

GGGAACCTGCGATCCTGACGGCTGTGACTTCAACCCTTACCGCATGGGCAACACTTCTTTCT

ACGGGCCTGGCAAGATCATCGATACCACCAAGCCCTTCACTGTCGTGACGCAGTTCCTCACT

GATGATGGTACGGATACTGGAACTCTCAGCGAGATCAAGCGCTTCTACATCCAGAACAGCA

ACGTCATTCCGCAGCCCAACTCGGACATCAGTGGCGTGACCGGCAACTCGATCACGACGGA

GTTCTGCACTGCTCAGAAGCAGGCCTTTGGCGACACGGACGACTTCTCTCAGCACGGTGGCC

TGGCCAAGATGGGAGCGGCCATGCAGCAGGGTATGGTCCTGGTGATGAGTTTGTGGGACGA

CTACGCCGCGCAGATGCTGTGGTTGGATTCCGACTACCCGACGGATGCGGACCCCACGACCC

CTGGTATTGCCCGTGGAACGTGTCCGACGGACTCGGGCGTCCCATCGGATGTCGAGTCGCAG

AGCCCCAACTCCTACGTGACCTACTCGAACATTAAGTTTGGTCCGATCAACTCGACCTTCAC

CGCTTCGTGA (SEQ ID NO: 125)
<u>MLRRALLLSSSAILAVKA</u>QQAGTATAENHPPLTWQECTAPGSCTTQNGAVVLDANWRWVHDV

NGYTNCYTGNTWDPTYCPDDETCAQNCALDGADYEGTYGVTSSGSSLKLNEVTGSNVGSRLYL

LQDDSTYQIFKLLNREFSEDVDVSNLPCGENGALYFVAMDADGGVSKYPNNKAGAKYGTGYCD

SQCPRDLKFIDGEANVEGWQPSSNNANTGIGDHGSCCAEMDVWEANSISNAVTPHPCDTPGQT

MCSGDDCGGTYSNDRYAGTCDPDGCDFNPYRMGNTSFYGPGKIIDTTKPFTVVTQFLTDDGTDT

GTLSEIKRFYIQNSNVIPQPNSDISGVTGNSITTEFCTAQKQAFGDTDDFSQHGGLAKMGAAMQQ

GMVLVMSLWDDYAAQMLWLDSDYPTDADPTTPGIARGTCPTDSGVPSDVESQSPNSYVTYSNI

KFGPINSTFTAS (SEQ ID NO: 126)
QQAGTATAENHPPLTWQECTAPGSCTTQNGAVVLDANWRWVHDVNGYTNCYTGNTWDPTYC

PDDETCAQNCALDGADYEGTYGVTSSGSSLKLNFVTGSNVGSRLYLLQDDSTYQIFKLLNREFSF

DVDVSNLPCGLNGALYFVAMDADGGVSKYPNNKAGAKYGTGYCDSQCPRDLKFIDGEANVEG

WQPSSNNANTGIGDHGSCCAEMDVWEANSISNAVTPHPCDTPGQTMCSGDDCGGTYSNDRYA

-continued

```
GTCDPDGCDFNPYRMGNTSFYGPGKIIDTTKPFTVVTQFLTDDGTDTGTLSEIKRFYIQNSNVIPQ

PNSDISGVIGNSITTEFCTAQKQAFGDTDDESQHGGLAKMGAAMQQGMVLVMSLWDDYAAQM

LWLDSDYPTDADPTTPGIARGTCPTDSGVPSDVESQSPNSYVTYSNIKFGPINSTFTAS
```

The polynucleotide (SEQ ID NO:127) and amino acid (SEQ ID NO:128) sequences of wild-type *M. thermophila* CBH1a are provided below. The signal sequence is shown underlined in SEQ ID NO:128. SEQ ID NO:129 provides the sequence of this CBH1a, without the signal sequence.

(SEQ ID NO: 127)
```
ATGTACGCCAAGTTCGCGACCCTCGCCGCCCTTGTGGCTGGCGCCGCTGCTCAGAACGCCTG

CACTCTGACCGCTGAGAACCACCCCTCGCTGACGTGGTCCAAGTGCACGTCTGGCGGCAGCT

GCACCAGCGTCCAGGGTTCCATCACCATCGACGCCAACTGGCGGTGGACTCACCGGACCGAT

AGCGCCACCAACTGCTACGAGGGCAACAAGTGGGATACTTCGTACTGCAGCGATGGTCCTTC

TTGCGCCTCCAAGTGCTGCATCGACGGCGCTGACTACTCGAGCACCTATGGCATCACCACGA

GCGGTAACTCCCTGAACCTCAAGTTCGTCACCAAGGGCCAGTACTCGACCAACATCGGCTCG

CGTACCTACCTGATGGAGAGCGACACCAAGTACCAGATGTTCCAGCTCCTCGGCAACGAGTT

CACCTTCGATGTCGACGTCTCCAACCTCGGCTGCGGCCTCAATGGCGCCCTCTACTTCGTGTC

CATGGATGCCGATGGTGGCATGTCCAAGTACTCGGGCAACAAGGCAGGTGCCAAGTACGGT

ACCGGCTACTGTGATTCTCAGTGCCCCCGCGACCTCAAGTTCATCAACGGCGAGGCCAACGT

AGAGAACTGGCAGAGCTCGACCAACGATGCCAACGCCGGCACGGGCAAGTACGGCAGCTGC

TGCTCCGAGATGGACGTCTGGGAGGCCAACAACATGGCCGCCGCCTTCACTCCCCACCCTTG

CACCGTGATCGGCCAGTCGCGCTGCGAGGGCGACTCGTGCGGCGGTACCTACAGCACCGAC

CGCTATGCCGGCATCTGCGACCCCGACGGATGCGACTTCAACTCGTACCGCCAGGGCAACAA

GACCTTCTACGGCAAGGGCATGACGGTCGACACGACCAAGAAGATCACGGTCGTCACCCAG

TTCCTCAAGAACTCGGCCGGCGAGCTCTCCGAGATCAAGCGGTTCTACGTCCAGAACGGCAA

GGTCATCCCCAACTCCGAGTCCACCATCCCGGGCGTCGAGGGCAACTCCATCACCCAGGACT

GGTGCGACCGCCAGAAGGCCGCCTTCGGCGACGTGACCGACTTCCAGGACAAGGGCGGCAT

GGTCCAGATGGGCAAGGCCCTCGCGGGCCCATGGTCCTCGTCATGTCCATCTGGGACGACC

ACGCCGTCAACATGCTCTGGCTCGACTCCACCTGGCCCATCGACGGCGCCGGCAAGCCGGGC

GCCGAGCGCGGTGCCTGCCCCACCACCTCGGGCGTCCCCGCTGAGGTCGAGGCCGAGGCCC

CCAACTCCAACGTCATCTTCTCCAACATCCGCTTCGGCCCCATCGGCTCCACCGTCTCCGGCC

TGCCCGACGGCGGCAGCGGCAACCCCAACCCGCCCGTCAGCTCGTCCACCCCGGTCCCCTCC

TCGTCCACCACATCCTCCGGTTCCTCCGGCCCGACTGGCGGCACGGGTGTCGCTAAGCACTA

TGAGCAATGCGGAGGAATCGGGTTCACTGGCCCTACCCAGTGCGAGAGCCCCTACACTTGCA

CCAAGCTGAATGACTGGTACTCGCAGTGCCTGTAA
```

(SEQ ID NO: 128)
```
MYAKFATLAALVAGAAAQNACTLTAENHPSLTYSKCTSGGSCTSVQGSITIDANWRWTHRTDS

ATNCYEGNKWDTSWCSDGPSCASKCCIDGADYSSTYGITTSGNSLNLKFVTKGQYSTNIGSRTY

LMESDTKYQMFQLLGNEFTFDVDVSNLGCGLNGALYFVSMDADGGMSKYSGNKAGAKYGTG

YCDSQCPRDLKFINGEANVENWQSSINDANAGTGKYGSCCSEMDVWEANNMAAAFTPFIPCTVI

GQSRCEGDSCGGTYSTDRYAGICDPDGCDFNSYRQGNKTFYGKGMTVDTTKKITVVTQFLKNS

AGELSELECRFYVQNGKVIPNSESTIPGVEGNSITQDWCDRQKAAFGDVTDFQDKGGMVQMGICA
```

```
LAGPMVLVMSIWDDHAVNMLWLDSTWPIDGAGKPGAERGACPTTSGVPAEVEAEAPNSNVIFS

NIRFGPIGSTVSGLPDGGSGNPNPPVSSSTPVPSSSTTSSGSSGPTGGTGVAKHYEQCGGIGFTGPT

QCESPYTCTKLNDWYSQCL
```

(SEQ ID NO: 129)
```
QNACTLTAENHPSLTYSKCTSGGSCTSVQGSITIDANWRWTHRTDSAINCYEGNKWDTSWCSD

GPSCASKCCIDGADYSSTYGITTSGNSLNLKFVTKGQYSTNIGSRTYLMESDTKYQMFQLLGNEF

TFDVDVSNLGCGLNGALYFVSMDADGGMSKYSGNKAGAKYGTGYCDSQCPRDLKFINGEANV

ENWQSSTNDANAGTGKYGSCCSEMDVWEANNMAAAFTPHPCTVIGQSRCEGDSCGGTYSTDR

YAGICDPDGCDFNSYRQGNKTFYGKGMTVDTTKKITVVTQFLKNSAGELSEIKRFYVQNGKVIP

NSESTIPGVEGNSITQDWCDRQKAAFGDVTDFQDKGGMVQMGKALAGPMVLVMSIWDDHAVN

MLWLDSTWPIDGAGKPGAERGACPTTSGVPAEVEALAPNSNVITSNIRFGPIGSTVSGLPDGGSG

NPNPPVSSSTPVPSSSTTSSGSSGPTGGTGVAKHYEQCGGIGFTGPTQCESPYTCTKLNDWYSQCL
```

The polynucleotide (SEQ ID NO:130) and amino acid (SEQ ID NO:131) sequences of a *M. thermophila* CBH1a variant ("Variant 145") are provided below. The signal sequence is shown underlined in SEQ ID NO:131. SEQ ID NO:132 provides the sequence of this CBH1a, without the signal sequence.

(SEQ ID NO: 130)
```
ATGTACGCCAAGTTCGCGACCCTCGCCGCCCTTGTGGCTGGCGCCGCTGCTCAGAACGCCTG

CACTCTGACCGCTGAGAACCACCCCTCGCTGACGTGGTCCAAGTGCACGTCTGGCGGCAGCT

GCACCAGCGTCCAGGGTTCCATCACCATCGACGCCAACTGGCGGTGGACTCACCGGACCGAT

AGCGCCACCAACTGCTACGAGGGCAACAAGTGGGATACTTCGTGGTGCAGCGATGGTCCTTC

TTGCGCCTCCAAGTGCTGCATCGACGGCGCTGACTACTCGAGCACCTATGGCATCACCACGA

GCGGTAACTCCCTGAACCTCAAGTTCGTCACCAAGGGCCAGTACTCGACCAACATCGGCTCG

CGTACCTACCTGATGGAGAGCGACACCAAGTACCAGATGTTCCAGCTCCTCGGCAACGAGTT

CACCTTCGATGTCGACGTCTCCAACCTCGGCTGCGGCCTCAATGGCGCCCTCTACTTCGTGTC

CATGGATGCCGATGGTGGCATGTCCAAGTACTCGGGCAACAAGGCAGGTGCCAAGTACGGT

ACCGGCTACTGTGATTCTCAGTGCCCCCGCGACCTCAAGTTCATCAACGGCGAGGCCAACGT

AGAGAACTGGCAGAGCTCGACCAACGATGCCAACGCCGGCACGGGCAAGTACGGCAGCTGC

TGCTCCGAGATGGACGTCTGGGAGGCCAACAACATGGCCGCCGCCTTCACTCCCCACCCTTG

CACCGTGATCGGCCAGTCGCGCTGCGAGGGCGACTCGTGCGGCGGTACCTACAGCACCGAC

CGCTATGCCGGCATCTGCGACCCCGACGGATGCGACTTCAACTCGTACCGCCAGGGCAACAA

GACCTTCTACGGCAAGGGCATGACGGTCGACACGACCAAGAAGATCACGGTCGTCACCCAG

TTCCTCAAGAACTCGGCCGGCGAGCTCTCCGAGATCAAGCGGTTCTACGTCCAGAACGGCAA

GGTCATCCCCAACTCCGAGTCCACCATCCCGGGCGTCGAGGGCAACTCCATCACCCAGGACT

GGTGCGACCGCCAGAAGGCCGCCTTCGGCGACGTGACCGACTTCCAGGACAAGGGCGGCAT

GGTCCAGATGGGCAAGGCCCTCGCGGGGCCCATGGTCCTCGTCATGTCCATCTGGGACGACC

ACGCCGTCAACATGCTCTGGCTCGACTCCACCTGGCCCATCGACGGCGCCGGCAAGCCGGGC

GCCGAGCGCGGTGCCTGCCCCACCACCTCGGGCGTCCCCGCTGAGGTCGAGGCCGAGGCCC

CCAACTCCAACGTCATCTTCTCCAACATCCGCTTCGGCCCCATCGGCTCCACCGTCTCCGGCC

TGCCCGACGGCGGCAGCGGCAACCCCAACCCGCCCGTCAGCTCGTCCACCCCGGTCCCCTCC

TCGTCCACCACATCCTCCGGTTCCTCCGGCCCGACTGGCGGCACGGGTGTCGCTAAGCACTA

TGAGCAATGCGGAGGAATCGGGTTCACTGGCCCTACCCAGTGCGAGAGCCCCTACACTTGCA
```

```
CCAAGCTGAATGACTGGTACTCGCAGTGCCTGTAA
```

(SEQ ID NO: 131)
```
MYAKFATLAALVAGAAAQNACTLTAENHPSLTWSKCTSGGSCTSVQGSITIDANWRWTHRTDS
ATNCYEGNKWDTSWCSDGPSCASKCCIDGADYSSTYGITTSGNSLNLKFVTKGQYSTNIGSRTY
LMESDTKYQMFQLLGNEFTFDVDVSNLGCGLNGALYFVSMDADGGMSKYSGNKAGAKYGTG
YCDSQCPRDLKFINGEANVENWQSSTNDANAGTGKYGSCCSEMDVWEANNMAAAFTPFIPCTVI
GQSRCEGDSCGGTYSTDRYAGICDPDGCDFNSYRQGNKTFYGKGMTVDTTKKITVVTQFLKNS
AGELSEIKRFYVQNGKVIPNSESTIPGVEGNSITQDWCDRQKAAFGDVTDFQDKGGMVQMGKA
LAGPMVLVMSIWDDHAVNMLWLDSTWPIDGAGKPGAERGACPTTSGVPAEVEAEAPNSNVIFS
NIRFGPIGSTVSGLPDGGSGNPNPPVSSSTPVPSSSTTSSGSSGPTGGTGVAKHYEQCGGIGFTGPT
QCESPYTCTKLNDWYSQCL
```

(SEQ ID NO: 132)
```
QNACTLTAENHPSLTWSKCTSGGSCTSVQGSITIDANWRWTHRTDSATNCYEGNKWDTSWCSD
GPSCASKCCIDGADYSSTYGITTSGNSLNLKFVTKGQYSTNIGSRTYLMESDTKYQMFQLLGNEF
TFDVDVSNLGCGLNGALYFVSMDADGGMSKYSGNKAGAKYGTGYCDSQCPRDLKFINGEANV
ENWQSSTNDANAGTGKYGSCCSEMDVWEANNMAAAFTPHPCTVIGQSRCEGDSCGGTYSTDR
YAGICDPDGCDFNSYRQGNKTFYGKGMTVDTTKKITVVTQFLKNSAGELSEIKRFYVQNGKVIP
NSESTIPGVEGNSITQDWCDRQKAAFGDVTDFQDKGGMVQMGICALAGPMVLVMSIWDDHAVN
MLWLDSTWPIDGAGKPGAERGACPTTSGVPAEVEAEAPNSNVIHNERFGPIGSTVSGLPDGGSG
NPNPPVSSSTPVPSSSTTSSGSSGPTGGTGVAKHYEQCGGIGFTGPTQCESPYTCTKLNDWYSQCL
```

The polynucleotide (SEQ ID NO:133) and amino acid (SEQ ID NO:134) sequences of a *M. thermophila* CBH1a variant ("Variant 983") are provided below. The signal sequence is shown underlined in SEQ ID NO:134. SEQ ID NO:135 provides the sequence of this CBH1a variant, without the signal sequence.

(SEQ ID NO: 133)
```
ATGTACGCCAAGTTCGCGACCCTCGCCGCCCTTGTGGCTGGCGCCGCTGCTCAGAACGCCTG
CACTCTGAACGCTGAGAACCACCCCTCGCTGACGTGGTCCAAGTGCACGTCTGGCGGCAGCT
GCACCAGCGTCCAGGGITCCATCACCATCGACGCCAACTGGCGGTGGACTCACCGGACCGAT
AGCGCCACCAACTGCTACGAGGGCAACAAGTGGGATACTTCGTACTGCAGCGATGGTCCTTC
TTGCGCCTCCAAGTGCTGCATCGACGGCGCTGACTACTCGAGCACCTATGGCATCACCACGA
GCGGTAACTCCCTGAACCTCAAGTTCGTCACCAAGGGCCAGTACTCGACCAACATCGGCTCG
CGTACCTACCTGATGGAGAGCGACACCAAGTACCAGATGTTCCAGCTCCTCGGCAACGAGTT
CACCTTCGATGTCGACGTCTCCAACCTCGGCTGCGGCCTCAATGGCGCCCTCTACTTCGTGTC
CATGGATGCCGATGGTGGCATGTCCAAGTACTCGGGCAACAAGGCAGGTGCCAAGTACGGT
ACCGGCTACTGTGATTCTCAGTGCCCCCGCGACCTCAAGTTCATCAACGGCGAGGCCAACGT
AGAGAACTGGCAGAGCTCGACCAACGATGCCAACGCCGGCACGGGCAAGTACGGCAGCTGC
TGCTCCGAGATGGACGTCTGGGAGGCCAACAACATGGCCGCCGCCTTCACTCCCCACCCTTG
CACCGTGATCGGCCAGTCGCGCTGCGAGGGCGACTCGTGCGGCGGTACCTACAGCACCGAC
CGCTATGCCGGCATCTGCGACCCCGACGGATGCGACTTCAACTCGTACCGCCAGGGCAACAA
GACCTTCTACGGCAAGGGCATGACGGTCGACACGACCAAGAAGATCACGGTCGTCACCCAG
TTCCTCAAGAACTCGGCCGGCGAGCTCTCCGAGATCAAGCGGTTCTACGTCCAGAACGGCAA
GGTCATCCCCAACTCCGAGTCCACCATCCCGGGCGTCGAGGGCAACTCCATCACCCAGGAGT
ACTGCGACCGCCAGAAGGCCGCCTTCGGCGACGTGACCGACTTCCAGGACAAGGGCGGCAT
```

-continued

```
GGTCCAGATGGGCAAGGCCCTCGCGGGGCCCATGGTCCTCGTCATGTCCATCTGGGACGACC

ACGCCGACAACATGCTCTGGCTCGACTCCACCTGGCCCATCGACGGCGCCGGCAAGCCGGG

CGCCGAGCGCGGTGCCTGCCCCACCACCTCGGGCGTCCCCGCTGAGGTCGAGGCCGAGGCC

CCCAACTCCAACGTCATCTTCTCCAACATCCGCTTCGGCCCCATCGGCTCCACCGTCTCCGGC

CTGCCCGACGGCGGCAGCGGCAACCCCAACCCGCCCGTCAGCTCGTCCACCCCGGTCCCCTC

CTCGTCCACCACATCCTCCGGTTCCTCCGGCCCGACTGGCGGCACGGGTGTCGCTAAGCACT

ATGAGCAATGCGGAGGAATCGGGTTCACTGGCCCTACCCAGTGCGAGAGCCCCTACACTTGC

ACCAAGCTGAATGACTGGTACTCGCAGTGCCTGTAA
```

```
                                                      (SEQ ID NO: 134)
MYAKFATLAALVAGAAAQNACTLNAENHPSLTWSKCTSGGSCTSVQGSITIDANWRWTHRTDS

ATNCYEGNKWDTSYCSDGPSCASKCCIDGADYSSTYGITTSGNSLNLKEVTKGQYSTNIGSRTYL

MESDTKYQMFQLLGNEFTFDVDVSNLGCGLNGALYFVSMDADGGMSKYSGNKAGAKYGTGY

CDSQCPRDLKENGEANVENWQSSTNDANAGTGKYGSCCSEMDVWEANNMAAAFTPHPCTVIG

QSRCEGDSCGGTYSTDRYAGICDPDGCDENSYRQGNKTFYGKGMTVDTTKKITVVTQFLKNSA

GELSETKREYVQNGKVIPNSESTIPGVEGNSITQEYCDRQKAAFGDVTDFQDKGGMVQMGKALA

GPMVLVMSIWDDHADNMLWLDSTWPIDGAGKPGAERGACPTTSGVPAEVEAEAPNSNVIFSNI

RFGPIGSTVSGLPDGGSGNPNPPVSSSTPVPSSSTTSSGSSGPTGGTGVAKHYEQCGGIGFTGPTQC

ESPYTCTKLNDWYSQCL
```

```
                                                      (SEQ ID NO: 135)
QNACTLNAENHPSLTWSKCTSGGSCTSVQGSITEDANWRWTHRTDSATNCYEGNKWDTSYCSD

GPSCASKCCIDGADYSSTYGITTSGNSLNLKFVIKGQYSTNIGSRTYLMESDTKYQMFQLLGNEF

TEDVDVSNLGCGLNGALYFVSMDADGGMSKYSGNKAGAKYGTGYCDSQCPRDLKEINGEANV

ENWQSSTNDANAGTGKYGSCCSEMDVWEANNMAAAFTPLIPCTVIGQSRCEGDSCGGTYSTDR

YAGICDPDGCDFNSYRQGNKTFYGKGMTVDTTKKITVVTQFLKNSAGELSEIKRFYVQNGKVIP

NSESTIPGVEGNSITQEYCDRQKAAFGDVTDFQDKGGMVQMGKALAGPMVLVMSIWDDHADN

MLWLDSTWPIDGAGKPGAERGACPTTSGVPAEVEALAPNSNVIFSNIREGPIGSTVSGLPDGGSG

NPNPPVSSSTPVPSSSTTSSGSSGPTGGTGVAKHYEQCGGIGFTGPTQCESPYTCTKLNDWYSQCL
```

The polynucleotide (SEQ ID NO:136) and amino acid (SEQ ID NO:137) sequences of wild-type *M. thermophila* CBH2b are provided below. The signal sequence is shown underlined in SEQ ID NO:137. SEQ ID NO:138 provides the sequence of this CBH2b, without the signal sequence.

```
                                                      (SEQ ID NO: 136)
ATGGCCAAGAAGCTTTTCATCACCGCCGCGCTTGCGGCTGCCGTGTTGGCGGCCCCCGTCAT

TGAGGAGCGCCAGAACTGCGGCGCTGTGTGGACTCAATGCGGCGGTAACGGGTGGCAAGGT

CCCACATGCTGCGCCTCGGGCTCGACCTGCGTTGCGCAGAACGAGTGGTACTCTCAGTGCCT

GCCCAACAGCCAGGTGACGAGTTCCACCACTCCGTCGTCGACTTCCACCTCGCAGCGCAGCA

CCAGCACCTCCAGCAGCACCACCAGGAGCGGCAGCTCCTCCTCCTCCTCCACCACGCCCCG

CCCGTCTCCAGCCCCGTGACCAGCATTCCCGGCGGTGCGACCTCCACGGCGAGCTACTCTGG

CAACCCCTTCTCGGGCGTCCGGCTCTTCGCCAACGACTACTACAGGTCCGAGGTCCACAATC

TCGCCATTCCTAGCATGACTGGTACTCTGGCGGCCAAGGCTTCCGCCGTCGCCGAAGTCCCT

AGCTTCCAGTGGCTCGACCGGAACGTCACCATCGACACCCTGATGGTCCAGACTCTGTCCCA
```

-continued

```
GGTCCGGGCTCTCAATAAGGCCGGTGCCAATCCTCCCTATGCTGCCCAACTCGTCGTCTACG

ACCTCCCCGACCGTGACTGTGCCGCCGCTGCGTCCAACGGCGAGTTTTCGATTGCAAACGGC

GGCGCCGCCAACTACAGGAGCTACATCGACGCTATCCGCAAGCACATCATTGAGTACTCGG

ACATCCGGATCATCCTGGTTATCGAGCCCGACTCGATGGCCAACATGGTGACCAACATGAAC

GTGGCCAAGTGCAGCAACGCCGCGTCGACGTACCACGAGTTGACCGTGTACGCGCTCAAGC

AGCTGAACCTGCCCAACGTCGCCATGTATCTCGACGCCGGCCACGCCGGCTGGCTCGGCTGG

CCCGCCAACATCCAGCCCGCCGCCGAGCTGTTTGCCGGCATCTACAATGATGCCGGCAAGCC

GGCTGCCGTCCGCGGCCTGGCCACTAACGTCGCCAACTACAACGCCTGGAGCATCGCTTCGG

CCCCGTCGTACACGTCGCCTAACCCTAACTACGACGAGAAGCACTACATCGAGGCCTTCAGC

CCGCTCTTGAACTCGGCCGGCTTCCCCGCACGCTTCATTGTCGACACTGGCCGCAACGGCAA

ACAACCTACCGGCCAACAACAGTGGGGTGACTGGTGCAATGTCAAGGGCACCGGCTTTGGC

GTGCGCCCGACGGCCAACACGGGCCACGAGCTGGTCGATGCCTTTGTCTGGGTCAAGCCCGG

CGGCGAGTCCGACGGCACAAGCGACACCAGCGCCGCCCGCTACGACTACCACTGCGGCCTG

TCCGATGCCCTGCAGCCTGCCCCCGAGGCTGGACAGTGGTTCCAGGCCTACTTCGAGCAGCT

GCTCACCAACGCCAACCCGCCCTTCTAA
```

(SEQ ID NO: 137)
MAKKEFITAALAAAVLAAPVIEERQNCGAVWTQCGGNGWQGPTCCASGSTCVAQNEWYSQCL

PNSQVTSSTTPSSTSTSQRSTSTSSSTTRSGSSSSSSTTPPPVSSPVTSIPGGATSTASYSGNPFSGVRL

FANDYYRSEVHNLAIPSMTGTLAAKASAVAEVPSFQWLDRNVTIDTLMVQTESQVRALNKAGA

NPPYAAQLVVYDLPDRDCAAAASNGEFSIANGGAANYRSYIDAIRKHIIEYSDIRIILVIEPDSMAN

MVTNMNVAKCSNAASTYHELTVYALKQENLPNVAMYLDAGHAGWEGWPANIQPAAELFAGI

YNDAGKPAAVRGLATNVANYNAWSIASAPSYTSPNPNYDEKHYIEAFSPLLNSAGFPARFIVDTG

RNGKQPTGQQQWGDWCNVKGTGEGVRPTANTGHELVDAFVWVKPGGESDGTSDTSAARYDY

HCGLSDALQPAPEAGQWFQAYFEQLLTNANPPF (SEQ ID NO: 138)
APVIEERQNCGAVWTQCGGNGWQGPTCCASGSTCVAQNEWYSQCLPNSQVTSSTTPSSTSTSQR

STSTSSSTTRSGSSSSSSTTPPPVSSPVTSIPGGATSTASYSGNPFSGVRLFANDYYRSEVHNLAIPS

MTGTLAAKASAVAEVPSFQWLDRNVTIDTLMVQTLSQVRALNKAGANPPYAAQLVVYDLPDR

DCAAAASNGEFSIANGGAANYRSYIDAIRKHIIEYSDIRIILVIEPDSMANMVTNMNVAKCSNAAS

TYHELTVYALKQLNLPNVAMYLDAGHAGWLGWPANIQPAAELFAGIYNDAGKPAAVRGLATN

VANYNAWSIASAPSYTSPNPNYDEKHYIEAFSPLLNSAGFPARFIVDTGRNGKQPTGQQQWGDW

CNVKGTGEGVRPTANTGHELVDAFVWVKPGGESDGTSDTSAARYDYHCGLSDALQPAPEAGQ

WFQAYFEQLLTNANPPF

The polynucleotide (SEQ ID NO:139) and amino acid (SEQ ID NO:140) sequences of a *M. thermophila* CBH2b variant ("Variant 196") are provided below. The signal sequence is shown underlined in SEQ ID NO:140. SEQ ID NO:141 provides the sequence of this CBH2b variant, without the signal sequence.

(SEQ ID NO: 139)
```
ATGGCCAAGAAGCTTTTCATCACCGCCGCGCTTGCGGCTGCCGTGTTGGCGGCCCCCGTCAT

TGAGGAGCGCCAGAACTGCGGCGCTGTGTGGACTCAATGCGGCGGTAACGGGTGGCAAGGT

CCCACATGCTGCGCCTCGGGCTCGACCTGCGTTGCGCAGAACGAGTGGTACTCTCAGTGCCT

GCCCAACAGCCAGGTGACGAGTTCCACCACTCCGTCGTCGACTTCCACCTCGCAGCGCAGCA

CCAGCACCTCCAGCAGCACCACCAGGAGCGGCAGCTCCTCCTCCTCCTCCACCACGCCCACC
```

```
CCCGTCTCCAGCCCCGTGACCAGCATTCCCGGCGGTGCGACCTCCACGGCGAGCTACTCTGG

CAACCCCTTCTCGGGCGTCCGGCTCTTCGCCAACGACTACTACAGGTCCGAGGTCCACAATC

TCGCCATTCCTAGCATGACTGGTACTCTGGCGGCCAAGGCTTCCGCCGTCGCCGAAGTCCCT

AGCTTCCAGTGGCTCGACCGGAACGTCACCATCGACACCCTGATGGTCCCGACTCTGTCCCG

CGTCCGGGCTCTCAATAAGGCCGGTGCCAATCCTCCCTATGCTGCCCAACTCGTCGTCTACG

ACCTCCCCGACCGTGACTGTGCCGCCGCTGCGTCCAACGGCGAGTTTTCGATTGCAAACGGC

GGCGCCGCCAACTACAGGAGCTACATCGACGCTATCCGCAAGCACATCATTGAGTACTCGG

ACATCCGGATCATCCTGGTTATCGAGCCCGACTCGATGGCCAACATGGTGACCAACATGAAC

GTGGCCAAGTGCAGCAACGCCGCGTCGACGTACCACGAGTTGACCGTGTACGCGCTCAAGC

AGCTGAACCTGCCCAACGTCGCCATGTATCTCGACGCCGGCCACGCCGGCTGGCTCGGCTGG

CCCGCCAACATCCAGCCCGCCGCCGAGCTGTTTGCCGGCATCTACAATGATGCCGGCAAGCC

GGCTGCCGTCCGCGGCCTGGCCACTAACGTCGCCAACTACAACGCCTGGAGCATCGCTTCGG

CCCCGTCGTACACGTCGCCTAACCCTAACTACGACGAGAAGCACTACATCGAGGCCTTCAGC

CCGCTCTTGAACTCGGCCGGCTTCCCCGCACGCTTCATTGTCGACACTGGCCGCAACGGCAA

ACAACCTACCGGCCAACAACAGTGGGGTGACTGGTGCAATGTCAAGGGCACCGGCTTTGGC

GTGCGCCCGACGGCCAACACGGGCCACGAGCTGGTCGATGCCTTTGTCTGGGTCAAGCCCGG

CGGCGAGTCCGACGGCACAAGCGACACCAGCGCCGCCCGCTACGACTACCACTGCGGCCTG

TCCGATGCCCTGCAGCCTGCCCCCGAGGCTGGACAGTGGTTCCAGGCCTACTTCGAGCAGCT

GCTCACCAACGCCAACCCGCCCTTCTAA
```

(SEQ ID NO: 140)

<u>MAKKLFITAALAAAVLA</u>APVIEERQNCGAVWTQCGGNGWQGPTCCASGSTCVAQNEWYSQCL

PNSQVTSSTTPSSTSTSQRSTSTSSSTTRSGSSSSSSTTPTPVSSPVTSIPGGATSTASYSGNPFSGVR

LFANDYYRSEVHNLAIPSMTGTLAAKASAVAEVPSFQWLDRNVTIDTLMVPTLSRVRALNKAG

ANPPYAAQLVVYDLPDRDCAAAASNGEFSIANGGAANYRSYIDAIRKHIIEYSDIRIILVIEPDSMA

NMVTNMNVAKCSNAASTYHELTVYALKQLNLPNVAMYLDAGHAGWLGWPANIQPAAELFAG

IYNDAGKPAAVRGLATNVANYNAWSIASAPSYTSPNPNYDEKHYIEAFSPLLNSAGFPARFIVDT

GRNGKQPTGQQQWGDWCNVKGTGFGVRPTANTGHELVDAFVWVKPGGESDGTSDTSAARYD

YHCGLSDALQPAPEAGQWFQAYFEQLLTNANPPF (SEQ ID NO: 141)
APVIEERQNCGAVWTQCGGNGWQGPTCCASGSTCVAQNEWYSQCLPNSQVTSSTTPSSTSTSQR

STSTSSSTTRSGSSSSSSTTPTPVSSPVTSIPGGATSTASYSGNPFSGVRLFANDYYRSEVHNLAIPS

MTGTLAAKASAVAEVPSFQWLDRNVTIDTLMVPTLSRVRALNKAGANPPYAAQLVVYDLPDRD

CAAAASNGEFSIANGGAANYRSYIDAIRKHIIEYSDIRIILVIEPDSMANMVTNMNVAKCSNAAST

YHELTVYALKQLNLPNVAMYLDAGHAGWEGWPANIQPAAELFAGIYNDAGKPAAVRGLATNV

ANYNAWSIASAPSYTSPNPNYDEKHYIEAFSPLLNSAGFPARFIVDTGRNGKQPTGQQQWGDWC

NVKGTGFGVRPTANTGHELVDAFVWVKPGGESDGTSDTSAARYDYHCGLSDALQPAPEAGQW

FQAYFEQLLTNANPPF

The polynucleotide (SEQ ID NO:142) and amino acid (SEQ ID NO:143) sequences of a *M. thermophila* CBH2b variant ("Variant 287") are provided below. The signal sequence is shown underlined in SEQ ID NO:143. SEQ ID NO:144 provides the sequence of this CBH2b variant, without the signal sequence.

(SEQ ID NO: 142)
```
ATGGCCAAGAAGCTTTTCATCACCGCCGCGCTTGCGGCTGCCGTGTTGGCGGCCCCCGTCAT
TGAGGAGCGCCAGAACTGCGGCGCTGTGTGGACTCAATGCGGCGGTAACGGGTGGCAAGGT
CCCACATGCTGCGCCTCGGGCTCGACCTGCGTTGCGCAGAACGAGTGGTACTCTCAGTGCCT
GCCCAACAGCCAGGTGACGAGTTCCACCACTCCGTCGTCGACTTCCACCTCGCAGCGCAGCA
CCAGCACCTCCAGCAGCACCACCAGGAGCGGCAGCTCCTCCTCCTCCTCCACCACGCCCCCG
CCCGTCTCCAGCCCCGTGACCAGCATTCCCGGCGGTGCGACCTCCACGGCGAGCTACTCTGG
CAACCCCTTCTCGGGCGTCCGGCTCTTCGCCAACGACTACTACAGGTCCGAGGTCCACAATC
TCGCCATTCCTAGCATGACTGGTACTCTGGCGGCCAAGGCTTCCGCCGTCGCCGAAGTCCCT
AGCTTCCAGTGGCTCGACCGGAACGTCACCATCGACACCCTGATGGTCCCGACTCTGTCCCG
CGTCCGGGCTCTCAATAAGGCCGGTGCCAATCCTCCCTATGCTGCCCAACTCGTCGTCTACG
ACCTCCCCGACCGTGACTGTGCCGCCGCTGCGTCCAACGGCGAGTTTTCGATTGCAAACGGC
GGCGCCGCCAACTACAGGAGCTACATCGACGCTATCCGCAAGCACATCAAGGAGTACTCGG
ACATCCGGATCATCCTGGTTATCGAGCCCGACTCGATGGCCAACATGGTGACCAACATGAAC
GTGGCCAAGTGCAGCAACGCCGCGTCGACGTACCACGAGTTGACCGTGTACGCGCTCAAGC
AGCTGAACCTGCCCAACGTCGCCATGTATCTCGACGCCGGCCACGCCGGCTGGCTCGGCTGG
CCCGCCAACATCCAGCCCGCCGCCGAGCTGTTTGCCGGCATCTACAATGATGCCGGCAAGCC
GGCTGCCGTCCGCGGCCTGGCCACTAACGTCGCCAACTACAACGCCTGGAGCATCGCTTCGG
CCCCGTCGTACACGTCGCCTAACCCTAACTACGACGAGAAGCACTACATCGAGGCCTTCAGC
CCGCTCTTGAACGACGCCGGCTTCCCCGCACGCTTCATTGTCGACACTGGCCGCAACGGCAA
ACAACCTACCGGCCAACAACAGTGGGGTGACTGGTGCAATGTCAAGGGCACCGGCTTTGGC
GTGCGCCCGACGGCCAACACGGGCCACGAGCTGGTCGATGCCTTTGTCTGGGTCAAGCCCGG
CGGCGAGTCCGACGGCACAAGCGACACCAGCGCCGCCCGCTACGACTACCACTGCGGCCTG
TCCGATGCCCTGCAGCCTGCCCCCGAGGCTGGACAGTGGTTCCAGGCCTACTTCGAGCAGCT
GCTCACCAACGCCAACCCGCCCTTCTAA
```

(SEQ ID NO: 143)
<u>MAKKLFITAALAAAVLAAPV</u>IEERQNCGAVWTQCGGNGWQGPTCCASGSTCVAQNEWYSQCL
PNSQVTSSTTPSSTSTSQRSTSTSSSTTRSGSSSSSSTTPPPVSSPVTSIPGGATSTASYSGNPFSGVRL
FANDYYRSEVHNLAIPSMTGTLAAKASAVAEVPSFQWLDRNVTIDTLMVPTLSRVRALNKAGA
NPPYAAQLVVYDLPDRDCAAAASNGEFSIANGGAANYRSYIDAIRKHIKEYSDIRIILVIEPDSMA
NMVTNMNVAKCSNAASTYHELTVYALKQLNLPNVAMYLDAGHAGWLGWPANIQPAAELFAG
IYNDAGKPAAVRGLATNVANYNAWSIASAPSYTSPNPNYDEKHYIEAFSPLLNDAGFPARFIVDT
GRNGKQPTGQQQWGDWCNVKGTGFGVRPTANTGHELVDAFVWVKPGGESDGTSDTSAARYD
YHCGLSDALQPAPEAGQWFQAYFEQLLTNANPPF (SEQ ID NO: 144)
APVIEERQNCGAVWTQCGGNGWQGPTCCASGSTCVAQNEWYSQCLPNSQVTSSTTPSSTSTSQR
STSTSSSTTRSGSSSSSSTTPPPVSSPVTSIPGGATSTASYSGNPFSGVRLFANDYYRSEVHNLAIPS
MTGTLAAKASAVAEVPSFQWLDRNVTIDTLMVPTLSRVRALNKAGANPPYAAQLVVYDLPDRD
CAAAASNGEFSIANGGAANYRSYIDAERKHIKEYSDIRIILVIEPDSMANMVTNMNVAKCSNAAS
TYHELTVYALKQLNLPNVAMYLDAGHAGWLGWPANIQPAAELFAGIYNDAGKPAAVRGLATN

-continued

```
VANYNAWSIASAPSYTSPNPNYDEKHYIEAFSPLLNDAGFPARFIVDTGRNGKQPTGQQQWGDW
CNVKGTGFGVRPTANTGHELVDAFVWVKPGGESDGTSDTSAARYDYHCGLSDALQPAPEAGQ
WFQAYFEQLLTNANPPF
```

The polynucleotide (SEQ ID NO:145) and amino acid (SEQ ID NO:146) sequences of a *M. thermophila* CBH2b variant ("Variant 962") are provided below. The signal sequence is shown underlined in SEQ ID NO:146. SEQ ID NO:147 provides the sequence of this CBH2b variant, without the signal sequence.

```
                                                        (SEQ ID NO: 145)
ATGGCCAAGAAGCTTTTCATCACCGCCGCGCTTGCGGCTGCCGTGTTGGCGGCCCCCGTCAT

TGAGGAGCGCCAGAACTGCGGCGCTGTGTGGACTCAATGCGGCGGTAACGGGTGGCAAGGT

CCCACATGCTGCGCCTCGGGCTCGACCTGCGTTGCGCAGAACGAGTGGTACTCTCAGTGCCT

GCCCAACAGCCAGGTGACGAGTTCCACCACTCCGTCGTCGACTTCCACCTCGCAGCGCAGCA

CCAGCACCTCCAGCAGCACCACCAGGAGCGGCAGCTCCTCCTCCTCCTCCACCACGCCCACC

CCCGTCTCCAGCCCCGTGACCAGCATTCCCGGCGGTGCGACCTCCACGGCGAGCTACTCTGG

CAACCCCTTCTCGGGCGTCCGGCTCTTCGCCAACGACTACTACAGGTCCGAGGTCATGAATC

TCGCCATTCCTAGCATGACTGGTACTCTGGCGGCCAAGGCTTCCGCCGTCGCCGAAGTCCCT

AGCTTCCAGTGGCTCGACCGGAACGTCACCATCGACACCCTGATGGTCACCACTCTGTCCCA

GGTCCGGGCTCTCAATAAGGCCGGTGCCAATCCTCCCTATGCTGCCCAACTCGTCGTCTACG

ACCTCCCCGACCGTGACTGTGCCGCCGCTGCGTCCAACGGCGAGTTTTCGATTGCAAACGGC

GGCAGCGCCAACTACAGGAGCTACATCGACGCTATCCGCAAGCACATCATTGAGTACTCGG

ACATCCGGATCATCCTGGTTATCGAGCCCGACTCGATGGCCAACATGGTGACCAACATGAAC

GTGGCCAAGTGCAGCAACGCCGCGTCGACGTACCACGAGTTGACCGTGTACGCGCTCAAGC

AGCTGAACCTGCCCAACGTCGCCATGTATCTCGACGCCGGCCACGCCGGCTGGCTCGGCTGG

CCCGCCAACATCCAGCCCGCCGCCGAGCTGTTTGCCGGCATCTACAATGATGCCGGCAAGCC

GGCTGCCGTCCGCGGCCTGGCCACTAACGTCGCCAACTACAACGCCTGGAGCATCGCTTCGG

CCCCGTCGTACACGCAGCCTAACCCTAACTACGACGAGAAGCACTACATCGAGGCCTTCAGC

CCGCTCTTGAACTCGGCCGGCTTCCCCGCACGCTTCATTGTCGACACTGGCCGCAACGGCAA

ACAACCTACCGGCCAACAACAGTGGGGTGACTGGTGCAATGTCAAGGGCACCGGCTTTGGC

GTGCGCCCGACGGCCAACACGGGCCACGAGCTGGTCGATGCCTTTGTCTGGGTCAAGCCCGG

CGGCGAGTCCGACGGCACAAGCGACACCAGCGCCGCCCGCTACGACTACCACTGCGGCCTG

TCCGATGCCCTGCAGCCTGCCCCCGAGGCTGGACAGTGGTTCCAGGCCTACTTCGAGCAGCT

GCTCACCAACGCCAACCCGCCCTTCTAA
                                                        (SEQ ID NO: 146)
MAKKLFITAALAAAVLAAPVIEERQNCGAVWTQCGGNGWQGPTCCASGSTCVAQNEWYSQCL

PNSQVTSSTTPSSTSTSQRSTSTSSSTTRSGSSSSSSTTPTPVSSPVTSIPGGATSTASYSGNPFSGVR

LFANDYYRSEVMNLAIPSMTGTLAAKASAVAEVPSFQWLDRNVTIDTLMVTTLSQVRALNKAG

ANPPYAAQLVVYDLPDRDCAAAASNGEFSIANGGSANYRSYIDAIRKHIIEYSDIRIILVIEPDSMA

NMVTNMNVAKCSNAASTYHELTVYALKQLNLPNVAMYLDAGHAGWLGWPANIQPAAELFAG

IYNDAGKPAAVRGLATNVANYNAWSIASAPSYTQPNPNYDEKHYIEAFSPLINSAGFPARFIVDT

GRNGKQPTGQQQWGDWCNVKGTGFGVRPTANTGHELVDAFVWVKPGGESDGTSDTSAARYD

YHCGLSDALQPAPEAGQWFQAYFEQLLTNANPPF
```

```
                                                          (SEQ ID NO: 147)
APVIEERQNCGAVWTQCGGNGWQGPTCCASGSTCVAQNEWYSQCLPNSQVTSSTTPSSTS

TSQRSTSTSSSTTRSGSSSSSSTTPTPVSSPVTSIPGGATSTASYSGNPFSGVRLFANDY

YRSEVMNLAIPSMTGTLAAKASAVAEVPSFQWLDRNVTIDTLMVTTLSQVRALNKAGANP

PYAAQLVVYDLPDRDCAAAASNGEFSIANGGSANYRSYIDAIRKHUIEYSDIRIILVIEP

DSMANMVTNMNVAKCSNAASTYHELTVYALKQLNLPNVAMYLDAGHAGWLGWPANIQPAA

ELFAGIYNDAGKPAAVRGLATNVANYNAWSIASAPSYTQPNPNYDEKHYIEAFSPLLNSA

GFPARFIVDTGRNGKQPTGQQQWGDWCNVKGTGFGVRPTANTGHELVDAFVWVKPGGESD

GTSDTSAARYDYHCGLSDALQPAPEAGQWFQAYFEQLLTNANPPF
```

The polynucleotide (SEQ ID NO:148) and amino acid (SEQ ID NO:149) sequences of another wild-type *M. thermophila* xylanase ("Xyl3") are provided below. The signal sequence is shown underlined in SEQ ID NO:149. SEQ ID NO:150 provides the sequence of this xylanase without the signal sequence.

```
                                                          (SEQ ID NO: 148)
ATGCACTCCAAAGCTTTCTTGGCAGCGCTTCTTGCGCCTGCCGTCTCAGGGCAACTGAACGA

CCTCGCCGTCAGGGCTGGACTCAAGTACTTTGGTACTGCTCTTAGCGAGAGCGTCATCAACA

GTGATACTCGGTATGCTGCCATCCTCAGCGACAAGAGCATGTTCGGCCAGCTCGTCCCCGAG

AATGGCATGAAGTGGGATGCTACTGAGCCGTCCCGTGGCCAGTTCAACTACGCCTCGGGCGA

CATCACGGCCAACACGGCCAAGAAGAATGGCCAGGGCATGCGTTGCCACACCATGGTCTGG

TACAGCCAGCTCCCGAGCTGGGTCTCCTCGGGCTCGTGGACCAGGGACTCGCTCACCTCGGT

CATCGAGACGCACATGAACAACGTCATGGGCCACTACAAGGGCCAATGCTACGCCTGGGAT

GTCATCAACGAGGCCATCAATGACGACGGCAACTCCTGGCGCGACAACGTCTTTCTCCGGAC

CTTTGGGACCGACTACTTCGCCCTGTCCTTCAACCTAGCCAAGAAGGCCGATCCCGATACCA

AGCTGTACTACAACGACTACAACCTCGAGTACAACCAGGCCAAGACGGACCGCGCTGTTGA

GCTCGTCAAGATGGTCCAGGCCGCCGGCGCGCCCATCGACGGTGTCGGCTTCCAGGGCCACC

TCATTGTCGGCTCGACCCCGACGCGCTCGCAGCTGGCCACCGCCCTCCAGCGCTTCACCGCG

CTCGGCCTCGAGGTCGCCTACACCGAGCTCGACATCCGCCACTCGAGCCTGCCGGCCTCTTC

GTCGGCGCTCGCGACCCAGGGCAACGACTTCGCCAACGTGGTCGGCTCTTGCCTCGACACCG

CCGGCTGCGTCGGCGTCACCGTCTGGGGCTTCACCGATGCGCACTCGTGGATCCCGAACACG

TTCCCCGGCCAGGGCGACGCCCTGATCTACGACAGCAACTACAACAAGAAGCCCGCGTGGA

CCTCGATCTCGTCCGTCCTGGCCGCCAAGGCCACCGGCGCCCCGCCCGCCTCGTCCTCCACC

ACCCTCGTCACCATCACCACCCCTCCGCCGGCATCCACCACCGCCTCCTCCTCCTCCAGTGCC

ACGCCCACGAGCGTCCCGACGCAGACGAGGTGGGGACAGTGCGGCGGCATCGGATGGACGG

GGCCGACCCAGTGCGAGAGCCCATGGACCTGCCAGAAGCTGAACGACTGGTACTGGCAGTG

CCTG
                                                          (SEQ ID NO: 149)
MHSKAFLAALLAPAVSGQLNDLAVRAGLKYFGTALSESVINSDTRYAAILSDKSMFGQLVPENG

MKWDATEPSRGQFNYASGDITANTAKKNGQGMRCHTMVWYSQLPSWVSSGSWTRDSLTSVIE

THMNNVMGHYKGQCYAWDVINEAINDDGNSWRDNVFLRTFGTDYFALSFNLAKKADPDTKLY

YNDYNLEYNQAKTDRAVELVKMVQAAGAPIDGVGFQGHLIVGSTPTRSQLATALQRFTALGLE

VAYTELDIRHSSLPASSSALATQGNDFANVVGSCLDTAGCVGVTVWGFTDAHSWIPNTFPGQGD

ALIYDSNYNKKPAWTSISSVLAAKATGAPPASSSTTLVTITTPPPASTTASSSSSATPTSVPTQTRW

GQCGGIGWTGPTQCESPWTCQKLNDWYWQCL
```

(SEQ ID NO: 150)
```
QLNDLAVRAGLKYFGTALSESVINSDTRYAAILSDKSMFGQLVPENGMKWDATEPSRGQFNYAS

GDITANTAKKNGQGMRCHTMVWYSQLPSWVSSGSWTRDSLTSVIETHMNNVMGHYKGQCYA

WDVINEAINDDGNSWRDNVFLRTFGTDYFALSFNLAKKADPDTKLYYNDYNLEYNQAKTDRA

VELVKMVQAAGAPIDGVGFQGHLIVGSTPTRSQLATALQRFTALGLEVAYTELDIRHSSLPASSS

ALATQGNDFANVVGSCLDTAGCVGVTVWGFTDAHSWIPNTFPGQGDALIYDSNYNKKPAWTSI

SSVLAAKATGAPPASSSTTLVTITTPPPASTTASSSSSATPTSVPTQTRWGQCGGIGWTGPTQCESP

WTCQKLNDWYWQCL
```

The polynucleotide (SEQ ID NO:151) and amino acid (SEQ ID NO:152) sequences of a wild-type *M. thermophila* xylanase ("Xyl 2") are provided below. The signal sequence is shown underlined in SEQ ID NO:152. SEQ ID NO:153 provides the sequence of this xylanase without the signal sequence.

(SEQ ID NO: 151)
```
ATGGTCTCGTTCACTCTCCTCCTCACGGTCATCGCCGCTGCGGTGACGACGGCCAGCCCTCTC

GAGGTGGTCAAGCGCGGCATCCAGCCGGGCACGGGCACCCACGAGGGGTACTTCTACTCGT

TCTGGACCGACGGCCGTGGCTCGGTCGACTTCAACCCCGGGCCCCGCGGCTCGTACAGCGTC

ACCTGGAACAACGTCAACAACTGGGTTGGCGGCAAGGGCTGGAACCCGGGCCCGCCGCGCA

AGATTGCGTACAACGGCACCTGGAACAACTACAACGTGAACAGCTACCTCGCCCTGTACGG

CTGGACTCGCAACCCGCTGGTCGAGTATTACATCGTGGAGGCATACGGCACGTACAACCCCT

CGTCGGGCACGGCGCGGCTGGGCACCATCGAGGACGACGGCGGCGTGTACGACATCTACAA

GACGACGCGGTACAACCAGCCGTCCATCGAGGGGACCTCCACCTTCGACCAGTACTGGTCCG

TCCGCCGCCAGAAGCGCGTCGGCGGCACTATCGACACGGGCAAGCACTTTGACGAGTGGAA

GCGCCAGGGCAACCTCCAGCTCGGCACCTGGAACTACATGATCATGGCCACCGAGGGCTAC

CAGAGCTCTGGTTCGGCCACTATCGAGGTCCGGGAGGCC
```

(SEQ ID NO: 152)
```
MVSFTLLLTVIAAAVTTASPLEVVKRGIQPGTGTHEGYFYSFWTDGRGSVDFNPGPRGSYSVTW

NNVNNWVGGKGWNPGPPRKIAYNGTWNNYNVNSYLALYGWTRNPLVEYYIVEAYGTYNPSS

GTARLGTIEDDGGVYDIYKTTRYNQPSIEGTSTFDQYWSVRRQKRVGGTIDTGKHFDEWKRQGN

LQLGTWNYMIMATEGYQSSGSATIEVREA
```

(SEQ ID NO: 153)
```
MVSFTLLLTVIAAAVTTASPLEVVKRGIQPGTGTHEGYFYSFWTDGRGSVDFNPGPRGSYSVTW

NNVNNWVGGKGWNPGPPRKIAYNGTWNNYNVNSYLALYGWTRNPLVEYYIVEAYGTYNPSS

GTARLGTIEDDGGVYDIYKTTRYNQPSIEGTSTFDQYWSVRRQKRVGGTIDTGKHFDEWKRQGN

LQLGTWNYMIMATEGYQSSGSATIEVREA
```

The polynucleotide (SEQ ID NO:154) and amino acid (SEQ ID NO:155) sequences of another wild-type *M. thermophila* xylanase ("Xyl1") are provided below. The signal sequence is shown underlined in SEQ ID NO:155. SEQ ID NO:156 provides the sequence of this xylanase without the signal sequence.

(SEQ ID NO: 154)
```
ATGCGTACTCTTACGTTCGTGCTGGCAGCCGCCCCGGTGGCTGTGCTTGCCCAATCTCCTCTG

TGGGGCCAGTGCGGCGGTCAAGGCTGGACAGGTCCCACGACCTGCGTTTCTGGCGCAGTATG

CCAATTCGTCAATGACTGGTACTCCCAATGCGTGCCCGGATCGAGCAACCCTCCTACGGGCA
```

-continued

```
CCACCAGCAGCACCACTGGAAGCACCCCGGCTCCTACTGGCGGCGGCGGCAGCGGAACCGG

CCTCCACGACAAATTCAAGGCCAAGGGCAAGCTCTACTTCGGAACCGAGATCGATCACTACC

ATCTCAACAACAATGCCTTGACCAACATTGTCAAGAAAGACTTTGGTCAAGTCACTCACGAG

AACAGCTTGAAGTGGGATGCTACTGAGCCGAGCCGCAATCAATTCAACTTTGCCAACGCCGA

CGCGGTTGTCAACTTTGCCCAGGCCAACGGCAAGCTCATCCGCGGCCACACCCTCCTCTGGC

ACTCTCAGCTGCCGCAGTGGGTGCAGAACATCAACGACCGCAACACCTTGACCCAGGTCATC

GAGAACCACGTCACCACCCTTGTCACTCGCTACAAGGGCAAGATCCTCCACTGGGACGTCGT

TAACGAGATCTTTGCCGAGGACGGCTCGCTCCGCGACAGCGTCTTCAGCCGCGTCCTCGGCG

AGGACTTTGTCGGCATCGCCTTCCGCGCCGCCCGCGCCGCCGATCCCAACGCCAAGCTCTAC

ATCAACGACTACAACCTCGACATTGCCAACTACGCCAAGGTGACCCGGGGCATGGTCGAGA

AGGTCAACAAGTGGATCGCCCAGGGCATCCCGATCGACGGCATCGGCACCCAGTGCCACCT

GGCCGGGCCCGGCGGGTGGAACACGGCCGCCGGCGTCCCCGACGCCCTCAAGGCCCTCGCC

GCGGCCAACGTCAAGGAGATCGCCATCACCGAGCTCGACATCGCCGGCGCCTCCGCCAACG

ACTACCTCACCGTCATGAACGCCTGCCTCCAGGTCTCCAAGTGCGTCGGCATCACCGTCTGG

GGCGTCTCTGACAAGGACAGCTGGAGGTCGAGCAGCAACCCGCTCCTCTTCGACAGCAACT

ACCAGCCAAAGGCGGCATACAATGCTCTGATTAATGCCTTGTAA
```

(SEQ ID NO: 155)
<u>MRTLTFVLAAAPVAVLAQSPLWGQCGGQGWTGPTTCVSGAVCQFVNDWYSQCVPGSSNPPTG</u>

TTSSTTGSTPAPTGGGGSGTGLHDKFKAKGKLYFGTEIDHYHLNNNALTNIVKKDFGQVTHENS

LKWDATEPSRNQFNFANADAVVNFAQANGKLIRGHTLLWHSQLPQWVQNINDRNTLTQVIENH

VTTLVTRYKGKILHWDVVNEIFAEDGSLRDSVFSRVLGEDFVGIAFRAARAADPNAKLYINDYN

LDIANYAKVTRGMVEKVNKWIAQGIPIDGIGTQCHLAGPGGWNTAAGVPDALKALAAANVKEI

AITELDIAGASANDYLTVMNACLQVSKCVGITVWGVSDKDSWRSSSNPLLFDSNYQPKAAYNA

LINAL (SEQ ID NO: 156)
QSPLWGQCGGQGWTGPTTCVSGAVCQFVNDWYSQCVPGSSNPPTGTTSSTTGSTPAPTGGGGS

GTGLHDKFKAKGKLYEGTEIDHYHLNNNALTNIVKKDFGQVTHENSLKWDATEPSRNQFNFAN

ADAVVNFAQANGKLIRGHTLLWHSQLPQWVQNINDRNTLTQVIENHVTTLVTRYKGKILHWDV

VNEIFAEDGSLRDSVFSRVLGEDFVGIAFRAARAADPNAKLYINDYNLDIANYAKVTRGMVEKV

NKWIAQGIPIDGIGTQCHLAGPGGWNTAAGVPDALKALAAANVKEIAITELDIAGASANDYLTV

MNACLQVSKCVGITVWGVSDKDSWRSSSNPLLFDSNYQPKAAYNALINAL

The polynucleotide (SEQ ID NO:157) and amino acid (SEQ ID NO:158) sequences of another wild-type *M. thermophila* xylanase ("Xyl6") are provided below. The signal sequence is shown underlined in SEQ ID NO:158. SEQ ID NO:159 provides the sequence of this xylanase without the signal sequence.

(SEQ ID NO: 157)
```
ATGGTCTCGCTCAAGTCCCTCCTCCTCGCCGCGGCGGCGACGTTGACGGCGGTGACGGCGCG

CCCGTTCGACTTTGACGACGGCAACTCGACCGAGGCGCTGGCCAAGCGCCAGGTCACGCCC

AACGCGCAGGGCTACCACTCGGGCTACTTCTACTCGTGGTGGTCCGACGGCGGCGGCCAGGC

CACCTTCACCCTGCTCGAGGGCAGCCACTACCAGGTCAACTGGAGGAACACGGGCAACTTTG

TCGGTGGCAAGGGCTGGAACCCGGGTACCGGCCGGACCATCAACTACGGCGGCTCGTTCAA

CCCGAGCGGCAACGGCTACCTGGCCGTCTACGGCTGGACGCACAACCCGCTGATCGAGTACT

ACGTGGTCGAGTCGTACGGGACCTACAACCCGGGCAGCCAGGCCCAGTACAAGGGCAGCTT
```

```
CCAGAGCGACGGCGGCACCTACAACATCTACGTCTCGACCCGCTACAACGCGCCCTCGATCG

AGGGCACCCGCACCTTCCAGCAGTACTGGTCCATCCGCACCTCCAAGCGCGTCGGCGGCTCC

GTCACCATGCAGAACCACTTCAACGCCTGGGCCCAGCACGGCATGCCCCTCGGCTCCCACGA

CTACCAGATCGTCGCCACCGAGGGCTACCAGAGCAGCGGCTCCTCCGACATCTACGTCCAGA

CTCACTAG
```

(SEQ ID NO: 158)
```
MVSLKSLLLAAAATLTAVTARPFDFDDGNSTEALAKRQVTPNAQGYHSGYFYSWWSDGGGQA

TFTLLEGSHYQVNWRNTGNFVGGKGWNPGTGRTINYGGSFNPSGNGYLAVYGWTHNPLIEYYV

VESYGTYNPGSQAQYKGSFQSDGGTYNIYVSTRYNAPSIEGTRTFQQYWSIRTSKRVGGSVTMQ

NHFNAWAQHGMPLGSHDYQIVATEGYQSSGSSDIYVQTH
```

(SEQ ID NO: 159)
```
RPFDFDDGNSTEALAKRQVTPNAQGYHSGYFYSWWSDGGGQATFTLLEGSHYQVNWRNTGNF

VGGKGWNPGTGRTINYGGSFNPSGNGYLAVYGWTHNPLIEYYVVESYGTYNPGSQAQYKGSFQ

SDGGTYNIYVSTRYNAPSIEGTRTFQQYWSIRTSKRVGGSVTMQNHFNAWAQHGMPLGSHDYQI

VATEGYQSSGSSDIYVQTH
```

The polynucleotide (SEQ ID NO:160) and amino acid (SEQ ID NO:161) sequences of another wild-type *M. thermophila* xylanase ("Xyl5") are provided below. The signal sequence is shown underlined in SEQ ID NO:161. SEQ ID NO:162 provides the sequence of this xylanase, without the signal sequence.

(SEQ ID NO: 160)
```
ATGGTTACCCTCACTCGCCTGGCGGTCGCCGCGGCGGCCATGATCTCCAGCACTGGCCTGGC

TGCCCCGACGCCCGAAGCTGGCCCCGACCTTCCCGACTTTGAGCTCGGGGTCAACAACCTCG

CCCGCCGCGCGCTGGACTACAACCAGAACTACAGGACCAGCGGCAACGTCAACTACTCGCC

CACCGACAACGGCTACTCGGTCAGCTTCTCCAACGCGGGAGATTTTGTCGTCGGGAAGGGCT

GGAGGACGGGAGCCACCAGAAACATCACCTTCTCGGGATCGACACAGCATACCTCGGGCAC

CGTGCTCGTCTCCGTCTACGGCTGGACCCGGAACCCGCTGATCGAGTACTACGTGCAGGAGT

ACACGTCCAACGGGGCCGGCTCCGCTCAGGGCGAGAAGCTGGGCACGGTCGAGAGCGACGG

GGGCACGTACGAGATCTGGCGGCACCAGCAGGTCAACCAGCCGTCGATCGAGGGCACCTCG

ACCTTCTGGCAGTACATCTCGAACCGCGTGTCCGGCCAGCGGCCCAACGGCGGCACCGTCAC

CCTCGCCAACCACTTCGCCGCCTGGCAGAAGCTCGGCCTGAACCTGGGCCAGCACGACTACC

AGGTCCTGGCCACCGAGGGCTGGGGCAACGCCGGCGGCAGCTCCCAGTACACCGTCAGCGG

CTGA
```

(SEQ ID NO: 161)
```
MVTLTRLAVAAAAMESSTGLAAPTPEAGPDLPDFELGVNNLARRALDYNQNYRTSGNVNYSPT

DNGYSVSFSNAGDFVVGKGWRTGATRNITFSGSTQHTSGTVLVSVYGWTRNPLIEYYVQEYTSN

GAGSAQGEKLGTVESDGGTYEIWRHQQVNQPSIEGTSTFWQYISNRVSGQRPNGGTVTLANHFA

AWQKLGLNLGQHDYQVLATEGWGNAGGSSQYTVSG
```

(SEQ ID NO: 162)
```
APTPEAGPDLPDFELGVNNLARRALDYNQNYRTSGNVNYSPTDNGYSVSFSNAGDFVVGKGWR

TGATRNIFFSGSTQHTSGTVLVSVYGWTRNPLIEYYVQEYTSNGAGSAQGEKLGTVESDGGTYEI

WRHQQVNQPSIEGTSTFWQYISNRVSGQRPNGGTVTLANHFAAWQKLGLNLGQHDYQVLATE

GWGNAGGSSQYTVSG
```

The polynucleotide (SEQ ID NO:163) and amino acid (SEQ ID NO:164) sequences of a wild-type *M. thermophila* beta-xylosidase are provided below. The signal sequence is shown underlined in SEQ ID NO:164. SEQ ID NO:165 provides the sequence of this xylanase without the signal sequence.

(SEQ ID NO: 163)
```
ATGTTCTTCGCTTCTCTGCTGCTCGGTCTCCTGGCGGGCGTGTCCGCTTCACCGGGACACGGG
CGGAATTCCACCTTCTACAACCCCATCTTCCCCGGCTTCTACCCCGATCCGAGCTGCATCTAC
GTGCCCGAGCGTGACCACACCTTCTTCTGTGCCTCGTCGAGCTTCAACGCCTTCCCGGGCATC
CCGATTCATGCCAGCAAGGACCTGCAGAACTGGAAGTTGATCGGCCATGTGCTGAATCGCA
AGGAACAGCTTCCCCGGCTCGCTGAGACCAACCGGTCGACCAGCGGCATCTGGGCACCCAC
CCTCCGGTTCCATGACGACACCTTCTGGTTGGTCACCACACTAGTGGACGACGACCGGCCGC
AGGAGGACGCTTCCAGATGGGACAATATTATCTTCAAGGCAAAGAATCCGTATGATCCGAG
GTCCTGGTCCAAGGCCGTCCACTTCAACTTCACTGGCTACGACACGGAGCCTTTCTGGGACG
AAGATGGAAAGGTGTACATCACCGGCGCCCATGCTTGGCATGTTGGCCCATACATCCAGCAG
GCCGAAGTCGATCTCGACACGGGGCCGTCGGCGAGTGGCGCATCATCTGGAACGGAACGG
GCGGCATGGCTCCTGAAGGGCCGCACATCTACCGCAAAGATGGOTGGTACTACTTGCTGGCT
GCTGAAGGGGGGACCGGCATCGACCATATGGTGACCATGGCCCGGTCGAGAAAAATCTCCA
GTCCTTACGAGTCCAACCCAAACAACCCCGTGTTGACCAACGCCAACACGACCAGTTACTTT
CAAACCGTCGGGCATTCAGACCTGTTCCATGACAGACATGGGAACTGGTGGGCAGTCGCCCT
CTCCACCCGCTCCGGTCCAGAATATCTTCACTACCCCATGGGCCGCGAGACCGTCATGACAG
CCGTGAGCTGGCCGAAGGACGAGTGGCCAACCTTCACCCCCATATCTGGCAAGATGAGCGG
CTGGCCGATGCCTCCTTCGCAGAAGGACATTCGCGGAGTCGGCCCCTACGTCAACTCCCCCG
ACCCGGAACACCTGACCTTCCCCCGCTCGGCGCCCCTGCCGGCCCACCTCACCTACTGGCGA
TACCCGAACCCGTCCTCCTACACGCCGTCCCCGCCCGGGCACCCCAACACCCTCCGCCTGAC
CCCGTCCCGCCTGAACCTGACCGCCCTCAACGGCAACTACGCGGGGCCGACCAGACCTTCG
TCTCGCGCCGGCAGCAGCACACCCTCTTCACCTACAGCGTCACGCTCGACTACGCGCCGCGG
ACCGCCGGGGAGGAGGCCGGCGTGACCGCCTTCCTGACGCAGAACCACCACCTCGACCTGG
GCGTCGTCCTGCTCCCTCGCGGCTCCGCCACCGCGCCCTCGCTGCCGGGCCTGAGTAGTAGT
ACAACTACTACTAGTAGTAGTAGTCGTCCGGACGAGGAGGAGGAGCGCGAGGCGGGCG
AAGAGGAAGAAGAGGGCGGACAAGACTTGATGATCCCGCATGTGCGGTTCAGGGGCGAGTC
GTACGTGCCCGTCCCGGCGCCCGTCGTGTACCCGATACCCCGGGCCTGGAGAGGCGGGAAG
CTTGTGTTAGAGATCCGGGCTTGTAATTCGACTCACTTCTCGTTCCGTGTCGGGCCGGACGGG
AGACGGTCTGAGCGGACGGTGGTCATGGAGGCTTCGAACGAGGCCGTTAGCTGGGGCTTTA
CTGGAACGCTGCTGGGCATCTATGCGACCAGTAATGGTGGCAACGGAACCACGCCGGCGTA
TTTTTCGGATTGGAGGTACACACCATTGGAGCAGTTTAGGGAT
```

(SEQ ID NO: 164)
<u>MFFASLLLGLLAGVSAS</u>PGHGRNSTFYNPIFPGFYPDPSCIYVPERDHTFFCASSSFNAFPGIPIHAS
KDLQNWKLIGHVLNRKEQLPRLAETNRSTSGIWAPTLRFHDDTFWLVTTLVDDDRPQEDASRW
DNIIFKAKNPYDPRSWSKAVHFNFTGYDTEPFWDEDGKVYTTGAHAWHVGPYIQQAEVDLDTG
AVGEWRIIWNGTGGMAPEGPHIYRKDGWYYLLAAEGGTGIDHMVTMARSRKISSPYESNPNNP
VLTNANTTSYFQTVGHSDLFHDRHGNWWAVALSTRSGPEYLHYPMGRETVMTAVSWPKDEWP
TFTPISGKMSGWPMPPSQKDIRGVGPYVNSPDPEHLTFPRSAPLPAHLTYWRYPNPSSYTPSPPGH
PNTLRLTPSRLNLTALNGNYAGADQTFVSRRQQHTLFTYSVTLDYAPRTAGEEAGVTAFLTQNH

-continued

```
HLDLGVVLLPRGSATAPSLPGLSSSTTTTSSSSSRPDEEEEREAGEEEEEGGQDLMIPHVRFRGESY

VPVPAPVVYPIPRAWRGGKLVLEIRACNSTHFSFRVGPDGRRSERTVVMEASNEAVSWGFTGTL

LGIYATSNGGNGTTPAYFSDWRYTPLEQFRD
```

(SEQ ID NO: 165)
```
SPGHGRNSTFYNPIFPGFYPDPSCIYVPERDHTFECASSSFNAFPGIPIHASKDLQNWKLIGHVLNR

KEQLPRLAETNRSTSGIWAPTLRFHDDTFWLVTTLVDDDRPQEDASRWDNIIFKAKNPYDPRSW

SKAVHFNFTGYDTEPFWDEDGKVYITGAHAWHVGPYIQQAEVDLDTGAVGEWRIIWNGTGGM

APEGPHIYRKDGWYYLLAAEGGTGIDHMVTMARSRKISSPYESNPNNPVLTNANTTSYFQTVGH

SDLFHDRHGNWWAVALSTRSGPEYLHYPMGRETVMTAVSWPKDEWPTFTPISGKMSGWPMPP

SQKDIRGVGPYVNSPDPEHLTFPRSAPLPAHLTYWRYPNPSSYTPSPPGHPNTLRLTPSRLNLTAL

NGNYAGADQTFVSRRQQHTLFTYSVTLDYAPRTAGEEAGVTAFLTQNHHLDLGVVLLPRGSAT

APSLPGLSSSTTTTSSSSSRPDEEEEREAGEEEEEGGQDLMIPHVRFRGESYVPVPAPVVYPIPRAW

RGGKLVLEIRACNSTHFSFRVGPDGRRSERTVVMEASNEAVSWGFTGTLLGIYATSNGGNGTTP

AYFSDWRYTPLEQFRD
```

The polynucleotide (SEQ ID NO:166) and amino acid (SEQ ID NO:167) sequences of a wild-type *M. thermophila* acetylxylan esterase ("Axe3") are provided below. The signal sequence is shown underlined in SEQ ID NO:167. SEQ ID NO:168 provides the sequence of this acetylxylan esterase without the signal sequence.

(SEQ ID NO: 166)
```
ATGAAGCTCCTGGGCAAACTCTCGGCGGCACTCGCCCTCGCGGGCAGCAGGCTGGCTGCCGC

GCACCCGGTCTTCGACGAGCTGATGCGGCCGACGGCGCCGCTGGTGCGCCCGCGGGCGGCC

CTGCAGCAGGTGACCAACTTTGGCAGCAACCCGTCCAACACGAAGATGTTCATCTACGTGCC

CGACAAGCTGGCCCCCAACCCGCCCATCATAGTGGCCATCCACTACTGCACCGGCACCGCCC

AGGCCTACTACTCGGGCTCCCCTTACGCCCGCCTCGCCGACCAGAAGGGCTTCATCGTCATC

TACCCGGAGTCCCCCTACAGCGGCACCTGTTGGGACGTCTCGTCGCGCGCCGCCCTGACCCA

CAACGGCGGCGGCGACAGCAACTCGATCGCCAACATGGTCACCTACACCCTCGAAAAGTAC

AATGGCGACGCCAGCAAGGTCTTTGTCACCGGCTCCTCGTCCGGCGCCATGATGACGAACGT

GATGGCCGCCGCGTACCCGGAACTGTTCGCGGCAGGAATCGCCTACTCGGGCGTGCCCGCCG

GCTGCTTCTACAGCCAGTCCGGAGGCACCAACGCGTGGAACAGCTCGTGCGCCAACGGGCA

GATCAACTCGACGCCCCAGGTGTGGGCCAAGATGGTCTTCGACATGTACCCGGAATACGAC

GGCCCGCGCCCCAAGATGCAGATCTACCACGGCTCGGCCGACGGCACGCTCAGACCCAGCA

ACTACAACGAGACCATCAAGCAGTGGTGCGGCGTCTTCGGCTTCGACTACACCCGCCCCGAC

ACCACCCAGGCCAACTCCCCGCAGGCCGGCTACACCACCTACACCTGGGGCGAGCAGCAGC

TCGTCGGCATCTACGCCCAGGGCGTCGGACACACGGTCCCCATCCGCGGCAGCGACGACAT

GGCCTTCTTTGGCCTGTGA
```

(SEQ ID NO: 167)
```
MKLLGKLSAALALAGSRLAAAHPVFDELMRPTAPLVRPRAALQQVTNFGSNPSNTKMFIYVPDK

LAPNPPIIVAIHYCTGTAQAYYSGSPYARLADQKGFIVIYPESPYSGTCWDVSSRAALTHNGGGDS

NSIANMVTYTLEKYNGDASKVFVTGSSSGAMMTNVMAAAYPELFAAGIAYSGVPAGCFYSQSG

GTNAWNSSCANGQINSTPQVWAKMVFDMYPEYDGPRPKMQIYHGSADGTLRPSNYNETIKQW

CGVFGFDYTRPDTTQANSPQAGYTTYTWGEQQLVGIYAQGVGHTVPIRGSDDMAFFGL
```

```
                                                     (SEQ ID NO: 168)
HPVFDELMRPTAPLVRPRAALQQVTNFGSNPSNTKMFIYVPDKLAPNPPIIVAIHYCTGTAQAYY

SGSPYARLADQKGFIVIYPESPYSGTCWDVSSRAALTHNGGGDSNSIANMVTYTLEKYNGDASK

VFVTGSSSGAMMTNVMAAAYPELFAAGIAYSGVPAGCFYSQSGGTNAWNSSCANGQINSTPQV

WAKMVFDMYPEYDGPRPKMQIYHGSADGTLRPSNYNETIKQWCGVFGFDYTRPDTTQANSPQ

AGYTTYTWGEQQLVGIYAQGVGHTVPIRGSDDMAFFGL
```

The polynucleotide (SEQ ID NO:169) and amino acid (SEQ ID NO:170) sequences of a wild-type *M. thermophila* ferulic acid esterase ("FAE") are provided below. The signal sequence is shown underlined in SEQ ID NO:170. SEQ ID NO:171 provides the sequence of this xylanase without the signal sequence identified as having GH61 activity. It was designated "GH61a". FIG. 1 shows the improvement in glucose yield resulting from having GH61a present in a reaction where crystalline cellulose undergoes saccharification by cellulase enzymes that are contained in culture broth from *M. thermophila* cells.

```
                                                     (SEQ ID NO: 169)
ATGATCTCGGTTCCTGCTCTCGCTCTGGCCCTTCTGGCCGCCGTCCAGGTCGTCGAGTCTGCC

TCGGCTGGCTGTGGCAAGGCGCCCCCTTCCTCGGGCACCAAGTCGATGACGGTCAACGGCAA

GCAGCGCCAGTACATTCTCCAGCTGCCCAACAACTACGACGCCAACAAGGCCCACAGGGTG

GTGATCGGGTACCACTGGCGCGACGGATCCATGAACGACGTGGCCAACGGCGGCTTCTACG

ATCTGCGGTCCCGGGCGGGCGACAGCACCATCTTCGTTGCCCCCAACGGCCTCAATGCCGGA

TGGGCCAACGTGGGCGGCGAGGACATCACCTTTACGGACCAGATCGTAGACATGCTCAAGA

ACGACCTCTGCGTGGACGAGACCCAGTTCTTTGCTACGGGCTGGAGCTATGGCGGTGCCATG

AGCCATAGCGTGGCTTGTTCTCGGCCAGACGTCTTCAAGGCCGTCGCGGTCATCGCCGGGGC

CCAGCTGTCCGGCTGCGCCGGCGGCACGACGCCCGTGGCGTACCTAGGCATCCACGGAGCC

GCCGACAACGTCCTGCCCATCGACCTCGGCCGCCAGCTGCGCGACAAGTGGCTGCAGACCA

ACGGCTGCAACTACCAGGGCGCCCAGGACCCCGCGCCGGGCCAGCAGGCCCACATCAAGAC

CACCTACAGCTGCTCCCGCGCGCCCGTCACCTGGATCGGCCACGGGGGCGGCCACGTCCCCG

ACCCCACGGGCAACAACGGCGTCAAGTTTGCGCCCCAGGAGACCTGGGACTTCTTTGATGCC

GCCGTCGGAGCGGCCGGCGCGCAGAGCCCGATGACATAA (SEQ ID NO: 170)
MISVPALALALLAAVQVVESASAGCGKAPPSSGTKSMTVNGKQRQYILQLPNNYDANKAHRVV

IGYHWRDGSMNDVANGGFYDLRSRAGDSTIFVAPNGLNAGWANVGGEDITFTDQIVDMLKNDL

CVDETQFFATGWSYGGAMSHSVACSRPDVFKAVAVIAGAQLSGCAGGTTPVAYLGIHGAADNV

LPIDLGRQLRDKWLQTNGCNYQGAQDPAPGQQAHIKTTYSCSRAPVTWIGHGGGHVPDPTGNN

GVKFAPQETWDFFDAAVGAAGAQSPMT (SEQ ID NO: 171)
ASAGCGKAPPSSGTKSMTVNGKQRQYILQLPNNYDANKAHRVVIGYHWRDGSMNDVANGGFY

DLRSRAGDSTIFVAPNGLNAGWANVGGEDITFTDQIVDMLKNDLCVDETQFFATGWSYGGAMS

HSVACSRPDVFKAVAVIAGAQLSGCAGGTTPVAYLGIHGAADNVLPIDLGRQLRDKWLQTNGC

NYQGAQDPAPGQQAHIKTTYSCSRAPVTWIGHGGGHVPDPTGNNGVKFAPQETWDFFDAAVG

AAGAQSPMT
```

Example 1

Gene Acquisition and Construction of Expression Vectors

A protein from a strain of *M. thermophila* having the amino acid sequence provided in SEQ ID NO:2 was previously In this Example, the wild type GH61a gene from *M. thermophila* was isolated from the genome and the DNA sequence verified. The gene was cloned into a *Saccharomyces cerevisiae*/*M. thermophila* shuttle vector pYTDX60 using Pml1 cloning sites, using standard methods known in the art. The signal peptide and gene were under the control of a yeast transcription elongation factor 1 promoter (pTEF1). The vector contained the REP2, rep1 and protein D (partial) origin of replication for *S. cerevisiae* and a URA3 resistance marker.

The resulting plasmid (pYTDX60-GH61a) was transformed into *S. cerevisiae* INVSC1 strain and the transformed host cells were grown in Costar 96 deep well plates for GH61a protein production. The GH61a sequence from the transformants were verified as the wild type GH61a DNA sequence (SEQ ID NO:1) and the encoded polypeptide (SEQ ID NO:2).

Example 2

Shake Flask Procedure

A single colony of *S. cerevisiae* containing a plasmid with the GH61a gene was inoculated into 3 mL synthetic defined-uracil (SD-ura) broth (2 g/L synthetic drop-out minus uracil without yeast nitrogen base (US Biological), 5 g/L ammonium sulfate, 0.1 g/L calcium chloride, 2 mg/L inositol, 0.5 g/L magnesium sulfate, 1 g/L potassium phosphate monobasic ($KH_2PO_4$), 0.1 g/L sodium chloride) containing 6% glucose. Cells were grown overnight (at least 21 hrs) in an incubator at 30° C. with shaking at 250 rpm. Then, 500 µL of the overnight culture was diluted into either 50 mL SD-ura medium or modified galactose expression medium (30 g/L galactose, 6.7 g/L yeast nitrogen base without amino acids, 5 g/L ammonium sulfate, 24 g/L amino acid mix minus uracil, 10 g/L potassium phosphate monobasic ($KH_2PO_4$) and 0.38% vitamin mix) containing 2% glucose in a 250 mL baffled sterile shake flask and incubated at 37° C. (for SD-ura medium) or 30° C. (for modified galactose expression medium) for 48 hours. Cells were pelleted by centrifugation (4000 rpm, 15 min, 4° C.). The clear media supernatant containing the secreted GH61a enzyme was collected and stored at 4° C. until used.

Example 3

GH61 Activity Assays

In some experiments, GH61 activity was determined using a biomass assay. The substrate was wheat straw that had been pretreated under acidic conditions (hereinafter referred to as "pretreated wheat straw"). The reaction was carried out in a total volume of 77 µL in the presence of 10 mg of pre-treated wheat straw, with 62 µL of 1×~20× concentrated clear media supernatant ("broth") containing *S. cerevisiae*-produced *M. thermophila* GH61a enzyme and 15 µL of sodium acetate buffer (pH 5.0), *M. thermophila*-produced cellobiohydrolase 1a (CBH1a), cellobiohydrolase 2b (CBH2b) and beta-glucosidase. The final concentration of sodium acetate was 150 mM and the enzyme loads of CBHs and beta-glucosidase were approximately 0.0025%~0.0125% (CBH1a and CBH2b in 1:1 ratio) and 0.01 to 0.02% with respect to substrate glucan mass in the biomass substrate, respectively.

Some experiments were also performed in the presence of inhibitors that may arise through the routine preparation or pre-treatment of a cellulose substrate. In this way, GH61 protein variants can be identified that are more resistant to the presence of such inhibitors, and therefore find use with a wider range of feedstocks and have wider applicability in the processing of biomass from different sources.

In some experiments, the pretreatment filtrate was obtained by washing pretreated substrate solids with water. The GH61 activity assay was carried out with 50 µL of GH61a containing supernatant, 12 µL of pretreatment filtrate, and 15 µL of sodium acetate buffer mixed with CBH1a, CBH2b and beta-glucosidase isolated from *M. thermophila*. Background negative controls were obtained by using media supernatant from cultures of cells without the GH61a gene in the plasmid. Thus, the negative controls represent activities of CBH1a, CBH2b and beta-glucosidase in the absence of GH61a. The reaction was incubated at 50 to 60° C. for 24 to 72 hours with shaking, and then quenched by adding 130 µL $H_2O$ at room temperature.

Some experiments were carried out in a total volume of 360 µL in the presence of 10 mg of pre-treated wheat straw and 40 µL filtrate (11% total volume), with 262 µL of clear media supernatant containing *S. cerevisiae*-produced *M. thermophila* GH61a enzyme and 48 µL of sodium acetate buffer (pH 5; supplemented with $CuSO_4$) mixed with *M. thermophila*-produced CBH1a, CBH2b and β-glucosidase. The final concentrations of sodium acetate and $CuSO_4$ were 128 mM and 15 µM, respectively, and the enzyme loads of CBH's and beta-glucosidase were 0.01% (CBH1a and CBH2b in 1:1 ratio) and 0.02% with respect to substrate glucan mass in the biomass substrate, respectively. Background negative controls were obtained by using media supernatant from cultures of *S. cerevisiae* cells without the GH61a gene in the plasmid. Thus, the negative controls represent glucose production by CBH1a, CBH2b and beta-glucosidase in the absence of GH61a. The reaction was incubated at 55° C. for 72 hours with shaking.

The GH61 activity in the reaction mixture was measured by monitoring glucose production, as determined using an enzymatic glucose assay kit (K-GLUC, Megazyme). In a total volume of 200 µL, 20 µL of GH61a reaction mixture was added to 180 µL of 2× concentrated glucose determination reagent (GOPOD Reagent™, supplied as part of the K-GLUC assay kit). The reaction was incubated at room temperature for 30 minutes and the absorbance of the solution was measured at 510 nm. The glucose oxidase enzyme in the GOPOD reagent reacts with glucose and produces hydrogen peroxide, which then reacts with the 4-aminoantipyrine in the reagent to produce a quinoneimine dye. The amount of quinoneimine dye was measured spectrophotometrically at 510 nm to calculate the total amount of D-glucose in the reaction mixture. The total amount of glucose in the reaction mixture was also measured using an AGILENT® HPLC 1200 equipped with an AMINEX™ HPX-87H ion exclusion column (300 mm×7.8 mm+Bio-Rad) with 5 mM sulfuric acid in water as eluent at a flow rate of 0.6 mL/min at 65° C. The retention time of glucose was 9.5 minutes.

Detectable amounts of glucose, as a measure of GH61 activity, were observed under high throughput screening conditions (pH 5, 55° C.). GH61a specific activity in the reaction mixture (which also comprised CBH1a, CBH2b and beta-glucosidase) was determined by subtracting the amount of glucose in the negative control reaction (comprising CBH1a, CBH2b and BGL, but not GH61a) from the total glucose measurement.

Example 4

High Throughput Assays to Identify Improved GH61a Variants

Plasmid libraries containing variant GH61a genes were transformed into *S. cerevisiae* INVSC1 strain and plated on SD-ura agar plate containing 2% glucose. After incubation for at least 48 hours at 30° C., colonies were picked using a Q-Bot® robotic colony picker (Genetix) into shallow, 96-well well microtiter plates containing 200 µL SD-ura media and 6% glucose. Cells were grown for at least 21 hours at 30° C. with shaking at 250 rpm and 85% humidity. Then, 20 μL of the overnight culture was transferred into 96-deep well microtiter plates containing 380 μL SD-ura medium with 2% glucose as described in Example 2. In some cases, 15 μL of the overnight culture was transferred into 96-deep well microtiter plates containing 285 μL modified galactose expression medium with 2% glucose as described in Example 2. The plates were incubated at 37° C. (for SD-ura medium) or 30° C. (for modified galactose expression medium) with shaking at 250 rpm and 85% humidity for 48 hours. The deep well plates were centrifuged at 4000 rpm for 15 minutes and the clear media supernatant containing the secreted GH61a enzyme was used for the high throughput biomass assay.

The GH61a libraries were screened for thermoactivity using a biomass-based high throughput method using the assays described in Example 3.

Example 5

Improved GH61 Activity of Engineered GH61a Variants

Improved GH61a variants were identified from the high throughput screening of various GH61a variant libraries as described in the previous Example. The screening was done by measuring thermoactivity of these variants compared with that of the parental GH61a enzyme (expressed from GH61a DNA; SEQ ID NO:1). The high throughput (HTP) saccharification reactions were conducted at pH 5, 55° C. for 24-72 hrs, using 50 g/L pretreated wheat straw, 0.0025-0.01% of mixture of CBH1a and CBH2b (1:1 ratio), and 0.01 to 0.02% of beta-glucosidase.

Example 6

Shake Flask Validation of Improved GH61a Variants

Figure 2:
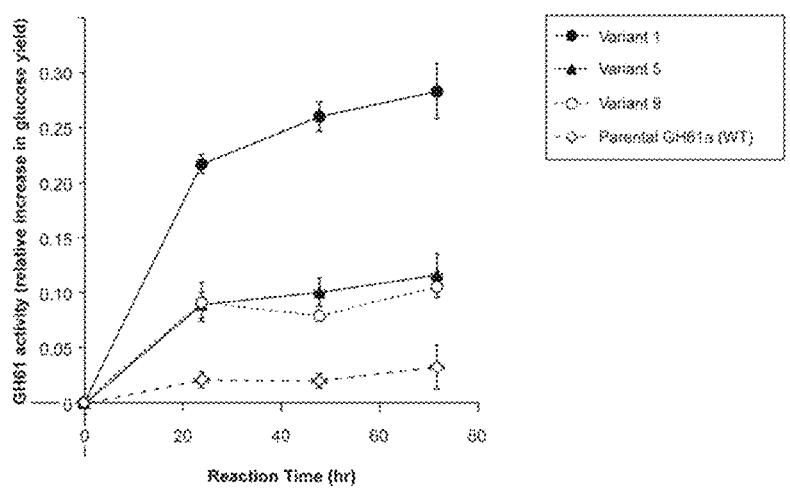
FIG. 2 shows specific GH61 activity observed in a reaction where a wheat straw substrate was hydrolyzed by cellulase enzymes CBH1, CBH2, and beta-glucosidase. The results show that GH61a Variants 5 and 9 have a 2.0 to 2.9 fold improvement over the parental GH61 sequence (SEQ ID NO:2); and Variant 1 has a 3.0 to 3.9 fold improvement.

Improved GH61a variants identified in the high throughput screening (as described in the previous Example) were prepared using the shake flask procedure described above. GH61 activities were determined using a biomass assay as described above, in which normalized concentrations of GH61a variants were used for direct comparison of the specific activities of the GH61a variants. Reactions were quenched at different time points between 24 to 72 hours and glucose levels measured for time-course analysis. FIG. 2 shows time course results for three GH61a variants. FIG. 2 also shows specific activities observed under the following assay conditions: pH 5.0, and 55° C., utilizing 50 g/L pretreated wheat straw, 0.0025%~0.0125% of mixture of CBH1a and CBH2b (1:1 ratio) and 0.01 to 0.02% of beta-galactosidase. The protein concentration was normalized in reactions. In this Figure, N=3; error bars represent ±1 standard deviation. GH61 activity is shown as the increase in glucose production by the enzyme combination [CBH1a+CBH2b+BGL1] supplemented by the GH61 protein, minus the glucose production by the same enzyme combination in the absence of the GH61 protein.

The results show that Variants 5 and 9 (SEQ ID NOS:6 and 8) have a 2.0 to 2.9 fold improvement over the native GH61a (SEQ ID NO:2); and Variant 1 has a 3.0 to 3.9 fold improvement over GH61a (SEQ ID NO:2).

Substitutions improving GH61 activity are compiled in Table 6-1 below. This table shows GH61a variants derived from the native GH61a enzyme (SEQ ID NO:2) that were shown to have improved thermoactivity. Improvement in GH61 activity in relation to the parental GH61a protein (SEQ ID NO:2) is indicated with the following scale:

+=1.1 to 1.9 fold improvement compared with wild-type (SEQ ID NO:2)
++=2.0 to 2.9 fold improvement compared with wild-type
+++=3.0 to 3.9 fold improvement compared with wild-type

TABLE 6-1

GH61 Variants with Improved Activity

| Var. No. | Amino Acid Changes | Silent Nucleotide Changes | Improvement in GH61 Activity |
|---|---|---|---|
| 1 | N35G/E104H/A168P (SEQ ID NO: 4) | t60c/c573g | +++ |
| 2 | W42P/E104H/K167A | t60c/c573g/g1026a | ++ |
| 3 | N35G/W42P/V97Q/A191N | | ++ |
| 4 | W42P/E104H | c573g | ++ |
| 5 | E104H/K167A | t60c/c291a/c573g | ++ |
| 6 | W42P/A191N | t60c/c291a | ++ |
| 7 | N35G/W42P/A191N | t60c/c291a | ++ |
| 8 | H20D | | ++ |
| 9 | V97Q/A191N | | ++ |
| 10 | N35G/E104H/A191N | t60c/c876t | ++ |
| 11 | E104H | | ++ |
| 12 | E104Q | | + |
| 13 | H20D/E104D/Q190H/Y192H | | + |
| 14 | H20D/Q190E/Y192Q | a312g | + |
| 15 | H20D/E104C | | + |
| 16 | H20D/P103H/E104C | | + |
| 17 | H20D/P103H | a312g | + |
| 18 | N35G/E104H | t60c/c573g | + |
| 19 | H20D/P103H/E104Q/Q190E | | + |
| 20 | H20D/P103H/E104C/Y192Q | | + |
| 21 | E104D | t60c | + |
| 22 | N35G/W42P | t60c/c573g | + |
| 23 | A137P | | + |
| 24 | H20D/P103H/E104Q | | + |
| 25 | P103E/E104D | t60c | + |
| 26 | N35G/F68Y/A191N | t379a/c380g/g381c | + |
| 27 | W42P/A168P | | + |
| 28 | H20D/E104C/Q190E/Y192Q | | + |
| 29 | A142W | | + |
| 30 | N35G | | + |
| 31 | H20C/Q190E | | + |
| 32 | W42P/A212P/T236P | | + |
| 33 | N35G/W42P/V97Q/K167A/A168P | t60c/c573g | + |
| 34 | V97Q/A168P | c573g | + |
| 35 | S232A | | + |
| 36 | W42P/E104H/K167A/A168P/Q190E | c573g | + |
| 37 | W42P/A168P/A212P/T236P | | + |
| 38 | N35G/V97Q/K167A | | + |
| 39 | N35G/V97Q | | + |
| 40 | N35G/A191N | | + |
| 41 | S127T/K167A/A191N | | + |
| 42 | W42P | | + |
| 43 | W42P/E104C/K167A/A168P | t60c/c291a/c573g | + |
| 44 | K167Q | | + |
| 45 | W131V | | + |
| 46 | E176C | | + |
| 47 | K167I/P273S | c300t | + |
| 48 | W42P/T87P | | + |
| 49 | W42P/A212P | | + |
| 50 | K133H | | + |
| 51 | D165N | | + |
| 52 | D165A | | + |
| 53 | A168D | | + |
| 54 | K218T | | + |
| 55 | P45T | | + |
| 56 | Q44V | | + |
| 57 | S164W | | + |
| 58 | I177F | | + |
| 59 | A191N | | + |
| 60 | I134P | | + |
| 61 | K133F | | + |

TABLE 6-1-continued

GH61 Variants with Improved Activity

| Var. No. | Amino Acid Changes | Silent Nucleotide Changes | Improvement in GH61 Activity |
|---|---|---|---|
| 62 | I134D | | + |
| 63 | N35G/K167A | t60c/c291a/c573g | + |
| 64 | I162R | | + |
| 65 | N35G/K167A | t204c/t379a/t380g/g381c/c385t | + |
| 66 | D165W/A246T | | + |
| 67 | I162L | | + |
| 68 | S164M | | + |
| 69 | F132D/A244D | | + |
| 70 | H181Q | | + |
| 71 | I177G | g1026a | + |
| 72 | L166W | | + |
| 73 | I162F | | + |
| 74 | I134V | | + |
| 75 | E176Q | | + |
| 76 | H181S | | + |
| 77 | I178A | | + |
| 78 | K167A | | + |
| 79 | V172K | | + |
| 80 | I177H | | + |
| 81 | I134N | | + |
| 82 | K133Y | | + |
| 83 | N35G/Y139L | | + |
| 84 | A168G | | + |
| 85 | T12A/I162G | c246t | + |
| 86 | D165E | | + |
| 87 | D165M | | + |
| 88 | I134M | | + |
| 89 | A168P | | + |
| 90 | I177D | | + |
| 91 | S164P | | + |
| 92 | H175T | | + |
| 93 | N187K/S330R | c597g | + |
| 94 | H175R | | + |
| 95 | L166H | | + |
| 96 | I178L | | + |
| 97 | L173H | | + |
| 98 | I177T | | + |
| 99 | N170Y | | + |
| 100 | H175S | | + |
| 101 | K167T | | + |
| 102 | L166R | | + |
| 103 | V172Y | | + |
| 104 | P163S/E176D | | + |
| 105 | S164I | | + |
| 106 | H175M | | + |
| 107 | A168N | | + |
| 108 | A179W | | + |
| 109 | W131K/H175Q | g1026a | + |
| 110 | Y171A | | + |
| 111 | N170H | | + |
| 112 | P163R | | + |
| 113 | A168C | | + |
| 114 | G169T | | + |
| 115 | R174F | | + |
| 116 | W131Y | | + |
| 117 | I134L | | + |
| 118 | I177V | | + |
| 119 | K167E | | + |
| 120 | H175C | | + |
| 121 | W131I | | + |
| 122 | W42P/A143P | | + |
| 123 | I178G | c72t | + |
| 124 | N170P | | + |
| 125 | A179D/N317K | c732g/c843t/c882t/c909t/c912g | + |
| 126 | I162V | | + |
| 127 | I178M | | + |
| 128 | V172A | | + |
| 129 | K167A/A191N | t60c/c291a | + |
| 130 | F132A | | + |
| 131 | P163E | | + |
| 132 | F132M | | + |
| 133 | A179G | | + |
| 134 | I177S | | + |
| 135 | K167A | g921a | + |
| 136 | K167F | | + |
| 137 | A168I | | + |
| 138 | A179N | | + |
| 139 | I134A | c792t | + |
| 140 | K167E | g972t | + |
| 141 | R174K | | + |
| 142 | S164F | | + |
| 143 | V172L | | + |
| 144 | A168H | | + |
| 145 | I134T | | + |
| 146 | K167H | | + |
| 147 | L166A | | + |
| 148 | S164R | | + |
| 149 | R174C | | + |
| 150 | A179P | | + |
| 151 | G169R | g1026a | + |
| 152 | L173M | | + |
| 153 | D165K | | + |
| 154 | E176S | | + |
| 155 | F132L | | + |
| 156 | F132I/A179I | | + |
| 157 | F132P | | + |
| 158 | S164Q | | + |
| 159 | V172Q | | + |
| 160 | W131D | | + |
| 161 | W131Q | | + |
| 162 | A179H | | + |
| 163 | I134H/G270S | | + |
| 164 | N170G | | + |
| 165 | A168T | | + |
| 166 | A179C | | + |
| 167 | K133N | | + |
| 168 | K167L | | + |
| 169 | L180M | | + |
| 170 | W131F | | + |
| 171 | I134W | g1026a | + |
| 172 | I178H | | + |
| 173 | N170A | | + |
| 174 | V172H | | + |
| 175 | A168H/S205N | | + |
| 176 | I134H | g921a | + |
| 177 | S164C | | + |
| 178 | S164K | | + |
| 179 | I177C | | + |
| 180 | I178Q | | + |
| 181 | L180W | | + |
| 182 | I177M | | + |
| 183 | R174D | | + |
| 184 | V172M | | + |
| 185 | A179M | | + |
| 186 | H175Y | | + |
| 187 | I178P | | + |
| 188 | L173A | | + |
| 189 | N170E | | + |
| 190 | N170F | | + |
| 191 | N35G/A191N/T258I/T323P/G328A/C341R | t379a/c380g/g381c/c454a/c456a/c732t/c843t/c849t | + |
| 192 | A168R | | + |
| 193 | D165I | | + |
| 194 | I162M | | + |
| 195 | K167V | | + |
| 196 | A179S | | + |
| 197 | E176N | | + |
| 198 | I134L/P322L | | + |
| 199 | P163L | | + |
| 200 | H181D | | + |
| 201 | N170S | | + |
| 202 | R174G | | + |
| 203 | I177R | | + |
| 204 | K167C | | + |
| 205 | L166Q | | + |

TABLE 6-1-continued

GH61 Variants with Improved Activity

| Var. No. | Amino Acid Changes | Silent Nucleotide Changes | Improvement in GH61 Activity |
|---|---|---|---|
| 206 | P163I | | + |
| 207 | S164L/L166I | | + |
| 208 | Y171R | | + |
| 209 | F132P/Q190E/A191T | | + |
| 210 | F132Q | | + |
| 211 | I134C | | + |
| 212 | I177A | | + |
| 213 | E176R | | + |
| 214 | G169A | | + |
| 215 | G169K | | + |
| 216 | H181A | | + |
| 217 | I177L | | + |
| 218 | A168G | | + |
| 219 | A179R | | + |
| 220 | D165T | | + |
| 221 | K167R | | + |
| 222 | L166V | | + |
| 223 | N170C | | + |
| 224 | I178R | | + |
| 225 | R174H | | + |
| 226 | S164H | | + |
| 227 | W131R/L166I | | + |
| 228 | I162A/A191T | | + |
| 229 | L173F | | + |
| 230 | N170Q | | + |
| 231 | I177P | | + |
| 232 | R174N | | + |
| 233 | V172K/S215W | | + |
| 234 | D165R | | + |
| 235 | G239D | c520a/c522g | + |
| 236 | H175V | | + |
| 237 | H181R | | + |
| 238 | I134Y | | + |
| 239 | V172F | | + |
| 240 | V172G | | + |

Table 6-2 shows GH61a variants derived from the GH61a protein designated "Variant 1" in Table 6-1 with improved thermoactivity. The second-round variants usually retained the alterations of Variant 1 compared with wild-type GH61a (N35G/E104H/A168P), along with additional alterations. Improvement in GH61 activity in relation to Variant 1 (SEQ ID NO:4) is indicated in Table 6-2 according to the following scale:

*=0.5 to 1.0 fold improvement compared with Variant 1 (SEQ ID NO:4)
+=1.1 to 1.9 fold improvement compared with Variant 1;
++=2.0 to 2.9 fold improvement compared with Variant 1

TABLE 6-2

GH61 Variants with Improved Activity Compared to Variant 1

| Variant Number | Amino Acid Changes | Silent Nucleotide Changes | GH61 Activity Improvement |
|---|---|---|---|
| 241 | N35G/T40A/E104H/A168P/P327M | t60c/c573g | ++ |
| 242 | N35G/P45D/E104H/A168P/N317R | t60c/c573g | ++ |
| 243 | N35G/E104H/A168P/N317R | t60c/c573g | + |
| 244 | N35G/E104H/A168P/N317L | t60c/c573g | + |
| 245 | N35G/T54H/E104H/A168P | t60c/c573g | + |
| 246 | N35G/E104H/A168P/N317D/S329Y | t60c/c573g | + |
| 247 | N35G/E104H/A137S/A168P/S232E | t60c/c573g | + |
| 248 | N35G/E104H/A168P/N317R/T320A | t60c/c573g | + |
| 249 | N35G/E104H/A168P/D234E | t60c/c573g | + |
| 250 | N35G/T40S/E104H/A142G/A168P | t60c/c573g | + |
| 251 | N35G/T40S/S78C/V88I/E104H/S128K/A168P/D234M | t60c/c573g | + |
| 252 | N35G/E104H/A168P/S330V | t60c/c573g | + |
| 253 | N35G/E104H/A168P/G203E/P266S | t60c/c573g | + |
| 254 | N35G/E104H/A168P/D234N | t60c/c573g | + |
| 255 | N35G/E104H/A168P/S286N/S329H | t60c/c573g | + |
| 256 | N35G/E104H/A168P/S330H | t60c/c573g | + |
| 257 | N35G/E104H/A168P/W337R | t60c/c573g | + |
| 258 | N35G/N66D/E104H/S164E/A168P/G267T | t60c/c573g | + |
| 259 | N35G/E104H/A168P/P233V | t60c/c573g | + |
| 260 | R34E/N35G/E104H/R145T/A168P | t60c/c573g | + |
| 261 | S24Q/N35G/E104H/A168P/V237I | t60c/c573g | + |
| 262 | Y32S/N35G/E64S/E104H/A168P | t60c/c573g | + |
| 263 | N35G/E104H/A168P/V333R | t60c/c573g | + |
| 264 | N35G/E104H/G144S/A168P/V333Q | t60c/c573g | + |
| 265 | V28H/N35G/P45K/E104H/A168P | t60c/c573g | + |
| 266 | N35G/E104H/A168P/P327K | t60c/c573g | + |
| 267 | N35G/N66Q/E104H/A168 | t60c/c573g | + |
| 268 | N35G/E104H/A168P/G203E | t60c/c573g | + |
| 269 | N35G/E104H/A168P/S339W | t60c/c573g | + |
| 270 | N35G/P45K/N46E/E104H/A150Y/A168P | t60c/c573g | + |
| 271 | N35G/E104H/R130S/A168P | t60c/c573g | + |
| 272 | N35G/E104H/R145T/A168P | t60c/c573g/g891a | + |
| 273 | N35G/E104H/A168P/S231K | t60c/c573g | + |
| 274 | N35G/T40A/E104H/A168P/D234E/P327M | t60c/c573g | + |
| 275 | N35G/E104H/A168P/S231H | t60c/c573g | + |
| 276 | N35G/E104H/A168P/N317M | t60c/c573g | + |
| 277 | N35G/E104H/A168P/S330Y | t60c/c573g | + |

TABLE 6-2-continued

GH61 Variants with Improved Activity Compared to Variant 1

| Variant Number | Amino Acid Changes | Silent Nucleotide Changes | GH61 Activity Improvement |
|---|---|---|---|
| 278 | N35G/E104H/A168P/S329I | t60c/c573g | + |
| 279 | N35G/E104H/A168P/S329R | t60c/c573g | + |
| 280 | N35G/N66D/E104H/A168P/P322R/S329L | t60c/c573g | + |
| 281 | N35G/E104H/A168P/P327F | t60c/c288t/c573g | + |
| 282 | N35G/P45D/E104H/A168P | t60c/c573g | + |
| 283 | N35G/E104H/A168P/S332R | t60c/c573g | + |
| 284 | N35G/E104H/A116S/A168P | t60c/c573g | + |
| 285 | N35G/T40A/E104H/A168P/V230I/P327M | t60c/c573g | + |
| 286 | N35G/T49A/E104H/A168P | t60c/c573g | + |
| 287 | N35G/E104H/A168P/N317T | t60c/c573g | + |
| 288 | N35G/N46Y/E104H/A168P | t60c/c573g | + |
| 289 | N35G/E104H/A168P/G203V | t60c/c573g | + |
| 290 | N35G/E104H/A168P/S329L | t60c/c573g | + |
| 291 | N35G/E104H/R145N/A168P/S329H | t60c/c573g | + |
| 292 | N35G/A56S/E104H/A168P | t60c/c573g | + |
| 293 | N35G/T40S/T49R/E104H/A168P/D234E/P327M | t60c/c573g | + |
| 294 | N35G/E104H/Q161R/A168P | t60c/c573g | + |
| 295 | N35G/E104H/A168P/S332F | t60c/c573g | + |
| 296 | N35G/P45R/T49A/E104H/A168P/N317R/T320A | t60c/c573g | + |
| 297 | N35G/E104H/A168P/V237I | t60c/c573g | + |
| 298 | N35G/Q44K/T80V/E104H/A168P | t60c/c573g | + |
| 299 | N35G/E104H/A168P/E336S | t60c/c573g | + |
| 300 | N35G/E104H/A168P/P233T | t60c/c573g | + |
| 301 | N35G/E104H/A168P/S329Y | t60c/c573g | + |
| 302 | N35G/E104H/A168P/P327L | t60c/c573g | + |
| 303 | N35G/E104H/A168P/N317I | t60c/c573g | + |
| 304 | N35G/E104H/R130H/A168P | t60c/c573g | + |
| 305 | N35G/Q44K/E104H/A168P | t60c/c573g | + |
| 306 | N35G/N66D/E104H/A168P | t60c/c573g | + |
| 307 | N35G/E104H/A168P/S329V | t60c/c573g | + |
| 308 | N35G/E104H/A168P/W337F | t60c/c573g | + |
| 309 | N35G/E104H/A168P/N317H | t60c/c573g | + |
| 310 | N35G/T40L/E104H/S128K/A168P | t60c/c573g | + |
| 311 | N35G/E104H/A168P/A326V | t60c/c573g | + |
| 312 | N35G/T80V/E104H/A168P/P303T | t60c/c573g | + |
| 313 | N35G/E104H/A168P/S231A/S295L | t60c/c573g | + |
| 314 | N35G/E104H/A116Q/A168P | t60c/c573g | + |
| 315 | N35G/E104H/A168P/S330C | t60c/c573g | + |
| 316 | N35G/T40S/E101T/E104H/A168P/P327M | t60c/c573g | + |
| 317 | N35G/E104H/A168P/A326Q | t60c/c573g | + |
| 318 | N35G/N46R/E104H/A168P | t60c/c573g | + |
| 319 | N35G/P45K/E104H/A168P/A219R/S232E | t60c/c573g | + |
| 320 | S24Q/N35G/E104H/A168P/V237I/P303T | t60c/c573g | + |
| 321 | N35G/E104H/A168P/G203E/T281A | t60c/c573g | + |
| 322 | N35G/A56N/E104H/A168P | t60c/c573g | + |
| 323 | N35G/E104H/A168P/E336G | t60c/c573g | + |
| 324 | N35G/E104H/A168P/E336R | t60c/c573g | + |
| 325 | N35G/T40S/E104H/S128K/A142G/A168P | t60c/c573g | + |
| 326 | N35G/Q44K/S67T/E104H/A168P | t60c/c198t/c573g | + |
| 327 | N35G/E104H/A168P/N317A | t60c/c573g | + |
| 328 | N35G/E104H/G155N/A168P | t60c/c573g | + |
| 329 | N35G/E104H/Q161E/A168P | t60c/c573g | + |
| 330 | N35G/E104H/N118S/A168P | t60c/c573g | + |
| 331 | N35G/P45T/V97Q/E104H/A168P/G267S | t60c/c573g | + |
| 332 | V28H/N35G/E104H/A168P | t60c/c573g | + |
| 333 | N35G/E104H/A168P/Q184L | t60c/c573g | + |
| 334 | N35G/E104H/A168P/N317V | t60c/c573g | + |
| 335 | N35G/Q44L/E104H/A168P | t60c/c573g | + |
| 336 | N35G/E104H/A168P/S330G | t60c/c573g | + |
| 337 | N35G/E104H/A168P/T320A/V333W | t60c/c573g | + |
| 338 | N35G/E104H/A168P/E336A | t60c/c573g | + |
| 339 | N35G/E104H/A168P/N335S | t60c/c573g | + |
| 340 | N35G/N66M/E104H/A168P | t60c/c573g | + |
| 341 | N35G/T54G/E104H/A168P | t60c/c573g | + |
| 342 | N35G/E104H/A168P/N317S | t60c/c573g | + |
| 343 | N35G/E64L/E104H/A168P | t60c/c573g | + |
| 344 | N35G/E104H/S164E/A168P/A271T | t60c/c573g | + |
| 345 | N35G/N66A/E104H/A168P | t60c/c573g | + |
| 346 | N35G/G83R/E104H/A168P | t60c/c573g | + |
| 347 | N35G/E104H/A168P/N317Q/T320A | t60c/c573g | + |
| 348 | N35G/E104H/K141A/A168P | t60c/c573g | + |
| 349 | N35G/P71T/E104H/A168P | t60c/c573g | + |

TABLE 6-2-continued

GH61 Variants with Improved Activity Compared to Variant 1

| Variant Number | Amino Acid Changes | Silent Nucleotide Changes | GH61 Activity Improvement |
|---|---|---|---|
| 350 | N35G/P71S/E104H/A168P | t60c/c573g | + |
| 351 | N35G/E104H/R130G/A168P | t60c/c573g | + |
| 352 | N35G/E104H/R145Q/A168P | t60c/c573g | + |
| 353 | N35G/T70A/E104H/A168P | t60c/c573g | + |
| 354 | N35G/E104H/A168P/K218R | t60c/c573g | + |
| 355 | N35G/E104H/A168P/Q184E | t60c/c573g | + |
| 356 | N35G/E104H/R130K/A168P | t60c/c573g | + |
| 357 | N35G/Q58H/E104H/A168P | t60c/c573g | + |
| 358 | Y32S/N35G/E104H/A168P | t60c/c573g | + |
| 359 | N35G/E104H/A168P/S329T | t60c/c573g | + |
| 360 | N35G/E104H/A168P/S330I | t60c/c573g | + |
| 361 | Y32S/N35G/P71A/E104H/A168P | t60c/c573g | + |
| 362 | N35G/E104H/A168P/S330T | t60c/c573g | + |
| 363 | N35G/G82A/E104H/A168P | t60c/c573g | + |
| 364 | N35G/T80V/E104H/A168P | t60c/c573g | + |
| 365 | N35G/E104H/A168P/S295T | t60c/c573g | + |
| 366 | N35G/N66G/E104H/A168P | t60c/c573g | + |
| 367 | N35G/E104H/R145L/A168P | t60c/c573g | + |
| 368 | N35G/S67H/E104H/A168P/V230M | t60c/c573g | + |
| 369 | N35G/E104H/G136E/A168P | t60c/c573g | + |
| 370 | N35G/T54S/E104H/A168P | t60c/c573g | + |
| 371 | N35G/P45S/E104H/A168P | t60c/c573g | + |
| 372 | N35G/E104H/A168P/A326M | t60c/c573g/c882t | + |
| 373 | N35G/N66D/N95E/E104H/S164E/A168P/G267D | t60c/c573g | + |
| 374 | N35G/E104H/A168P/S332C | t60c/c573g | + |
| 375 | N35G/E104H/S128L/A168P | t60c/c573g | + |
| 376 | N35G/T54W/E104H/A168P | t60c/c573g | + |
| 377 | N35G/E104H/A168P/G268A/G269A/G270A | t60c/c573g | + |
| 378 | N35G/Q44K/E104H/A168P/S231T | t60c/c573g | + |
| 379 | R34E/N35G/E104H/A168P/A280D | t60c/c573g | + |
| 380 | N35G/E104H/A168P/A297T | t60c/g399a/c573g | + |
| 381 | N35G/E104H/K141P/R145Q/A168P | t60c/c573g | + |
| 382 | N35G/P45E/E104H/K141R/A168P | t60c/c573g | + |
| 383 | N35G/N66T/E104H/A168P | t60c/c573g | + |
| 384 | N35G/E104H/S164E/A168P/S295D | t60c/c573g | + |
| 385 | N35G/E104H/A168P/N317F | t60c/c573g | + |
| 386 | N35G/E104H/A168P/N317Q | t60c/c573g | + |
| 387 | N35G/T40G/T49R/S78C/E104H/A142G/A168P | t60c/c573g | + |
| 388 | N35G/G82S/E104H/A168P | t60c/c573g | + |
| 389 | N35G/Q58P/E104H/A168P | t60c/c573g | + |
| 390 | N35G/N46R/E104H/A168P/G203E/A263V | t60c/c573g | + |
| 391 | N35G/P45R/E104H/A168P | t60c/c573g | + |
| 392 | N35G/S67G/E104H/A168P | t60c/c573g | + |
| 393 | N35G/E104H/A168P/R199E | t60c/c573g | + |
| 394 | N35G/G69T/E104H/A168P | t60c/c573g | + |
| 395 | N35G/E104H/A168P/G203E/G268A/G269A/G270A | t60c/c573g | + |
| 396 | N35G/E104H/A168P/P266S | t60c/c573g | + |
| 397 | N35G/E104H/A168P/V324M | t60c/c573g | + |
| 398 | N35G/E104H/A168P/G245A | t60c/c573g | + |
| 399 | N35G/N66R/E104H/A168P | t60c/c573g | + |
| 400 | N35G/E104H/A168P/T236E | t60c/c573g | + |
| 401 | S24Q/N35G/Q44K/T80H/E104H/A168P | t60c/c573g | + |
| 402 | N35G/E104H/S128D/A168P | t60c/c573g | + |
| 403 | N35G/N66D/S78D/E104H/A168P/S253D | t60c/c573g | + |
| 404 | N35G/E104H/R130Y/A168P | t60c/c573g | + |
| 405 | N35G/E104H/A168P/K310I | t60c/c573g | + |
| 406 | N35G/E104H/R145E/A168P | t60c/c573g | + |
| 407 | N35G/N66D/E104H/S164E/A168P/S282D | t60c/c573g | + |
| 408 | N35G/E104H/K141P/A168P | t60c/c573g | + |
| 409 | N35G/E104H/A168P/Q184R | t60c/c573g | + |
| 410 | N35G/E104H/A168P/S231T | t60c/c573g | + |
| 411 | N35G/N66V/E104H/A168P | t60c/c573g | + |
| 412 | N35G/E104H/A142L/A168P | t60c/c573g | + |
| 413 | N35G/E104H/R145H/A168P | t60c/c573g | + |
| 414 | N35G/E104H/A168P/K218L | t60c/c573g | + |
| 415 | N35G/E104H/K141T/A168P | t60c/c573g | + |
| 416 | N35G/E104H/A168P/P233F | t60c/c573g | + |
| 417 | N35G/T40S/E104H/A168P/P327M | t60c/c573g | + |
| 418 | N35G/T54M/E104H/A168P | t60c/c573g | + |
| 419 | S24T/N35G/E104H/S164E/A168P | t60c/c573g | + |
| 420 | N35G/P45T/E104H/A168P | t60c/c573g | + |

TABLE 6-2-continued

GH61 Variants with Improved Activity Compared to Variant 1

| Variant Number | Amino Acid Changes | Silent Nucleotide Changes | GH61 Activity Improvement |
|---|---|---|---|
| 421 | N35G/N66D/E104H/S164E/A168P/S231T/S253T | t60c/c573g | + |
| 422 | N35G/G69H/E104H/A168P | t60c/c573g | + |
| 423 | N35G/E104H/S128Y/A168P | t60c/c573g | + |
| 424 | N35G/T49Q/E104H/A168P | t60c/c573g | + |
| 425 | N35G/T49A/E104H/A168P/Q184H | t60c/c573g | + |
| 426 | N35G/E104H/A168P/G203Y | t60c/c573g | + |
| 427 | N35G/Q44K/N66V/E104H/A168P | t60c/c573g | + |
| 428 | N35G/E104H/A137M/A168P | t60c/c573g | + |
| 429 | N35G/E104H/A168P/P327C | t60c/c573g | + |
| 430 | N35G/E104H/A168P/T236R | t60c/c573g | + |
| 431 | N35G/I51A/E104H/A168P | t60c/c573g | + |
| 432 | N35G/S67H/E104H/A168P | t60c/c573g | + |
| 433 | N35G/E104H/A168P/A326C | t60c/c573g | + |
| 434 | N35G/T49A/E104H/S128N/A168P | t60c/c573g | + |
| 435 | N35G/T49R/E104H/A168P/K218L/N317Q | t60c/c573g | + |
| 436 | N35G/E104H/A168P/P266S/G267V | t60c/c573g | + |
| 437 | N35G/E104H/A168P/V237I/P303T | t60c/c573g | + |
| 438 | N35G/T49E/E104H/A168P | t60c/c573g | + |
| 439 | N35G/P45R/E104H/A168P/T320A | t60c/c573g | + |
| 440 | N35G/N66L/E104H/A168P | t60c/c573g | + |
| 441 | N35G/P45R/E104H/A168P/K218L/N317Q | t60c/c573g | + |
| 442 | N35G/E104H/R145V/A168P | t60c/c573g | + |
| 443 | N35G/N66D/E104H/A168P/R290K | t60c/c573g | + |
| 444 | N35G/T80L/E104H/A168P | t60c/c573g | + |
| 445 | N35G/A55G/E104H/A168P | t60c/c573g | + |
| 446 | N35G/E104H/A168P/S330A | t60c/c573g | + |
| 447 | N35G/E104H/K141N/A168P/P266S | t60c/c573g | + |
| 448 | N35G/E104H/A142S/A168P | t60c/c573g | + |
| 449 | N35G/E104H/A168P/Q184G | t60c/c573g | + |
| 450 | N35G/E104H/N118E/A168P | t60c/c573g | + |
| 451 | N35G/E104H/A168P/A212M | t60c/c573g | + |
| 452 | N35G/E104H/A168P/G267D | t60c/c573g | + |
| 453 | N35G/K93N/E104H/R130Y/A168P | t60c/c573g | + |
| 454 | N35G/P45R/T49Y/E104H/A168P/N317D | t60c/c573g | + |
| 455 | N35G/E104H/A168P/S329Q | t60c/c573g | + |
| 456 | N35G/E104H/A168P/V230Q | t60c/c573g | + |
| 457 | N35G/P45K/E104H/A168P/A219R | t60c/c573g | + |
| 458 | N35G/E104H/A142G/A168P | t60c/c573g | + |
| 459 | N35G/E104H/A168P/S205T | t60c/c573g | + |
| 460 | N35G/S78D/E104H/S164E/A168P | t60c/c573g | + |
| 461 | N35G/E104H/R130E/A168P | t60c/c573g | + |
| 462 | N35G/E104H/A168P/Q184H | t60c/c573g | + |
| 463 | N35G/E104H/A116P/A168P | t60c/c573g | + |
| 464 | N35G/E104H/A142D/A168P | t60c/c573g | + |
| 465 | V28H/N35G/N46E/Q58H/E104H/A168P | t60c/c573g | + |
| 466 | N35G/E104H/A168P/A280T | t60c/c573g | + |
| 467 | R34E/N35G/E104H/A168P/A280T | t60c/c573g | + |
| 468 | N35G/E104H/A168P/E336L | t60c/c573g | + |
| 469 | N35G/T49D/E104H/A168P | t60c/c573g | + |
| 470 | N35G/E104H/A168P/A219T | t60c/c573g | + |
| 471 | N35G/E104H/A142W/A168P | t60c/c573g | + |
| 472 | N35G/E104H/A168P/P303T/G305D | t60c/c573g | + |
| 473 | N35G/Q44V/E104H/A168P | t60c/c573g | + |
| 474 | N35G/E104H/A168P/N187D | t60c/c573g | + |
| 475 | N35G/E104H/G136H/A168P | t60c/c573g | + |
| 476 | S24Q/N35G/Q44K/E104H/A168P/P303T/S332D | t60c/c573g | + |
| 477 | N35G/E104H/A168P/Q184N | t60c/c573g | + |
| 478 | N35G/E104H/A168P/S332L | t60c/c573g | + |
| 479 | S24T/N35G/N66D/S78D/E104H/A168P/S205T/S253T | t60c/c573g | + |
| 480 | N35G/E104H/A168P/P327A | t60c/c573g | + |
| 481 | N35G/T40A/T49Q/S78C/E104H/A168P | t60c/c573g | + |
| 482 | N35G/T40L/E104H/A142G/A168P | t60c/c573g | + |
| 483 | N35G/T49Y/E104H/A168P/N317R | t60c/c573g | + |
| 484 | R34E/N35G/K93T/E104H/R130E/R145T/A168P/R199E/K218T/A280D | t60c/c573g | + |

Example 7

Selection of Further GH61 Candidates for Strain Improvement

This example illustrates the selection of potential candidates to further improve whole cellulase broth activity of *M. thermophila* cultures on different types of pretreated substrates like pretreated corn stover and pretreated wheat straw.

In this Example, *M. thermophila*-produced and purified GH61a, GH61p, GH61f, GH61n, CBH1a, CBH2b, AXE3, FAE, and Xyl3, were used to supplement the activity present in culture broths (i.e., "whole broth cellulase base") of the *M. thermophila* strain CF-416 prepared using standard methods known in the art. The broth cellulase base was fixed to 0.5% protein and the single purified enzyme was added at 0.4% (wt added protein/wt glucan) to the saccharification reactions. The whole cellulase broth base and individual enzymes were characterized by standard BCA assays for total protein quantification.

The saccharification reactions were carried out at 74 g/L glucan load of pretreated wheat straw (PWS) or pretreated corn stover (PCS) at pH 5.0, 55° C. at 950 rpm in the presence of 50 µM copper in high throughput (HTP) 96 deep well plates. Glucose analysis was carried out by the glucose oxidase assay as described above. In each case, the fold improvement was calculated using the formula Fold Improvement=[Total Glucose Production with addition of 0.4% single enzyme to the whole cellulase broth base]/[glucose production from the 0.5% whole cellulase broth base]. The results are provided in Table 10-1. In this Table, the fold improvements were ranked from 0 to 3; fold improvements less than 1.2× are indicated by "0," fold improvements of >1.2 to <1.5 are indicated by "1," fold improvements of ≥1.5× to <1.7× improvements are indicated by "2," and fold improvements ≥1.7 are indicated by "3."

As indicated by the results in the Table, the greatest benefit was observed using GH61p on pre-treated corn stover (PCS), and GH61a on pre-treated wheatstraw (PWS), indicating that GH61 activity is increases the cellulolytic activity of the reaction mix. In addition to the enzymes listed in Table 10-1, EG1b, Xyl1, Xyl6, beta-xylosidase, and another xylanase were also tested, but did not show any improvement under the test conditions.

TABLE 7-1

Fold Improvement

| Whole broth cellulases from | Fold Improvement Over Whole Cellulase Broth Tested on PCS | Fold Improvement Over Whole Cellulase Broth Tested on PWS |
|---|---|---|
| CF-416 | 1 | 1 |
| CBH1a | 1 | 3 |
| CBH2b | 1 | 1 |
| GH61a | 2 | 3 |
| GH61p | 3 | 2 |
| GH61f | 1 | 1 |
| GH61n | 1 | 1 |
| AXE3 | 0 | 1 |
| FAE | 1 | 1 |
| Xyl3 | 0 | 1 |

Example 8

Improvement of GH61 Activity by Copper(II) Ions

This example illustrates the enhancement in GH61 activity with the addition of copper(II) ion to the saccharification reaction.

Purified *M. thermophila*-produced GH61a or *S. cerevisiae* supernatant containing *M. thermophila*-GH61a was pre-incubated with different amounts of copper(II) ($CuSO_4$) at concentrations of 0 to 100 µM at ambient temperature for 30 min. The biomass assay was then performed in a total volume of 300 µL, in the presence of 10 mg of pre-treated wheat straw, using 2614 of copper-treated GH61 samples, 39 µL of sodium acetate buffer (pH 5), *M. thermophila*-produced CBH1a, CBH2b and β-glucosidase. The final concentration of sodium acetate was 120 mM and the enzyme loads of CBHs and β-glucosidase (CBH1a and CBH2b in 1:1 ratio) were 0.01% and 0.02% with respect to substrate glucan mass in the biomass substrate, respectively. Background (negative) controls were obtained by using either water or media supernatant from cultures of *S. cerevisiae* cells without the GH61a gene in the plasmid. Thus, the negative controls represent activities of CBH1a, CBH2b and beta-glucosidase in the absence of GH61a. The reaction was incubated at 55° C. for 72 hours with shaking. The GH61a activity in the reaction mixture was measured by monitoring glucose production using a glucose oxidase/peroxidase-based glucose assay.

Some experiments were also performed without pre-incubating GH61 with copper(II), but instead, by directly adding different amounts of copper(II) ($CuSO_4$) to the biomass assay reactions as described herein.

Figure 3:
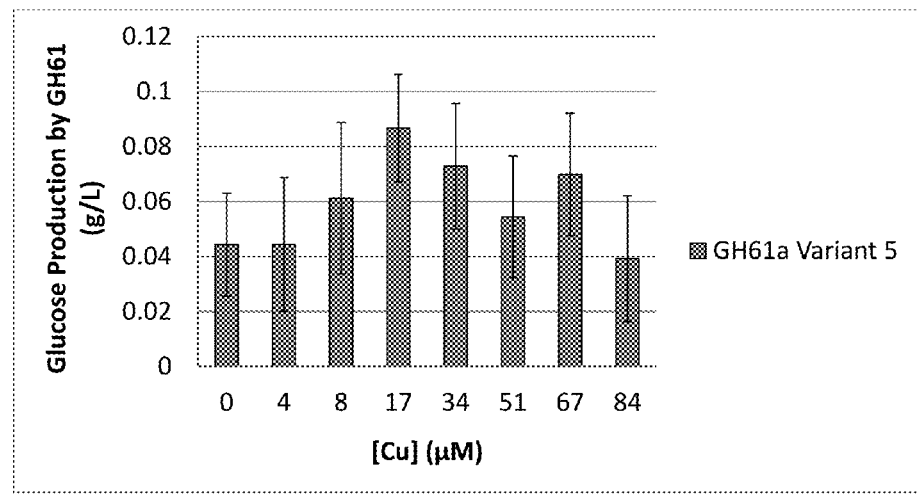
FIG. 3 shows the increase in glucose production in the presence of GH61 protein when $Cu^{++}$ is included the reaction. In this Figure, n=4; and mean±SD. Panel A shows the increase with a GH61 variant protein "Variant 5," while Panel B shows the increase with the wild-type GH61a protein (SEQ ID NO:2).
Figure 3:
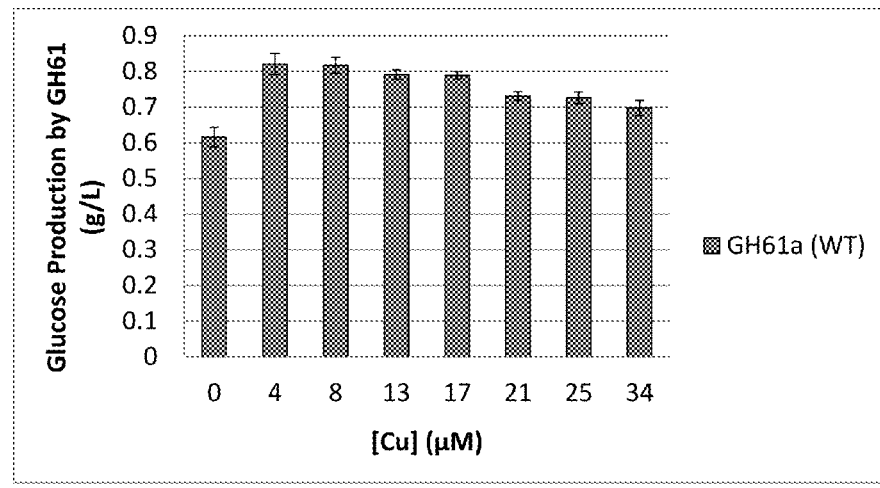

FIG. 3 shows activity of *M. thermophila*-GH61a pre-incubated with different amounts of copper(II) ion. Biomass assays were performed with (A) *S. cerevisiae*-produced *M. thermophila* GH61a Variant 5, and (B) *M. thermophila*-produced wild-type GH61a. Glucose production after 72 h incubation at pH 5, 55° C. was determined by the glucose assay. The data in this Figure indicate GH61a-only activity, in which the amount of glucose produced in control reaction containing CBH and β-glucosidase was subtracted from the total amount of glucose produced in the reactions with GH61a. In this Figure, N=4; and the error bars represent ±1 standard deviation. Copper concentrations shown are with respect to the total reaction volume.

The results indicate that the activities of *M. thermophila*-produced GH61a and *S. cerevisiae* supernatant containing *M. thermophila*-GH61a are improved by pre-incubation with copper(II) ions under the conditions tested. Similar results were obtained when copper(II) was directly added to the biomass assay reactions.

Example 9

Further Evaluation of Copper Requirements in Saccharification Reactions

Figure 4:
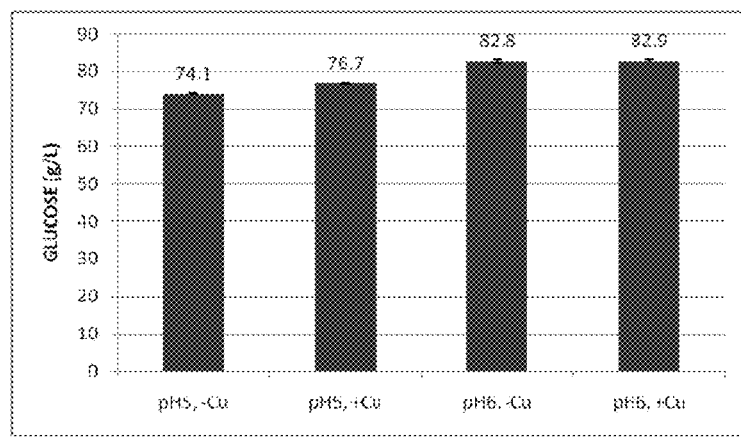
FIG. 4 shows activity of GH61a pre-incubated with 0 or 50 µM $CuSO_4$, copper(II) ion at either saccharification pH 5.0 or pH 6.0. Panel A shows glucose production, while Panel B shows the total production of C5 sugars.
Figure 4:
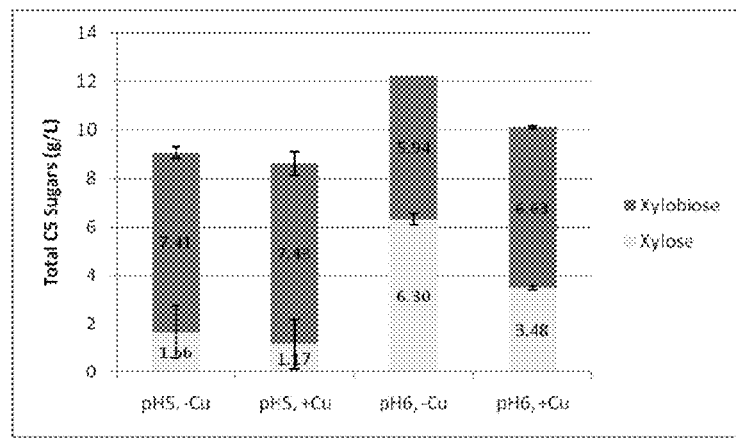

This Example describes experiments designed to determine the effects of added copper in saccharification reactions. The saccharification reactions were run in 30 g shake flasks (250 mL flasks) using 82 g/kg glucan of acid-pretreated corn stover and whole broth enzymes produced by *M. thermophila* strain CF-416 (produced using standard methods known in the art) at a 0.81% total enzyme load with respect to glucan. The reactions were conducted at pH 5.0 or pH 6.0, 55° C. and 250 rpm mixing, with supplementation of either 0 or 50 µM $CuSO_4$, copper(II) with respect to the total reaction volume. A pH trim was also performed using 2M NaOH at time intervals of 1, 4, 7, 22, 24 29, 46, 52, 70, 75 and 96 hrs, to maintain the pH at the desired value of pH 5.0 or pH 6.0. Samples were removed at 72 hours and the total amount of glucose in the reaction mixture was determined using standard HPLC methods and equipment as known in the art. The results indicated that under the conditions described herein, the effect of copper is dependent on saccharification pH. As shown in FIG. 4, Panel A, at a saccharification pH of pH 5.0, the addition of copper caused an increase in glucose yields by ~3.5% while this effect was not observed when the saccharification was carried out at pH 6.0. Also, the addition of copper may cause a decrease in the total amounts of C5 sugars that are produced as shown in FIG. 4, Panel B.

Example 10

Effect of Reducing Agents on the Cellulolytic Activity of GH61a

This Example provides experiments conducted to determine the effect of adding reducing agents (e.g., gallic acid and ascorbic acid) to saccharification reactions. In these experiments, enhancement of GH61 activity was tested using Variant 1 (SEQ ID NO:5) in the presence of reducing agents (specifically, ascorbic acid or gallic acid) and pretreatment filtrate, which contains various reducing agents from lignin degradation. Reactions were performed on cellulosic substrates, AVICEL® PH microcrystalline cellulose and phosphoric acid swollen cellulose (PASC), with purified $M.$ $thermophila$-produced GH61 Variant 1 and beta-glucosidase at 0.3% and 0.08% respectively, with respect to substrate glucan mass, and 128 mM sodium acetate buffer (pH 5) supplemented with 30 µM $CuSO_4$. Thus, reactions were performed with 0.3% GH61a and 0.08% BGL, where % enzyme loads are with respect to substrate glucan mass (36 g/L AVICEL® cellulose and 5 g/L PASC). Background (negative) controls were beta-glucosidase-only reactions tested in the absence of GH61a. Glucose production after 48 h incubation at pH 5, 55° C. was determined by glucose oxidase/peroxidase-based or HPLC-based glucose assay glucose assay, using methods known in the art.

Figure 5:
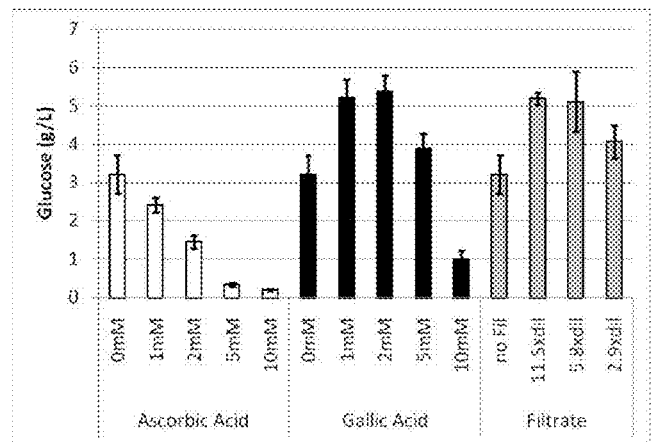
FIG. 5 shows activity of M. thermophila-produced GH61a Variant 1 on cellulosic substrates. Panel A shows the results on AVICEL® PH microcrystalline cellulose, and Panel B shows the results on phosphoric acid swollen cellulose (PASC), in the presence of ascorbic acid, gallic acid and pretreatment filtrate.
Figure 5:
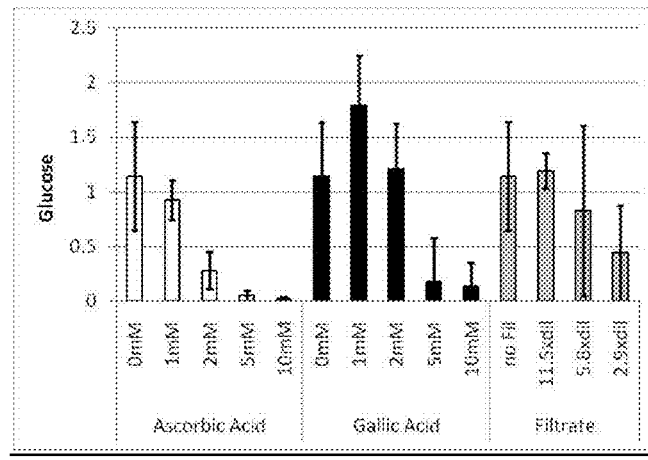

FIG. 5 shows the activity of $M.$ $thermophila$-produced GH61a Variant 1 on cellulosic substrates in the presence of ascorbic acid, gallic acid and pretreatment filtrate. Panel A shows the results for AVICEL® PH microcrystalline cellulose and Panel B shows the results for PASC. GH61-only activity is also shown, these results were obtained by subtracting the amount of glucose produced in the beta-glucosidase-only control reaction from the total amount of glucose produced in the reaction that included GH61a. Filtrate dilutions are indicated in this Figure, where undiluted filtrate equals 72% of the total reaction volume. In this Figure, N=4; and the error bars represent ±1 standard deviation.

The results indicate that supplementing the GH61a reaction with gallic acid improved the GH61 activity in generating soluble sugars from AVICEL® cellulose and PASC, which were then hydrolyzed by beta-glucosidase to generate glucose monomers. The improvement was also observed with diluted pretreatment filtrate, which suggests that the filtrate may contain gallic acid or gallic acid-like reductants that can beneficially impact GH61 activity.

Example 11

Evaluation of Oxygen Limitation in Saccharification Reactions

This example describes experiments conducted to determine if oxygen is a limiting factor in saccharification reactions. To investigate the level of oxygen required in the overall saccharification efficiency, two shake flask reactions were performed, in which one was left closed throughout the 72 hour reaction, while the other was opened at 4 hrs and 24 hrs for 10 seconds to provide fresh air. The reactions were run in 30 g shake flasks (250 mL flasks) using 87 g/kg glucan and $M.$ $thermophila$ CF-416 whole broth cellulases. The total protein content in each reaction was 0.81% total enzyme load with respect to glucan. The reactions were conducted at pH 5.0, 55° C. and 250 rpm mixing, with supplementation of 50 µM $CuSO_4$. Samples were removed at 72 hours and glucose yields were measured by monitoring glucose production using a glucose oxidase/peroxidase-based glucose assay. The results indicated that under the reaction conditions tested, oxygen was not a limiting factor as the two reactions (control vs. the reaction with air supplemented) yielded similar levels of glucose.

Example 12

Enhancement of Saccharification Efficiency by Addition of Surfactants

This example illustrates the enhancement of overall saccharification yield with the addition of surfactants such as TWEEN®-20 and PEG-4000. Experiments were designed to monitor the enhancement in cellulase activity with different concentrations of TWEEN®-20 or PEG-4000 in the biomass assay. The biomass assay was performed in a total volume of 90 µL, including 10 mg of pre-treated wheat straw, 64.8 µL (72% by volume) of filtrate (or $H_2O$ for no filtrate conditions), and 11.6 µL of a mixture of sodium acetate buffer (pH 5.0, supplemented with $CuSO_4$), $M.$ $thermophila$-produced cellobiohydrolase 1a (CBH1a), cellobiohydrolase 2b (CBH2b), beta-glucosidase (BGL), and glycoside hydrolase type 61 (GH61a). The final concentration of sodium acetate was 128 mM (with 30 µM $CuSO_4$) and the enzyme loads of CBH1a, CBH2b, BGL and GH61a were 0.15%, 0.15%, 0.08% and 0.3% with respect to the substrate glucan mass in the biomass substrate, respectively. Water was used in place of the enzymes as a negative control. Herein, "1× filtrate" indicates 72% of filtrate (i.e., the filtered liquid portion of pre-treated substrate) in the total reaction volume. The amount of glucose in the filtrate background was subtracted from the test data (N=2; Error bars in the Figures represent ±1 standard deviation). The reaction was incubated at 55° C. for 72 hours at pH 5, with shaking at 950 rpm, then was quenched by adding 180 µL of water. The total cellulase activity in the reaction mixture was measured by monitoring glucose production using a glucose oxidase/peroxidase-based glucose assay as known in the art. The results indicate that the total glucose production in the saccharification reaction was enhanced with the addition of TWEEN®-20 or PEG-4000.

Figure 6:
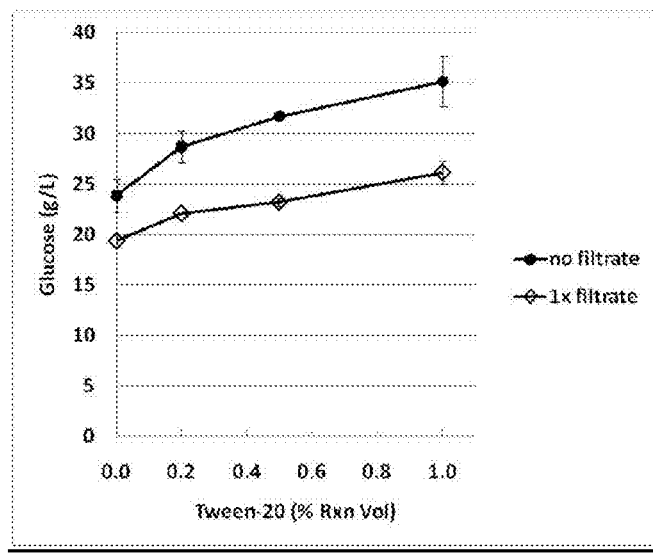
FIG. 6 provides results showing the effects of surfactants on saccharification. Panel A shows enzymatic hydrolysis activity of a cellulase mixture in the presence of TWEEN®-20, while Panel B shows the enzymatic hydrolysis activity of a cellulase mixture in the presence of PEG-4000.
Figure 6:
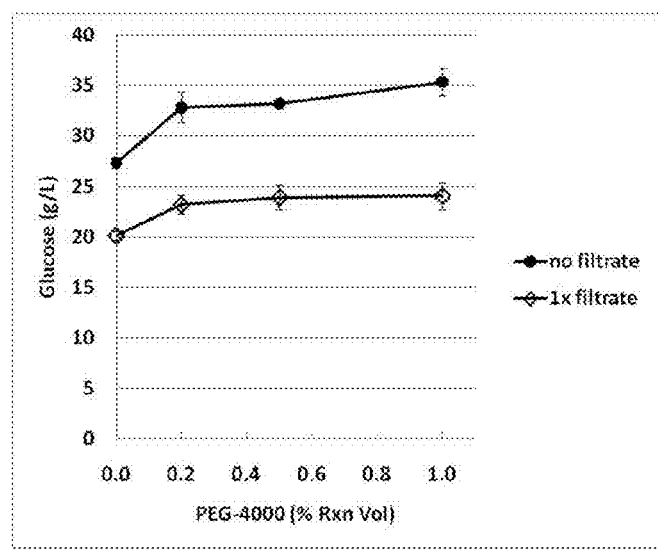

FIG. 6, Panel A, shows enzymatic hydrolysis activity of the cellulase mixture in the presence of TWEEN®-20. Data shown are total glucose produced by a mixture of GH61a, CBH1a, CBH2b, and BGL at 0.3%, 0.15%, 0.15%, and 0.08% with respect to the substrate glucan mass in the biomass substrate, respectively. In this Figure, TWEEN®-20 concentrations are expressed as % total reaction volume.

FIG. 6, Panel B, shows enzymatic hydrolysis activity of the cellulase mixture in the presence of PEG-4000. In this Figure, PEG-4000 concentrations are expressed as % total reaction volume.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

We claim:

1. A glycoside hydrolase 61 (GH61) variant protein comprising an amino acid sequence that is at least at least 90%, identical to SEQ ID NO:2 or a fragment of SEQ ID NO:2 having GH61 activity, wherein the amino acid sequence of the variant protein has one or more amino acid substitutions with respect to SEQ ID NO:2 or said fragment.

2. The GH61 variant protein of claim 1, wherein said GH61 variant protein is at least 95% identical to SEQ ID NO:2 or a fragment of SEQ ID NO:2 having GH61 activity.

3. The GH61 variant protein of claim 1, wherein said GH61 variant protein has increased thermoactivity, thermostability, and/or activity as compared to the GH61 wild-type protein of SEQ ID NO:2.

4. The GH61 variant protein of claim 1, wherein said GH61 variant protein comprises at least one substitution(s) at one or more of the following amino acid positions: H20, N35, W42, Q44, P45, F68, T87, V97, P103, E104, S127, W131, F132, K133, I134, A137, Y139, A142, A143, I162, P163, S164, D165, L166, K167, A168, G169, N170, Y171, V172, L173, R174, H175, E176, I177, I178, A179, L180, H181, Q190, A191, Y192, Y192, S205, A212, S215, K218, S232, T236, G239, A244, A246, T258, G270, P273, N317, P322, T323, G328, S330, and/or C341, wherein the amino acid positions are numbered with reference to SEQ ID NO:2.

5. The GH61 variant protein of claim 4, wherein said GH61 variant protein comprises at least one substitution(s) at one or more of the following amino acid positions: H20, N35, W42, E104, I134, S164, K167, A168, V172, I177, A179, and/or A191, wherein the amino acid positions are numbered with reference to SEQ ID NO:2.

6. The GH61 variant protein of claim 1, wherein said GH61 variant protein comprises the substitution set N35/E104/A168, wherein the amino acid positions are numbered with reference to SEQ ID NO:2.

7. The GH61 variant protein of claim 1, wherein said amino acid substitution(s) comprise one or more of the following substitutions numbered with reference to SEQ ID NO:2: N35G, E104C/D/H/Q, and A168P/X, wherein the amino acid positions are numbered with reference to SEQ ID NO:2.

8. The GH61 variant protein of claim 1, wherein said GH61 variant protein comprises one or more of the following substitutions: N35G, E104H, and A168P, wherein the amino acid positions are numbered with reference to SEQ ID NO:2.

9. The GH61 variant protein of claim 1, wherein said GH61 variant protein comprises the substitution set N35G/E104H/A168P, wherein the amino acid positions are numbered with reference to SEQ ID NO:2.

10. The GH61 variant protein of claim 1, wherein said variant protein comprises the sequence set forth in any of SEQ ID NOS:4, 6, and/or 8.

11. The GH61 variant protein of claim 1, wherein said GH61 variant protein is encoded by at least one polynucleotide sequence set forth in SEQ ID NOS:3, 5, and/or 7.

12. The GH61 variant protein of claim 1, wherein said GH61 variant protein, comprises at least one substitution(s) at one or more of the following amino acid positions: S24, V28, Y32, R34, N35, T40, Q44, P45, N46, T49, I51, T54, A55, A56, Q58, E64, N66, S67, G69, T70, P71, S78, T80, G82, G83, V88, K93, N95, E101, E104, A116, N118, S128, R130, G136, A137, K141, A142, G144, R145, A150, G155, Q161, S164, A168, Q184, N187, R199, G203, S205, A212, K218, A219, V230, S231, S232, P233, D234, T236, V237, G245, S253, A263, P266, G267, G268, G269, G270, A271, A280, T281, S282, R290, S295, A297, P303, G305, K310, N317, T320, V324, A326, P327, S329, S330, S332, V333, E336, W337, and/or S339, wherein the amino acid positions are numbered with reference to SEQ ID NO:2.

13. The GH61 variant protein of claim 1, wherein said GH61 variant protein comprises a plurality of amino acid substitutions.

14. The GH61 variant protein of claim 1, wherein said GH61 variant protein comprises a polypeptide sequence that is at least 90% identical to any of SEQ ID NOS:2, 3, 5, 6, 8, and/or 9, and/or a biologically active fragment of any of SEQ ID NOS: 2, 3, 5, 6, 8, and/or 9, wherein said fragment has GH61 activity.

15. A GH61 variant protein comprising an amino acid sequence that is at least 90% identical to SEQ ID NO:5, or a fragment of SEQ ID NO:5, having GH61 activity, wherein the amino acid sequence of the variant protein has one or more amino acid substitutions with respect to SEQ ID NO:2 or said fragment, and wherein the substitution(s) in the amino acid sequence result in the variant protein having increased GH61 activity in a reaction where crystalline cellulose undergoes saccharification by cellulase enzymes that are contained in culture broth from *M. thermophile cells*, compared with a reference protein comprising SEQ ID NO:2, or said fragment, without any of said substitutions.

16. An enzyme composition comprising at least one GH61 variant protein as set forth in claim 1.

17. The enzyme composition of claim 16, further comprising one or more enzymes selected from wild-type GH61 enzymes, endoglucanases (EG), β-glucosidases (BGL), Type 1 cellobiohydrolases (CBH1), and/or Type 2 cellobiohydrolases (CBH2), cellulases, hemicellulases, xylanases, xylosidases, amylases, glucoamylases, proteases, esterases, and lipases.

18. The enzyme composition of claim 17, further comprising at least one adjunct material.

19. The enzyme composition of claim 18, wherein said adjunct material is selected from divalent metal cations, reductants, surfactants, buffers, culture media, and enzyme stabilizing systems.

20. The composition of claim 16, wherein the cellulosic substrate is selected from wheat grass, wheat straw, barley straw, sorghum, rice grass, sugarcane straw, bagasse, switchgrass, corn stover, corn fiber, grains, or any combination thereof.

21. A composition comprising at least one variant GH61 protein of claim 1, one or more cellulase enzymes, a cellulosic substrate, and $Cu^{++}$, wherein the variant GH61 protein is at least 90% identical to SEQ ID NO:5, and/or a biologically fragment thereof with GH61 activity.

22. A composition comprising at least one GH61 protein of claim 1, one or more cellulase enzymes, a cellulosic substrate, and gallic acid, wherein the GH61 protein is at least 90% SEQ ID NO:5, and/or a biologically fragment thereof with GH61 activity.

23. A GH61 variant protein encoded by a polynucleotide, wherein the protein comprises an amino acid sequence that is at least or about 85% identical to any of SEQ ID NO:5, or a fragment of SEQ ID NO:5, having GH61 activity, wherein the amino acid sequence of the variant protein has one or more amino acid substitutions with respect to SEQ ID NO:2, or said fragment, and wherein the polynucleotide encoding the GH61 variant protein comprises at least one mutation set comprising t60c/c573g, wherein the nucleotide positions are numbered with reference to SEQ ID NO:1.

* * * * *

UNITED STATES PATENT AND TRADEMARK OFFICE
CERTIFICATE OF CORRECTION

PATENT NO. : 8,877,474 B2  Page 1 of 1
APPLICATION NO. : 13/592024
DATED : November 4, 2014
INVENTOR(S) : Yang et al.

It is certified that error appears in the above-identified patent and that said Letters Patent is hereby corrected as shown below:

In the Claims

In Column 467, Claim 1, line 38, replace "that is at least at least" with "that is at least".

In Column 467, Claim 4, line 58, replace "A191, Y192, Y192" with "A191, Y192".

In Column 470, Claim 22, lines 20-21, replace "90% SEQ ID NO:5" with "90% identical to SEQ ID NO:5".

Signed and Sealed this
Thirty-first Day of March, 2015

Michelle K. Lee
*Director of the United States Patent and Trademark Office*